US008821850B2

(12) United States Patent
Yurkovetskiy et al.

(10) Patent No.: US 8,821,850 B2
(45) Date of Patent: Sep. 2, 2014

(54) PROTEIN-POLYMER-DRUG CONJUGATES

(71) Applicant: Mersana Therapeutics, Inc., Cambridge, MA (US)

(72) Inventors: Aleksandr Yurkovetskiy, Littleton, MA (US); Mao Yin, Needham, MA (US); Timothy B. Lowinger, Carlisle, MA (US); Joshua D. Thomas, Natick, MA (US); Charles E. Hammond, Billerica, MA (US); Cheri A. Stevenson, Haverhill, MA (US); Natalya D. Bodyak, Brookline, MA (US); Patrick R. Conlon, Wakefield, MA (US); Dmitry R. Gumerov, Waltham, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 0 days.

(21) Appl. No.: 14/157,154

(22) Filed: Jan. 16, 2014

(65) Prior Publication Data

US 2014/0134127 A1    May 15, 2014

Related U.S. Application Data

(63) Continuation of application No. 13/710,335, filed on Dec. 10, 2012, which is a continuation-in-part of application No. 13/493,899, filed on Jun. 11, 2012, now Pat. No. 8,685,383.

(60) Provisional application No. 61/618,499, filed on Mar. 30, 2012, provisional application No. 61/605,618, filed on Mar. 1, 2012, provisional application No. 61/566,935, filed on Dec. 5, 2011, provisional application No. 61/513,234, filed on Jul. 29, 2011, provisional application No. 61/501,000, filed on Jun. 24, 2011, provisional application No. 61/495,771, filed on Jun. 10, 2011.

(51) Int. Cl.
| | |
|---|---|
| *A61K 31/74* | (2006.01) |
| *A61K 47/48* | (2006.01) |
| *A61K 38/04* | (2006.01) |
| *C08G 63/48* | (2006.01) |
| *C08G 63/91* | (2006.01) |
| *C08G 6/00* | (2006.01) |
| *C08G 65/332* | (2006.01) |
| *C08G 65/333* | (2006.01) |
| *C08G 65/334* | (2006.01) |

(52) U.S. Cl.
CPC ............ *C08G 6/00* (2013.01); *A61K 47/48192* (2013.01); *C08G 65/3324* (2013.01); *C08G 65/33396* (2013.01); *C08G 65/334* (2013.01); *A61K 47/48692* (2013.01); *A61K 47/48507* (2013.01); *A61K 47/48246* (2013.01)
USPC ....... 424/78.17; 530/330; 525/54.1; 525/411; 525/413

(58) Field of Classification Search
CPC .................. A61K 47/48692; A61K 47/48246; A61K 47/48192; C08G 65/33396; C08G 65/334
See application file for complete search history.

(56) References Cited

U.S. PATENT DOCUMENTS

| | | | |
|---|---|---|---|
| 6,080,751 A * | 6/2000 | Stehlin et al. ................. 514/283 |
| 6,822,086 B1 | 11/2004 | Papisov | |
| 7,160,924 B2 | 1/2007 | Kinstler et al. | |
| 7,276,497 B2 | 10/2007 | Chari et al. | |
| 7,553,816 B2 | 6/2009 | Senter et al. | |
| 7,790,150 B2 | 9/2010 | Papisov et al. | |
| 7,977,465 B2 | 7/2011 | Ng et al. | |
| 8,030,459 B2 | 10/2011 | Papisov et al. | |
| 8,034,959 B2 | 10/2011 | Ng et al. | |
| 2002/0082362 A1 | 6/2002 | Brocchini et al. | |
| 2004/0105840 A1 | 6/2004 | Kinstler et al. | |
| 2004/0166089 A1 | 8/2004 | Yu et al. | |
| 2005/0049387 A1 | 3/2005 | Van et al. | |
| 2005/0169933 A1 | 8/2005 | Steeves et al. | |
| 2007/0190018 A1 | 8/2007 | Papisov | |
| 2008/0176958 A1 | 7/2008 | Davis et al. | |
| 2009/0148396 A1 | 6/2009 | Akullian et al. | |

(Continued)

FOREIGN PATENT DOCUMENTS

| | | |
|---|---|---|
| WO | WO 0110468 A2 | 2/2001 |
| WO | WO 2004009774 A2 | 1/2004 |

(Continued)

OTHER PUBLICATIONS

Burke et al., "Design, Synthesis, and Biological Evaluation of Antibody-Drug Conjugates Comprised of Potent Camptothecin Analogues." *Bioconj. Chem.* 20.6(2009):1242-1250.

(Continued)

*Primary Examiner* — Marcela M Cordero Garcia
*Assistant Examiner* — Sergio Coffa
(74) *Attorney, Agent, or Firm* — Cooley LLP

(57) ABSTRACT

A drug conjugate is provided herein. The conjugate comprises a protein based recognition-molecule (PBRM) and a polymeric carrier substituted with one or more -$L^D$-D, the protein based recognition-molecule being connected to the polymeric carrier by $L^P$. Each occurrence of D is independently a therapeutic agent having a molecular weight ≤5 kDa. $L^D$ and $L^P$ are linkers connecting the therapeutic agent and PBRM to the polymeric carrier respectively. Also disclosed are polymeric scaffolds useful for conjugating with a PBRM to form a polymer-drug-PBRM conjugate described herein, compositions comprising the conjugates, methods of their preparation, and methods of treating various disorders with the conjugates or their compositions.

18 Claims, 10 Drawing Sheets

(56) References Cited

U.S. PATENT DOCUMENTS

| | | |
|---|---|---|
| 2010/0129314 A1 | 5/2010 | Singh et al. |
| 2010/0203007 A1 | 8/2010 | Li et al. |
| 2010/0305149 A1 | 12/2010 | Yurkovetskiy et al. |
| 2011/0020343 A1 | 1/2011 | Senter et al. |
| 2011/0070248 A1 | 3/2011 | Ichikawa et al. |
| 2011/0243880 A1 | 10/2011 | Yurkovetskiy et al. |

FOREIGN PATENT DOCUMENTS

| | | |
|---|---|---|
| WO | WO 2005081711 A2 | 9/2005 |
| WO | WO 2006044986 A1 | 4/2006 |
| WO | WO 2007008848 A2 | 1/2007 |
| WO | WO 2007103288 A2 | 9/2007 |
| WO | WO 2007109567 A1 | 9/2007 |
| WO | WO 2007140371 A2 | 12/2007 |
| WO | WO 2008052187 A2 | 5/2008 |
| WO | WO 2008076333 A2 | 6/2008 |
| WO | WO 2009052249 A1 | 4/2009 |
| WO | WO 2009117531 A1 | 9/2009 |
| WO | WO 2010114940 A1 | 10/2010 |
| WO | WO 2010126552 A1 | 11/2010 |
| WO | WO 2010138719 A1 | 12/2010 |
| WO | WO 2011120053 A1 | 9/2011 |
| WO | WO 2012066581 A1 | 5/2012 |

OTHER PUBLICATIONS

Hamblett et al., "Effects of Drug Loading on the Antitumor Activity of a Monoclonal Antibody Drug Conjugate." *Clin. Cancer Res.* 10(2004);7063-7070.

Lambert et al. "Drug-Conjugated Monoclonal Antibodies for the Treatment of Cancer." *Curr. Opin. Pharmacal.* 5(2005):543-549.

Lash, "Making the Case for Antibody-Drug Conjugates." In Vivo. 28.11 (2010):32-38. (Article #201 0800200).

Noguchi et al., "Preparation and Properties of the Immunoconjugate Composed of Anti-Human Colon Cancer Monoclonal Antibody and Mitomycin C-Dextran Conjugate." *Bioconj. Chem.* 3.2(1992): 132-137.

Senter, "Potent Antibody Drug Conjugates for Cancer Therapy." *Curr. Opin. Chem. Bioi.* 13(2009): 1-10.

Ulbrich et al. "HPMA Copolymers With pH-Controlled Release of Doxorubicin." *J. Control. Release.* 87.1-3(2003):33-4 7.

Yurkovetskiy et al., "Fully Degradable Hydrophilic Polyals for Protein Modification." *Biomacromol.* 6.5(2005):2648-2658.

\* cited by examiner

Table 1

|  | At least one polymer attached to one PBRM, PBRM MW > 40 kDa | | |
|---|---|---|---|
| Starting/unmodified PHF MW range, kDa | Acceptable Range | Preferable Range | Most preferable |
|  | 2-40 kDa | 6-20 kDa | 8-15 kDa |
| $m+m_1+m_2+m_3+m_4$ | 15-300 | 45-150 | 60-110 |
| $m_1+m_2$ | 3-140 | 7-75 | 7-55 |
| $m_2$ | 1-40 | 2-20 | 2-15 |
| $m_3+m_4$ | 1-18 | 1-9 | 1-7 |
| $m_4$ | 1-10 | 1-10 | 1-10 |
| Polymer/PBRM ratio | 1-10 | 1-10 | 1-10 |

Table 2

|  | At least one PBRM is attached to one polymer PBRM MW <200 kDa | | |
|---|---|---|---|
| Starting/unmodified PHF MW range, kDa | Acceptable Range | Preferable Range | Most preferable |
|  | 20-300 kDa | 40-150 kDa | 50-100 kDa |
| $m+m_1+m_2+m_3+m_4$ | 150-2200 | 300-1100 | 370-740 |
| $m_1+m_2$ | 14-660 | 20-330 | 22-220 |
| $m_2$ | 3-300 | 4-150 | 5-100 |
| $m_3+m_4$ | 1-110 | 1-75 | 1-40 |
| $m_4$ | 1-60 | 1-30 | 1-20 |
| Polymer/PBRM ratio | 0.0167-1.0 | 0.0333-1.0 | 0.05-1.0 |

Table 3

|  | At least one PBRM is attached to one polymer PBRM MW <200 kDa, PBRM MW preferably < 80 kDa, PBRM MW more preferably 30-70 kDa, 20-30 kDa, or 4-20 kDa | | |
|---|---|---|---|
| Starting/unmodified PHF MW range, kDa | Acceptable Range | Preferable Range | Most preferable |
|  | 20-300 kDa | 20-150 kDa | 30-100 kDa |
| $m+m_1+m_2+m_3+m_4$ | 150-2200 | 150-1100 | 220-740 |
| $m_1+m_2$ | 14-660 | 14-330 | 18-220 |
| $m_2$ | 3-300 | 3-150 | 3-100 |
| $m_3+m_4$ | 1-110 | 1-55 | 1-40 |
| $m_4$ | 1-60 | 1-30 | 1-20 |
| Polymer/PBRM ratio | 0.0167-1.0 | 0.0333-1.0 | 0.05-1.0 |

Figure 10

PROTEIN-POLYMER-DRUG CONJUGATES

RELATED APPLICATIONS

This application is a continuation of U.S. patent application Ser. No. 13/710,355, filed Dec. 10, 2012, which is a continuation-in-part of U.S. patent application Ser. No. 13/493,899, filed Jun. 11, 2012, which claims the benefit of and priority under 35 USC §119(e) to U.S. Patent Application Nos. 61/495,771, filed Jun. 10, 2011; 61/501,000, filed Jun. 24, 2011; 61/513,234, filed Jul. 29, 2011; 61/566,935, filed Dec. 5, 2011; 61/605,618, filed Mar. 1, 2012; and 61/618,499, filed Mar. 30, 2012. The contents of each of these applications are hereby incorporated by reference in their entireties.

BACKGROUND OF THE INVENTION

Traditionally, pharmaceuticals have primarily consisted of small molecules that are dispensed orally (as solid pills and liquids) or as injectables. Over the past three decades, formulations (i.e., compositions that control the route and/or rate of drug delivery and allow delivery of the therapeutic agent at the site where it is needed) have become increasingly common and complex. Nevertheless, many questions and challenges regarding the development of new treatments as well as the mechanisms with which to administer them remain to be addressed. For example, many drugs exhibit limited or otherwise reduced potencies and therapeutic effects because they are either generally subject to partial degradation before they reach a desired target in the body, or accumulate in tissues other than the target, or both.

One objective in the field of drug delivery systems, therefore, is to deliver medications intact to specifically targeted areas of the body through a system that can stabilize the drug and control the in vivo transfer of the therapeutic agent utilizing either physiological or chemical mechanisms, or both.

Antibody-drug conjugates have been developed as target-specific therapeutic agents. Antibodies against various cancer cell-surface antigens have been conjugated with different cytotoxic agents that inhibit various essential cellular targets such as microtubules (maytansinoids, auristatins, taxanes: U.S. Pat. Nos. 5,208,020; 5,416,064; 6,333,410; 6,441,163; 6,340,701; 6,372,738; 6,436,931; 6,596,757; and 7,276,497); DNA (calicheamicin, doxorubicin, CC-1065 analogs; U.S. Pat. Nos. 5,475,092; 5,585,499; 5,846,545; 6,534,660; 6,756,397; and 6,630,579). Antibody conjugates with some of these cytotoxic drugs are actively being investigated in the clinic for cancer therapy (Ricart, A. D., and Tolcher, A. W., 2007, *Nature Clinical Practice*, 4, 245-255; Krop et al., 2010, *J. Clin. Oncol.*, 28, 2698-2704). However, existing antibody-drug conjugates have exhibited a few limitations. A major limitation is their inability to deliver a sufficient concentration of drug to the target site because of the limited number of targeted antigens and the relatively moderate cytotoxicity of cancer drugs like methotrexate, daunorubicin, maytansinoids, taxanes, and vincristine. One approach to achieving significant cytotoxicity is by linkage of a large number of drug molecules either directly or indirectly to the antibody. However such heavily modified antibodies often display impaired binding to the target antigen and fast in vivo clearance from the blood stream. Therefore, there is a need to improve the ability to deliver a sufficient concentration of a drug to the target such that maximum cytotoxicity for the drug is achieved.

SUMMARY OF THE INVENTION

The present invention relates to a protein-polymer-drug conjugate that is biodegradable, biocompatible and exhibits high drug load as well as strong binding to target antigen. The present invention also relates to a polymeric scaffold useful to conjugate with a protein based recognition-molecule (PBRM) so as to obtain the protein-polymer-drug conjugate.

In one aspect, the invention relates to a polymeric scaffold of Formula (Ia) useful to conjugate with a protein based recognition-molecule (PBRM) that has a molecular weight of less than 80 kDa, wherein the scaffold comprises a polymeric carrier:

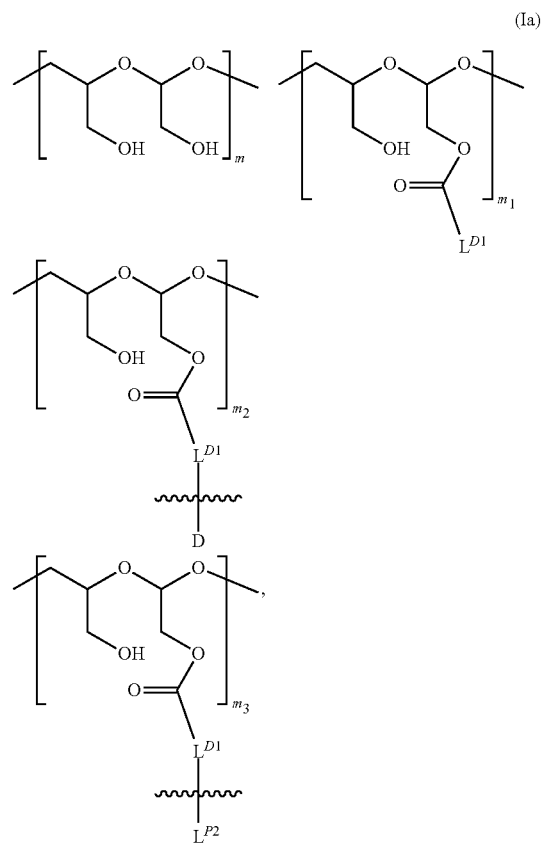

further wherein:

the polymeric carrier is PHF having a molecular weight ranging from 20 kDa to 150 kDa;

each occurrence of D is independently a therapeutic agent having a molecular weight of ≤5 kDa;

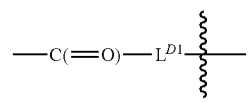

is a linker that contains a biodegradable bond so that when the bond is broken, D is released from the polymeric carrier in an active form for its intended therapeutic effect; in which $L^{D1}$ is a carbonyl-containing moiety, and the

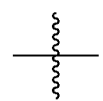

between $L^{D1}$ and D denotes direct or indirect attachment of D to $L^{D1}$;

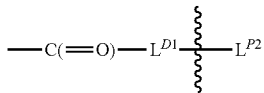

is a linker distinct from the linker

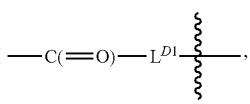

in which $L^{P2}$ is a moiety containing a functional group that is capable of forming a covalent bond with a functional group of a PBRM, and the

between $L^{D1}$ and $L^{P2}$ denotes direct or indirect attachment of $L^{P2}$ to $L^{D1}$;

m is an integer from 1 to 1100,
$m_1$ is an integer from 1 to 330,
$m_2$ is an integer from 3 to 150,
$m_3$ is an integer from 1 to 55, and
the sum of m, $m_1$, $m_2$ and $m_3$ ranges from 150 to about 1100.

The scaffold of (Ia) can include one or more of the following features:

The PHF has a molecular weight ranging from 30 kDa to 100 kDa, $m_2$ is an integer from 3 to about 100, $m_3$ is an integer from 1 to 40, and $m_1$ is an integer from 1 to 220.

The functional group of $L^{P2}$ is selected from —$SR^p$, —S—S-LG, maleimido, and halo, in which LG is a leaving group and $R^p$ is H or a sulfur protecting group.

$L^{D1}$ comprises —X—$(CH_2)_v$—C(=O)— with X directly connected to the carbonyl group of

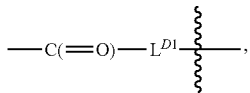

in which X is $CH_2$, O, or NH, and v is an integer from 1 to 6.

$L^{P2}$ contains a biodegradable bond.

The scaffold further comprises a PBRM connected to the polymeric carrier via $L^P$.

The scaffold is of Formula (Ib):

(Ib)

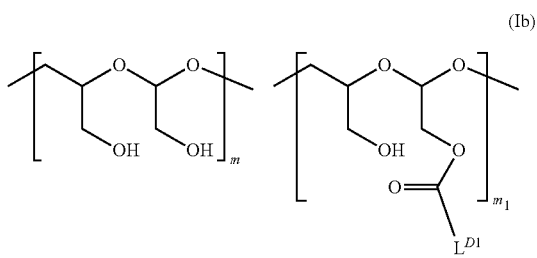

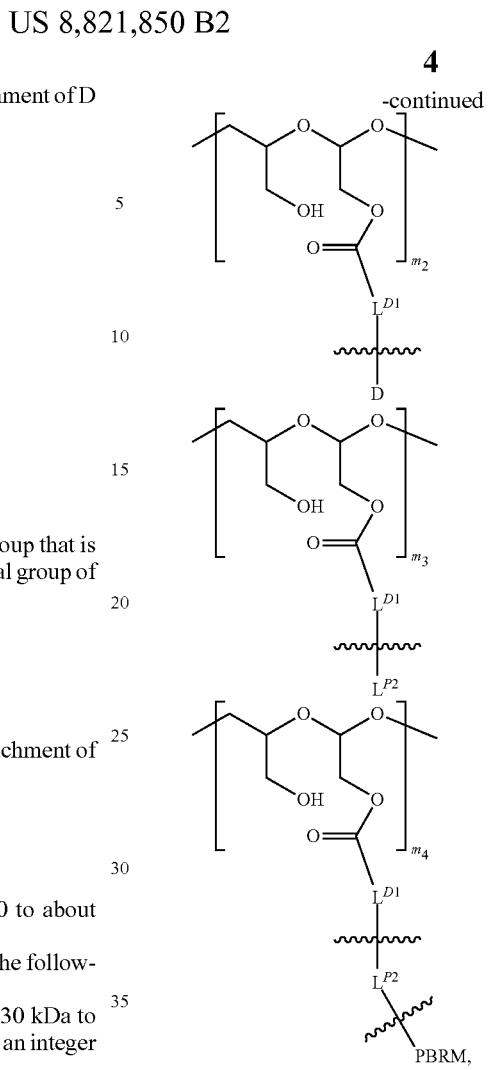

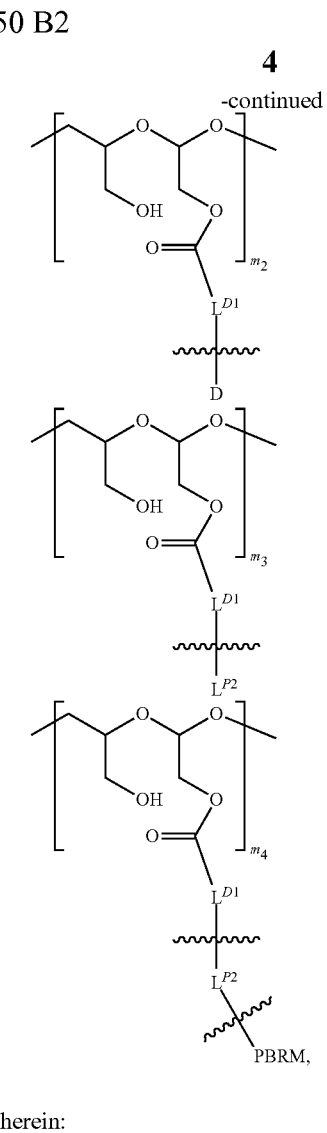

wherein:

between $L^{P2}$ and PBRM denotes direct or indirect attachment of PBRM to $L^{P2}$, each occurrence of PBRM independently has a molecular weight of less than 80 kDa, m is an integer from 1 to 1100,
$m_1$ is an integer from 1 to 330,
$m_2$ is an integer from 3 to 150,
$m_3$ is an integer from 0 to 55,
$m_4$ is an integer from 1 to 30; and
the sum of m, $m_1$, $m_2$, $m_3$ and $m_4$ ranges from 150 to 1100.

The scaffold of Formula (Ib) can include one or more of the following features:

The PHF has a molecular weight ranging from 30 kDa to 100 kDa, $m_1$ is an integer from 1 to 220, $m_2$ is an integer from 3 to 100, $m_3$ is an integer from 0 to 40, and $m_4$ is an integer from 1 to 20, and the sum of $m_1$ and $m_2$ is an integer from 18 to 220, and the sum of $m_3$ and $m_4$ is an integer from 1 to 40.

$m_2$ is an integer from 3 to about 150.
$m_4$ is an integer from 1 to about 10.
The sum of $m_1$ and $m_2$ is an integer from 14 to 330.
The sum of $m_3$ and $m_4$ is an integer from 1 to 55.

Each occurrence of PBRM independently has a molecular weight of about 30-70 kDa, and $m_2$ is an integer from 3 to 100.

Each occurrence of PBRM independently has a molecular weight of about 20-30 kDa, and $m_2$ is an integer from 3 to 150.

Each occurrence of PBRM independently has a molecular weight of about 4-20 kDa, and $m_2$ is an integer from 3 to 150.

The ratio of $m_2$ to $m_4$ is between 5:1 and 40:1.

Other features of scaffold of Formula (Ia) or (Ib) include those described herein where applicable.

In another aspect, the invention features a polymeric scaffold useful to conjugate with a PBRM. The scaffold comprises a polymeric carrier, one or more -$L^D$-D connected to the polymeric carrier, and one or more $L^P$ connected to the polymeric carrier which is suitable for connecting a PBRM to the polymeric carrier, wherein:

each occurrence of D is independently a therapeutic agent having a molecular weight ≤5 kDa;

the polymeric carrier is a polyacetal or polyketal, $L^D$ is a linker having the structure:

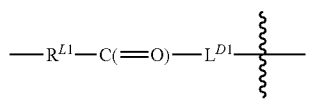

with $R^{L1}$ connected to an oxygen atom of the polymeric carrier and $L^{D1}$ connected to D, and

denotes direct or indirect attachment of D to $L^{D1}$, and $L^D$ contains a biodegradable bond so that when the bond is broken, D is released from the polymeric carrier in an active form for its intended therapeutic effect;

$L^{D1}$ is a carbonyl-containing moiety;

$L^P$ is a linker different from $L^D$ and having the structure: —$R^{L2}$—C(=O)-$L^{P1}$ with $R^{L2}$ connected to an oxygen atom of the polymeric carrier and $L^{P1}$ suitable for connecting directly or indirectly to a PBRM;

each of $R^{L1}$ and $R^{L2}$ independently is absent, alkyl, heteroalkyl, cycloalkyl, or heterocyclo alkyl; and $L^{P1}$ is a moiety containing a functional group that is capable of forming a covalent bond with a functional group of a PBRM.

The polymeric scaffold can include one or more of the following features.

$L^P$ is a linker having the structure:

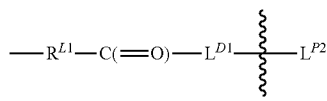

in which $L^{P2}$ is a moiety containing a functional group that is capable of forming a covalent bond with a functional group of a PBRM, and

denotes direct or indirect attachment of $L^{P2}$ to $L^{D1}$.

The functional group of $L^{P1}$ or $L^{P2}$ is selected from —$SR^p$, —S—S-LG, maleimido, and halo, in which LG is a leaving group and $R^p$ is H or a sulfur protecting group.

$L^{D1}$ comprises —X—(CH$_2$)$_v$—C(=O)— with X directly connected to the carbonyl group of $R^{L1}$—C(=O), in which X is CH$_2$, O, or NH, and v is an integer from 1 to 6.

$L^{P1}$ or $L^{P2}$ contains a biodegradable bond.

Each of $R^{L1}$ and $R^{L2}$ is absent.

The polymeric carrier of the scaffold of the invention is a polyacetal, e.g., a PHF having a molecular weight (i.e., MW of the unmodified PHF) ranging from about 2 kDa to about 300 kDa.

For conjugating a PBRM having a molecular weight of 40 kDa or greater (e.g., 80 kDa or greater), the polymeric carrier of the scaffold of the invention is a polyacetal, e.g., a PHF having a molecular weight (i.e., MW of the unmodified PHF) ranging from about 2 kDa to about 40 kDa (e.g., about 6-20 kDa or about 8-15 kDa).

For conjugating a PBRM having a molecular weight of 200 kDa or less (e.g., 80 kDa or less), the polymeric carrier of the scaffold of the invention is a polyacetal, e.g., a PHF having a molecular weight (i.e., MW of the unmodified PHF) ranging from about 20 kDa to about 300 kDa (e.g., about 40-150 kDa or about 50-100 kDa).

The scaffold is of Formula (Ia):

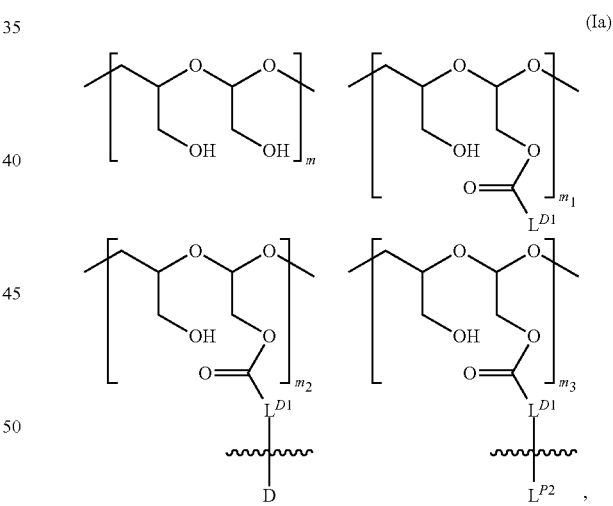

(Ia)

wherein:
m is an integer from 1 to about 2200,
$m_1$ is an integer from 1 to about 660,
$m_2$ is an integer from 1 to about 300,
$m_3$ is an integer from 1 to about 110, and
the sum of m, $m_1$, $m_2$ and $m_3$ ranges from about 15 to about 2200.

When the PHF in Formula (Ia) has a molecular weight ranging from about 2 kDa to about 40 kDa (i.e., the sum of m, $m_1$, $m_2$, and $m_3$ ranging from about 15 to about 300), $m_2$ is an integer from 1 to about 40, $m_3$ is an integer from 1 to about 18, and/or $m_1$ is an integer from 1 to about 140 (e.g., $m_1$ being about 1-90).

When the PHF in Formula (Ia) has a molecular weight ranging from about 6 kDa to about 20 kDa (i.e., the sum of m, $m_1$, $m_2$, and $m_3$ ranging from about 45 to about 150), $m_2$ is an integer from 2 to about 20, $m_3$ is an integer from 1 to about 9, and/or $m_1$ is an integer from 1 to about 75 (e.g., $m_1$ being about 4-45).

When the PHF in Formula (Ia) has a molecular weight ranging from about 8 kDa to about 15 kDa (i.e., the sum of m, $m_1$, $m_2$, and $m_3$ ranging from about 60 to about 110), $m_2$ is an integer from 2 to about 15, $m_3$ is an integer from 1 to about 7, and/or $m_1$ is an integer from 1 to about 55 (e.g., $m_1$ being about 4-30).

When the PHF in Formula (Ia) has a molecular weight ranging from 20 kDa to 300 kDa (i.e., the sum of m, $m_1$, $m_2$, and $m_3$ ranging from about 150 to about 2200), $m_2$ is an integer from 3 to about 300, $m_3$ is an integer from 1 to about 110, and/or $m_1$ is an integer from 1 to about 660 (e.g., $m_1$ being about 10-250).

When the PHF in Formula (Ia) has a molecular weight ranging from about 50 kDa to about 100 kDa (i.e., the sum of m, $m_1$, $m_2$, and $m_3$ ranging from about 370 to about 740), $m_2$ is an integer from 5 to about 100, $m_3$ is an integer from 1 to about 40, and/or $m_1$ is an integer from 1 to about 220 (e.g., $m_1$ being about 15-80).

The scaffold further comprises a PBRM connected to the polymeric carrier via $L^P$.

One or more PBRMs are connected to one drug-carrying polymeric carrier.

The scaffold (e.g., a PBRM-polymer-drug conjugate) is of Formula (Ib):

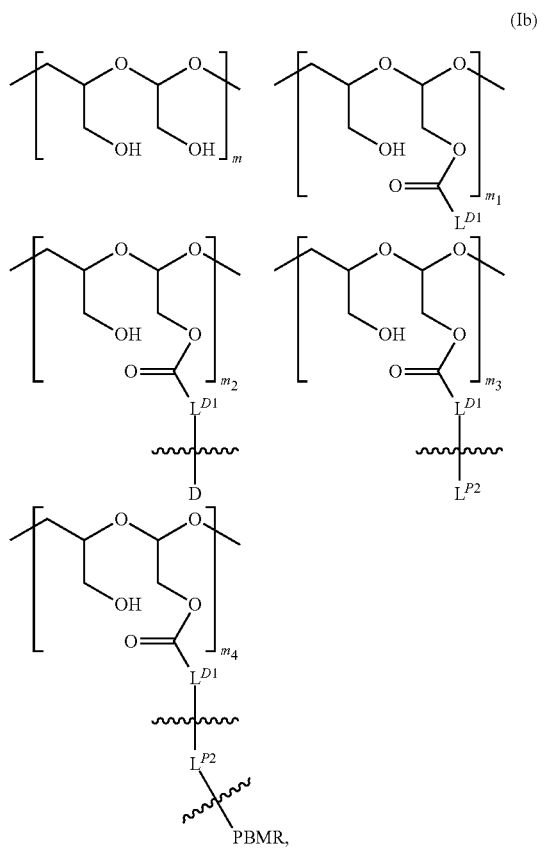

(Ib)

wherein:

between $L^{P2}$ and PBRM denotes direct or indirect attachment of PBRM to $L^{P2}$, each occurrence of PBRM independently has a molecular weight of less than 200 kDa, m is an integer from 1 to about 2200, $m_1$ is an integer from 1 to about 660, $m_2$ is an integer from 3 to about 300, $m_3$ is an integer from 0 to about 110, $m_4$ is an integer from 1 to about 60; and the sum of m, $m_1$, $m_2$, $m_3$ and $m_4$ ranges from about 150 to about 2200.

In Formula (Ib), $m_1$ is an integer from about 10 to about 660 (e.g., about 10-250).

When the PHF in Formula (Ib) has a molecular weight ranging from about 50 kDa to about 100 kDa (i.e., the sum of m, $m_1$, $m_2$, $m_3$, and $m_4$ ranging from about 370 to about 740), $m_2$ is an integer from 5 to about 100, $m_3$ is an integer from 1 to about 40, $m_4$ is an integer from 1 to about 20, and/or $m_1$ is an integer from 1 to about 220 (e.g., $m_1$ being about 15-80).

Alternatively or additionally, one or more drug-carrying polymeric carriers are connected to one PBRM. The scaffold (e.g., a PBRM-polymer-drug conjugate) comprises a PBRM with a molecular weight of greater than 40 kDa and one or more D-carrying polymeric carriers connected to the PBRM, in which each of the D-carrying polymeric carrier independently is of Formula (Ic):

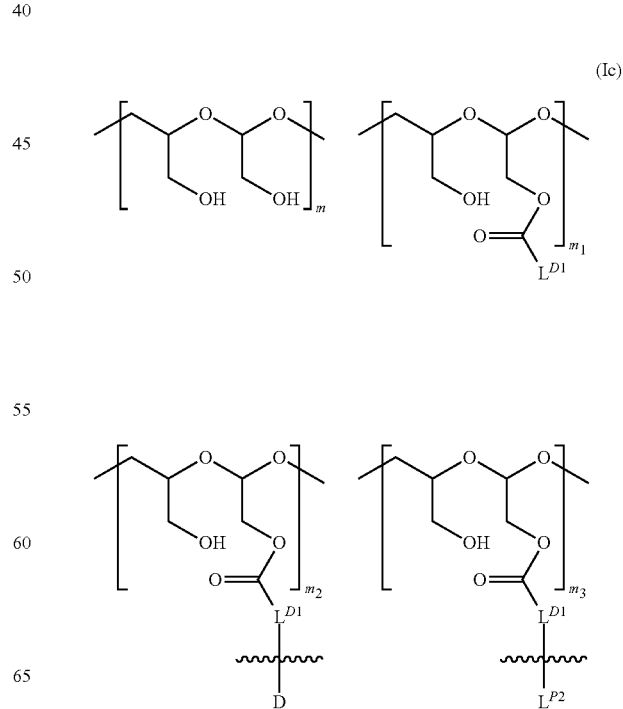

(Ic)

-continued

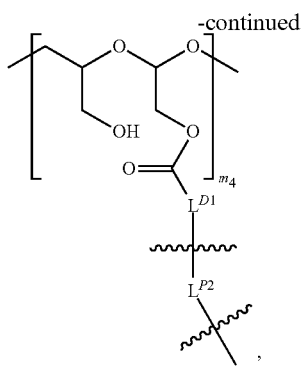

wherein:
terminal

attached to $L^{P2}$ denotes direct or indirect attachment of $L^{P2}$ to PBRM such that the D-carrying polymeric carrier is connected to the PBRM, m is an integer from 1 to 300,
$m_1$ is an integer from 1 to 140,
$m_2$ is an integer from 1 to 40,
$m_3$ is an integer from 0 to 18,
$m_4$ is an integer from 1 to 10; and
the sum of m, $m_1$, $m_2$, $m_3$, and $m_4$ ranges from 15 to 300; provided that the total number of $L^{P2}$ attached to the PBRM is 10 or less.

In Formula (Ic), $m_1$ is an integer from 1 to about 120 (e.g., about 1-90) and/or $m_3$ is an integer from 1 to about 10 (e.g., about 1-8).

When the PHF in Formula (Ic) has a molecular weight ranging from about 6 kDa to about 20 kDa (i.e., the sum of m, $m_1$, $m_2$, $m_3$, and $m_4$ ranging from about 45 to about 150), $m_2$ is an integer from 2 to about 20, $m_3$ is an integer from 1 to about 9, and/or $m_1$ is an integer from 1 to about 75 (e.g., $m_1$ being about 4-45).

When the PHF in Formula (Ic) has a molecular weight ranging from about 8 kDa to about 15 kDa (i.e., the sum of m, $m_1$, $m_2$, $m_3$, and $m_4$ ranging from about 60 to about 110), $m_2$ is an integer from 2 to about 15, $m_3$ is an integer from 1 to about 7, and/or $m_1$ is an integer from 1 to about 55 (e.g., $m_1$ being about 4-30).

Each occurrence of D independently is selected from vinca alkaloids, auristatins, tubulysins, duocarmycins, kinase inhibitors, MEK inhibitors, KSP inhibitors, and analogs thereof.

$L^D$ is —$R^{L1}$—C(=O)—$X^D$-$M^{D1}$-$Y^D$-$M^{D2}$-$Z^D$-$M^{D3}$-$Q^D$-$M^{D4}$- with $M^{D4}$ directly connected to D, in which $X^D$ is —O—, —S—, —N($R^1$)—, or absent, in which $R^1$ is hydrogen, an aliphatic, heteroaliphatic, carbocyclic, or heterocycloalkyl moiety, —C(=O)$R^{1B}$, —C(=O)O$R^{1B}$, or —SO$_2R^{1B}$, or —N($R^1$)— is a heterocycloalkyl moiety, wherein $R^{1B}$ is hydrogen, an aliphatic, heteroaliphatic, carbocyclic, or heterocycloalkyl moiety;

each of $Y^D$, $Z^D$, and $Q^D$, independently, is absent or a biodegradable linker moiety selected from the group consisting of —S—S—, —C(=O)O—, —C(=O)N$R^2$—, —OC(=O)—, —N$R^2$C(=O)—, —OC(=O)O—, —OC(=O) N$R^2$—, —N$R^2$C(=O)O—, —N$R^2$C(=O)N$R^3$—, —C(O$R^2$)O—, —C(O$R^2$)S—, —C(O$R^2$)N$R^3$—, —C(S$R^2$)O—, —C(S$R^2$)S—, C(S$R^2$)N$R^3$—, —C(N$R^2R^3$)O—, —C(N$R^2R^3$)S—, —C(N$R^2R^3$)N$R^4$—, —C(=O)S—, —SC(=O)—, —SC(=O)S—, —OC(=O)S—, —SC(=O)O—, —C(=S)S—, —SC(=S)—, —OC(=S)—, —C(=S)O—, —SC(=S)O—, —OC(=S)S—, —OC(=S)O—, —SC(=S)S—, —C(=N$R^2$)O—, —C(=N$R^2$)S—, —C(=N$R^2$)N$R^3$—, —OC(=N$R^2$)—, —SC(=N$R^2$)—, —N$R^3$C(=N$R^2$)—, —N$R^2$SO$_2$—, N$R^2$N$R^3$—, —C(=O)N$R^2$N$R^3$—, —N$R^2$N$R^3$C(=O)—, —OC(=O)N$R^2$N$R^3$—, —N$R^2$N$R^3$C(=O)O—, —C(=S)N$R^2$N$R^3$—, —N$R^2$N$R^3$C(=S)—, —C(=N$R^4$)N$R^2$N$R^3$—, —N$R^2$N$R^3$C(=N$R^4$)—, —O(N=C$R^3$)—, —(C$R^3$=N)O—, —C(=O)N$R^2$—(N$R^3$)—, —(C$R^3$=N)—N$R^2$C(=O)—, —SO$_3$—, —N$R^2$SO$_2$N$R^3$—, —SO$_2$N$R^2$—, and polyamide, wherein each occurrence of $R^2$, $R^3$, and $R^4$ independently is hydrogen or an aliphatic, heteroaliphatic, carbocyclic, or heterocyclic moiety, or each occurrence of —N$R^2$— or —N$R^2$N$R^3$— is a heterocycloalkyl moiety; and each of $M^{D1}$, $M^{D2}$, $M^{D3}$, and $M^{D4}$ independently, is absent or a non-biodegradable linker moiety selected from the group consisting of alkyl, alkenyl, alkynyl, heteroalkyl, heteroalkenyl, heteroalkynyl, a carbocyclic moiety, a heterocyclic moiety, and a combination thereof, and each of $M^{D1}$, $M^{D2}$, and $M^{D3}$ optionally contains one or more —(C=O)— but does not contain any said biodegradable linker moiety;

provided that for each $L^{D1}$, at least one of $X^D$, $Y^D$, $Z^D$, and $Q^D$ is not absent.

Each

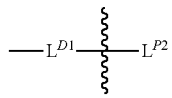

when not connected to PBRM, independently comprises a terminal group $W^P$, in which each $W^P$ independently is:

(1)
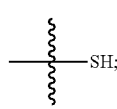

(2)
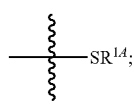

(3)
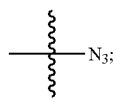

(4)
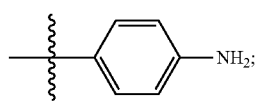

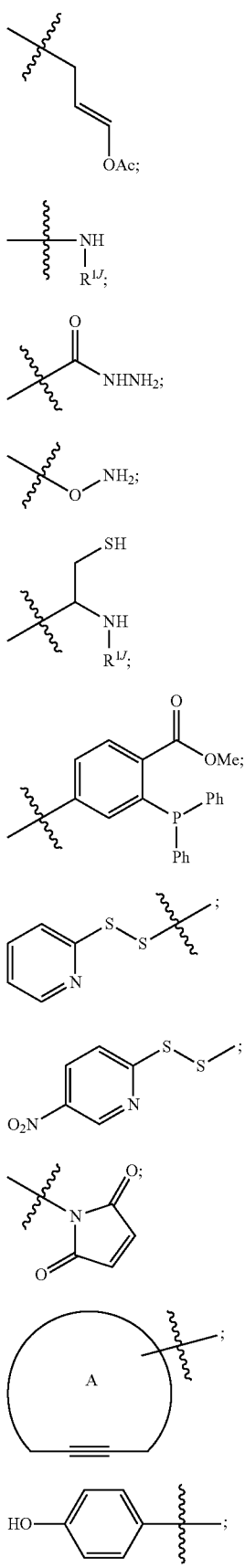
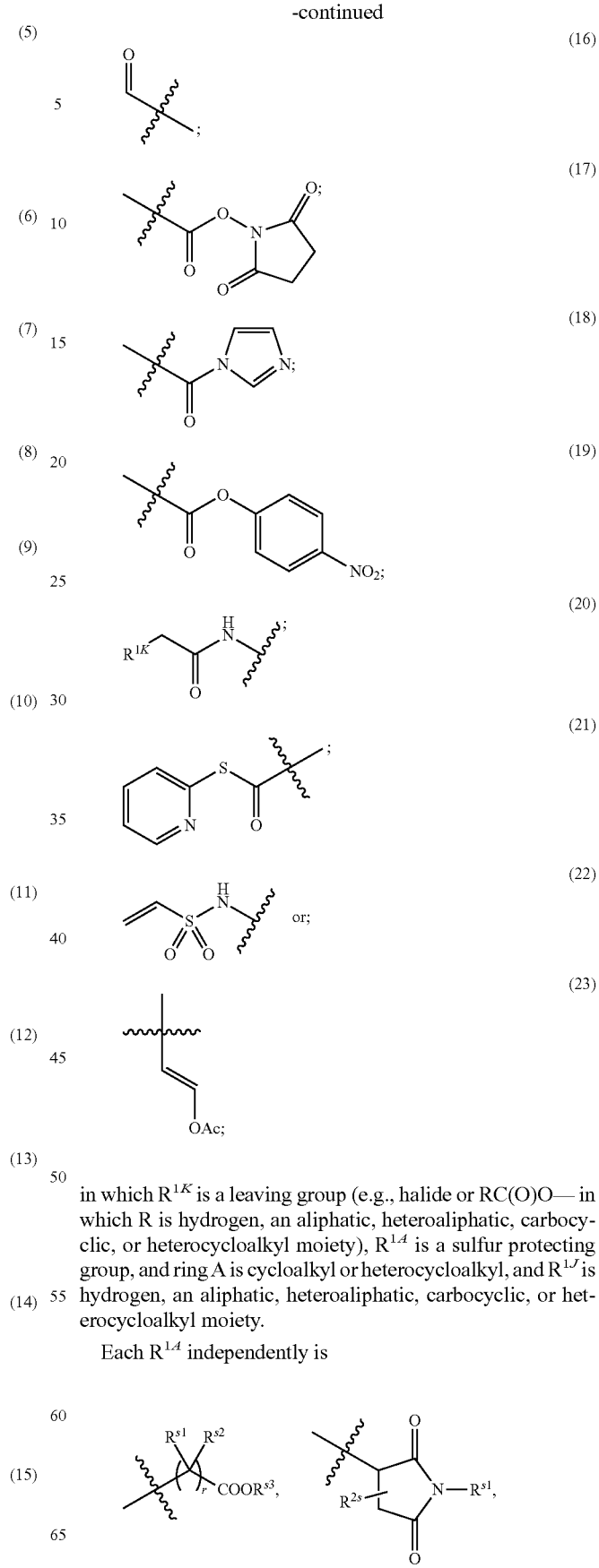
in which $R^{1K}$ is a leaving group (e.g., halide or RC(O)O— in which R is hydrogen, an aliphatic, heteroaliphatic, carbocyclic, or heterocycloalkyl moiety), $R^{1A}$ is a sulfur protecting group, and ring A is cycloalkyl or heterocycloalkyl, and $R^{1J}$ is hydrogen, an aliphatic, heteroaliphatic, carbocyclic, or heterocycloalkyl moiety.
Each $R^{1A}$ independently is -continued

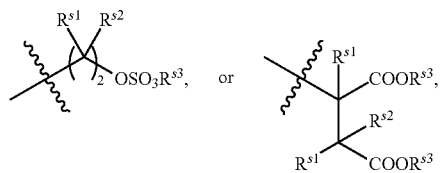

in which r is 1 or 2 and each of $R^{s1}$, $R^{s2}$, and $R^{s3}$ is hydrogen, an aliphatic, heteroaliphatic, carbocyclic, or heterocycloalkyl moiety.

Each

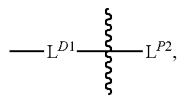

when connected to PBRM, independently is $-X^P-M^{P1}-Y^P-M^{P2}-Z^P-M^{P3}-Q^P-M^{P4}-$, with $X^P$ directly connected to the carbonyl group of $R^{L1}-C(=O)$ and $M^{P4}$ directly connected to PBRM, in which:

$X^P$ is $-O-$, $-S-$, $-N(R^1)-$, or absent, in which $R^1$ is hydrogen, an aliphatic, heteroaliphatic, carbocyclic, or heterocycloalkyl moiety, $-C(=O)R^{1B}$, $-C(=O)OR^{1B}$, or $-SO_2R^{1B}$, or $-N(R^1)-$ is a heterocycloalkyl moiety, wherein $R^{1B}$ is hydrogen, an aliphatic, heteroaliphatic, carbocyclic, or heterocycloalkyl moiety;

each of $Y^P$, $Z^P$, and $Q^P$, independently, is absent or a biodegradable linker moiety selected from the group consisting of $-S-S-$, $-C(=O)O-$, $-C(=O)NR^2-$, $-OC(=O)-$, $-NR^2C(=O)-$, $-OC(=O)O-$, $-OC(=O)NR^2-$, $-NR^2C(=O)O-$, $-NR^2C(=O)NR^3-$, $-C(OR^2)O-$, $-C(OR^2)S-$, $-C(OR^2)NR^3-$, $-C(SR^2)O-$, $-C(SR^2)S-$, $C(SR^2)NR^3-$, $-C(NR^2R^3)O-$, $-C(NR^2R^3)S-$, $-C(NR^2R^3)NR^4-$, $-C(=O)S-$, $-SC(=O)-$, $-SC(=O)S-$, $-OC(=O)S-$, $-SC(=O)O-$, $-C(=S)S-$, $-SC(=S)-$, $-OC(=S)-$, $-C(=S)O-$, $-SC(=S)O-$, $-OC(=S)S-$, $-OC(=S)O-$, $-SC(=S)S-$, $-C(=NR^2)O-$, $-C(=NR^2)S-$, $-C(=NR^2)NR^3-$, $-OC(=NR^2)-$, $-SC(=NR^2)-$, $-NR^3C(=NR^2)-$, $-NR^2SO_2-$, $NR^2NR^3-$, $-C(=O)NR^2NR^3-$, $-NR^2NR^3C(=O)-$, $-OC(=O)NR^2NR^3-$, $-NR^2NR^3C(=O)O-$, $-C(=S)NR^2NR^3-$, $-NR^2NR^3C(=S)-$, $-C(=NR^4)NR^2NR^3-$, $-NR^2NR^3C(=NR^4)-$, $-O(NR^3)-$, $-(CR^3=N)O-$, $-C(=O)NR^2-(N=CR^3)-$, $-(CR^3=N)-NR^2C(=O)-$, $-SO_3-$, $-NR^2SO_2NR^3-$, $-SO_2NR^2-$, and polyamide, wherein each occurrence of $R^2$, $R^3$, and $R^4$ independently is hydrogen or an aliphatic, heteroaliphatic, carbocyclic, or heterocyclic moiety, or each occurrence of $-NR^2-$ or $-NR^2NR^3-$ is a heterocycloalkyl moiety; and each of $M^{P1}$, $M^{P2}$, $M^{P3}$, and $M^{P4}$ independently, is absent or a non-biodegradable linker moiety selected from the group consisting of alkyl, alkenyl, alkynyl, heteroalkyl, heteroalkenyl, heteroalkynyl, a carbocyclic moiety, a heterocyclic moiety, and a combination thereof, and each of $M^{P1}$, $M^{P2}$, and $M^{P3}$ optionally contains one or more $-(C=O)-$ but does not contain any said biodegradable linker moiety;

provided that for each

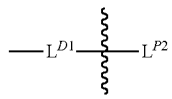

connected to PBRM, at least one of $X^P$, $Y^P$, $Z^P$, and $Q^P$ is not absent.

Each of $M^{D1}$ and $M^{P1}$ independently is $C_{1-6}$ alkyl or $C_{1-6}$ heteroalkyl.

Each of $M^{D2}$, $M^{D3}$, $M^{D4}$, $M^{P2}$, $M^{P3}$, and $M^{P4}$, independently is absent, $C_{1-6}$ alkyl, cycloalkyl, heteroalkyl, heterocycloalkyl, or a combination thereof.

In each

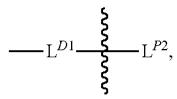

at most one of $M^{P2}$ and $M^{P3}$ has one of the following structures:

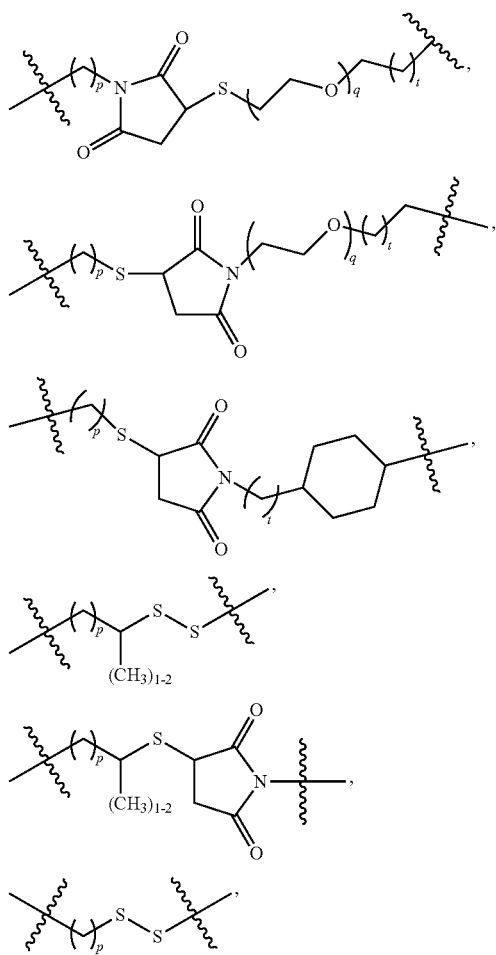

-continued

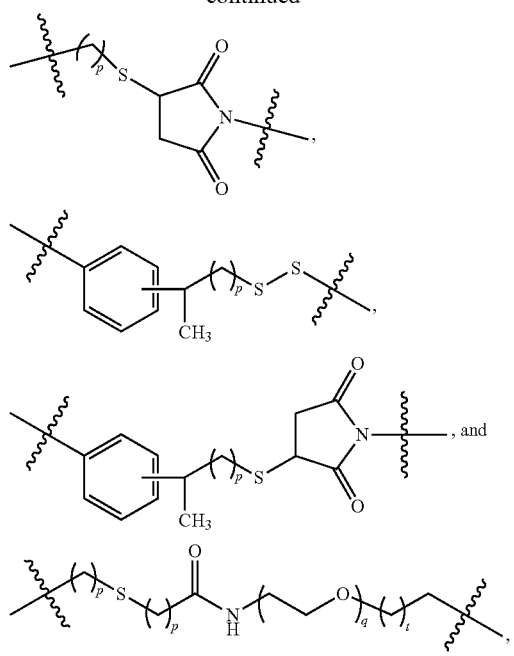

in which q is an integer from 0 to 12 and each of p and t independently is an integer from 0 to 3.

Also within the scope of the invention is a method of preparing a scaffold described above. The method comprises providing a polymeric carrier that is substituted with one or more -$L^D$-D and one or more —$R^{L1}$—C(=O)-$L^{D1}$, and reacting the polymeric carrier with a compound containing an $L^{P2}$ moiety to produce the scaffold comprising a polymeric carrier substituted both with one or more -$L^D$-D and with one or more

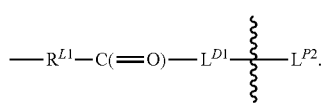

Alternatively, the method comprises providing a polymeric carrier that is substituted with one or more

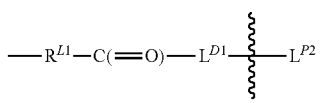

and one or more —$R^{L1}$—C(=O)-$L^{D1}$, and reacting the polymeric carrier with D containing a functional group that is capable of forming a covalent bond with —$R^{L1}$—C(=O)-$L^{D1}$ to produce the scaffold comprising a polymeric carrier substituted both with one or more -$L^D$-D and with one or more

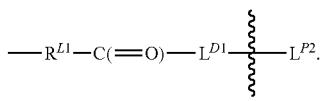

The invention also features a compound of Formula (XII) or (XIIa):

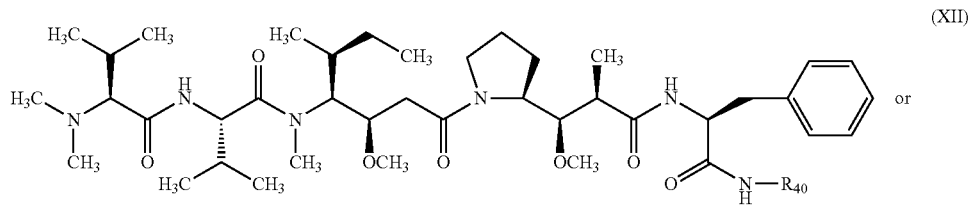
(XII)

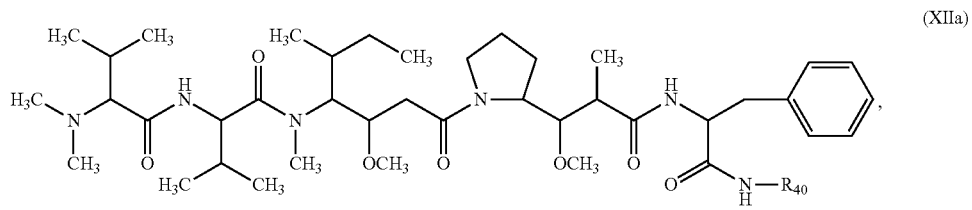
(XIIa)

or a pharmaceutically acceptable salt thereof, wherein:

$R_{40}$ is selected from the group consisting of

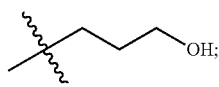
(1)

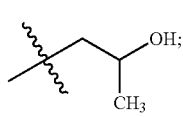
(2)

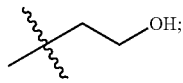
(3)

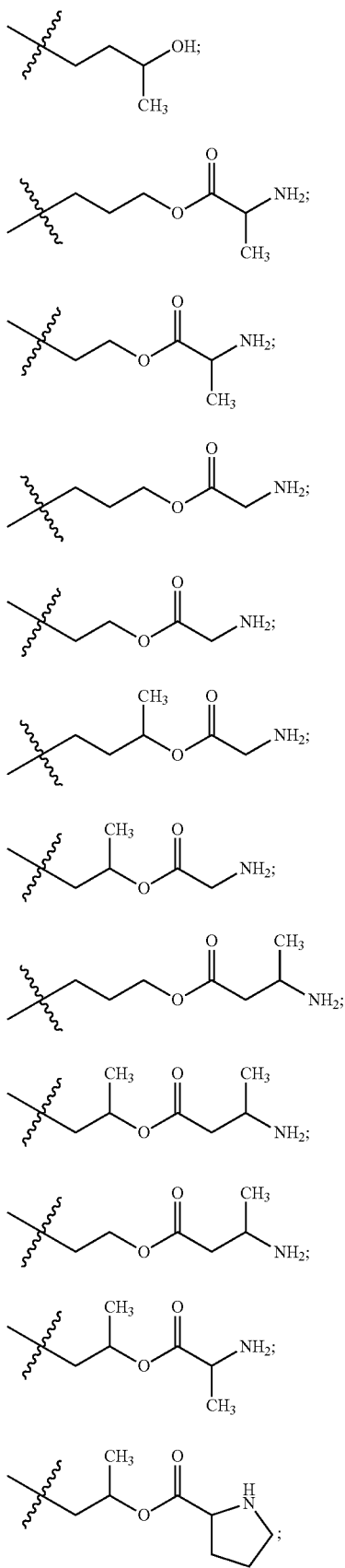

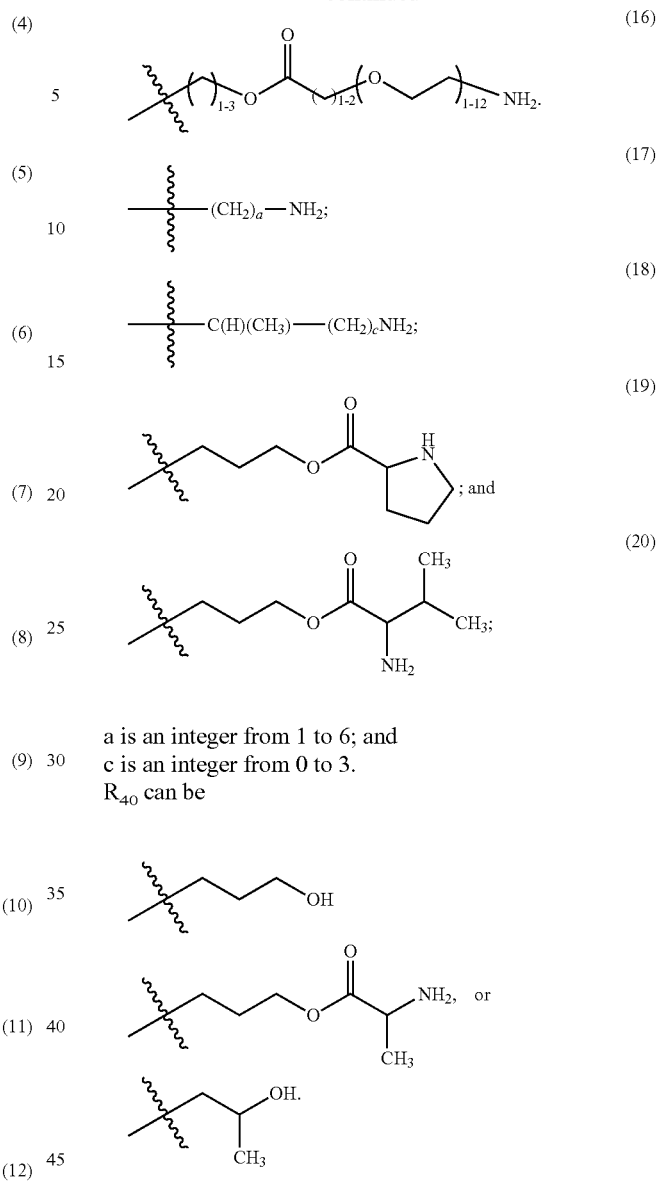

a is an integer from 1 to 6; and
c is an integer from 0 to 3.

$R_{40}$ can be

In another aspect, the invention features a polymeric scaffold useful to conjugate with both a protein based recognition-molecule (PBRM) and a therapeutic agent (D). The scaffold (i.e., the one free of any D) comprises a polymeric carrier, one or more $L^P$ connected to the polymeric carrier which is suitable for connecting a PBRM to the polymeric carrier, and one or more —$R^{L1}$—C(=O)-$L^{D1}$ connected to the polymeric carrier via $R^{L1}$, wherein:

the polymeric carrier is a polyacetal or polyketal, $R^{L1}$ is connected to an oxygen atom of the polymeric carrier, $L^{D1}$ is a linker suitable for connecting a D molecule to the polymeric carrier, in which each occurrence of D is independently a therapeutic agent having a molecular weight ≤5 kDa;

$L^P$ is a linker different from —$R^{L1}$—C(=O)-$L^{D1}$, and having the structure: —$R^{L2}$—C(=O)-$L^{P1}$ with $R^{L2}$ connected to an oxygen atom of the polymeric carrier and $L^{P1}$ suitable for connecting to a PBRM;

each of $R^{L1}$ and $R^{L2}$ independently is absent, alkyl, heteroalkyl, cycloalkyl, or heterocycloalkyl;

$L^{D1}$ is a moiety containing a functional group that is capable of forming a covalent bond with a functional group of D, and $L^{P1}$ is a moiety containing a functional group that is capable of forming a covalent bond with a functional group of a PBRM.

The D-free scaffold useful to conjugate with a PBRM and a D can have one or more of the following features.

$L^P$ is a linker having the structure:

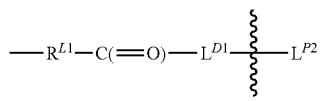

in which $L^{P2}$ is a moiety containing a functional group that is capable of forming a covalent bond with a functional group of a PBRM, and

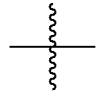

denotes direct or indirect attachment of $L^{P2}$ to $L^{D1}$.

The functional group of $L^{P1}$ or $L^{P2}$ is selected from —$SR^p$, —S—S-LG, maleimido, and halo, in which LG is a leaving group and $R^p$ is H or a sulfur protecting group.

$L^{D1}$ comprises —X—$(CH_2)_v$—C(=O)— with X directly connected to the carbonyl group of $R^{L1}$—C(=O), in which X is $CH_2$, O, or NH, and v is an integer from 1 to 6.

$L^{P1}$ or $L^{P2}$ contains a biodegradable bond.

Each of $R^{L1}$ and $R^{L2}$ is absent.

The polymeric carrier of the D-free scaffold is a polyacetal, e.g., a PHF having a molecular weight (i.e., MW of the unmodified PHF) ranging from about 2 kDa to about 300 kDa.

For conjugating a PBRM having a molecular weight of 40 kDa or greater (e.g., 80 kDa or greater), the polymeric carrier of the D-free scaffold is a polyacetal, e.g., a PHF having a molecular weight (i.e., MW of the unmodified PHF) ranging from about 2 kDa to about 40 kDa (e.g., about 6-20 kDa or about 8-15 kDa).

For conjugating a PBRM having a molecular weight of 200 kDa or less (e.g., 80 kDa or less), the polymeric carrier of the D-free scaffold of the invention is a polyacetal, e.g., a PHF having a molecular weight (i.e., MW of the unmodified PHF) ranging from about 20 kDa to about 300 kDa (e.g., about 40-150 kDa or about 50-100 kDa).

The D-free scaffold is of Formula (Id):

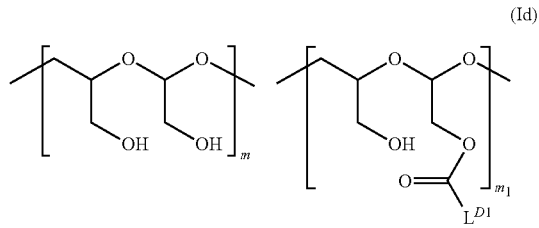

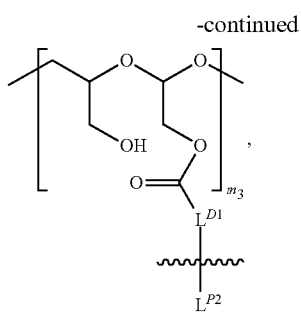

wherein:

m is an integer from 1 to about 2200, $m_1$ is an integer from 1 to about 660, $m_3$ is an integer from 1 to about 110, and the sum of m, $m_1$, and $m_3$ ranges from about 15 to about 2200.

When the PHF in Formula (Id) has a molecular weight ranging from about 2 kDa to about 40 kDa (i.e., the sum of m, $m_1$, and $m_3$ ranging from about 15 to about 300), $m_3$ is an integer from 1 to about 18, and/or $m_1$ is an integer from 1 to about 140 (e.g., $m_1$ being about 2-120).

When the PHF in Formula (Id) has a molecular weight ranging from about 6 kDa to about 20 kDa (i.e., the sum of m, $m_1$, and $m_3$ ranging from about 45 to about 150), $m_3$ is an integer from 1 to about 9, and/or $m_1$ is an integer from 1 to about 75 (e.g., $m_1$ being about 6-60).

When the PHF in Formula (Id) has a molecular weight ranging from about 8 kDa to about 15 kDa (i.e., the sum of m, $m_1$, and $m_3$ ranging from about 60 to about 110), $m_3$ is an integer from 1 to about 7, and/or $m_1$ is an integer from 1 to about 55 (e.g., $m_1$ being about 6-45).

When the PHF in Formula (Id) has a molecular weight ranging from 20 kDa to 300 kDa (i.e., the sum of m, $m_1$, and $m_3$ ranging from about 150 to about 2200), $m_3$ is an integer from 1 to about 110, and/or $m_1$ is an integer from 1 to about 660 (e.g., $m_1$ being about 13-550).

When the PHF in Formula (Id) has a molecular weight ranging from about 50 kDa to about 100 kDa (i.e., the sum of m, $m_1$, and $m_3$ ranging from about 370 to about 740), $m_3$ is an integer from 1 to about 40, and/or $m_1$ is an integer from 1 to about 220 (e.g., $m_1$ being about 20-180).

The D-free scaffold further comprises a PBRM connected to the polymeric carrier via $L^P$.

One or more PBRMs are connected to one D-free polymeric carrier.

The D-free scaffold is of Formula (Ie):

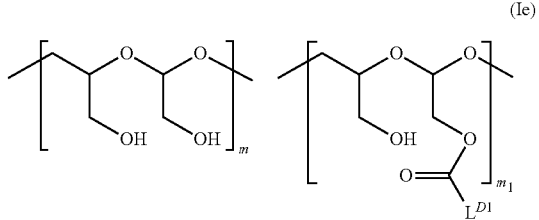

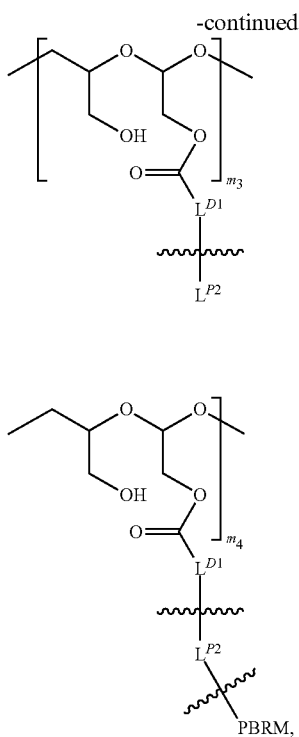

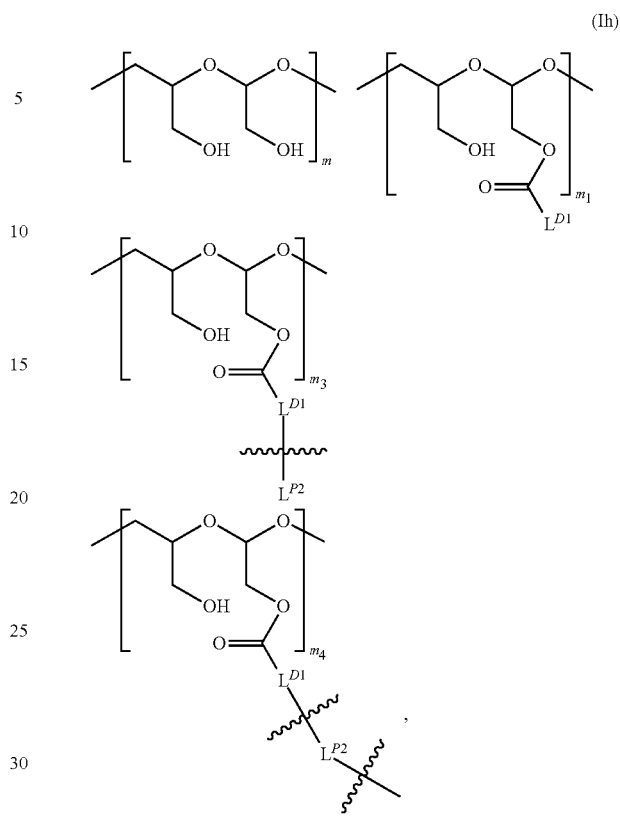

wherein:

between $L^{P2}$ and PBRM denotes direct or indirect attachment of PBRM to $L^{P2}$, PBRM has a molecular weight of less than 200 kDa, m is an integer from 1 to 2200, $m_1$ is an integer from 1 to 660, $m_3$ is an integer from 0 to 110, $m_4$ is an integer from 1 to about 60; and the sum of m, $m_1$, $m_2$, $m_3$ and $m_4$ ranges from about 150 to about 2200.

In Formula (Ie), $m_1$ is an integer from about 10 to about 660 (e.g., about 14-550).

When the PHF in Formula (Ie) has a molecular weight ranging from about 50 kDa to about 100 kDa (i.e., the sum of m, $m_1$, $m_3$, and $m_4$ ranging from about 370 to about 740), $m_3$ is an integer from 1 to about 40, $m_4$ is an integer from 1 to about 20, and/or $m_1$ is an integer from 1 to about 220 (e.g., $m_1$ being about 20-180).

Alternatively or additionally, one or more D-free polymeric carriers are connected to one PBRM. The scaffold comprises a PBRM with a molecular weight of greater than 40 kDa and one or more polymeric carriers connected to the PBRM, in which each of the polymeric carrier independently is of Formula (Ih):

wherein:
terminal attached to $L^{P2}$ denotes direct or indirect attachment of $L^{P2}$ to PBRM such that the D-carrying polymeric carrier is connected to the PBRM, m is an integer from 1 to 300, $m_1$ is an integer from 1 to 140, $m_3$ is an integer from 0 to 18, $m_4$ is an integer from 1 to 10; and the sum of m, $m_1$, $m_3$, and $m_4$ ranges from 15 to 300; provided that the total number of $L^{P2}$ attached to the PBRM is 10 or less In Formula (Ih), $m_1$ is an integer from 2 to about 130 (e.g., about 3-120) and/or $m_3$ is an integer from 1 to about 10 (e.g., about 1-8).

When the PHF in Formula (Ih) has a molecular weight ranging from about 6 kDa to about 20 kDa (i.e., the sum of m, $m_1$, $m_3$, and $m_4$ ranging from about 45 to about 150), $m_3$ is an integer from 1 to about 9, and/or $m_1$ is an integer from 6 to about 75 (e.g., $m_1$ being about 7-60).

When the PHF in Formula (Ih) has a molecular weight ranging from about 8 kDa to about 15 kDa (i.e., the sum of m, $m_1$, $m_3$, and $m_4$ ranging from about 60 to about 110), $m_3$ is an integer from 1 to about 7, and/or $m_1$ is an integer from 6 to about 55 (e.g., $m_1$ being about 7-45).

As used herein, the terms "polymeric scaffold" or simply "scaffold" and "conjugate" are used interchangeably when the scaffold comprises one or more PBRM and one or more D molecules.

In yet another aspect, the invention encompasses a conjugate comprising a polymeric carrier, one or more -$L^D$-D connected to the polymeric carrier, and a protein based recognition-molecule (PBRM) connected to the polymeric carrier via $L^P$, wherein:

each occurrence of D is independently a therapeutic agent (e.g., a drug) having a molecular weight ≤5 kDa;

the polymeric carrier is a polyacetal or polyketal, $L^D$ is a linker having the structure: —$R^{L1}$—C(=O)—$X^D$-$M^{D1}$-$Y^D$-$M^{D2}$-$Z^D$-$M^{D3}$-$Q^D$-$M^{D4}$-, with $R^{L1}$ connected to an oxygen atom of the polymeric carrier and $M^{D4}$ connected to D;

$L^P$ is a linker having the structure: —$R^{L2}$—C(=O)—$X^P$-$M^{P1}$-$Y^P$-$M^{P2}$-$Z^P$-$M^{P3}$-$Q^P$-$M^{P4}$-, with $R^{L2}$ connected to an oxygen atom of the polymeric carrier and $M^{P4}$ connected to the protein based recognition-molecule;

each of $R^{L1}$ and $R^{L2}$ independently is absent, alkyl, cycloalkyl, heteroalkyl, or heterocycloalkyl;

each of $X^D$ and $X^P$, independently is —O—, —S—, —N($R^1$)—, or absent, in which $R^1$ is hydrogen, an aliphatic, heteroaliphatic, carbocyclic, or heterocycloalkyl moiety, —C(=O)$R^{1B}$, —C(=O)O$R^{1B}$, —SO$_2R^{1B}$ or —N($R^1$)— is a heterocycloalkyl moiety, wherein $R^{1B}$ is hydrogen, an aliphatic, heteroaliphatic, carbocyclic, or heterocycloalkyl moiety;

each of $Y^D$, $Y^P$, $Z^D$, $Z^P$, $Q^D$, and $Q^P$, independently, is absent or a biodegradable linker moiety selected from the group consisting of —S—S—, —C(=O)O—, —C(=O)NR$^2$—, —OC(=O)—, —NR$^2$C(=O)—, —OC(=O)O—, —OC(=O)NR$^2$—, —NR$^2$C(=O)O—, —NR$^2$C(=O)NR$^3$—, —C(OR$^2$)O—, —C(OR$^2$)S—, —C(OR$^2$)NR$^3$—, —C(SR$^2$)O—, —C(SR$^2$)S—, C(SR$^2$)NR$^3$—, —C(NR$^2$R$^3$)O—, —C(NR$^2$R$^3$)S—, —C(NR$^2$R$^3$)NR$^4$—, —C(=O)S—, —SC(=O)—, —SC(=O)S—, —OC(=O)S—, —SC(=O)O—, —C(=S)S—, —SC(=S)—, —OC(=S)—, —C(=S)O—, —SC(=S)O—, —OC(=S)S—, —OC(=S)O—, —SC(=S)S—, —C(=NR$^2$)O—, —C(=NR$^2$)S—, —C(=NR$^2$)NR$^3$—, —OC(=NR$^2$)—, —SC(=NR$^2$)—, —NR$^2$C(=NR$^2$)—, —NR$^2$SO$_2$—, NR$^2$NR$^3$—, —C(=O)NR$^2$NR$^3$—, —NR$^2$NR$^3$C(=O)—, —OC(=O)NR$^2$NR$^3$—, —NR$^2$NR$^3$C(=O)O—, —C(=S)NR$^2$NR$^3$—, —NR$^2$NR$^3$C(=S)—, —C(=NR$^4$)NR$^2$NR$^3$—, —NR$^2$NR$^3$C(=NR$^4$)—, —O(N=CR$^3$)—, —(CR$^3$=N)O—, —C(=O)NR$^2$—(NR$^3$)—, —(CR$^3$=N)—NR$^2$C(=O)—, —SO$_3$—, —NR$^2$SO$_2$NR$^3$—, —SO$_2$NR$^2$—, and polyamide, wherein each occurrence of R$^2$, R$^3$, and R$^4$ independently is hydrogen or an aliphatic, heteroaliphatic, carbocyclic, or heterocyclic moiety, or each occurrence of —NR$^2$— or —NR$^2$NR$^3$— is a heterocycloalkyl moiety; and each of $M^{D1}$, $M^{D2}$, $M^{D3}$, $M^{D4}$, $M^{P1}$, $M^{P2}$, $M^{P3}$ and $M^{P4}$, independently, is absent or a non-biodegradable linker moiety selected from the group consisting of alkyl, alkenyl, alkynyl, heteroalkyl, heteroalkenyl, heteroalkynyl, a carbocyclic moiety, a heterocyclic moiety, and a combination thereof, and each of $M^{D1}$, $M^{D2}$, $M^{D3}$, $M^{P1}$, $M^{P2}$, and $M^{P3}$ optionally contains one or more —(C=O)— but does not contain any said biodegradable linker moiety;

provided that for each $L^D$, at least one of $X^D$, $Y^D$, $Z^D$, and $Q^D$ is not absent, and for each $L^P$, at least one of $X^P$, $Y^P$, $Z^P$, and $Q^P$ is not absent.

The conjugate can include one or more of the following features.

The polymeric carrier can be a polyacetal, e.g., PHF.

For each $L^D$, $M^{D1}$ is not absent when $X^D$ is absent.

For each $L^P$, $M^{P1}$ is not absent when $X^P$ is absent.

The polymeric carrier can be further substituted with one or more —$R^{L1}$—C(=O)—$X^D$-$M^{D1}$-$Y^D$-$M^{D2}$-$W^D$, in which each $W^D$ independently is:

(1)

(2)

(3)

(4)
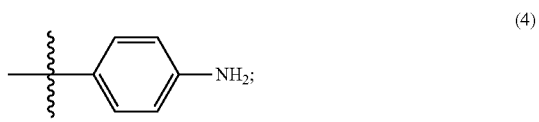

(5)

(6)

(7)

(8)

(9)

(10)
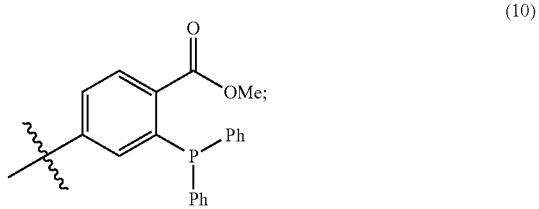

-continued
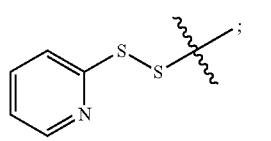(11)
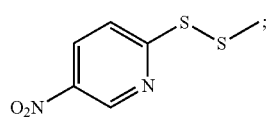(12)
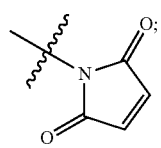(13)
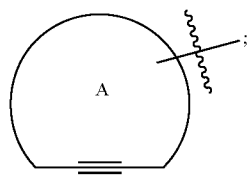(14)
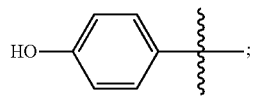(15)
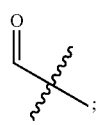(16)
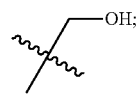(17)
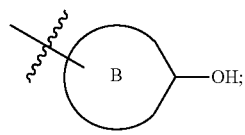(18)
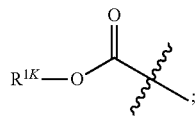(19)
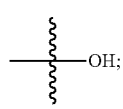(20)
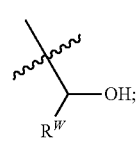(21)
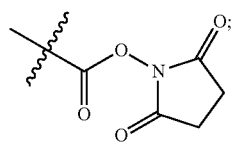(22)
-continued
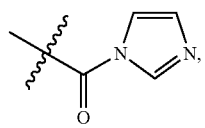(23)
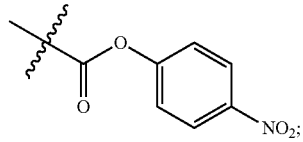(24)
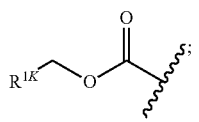(25)
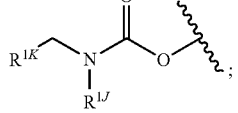(26)
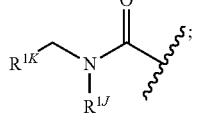(27)
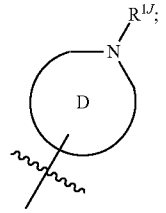(28)
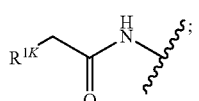(29)
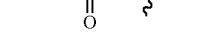(30)
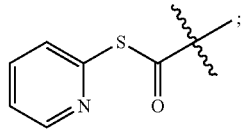(31)
—COOH; or (32)
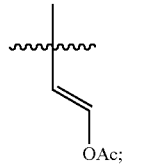(33)
in which $R^{1A}$ is a sulfur protecting group, each of ring A and B, independently, is cycloalkyl or heterocycloalkyl, $R^W$ is an aliphatic, heteroaliphatic, carbocyclic or heterocycloalkyl moiety; ring D is heterocycloalkyl; $R^{1J}$ is hydrogen, an aliphatic, heteroaliphatic, carbocyclic, or heterocycloalkyl moiety; and $R^{1K}$ is a leaving group (e.g., halide or RC(O)O— in which R is hydrogen, an aliphatic, heteroaliphatic, carbocyclic, or heterocycloalkyl moiety).
The polymeric carrier can be further substituted with one or more —$R^{L2}$—C(=O)—$X^P$-$M^{P1}$-$Y^P$-$M^{P2}$-$W^P$, in which each $W^P$ independently is:
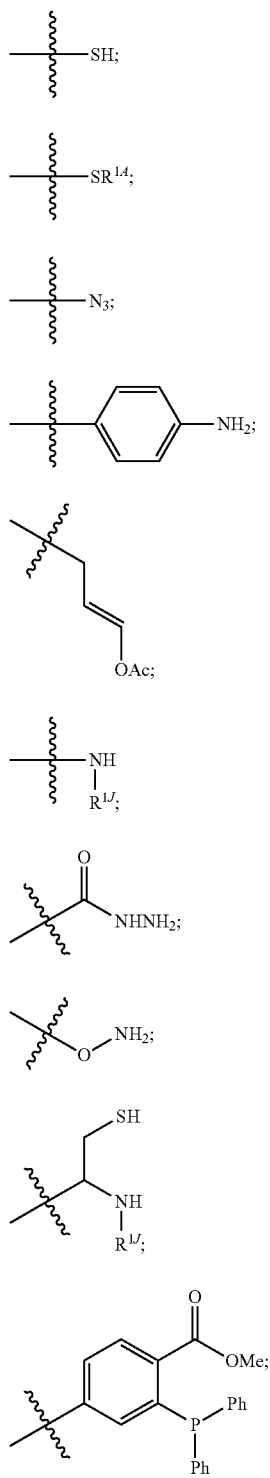
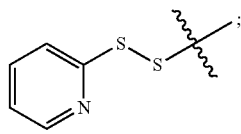
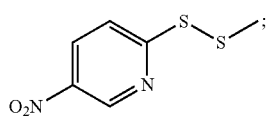
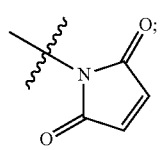
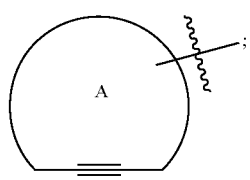
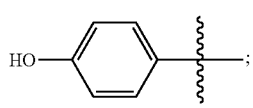
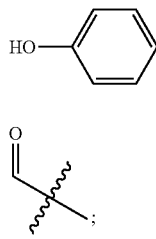
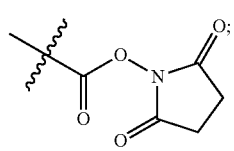
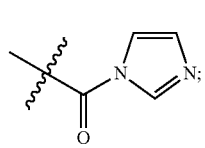
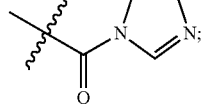
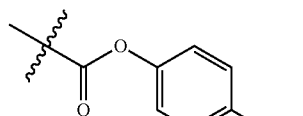
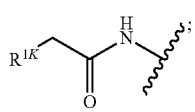
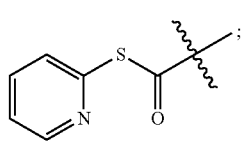

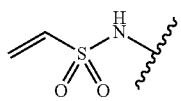

(22)

or;

(23)

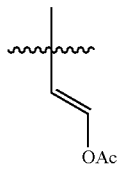

in which $R^{1K}$ is a leaving group (e.g., halide or RC(O)O— in which R is hydrogen, an aliphatic, heteroaliphatic, carbocyclic, or heterocycloalkyl moiety), $R^{1A}$ is a sulfur protecting group, and ring A is cycloalkyl or heterocycloalkyl, and $R^1$ is hydrogen, an aliphatic, heteroaliphatic, carbocyclic, or heterocycloalkyl moiety. For example, $R^{1A}$ is

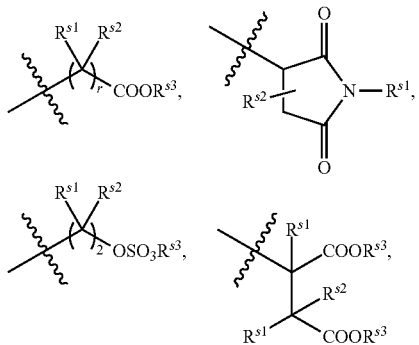

in which r is 1 or 2 and each of $R^{s1}$, $R^{s2}$, and $R^{s3}$ is hydrogen, an aliphatic, heteroaliphatic, carbocyclic, or heterocycloalkyl moiety.

Ring A can be $C_{3-8}$ cycloalkyl or 5-19 membered heterocycloalkyl.

Ring A can be

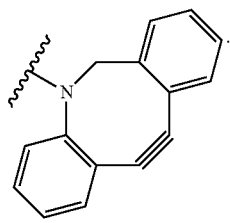 [SMILES: *N1Cc2ccccc2C#Cc2ccccc21]

Ring B can be $C_{3-8}$ cycloalkyl or 3-12 membered heterocycloalkyl.

Ring D can be piperazinyl or piperidinyl.

Each of $R^{s1}$, $R^{s2}$, and $R^{s3}$ can be hydrogen or $C_{1-6}$ alkyl.

Each PBRM independently can be a peptide, a peptide mimetic, an antibody, or an antibody fragment.

Each of $M^{D1}$ and $M^{P1}$ independently can be $C_{1-6}$ alkyl or $C_{1-6}$ heteroalkyl.

Each of $M^{D2}$, $M^{D3}$, $M^{D4}$, $M^{P2}$, $M^{P3}$, and $M^{P4}$, independently can be absent, $C_{1-6}$ alkyl, cycloalkyl, heteroalkyl, heterocycloalkyl, or a combination thereof.

For each $L^D$, at most two of $M^{D2}$, $M^{D3}$, and $M^{D4}$ can be absent.

For each $L^P$, at most two of $M^{P2}$, $M^{P3}$, and $M^{P4}$ can be absent.

For each $L^D$, at most one of $M^{D2}$ and $M^{D3}$ can have one of the following structures:

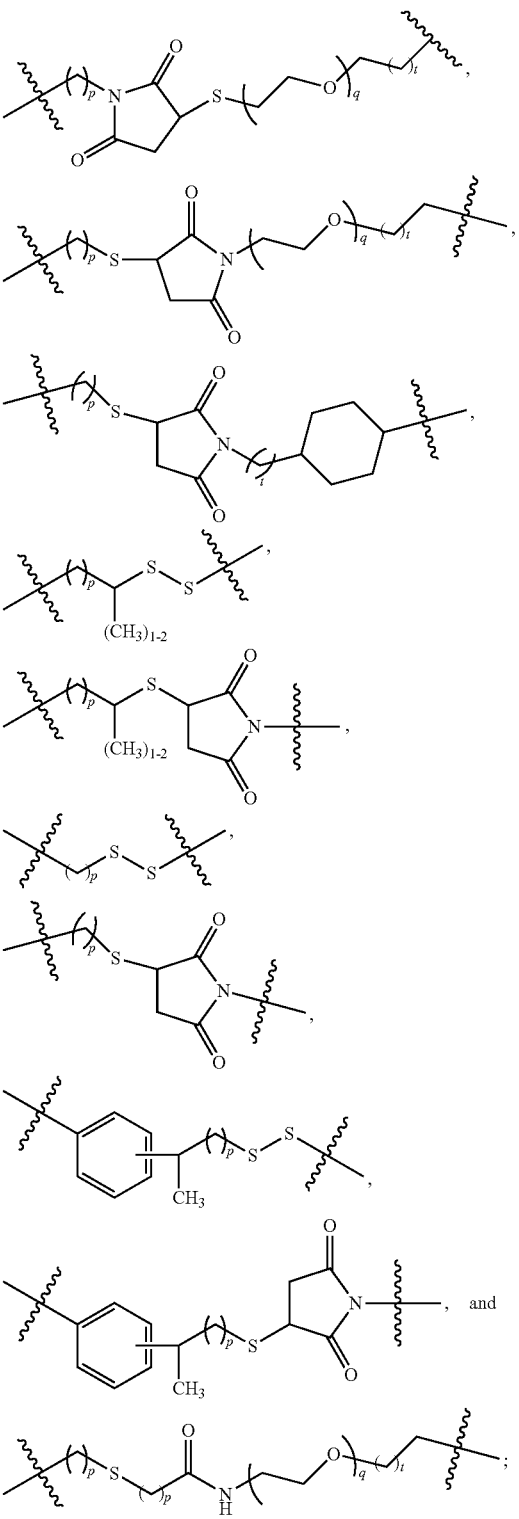

in which q is an integer from 0 to 12 and each of p and t independently is an integer from 0 to 3.

For each $L^P$, at most one of $M^{P2}$ and $M^{P3}$ can have one of the following structures:
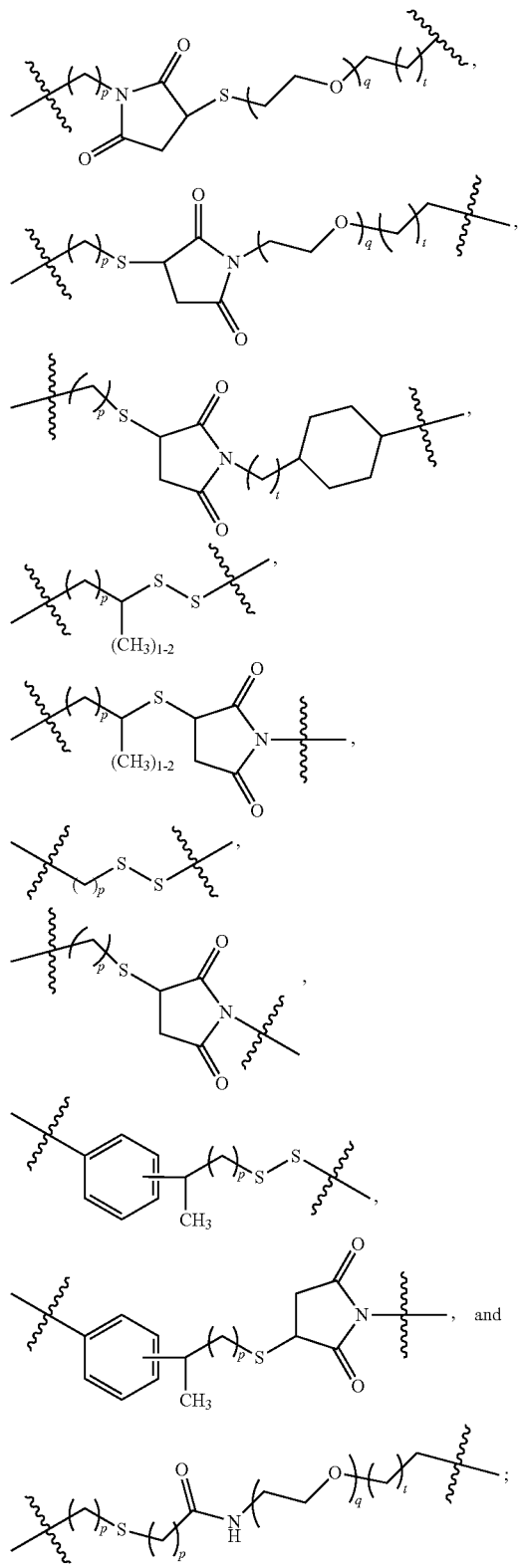
in which q is an integer from 0 to 12 and each of p and t independently is an integer from 0 to 3.
For each $L^D$, each of -$M^{D2}$-$Z^D$—, —$Z^D$-$M^{D3}$-, —$Z^D$-$M^{D2}$-, and -$M^{D3}$-$Z^D$—, independently can have one of the following structures:
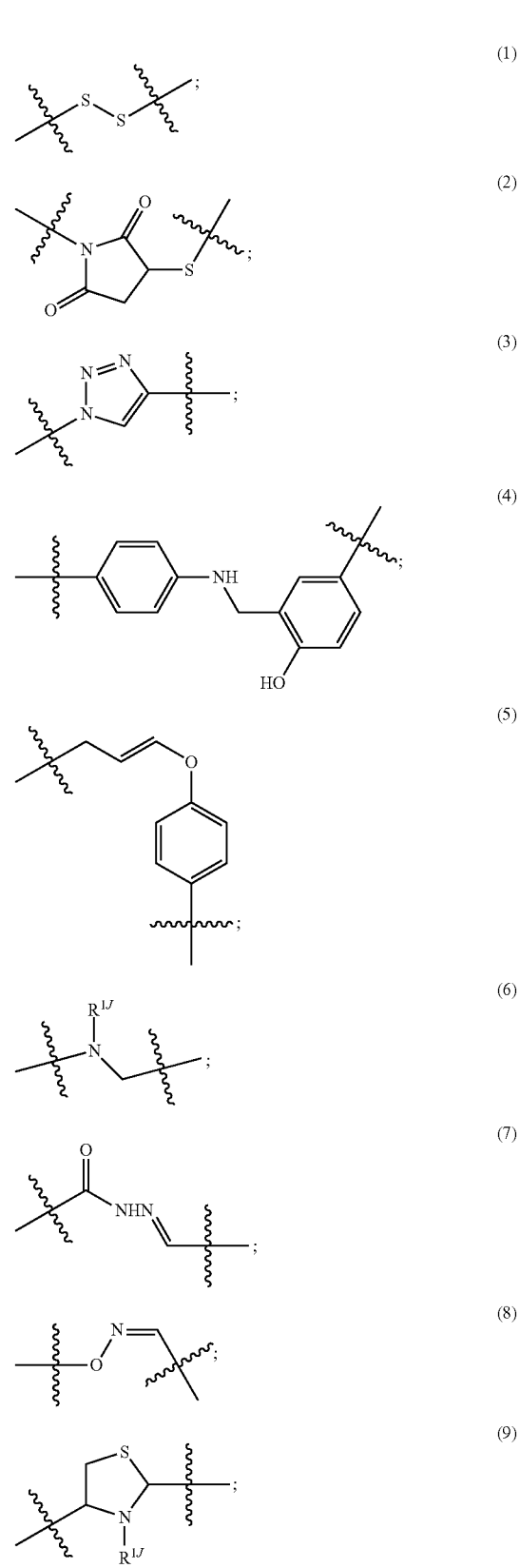

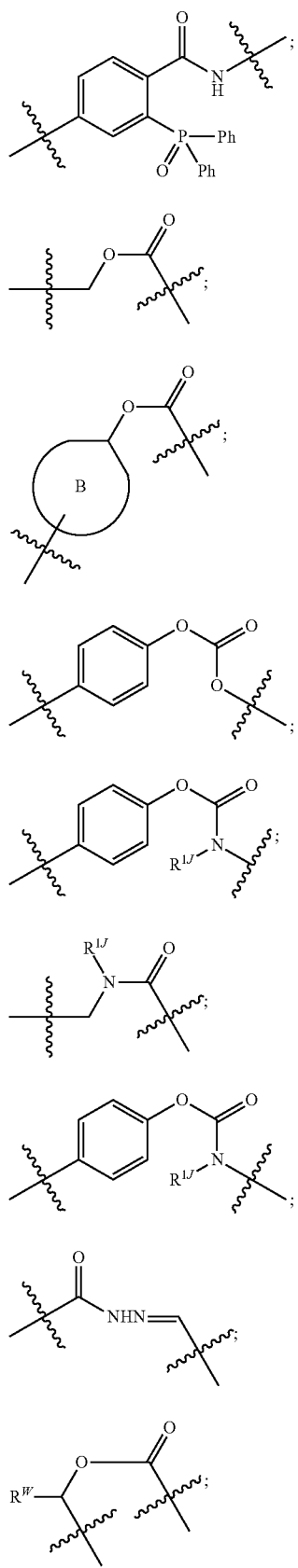

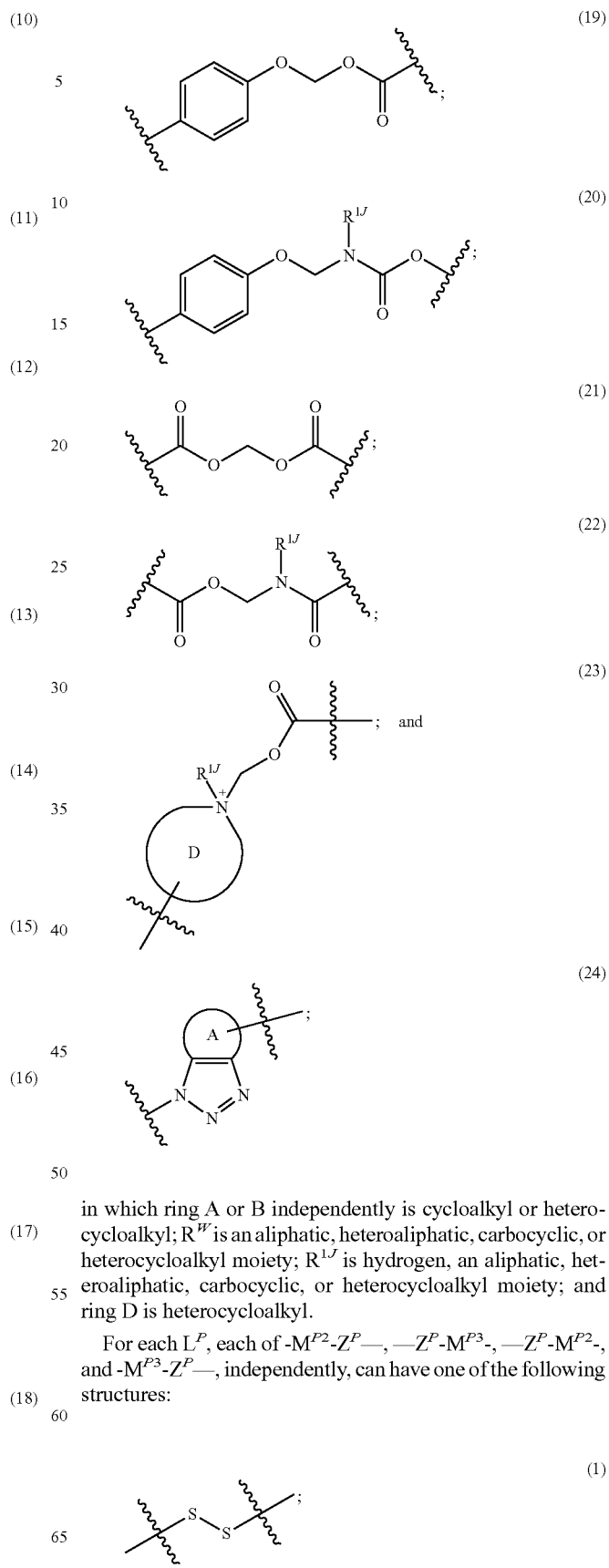

in which ring A or B independently is cycloalkyl or heterocycloalkyl; $R^W$ is an aliphatic, heteroaliphatic, carbocyclic, or heterocycloalkyl moiety; $R^{1J}$ is hydrogen, an aliphatic, heteroaliphatic, carbocyclic, or heterocycloalkyl moiety; and ring D is heterocycloalkyl.

For each $L^P$, each of -$M^{P2}$-$Z^P$—, —$Z^P$-$M^{P3}$-, —$Z^P$-$M^{P2}$-, and -$M^{P3}$-$Z^P$—, independently, can have one of the following structures:

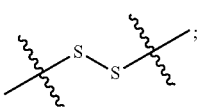

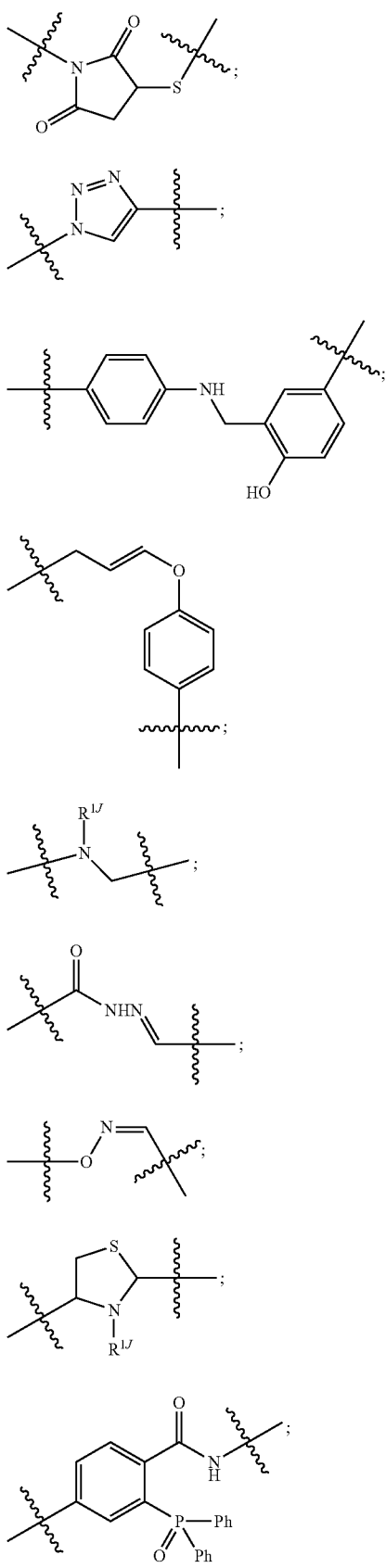

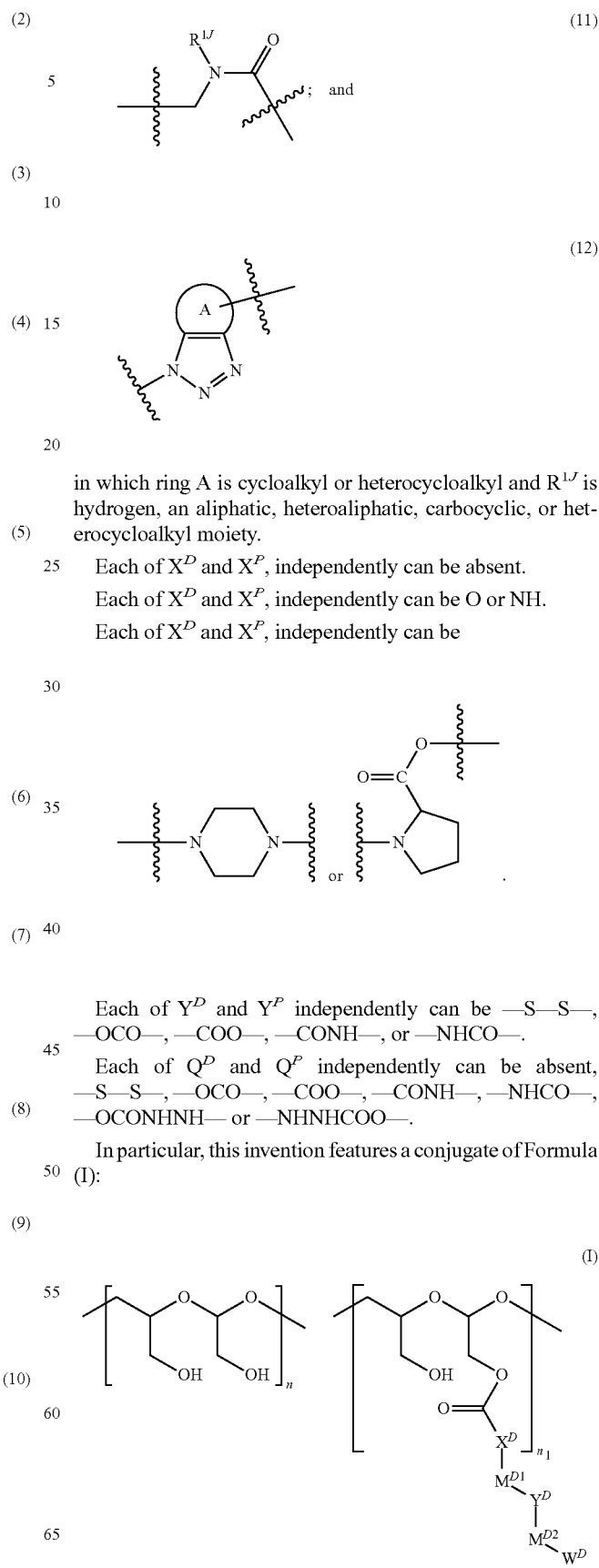

in which ring A is cycloalkyl or heterocycloalkyl and $R^{1J}$ is hydrogen, an aliphatic, heteroaliphatic, carbocyclic, or heterocycloalkyl moiety.

Each of $X^D$ and $X^P$, independently can be absent.

Each of $X^D$ and $X^P$, independently can be O or NH.

Each of $X^D$ and $X^P$, independently can be

Each of $Y^D$ and $Y^P$ independently can be —S—S—, —OCO—, —COO—, —CONH—, or —NHCO—.

Each of $Q^D$ and $Q^P$ independently can be absent, —S—S—, —OCO—, —COO—, —CONH—, —NHCO—, —OCONHNH— or —NHNHCOO—.

In particular, this invention features a conjugate of Formula (I):

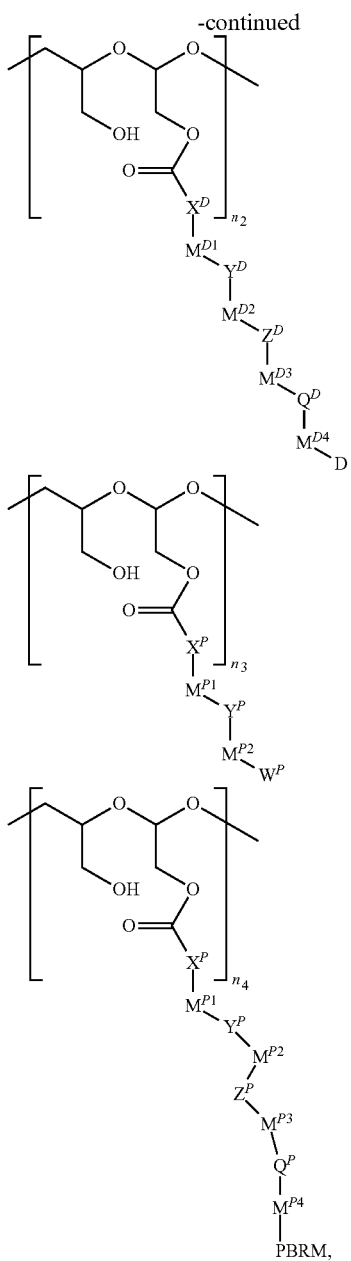

wherein each of n, $n_1$, $n_2$, $n_3$, and $n_4$, is the molar fraction of the corresponding polymer unit ranging between 0 and 1; $n+n_1+n_2+n_3+n_4=1$; provided that none of n, $n_2$, and $n_4$ is 0.

In Formula (I) above, the disconnection or gap between the polyacetal units indicates that the units can be connected to each other in any order. In other words, the appending groups that contain D, PBRM, $W^D$, and $W^P$, can be randomly distributed along the polymer backbone.

In the protein-polymer-drug conjugate of Formula (I), each D can be the same or different moiety and each PBRM can be the same or different moiety.

The ratio between $n_2$ and $n_4$ can be greater than 1:1, and up to 200:1 (e.g., up to 100:1), e.g., between 2:1 and 40:1; between 5:1 and 20:1; between 10:1 and 50:1, between 25:1 and 50:1, or between 30:1 and 50:1.

The ratio between $n_2$ and $n_4$ can be about 50:1, 40:1, 25:1, 20:1, 10:1, 5:1 or 2:1.

For example the ratio between D and PBRM can be greater than 1:1, and up to 200:1 (e.g., up to 100:1), e.g., between 2:1 and 40:1; between 5:1 and 20:1; between 10:1 and 50:1, between 25:1 and 50:1, or between 30:1 and 50:1. Examples of PBRM include but are not limited to, full length antibodies such as IgG and IgM, antibody fragments such as Fabs, scFv, camelids, Fab2, and the like, small proteins, and peptides.

In one embodiment the ratio between D and PBRM can be about 50:1, 40:1, 25:1, 20:1, 15:1, 10:1, 9:1, 8:1, 7:1, 6:1, 5:1, 4:1, 3:1, or 2:1.

In another embodiment the ratio between D and PBRM can be about 25:1, 20:1, 15:1, 10:1, 5:1 or 2:1.

In another aspect, the invention provides compositions comprising the conjugates, methods for their preparation, and methods of use thereof in the treatment of various disorders, including, but not limited to cancer.

The invention also features a drug-polymer conjugate (e.g., therapeutic agent-polymer conjugate) that is similar to the protein-polymer-drug conjugate described above except that drug-polymer conjugate does not contain a PBRM. In this embodiment the polymer-drug conjugate may comprise a plurality of drug moieties in which each D can be the same or different. In this embodiment, $n_4$ is 0 in the conjugate of Formula (I). The methods of producing the drug-polymer conjugates and methods of treating various disorders (e.g., cancer) are also contemplated and described herein.

The invention also features a protein-polymer conjugate (e.g., PBRM-polymer conjugate) that is similar to the protein-polymer-drug conjugate described above except that protein-polymer conjugate does not contain a drug. In this embodiment the protein-polymer conjugate may comprise a plurality of protein moieties in which each PBRM can be the same or different. In this embodiment, $n_2$ is 0 in the conjugate of Formula (I). The methods of producing the drug-polymer conjugates or polymeric scaffolds and methods of treating various disorders (e.g., cancer) are also contemplated and described herein. The target cancer can be anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, or gastric cancer.

The invention further relates to a pharmaceutical composition comprising a polymeric scaffold or conjugate described herein and a pharmaceutically acceptable carrier.

In yet another aspect, the invention relates to a method of diagnosing a disorder in a subject suspected of having the disorder. The method comprises administering an effective amount of the conjugate described herein to the subject suspected of having the disorder or performing an assay to detect a target antigen/receptor in a sample from the subject so as to determine whether the subject expresses target antigen or receptor.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

One of the advantages of the present invention is that the protein-polymer-drug conjugates or the polymeric scaffolds described herein greatly enhances the bioavailability of the drugs to be delivered and/or enhances the bioavailability of the protein attached to the polymeric carrier. Another advantage of the present invention is that the efficacy of the protein-polymer-drug conjugates described herein increases or at least remains substantially the same with increases in the drug load of the conjugates. Yet another advantage of the present invention is that the protein-polymer conjugates via thiol conjugation to the cysteine moiety of the protein exhibits substantially improved stability. Other features and advantages of the invention will be apparent from the following detailed description and claims.

BRIEF DESCRIPTION OF FIGURES

FIG. 10 is a group of tables listing "m" values per PHF scaffold and polymer/PBRM ratios of embodiments of the invention. Table 1 relates to PBRM-drug polymer conjugates in which the PBRMs have a molecular weight of 40 kDa or greater (e.g., 60 kDa or greater, 80 kDa or greater, 100 kDa or greater, 120 kDa or greater, 140 kDa or greater, 160 kDa or greater or 180 kDa or greater) and one or more PHF-Drug scaffolds are attached to one PBRM, Tables 2 and 3 relate to PBRM-drug polymer conjugates in which the PBRMs have a molecular weight of 200 kDa or less (e.g., 120 kDa or less, 80 kDa or less, 60 kDa or less, 40 kDa or less, 20 kDa or less or 10 kDa or less) and one or more PBRMs are attached to one PHF-Drug scaffold.

DETAILED DESCRIPTION OF CERTAIN PREFERRED EMBODIMENTS OF THE INVENTION

Figure 1:
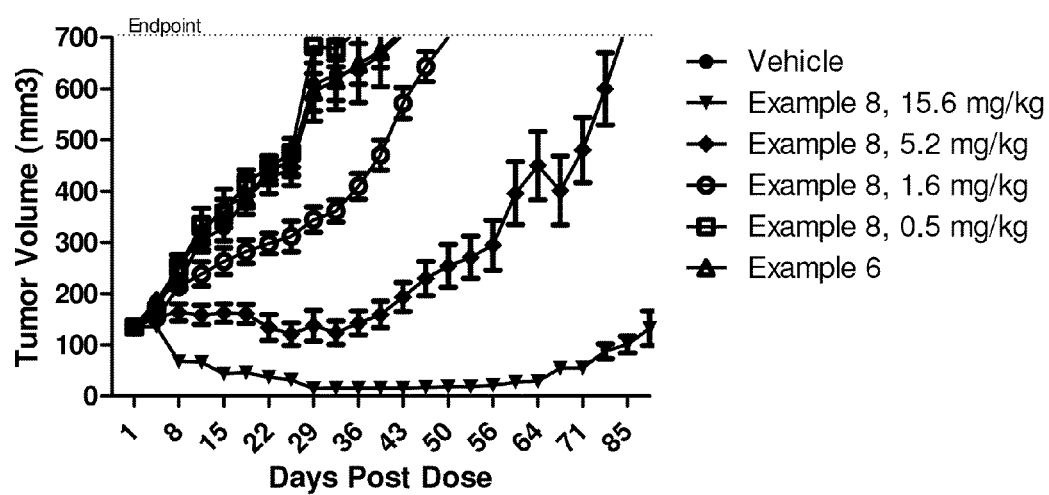
FIG. 1 is a graph showing the tumor response in mice inoculated subcutaneously with NCI-N87 cells (n=10 for each group) after IV administration of vehicle, PBRM-drug polymer conjugate PHF-GA-(HPV-Alanine)-(Trastuzumab-M-(PEG)$_{12}$), (Example 8, HPV:trastuzumab about 16:1 to 18:1) at 15.6 mg/kg, 5.2 mg/kg, 1.6 mg/kg and 0.5 mg/kg respectively and drug polymer conjugate PHF-GA-(HPV-Alanine)-SH (Example 6) (dosed at a Vinca dose that was equivalent to that present in Example 8 at 15.6 mg/kg) dosed once every week for 3 weeks on day 1, day 8 and day 15 respectively.

The present invention provides novel protein-polymer-drug conjugates, polymeric scaffolds for making the conjugates, synthetic methods for making the conjugates or polymeric scaffolds, pharmaceutical compositions containing them and various uses of the conjugates.

The present invention also provides novel polymer-drug conjugates, synthetic methods for making the conjugates, pharmaceutical compositions containing them and various uses of the conjugates.

The present invention further provides novel drug derivatives, synthetic methods for making the derivatives, pharmaceutical compositions containing them and various uses of the drug derivatives.

Definition/Terminology

Certain compounds of the present invention, and definitions of specific functional groups are also described in more detail herein. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups.

The use of the articles "a", "an", and "the" in both the following description and claims are to be construed to cover both the singular and the plural, unless otherwise indicated herein or clearly contradicted by context. The terms "comprising", "having", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of:"

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6".

"Protecting group": as used herein, the term protecting group means that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, certain exemplary oxygen protecting groups may be utilized. These oxygen protecting groups include, but are not limited to methyl ethers, substituted methyl ethers (e.g., MOM (methoxymethyl ether), MTM (methylthiomethyl ether), BOM (benzyloxymethyl ether), and PMBM (p-methoxybenzyloxymethyl ether)), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, and TBDPS (t-butyldiphenyl silyl ether), esters (e.g., formate, acetate, benzoate (Bz), trifluoroacetate, and dichloroacetate), carbonates, cyclic acetals and ketals. In certain other exemplary embodiments, nitrogen protecting groups are utilized. Nitrogen protecting groups, as well as protection and deprotection methods are known in the art. Nitrogen protecting groups include, but are not limited to, carbamates (including methyl, ethyl and substituted ethyl carbamates (e.g., Troc), amides, cyclic imide derivatives, N-Alkyl and N-Aryl amines, imine derivatives, and enamine derivatives. In yet other embodiments, certain exemplary sulphur protecting groups may be utilized. The sulfur protecting groups include, but are not limited to those oxygen protecting group describe above as well as aliphatic carboxylic acid (e.g., acrylic acid), maleimide, vinyl sulfonyl, and optionally substituted maleic acid. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

"Leaving group" refers to a molecular fragment that departs with a pair of electrons in heterolytic bond cleavage. Leaving groups can be anions or neutral molecules. Leaving groups include, but are not limited to halides such as Cl$^-$, Br$^-$, and I$^-$, sulfonate esters, such as para-toluenesulfonate ("tosylate", TsO$^-$), and RC(O)O— in which R is hydrogen, an aliphatic, heteroaliphatic, carbocyclic, or heterocycloalkyl moiety.

All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

"Antibody" refers to an immunoglobulin molecule of the class IgG including but not limited to IgG subclasses (IgG1, 2, 3 and 4) and class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, intracellular antibodies ("intrabodies"), recombinant antibodies, anti-idiotypic antibodies, domain antibodies, linear antibody, multispecific antibody, antibody fragments, such as, Fv, Fab, Fab', Fab'-SH, F(ab')$_2$, single chain variable fragment antibodies (scFv), Fc, pFc', scFvFc, disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, dual-affinity antibodies such as, dual-affinity retargeting proteins (DART™), divalent (or bivalent) single-chain variable fragments (di-scFvs, bi-scFvs) including but not limited to minibodies, diabodies, triabodies or tribodies, tetrabodies, and the like, and multivalent antibodies. "Antibody fragment" refers to at least a portion of the variable region of the immunoglobulin molecule that binds to its target, i.e., the antigen-binding region. As used herein, the term "antibody" refers to both the full-length antibody and antibody fragments unless otherwise specified.

"Protein based recognition-molecule" or "PBRM" refers to a molecule that recognizes and binds to a cell surface marker or receptor such as, a transmembrane protein, surface immobilized protein, or protoglycan. Examples of PBRMs include but are not limited to, antibodies (e.g., Trastuzumab, Cetuximab, Rituximab, Bevacizumab, Epratuzumab, Veltuzumab, Labetuzumab) or peptides (LHRH receptor targeting peptides, EC-1 peptide), lipocalins, such as, for example, anticalins, proteins such as, for example, interferons, lymphokines, growth factors, colony stimulating factors, and the like, peptides or peptide mimics, and the like. The protein based recognition molecule, in addition to targeting the modified polymer conjugate to a specific cell, tissue or location, may also have certain therapeutic effect such as antiproliferative (cytostatic and/or cytotoxic) activity against a target cell or pathway. The protein based recognition molecule comprises or may be engineered to comprise at least one chemically reactive group such as, —COOH, primary amine, secondary amine —NHR, —SH, or a chemically reactive amino acid moiety or side chains such as, for example, tyrosine, histidine, cysteine, or lysine.

"Biocompatible" as used herein is intended to describe compounds that exert minimal destructive or host response effects while in contact with body fluids or living cells or tissues. Thus a biocompatible group, as used herein, refers to an aliphatic, cycloalkyl, heteroaliphatic, heterocycloalkyl, aryl, or heteroaryl moiety, which falls within the definition of the term biocompatible, as defined above and herein. The term "Biocompatibility" as used herein, is also taken to mean that the compounds exhibit minimal interactions with recognition proteins, e.g., naturally occurring antibodies, cell proteins, cells and other components of biological systems, unless such interactions are specifically desirable. Thus, substances and functional groups specifically intended to cause the above minimal interactions, e.g., drugs and prodrugs, are considered to be biocompatible. Preferably (with exception of compounds intended to be cytotoxic, such as, e.g., antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity and/or other such adverse effects. In the above sentence, the term "normal cells" refers to cells that are not intended to be destroyed or otherwise significantly affected by the compound being tested.

"Biodegradable": As used herein, "biodegradable" polymers are polymers that are susceptible to biological processing in vivo. As used herein, "biodegradable" compounds or moieties are those that, when taken up by cells, can be broken down by the lysosomal or other chemical machinery or by hydrolysis into components that the cells can either reuse or dispose of without significant toxic effect on the cells. The term "biocleavable" as used herein has the same meaning of "biodegradable". The degradation fragments preferably induce little or no organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the biodegradable protein-polymer-drug conjugates (or their components, e.g., the biodegradable polymeric carrier and the linkers between the carrier and the antibody or the drug molecule) described herein, for example, include exposure of the biodegradable conjugates to water at a temperature and a pH of lysosomal intracellular compartment. Biodegradation of some protein-polymer-drug conjugates (or their components, e.g., the biodegradable polymeric carrier and the linkers between the carrier and the antibody or the drug molecule), can also be enhanced extracellularly, e.g., in low pH regions of the animal body, e.g., an inflamed area, in the close vicinity of activated macrophages or other cells releasing degradation facilitating factors. In certain preferred embodiments, the effective size of the polymer carrier at pH~7.5 does not detectably change over 1 to 7 days, and remains within 50% of the original polymer size for at least several weeks. At pH~5, on the other hand, the polymer carrier preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolization or excretion of polymer fragments by the cells. In preferred embodiments, the polymers and polymer biodegradation byproducts are biocompatible.

"Bioavailability": The term "bioavailability" refers to the systemic availability (i.e., blood/plasma levels) of a given amount of drug or compound administered to a subject. Bioavailability is an absolute term that indicates measurement of both the time (rate) and total amount (extent) of drug or compound that reaches the general circulation from an administered dosage form.

"Hydrophilic": The term "hydrophilic" as it relates to substituents on the polymer monomeric units does not essentially differ from the common meaning of this term in the art, and denotes chemical moieties which contain ionizable, polar, or polarizable atoms, or which otherwise may be solvated by water molecules. Thus a hydrophilic group, as used herein, refers to an aliphatic, cycloalkyl, heteroaliphatic, heterocycloalkyl, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In preferred embodiments of the present invention, at least one of the polymer monomeric units include a carboxyl group (COOH), an aldehyde group (CHO), a methylol ($CH_2OH$) or a glycol (for example, $CHOH$—$CH_2OH$ or $CH$—$(CH_2OH)_2$).

The term "hydrophilic" as it relates to the polymers of the invention generally does not differ from usage of this term in the art, and denotes polymers comprising hydrophilic functional groups as defined above. In a preferred embodiment, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

"Polymeric Carrier": The term polymeric carrier, as used herein, refers to a polymer or a modified polymer, which is suitable for covalently attaching to or can be covalently attached to one or more drug molecules with a designated linker and/or one or more PBRMs with a designated linker.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Polysaccharide", "carbohydrate" or "oligosaccharide": The terms "polysaccharide", "carbohydrate", or "oligosaccharide" are known in the art and refer, generally, to substances having chemical formula $(CH_2O)_n$, where generally n>2, and their derivatives. Carbohydrates are polyhydroxyaldehydes or polyhydroxyketones, or change to such substances on simple chemical transformations, such as hydrolysis, oxidation or reduction. Typically, carbohydrates are present in the form of cyclic acetals or ketals (such as, glucose or fructose). These cyclic units (monosaccharides) may be connected to each other to form molecules with few (oligosaccharides) or several (polysaccharides) monosaccharide units. Often, carbohydrates with well defined number, types and positioning of monosaccharide units are called oligosaccharides, whereas carbohydrates consisting of mixtures of molecules of variable numbers and/or positioning of monosaccharide units are called polysaccharides. The terms "polysaccharide", "carbohydrate", and "oligosaccharide", are used herein interchangeably. A polysaccharide may include natural sugars (e.g., glucose, fructose, galactose, mannose, arabinose, ribose, and xylose) and/or derivatives of naturally occurring sugars (e.g., 2'-fluororibose, 2'-deoxyribose, and hexose).

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred embodiments, the small molecule is a drug and the small molecule is referred to as "drug molecule" or "drug" or "therapeutic agent". In certain embodiments, the drug molecule has MW less than or equal to about 5 kDa. In other embodiments, the drug molecule has MW less than or equal to about 1.5 kDa. In embodiments, the drug molecule is selected from vinca alkaloids, auristatins, tubulysins, duocarmycins, kinase inhibitors, MEK inhibitors, KSP inhibitors, and analogs thereof. Preferably, though not necessarily, the drug is one that has already been deemed safe and effective for use by an appropriate governmental agency or body, e.g., the FDA. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered suitable for use with the present hydrophilic polymers.

Classes of drug molecules that can be used in the practice of the present invention include, but are not limited to, anti-cancer substances, radionuclides, vitamins, anti-AIDS substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. Many large molecules are also drugs.

A more complete, although not exhaustive, listing of classes and specific drugs suitable for use in the present invention may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, both of which are incorporated herein by reference. In preferred embodiments, the drug used in this invention is a therapeutic agent that has antiproliferative (cytostatic and/or cytotoxic) activity against a target cell or pathway. The drug may have a chemically reactive group such as, for example, —COOH, primary amine, secondary amine —NHR, —OH, —SH, —C(O)H, —C(O)R, —C(O)NHR$^{2b}$, C(S)OH, —S(O)$_2$OR$^{2b}$, —P(O)$_2$OR$^{2b}$, —CN, —NC or —ONO, in which R is an aliphatic, heteroaliphatic, carbocyclic or heterocycloalkyl moiety and R$^{2b}$ is a hydrogen, an aliphatic, heteroaliphatic, carbocyclic, or heterocyclic moiety.

"Drug derivative" or "modified drug" or the like as used herein, refers to a compound that comprises the drug molecule intended to be delivered by the conjugate of the invention and a functional group capable of attaching the drug molecule to the polymeric carrier.

"Active form" as used herein refers to a form of a compound that exhibits intended pharmaceutical efficacy in vivo or in vitro. In particular, when a drug molecule intended to be delivered by the conjugate of the invention is released from the conjugate, the active form can be the drug itself or its derivatives, which exhibit the intended therapeutic properties. The release of the drug from the conjugate can be achieved by cleavage of a biodegradable bond of the linker which attaches the drug to the polymeric carrier. The active drug derivatives accordingly can comprise a portion of the linker.

"Diagnostic label": As used herein, the term diagnostic label refers to an atom, group of atoms, moiety or functional group, a nanocrystal, or other discrete element of a composition of matter, that can be detected in vivo or ex vivo using analytical methods known in the art. When associated with a conjugate of the present invention, such diagnostic labels permit the monitoring of the conjugate in vivo. Alternatively or additionally, constructs and compositions that include diagnostic labels can be used to monitor biological functions or structures. Examples of diagnostic labels include, without limitation, labels that can be used in medical diagnostic procedures, such as, radioactive isotopes (radionuclides) for gamma scintigraphy and Positron Emission Tomography (PET), contrast agents for Magnetic Resonance Imaging (MRI) (for example paramagnetic atoms and superparamagnetic nanocrystals), contrast agents for computed tomography and other X-ray-based imaging methods, agents for ultrasound-based diagnostic methods (sonography), agents for neutron activation (e.g., boron, gadolinium), fluorophores for various optical procedures, and, in general moieties which can emit, reflect, absorb, scatter or otherwise affect electromagnetic fields or waves (e.g., gamma-rays, X-rays, radio-waves, microwaves, light), particles (e.g., alpha particles, electrons, positrons, neutrons, protons) or other forms of radiation, e.g., ultrasound.

"Aliphatic": In general, the term aliphatic, as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. In certain embodiments, as used herein, "lower alkyl" is used to indicate those alkyl groups (substituted, unsubstituted, branched or unbranched) having about 1-6 carbon atoms. "Substituted alkyl" refers to alkyl groups that are substituted with one or more functional groups. Substituents include, but are not limited to, any of the substituents mentioned below, i.e., the substituents recited below resulting in the formation of a stable compound.

"Alkenyl": the term alkenyl denotes a monovalent group derived from a hydrocarbon moiety having at least one carbon-carbon double bond by the removal of a single hydrogen atom. "Substituted alkenyl" groups are substituted with one or more functional groups. Substituents include, but are not limited to, any of the substituents mentioned below, i.e., the substituents recited below resulting in the formation of a stable compound. Alkenyl groups include, for example, ethenyl, propenyl, butenyl, 1-methyl-2-buten-1-yl, and the like.

"Alkynyl": the term alkynyl as used herein refers to a monovalent group derived from a hydrocarbon having at least one carbon-carbon triple bond by the removal of a single hydrogen atom. "Substituted alkenyl" groups are substituted with one or more functional groups. Substituents include, but are not limited to, any of the substituents mentioned below, i.e., the substituents recited below resulting in the formation of a stable compound. Representative alkynyl groups include ethynyl, 2-propynyl(propargyl), 1-propynyl, and the like.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl(propargyl), 1-propynyl and the like.

"Alkylene" as used herein, the term alkylene by itself or part of another term refers to a saturated, branched or straight chain having two monovalent radical centers derived by the removal of two hydrogen atoms from the same or two different carbon atoms of a parent alkane. Alkylene radicals include, but are not limited to, methylene, 1,2, ethylene, 1,3-propyl, and the like. Suitable alkylenes include, but are not limited to methylene, ethylene, propylene, butylene, pentylene, hexylene, heptylene, octylene, nonylene, decalene, and the like. The term "cycloalkylene" similarly refers to bivalent cycloalkyl. Cycloalkylene radicals include, but are not limited to, 1,1-cyclopentylene, 1,2-cyclopentylene, 1,1-cyclobutylene, 1,3-cyclobutylene, etc.

"Heteroaliphatic": as used herein, the term heteroaliphatic refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted ("substituted heteroaliphatic") by independent replacement of one or more of the hydrogen atoms thereon with one or more moieties including, but not limited to aliphatic; heteroaliphatic; cycloalkyl; heterocycloalkyl; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$N_{O2}$; —CN; —$C_{F3}$; —$C_{H2}C_{F3}$; —$CHC_{12}$; —$C_{H2}OH$; —$C_{H2}C_{H2}OH$; —$C_{H2}N_{H2}$; —$C_{H2}S_{O2}C_{H3}$; - or -$G^{RG1}$ wherein G is —O—, —S—, —$N^{RG2}$—, —C(=O)—, —S(=O)—, —$S_{O2}$—, —C(=O)O—, —C(=O)$N^{RG2}$—, —OC(=O)—, —$N^{RG2}$C(=O)—, —OC(=O)O—, —OC(=O)$N^{RG2}$—, —$N^{RG2}$C(O)O—, —$N^{RG2}$C(=O)$N^{RG2}$—, —C(=S)—, —C(=S)S—, —SC(=S)—, —SC(=S)S—, —C(=$N^{RG2}$)—, —C(=$N^{RG2}$)O—, —C(=$N^{RG2}$)$N^{RG3}$—, —OC(=$N^{RG2}$)—, —$N^{RG2}$C(=$N^{RG3}$)—, —$N^{RG2}S_{O2}$—, —$N^{RG2}S_{O2}N^{RG3}$—, or —$S_{O2}N^{RG2}$—, wherein each occurrence of $RG1$, $RG2$ and $RG3$ independently includes, but is not limited to, hydrogen, halogen, or an aliphatic, heteroaliphatic, cycloalkyl, heterocycloalkyl, aryl, heteroaryl, alkylaryl, or alkylheteroaryl moiety, each of which is optionally substituted. Additional examples of generally applicable substituents are illustrated by the specific embodiments shown in the Examples that are described herein.

"Cycloalkyl": as used herein, the term cycloalkyl refers to a saturated or unsaturated nonaromatic hydrocarbon mono- or multi-ring system having 3 to 30 carbon atoms (e.g., $C_3$-$C_{10}$). Suitable cycloalkyls include, but are not limited to cyclopropyl, cyclobutyl, cyclopentyl, cyclohexyl, cycloheptyl, cyclooctyl, cyclopentenyl, cyclohexenyl, cycloheptenyl, cycloheptynyl, adamantyl, and the like.

"Heterocycloalkyl" as used herein refers to a saturated or unsaturated nonaromatic 3-8 membered monocyclic, 8-12 membered bicyclic, or 11-19 membered tricyclic ring system having one or more heteroatoms (such as O, N, S, or Se), unless specified otherwise. In certain embodiments, the term "heterocycloalkyl" refers to a non-aromatic 5-, 6-, 7- or 8-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocycloalkyl; rings may be fused to an aryl or heteroaryl ring. Examples of heterocycloalkyl groups include, but are not limited to, piperidinyl, piperazinyl, pyrrolidinyl, dioxanyl, tetrahydrofuranyl, tetrahydrothienyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydro-2H-pyranyl, 3,6-dihydro-2H-pyranyl, morpholinyl, and the like.

"Aryl": as used herein, refers to groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl": as used herein, refers to aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., NO and $S(O)_p$, where p=1 or 2). It is to be noted that total number of S and O atoms in the aromatic heterocycle is not more than 1. Examples of heteroaryl include pyridyl, pyrazinyl, pyrimidinyl, pyrrolyl, pyrazolyl, imidazolyl, thiazolyl, isothiazolyl, tetrazolyl, oxazolyl, isooxazolyl, thiadiazolyl, oxadiazolyl, thiophenyl, furanyl, quinolinyl, isoquinolinyl, tetrazolyl, pyridazinyl, quinazolinyl, dihydroquinazolyl, and tetrahydroquinazolyl and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

"Carbocycle" or "carbocyclic moiety" as used herein, is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

"Heterocycle" or "heterocyclic moiety" as used herein, includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Multiple-ring heterocycle can include fused, bridged or spiro rings.

The cycloalkyl, heterocycloalkyl, aryl, or heteroaryl ring (or the carbocyclic or heterocyclic group) can be substituted at one or more ring positions (e.g., the ring-forming carbon or heteroatom such as N) with such substituents as described above, for example, aliphatic; heteroaliphatic; cycloalkyl; heterocycloalkyl; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; - or -$Gr^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —NR—, —NR—, —NR—, or —$SO_2NR^{G2}$—, wherein each occurrence of $R^{G1}$, $R^{G2}$ and $R^{G3}$ independently includes, but is not limited to, hydrogen, halogen, or an aliphatic, heteroaliphatic, cycloalkyl, heterocycloalkyl, aryl, heteroaryl, alkylaryl, or alkylheteroaryl moiety, each of which is optionally substituted. Aryl and heteroaryl groups can also be fused or bridged with cycloalkyl or heterocyclic rings, which are not aromatic so as to form a multicyclic system (e.g., tetralin, methylenedioxyphenyl).

"Alkoxy" (or "alkyloxy"): as used herein, the term alkoxy (or alkyloxy) refers to an alkyl group, as previously defined, attached to the parent molecular moiety through an oxygen atom ("alkoxy"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy.

"Aryloxy": as used herein, the term aryloxy refers to an aryl group, as defined herein, attached to the parent molecular moiety through an oxygen atom. Examples of aryloxy groups include but are not limited to phenoxy and napthyloxy.

"Heteroaryloxy": as used herein, the term heteroaryloxy refers to a heteroaryl group, as defined herein, attached to the parent molecular moiety through an oxygen atom. Examples of heteroaryloxy groups include but are not limited to, quinolyloxy and isoquinolizinyloxy.

"Amine": the term amine refers to a group having the structure —N(R)$_2$ wherein each occurrence of R is independently hydrogen, or an aliphatic or heteroaliphatic moiety, or the R groups, taken together, may form a heterocyclic moiety. In certain instances, an amine group can be charged (protonized) or quarternized, e.g., —HN$^+$(R)$_2$ or —N$^+$(R)$_3$.

"Alkylamino": as used herein, the term alkylamino refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

"Alkylthio" (or "thioalkyl") means an alkyl group as defined herein with the indicated number of carbon atoms attached through a sulfur atom. $C_{1-6}$ alkylthio, is intended to include $C_1$, $C_2$, $C_3$, $C_4$, $C_5$, and $C_6$ alkylthio groups. $C_{1-8}$ alkylthio, is intended to include $C_1$, $C_2$, $C_3$, $C_4$, $C_5$, $C_6$, $C_7$, and $C_8$ alkylthio groups. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl alkylaryl, or an aryl or heteroaryl moieties.

"Thiocarbonyl" or "thiocarboxy" includes compounds and moieties which contain a carbon connected with a double bond to a sulfur atom.

"Thioether" includes moieties which contain a sulfur atom bonded to two carbon atoms or heteroatoms. Examples of thioethers include, but are not limited to alkthioalkyls, alkthioalkenyls and alkthioalkynyls. The term "alkthioalkyls" include moieties with an alkyl, alkenyl or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

"Arylthio" (or "thioaryl") means an aryl group as defined herein with the indicated number of carbon atoms attached through a sulfur atom.

"Carboxylic acid" as used herein refers to a compound comprising a group of formula —CO$_2$H.

"Dicarboxylic acid" refers to a compound comprising two groups of formula —CO$_2$H.

"Halo, halide and halogen": The terms halo, halide and halogen as used herein refer to an atom selected from fluorine, chlorine, bromine, and iodine.

"Methylol": The term methylol as used herein refers to an alcohol group of the structure —CH$_2$OH.

"Hydroxyalkyl": As used herein, the term hydroxyalkyl refers to an alkyl group, as defined above, bearing at least one OH group.

"Mercaptoalkyl": The term mercaptoalkyl as used therein refers to an alkyl group, as defined above, bearing at least one SH group.

"Acyl" includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aryl or heteroaryl moiety.

"Hydrocarbon": The term hydrocarbon, as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, heterocycloalkyl, aryl, heteroaryl, thioalkyl, and the like. As would be known to one skilled in this art, all valencies must be satisfied in making any substitutions.

"Alkylaryl" as used herein refers to an aryl group substituted with one or more alkyl groups (e.g., methylphenyl).

"Alkylarylamino" as used herein refers to —NR$^{G4}$R$^{G5}$, wherein R$^{G4}$ is alkyl, as defined herein, and R$^{G5}$ is an aryl, as defined herein, or at least one of R$^{G4}$ and R$^{G5}$ is an alkylaryl as defined herein.

"Substituted": The terms substituted, whether preceded by the term "optionally" or not, and substituent, as used herein, refers to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Examples of substituents include, but are not limited to aliphatic; heteroaliphatic; cycloalkyl; heterocycloalkyl; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; - or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an aliphatic, heteroaliphatic, cycloalkyl, heterocycloalkyl, aryl, heteroaryl, alkylaryl, or alkylheteroaryl moiety, each of which is optionally substituted. Additional examples of generally applicable substituents are illustrated by the specific embodiments shown in the Examples that are described herein.

The following are more general terms used throughout the present application:

"Animal": The term animal, as used herein, refers to humans as well as non-human animals, at any stage of development, including, for example, mammals, birds, reptiles, amphibians, fish, worms and single cells. Cell cultures and live tissue samples are considered to be pluralities of animals. Preferably, the non-human animal is a mammal (e.g., a rodent, a mouse, a rat, a rabbit, a monkey, a dog, a cat, a primate, or a pig). An animal may be a transgenic animal or a human clone. The term "subject" encompasses animals.

"Efficient amount": In general, as it refers to an active agent or drug delivery device, the term "efficient amount" refers to the amount necessary to elicit the desired biological response. As will be appreciated by those of ordinary skill in this art, the efficient amount of an agent or device may vary depending on such factors as the desired biological endpoint, the agent to be delivered, the composition of the encapsulating matrix, the target tissue, etc. For example, the efficient amount of microparticles containing an antigen to be delivered to immunize an individual is the amount that results in an immune response sufficient to prevent infection with an organism having the administered antigen.

"Natural amino acid" as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

"Unnatural amino acid" as used herein refers to any amino acid which is not a natural amino acid. This includes, for example, amino acids that comprise α-, β-, ω-, D-, L-amino acyl residues. More generally, the unnatural amino acid comprises a residue of the general formula

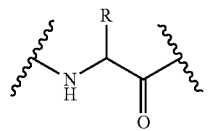

wherein the side chain R is other than the amino acid side chains occurring in nature. Exemplary unnatural amino acids, include, but are not limited to, sarcosine (N-methylglycine), citrulline (cit), homocitrulline, β-ureidoalanine, thiocitrulline, hydroxyproline, allothreonine, pipecolic acid (homoproline), α-aminoisobutyric acid, tert-butylglycine, tert-butylalanine, allo-isoleucine, norleucine, α-methylleucine, cyclohexylglycine, β-cyclohexylalanine, β-cyclopentylalanine, α-methylproline, phenylglycine, α-methylphenylalanine and homophenylalanine.

"Amino acyl": More generally, the term amino acyl, as used herein, encompasses natural amino acid and unnatural amino acids.

"Polyamide": refers to homo- or hetero-polymers of natural amino acid and unnatural amino acids. Illustrative homopolymers include, but are not limited to, poly-lysine, poly-arginine, poly-γ-glutaric acid, and the like. Illustrative heteropolymers include, but are not limited to, polymers comprising peptides fragments selected from peptidases, lysozymes, metalloproteinases, and the like.

"PHF" refers to poly(1-hydroxymethylethylene hydroxymethyl-formal).

As used herein, the terms "polymer unit", "monomeric unit", "monomer", "monomer unit", "unit" all refer to a repeatable structural unit in a polymer.

As used herein, "molecular weight" or "MW" of a polymer or polymeric carrier/scaffold or polymer conjugates refers to the weight average molecular weight unless otherwise specified.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention is intended to include all isomers of the compound, which refers to and includes, optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers.

Polymeric Carriers

In certain exemplary embodiments, the conjugates of the invention find use in biomedical applications, such as drug delivery and tissue engineering, and the carrier is biocompatible and biodegradable. In certain embodiments, the carrier is a soluble polymer, nanoparticle, gel, liposome, micelle, suture, implant, etc. In certain embodiments, the term "soluble polymer" encompasses biodegradable biocompatible polymer such as a polyal (e.g., hydrophilic polyacetal or polyketal). In certain other embodiments, the carrier is a fully synthetic, semi-synthetic or naturally-occurring polymer. In certain other embodiments, the carrier is hydrophilic.

In certain exemplary embodiments, the carriers used in the present invention are biodegradable biocompatible polyals comprising at least one hydrolysable bond in each monomer unit positioned within the main chain. This ensures that the degradation process (via hydrolysis/cleavage of the monomer units) will result in fragmentation of the polymer conjugate to the monomeric components (i.e., degradation), and confers to the polymer conjugates of the invention their biodegradable properties. The properties (e.g., solubility, bioadhesivity and hydrophilicity) of biodegradable biocompatible polymer conjugates can be modified by subsequent substitution of additional hydrophilic or hydrophobic groups. Examples of biodegradable biocompatible polymers suitable for practicing the invention can be found inter alia in U.S. Pat. Nos. 5,811,510; 5,863,990; 5,958,398; 7,838,619 and 7,790,150; and U.S. Publication No. 2006/0058512; each of the above listed patent documents is incorporated herein by reference in its entirety. Guidance on the significance, preparation, and applications of this type of polymers may be found in the above-cited documents. In certain embodiments, it is anticipated that the present invention will be particularly useful in combination with the above-referenced patent documents, as well as U.S. Pat. Nos. 5,582,172 and 6,822,086, each of the above listed patent documents is incorporated herein by reference in its entirety.

The conjugates of this invention are hydrophilic, hydrolysable and comprise drug molecules (e.g., vinca alkaloids or derivatives, non-natural camptothecin compounds or derivatives, auristatins, tubulysins, duocarmycins, PI3 kinases, MEK inhibitors, KSP inhibitors, and analogs thereof) and antibodies (e.g., Trastuzumab, Cetuximab, Rituximab, Bevacizumab, Epratuzumab, Veltuzumab, Labetuzumab) or peptides (LHRH receptor targeting peptides, EC-1 peptide) covalently attached to the polymer carrier via linkages that contain one or more biodegradable bonds. Thus, in certain exemplary embodiments, carriers suitable for practicing the present invention are polyals having at least one acetal/ketal oxygen atom in each monomer unit positioned within the main chain. As discussed above, this ensures that the degradation process (via hydrolysiscleavage of the polymer acetal/ketal groups) will result in fragmentation of the polyal conjugate to low molecular weight components (i.e., degradation).

In certain embodiments, biodegradable biocompatible polymer carriers, used for preparation of polymer conjugates of the invention, are naturally occurring polysaccharides, glycopolysaccharides, and synthetic polymers of polyglycoside, polyacetal, polyamide, polyether, and polyester origin and products of their oxidation, fictionalization, modification, cross-linking, and conjugation.

In certain other embodiments, the carrier is a hydrophilic biodegradable polymer selected from the group consisting of carbohydrates, glycopolysaccharides, glycolipids, glycoconjugates, polyacetals, polyketals, and derivatives thereof.

In certain exemplary embodiments, the carrier is a naturally occurring linear and/or branched biodegradable biocompatible homopolysaccharide selected from the group consisting of cellulose, amylose, dextran, levan, fucoidan, carraginan, inulin, pectin, amylopectin, glycogen and lixenan.

In certain other exemplary embodiments, the carrier is a naturally occurring linear and branched biodegradable biocompatible heteropolysaccharide selected from the group consisting of agarose, hyluronan, chondroitinsulfate, dermatansulfate, keratansulfate, alginic acid and heparin.

In yet other exemplary embodiments, the polymeric carrier comprises a copolymer of a polyacetal/polyketal and a hydrophilic polymer selected from the group consisting of polyacrylates, polyvinyl polymers, polyesters, polyorthoesters, polyamides, polypeptides, and derivatives thereof.

In yet another embodiment, the polymeric carrier is dextrin that is produced by the hydrolysis of a starch obtained from various natural products such as, for example, wheat, rice, maize and tapioca. Depending on the structure of the starch starting material each dextrin comprises a unique distribution of α-1,4 linkages and α-1,6 linkages. Since the rate of biodegradability of α-1,6 linkages is typically less than that for α-1,4 linkages, preferably the percentage of α-1,6 linkages is less than 10% and more preferably less than 5%. In one embodiment the molecular weight of the dextrin is in the range of about 1 kDa to about 200 kDa, more preferably from about 2 kDa to about 55 kDa.

In certain embodiments, the carrier comprises polysaccharides activated by selective oxidation of cyclic vicinal diols of 1,2-, 1,4-, 1,6-, and 2,6-pyranosides, and 1,2-, 1,5-, 1,6-furanosides, or by oxidation of lateral 6-hydroxy and 5,6-diol containing polysaccharides prior to conjugation with drug molecules or PBRMs.

In still other embodiments, the polymeric carrier comprises a biodegradable biocompatible polyacetal wherein at least a subset of the polyacetal repeat structural units have the following chemical structure:

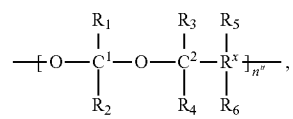

wherein for each occurrence of the n bracketed structure, one of $R_1$ and $R_2$ is hydrogen, and the other is a biocompatible group and includes a carbon atom covalently attached to $C^1$; $R^x$ is a carbon atom covalently attached to $C^2$; n" is an integer; each occurrence of $R_3$, $R_4$, $R_5$ and $R_6$ is a biocompatible group and is independently hydrogen or an organic moiety; and for each occurrence of the bracketed structure n, at least one of $R_1$, $R_2$, $R_3$, $R_4$, $R_5$ and $R_6$ comprises a functional group suitable for coupling. In certain embodiments, the functional group is a hydroxyl moiety.

In one embodiment, the polymeric carrier comprises activated hydrophilic biodegradable biocompatible polymers comprising from 0.1% to 100% polyacetal moieties whose backbone is represented by the following chemical structure:

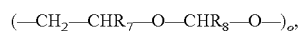

wherein:

$R_7$ and $R_8$ are independently hydrogen, hydroxyl, hydroxy alkyl (e.g., —CH$_2$OH, —CH(OH)—CH(OH), —CHO, —CH(OH)—CHO or -carbonyl; and o is an integer from 20 to 2000.

In yet other embodiments, the polymeric carrier comprises a biodegradable biocompatible polyketal wherein at least a subset of the polyketal repeatable structural units have the following chemical structure:

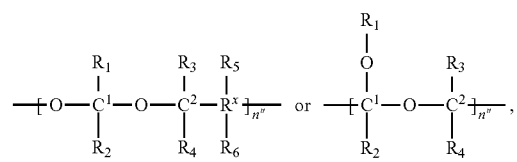

wherein each occurrence of $R_1$ and $R_2$ is a biocompatible group and $R^x$, $R_3$, $R_4$, $R_5$, $R_6$ and are as defined herein.

In certain embodiments, the ketal units are monomers of Formula (IIa) or (IIb):

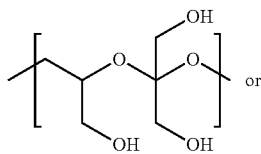

(IIa)

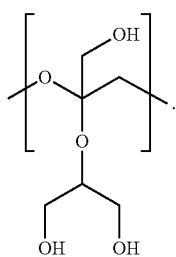

(IIb)

Biodegradable, biocompatible polyketal polymers and their methods of making have been described in U.S. Pat. Nos. 5,811,510, 7,790,150 and 7,838,619, which are hereby incorporated by reference in their entireties.

In one embodiment, the polymeric carrier can be obtained from partially oxidized dextran (β1→6)-D-glucose) followed by reduction. In this embodiment, the polymer comprises a random mixture of the unmodified dextran (A), partially oxidized dextran acetal units (B) and exhaustively dextran acetal units (C) of the following structures:

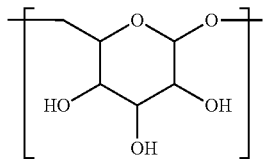

(A)

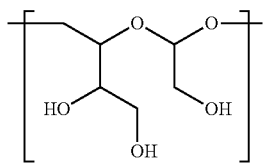

(B)

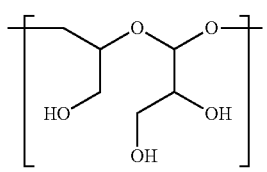

(B)

(C)

In another embodiment, the polymeric carrier comprises unmodified acetal units, i.e., polyacetal segments. In some embodiments, the polyacetals can be derived from exhaustively oxidized dextran followed by reduction. These polymers have been described in references, see, e.g., U.S. Pat. No. 5,811,510, which is hereby incorporated by reference for its description of polyacetals at column 2, line 65 to column 8, line 55 and their synthesis at column 10, line 45 to column 11, line 14. In one embodiment, the unmodified polyacetal polymer is a poly(hydroxymethylethylene hydroxymethyl formal) polymer (PHF).

In addition to poly(hydroxymethylethylene hydroxymethyl formal) polymers, the backbone of the polymeric carrier can also comprise co-polymers of poly(hydroxymethylethylene hydroxymethyl formal) blocks and other acetal or non-acetal monomers or polymers. For example, polyethylene glycol polymers are useful as a stealth agent in the polymer backbone because they can decrease interactions between polymer side chains of the appended functional groups. Such groups can also be useful in limiting interactions such as between serum factors and the modified polymer. Other stealth agent monomers for inclusion in the polymer backbone include, for example, ethyleneimine, methacrylic acid, acrylamide, glutamic acid, and combinations thereof.

The acetal or ketal units are present in the modified polymer in an amount effective to promote biocompatibility. The unmodified acetal or ketal unit can be described as a "stealth agent" that provides biocompatibility and solubility to the modified polymers. In addition, conjugation to a polyacetal or polyketal polymer can modify the susceptibility to metabolism and degradation of the moieties attached to it, and influence biodistribution, clearance and degradation.

The unmodified acetal units are monomers of Formula (III):

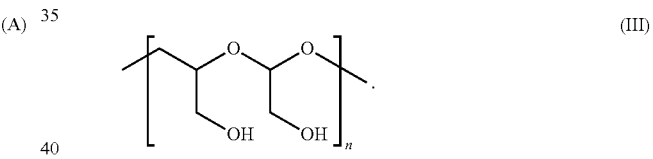

(III)

The molar fraction, n, of unmodified polyacetal units is the molar fraction available to promote biocompatibility, solubility and increase half-life, based on the total number of polymer units in the modified polymer. The molar fraction n may be the minimal fraction of unmodified monomer acetal units needed to provide biocompatibility, solubility, stability, or a particular half-life, or can be some larger fraction. The most desirable degree of cytotoxicity is substantially none, i.e., the modified polymer is substantially inert to the subject. However, as is understood by those of ordinary skill in the art, some degree of cytotoxicity can be tolerated depending on the severity of disease or symptom being treated, the efficacy of the treatment, the type and degree of immune response, and like considerations.

In one embodiment, the modified polymer backbone comprises units of Formula (IV):

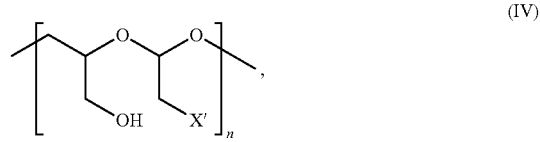

(IV)

wherein X' indicates the substituent for the hydroxyl group of the polymer backbone. As shown in Formula (IV) and the other formulae described herein, each polyacetal unit has a single hydroxyl group attached to the glycerol moiety of the unit and an X' group (or another substituent such as -$L^D$-D) attached to the glycolaldehyde moiety of the unit. This is for convenience only and it should be construed that the polymer having units of Formula (IV) and other formulae described herein can contain a random distribution of units having a X' group (or another substituent such as -$L^D$-D) attached to the glycolaldehyde moiety of the units and those having a single X' group (or another substituent such as -$L^D$-D) attached to the glycerol moiety of the units as well as units having two X' groups (or other substituents such as -$L^D$-D) with one attached to the glycolaldehyde moiety and the other attached to the glycerol moiety of the units.

In one embodiment, biodegradable biocompatible polyals suitable for practicing the present invention have a molecular weight of between about 0.5 and about 300 kDa. In a preferred embodiment of the present invention, the biodegradable biocompatible polyals have a molecular weight of between about 1 and about 300 kDa (e.g., between about 1 and about 200 kDa, between about 2 and about 300 kDa, between about 2 and about 200 kDa, between about 5 and about 100 kDa, between about 10 and about 70 kDa, between about 20 and about 50 kDa, between about 20 and about 300 kDa, between about 40 and about 150 kDa, between about 50 and about 100 kDa, between about 2 and about 40 kDa, between about 6 and about 20 kDa, or between about 8 and about 15 kDa).

In one embodiment, the biodegradable biocompatible polyals suitable for practicing the present invention are modified before conjugating with a drug or a PBRM. For example, the polyals may contain subunits of linkers $L^D$ or $L^P$, such as —C(=O)—X—(CH$_2$)$_v$—C(=O)— with X being CH$_2$, O, or NH, and v being an integer from 1 to 6. Table A below provides some examples of the modified polyals suitable for conjugating with a drug or PBRM or derivatives thereof. Unless otherwise specified, reference numbers in Tables A through E below correspond to the Example numbers described herein; the term "ND" means not determined; and X is CH$_2$, O, or NH.

TABLE A

| Ref # | Polymer Scaffold |
|---|---|
| Ex 2 | |
| Ex 1 | |

TABLE A-continued

| Ref # | Polymer Scaffold |
|---|---|
| X = CH$_2$ Ex 5<br>X = NH Ex 74 | |
| | |
| X = CH$_2$, Ex 12 | |

TABLE A-continued
| Ref # | Polymer Scaffold |
|---|---|
| X = CH$_2$<br>Ex 71 | 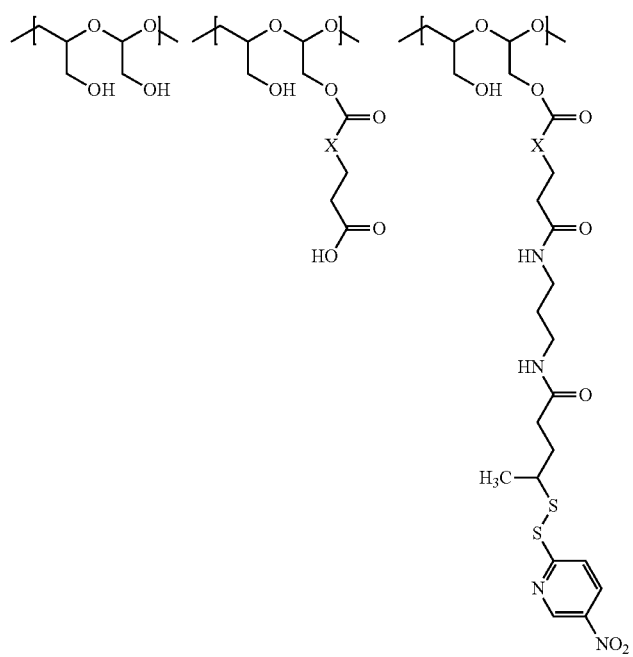 |

TABLE A-continued

| Ref # | Polymer Scaffold |
|---|---|
| X = CH$_2$ Ex 68 | |

TABLE A-continued
| Ref # | Polymer Scaffold |
|---|---|
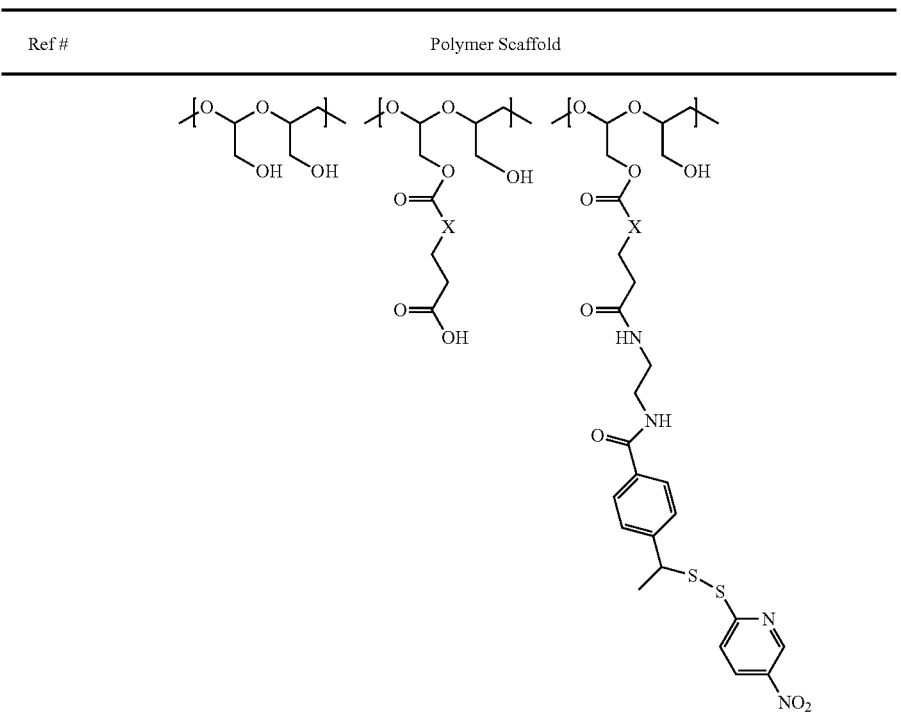
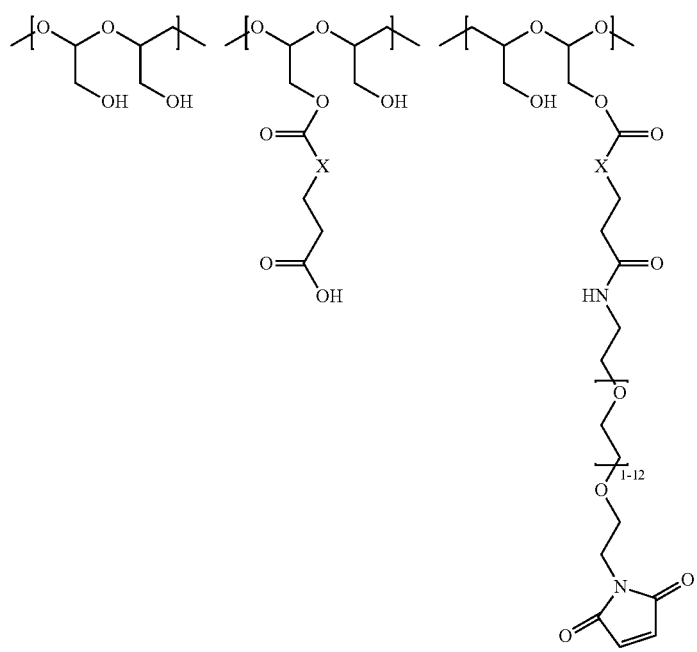

TABLE A-continued

| Ref # | Polymer Scaffold |
|---|---|

TABLE A-continued

| Ref # | Polymer Scaffold |
|---|---|
| | 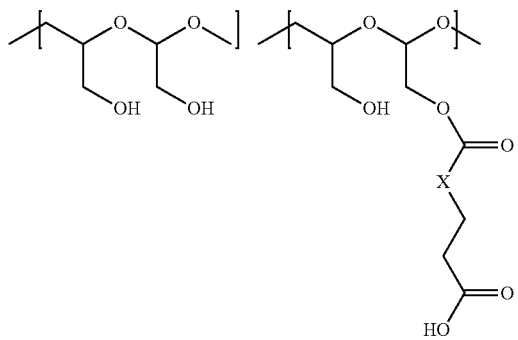 |

Therapeutic Agents

In certain embodiments, the therapeutic agent is a small molecule having a molecular weight preferably ≤about 5 kDa, more preferably ≤about 4 kDa, more preferably ≤about 3 kDa, most preferably ≤about 1.5 kDa or ≤about 1 kDa.

In certain embodiments, the therapeutic agent has an $IC_{50}$ of about less than 1 nM.

In another embodiment, the therapeutic agent has an $IC_{50}$ of about greater than 1 nM, for example, the therapeutic agent has an $IC_{50}$ of about 1 to 50 nM.

Some therapeutic agents having an $IC_{50}$ of greater than about 1 nM (e.g., "less potent drugs") are unsuitable for conjugation with a PBRM using art-recognized conjugation techniques. Without wishing to be bound by theory, such therapeutic agents have a potency that is insufficient for use in targeted PBRM-drug conjugates using conventional techniques as sufficient copies of the drug (i.e., more than 8) cannot be conjugated using art-recognized techniques without resulting in diminished pharmacokinetic and physiochemical properties of the conjugate. However sufficiently high loadings of these less potent drugs can be achieved using the conjugation strategies described herein thereby resulting in high loadings of the therapeutic agent while maintaining the desirable pharmacokinetic and physiochemical properties. Thus, the invention also relates to a PBRM-drug conjugate which includes a PBRM, PHF and at least eight therapeutic agent moieties, wherein the therapeutic agent has an $IC_{50}$ of greater than about 1 nM.

In certain embodiments, about 0.1 to about 25% monomers comprise a therapeutic agent, more preferably about 0.5 to about 20%, more preferably about 1 to about 15%, and even more preferably about 2 to about 10%.

The small molecule therapeutic agents used in this invention (e.g., antiproliferative (cytotoxic and cytostatic) agents capable of being linked to a polymer carrier) include cytotoxic compounds (e.g., broad spectrum), angiogenesis inhibitors, cell cycle progression inhibitors, PI3K/m-TOR/AKT pathway inhibitors, MAPK signaling pathway inhibitors, kinase inhibitors, protein chaperones inhibitors, HDAC inhibitors, PARP inhibitors, Wnt/Hedgehog signaling pathway inhibitors and RNA polymerase inhibitors.

Broad spectrum cytotoxins include, but are not limited to, DNA-binding or alkylating drugs, microtubule stabilizing and destabilizing agents, platinum compounds, and topoisomerase I inhibitors.

Exemplary DNA-binding or alkylating drugs include, CC-1065 and its analogs, anthracyclines (doxorubicin, epirubicin, idarubicin, daunorubicin) and its analogs, alkylating agents, such as calicheamicins, dactinomycines, mitromycines, pyrrolobenzodiazepines, and the like.

Exemplary CC-1065 analogs include duocarmycin SA, duocarmycin C1, duocarmycin C2, duocarmycin B2, DU-86, KW-2189, bizelesin, seco-adozelesin, and those described in U.S. Pat. Nos. 5,475,092; 5,595,499; 5,846,545; 6,534,660; 6,586,618; 6,756,397 and 7,049,316. Doxorubicin and its analogs include those described in U.S. Pat. No. 6,630,579. Calicheamicins include those described in U.S. Pat. Nos. 5,714,586 and 5,739,116. Duocarmycins include those described in U.S. Pat. Nos. 5,070,092; 5,101,038; 5,187,186; 6,548,530; 6,660,742; and 7,553,816 B2; and Li et al., *Tet Letts.*, 50:2932-2935 (2009). Pyrrolobenzodiazepines include those described in Denny, *Exp. Opin. Ther. Patents.*, 10(4):459-474 (2000).

Exemplary microtubule stabilizing and destabilizing agents include taxane compounds, such as paclitaxel, docetaxel; maytansinoids, auristatins and analogs thereof, tubulysin A and B derivatives, vinca alkaloid derivatives, epothilones and cryptophycins.

Exemplary maytansinoids or maytansinoid analogs include maytansinol and maytansinol analogs, maytansine or DM-1 and DM-4 are those described in U.S. Pat. Nos. 5,208,020; 5,416,064; 6,333,410; 6,441,163; 6,716,821; RE39,151 and 7,276,497. In certain embodiments, the cytotoxic agent is a maytansinoid, another group of anti-tubulin agents (ImmunoGen, Inc.; see also Chari et al., 1992, Cancer Res. 52:127-131), maytansinoids or maytansinoid analogs. Examples of suitable maytansinoids include maytansinol and maytansinol analogs. Suitable maytansinoids are disclosed in U.S. Pat.

Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Exemplary auristatins include auristatin E (also known as a derivative of dolastatin-10), auristatin EB (AEB), auristatin EFP (AEFP), monomethyl auristatin E (MMAE), monomethyl auristatin F (MMAF), auristatin F and dolastatin. Suitable auristatins are also described in U.S. Publication Nos. 2003/0083263, 2011/0020343, and 2011/0070248; PCT Application Publication Nos. WO 09/117,531, WO 2005/081711, WO 04/010957; WO 02/088172 and WO01/24763, and U.S. Pat. Nos. 7,498,298; 6,884,869; 6,323,315; 6,239,104; 6,124,431; 6,034,065; 5,780,588; 5,767,237; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, the disclosures of which are incorporated herein by reference in their entirety.

Exemplary tubulysin compounds include compounds described in U.S. Pat. Nos. 7,816,377; 7,776,814; 7,754,885; U.S. Publication Nos. 2011/0021568; 2010/004784; 2010/0048490; 2010/00240701; 2008/0176958; and PCT Application Nos. WO 98/13375; WO 2004/005269; WO 2008/138561; WO 2009/002993; WO 2009/055562; WO 2009/012958; WO 2009/026177; WO 2009/134279; WO 2010/033733; WO 2010/034724; WO 2011/017249; WO 2011/057805; the disclosures of which are incorporated by reference herein in their entirety.

Exemplary vinca alkaloids include vincristine, vinblastine, vindesine, and navelbine (vinorelbine). Suitable Vinca alkaloids that can be used in the present invention are also disclosed in U.S. Publication Nos. 2002/0103136 and 2010/0305149, and in U.S. Pat. No. 7,303,749 B 1, the disclosures of which are incorporated herein by reference in their entirety.

Exemplary epothilone compounds include epothilone A, B, C, D, E and F, and derivatives thereof. Suitable epothilone compounds and derivatives thereof are described, for example, in U.S. Pat. Nos. 6,956,036; 6,989,450; 6,121,029; 6,117,659; 6,096,757; 6,043,372; 5,969,145; and 5,886,026; and WO 97/19086; WO 98/08849; WO 98/22461; WO 98/25929; WO 98/38192; WO 99/01124; WO 99/02514; WO 99/03848; WO 99/07692; WO 99/27890; and WO 99/28324; the disclosures of which are incorporated herein by reference in their entirety.

Exemplary cryptophycin compounds are described in U.S. Pat. Nos. 6,680,311 and 6,747,021.

Exemplary platinum compounds include cisplatin (PLATINOL®), carboplatin (PARAPLATIN®), oxaliplatin (ELOXATINE®), iproplatin, ormaplatin, and tetraplatin.

Exemplary topoisomerase I inhibitors include camptothecin, camptothecin, derivatives, camptothecin analogs and non-natural camptothecins, such as, for example, CPT-11 (irinotecan), SN-38, topotecan, 9-aminocamptothecin, rubitecan, gimatecan, karenitecin, silatecan, lurtotecan, exatecan, diflomotecan, belotecan, lurtotecan and 539625. Other camptothecin compounds that can be used in the present invention include those described in, for example, J. Med. Chem., 29:2358-2363 (1986); J. Med. Chem., 23:554 (1980); J. Med. Chem., 30:1774 (1987).

Angiogenesis inhibitors include, but are not limited, MetAP2 inhibitors, VEGF inhibitors, PlGF inhibitors, VGFR inhibitors, PDGFR inhibitors, MetAP2 inhibitors. Exemplary VGFR and PDGFR inhibitors include sorafenib (Nexavar), sunitinib (Sutent) and vatalanib. Exemplary MetAP2 inhibitors include fumagillol analogs, meaning any compound that includes the fumagillin core structure, including fumagillamine, that inhibits the ability of MetAP-2 to remove $NH_2$-terminal methionines from proteins as described in Rodeschini et al., J. Org. Chem., 69, 357-373, 2004 and Liu, et al., Science 282, 1324-1327, 1998. Non limiting examples of "fumagillol analogs" are disclosed in J. Org. Chem., 69, 357, 2004; J. Org. Chem., 70, 6870, 2005; European Patent Application 0 354 787; J. Med. Chem., 49, 5645, 2006; Bioorg. Med. Chem., 11, 5051, 2003; Bioorg. Med. Chem., 14, 91, 2004; Tet. Lett. 40, 4797, 1999; WO99/61432; U.S. Pat. Nos. 6,603,812; 5,789,405; 5,767,293; 6,566,541; and 6,207,704.

Exemplary cell cycle progression inhibitors include CDK inhibitors such as, for example, BMS-387032 and PD0332991; Rho-kinase inhibitors such as, for example GSK429286; checkpoint kinase inhibitors such as, for example, AZD7762; aurora kinase inhibitors such as, for example, AZD1152, MLN8054 and MLN8237; PLK inhibitors such as, for example, BI 2536, BI6727 (Volasertib), GSK461364, ON-01910 (Estybon); and KSP inhibitors such as, for example, SB 743921, SB 715992 (ispinesib), MK-0731, AZD8477, AZ3146 and ARRY-520.

Exemplary PI3K/m-TOR/AKT signaling pathway inhibitors include phosphoinositide 3-kinase (PI3K) inhibitors, GSK-3 inhibitors, ATM inhibitors, DNA-PK inhibitors and PDK-1 inhibitors.

Exemplary PI3 kinases are disclosed in U.S. Pat. No. 6,608,053, and include BEZ235, BGT226, BKM120, CAL101, CAL263, demethoxyviridin, GDC-0941, GSK615, IC87114, LY294002, Palomid 529, perifosine, PF-04691502, PX-866, SAR245408, SAR245409, SF1126, Wortmannin, XL147 and XL765.

Exemplary AKT inhibitors include, but are not limited to AT7867.

Exemplary MAPK signaling pathway inhibitors include MEK, Ras, JNK, B-Raf and p38 MAPK inhibitors.

Exemplary MEK inhibitors are disclosed in U.S. Pat. No. 7,517,994 and include GDC-0973, GSK1120212, MSC1936369B, AS703026, R05126766 and R04987655, PD0325901, AZD6244, AZD 8330 and GDC-0973.

Exemplary B-raf inhibitors include CDC-0879, PLX-4032, and SB590885.

Exemplary B p38 MAPK inhibitors include BIRB 796, LY2228820 and SB 202190.

Receptor tyrosine kinases (RTK) are cell surface receptors which are often associated with signaling pathways stimulating uncontrolled proliferation of cancer cells and neoangiogenesis. Many RTKs, which over express or have mutations leading to constitutive activation of the receptor, have been identified, including, but not limited to, VEGFR, EGFR, FGFR, PDGFR, EphR and RET receptor family receptors. Exemplary specific RTK targets include ErbB2, FLT-3, c-Kit, and c-Met.

Exemplary inhibitors of ErbB2 receptor (EGFR family) include but not limited to AEE788 (NVP-AEE 788), BIBW2992, (Afatinib), Lapatinib, Erlotinib (Tarceva), and Gefitinib (Iressa).

Exemplary RTK inhibitors targeting more then one signaling pathway (multitargeted kinase inhibitors) include AP24534 (Ponatinib) that targets FGFR, FLT-3, VEGFR-PDGFR and Bcr-Abl receptors; ABT-869 (Linifanib) that targets FLT-3 and VEGFR-PDGFR receptors; AZD2171 that targets VEGFR-PDGFR, Flt-1 and VEGF receptors; CHR-258 (Dovitinib) that targets VEGFR-PDGFR, FGFR, Flt-3, and c-Kit receptors; Sunitinib (Sutent) that targets VEGFR, PDGFR, KIT, FLT-3 and CSF-IR; Sorafenib (Nexavar) and Vatalanib that target VEGFR, PDGFR as well as intracellular serine/threonine kinases in the Raf/Mek/Erk pathway.

Exemplary protein chaperon inhibitors include HSP90 inhibitors. Exemplary HSP90 inhibitors include 17AAG derivatives, BIIB021, BIIB028, SNX-5422, NVP-AUY-922 and KW-2478.

Exemplary HDAC inhibitors include Belinostat (PXD101), CUDC-101, Droxinostat, ITF2357 (Givinostat, Gavinostat), JNJ-26481585, LAQ824 (NVP-LAQ824, Dacinostat), LBH-589 (Panobinostat), MC1568, MGCD0103 (Mocetinostat), MS-275 (Entinostat), PCI-24781, Pyroxamide (NSC 696085), SB939, Trichostatin A and Vorinostat (SAHA).

Exemplary PARP inhibitors include iniparib (BSI 201), olaparib (AZD-2281), ABT-888 (Veliparib), AG014699, CEP 9722, MK 4827, KU-0059436 (AZD2281), LT-673, 3-aminobenzamide, A-966492, and AZD2461.

Exemplary Wnt/Hedgehog signaling pathway inhibitors include vismodegib (RG3616/GDC-0449), cyclopamine (11-deoxojervine) (Hedgehog pathway inhibitors) and XAV-939 (Wnt pathway inhibitor)

Exemplary RNA polymerase inhibitors include amatoxins. Exemplary amatoxins include α-amanitins, β-amanitins, γ-amanitins, ε-amanitins, amanullin, amanullic acid, amaninamide, amanin, and proamanullin.

In one embodiment the drug of the invention is a non-natural camptothecin compound, vinca alkaloid, kinase inhibitor (e.g., PI3 kinase inhibitor (GDC-0941 and PI-103)), MEK inhibitor, KSP inhibitor, RNA polymerse inhibitor, PARP inhibitor, docetaxel, paclitaxel, doxorubicin, duocarmycin, tubulysin, auristatin or a platinum compound. In specific embodiments, the drug is a derivative of SN-38, vindesine, vinblastine, PI-103, AZD 8330, auristatin E, auristatin F, a duocarmycin compound, tubulysin compound, or ARRY-520.

In another embodiment, the drug used in the invention is a combination of two or more drugs, such as, for example, PI3 kinases and MEK inhibitors; broad spectrum cytotoxic compounds and platinum compounds; PARP inhibitors and platinum compounds; broad spectrum cytotoxic compounds and PARP inhibitors.

In one embodiment, the Vinca alkaloid is a compound of Formula (V):

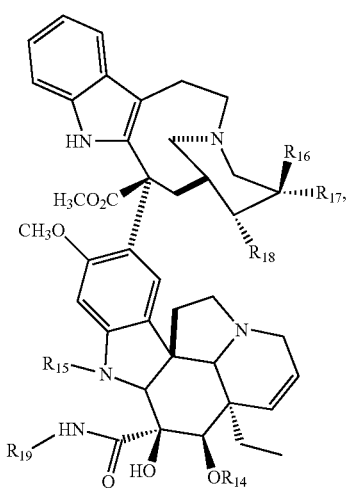

(V)

wherein:

$R_{14}$ is hydrogen, —C(O)—$C_{1-3}$ alkyl or —C(O)-chloro substituted $C_{1-3}$ alkyl;

$R_{15}$ is hydrogen, —$CH_3$ or —CHO;

when $R_{17}$ and $R_{18}$ are taken independently, $R_{18}$ is hydrogen, and either $R_{16}$ or $R_{17}$ is ethyl and the other is hydroxyl;

when $R_{17}$ and $R_{18}$ are taken together with the carbon to which they are attached to form an oxiran ring, $R_{16}$ is ethyl;

$R_{19}$ is hydrogen, OH, amino group, alkyl amino or —[C($R_{20}R_{21}$)]$_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NH_2$, —COOH, —$R_{82}$—C(O)($CH_2$)$_c$—C(H)($R_{23}$)—N(H)($R_{23}$), —$R_{82}$—C(O)($CH_2$)$_d$—($OCH_2$—$CH_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is hydrogen or $X^2$ and $NR_{77}$ form a nitrogen containing heterocyclic moiety;

$R_{82}$ is —NH or oxygen;

a is an integer from 1 to 6;

c is an integer from 0 to 3;

d is an integer from 1 to 3; and f is an integer from 1 to 12.

Further examples of Vinca alkaloids are described in US 2010/0305149 and US 2002/0103136.

In one embodiment the Vinca alkaloid of Formula (V) is a compound of Formula (VI):

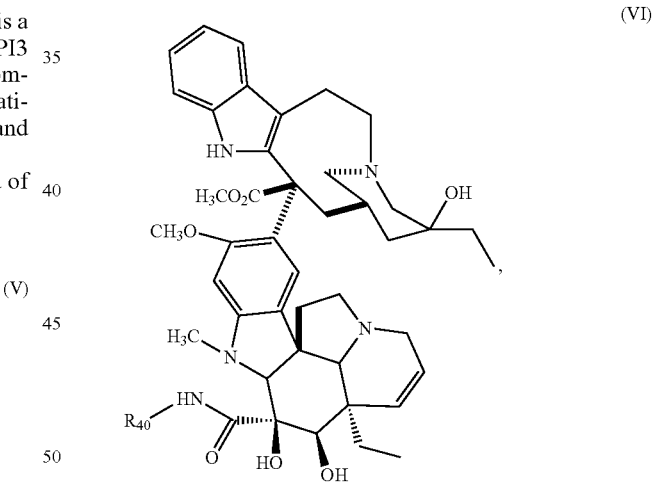

(VI)

wherein:

$R_{40}$ is hydrogen, —OH, —$NH_2$, or any of the following structures:

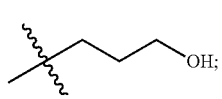

(1)

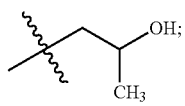

(2)

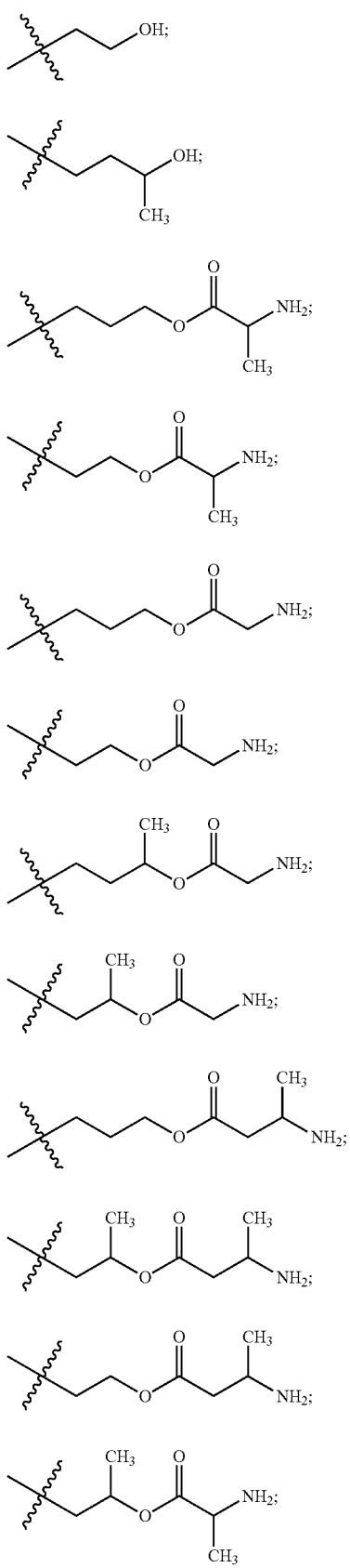
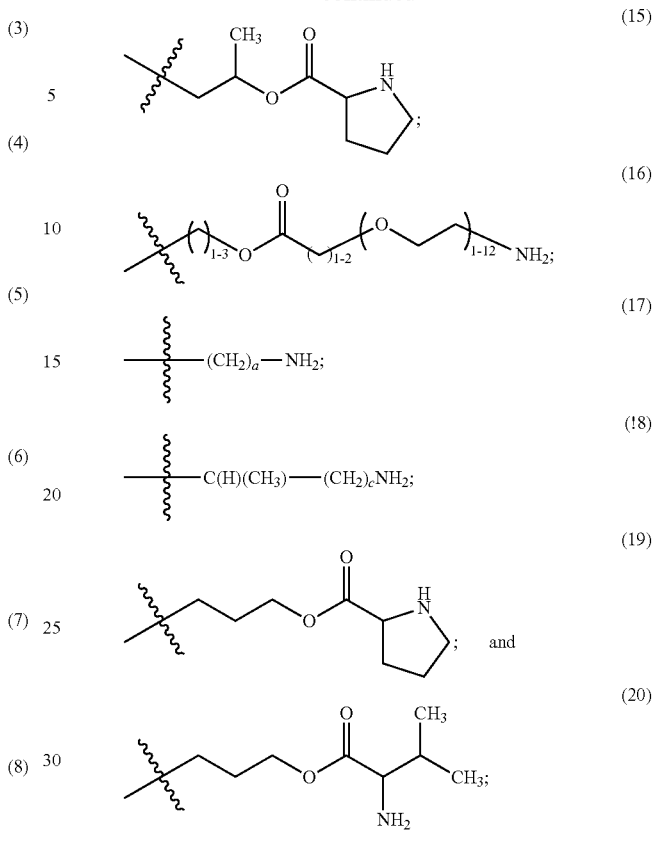
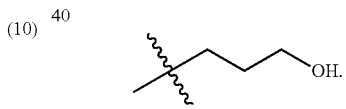
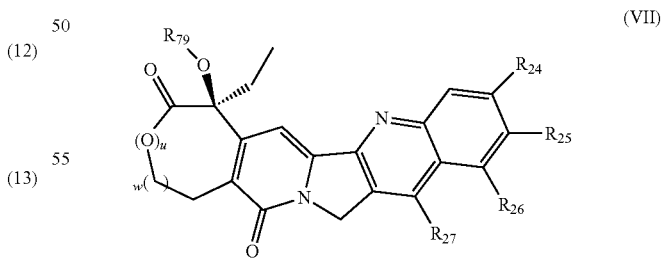
wherein:
a is an integer from 1 to 6; and
c is an integer from 0 to 3.
In one embodiment, $R_{40}$ is
In another embodiment, non-natural camptothecin is a compound of Formula (VII):
wherein:
$R_{24}$ is —H, —Cl, —F, —OH or alkyl; or $R_{24}$ and $R_{25}$, may be taken together to form an optionally substituted five- or six-membered ring;
$R_{25}$ is —H, —F, —OH, —CH$_3$, —CH=N—O-t-Butyl, —CH$_2$CH$_2$Si(CH$_3$)$_3$, —Si((CH$_3$)$_2$)-t-butyl, —O—C(O)—$R_{29}$;

$R_{29}$ is —$NH_2$, —$R_{28}$—$C_{1-6}$ alkyl-$R_{22}$, 5 to 12-membered heterocycloalkyl, $R_{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{26}$ is —H, —$CH_2$—$N(CH_3)_2$, $NH_2$, or $NO_2$;

$R_{27}$ is ethyl, N-methyl piperidine, cycloalkyl, —$CH_2CH_2NHCH(CH_3)_2$, or —N-4-methylcyclohexylamine;

$R_{79}$ is —H or —C(O)—$R_{28}$—[C($R_{20}R_{21}$)]$_a$—$R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NH_2$, —COOH, —$R_{82}$—C(O)($CH_2$)$_c$—C(H)($R_{23}$)—N(H)($R_{23}$), —$R_{82}$—C(O)($CH_2$)$_d$—(O$CH_2$—$CH_2$)$_f$—N(H)($R_{23}$), or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

or $R_{26}$ and $R_{27}$ when taken together with the two carbon atoms to which they attach and the third carbon atom connecting the two carbon atoms form an optionally substituted six-membered ring;

$R_{28}$ is absent, NH or oxygen;

a is an integer from 1 to 6;

c is an integer from 0 to 3;

d is an integer from 1 to 3;

f is an integer from 1 to 12;

u is an integer 0 or 1;

w is an integer 0 or 1; and with the proviso that the compound of Formula (VII) must contain at least one of $R_{29}$ and $R_{79}$.

In one embodiment the non-natural camptothecin compound of Formula (VII) is a compound of Formula (VIII) or Formula (XXV):

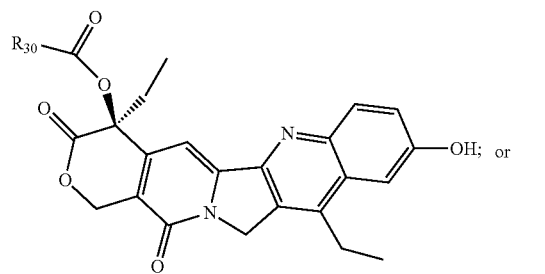

(VIII)

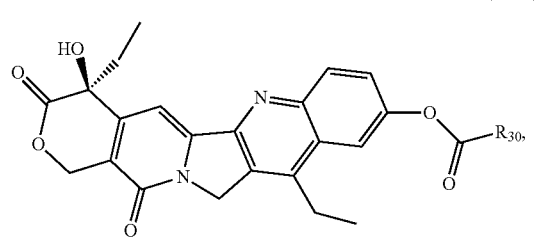

(XXV)

wherein $R_{30}$ is —$NH_2$, —$R_{28}$—$C_{1-6}$ alkyl-$R_{22}$, 5 to 12-membered heterocycloalkyl, $R_{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$;

$R_{28}$ is absent, NH or oxygen;

$R_{22}$ is —OH, —$NH_2$, —COOH, —$R_{82}$—C(O)($CH_2$)$_c$—C(H)($R_{23}$)—N(H)($R_{23}$), —$R_{82}$—C(O)($CH_2$)$_d$—(O$CH_2$—$CH_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

c is an integer from 0 to 3;

d is an integer from 1 to 3; and f is an integer from 1 to 12.

In some embodiments $R_{30}$ is any one of the following structures:

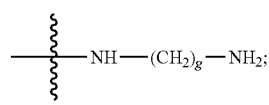

(1)

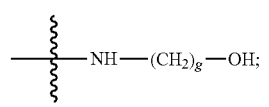

(2)

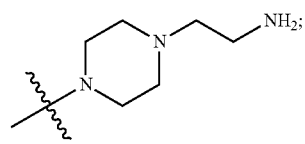

(3)

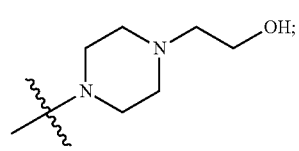

(4)

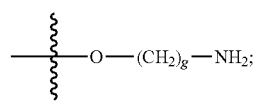

(5)

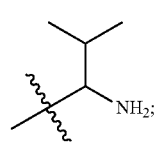

(6)

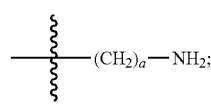

(7)

-continued (8)

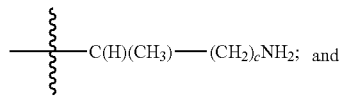
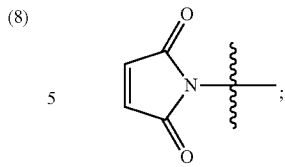

(9)

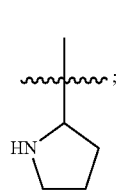

wherein:
a is an integer from 1 to 6;
c is an integer from 0 to 3; and
g is an integer from 2 to 6.

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

$R_9$ is absent, N—($R_{83}$) or oxygen;

$R_{83}$ is hydrogen or $CH_3$;

$R_{11}$ is:

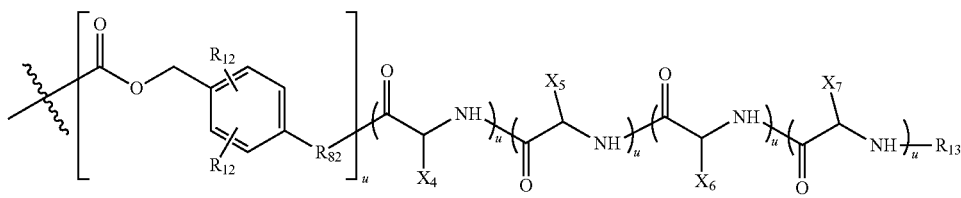

In another embodiment the PI3 kinase is a compound of Formula (IX):

(IX)

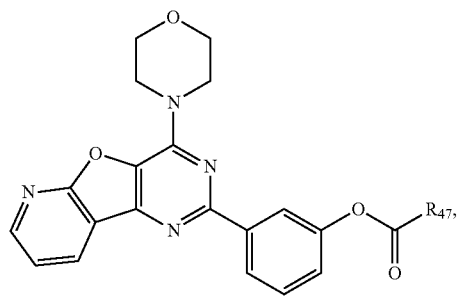

wherein $R_{47}$ is an amino group, —$R_9$—[$C(R_{20}R_{21})$]$_a$—$R_{10}$, —$R_9$—$C_{5-12}$ heterocycloalkyl-$C_{1-6}$ alkyl-$R_{10}$, 5 to 12-membered heterocycloalkyl, or —$R_9$—$C_{6-10}$ aryl;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{10}$ is —OH, —$NHR_{83}$, —N—($R_{83}$)$R_{11}$, —COOH, —$R_{82}$—C(O)(CH$_2$)$_c$—C(H)(R$_{23}$)—N(H)(R$_{23}$), —$R_{82}$—C(O)(CH$_2$)$_d$—(OCH$_2$—CH$_2$)$_f$—N(H)(R$_{23}$), —$R_{82}$—(C(O)—CH(X$^2$)—NH)$_d$—$R_{77}$ or —$R_{82}$—C(O)—[C(R$_{20}$R$_{21}$)]$_a$—$R_{82}$-$R_{83}$ or each $R_{12}$ independently is hydrogen, chloride, —$CH_3$ or —$OCH_3$;

$R_{13}$ is hydrogen or —C(O)—(CH$_2$)$_d$—(O—CH$_2$—CH$_2$)$_f$—NH$_2$;

$R_{82}$ is —NH or oxygen $X_4$ is the side chain of lysine, arginine, citrulline, alanine or glycine;

$X_5$ is the side chain of phenylalanine, valine, leucine, isoleucine or tryptophan;

each of $X_6$ and $X_7$ is independently the side chain of glycine, alanine, serine, valine or proline;

a is an integer from 1 to 6;

c is an integer from 0 to 3;

d is an integer from 1 to 3;

f is an integer from 1 to 12; and each u independently is an integer 0 or 1;

or $R_{11}$ is —$Y_u$—$W_q$—$R_{88}$, wherein:

Y is any one of the following structures:

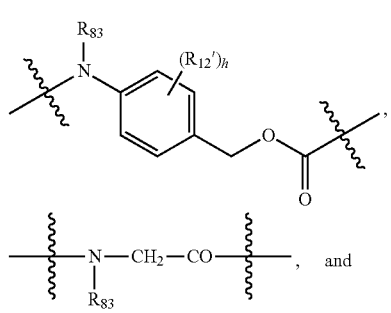

-continued

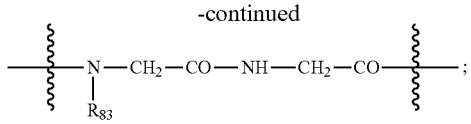

in each of which the terminal NR$_{83}$ group of Y is proximal to R$_{88}$;
R$_{83}$ is hydrogen or CH$_3$;
each W is an amino acid unit;
each R$_{12}$' independently is halogen, —C$_{1-8}$ alkyl, —O—C$_{1-8}$ alkyl, nitro or cyano;
R$_{88}$ is hydrogen or —C(O)—(CH$_2$)$_{ff}$—(NH—C(O))$_{aa}$-E$_j$(CH$_2$)$_{bb}$—R$_{85}$
R$_{85}$ is NH$_2$, OH or

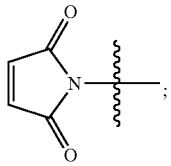

E is —CH$_2$— or —CH$_2$CH$_2$O—;
u is an integer 0 or 1;
q is an integer from 0 to 12;
aa is an integer 0 or 1;
bb is an integer 0 or 2;
ff is an integer from 0 to 10;
h is an integer from 0 to 4;
j is an integer from 0 to 12; and
when E is —CH$_2$—, bb is 0 and j is an integer from 0 to 10; and when E is —CH$_2$CH$_2$—O—, bb is 2 and j is an integer from 1 to 12;
or R$_{11}$ is

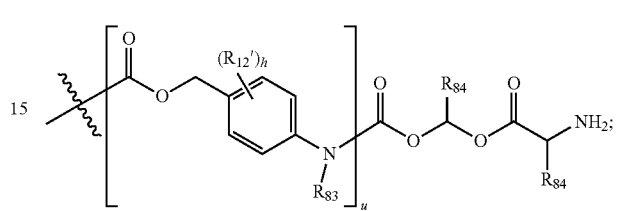

wherein:
R$_{83}$ is hydrogen or CH$_3$;
R$_{84}$ is C$_{1-6}$ alkyl or C$_{6-10}$ aryl;
each R$_{12}$' independently is halogen, —C$_{1-8}$ alkyl, —O—C$_{1-8}$ alkyl, nitro or cyano;
h is an integer from 0 to 4; and
u is an integer 0 or 1.
In some embodiments, R$_{11}$ is:

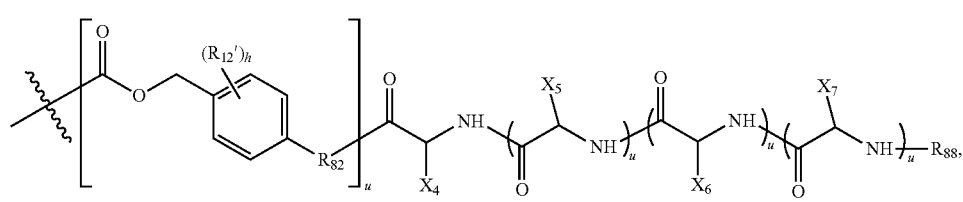

wherein:
each R$_{12}$' independently is chloride, —CH$_3$ or —OCH$_3$;
R$_{88}$ is hydrogen or —C(O)—(CH$_2$)$_{ff}$—(CH$_2$—CH$_2$O)$_j$—CH$_2$—CH$_2$—NH$_2$;
R$_{82}$ is —NH or oxygen
X$_4$ is the side chain of lysine, arginine, citrulline, alanine or glycine;
X$_5$ is the side chain of phenylalanine, valine, leucine, isoleucine or tryptophan;
each of X$_6$ and X$_7$ is independently the side chain of glycine, alanine, serine, valine or proline;
ff is an integer from 1 to 3;
j is an integer from 1 to 12
h is an integer from 0 to 4; and
each u independently is an integer 0 or 1.
In some embodiments,

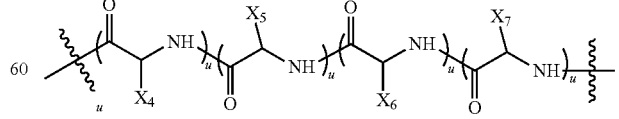

is citrulline-valine; lysine-phenylalanine; citrulline-phenylalanine; citrulline-leucine; citrulline-valine-glycine-glycine; glycine-phenylalanine-glycine-glycine; valine; proline; leucine or isoleucine.

In another embodiment, $R_{11}$ is any one of the following structures:
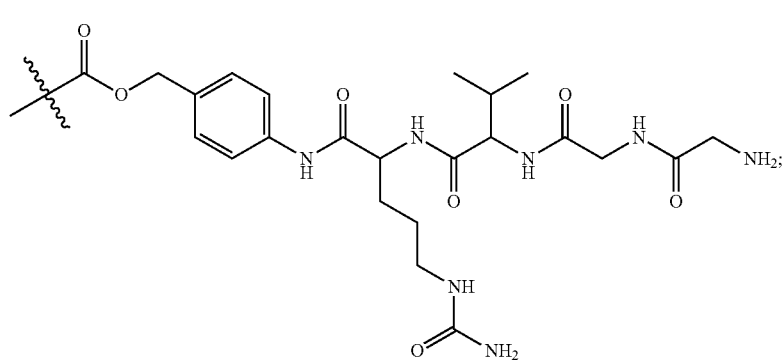
(1)
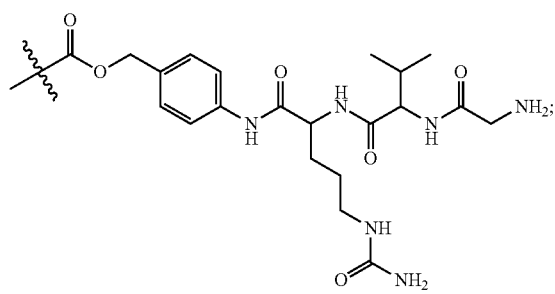
(2)
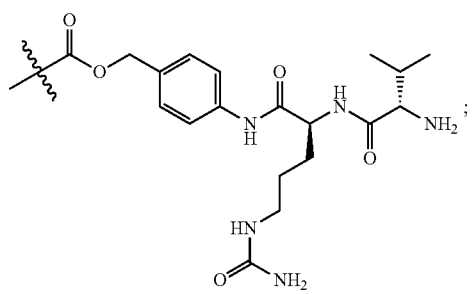
(3)
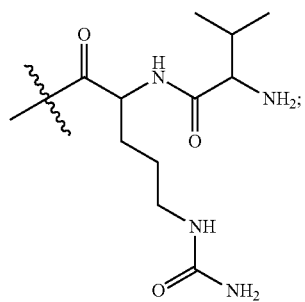
(4)
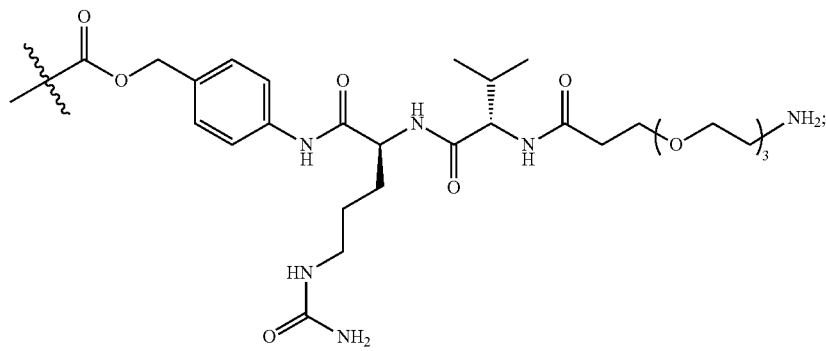
(5)
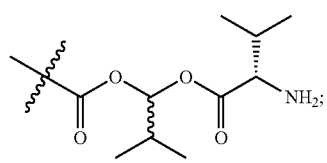
(6)
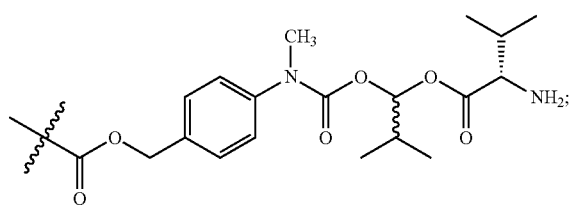
(7)

(8) 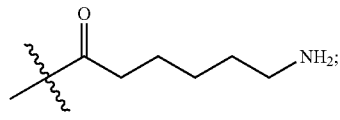
(9) 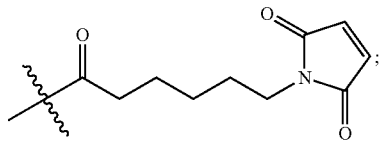
(10) 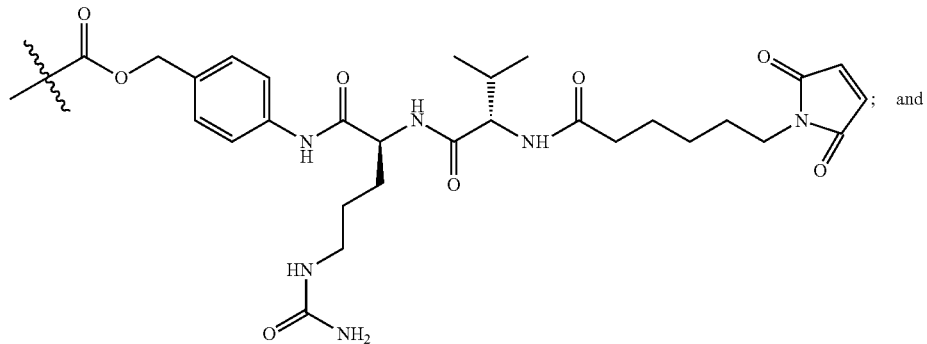 and
(11) 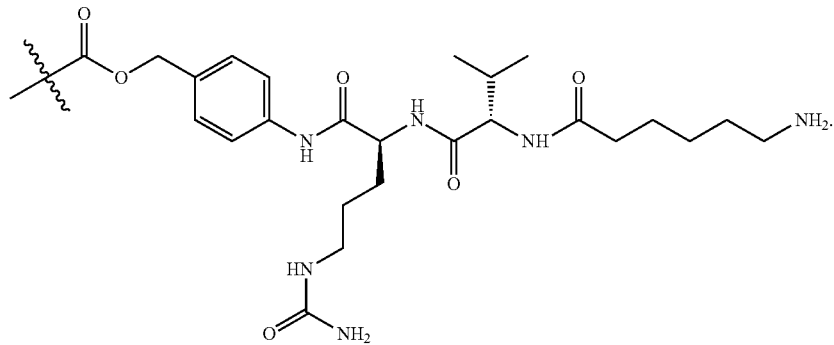
In some embodiments $R_{47}$ is any one of the following structures:
(1) $-NH-(CH_2)_g-NH_2;$
(2) $-NH-(CH_2)_g-OH;$
(3) 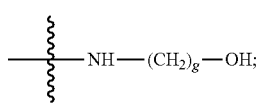
(4) 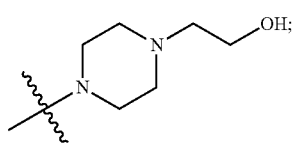
(5) $-O-(CH_2)_g-NH_2;$
(6) 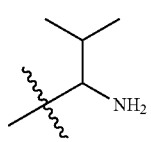
(7) $-(CH_2)_a-NH_2;$
(8) 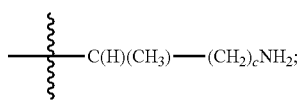

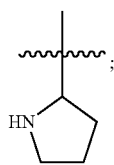
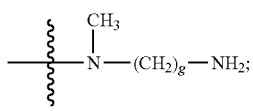
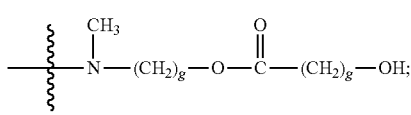
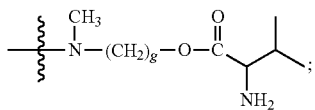

(19)


; or (20)

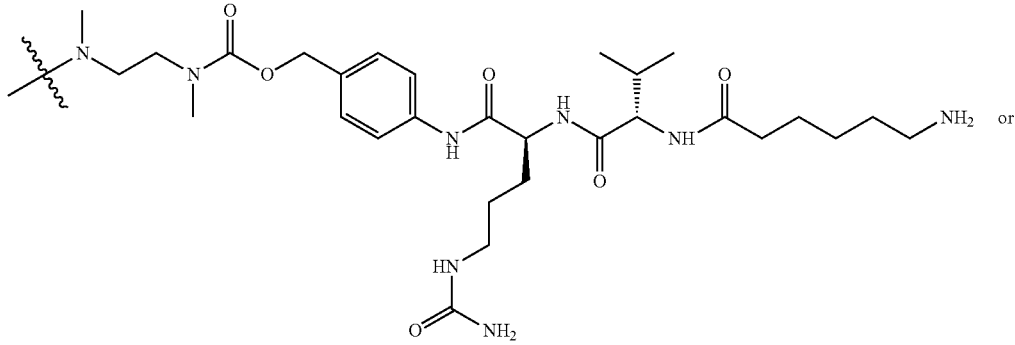

or (21)

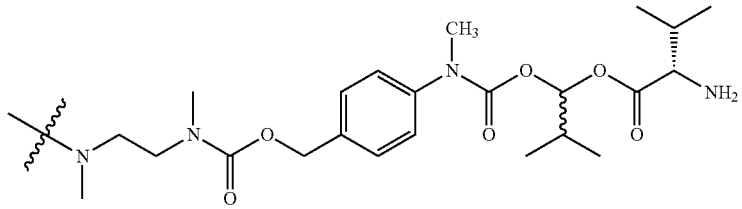

wherein:
a is an integer from 1 to 6;
c is an integer from 0 to 3; and
g is an integer from 2 to 6.

In another embodiment the auristatin is a compound of Formula (X):

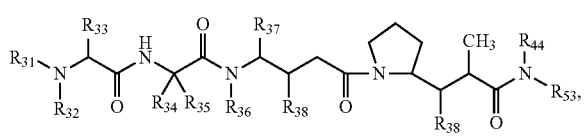

wherein:
each of $R_{31}$ and $R_{32}$ independently is hydrogen or $C_{1-8}$ alkyl and at most one of $R_{31}$ and $R_{32}$ is hydrogen;
$R_{33}$ is hydrogen, $C_{1-8}$ alkyl, $C_{3-8}$ carbocycle, $C_{6-10}$ aryl, $C_{1-8}$ alkyl-$C_{6-10}$ aryl, $X^1$—($C_{3-8}$ carbocycle), $C_{3-8}$ heterocycle or $X^1$—($C_{3-8}$ heterocycle);
$R_{34}$ is hydrogen, $C_{1-8}$ alkyl, $C_{3-8}$ carbocycle, $C_{6-10}$ aryl, $X^1$—$C_{6-10}$ aryl, $X^1$—($C_{3-8}$ carbocycle), $C_{3-8}$ heterocycle or $X^1$—($C_{3-8}$ heterocycle);
$R_{35}$ is hydrogen or methyl;
or $R_{34}$ and $R_{35}$, together with the carbon atom to which they attach form a carbocyclic ring having the formula —$(CR_{55}R_{41})_b$— wherein each of $R_{55}$ and $R_{41}$ independently is hydrogen or $C_{1-8}$ alkyl and b is an integer from 3 to 7;
$R_{36}$ is hydrogen or $C_{1-8}$ alkyl;
$R_{37}$ is hydrogen, $C_{1-8}$ alkyl, $C_{3-8}$ carbocycle, $C_{6-10}$ aryl, —$X^1$—$C_{6-10}$ aryl, —$X^1$—($C_{3-8}$ carbocycle), $C_{3-8}$ heterocycle or —$X^1$—($C_{3-8}$ heterocycle);
each $R_{38}$ independently is hydrogen, OH, $C_{1-8}$ alkyl, $C_{3-8}$ carbocycle or O—($C_{1-8}$ alkyl);
$R_{53}$ is: or $R_{54}$ $R_{39}$ is H, $C_{1-8}$ alkyl, $C_{6-10}$ aryl, —$X^1$—$C_{6-10}$ aryl, $C_{3-8}$ carbocycle, $C_{3-8}$ heterocycle, —$X^1$—$C_{3-8}$ heterocycle, —$C_{1-8}$ alkylene-$NH_2$, or $(CH_2)_2SCH_3$
each $X^1$ independently is $C_{1-10}$ alkylene or $C_{3-10}$ cycloalkylene;
$R_{44}$ is hydrogen or $C_{1-8}$ alkyl;
$R_{45}$ is $X^3$—$R_{42}$ or NH—$R_{19}$;
$X^3$ is O or S;
$R_{19}$ is hydrogen, OH, amino group, alkyl amino or —[C$(R_{20}R_{21})]_a$—$R_{22}$;

$R_{42}$ is an amino group, $C_{1-6}$ alkyl amino or $-[C(R_{20}R_{21})]_a-R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is $-OH$, $-NHR_{23}$, $-COOH$, $-R_{82}-C(O)(CH_2)_c-C(H)(R_{23})-N(H)(R_{23})$, $-R_{82}-C(O)(CH_2)_d-(OCH_2-CH_2)_f-N(H)(R_{23})$ or $-R_{82}-(C(O)-CH(X^2)-NH)_d-R_{77}$;

each $R_{23}$ independently is hydrogen, $C_{1-6}$ alkyl, $C_{6-10}$ aryl, $C_{3-8}$ cycloalkyl, $-COOH$, or $-COO-C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is $-NH$ or oxygen;

$R_{54}$ is $-C(R_{56})_2-C(R_{56})_2-C_{6-10}$ aryl, $-C(R_{56})_2-C(R_{56})_2-C_{3-8}$ heterocycle or $-C(R_{56})_2-C(R_{56})_2-C_{3-8}$ carbocycle;

$R_{56}$ is independently selected from H, OH, $C_{1-8}$ alkyl, $C_{3-8}$ carbocycle, $-O-C_{1-8}$ alkyl, $-O-C(O)-R_{29}$ and $-O-R_{23}-O-C_{1-6}$ alkyl-$NH_2$;

$R_{29}$ is an amino group, 5 to 12-membered heterocycloalkyl, $-R_{28}-C_{1-6}$ alkyl-$R_{22}$, $R_{28}-C_{5-12}$ heterocycloalkyl-$C_{1-6}$ alkyl-$R_{22}$, $-[C(R_{20}R_{21})]_a-R_{22}$, or $-R_{28}-C_{1-6}$ alkyl-$C_{6-12}$ aryl-$C_{1-6}$ alkyl-$R_{22}$; or $R_{29}$ is $R_{47}$ as defined herein;

$R_{28}$ is absent, NH or oxygen;

a is an integer from 1 to 6;

c is an integer from 0 to 3;

d is an integer from 1 to 3; and f is an integer from 1 to 12.

In some embodiments, in the auristatin compound of Formula (X):

$R_{39}$ is benzyl or

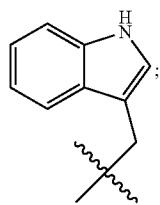 [SMILES: *Cc1c[nH]c2ccccc12]

and $R_{44}$ is hydrogen.

In another embodiment the auristatin is a compound of Formula (Xa):

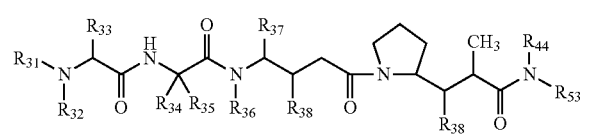

(Xa)

wherein:

$R_{33}$ through $R_{38}$, and $R_{44}$ are as defined herein, one of $R_{31}$ and $R_{32}$ is hydrogen or $C_{1-8}$ alkyl and the other is:

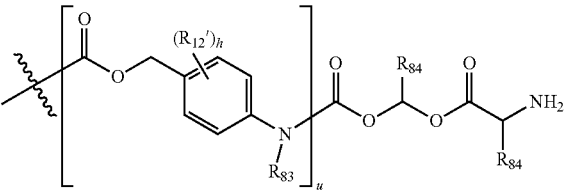

wherein:

$R_{83}$ is hydrogen or $CH_3$;

$R_{84}$ is $C_{1-6}$ alkyl or $C_{6-10}$ aryl;

each $R_{12}'$ independently is halogen, $-C_{1-8}$ alkyl, $-O-C_{1-8}$ alkyl, nitro or cyano;

h is an integer from 0 to 4; and u is an integer 0 or 1;

$R_{53}$ is:

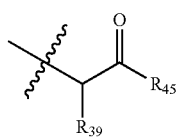

or $R_{54}$ $R_{39}$ is H, $C_{1-8}$ alkyl, $C_{6-10}$ aryl, $-X^1-C_{6-10}$ aryl, $C_{3-8}$ carbocycle, $C_{3-8}$ heterocycle, $-X^1-C_{3-8}$ heterocycle, $-C_{1-8}$ alkylene-$NH_2$, or $(CH_2)_2SCH_3$, each $X^1$ independently is $C_{1-10}$ alkylene or $C_{3-10}$ cycloalkylene;

$R_{45}$ is $X^3-R_{42}$ or $NH-R_{19}$;

$X^3$ is O or S;

$R_{19}$ is hydrogen, OH, amino group, alkyl amino or $-[C(R_{20}R_{21})]_a-R_{22}$;

$R_{42}$ is H, an amino group, $C_{1-6}$ alkyl amino or $-[C(R_{20}R_{21})]_a-R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is $-OH$, $-NHR_{23}$, $-COOH$, $-R_{82}-C(O)(CH_2)_c-C(H)(R_{23})-N(H)(R_{23})$, $-R_{82}-C(O)(CH_2)_d-(OCH_2-CH_2)_f-N(H)(R_{23})$ or $-R_{82}-(C(O)-CH(X^2)-NH)_d-R_{77}$;

each $R_{23}$ independently is hydrogen, $C_{1-6}$ alkyl, $C_{6-10}$ aryl, $C_{3-8}$ cycloalkyl, $-COOH$, or $-COO-C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is $-NH$ or oxygen;

$R_{54}$ is $-C(R_{56})_2-C(R_{56})_2-C_{6-10}$ aryl, $-C(R_{56})_2-C(R_{56})_2-C_{3-8}$ heterocycle or $-C(R_{56})_2-C(R_{56})_2-C_{3-8}$ carbocycle;

$R_{56}$ is independently selected from H, OH, $C_{1-8}$ alkyl, $C_{3-8}$ carbocycle, $-O-C_{1-8}$ alkyl, $-O-C(O)-R_{29}$ and $-O-R_{23}-O-C_{1-6}$ alkyl-$NH_2$;

$R_{29}$ is an amino group, 5 to 12-membered heterocycloalkyl, $-R_{28}-C_{1-6}$ alkyl-$R_{22}$, $R_{28}-C_{5-12}$ heterocycloalkyl-$C_{1-6}$ alkyl-$R_{22}$, $-[C(R_{20}R_{21})]_a-R_{22}$, or $-R_{28}-C_{1-6}$ alkyl-$C_{6-12}$ aryl-$C_{1-6}$ alkyl-$R_{22}$; or $R_{29}$ is $R_{47}$ as defined herein;

$R_{28}$ is absent, NH or oxygen;

a is an integer from 1 to 6;

c is an integer from 0 to 3;

d is an integer from 1 to 3; and f is an integer from 1 to 12.

In one embodiment, the auristatin compound of Formula (Xa) is a compound of Formula (XIa) or Formula (XIb):
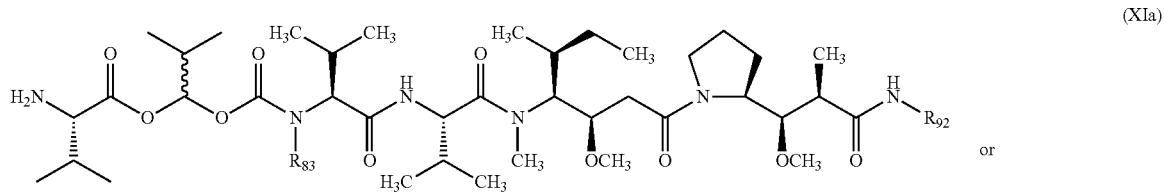
(XIa)
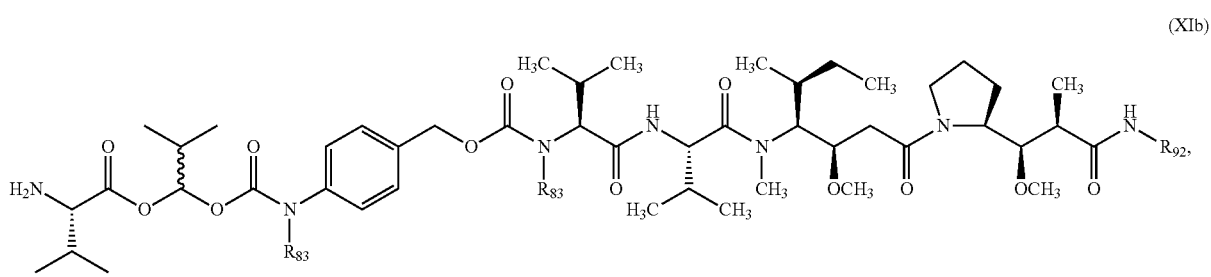
(XIb)
wherein:
R$_{92}$ is:
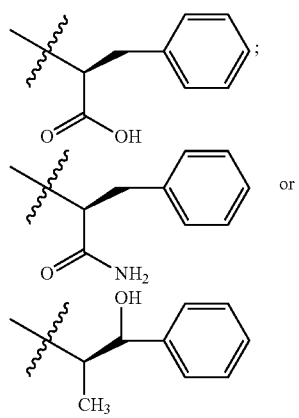
and
R$_{83}$ is hydrogen or CH$_3$.
In one embodiment the auristatin of Formula (X) is a compound of Formula (XI), Formula (XII) or Formula (XIII):
wherein the compound of Formula (XI) is:
wherein R$_{42}$ is —CH$_3$ or any one of the following structures:
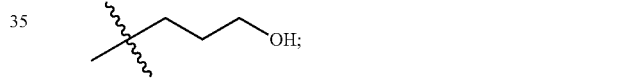
(1)
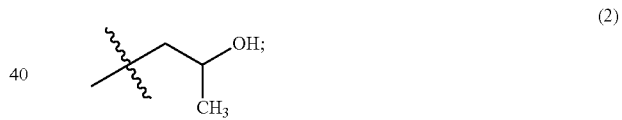
(2)
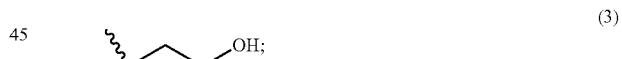
(3)
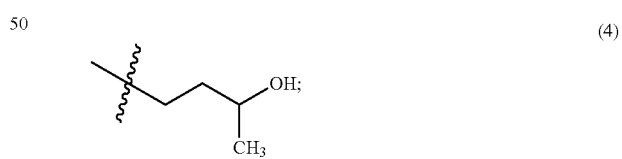
(4)
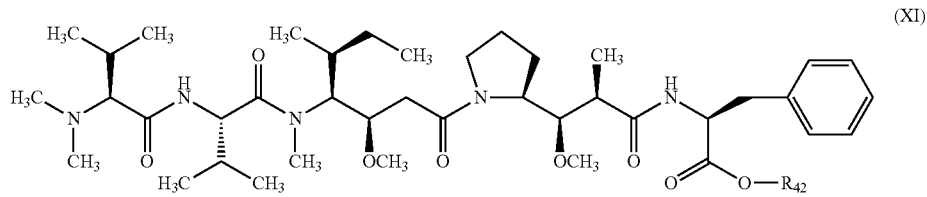
(XI)

-continued
(5) 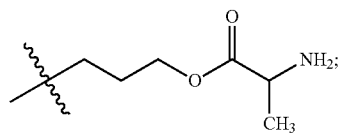
(6) 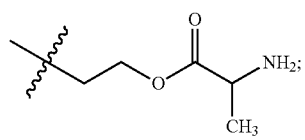
(7) 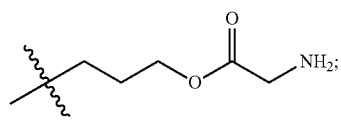
(7) 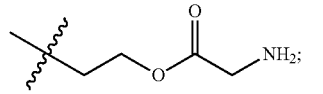
(9) 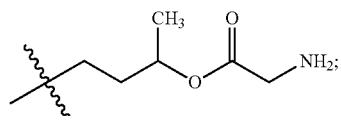
(10) 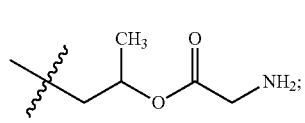
(11) 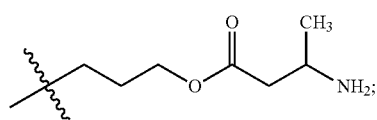
(12) 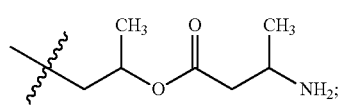
(13) 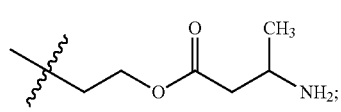
-continued
(14) 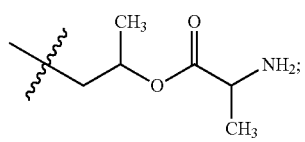
(15) 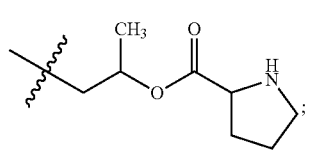
(16) 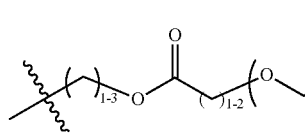
(17) 
(18) 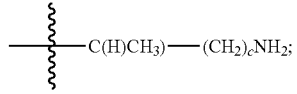
(19) 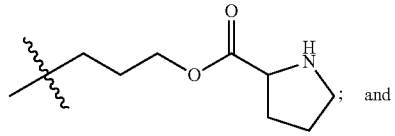
(20) 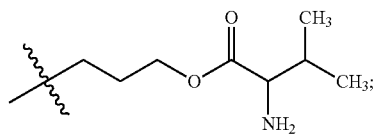
wherein:
a is an integer from 1 to 6; and
c is an integer from 0 to 3;
wherein the compound of Formula (XII) is:
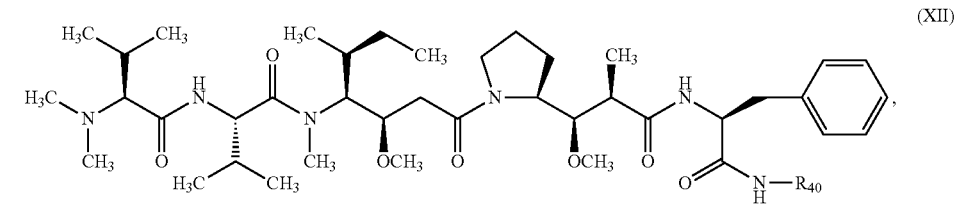
(XII)

wherein R$_{40}$ is hydrogen, —OH, —NH$_2$, or any of the following structures:
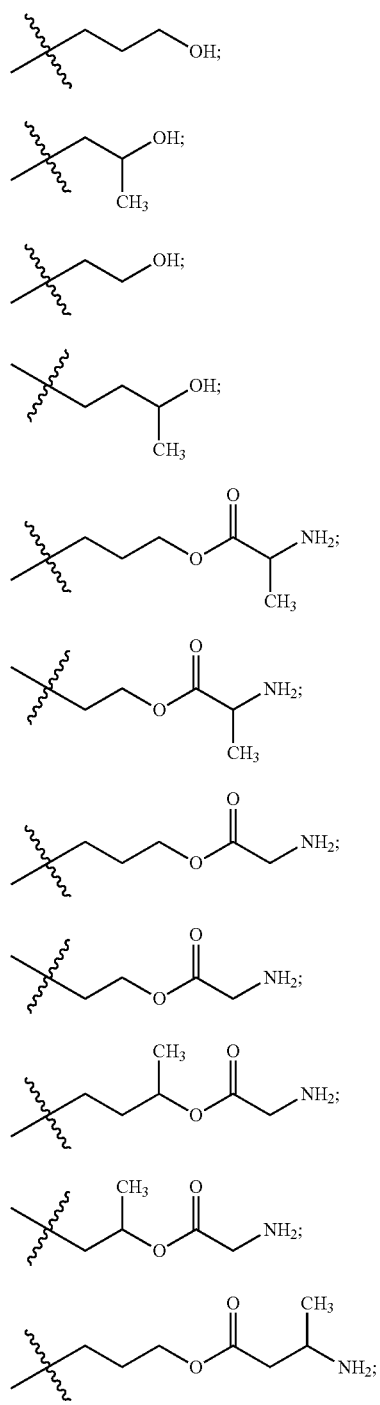
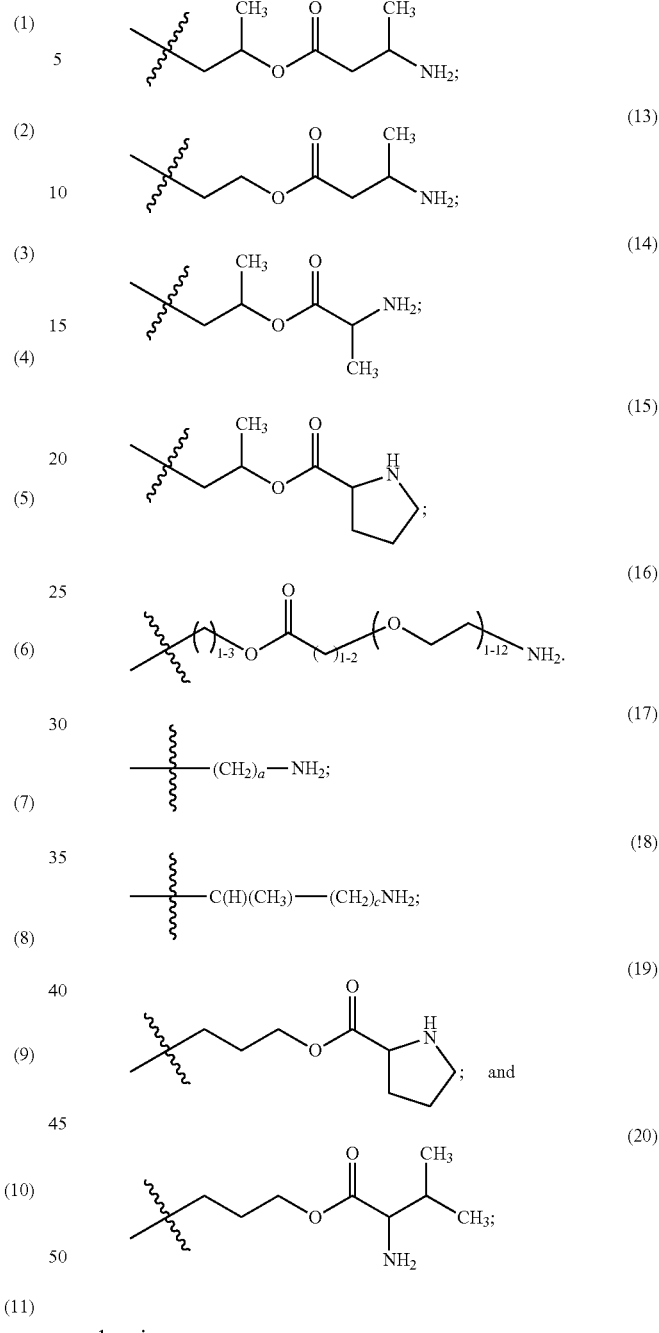
wherein:
a is an integer from 1 to 6; and
c is an integer from 0 to 3;
wherein the compound of Formula (XIII) is:
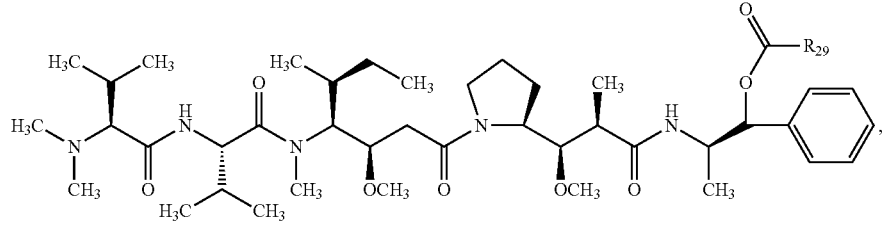

wherein $R_{29}$ is an amino group, 5 to 12-membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$, —$R_{28}$—[C($R_{20}R_{21}$)]$_a$—$R_{22}$, or —$R_{28}$—$C_{1-6}$ alkyl-$C_{6-12}$ aryl-$C_{1-6}$ alkyl-$R_{22}$; or $R_{29}$ is $R_{47}$ as defined herein;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —NHR$_{23}$, —COOH, —$R_{82}$—C(O)(CH$_2$)$_c$—C(H)(R$_{23}$)—N(H)(R$_{23}$), —$R_{82}$—C(O)(CH$_2$)$_d$—(OCH$_2$—CH$_2$)$_f$—N(H)(R$_{23}$) or —$R_{82}$—(C(O)—CH(X$^2$)—NH)$_d$—R$_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and NR$_{77}$ form a nitrogen containing cyclic compound;

$R_{82}$ is —NH or oxygen;

$R_{28}$ is absent, NH or oxygen;

a is an integer from 1 to 6;

c is an integer from 0 to 3;

d is an integer from 1 to 3; and f is an integer from 1 to 12.

In one embodiment, in Formula (XII), $R_{40}$ is

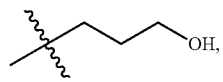

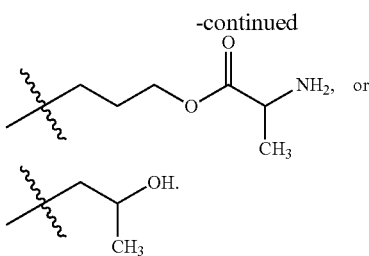

In one embodiment in the compound of Formula (XIII), $R_{29}$ is —NH$_2$, 5 membered heterocycloalkyl, —$R_{28}$—$C_{1-6}$ alkyl-$R_{22}$, $R_{28}$—$C_{5-12}$ heterocycloalkyl-$C_{1-6}$ alkyl-$R_{22}$ or —$R_{28}$—$C_{1-6}$ alkyl-$C_{6-12}$ aryl-$C_{1-6}$ alkyl-$R_{22}$; or $R_{29}$ is $R_{47}$ as defined herein;

$R_{28}$ is absent, NH or oxygen;

$R_{22}$ is —OH, —NHR$_{23}$, —COOH, —$R_{82}$—C(O)(CH$_2$)$_c$—C(H)(R$_{23}$)—N(H)(R$_{23}$), —$R_{82}$—C(O)(CH$_2$)$_d$—(OCH$_2$—CH$_2$)$_f$—N(H)(R$_{23}$) or —$R_{82}$—(C(O)—CH(X$^2$)—NH)$_d$—R$_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and NR$_{77}$ form a nitrogen containing cyclic compound;

$R_{82}$ is —NH or oxygen;

c is an integer from 0 to 3;

d is an integer from 1 to 3; and f is an integer from 1 to 12.

In yet another embodiment, $R_{29}$ is any one of the following structures:

(1)
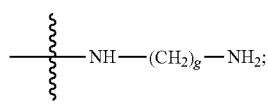

(2)
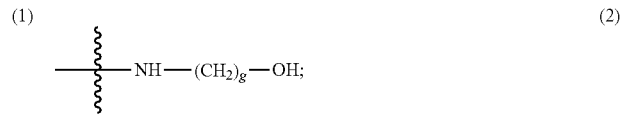

(3)
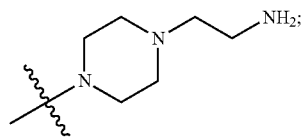

(4)
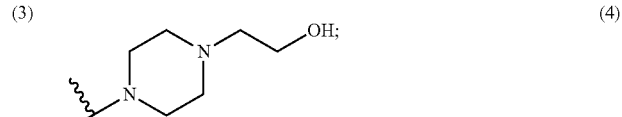

(5)
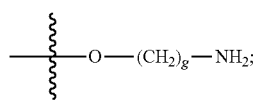

(6)

(7)
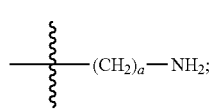

(8)
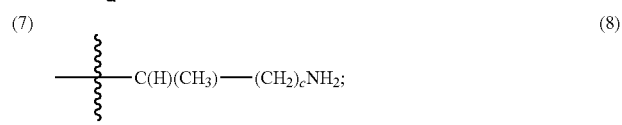

(9)
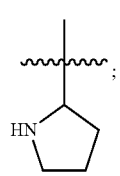

(10)
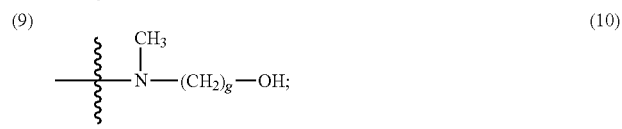

(11)
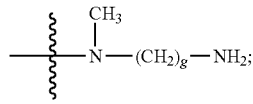

(12)
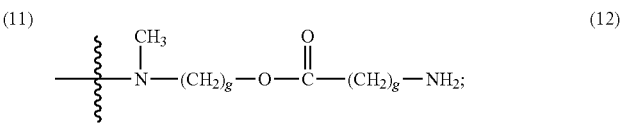

103 104
-continued
(13)
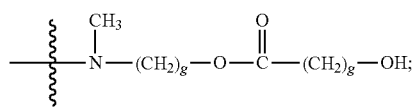
(14)
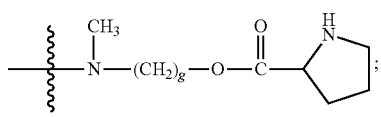
(15)
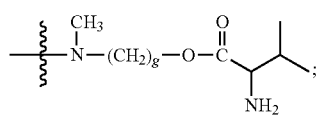
(16)
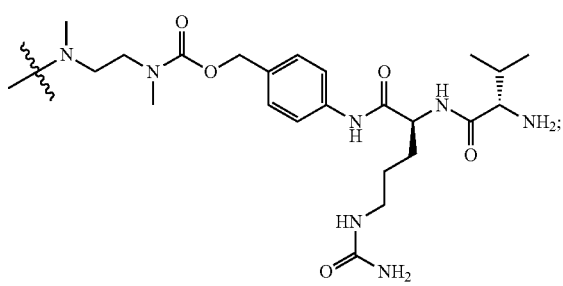 [SMILES: *N(C)CCN(C)C(=O)OCc1ccc(NC(=O)[C@H](CCCNC(N)=O)NC(=O)[C@@H](N)C(C)C)cc1]
(17)
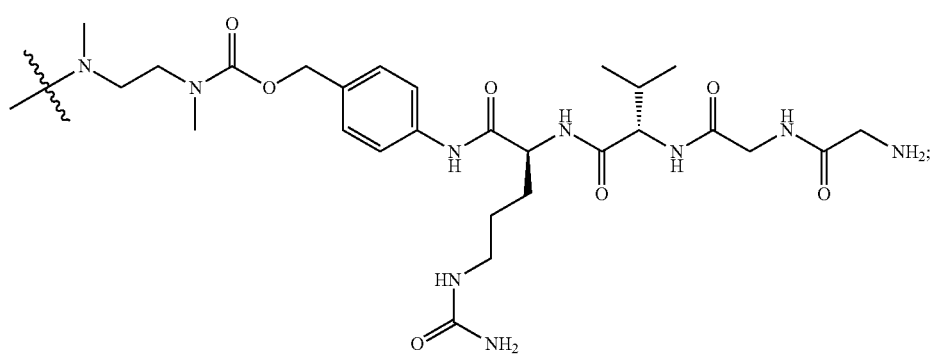
(18)
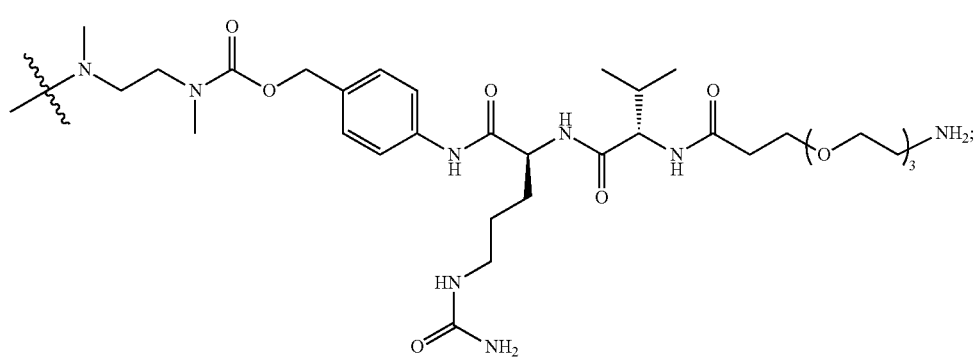
(19)
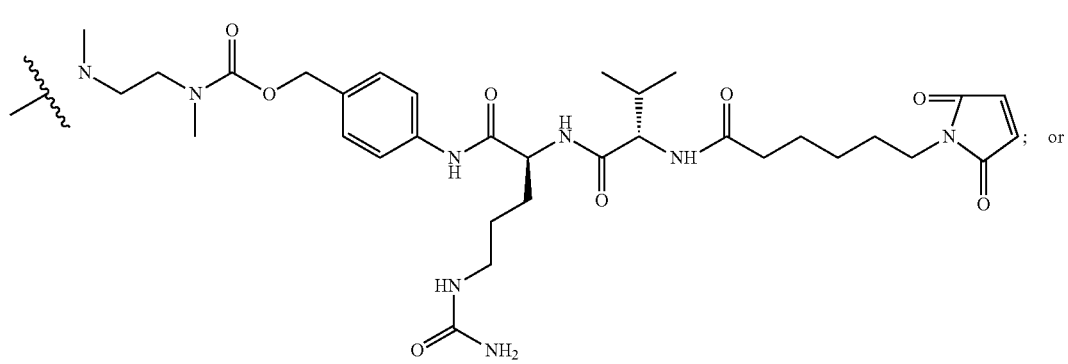

-continued

(20)
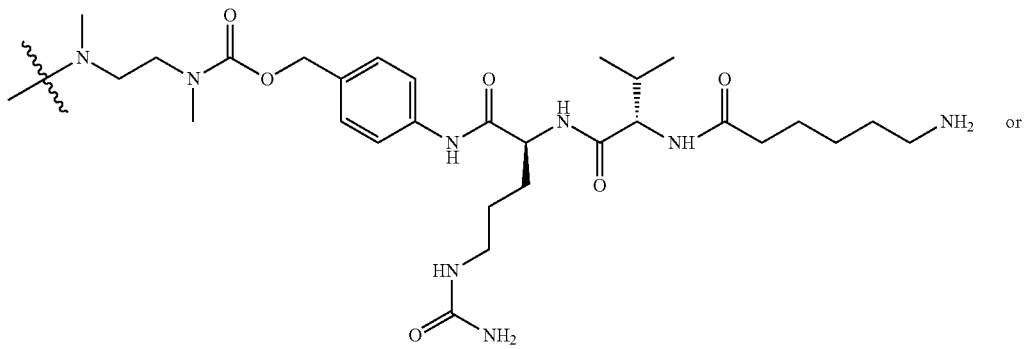

(21)
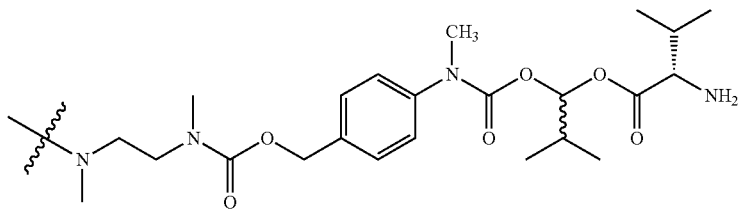

wherein:
a is an integer from 1 to 6;
c is an integer from 0 to 3; and
g is an integer from 2 to 6.

In one embodiment, the MEK inhibitor is a compound of Formula (XIV):

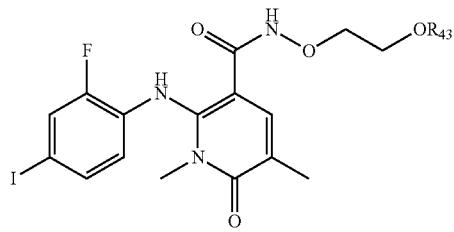
(XIV)

wherein $R_{43}$ is H or —$R_{46}$-$R_{47}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —$NH_2$, —COOH, —$R_{82}$—C(O)($CH_2$), C(H)($R_{23}$)—N(H)($R_{23}$), —$R_{82}$—C(O)($CH_2$)$_d$—(O$CH_2$—$CH_2$)$_f$—N(H)($R_{23}$) or —$R_{82}$—(C(O)—CH($X^2$)—NH)$_d$—$R_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

$R_{46}$ is —C(O)—; —C(O)—O—, —C(O)—NH—, or absent;

$R_{47}$ is as defined herein;

a is an integer from 1 to 6;

c is an integer from 0 to 3;

d is an integer from 1 to 3; and f is an integer from 1 to 12.

Further examples of the MEK inhibitor are disclosed in U.S. Pat. No. 7,517,994 B2.

In some embodiments $R_{43}$ is —C(O)—($CH_2$)$_a$—$NH_2$, or —C(O)—C(H)($CH_3$)—($CH_2$)$_c$—$NH_2$; in which a is an integer from 1 to 6; and c is an integer from 0 to 3.

In another embodiment, the duocarmycin compound is a compound of Formula (XV):

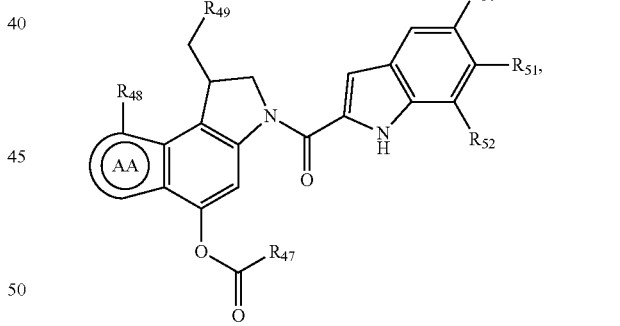
(XV)

wherein:
$R_{47}$ is as defined herein;
$R_{48}$ is hydrogen, —COO$C_{1-6}$ alkyl, —COOH, —$NH_2$ or —$CH_3$;
$R_{49}$ is Cl, Br or —OH;
$R_{50}$ is hydrogen, —$OCH_3$,

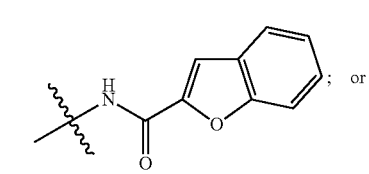
; or

-continued
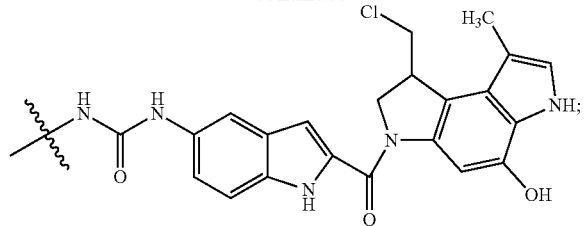
each of $R_{51}$ and $R_{52}$ independently is hydrogen or —$OCH_3$; and
ring AA is either a phenyl or pyrrolyl ring.
Further examples of duocarmycin compounds are disclosed in U.S. Pat. No. 7,553,816.
In one embodiment the duocarmycin compound of Formula (XV) is a compound of Formula (XVI), (XVII), (XVIII) or (XIX):
(XVI)
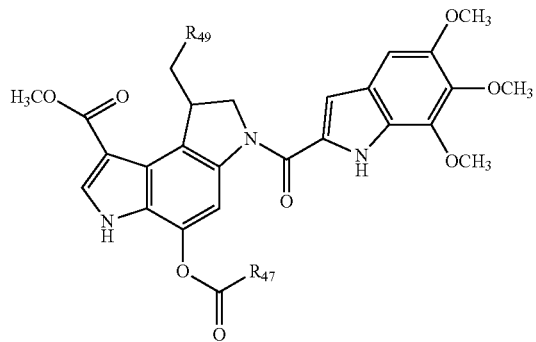
(XVII)
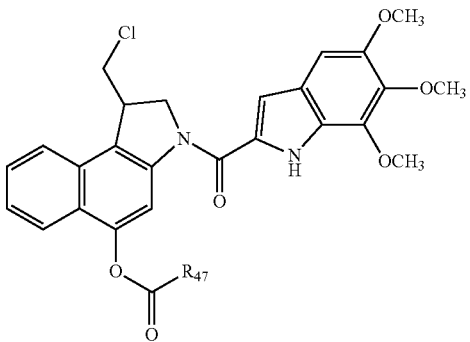
(XVIII)
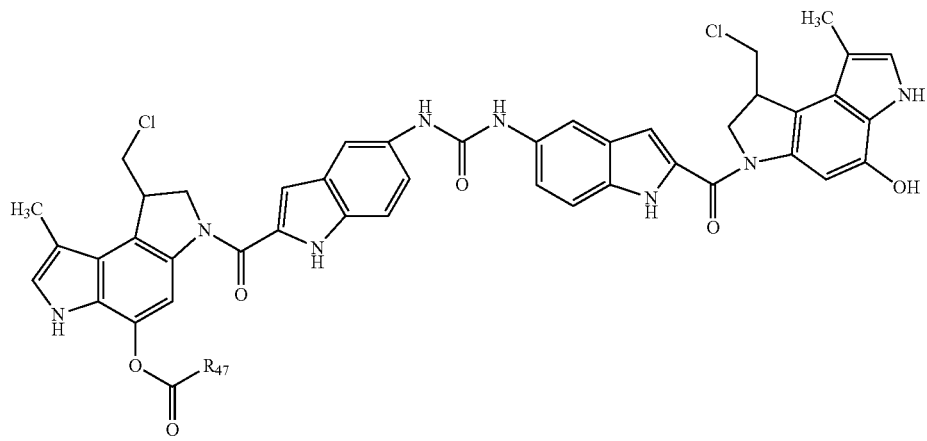
(XIX)
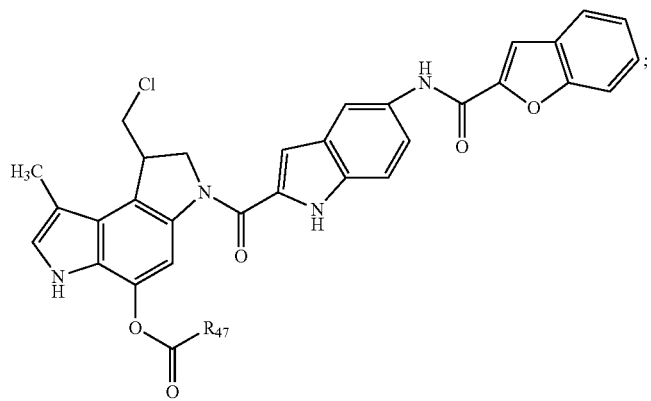

wherein:

$R_{49}$ is Cl, Br or —OH; and $R_{47}$ is as defined herein.

In another embodiment, the duocarmycin compound is a duocarmycin SA compound of Formula (XX): U.S. Pat. No. 5,101,038; or (XXI):

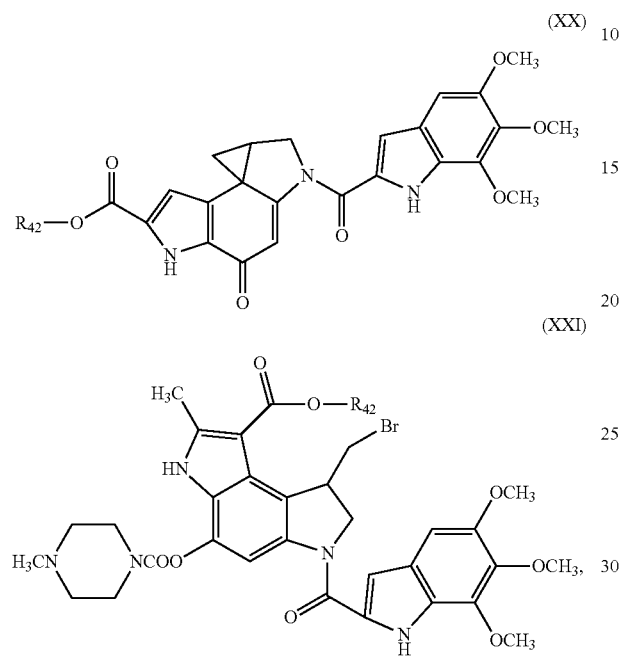

wherein:

$R_{42}$ is $C_{1-6}$ alkyl amino or —[C(R_{20}R_{21})]_a—R_{22}$;

each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{22}$ is —OH, —NH$_2$, —COOH, —R$_{82}$—C(O)(CH$_2$)$_c$—C(H)(R$_{23}$)—N(H)(R$_{23}$), —R$_{82}$—C(O)(CH$_2$)$_d$—(OCH$_2$—CH$_2$)$_f$—N(H)(R$_{23}$), or —R$_{82}$—(C(O)—CH(X$^2$)—NH)$_d$—R$_{77}$;

each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;

$X^2$ is a side chain of a natural or unnatural amino acid;

$R_{77}$ is a hydrogen or $X^2$ and $NR_{77}$ form a nitrogen containing cyclic compound;

$R_{82}$ is —NH or oxygen;

a is an integer from 1 to 6;

c is an integer from 0 to 3;

d is an integer from 1 to 3; and f is an integer from 1 to 12.

In some embodiments, $R_{42}$ is any one of the following structures:

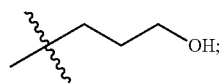
(1)

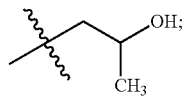
(2)

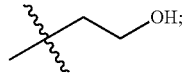
(3)

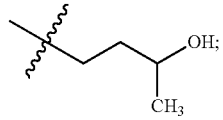
(4)

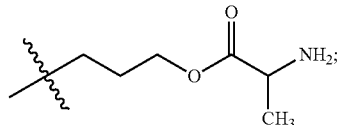
(5)

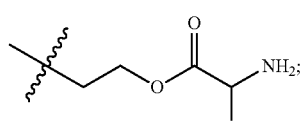
(6)

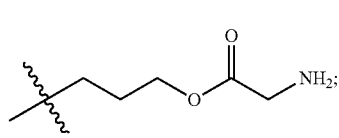
(7)

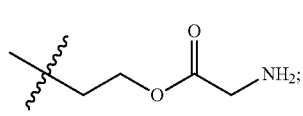
(8)

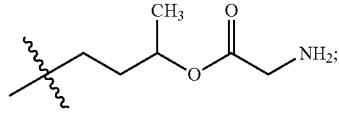
(9)

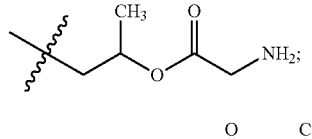
(10)

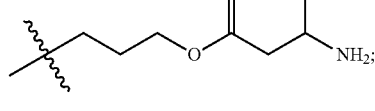
(11)

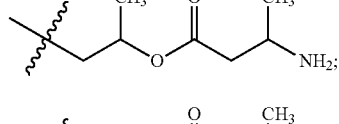
(12)

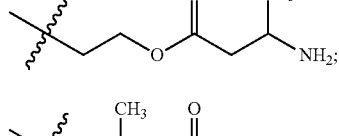
(13)

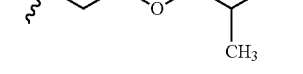
(14)

-continued

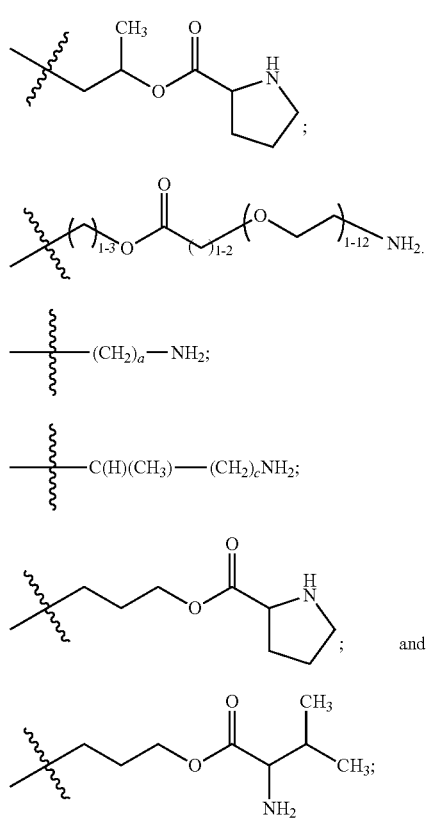

wherein:
a is an integer from 1 to 6; and
c is an integer from 0 to 3.

In another embodiment the tubulysin is a compound of Formula (XXII):

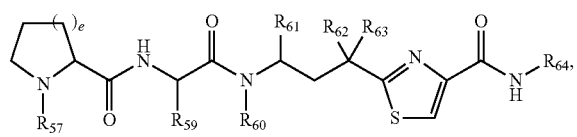

wherein:
$R_{57}$ is $C_{1-4}$ alkyl or —C(O)$R_{58}$;
$R_{58}$ is $C_{1-6}$ alkyl, $CF_3$ or $C_{6-10}$ aryl;
$R_{59}$ is $C_{1-6}$ alkyl;
$R_{60}$ is hydrogen, $C_{1-6}$ alkyl, $C_{2-7}$ alkenyl, —CH$_2$-phenyl, CH$_2$OR$_{65}$ or CH$_2$OCOR$_{66}$;
$R_{65}$ is hydrogen, $C_{1-6}$ alkyl, $C_{2-7}$ alkenyl, $C_{6-10}$ aryl or C(O)$R_{67}$;
$R_{67}$ is $C_{1-6}$ alkyl, $C_{2-6}$ alkenyl, $C_{6-10}$ aryl or heteroaryl;
$R_{66}$ is $C_{1-6}$ alkyl, —$C_6H_5$ or —CH$_2$-phenyl;
$R_{61}$ is $C_{1-6}$ alkyl;
$R_{62}$ is hydrogen, OH, O—$C_{1-4}$ alkyl or O—C(O)—$C_{1-4}$ alkyl;
$R_{63}$ is hydrogen, OH, O—$C_{1-4}$ alkyl, O—C(O)—$C_{1-4}$ alkyl, halogen or $C_{1-6}$ alkyl;
e is an integer from 1 to 3;

$R_{64}$ is:

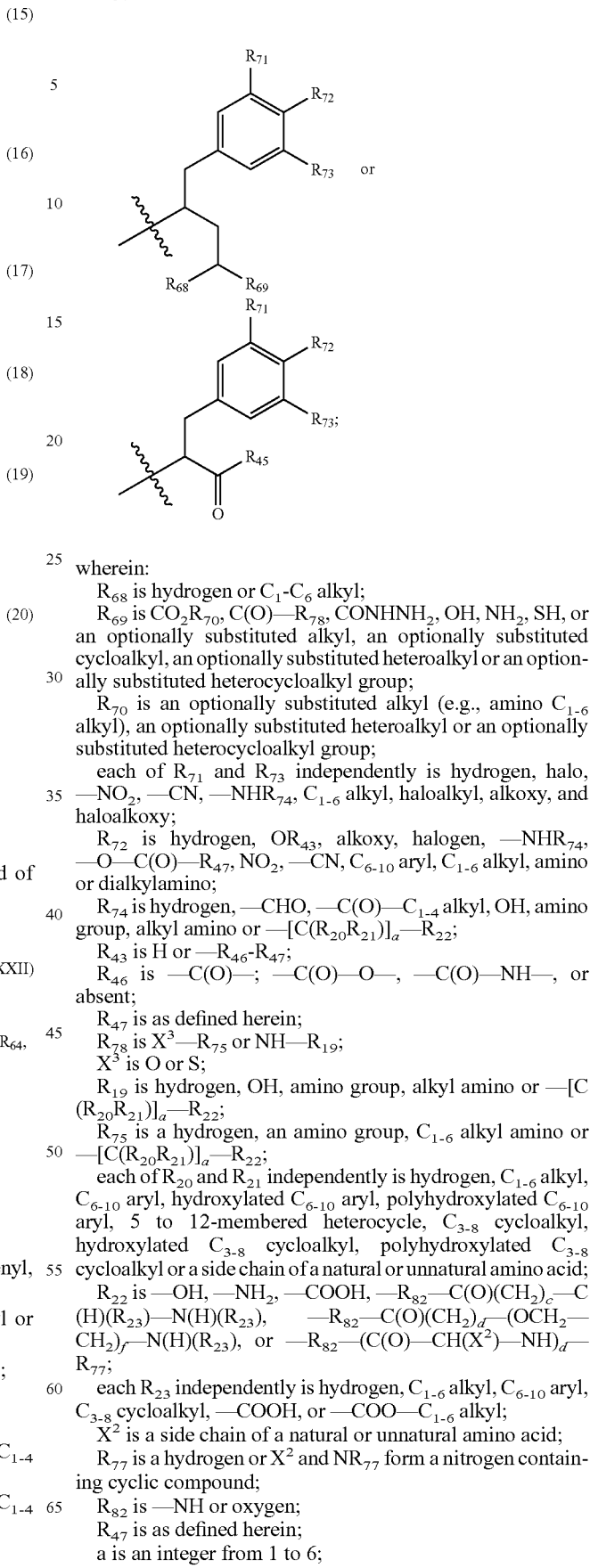

wherein:
$R_{68}$ is hydrogen or $C_1$-$C_6$ alkyl;
$R_{69}$ is CO$_2$R$_{70}$, C(O)—R$_{78}$, CONHNH$_2$, OH, NH$_2$, SH, or an optionally substituted alkyl, an optionally substituted cycloalkyl, an optionally substituted heteroalkyl or an optionally substituted heterocycloalkyl group;
$R_{70}$ is an optionally substituted alkyl (e.g., amino $C_{1-6}$ alkyl), an optionally substituted heteroalkyl or an optionally substituted heterocycloalkyl group;
each of $R_{71}$ and $R_{73}$ independently is hydrogen, halo, —NO$_2$, —CN, —NHR$_{74}$, $C_{1-6}$ alkyl, haloalkyl, alkoxy, and haloalkoxy;
$R_{72}$ is hydrogen, OR$_{43}$, alkoxy, halogen, —NHR$_{74}$, —O—C(O)—R$_{47}$, NO$_2$, —CN, $C_{6-10}$ aryl, $C_{1-6}$ alkyl, amino or dialkylamino;
$R_{74}$ is hydrogen, —CHO, —C(O)—$C_{1-4}$ alkyl, OH, amino group, alkyl amino or —[C(R$_{20}$R$_{21}$)]$_a$—R$_{22}$;
$R_{43}$ is H or —R$_{46}$-R$_{47}$;
$R_{46}$ is —C(O)—; —C(O)—O—, —C(O)—NH—, or absent;
$R_{47}$ is as defined herein;
$R_{78}$ is X$^3$—R$_{75}$ or NH—R$_{19}$;
$X^3$ is O or S;
$R_{19}$ is hydrogen, OH, amino group, alkyl amino or —[C(R$_{20}$R$_{21}$)]$_a$—R$_{22}$;
$R_{75}$ is a hydrogen, an amino group, $C_{1-6}$ alkyl amino or —[C(R$_{20}$R$_{21}$)]$_a$—R$_{22}$;
each of $R_{20}$ and $R_{21}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;
$R_{22}$ is —OH, —NH$_2$, —COOH, —R$_{82}$—C(O)(CH$_2$)$_c$—C(H)(R$_{23}$)—N(H)(R$_{23}$), —R$_{82}$—C(O)(CH$_2$)$_d$—(OCH$_2$—CH$_2$)$_f$—N(H)(R$_{23}$), or —R$_{82}$—(C(O)—CH(X$^2$)—NH)$_d$—R$_{77}$;
each $R_{23}$ independently is hydrogen, $C_{1-6}$ alkyl, $C_{6-10}$ aryl, $C_{3-8}$ cycloalkyl, —COOH, or —COO—$C_{1-6}$ alkyl;
$X^2$ is a side chain of a natural or unnatural amino acid;
$R_{77}$ is a hydrogen or $X^2$ and NR$_{77}$ form a nitrogen containing cyclic compound;
$R_{82}$ is —NH or oxygen;
$R_{47}$ is as defined herein;
a is an integer from 1 to 6;

c is an integer from 0 to 3;
d is an integer from 1 to 3;
f is an integer from 1 to 12; and
with the proviso that when $R_{69}$ is $C(O)-X^3-R_{75}$ or $C(O)-NH-R_{19}$, one or both of $R_{71}$ and $R_{73}$ are $-NHR_{74}$, and $R_{72}$ is $OR_{43}$, $-NHR_{74}$ or $-O-C(O)-R_{47}$, at least one of $R_{19}$, $R_{43}$, $R_{74}$ and $R_{75}$ cannot be hydrogen.

In some embodiments in the compound of Formula (XXII):
$R_{57}$ is $-CH_3$;
$R_{59}$ is sec-butyl;
$R_{60}$ is hydrogen, methyl, ethyl, propyl, iso-propyl or iso-butyl;
$R_{61}$ is iso-propyl,
$R_{62}$ is hydrogen;
$R_{63}$ is hydrogen, OH, $-O-C_3H_7$, $O-C(O)-CH_3$;
$R_{68}$ is hydrogen or $-CH_3$;
$R_{69}$ is $CO_2H$, $CO_2R_{70}$ or $C(O)-R_{78}$;
$R_{70}$ is $C_{1-6}$ alkyl amine;
each of $R_{71}$ and $R_{73}$ independently is hydrogen;
$R_{72}$ is hydrogen, $-OR_{43}$, OH, F, $-CH_3$ or $-OCH_3$;
$R_{78}$ is OH, $-OR_{75}$ or $-NHR_{40}$;
e is the integer 2;
$R_{40}$ is hydrogen, $-OH$, $-NH_2$, or any of the following structures:

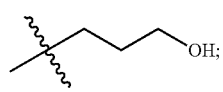 (1)

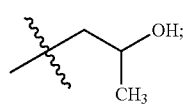 (2)

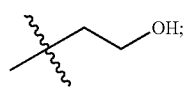 (3)

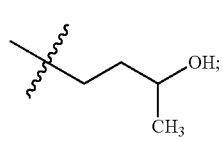 (4)

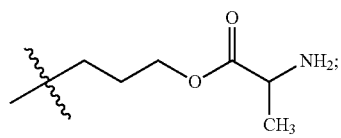 (5)

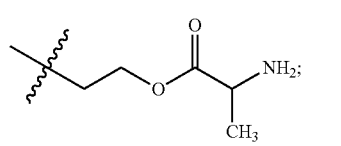 (6)

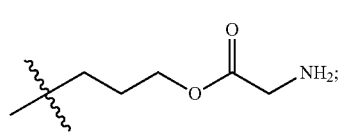 (7)

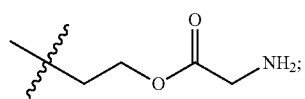 (8)

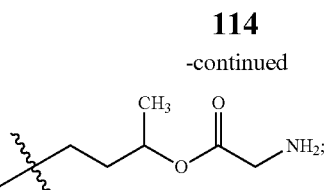 (9)

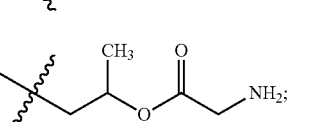 (10)

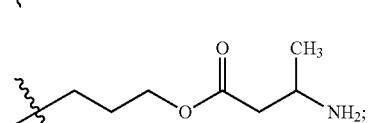 (11)

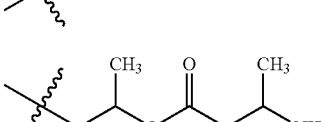 (12)

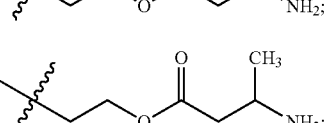 (13)

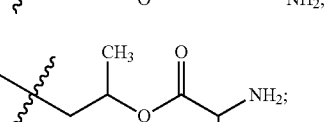 (14)

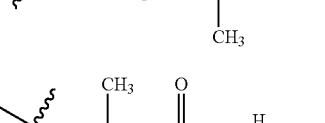 (15)

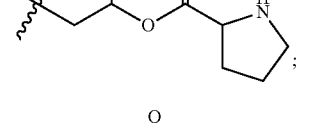 (16)

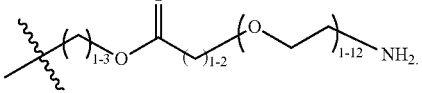 (17)

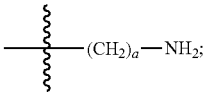 (18)

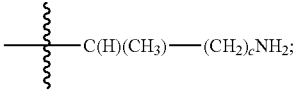 (19)

and

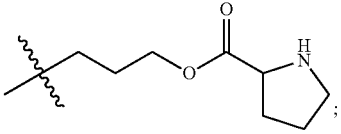 (20)

wherein:
a is an integer from 1 to 6;
c is an integer from 0 to 3;

$R_{75}$ is any one of the following structures:
(1) 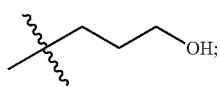
(2) 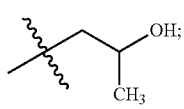
(3) 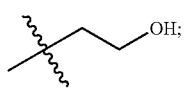
(4) 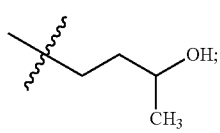
(5) 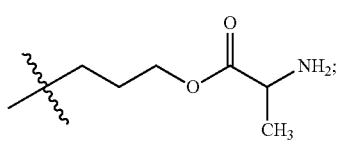
(6) 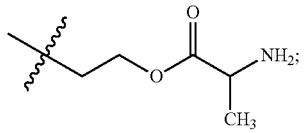
(7) 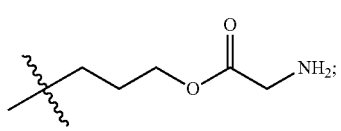
(8) 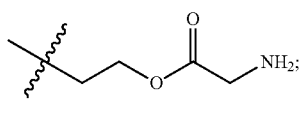
(9) 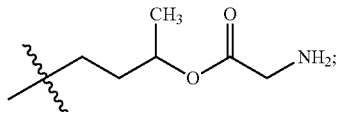
(10) 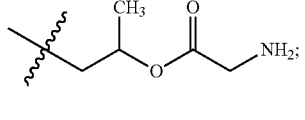
-continued
(11) 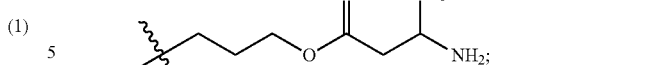
(12) 
(13) 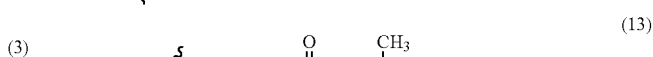
(14) 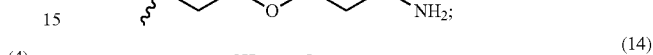
(15) 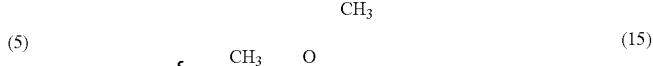
(16) 
(17) 
(18) 
wherein:
 a is an integer from 1 to 6; and
 c is an integer from 0 to 3;
 $R_{43}$ is hydrogen, —C(O)—$(CH_2)_a$—$NH_2$, or —C(O)—C(H)($CH_3$)—$(CH_2)_c$—$NH_2$;
wherein:
 a is an integer from 1 to 6;
 c is an integer from 0 to 3; and
 $R_{47}$ is any one of the following structures:
(1) 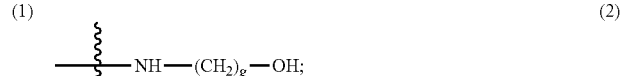
(2) 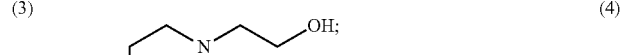
(3) 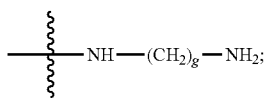
(4) 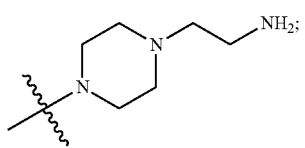

-continued
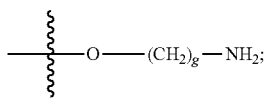 (5)
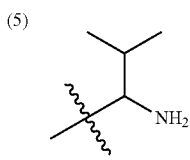 (6)
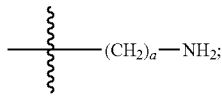 (7)
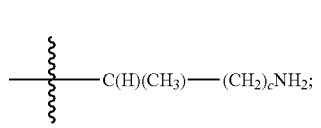 (8)
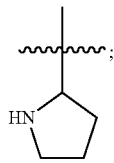 (10)
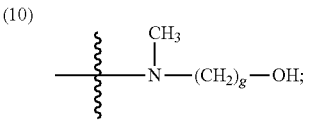 (9)
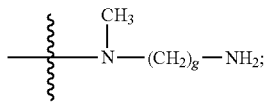 (11)
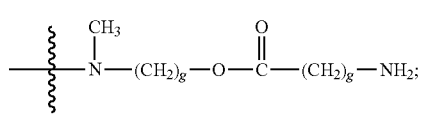 (12)
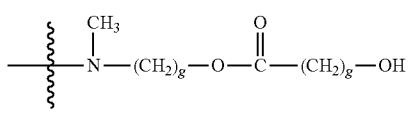 (13)
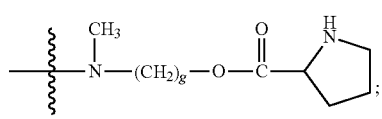 (14)
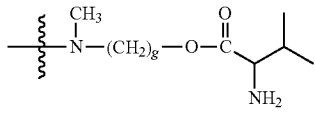 (15)
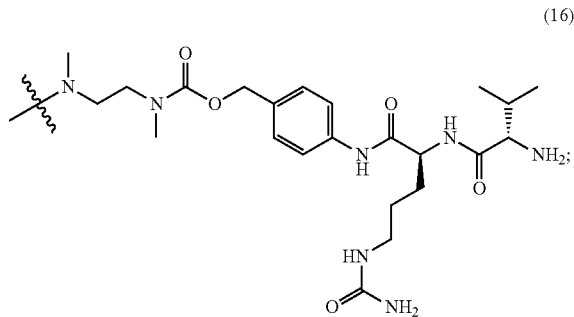 (16)
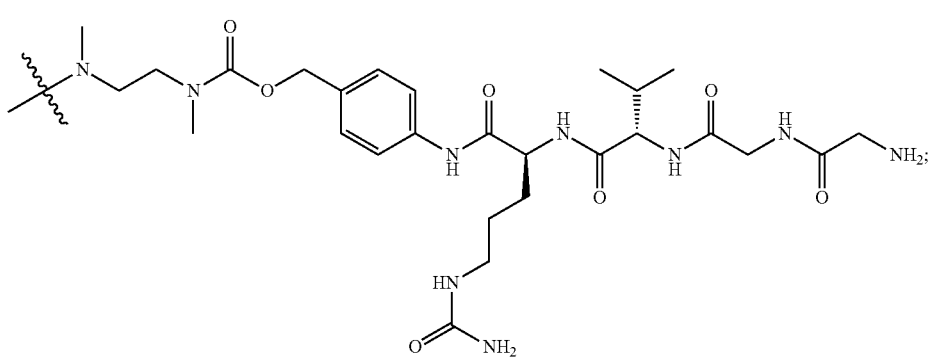 (17)

-continued
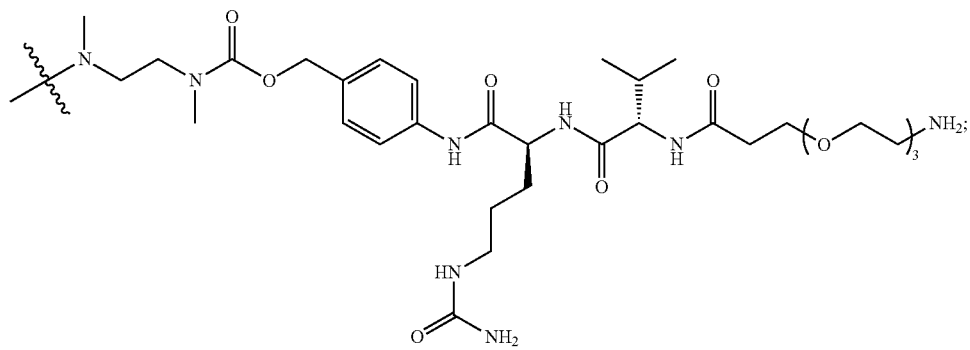
(18)
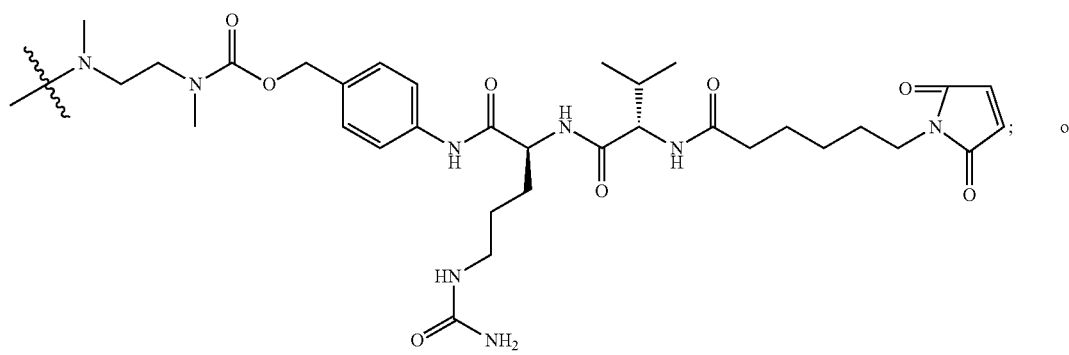
(19)
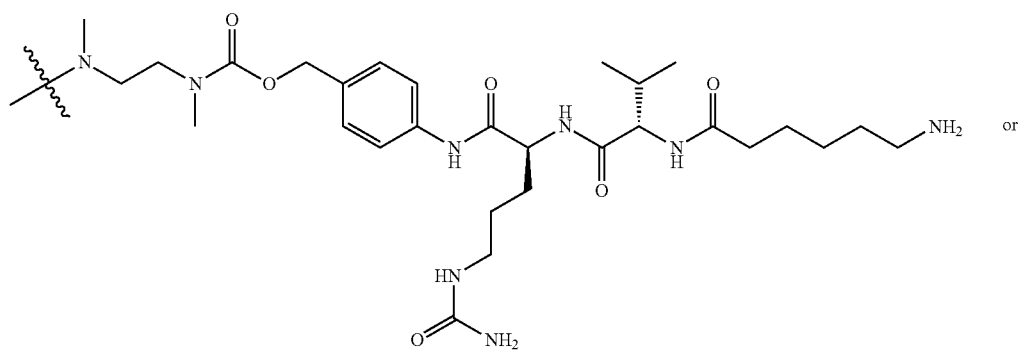
(20)
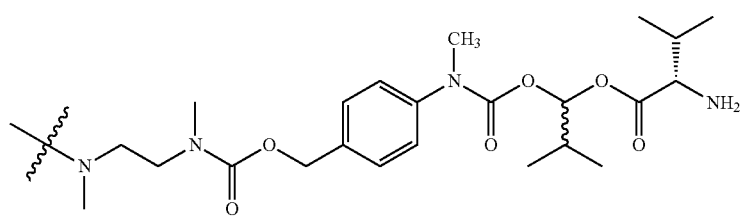
(21)

wherein:
 a is an integer from 1 to 6;
 c is an integer from 0 to 3; and
 g is an integer from 2 to 6;
with the proviso that if $R_{72}$ is —OH, then $R_{75}$ cannot be hydrogen; if $R_{69}$ is COOH then $R_{72}$ must be —$OR_{43}$ or —O—C(O)—$R_{47}$.
In some embodiments, the tubulysin of Formula (XXII) is a compound of Formula (XXIII) or (XXIV):
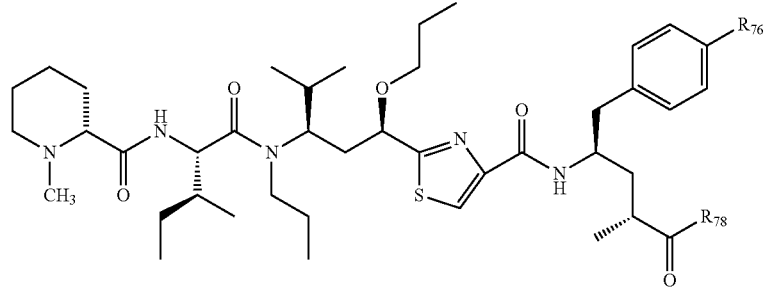
(XXIII)
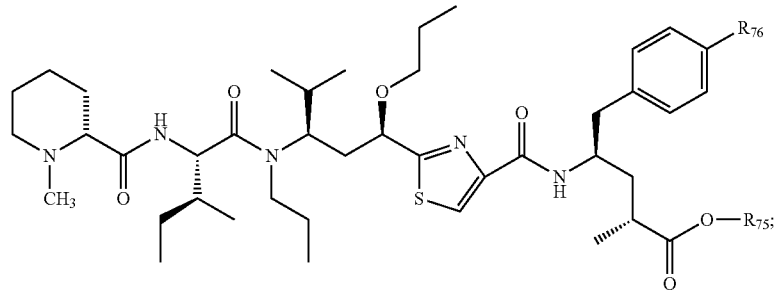
(XXIIIa)
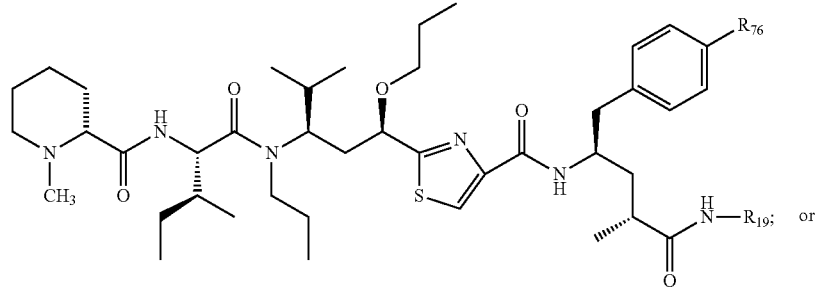
(XXIIIb)
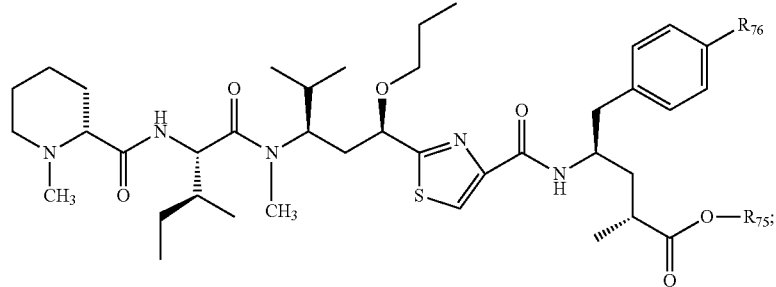
(XXIV)

wherein:

$R_{76}$ is hydrogen, OH, OCH$_3$, F, —OR$_{43}$ or —O—C(O)—R$_{47}$;

wherein $R_{78}$, $R_{75}$, $R_{19}$, $R_{47}$ and $R_{43}$ are as defined herein; and with the proviso that if $R_{76}$ is —OH, OCH$_3$ or F, then $R_{75}$ and $R_{19}$ cannot be hydrogen.

In one embodiment, $R_{47}$ is

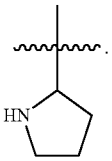

In another embodiment, $R_{47}$ is

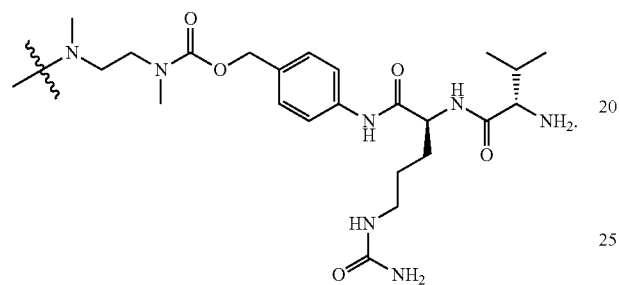

In yet another embodiment, $R_{47}$ is

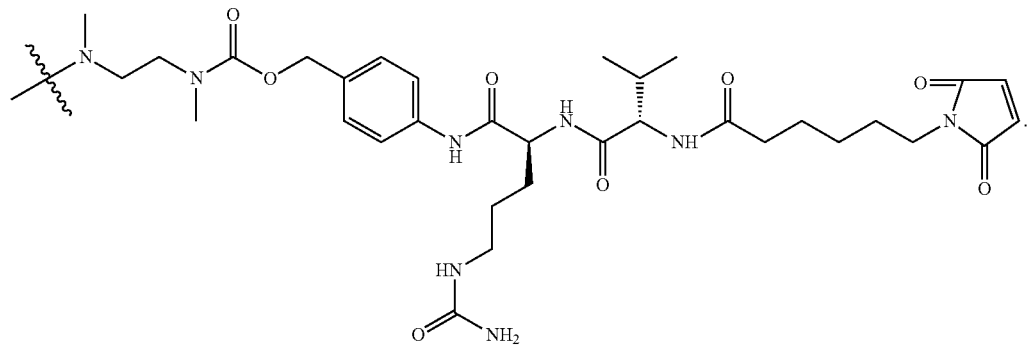 [SMILES: *N(C)CCN(C)C(=O)OCc1ccc(NC(=O)[C@H](CCCNC(N)=O)NC(=O)[C@@H](NC(=O)CCCCCN2C(=O)C=CC2=O)C(C)C)cc1]

In another embodiment, the KSP inhibitor compound is a compound of Formula (XXVI):

(XXVI)

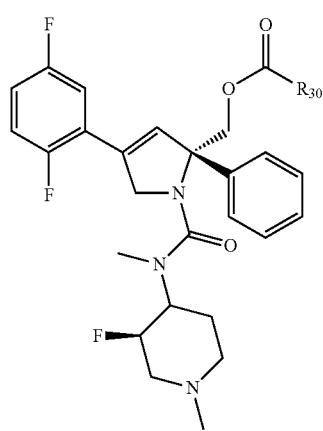

wherein $R_{30}$ is as defined herein.

In some embodiments $R_{30}$ is:

(1)

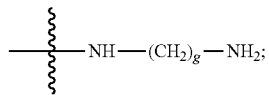
—NH—(CH$_2$)$_g$—NH$_2$;

(2)

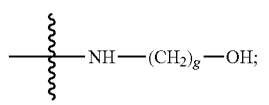
—NH—(CH$_2$)$_g$—OH;

(3)

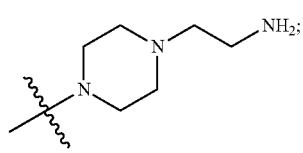

-continued (4)

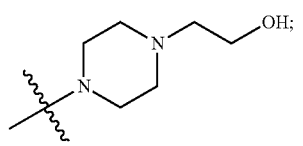

(5)

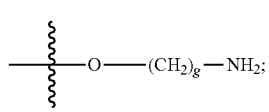
—O—(CH$_2$)$_g$—NH$_2$;

(6)

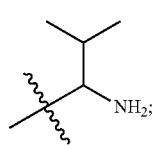

-continued

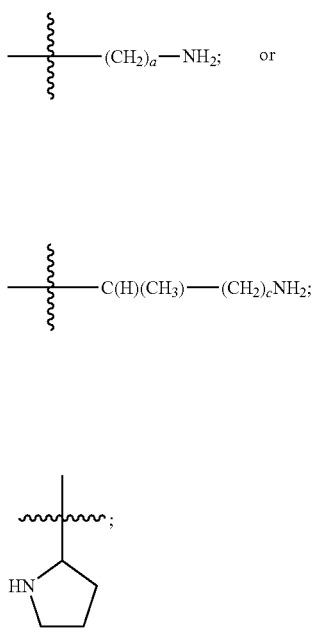

wherein:
a is an integer from 1 to 6;
c is an integer from 0 to 3; and
g is an integer from 2 to 6.

In another embodiment the KSP inhibitor compound is a compound of Formula (XXVII), (XXVIII) or (XXIX):

(XXVII)

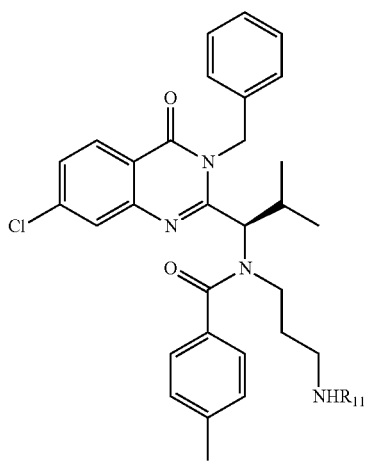

-continued (XXVIII)

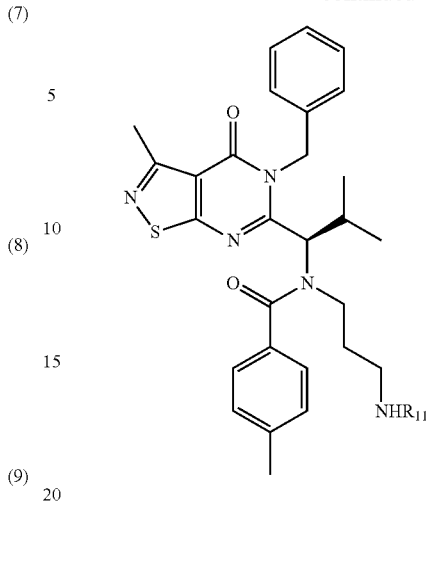

(XXIX)

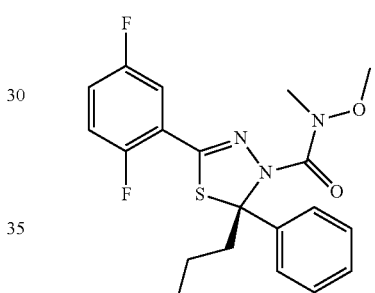

wherein:
$R_{11}$ is as defined herein.

One skilled in the art of therapeutic agents will readily understand that each of the therapeutic agents described herein can be modified in such a manner that the resulting compound still retains the specificity and/or activity of the original compound. The skilled artisan will also understand that many of these compounds can be used in place of the therapeutic agents described herein. Thus, the therapeutic agents of the present invention include analogues and derivatives of the compounds described herein.

Table B below provides more examples of the therapeutic agents and derivatives thereof suitable for conjugation to form the polymer-drug-protein conjugates or polymer-drug scaffolds of the invention. Spectral data of certain compounds are also provided (ND in the table means "not determined"). These examples may also be the active form of the drug when it is released from the conjugates in vitro or in vivo.

TABLE B
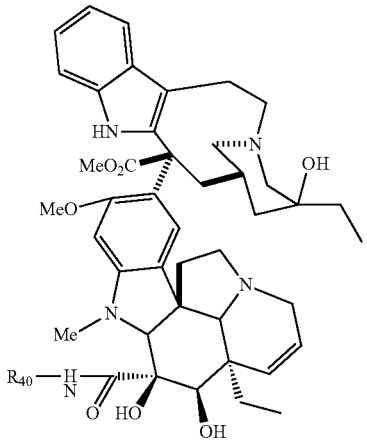
(VI)
| Ref # | R$_{40}$ |
|---|---|
| Ex 6 | 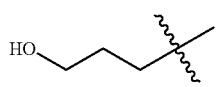 |
| Ex 22 | 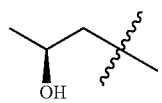 [SMILES: *C[C@H](C)O] |
| Ex 23 | 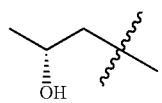 [SMILES: *C[C@@H](C)O] |
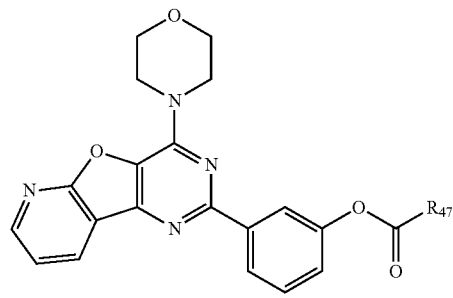
(IX)
| Ref # | R$_{47}$ | m/z |
|---|---|---|
| Ex 24 | 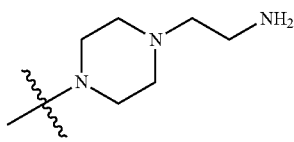 [SMILES: *N1CCN(CCN)CC1] | ND |
| Ex 25 | 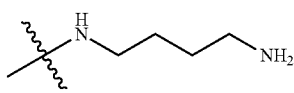 [SMILES: *NCCCCN] | ND |
Note: Ex 6 structure shown as 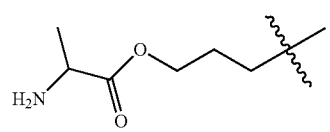

TABLE B-continued
| | | |
|---|---|---|
| Ex 30 | 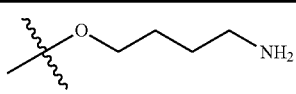 | ND |
| Ex 33 | 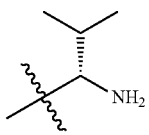 [SMILES: *[C@@H](N)C(C)C] | ND |
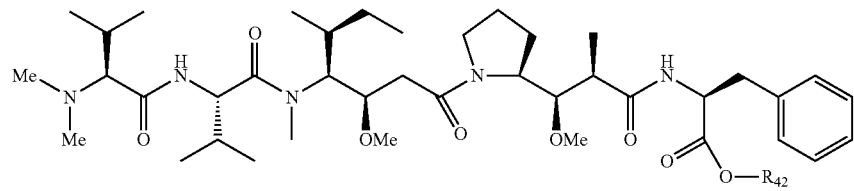
(XI)
| Ref # | R$_{42}$ | m/z |
|---|---|---|
| |  H —CH$_3$ | 760 |
| Ex 39 | 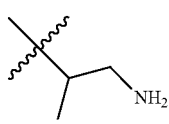 [SMILES: *C(C)CN] | 802.6 |
| | 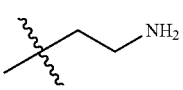 | 790 |
| Ex 64 | 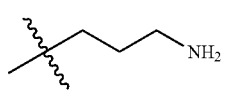 [SMILES: *CCCN] | 804 |
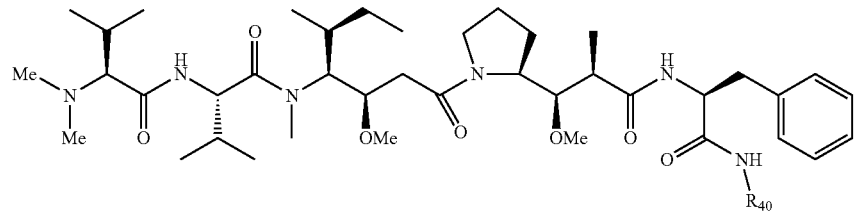
(XII)
| Ref # | R$_{40}$ | m/z |
|---|---|---|
| |  —H | |
| Ex 48 | 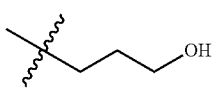 [SMILES: *CCCO] | 803.5 |
| | 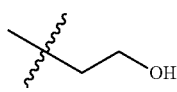 [SMILES: *CCO] | 789.1 |
| Ex 49 | 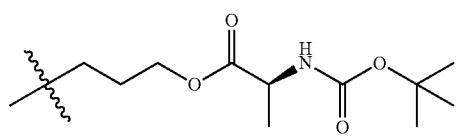 [SMILES: *CCCOC(=O)[C@H](C)NC(=O)OC(C)(C)C] | 974.2 |

TABLE B-continued
| | | |
|---|---|---|
| Ex 50 | 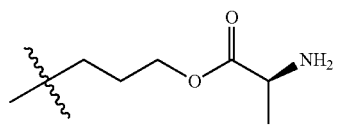 [SMILES: *CCCOC(=O)[C@H](C)N] | 874.5 |
| | 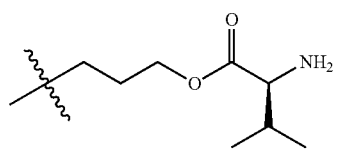 [SMILES: *CCCOC(=O)[C@@H](N)C(C)C] | 902.2 |
| | 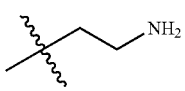 | ND |
| | 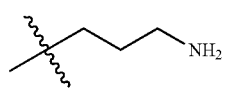 [SMILES: *CCCN] | ND |
| | —OH | 788 |
| Ex 61 | 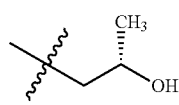 | 803.4 |
| Ex 62 | 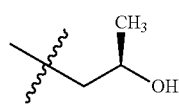 [SMILES: *C[C@@H](C)O] | 803.4 |
| | 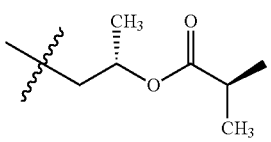 | 874.4 |
| | 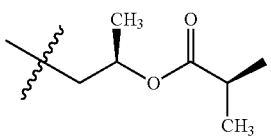 | 874.4 |
| | 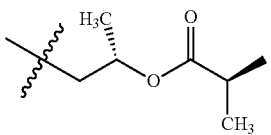 | 874.4 |
| | 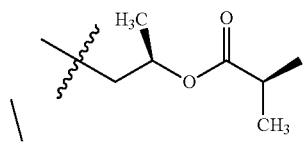 | 874.4 |
| | 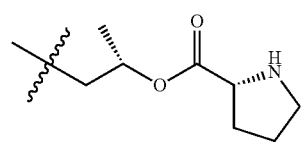 [SMILES: *C[C@H](C)OC(=O)[C@H]1CCCN1] | 900.2 |

TABLE B-continued
| Structure | m/z |
|---|---|
| 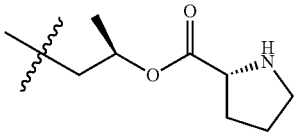 [SMILES: *C[C@@H](C)OC(=O)[C@H]1CCCN1] | 900.2 |
| 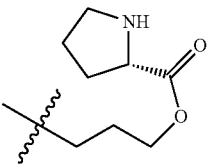 [SMILES: *CCCOC(=O)[C@@H]1CCCN1] | 900.5 |
| 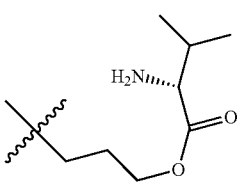 [SMILES: *CCCOC(=O)[C@H](N)C(C)C] | 900.5 |
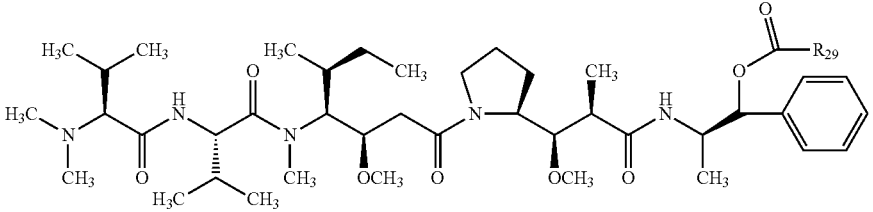
(XIII)
| —C(O)—R$_{29}$ | m/z |
|---|---|
| 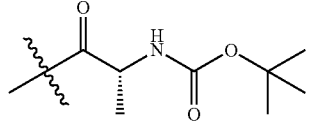 [SMILES: *C(=O)[C@@H](C)NC(=O)OC(C)(C)C] | 903.2 |
| 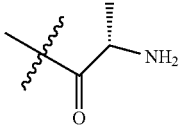 [SMILES: *C(=O)[C@H](C)N] | 803.1 |
| 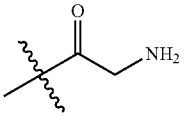 | 790 |
| 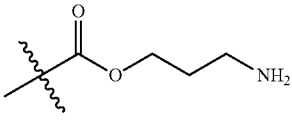 [SMILES: *C(=O)OCCCN] | 832.6 |
| 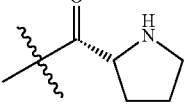 | 829.1 |
| 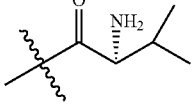 | 802 |

TABLE B-continued
(XIV)
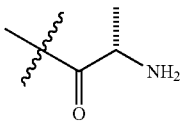
| Ref # | R43 | m/z |
|---|---|---|
| Ex 36 | 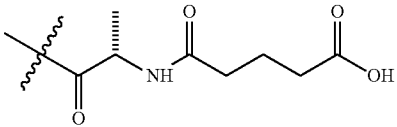 [SMILES: *C(=O)[C@H](C)NC(=O)CCCC(=O)O] | ND |
|  | 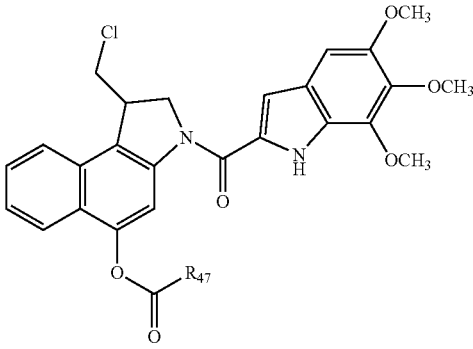 | 644.9 |
(XVII)
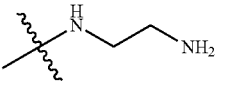
| R47 | m/z |
|---|---|
| 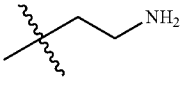 | 553.1 |
| 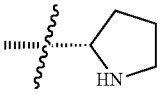 | 538.1 |
| 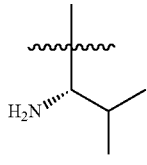 | 564.1 |
|  | 566.1 |

TABLE B-continued
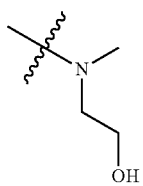 [SMILES: *N(C)CCO] 568.1
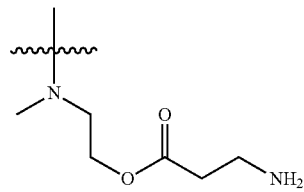 [SMILES: *N(C)CCOC(=O)CCN] ND
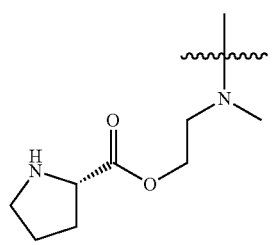 [SMILES: *N(C)CCOC(=O)[C@@H]1CCCN1] ND
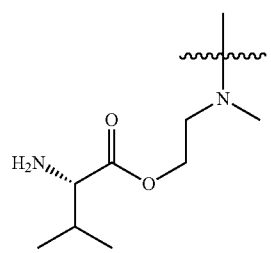 [SMILES: *N(C)CCOC(=O)[C@@H](N)C(C)C] 667.2
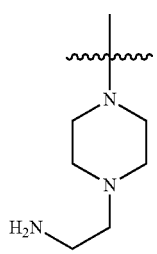 [SMILES: *N1CCN(CCN)CC1] 622.2
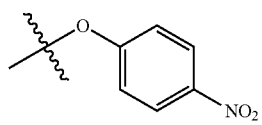 [SMILES: *Oc1ccc([N+](=O)[O-])cc1] 632.02

TABLE B-continued
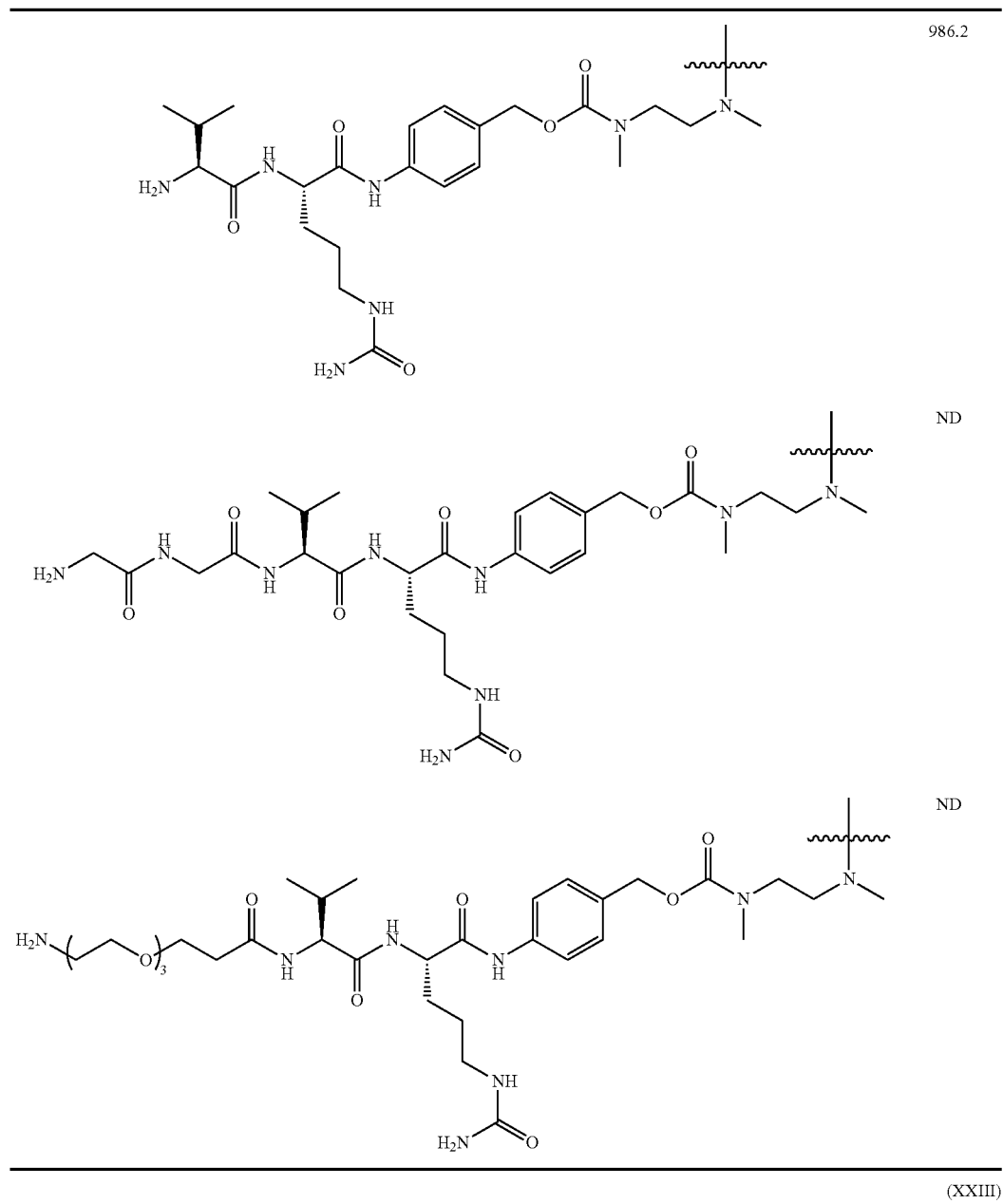
| Ref # | R$_{76}$ | —R$_{78}$ | m/z |
|---|---|---|---|
| | OH | —OH | 772.1 |
| | OH | —OCH$_3$ | 786.4 |
| | OH | —NH$_2$ | 771.4 |

US 8,821,850 B2
TABLE B-continued
| | | | |
|---|---|---|---|
| | OH | 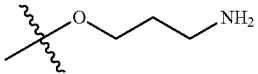 | 829.4 |
| | OH | 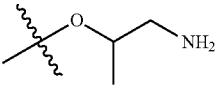 [SMILES: *OC(C)CN] | ND |
| | 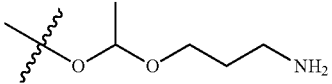 [SMILES: *OC(C)OCCCN] | OH | ND |
| | 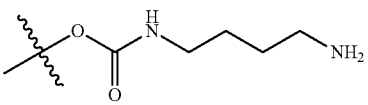 [SMILES: *OC(=O)NCCCCN] | —OCH₃ | 900.4 |
| | 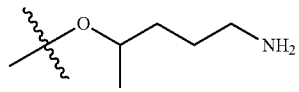 [SMILES: *OC(C)CCCN] | —OH | ND |
| | 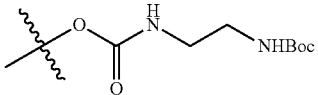 [SMILES: *OC(=O)NCCNC(=O)OC(C)(C)C] | —OCH₃ | ND |
| | 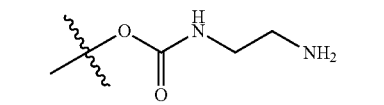 [SMILES: *OC(=O)NCCN] | —OCH₃ | ND |
| | 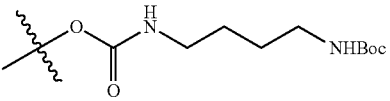 [SMILES: *OC(=O)NCCCCNC(=O)OC(C)(C)C] | —OCH₃ | 1000.5 |
| Ex 73 | 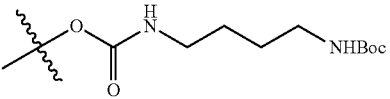 [SMILES: *OC(=O)NCCCCNC(=O)OC(C)(C)C] | —OH | 986.5 |
| Ex 63 | 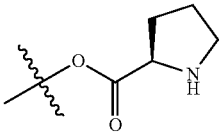 [SMILES: *OC(=O)[C@H]1CCCN1] | —OH | 869.4 |
| | 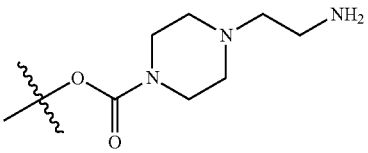 [SMILES: *OC(=O)N1CCN(CCN)CC1] | —OH | 927.3 |
| Ex 76 | 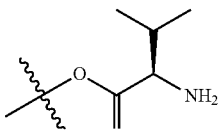 | —OH | 871.4 |
| Ex 42 | F | 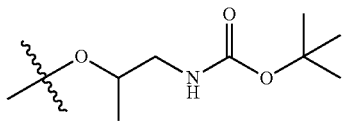 [SMILES: *OC(C)CNC(=O)OC(C)(C)C] | ND |

TABLE B-continued
| Ex 43 | F | 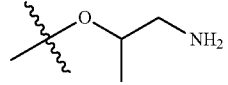 | ND |
| --- | --- | --- | --- |
| | 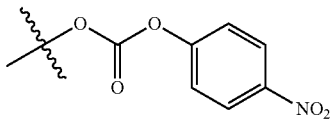 [SMILES: *OC(=O)Oc1ccc([N+](=O)[O-])cc1] | 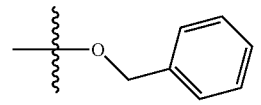 [SMILES: *OCc1ccccc1] | 1027.2 |
| | —OH | 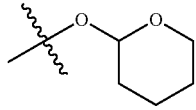 [SMILES: *OC1CCCCO1] | |
| Ex 73 | —OH | 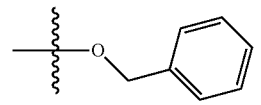 [SMILES: *OCc1ccccc1] | 862.5 |
| Ex 73 | 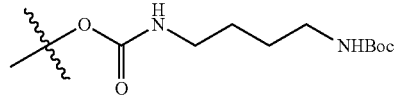 [SMILES: *OC(=O)NCCCCNC(=O)OC(C)(C)C] | 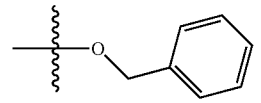 [SMILES: *OCc1ccccc1] | 1076.4 |
| Ex 73 | 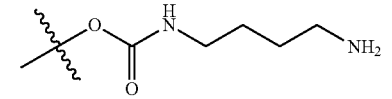 [SMILES: *OC(=O)NCCCCN] | —OH | 886.3 |
| Ex 79 | 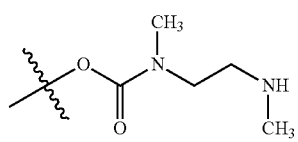 | —OH | 886.4 |
| Ex 79 | 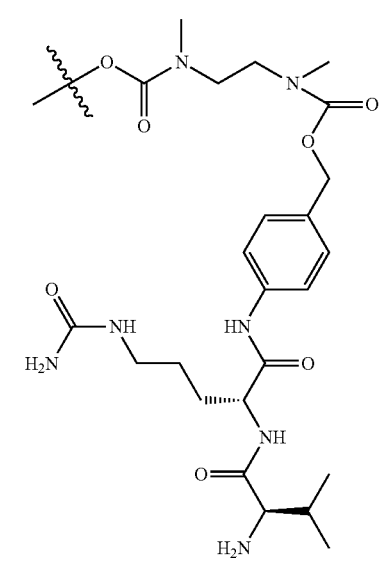 [SMILES: *OC(=O)N(C)CCN(C)C(=O)OCc1ccc(NC(=O)[C@@H](CCCNC(N)=O)NC(=O)[C@H](N)C(C)C)cc1] | —OH | 1291.7 |

TABLE B-continued
| Ex 82 | 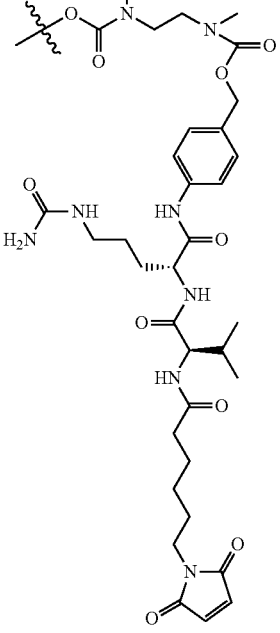 | —OH | 1316.7 |
|---|---|---|---|
| | | —OH | ND |

TABLE B-continued
(XXX)
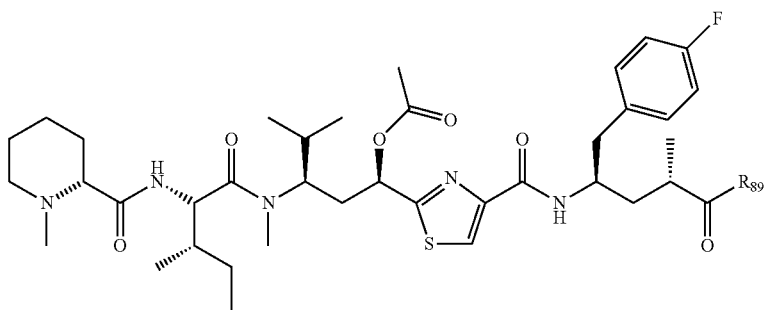
| Ref # | —R89 |
|---|---|
| Ex 45 | 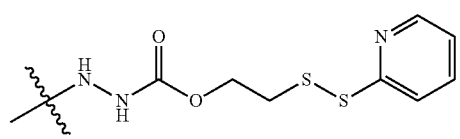 [SMILES: *NNC(=O)OCCSSc1ccccn1] |
| Ex 46 | 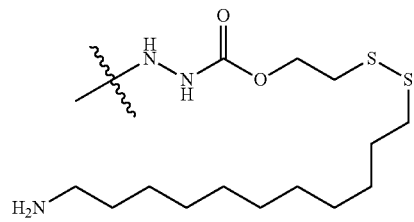 [SMILES: *NNC(=O)OCCSSCCCCCCCCCCCN] |
(XXVII)
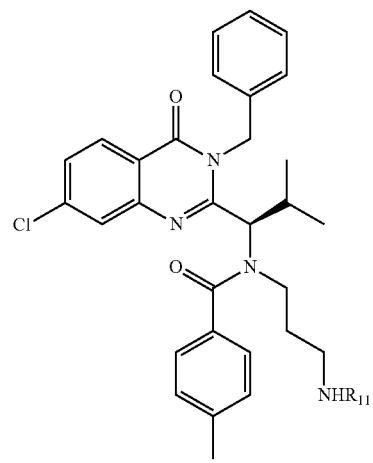

TABLE B-continued
(XXVIII)
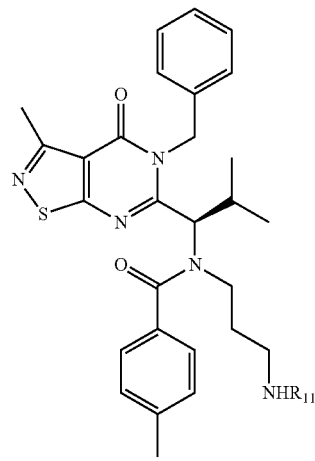
(XXIX)
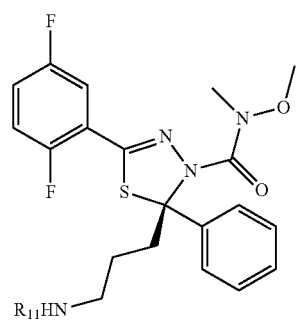
| Ref # | R₁₁ | m/z (XXVII) |
|---|---|---|
| Ex 84 | 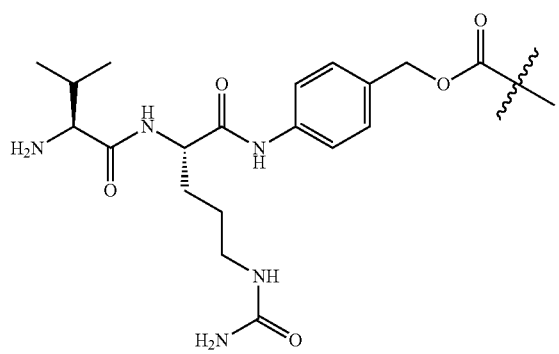 [SMILES: *C(=O)OCc1ccc(NC(=O)[C@H](CCCNC(N)=O)NC(=O)[C@@H](N)C(C)C)cc1] | 922.3 |
| Ex 87 | 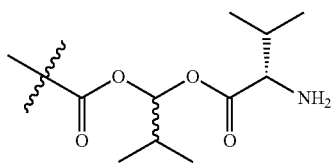 [SMILES: *C(=O)OC(OC(=O)[C@@H](N)C(C)C)C(C)C] | 732.2 |

| | |
|---|---|
| 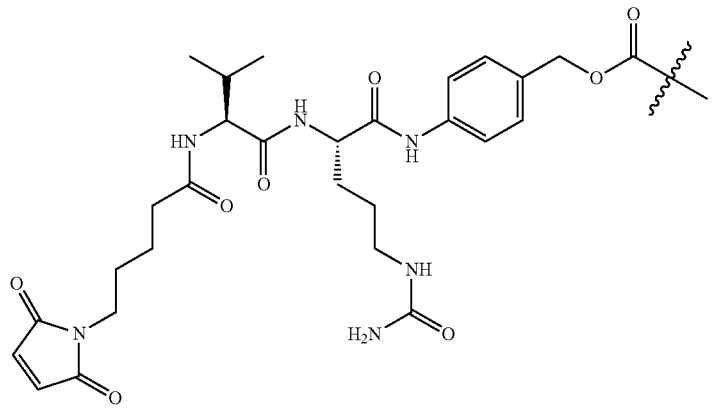 [SMILES: *C(=O)OCc1ccc(NC(=O)[C@H](CCCNC(N)=O)NC(=O)[C@@H](NC(=O)CCCCN2C(=O)C=CC2=O)C(C)C)cc1] | 1101.7 |
| 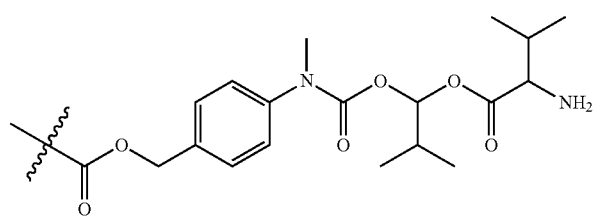 [SMILES: *C(=O)OCc1ccc(N(C)C(=O)OC(OC(=O)C(N)C(C)C)C(C)C)cc1] | ND |
| 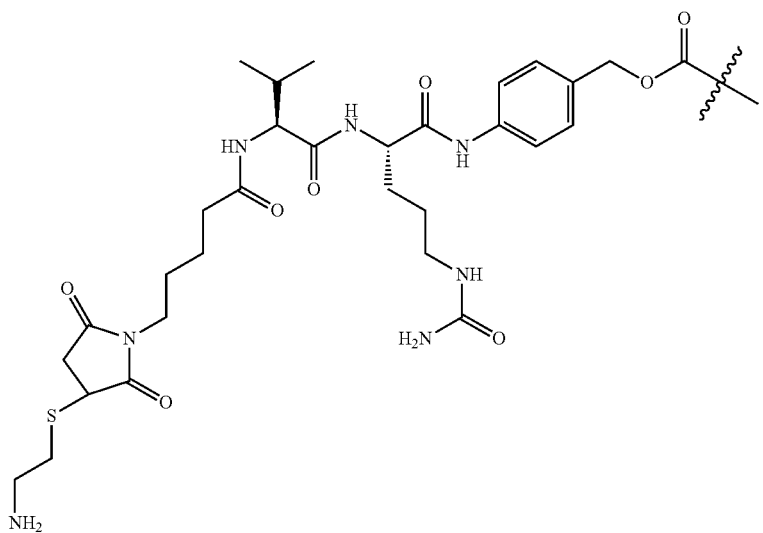 [SMILES: *C(=O)OCc1ccc(NC(=O)[C@H](CCCNC(N)=O)NC(=O)[C@@H](NC(=O)CCCCN2C(=O)CC(SCCN)C2=O)C(C)C)cc1] | ND |
| 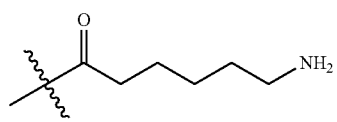 [SMILES: *C(=O)CCCCCN] | ND |
| 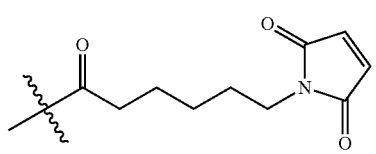 [SMILES: *C(=O)CCCCCN1C(=O)C=CC1=O] | ND |

TABLE B-continued

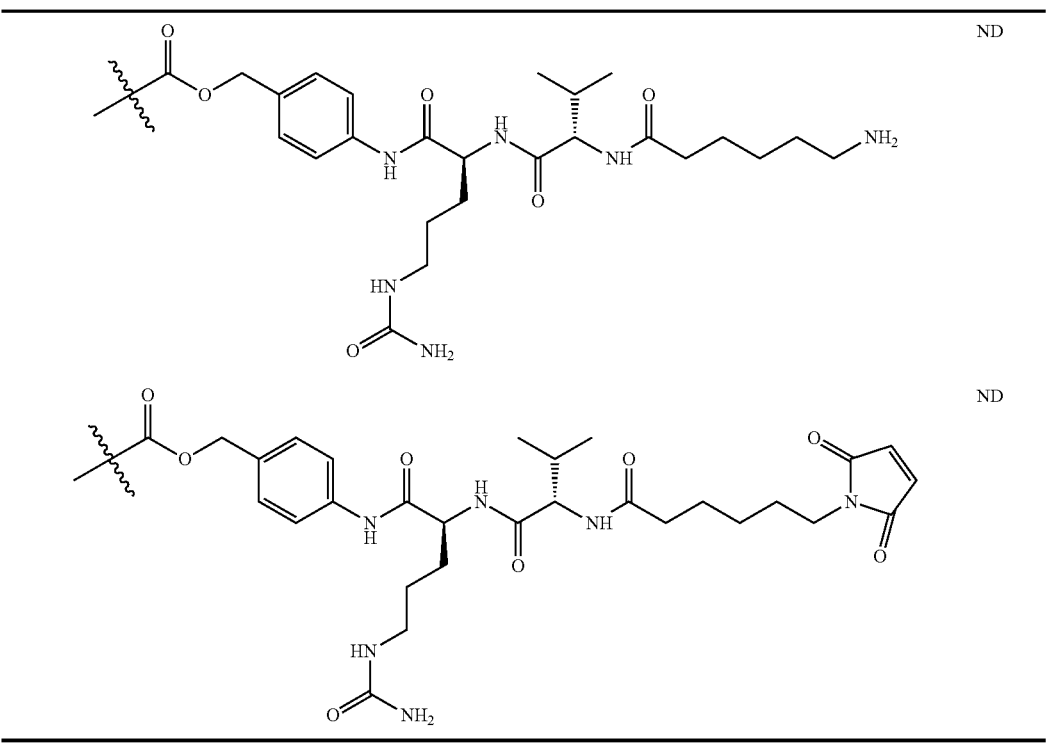

Protein-Based Recognition Molecules (PBRMs)

The protein-based recognition molecule directs the drug-polymer carrier conjugates to specific tissues, cells, or locations in a cell. The protein-based recognition molecule can direct the modified polymer in culture or in a whole organism, or both. In each case, the protein-based recognition molecule has a ligand that is present on the cell surface of the targeted cell(s) to which it binds with an effective specificity, affinity and avidity. In some embodiments, the protein-based recognition molecule targets the modified polymer to tissues other than the liver. In other embodiments the protein-based recognition molecule targets the modified polymer to a specific tissue such as the liver, kidney, lung or pancreas. The protein-based recognition molecule can target the modified polymer to a target cell such as a cancer cell, such as a receptor expressed on a cell such as a cancer cell, a matrix tissue, or a protein associated with cancer such as tumor antigen. Alternatively, cells comprising the tumor vasculature may be targeted. Protein-based recognition molecules can direct the polymer to specific types of cells such as specific targeting to hepatocytes in the liver as opposed to Kupffer cells. In other cases, protein-based recognition molecules can direct the polymer to cells of the reticular endothelial or lymphatic system, or to professional phagocytic cells such as macrophages or eosinophils. (In such cases the polymer itself might also be an effective delivery system, without the need for specific targeting).

In still other embodiments, the protein based recognition molecule can target the modified polymer to a location within the cell, such as the nucleus, the cytoplasm, or the endosome, for example. In specific embodiments, the protein based recognition molecule can enhance cellular binding to receptors, or cytoplasmic transport to the nucleus and nuclear entry or release from endosomes or other intracellular vesicles.

In specific embodiments the protein based recognition molecules include antibodies, proteins and peptides or peptide mimics.

Exemplary antibodies or antibodies derived from Fab, Fab2, scFv or camel antibody heavy-chain fragments specific to the cell surface markers, include, but are not limited to, 5T4, AOC3, C242, CA-125, CCL11, CCR 5, CD2, CD3, CD4, CD5, CD15, CD18, CD19, CD20, CD22, CD23, CD25, CD28, CD30, CD31, CD33, CD37, CD38, CD40, CD41, CD44, CD51, CD52, CD54, CD56, CD62E, CD62P, CD62L, CD70, CD74, CD80, CD125, CD138, CD141, CD147, CD152, CD 154, CD326, CEA, clumping factor, CTLA-4, EGFR, ErbB2, ErbB3, EpCAM, folate receptor, FAP, GD2, GD3, GPNMB, HGF, HER2, ICAM, IGF-1 receptor, VEGFR1, EphA2, TRPV1, CFTR, gpNMB, CA9, Cripto, ACE, APP, adrenergic receptor-beta2, Claudine 3, Mesothelin, IL-2 receptor, IL-4 receptor, IL-13 receptor, integrins (including $\alpha_4$, $\alpha_\nu\beta_3$, $\alpha_\nu\beta_5$, $\alpha_\nu\beta_6$, $\alpha_1\beta_4$, $\alpha_4\beta_1$, $\alpha_4\beta_7$, $\alpha_5\beta_1$, $\alpha_6\beta_4$, $\alpha_{IIb}\beta_3$ intergins), IFN-$\alpha$, IFN-$\gamma$, IgE, IgE, IGF-1 receptor, IL-1, IL-12, IL-23, IL-13, IL-22, IL-4, IL-5, IL-6, interferon receptor, ITGB2 (CD18), LFA-1 (CD11a), L-selectin (CD62L), mucin, MUC1, myostatin, NCA-90, NGF, PDGFR$\alpha$, phosphatidylserine, prostatic carcinoma cell, *Pseudomonas aeruginosa*, rabies, RANKL, respiratory syncytial virus, Rhesus factor, SLAMF7, sphingosine-1-phosphate, TAG-72, T-cell receptor, tenascin C, TGF-1, TGF-$\beta$2, TGF-$\beta$, TNF-$\alpha$, TRAIL-R1, TRAIL-R2, tumor antigen CTAA16.88, VEGF-A, VEGFR2, vimentin, and the like.

In one embodiment the antibodies or antibody derived from Fab, Fab2, scFv or camel antibody heavy-chain fragments specific to the cell surface markers include CA-125, C242, CD3, CD19, CD22, CD25, CD30, CD31, CD33, CD37, CD40, CD44, CD51, CD54, CD56, CD62E, CD62P, CD62L, CD70, CD138, CD141, CD326, CEA, CTLA-4, EGFR, ErbB2, ErbB3, FAP, folate receptor, IGF-1 receptor, GD3, GPNMB, HGF, HER2, VEGF-A, VEGFR2, VEGFR1, EphA2, EpCAM, 5T4, TAG-72, tenascin C, TRPV1, CFTR, gpNMB, CA9, Cripto, ACE, APP, PDGFR $\alpha$, phosphatidylserine, prostatic carcinoma cells, adrenergic receptor-beta2, Claudine 3, mucin, MUC1, Mesothelin, IL-2 receptor, IL-4 receptor, IL-13 receptor and integrins (including $\alpha_v\beta_3$, $\alpha_v\beta_5$, $\alpha_v\beta_6$, $\alpha_1\beta_4$, $\alpha_4\beta_1$, $\alpha_5\beta_1$, $\alpha_6\beta_4$ intergins), tenascin C, TRAIL-R2 and vimentin.

Exemplary antibodies include 3F8, abagovomab, abciximab (REOPRO), adalimumab (HUMIRA), adecatumumab, afelimomab, afutuzumab, alacizumab, ALD518, alemtuzumab (CAMPATH), altumomab, amatuximab, anatumomab, anrukinzumab, apolizumab, arcitumomab (CEA-SCAN), aselizumab, atlizumab (tocilizumab, Actemra, RoActemra), atorolimumab, bapineuzumab, basiliximab (Simulect), bavituximab, bectumomab (LYMPHOSCAN), belimumab (BENLYSTA), benralizumab, bertilimumab, besilesomab (SCINITIMUN), bevacizumab (AVASTIN), biciromab (FIBRISCINT), bivatuzumab, blinatumomab, brentuximab, briakinumab, canakinumab (ILARIS), cantuzumab, capromab, catumaxomab (REMOVAB), CC49, cedelizumab, certolizumab, cetuximab (ERBITUX), citatuzumab, cixutumumab, clenoliximab, clivatuzumab, conatumumab, CR6261, dacetuzumab, daclizumab (ZENAPAX), daratumumab, denosumab (PROLIA), detumomab, dorlimomab, dorlixizumab, ecromeximab, eculizumab (SOLIRIS), edobacomab, edrecolomab (PANOREX), efalizumab (RAPTIVA), efungumab (MYCOGRAB), elotuzumab, elsilimomab, enlimomab, epitumomab, epratuzumab, erlizumab, ertumaxomab (REXOMUN), etaracizumab (ABEGRIN), exbivirumab, fanolesomab (NEUTROSPEC), faralimomab, farletuzumab, felvizumab, fezakinumab, figitumumab, fontolizumab (HuZAF), foravirumab, fresolimumab, galiximab, gantenerumab, gavilimomab, gemtuzumab girentuximab, glembatumumab, golimumab (SIMPONI), gomiliximab, ibalizumab, ibritumomab, igovomab (INDIMACIS-125), imciromab (MYOSCINT), infliximab (REMICADE), intetumumab, inolimomab, inotuzumab, ipilimumab, iratumumab, keliximab, labetuzumab (CEA-CIDE), lebrikizumab, lemalesomab, lerdelimumab, lexatumumab, libivirumab, lintuzumab, lucatumumab, lumiliximab, mapatumumab, maslimomab, matuzumab, mepolizumab (BOSATRIA), metelimumab, milatuzumab, minretumomab, mitumomab, morolimumab, motavizumab (NUMAX), muromonab-CD3 (ORTHOCLONE OKT3), nacolomab, naptumomab, natalizumab (TYSABRI), nebacumab, necitumumab, nerelimomab, nimotuzumab (THERACIM), nofetumomab, ocrelizumab, odulimomab, ofatumumab (ARZERRA), olaratumab, omalizumab (XOLAIR), ontecizumab, oportuzumab, oregovomab (OVAREX), otelixizumab, pagibaximab, palivizumab (SYNAGIS), panitumumab (VECTIBIX), panobacumab, pascolizumab, pemtumomab (THERAGYN), pertuzumab (OMNITARG), pexelizumab, pintumomab, priliximab, pritumumab, PRO 140, rafivirumab, ramucirumab, ranibizumab (LUCENTIS), raxibacumab, regavirumab, reslizumab, rilotumumab, rituximab (RITUXAN), robatumumab, rontalizumab, rovelizumab (LEUKARREST), ruplizumab (ANTOVA), satumomab pendetide, sevirumab, sibrotuzumab, sifalimumab, siltuximab, siplizumab, solanezumab, sonepcizumab, sontuzumab, stamulumab, sulesomab (LEUKOSCAN), tacatuzumab (AFP-CIDE), tetraxetan, tadocizumab, talizumab, tanezumab, taplitumomab paptox, tefibazumab (AUREXIS), telimomab, tenatumomab, teneliximab, teplizumab, TGN1412, ticilimumab (tremelimumab), tigatuzumab, TNX-650, tocilizumab (atlizumab, ACTEMRA), toralizumab, tositumomab (BEXXAR), trastuzumab (HERCEPTIN), tremelimumab, tucotuzumab, tuvirumab, urtoxazumab, ustekinumab (STELERA), vapaliximab, vedolizumab, veltuzumab, vepalimomab, visilizumab (NUVION), voloximab (HUMASPECT), votumumab, zalutumumab (HuMEX-EGFr), zanolimumab (HuMAX-CD4), ziralimumab and zolimomab.

In some embodiments the antibodies are directed to cell surface markers for 5T4, CA-125, CEA, CD3, CD19, CD20, CD22, CD30, CD33, CD40, CD44, CD51, CTLA-4, EpCAM, HER2, EGFR, FAP, folate receptor, HGF, integrin $\alpha_v\beta_3$, integrin $\alpha_5\beta_1$, IGF-1 receptor, GD3, GPNMB, mucin, MUC1, phosphatidylserine, prostatic carcinoma cells, PDGFR $\alpha$, TAG-72, tenascin C, TRAIL-R2, VEGF-A and VEGFR2. In this embodiment the antibodies are abagovomab, adecatumumab, alacizumab, altumomab, anatumomab, arcitumomab, bavituximab, bevacizumab (AVASTIN), bivatuzumab, blinatumomab, brentuximab, cantuzumab, catumaxomab, capromab, cetuximab, citatuzumab, clivatuzumab, conatumumab, dacetuzumab, edrecolomab, epratuzumab, ertumaxomab, etaracizumab, farletuzumab, figitumumab, gemtuzumab, glembatumumab, ibritumomab, igovomab, intetumumab, inotuzumab, labetuzumab, lexatumumab, lintuzumab, lucatumumab, matuzumab, mitumomab, naptumomab estafenatox, necitumumab, oportuzumab, oregovomab, panitumumab, pemtumomab, pertuzumab, pritumumab, rituximab (RITUXAN), rilotumumab, robatumumab, satumomab, sibrotuzumab, taplitumomab, tenatumomab, tenatumomab, ticilimumab (tremelimumab), tigatuzumab, trastuzumab (HERCEPTIN), tositumomab, tremelimumab, tucotuzumab celmoleukin, voloximab and zalutumumab.

In specific embodiments the antibodies directed to cell surface markers for HER2 are pertuzumab or trastuzumab and for EGFR the antibody is cetuximab and for CD20 the antibody is rituximab and for VEGF-A is bevacizumab and for CD-22 the antibody is epratuzumab or veltuzumab and for CEA the antibody is labetuzumab.

Exemplary peptides or peptide mimics include integrin targeting peptides (RGD peptides), LHRH receptor targeting peptides, ErbB2 (HER2) receptor targeting peptides, prostate specific membrane bound antigen (PSMA) targeting peptides, lipoprotein receptor LRP1 targeting, ApoE protein derived peptides, ApoA protein peptides, somatostatin receptor targeting peptides, chlorotoxin derived peptides, and bombesin.

In specific embodiments the peptides or peptide mimics are LHRH receptor targeting peptides and ErbB2 (HER2) receptor targeting peptides Exemplary proteins comprise insulin, transferrin, fibrinogen-gamma fragment, thrombospondin, claudin, apolipoprotein E, Affibody molecules such as, for example, ABY-025, Ankyrin repeat proteins, ankyrin-like repeats proteins and synthetic peptides.

In some embodiments of the invention the protein drug polymer conjugates comprise broad spectrum cytotoxins in combination with cell surface markers for HER2 such as pertuzumab or trastuzumab; for EGFR such as cetuximab; for CEA such as labetuzumab; for CD20 such as rituximab; for VEGF-A such as bevacizumab; or for CD-22 such as epratuzumab or veltuzumab.

In other embodiments of the invention the protein-drug-polymer conjugates or protein-polymer conjugates used in the invention comprise combinations of two or more protein based recognition molecules, such as, for example, combination of bispecific antibodies directed to the EGF receptor (EGFR) on tumor cells and to CD3 and CD28 on T cells; combination of antibodies or antibody derived from Fab, Fab2, scFv or camel antibody heavy-chain fragments and peptides or peptide mimetics; combination of antibodies or antibody derived from Fab, Fab2, scFv or camel antibody heavy-chain fragments and proteins; combination of two bispecific antibodies such as CD3×CD19 plus CD28×CD22 bispecific antibodies.

Table C below provides more examples of the PBRM described hereof, which are suitable for conjugation to form the polymer-drug-protein conjugates or polymer-PBRM scaffolds of the invention.

TABLE C

| Ref # | PBRM |
|---|---|
| Ex 3 | 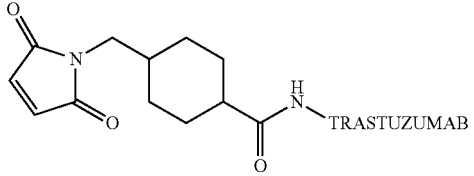 |
| Ex 4 | 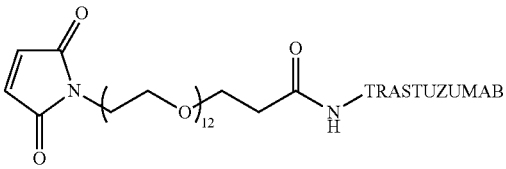 |
| Ex 53 | 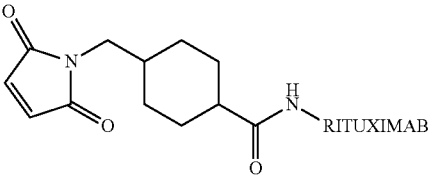 |
| Ex 60 | TRASTUZUMAB-Fab'-SH |
| | 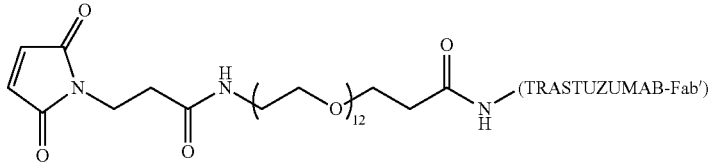 |
| Ex 10 | 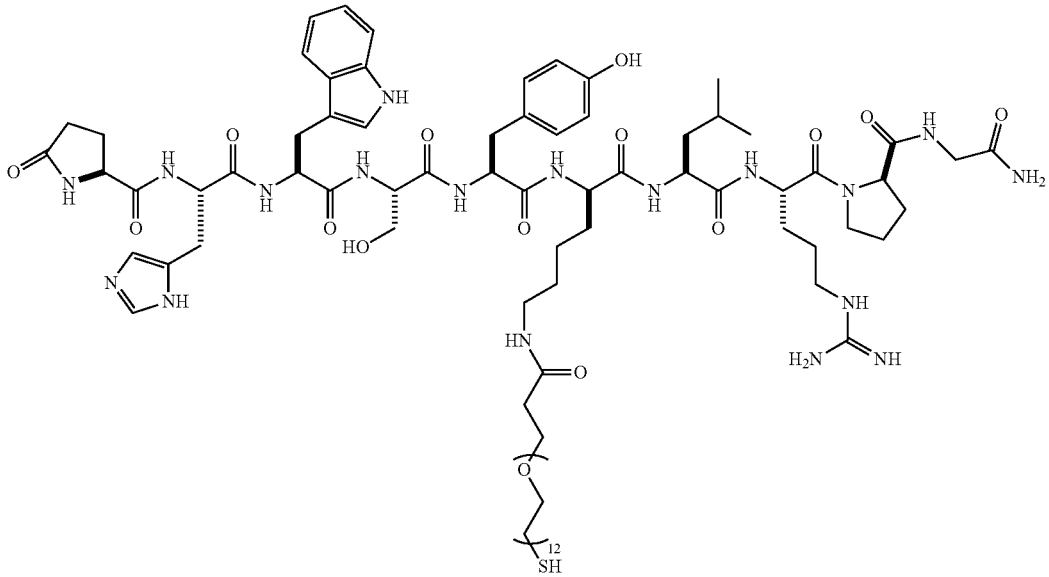 |

US 8,821,850 B2
159 160
TABLE C-continued
| Ref # | PBRM |
|---|---|
| Ex 14 | 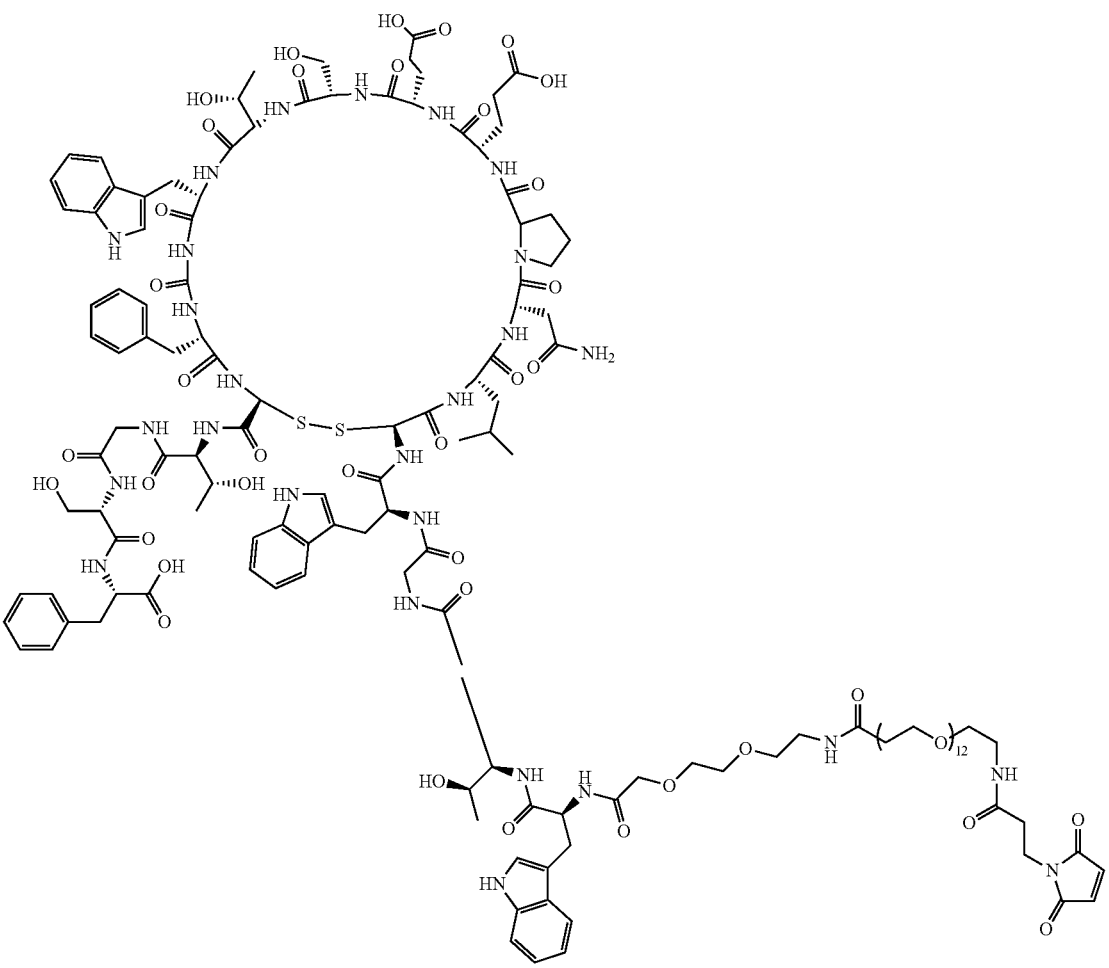 |
| Ex 16 | 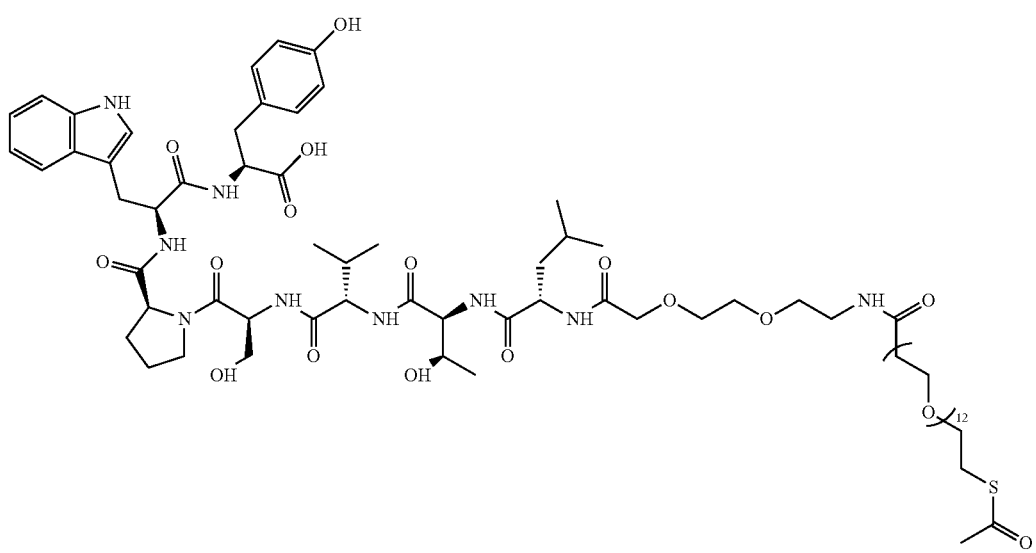 |
| Ex 91 | TRASTUZUMAB-Fab-SH |

Linkers ($L^D$ and $L^P$)

As described above, the drug or PBRM is connected to the polymeric carrier via a linker $L^D$ or $L^P$. In some embodiments, the linker is biocleavable/biodegradable under intracellular conditions, such that the cleavage of the linker releases the drug or PBRM from the polymer unit in the intracellular environment.

A linker is any chemical moiety that is capable of linking a drug or a PBRM to a polymer backbone through chemical bonds such that the drug or PBRM and the polymer are chemically coupled (e.g., covalently bonded) to each other. In some embodiments, the linker comprises a biodegradable linker moiety (e.g., a biodegradable bond such as an ester or amide bond).

In other embodiments, the linker $L^D$ or $L^P$ is biodegradable under mild conditions, i.e., conditions within a cell under which the activity of the drug is not affected. Examples of suitable biodegradable linker moiety include disulfide linkers, acid labile linkers, photolabile linkers, peptidase labile linkers, and esterase labile linkers.

In some embodiments, the linker $L^D$ or $L^P$ is biocleavable under reducing conditions (e.g., a disulfide linker). In this embodiment the drug or PBRM moiety is linked to the polymer through a disulfide bond. The linker molecule comprises a reactive chemical group that can react with the drug. Preferred reactive chemical groups for reaction with the drug or PBRM moiety are N-succinimidyl esters and N-sulfosuccinimidyl esters. Additionally the linker molecule comprises a reactive chemical group, preferably a dithiopyridyl group that can react with the drug to form a disulfide bond. In some embodiments the linker molecules include, for example, N-succinimidyl 3-(2-pyridyldithio)propionate (SPDP), N-succinimidyl 4-(2-pyridyldithio)butanoate (SPDB), N-succinimidyl 4-(2-pyridyldithio)pentanoate (SPP), N-succinimidyl-5-acetylthioacetate (SATA) and N-succinimidyl-oxycarbonyl-alpha-methyl-alpha-(2-pyridyl-dithio)toluene or 2,5-dioxopyrrolidin-1-yl 4-(1-(pyridin-2-yldisulfanyl)ethyl)benzoate (SMPT).

In other embodiments, the biocleavable linker $L^D$ or $L^P$ is pH-sensitive, i.e., sensitive to hydrolysis at certain pH values. Typically, the pH-sensitive linker is hydrolysable under acidic conditions. For example, an acid-labile linker that is hydrolysable in the lysosome or endosome (e.g., a hydrazone, semicarbazone, thiosemicarbazone, cis-aconitic amide, orthoester, acetal, ketal, or the like) can be used. Such linkers are relatively stable under neutral pH conditions, such as those in the blood, but are unstable at below pH 5.5 or 5.0, the approximate pH of the lysosome. In certain embodiments, the hydrolysable linker is a thioether linker (such as, e.g., a thioether attached to the therapeutic agent via an acylhydrazone bond).

In other embodiments the linker $L^D$ or $L^P$ is photo-labile and is useful at the body surface and in many body cavities that are accessible to light. Furthermore, $L^D$ or $L^P$ is biocleavable by infrared light which can penetrate tissue. Accordingly, $L^D$ or $L^P$ is useful for both applications on the body surface and in the tissue.

In some embodiments, the linker $L^D$ or $L^P$ is biocleavable by a cleaving agent that is present in the intracellular environment (e.g., within a lysosome or endosome or caveolea). The linker can be, for example, a peptidyl linker that is cleaved by an intracellular peptidase or protease enzyme, including, but not limited to, a lysosomal or endosomal protease.

In some embodiments the linker $L^D$ or $L^P$ is cleaved by esterases. Only certain esters can be cleaved by esterases present inside or outside cells. Esters are formed by the condensation of a carboxylic acid and an alcohol. Simple esters are esters produced with simple alcohols, such as aliphatic alcohols, and small cyclic and small aromatic alcohols.

In yet other embodiments, the linker $L^D$ or $L^P$ is not biocleavable and the drug is released by antibody degradation. See, for example, U.S. Pat. No. 7,498,298, which is incorporated by reference herein in its entirety and for all purposes.

Typically, the linker $L^D$ or $L^P$ is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of Polymer Drug Conjugate, are cleaved when the Polymer Drug Conjugate presents in an extracellular environment (e.g., in plasma) for 24 hours. Whether a linker is not substantially sensitive to the extracellular environment can be determined, for example, by incubating the Polymer Drug Conjugate with plasma for a predetermined time period (e.g., 2, 4, 8, 16, or 24 hours) and then quantitating the amount of free drug present in the plasma.

In embodiments, the linker $L^D$ has the structure: —$R^{L1}$—C(=O)—$X^D$-$M^{D1}$-$Y^D$-$M^{D2}$-$Z^D$-$M^{D3}$-$Q^D$-$M^{D4}$-, with $R^{L1}$ connected to an oxygen atom of the polymeric carrier and $M^{D4}$ connected to the drug molecule to be delivered.

In embodiments, the linker $L^P$ has the structure: —$R^{L2}$—C(=O)—$X^P$-$M^{P1}$-$Y^P$-$M^{P2}$-$Z^P$-$M^{P3}$-$Q^P$-$M^{P4}$-, with $R^{L2}$ connected to an oxygen atom of the polymeric carrier and $M^{P4}$ connected to the PBRM.

For example, each of $R^{L1}$ and $R^{L2}$ independently is absent, alkyl, alkenyl, alkynyl, cycloalkyl, heteroalkyl, heteroalkenyl, heteroalkynyl, heterocycloalkyl, aryl, or heteroaryl.

For example, each of $R^{L1}$ and $R^{L2}$ independently is absent, alkyl, cycloalkyl, heteroalkyl, or heterocycloalkyl.

For example, $R^{L1}$ is absent.

For example, $R^{L2}$ is absent.

For example, each of $X^D$ and $X^P$, independently is —O—, —S—, —N($R^1$)—, or absent, in which $R^1$ is hydrogen, an aliphatic, heteroaliphatic, carbocyclic, or heterocycloalkyl moiety, —C(=O)$R^{1B}$, —C(=O)O$R^{1B}$, —SO$_2R^{1B}$ or —N($R^1$)— is a heterocycloalkyl moiety, wherein $R^{1B}$ is hydrogen, an aliphatic, heteroaliphatic, carbocyclic, or heterocycloalkyl moiety.

For example, each of $Y^D$, $Y^P$, $Z^D$, $Z^P$, $Q^D$, and $Q^P$, independently, is absent or a biodegradable linker moiety selected from the group consisting of —S—S—, —C(=O)O—, —C(=O)NR$^2$—, —OC(=O)—, —NR$^2$C(=O)—, —OC(=O)O—, —OC(=O)NR$^2$—, —NR$^2$C(=O)O—, —NR$^2$C(=O)NR$^3$—, —C(OR$^2$)O—, —C(OR$^2$)S—, —C(OR$^2$)NR$^3$—, —C(SR$^2$)O—, —C(SR$^2$)S—, C(SR$^2$)NR$^3$—, —C(NR$^2$R$^3$)O—, —C(NR$^2$R$^3$)S—, —C(NR$^2$R$^3$)NR$^4$—, —C(=O)S—, —SC(=O)—, —SC(=O)S—, —OC(=O)S—, —SC(=O)O—, —C(=S)S—, —SC(=S)—, —OC(=S)—, —C(=S)O—, —SC(=S)O—, —OC(=S)S—, —OC(=S)O—, —SC(=S)S—, —C(=NR$^2$)O—, —C(=NR$^2$)S—, —C(=NR$^2$)NR$^3$—, —OC(=NR$^2$)—, —SC(=NR$^2$)—, —NR$^3$C(=NR$^2$)—, —NR$^2$SO$_2$—, —NR$^2$NR$^3$—, —C(=O)NR$^2$NR$^3$—, —NR$^2$NR$^3$C(=O)—, —OC(=O)NR$^2$NR$^3$—, —NR$^2$NR$^3$C(=O)O—, —C(=S)NR$^2$NR$^3$—, —NR$^2$NR$^3$C(=S)—, —C(=NR$^4$)NR$^2$NR$^3$—, —NR$^2$NR$^3$C(=NR$^4$)—, —O(N=CR$^3$)—, —(CR$^3$=N)O—, —C(=O)NR$^2$—(N=CR$^3$)—, —(CR$^3$=N)—NR$^2$C(=O)—, —SO$_3$—, —NR$^2$SO$_2$NR$^3$—, —SO$_2$NR$^2$—, and polyamide, wherein each occurrence of $R^2$, $R^3$, and $R^4$ independently is hydrogen or an aliphatic, heteroaliphatic, carbocyclic, or heterocyclic moiety, or each occurrence of —NR²— or —NR²NR³— is a heterocycloalkyl moiety.

For example, each of $M^{D1}$, $M^{D2}$, $M^{D3}$, $M^{D4}$, $M^{P1}$, $M^{P2}$, $M^{P3}$ and $M^{P4}$, independently, is absent or a non-biodegradable linker moiety selected from the group consisting of alkyl, alkenyl, alkynyl, cycloalkyl, heteroalkyl, heteroalkenyl, heteroalkynyl, heterocycloalkyl, aryl, heteroaryl, and a combination thereof and each of $M^{D1}$, $M^{D2}$, $M^{D3}$, $M^{P1}$, $M^{P2}$, and $M^{P3}$ optionally contains one or more —C(=O)— but does not contain any of the biodegradable linker moieties mentioned above.

For example, each of $M^{D1}$, $M^{D2}$, $M^{D3}$, $M^{D4}$, $M^{P1}$, $M^{P2}$, $M^{P3}$ And $M^{P4}$, Independently is $C_{1-6}$ alkyl, $C_{1-6}$ alkyl-C(O)—$C_{0-6}$ alkyl, $C_{1-6}$ alkyl-NH—$C_{0-6}$ alkyl, $C_{1-6}$ alkyl-O—$C_{0-6}$ alkyl, $C_{1-6}$ alkyl-S—$C_{0-6}$ alkyl, $C_{1-6}$ alkyl-C(O)—$C_{1-6}$ alkyl-NH, $C_{1-6}$ alkyl-C(O)—$C_{1-6}$ alkyl-O, $C_{1-6}$ alkyl-C(O)—$C_{1-6}$ alkyl-S, $C_{3-10}$ cycloalkyl-C(O)—$C_{0-6}$ alkyl, 3-19 membered heterocycloalkyl-C(O)—$C_{0-6}$ alkyl, aryl-C(O)—$C_{0-6}$ alkyl, $(CH_2CH_2O)_{1-12}$, and the like.

For example, for each $L^D$, $M^{D1}$ is not absent when $X^D$ is absent.

For example, for each $L^P$, $M^{P1}$ is not absent when $X^P$ is absent.

For example, for each $L^D$, at least one of $X^D$, $Y^D$, $Z^D$, and $Q^D$ is not absent.

For example, for each $L^P$, at least one of $X^P$, $Y^P$, $Z^P$, and $Q^P$ is not absent.

For example, each of $M^{D1}$ and $M^{P1}$ independently is $C_{1-6}$ alkyl or $C_{1-6}$ heteroalkyl.

For example, each of $M^{D2}$, $M^{D3}$, $M^{D4}$, $M^{P2}$, $M^{P3}$, and $M^{P4}$, independently is absent, $C_{1-6}$ alkyl, cycloalkyl, heteroalkyl, heterocycloalkyl, or a combination thereof.

For example, for each $L^D$, at most two of $M^{D2}$, $M^{D3}$, and $M^{D4}$ are absent.

For example, for each $L^P$, at most two of $M^{P2}$, $M^{P3}$, and $M^{P4}$ are absent.

For example, for each $L^D$, one of $M^{D2}$ and $M^{D3}$ has one of the following structures:

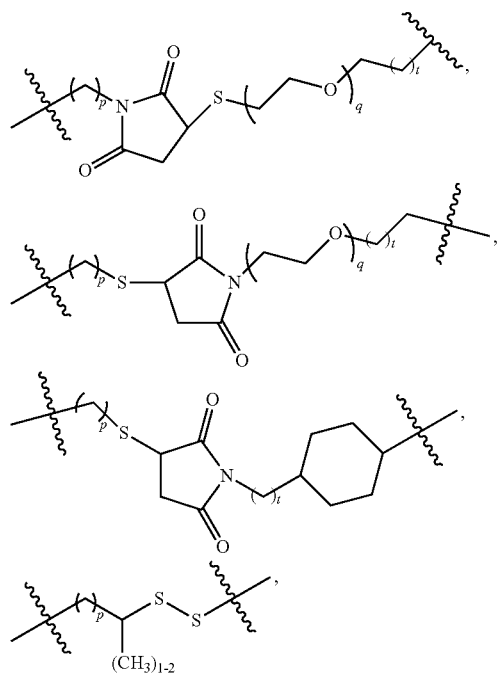

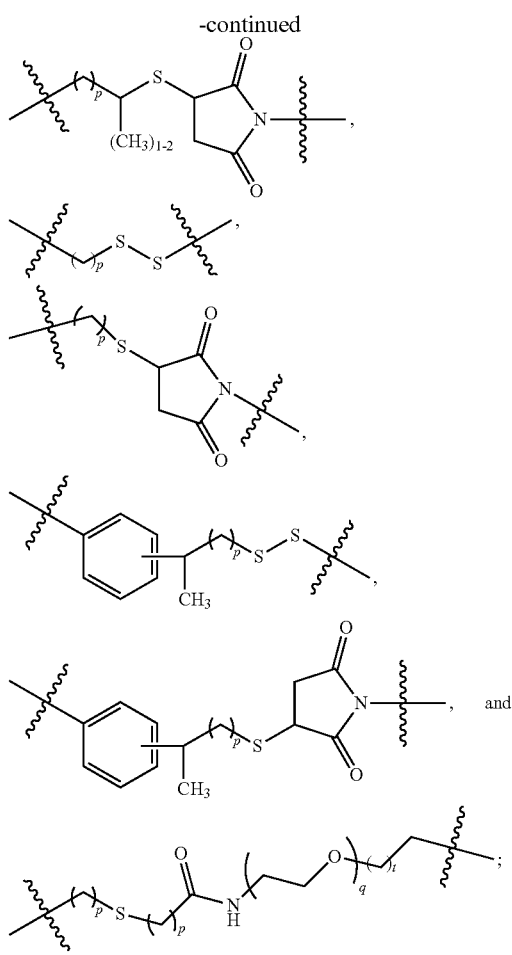

in which q is an integer from 0 to 12 and each of p and t independently is an integer from 0 to 3, and the other of $M^{D2}$ or $M^{D3}$ is either absent or a moiety different from the above, such as $C_{1-6}$ alkyl.

For example, for each $L^P$, one of $M^{P2}$ and $M^{P3}$ has one of the following structures:

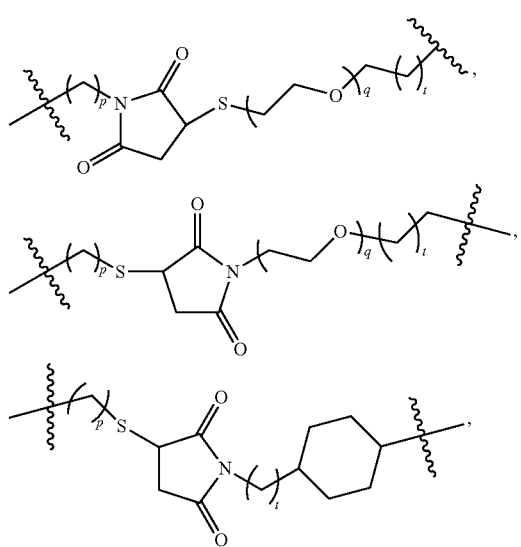

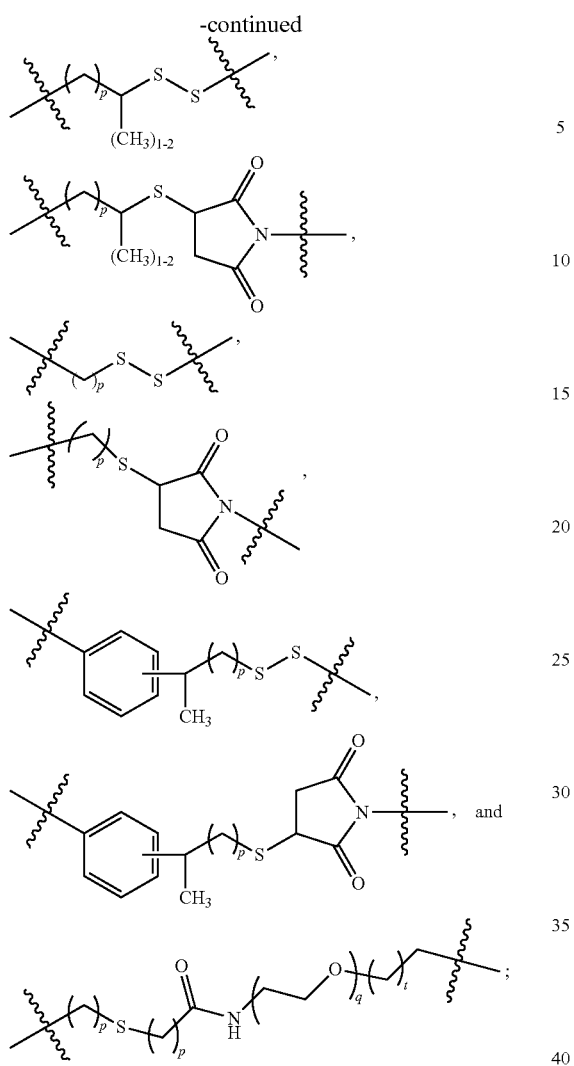

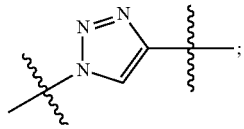
(3)

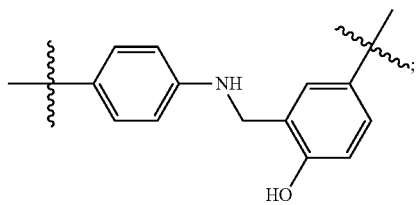
(4)

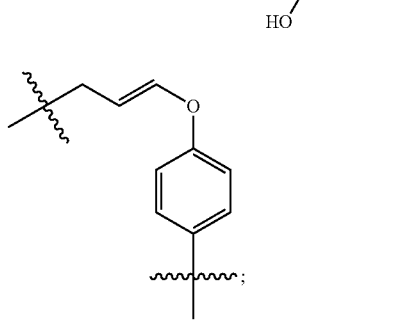
(5)

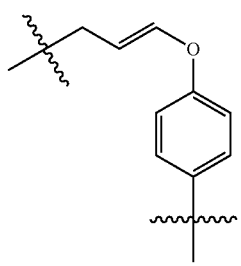
(6)

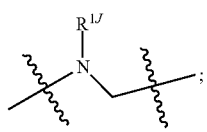
(7)

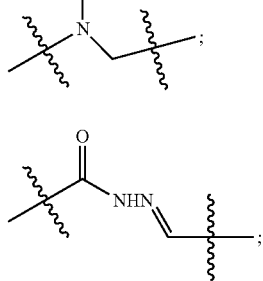
(8)

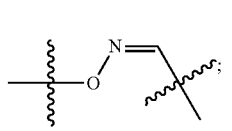
(9)

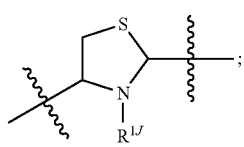

in which q is an integer from 0 to 12 and each of p and t independently is an integer from 0 to 3, and the other of $M^{P2}$ or $M^{P3}$ is either absent or a moiety different from the above, such as $C_{1\text{-}6}$ alkyl.

For example, p is 2.

For example, q is 0 or 12.

For example, t is 0 or 1.

For example, each of $-M^{D2}\text{-}Z^{D}-$, $-Z^{D}\text{-}M^{D3}-$, $-Z^{D}\text{-}M^{D2}$, or $M^{D3}\text{-}Z^{D}-$, independently has one of the following structures:

(1)
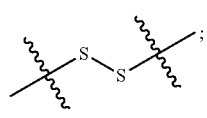

(2)
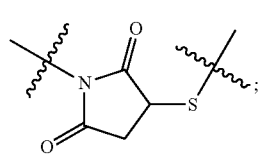

(10)
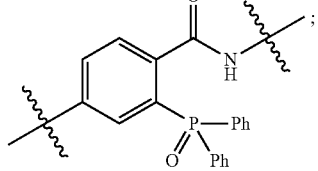

(11)
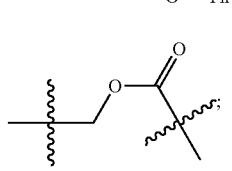

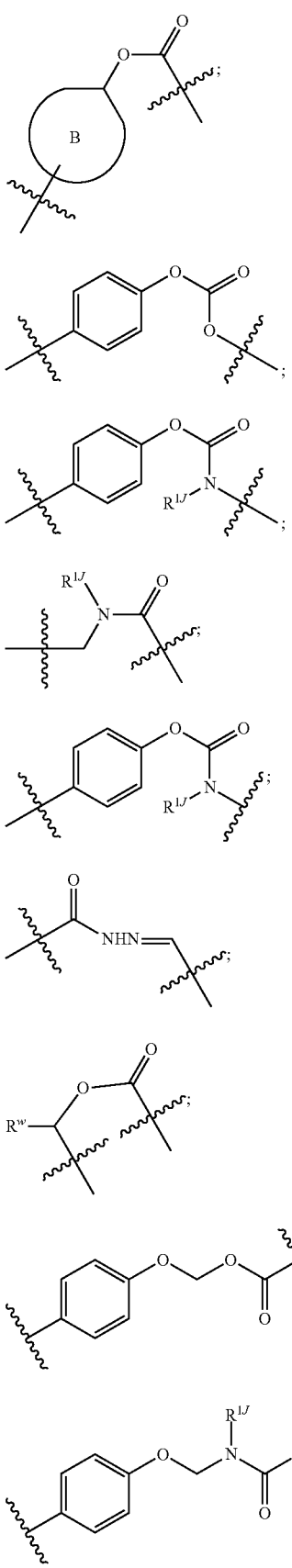

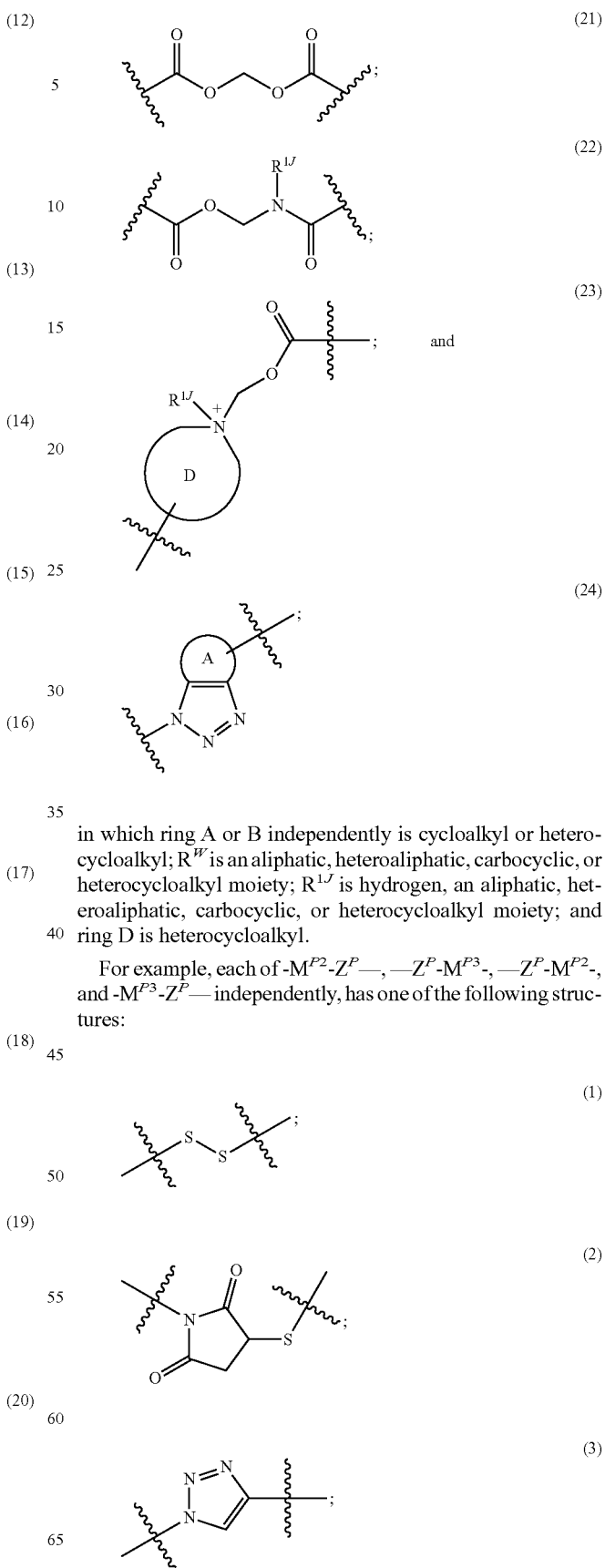

in which ring A or B independently is cycloalkyl or heterocycloalkyl; $R^W$ is an aliphatic, heteroaliphatic, carbocyclic, or heterocycloalkyl moiety; $R^{1J}$ is hydrogen, an aliphatic, heteroaliphatic, carbocyclic, or heterocycloalkyl moiety; and ring D is heterocycloalkyl.

For example, each of $-M^{P2}-Z^P-$, $-Z^P-M^{P3}-$, $-Z^P-M^{P2}-$, and $-M^{P3}-Z^P-$ independently, has one of the following structures:

-continued

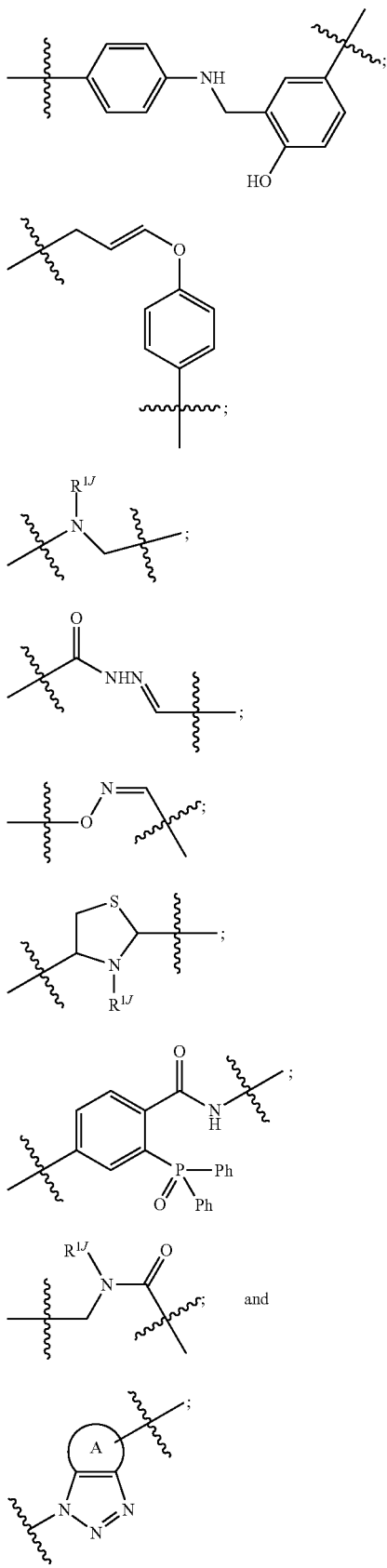

in which ring A is cycloalkyl or heterocycloalkyl and $R^{1J}$ is hydrogen, an aliphatic, heteroaliphatic, carbocyclic, or heterocycloalkyl moiety.

For example, ring A is 5-19 membered heterocycloalkyl, e.g.,

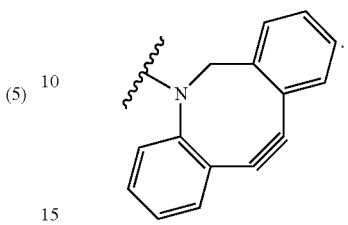

For example, ring A is $C_{3-8}$ cycloalkyl.
For example, ring D is piperazinyl or piperidinyl.
For example, $R^W$ is $C_{1-6}$ alkyl.
For example, $R^{1J}$ is hydrogen or $C_{1-6}$ alkyl.
For example, $Z^D$ is

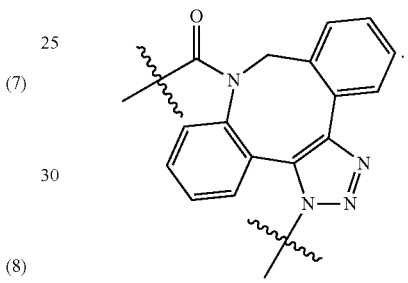

For example, $Z^P$ is

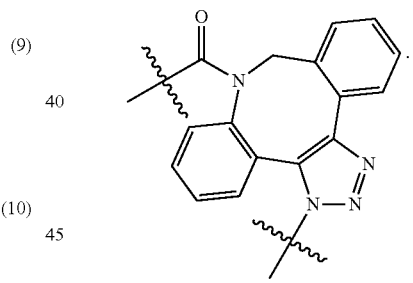

For example, $X^D$ is absent, O or NH.
For example, $X^P$ is absent, O or NH.
For example, each of $X^D$ and $X^P$, independently is

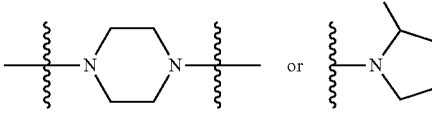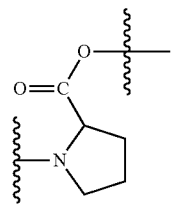

For example, each of $Y^D$ and $Y^P$ independently is —S—S—, —OCO—, —COO—, —CONH— or —NHCO—.
For example, each of $Q^D$ and $Q^P$ independently is absent, —S—S—, —OCO—, —COO—, —CONH—, —NHCO—, —OCONHNH—, or —NHNHCOO—.

For example, -L$^D$-D can have one of the following structures below, in which the wavy bond indicates that D (i.e., Drug) is either connected to the functional linker directly or via another moiety:
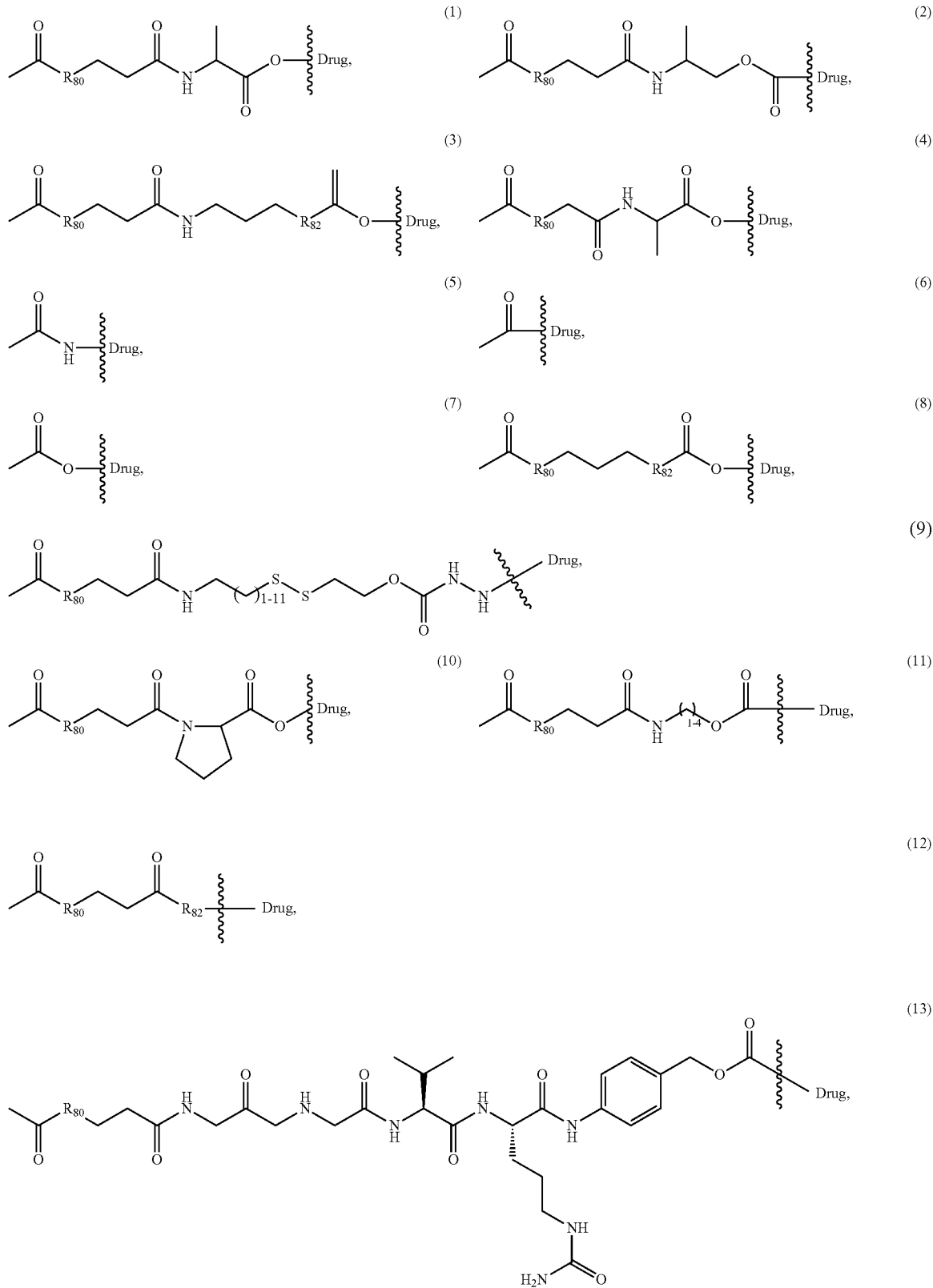

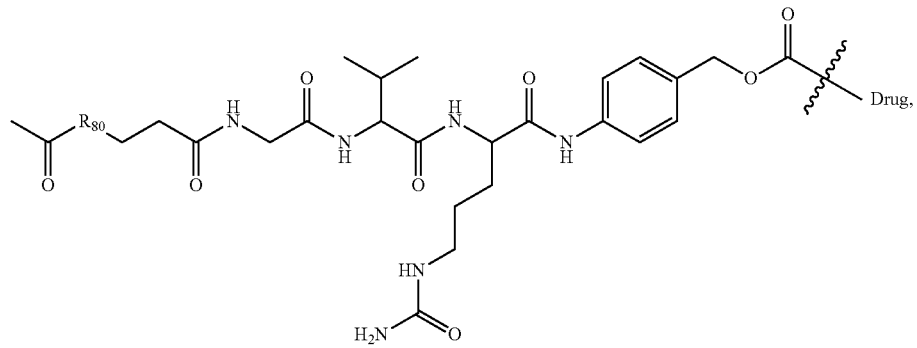
(14)
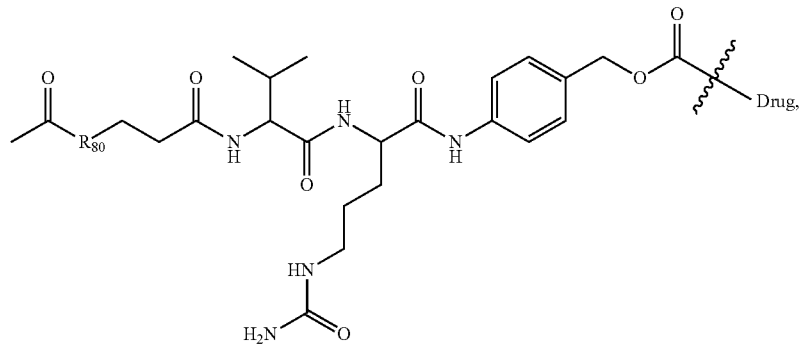
(15)
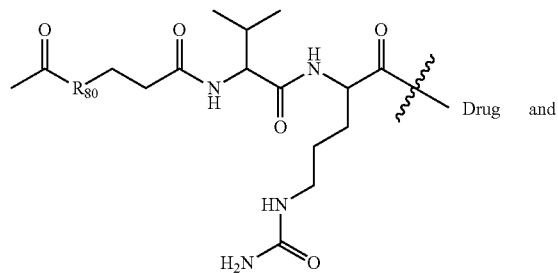
(16)
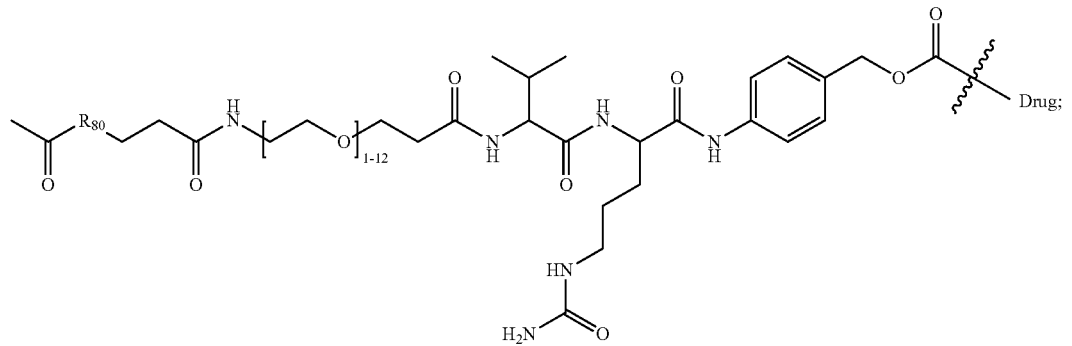
(17)

wherein $R_{80}$ is $CH_2$, —NH, or oxygen; and $R_{82}$ is —NH or oxygen.
For example, polymeric carrier-$L^P$-PBRM can have one of the following structures below:
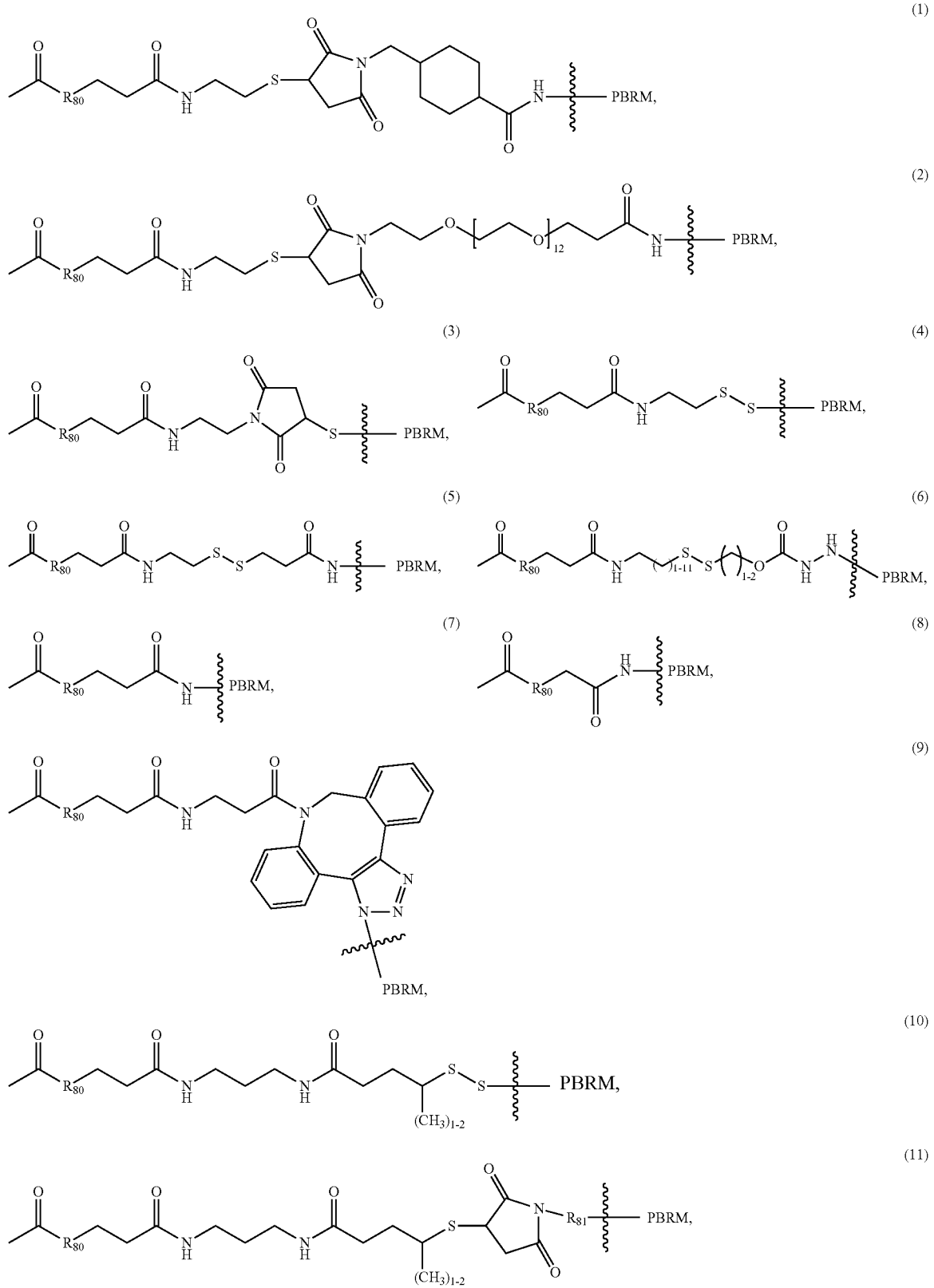

-continued
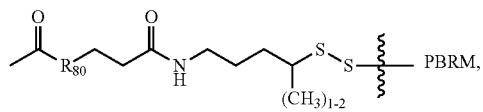 (12)
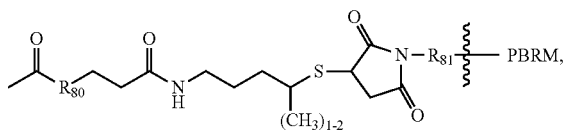 (13)
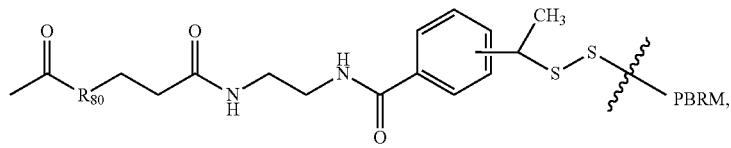 (14)
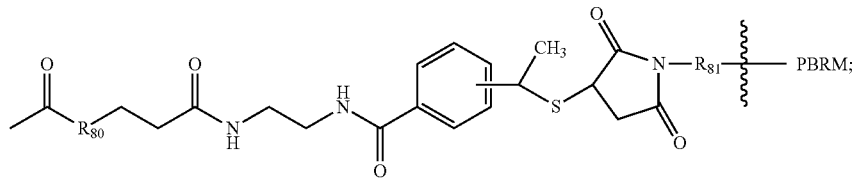 (15)
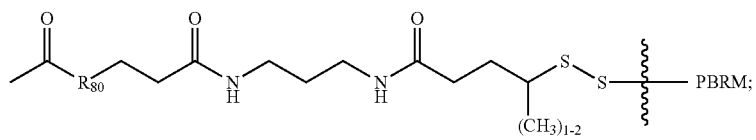 (16)
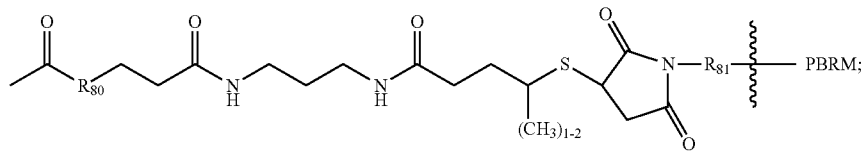 (17)
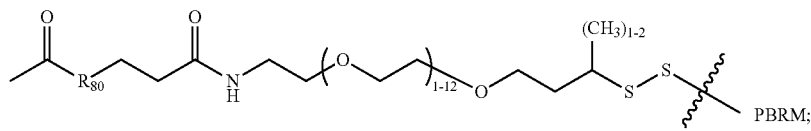 (18)
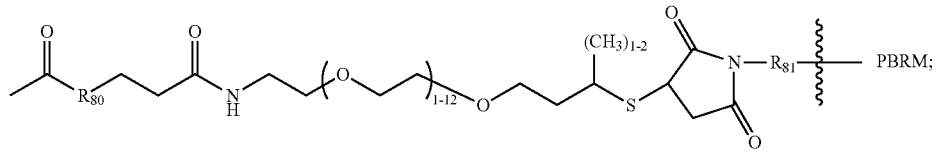 (19)
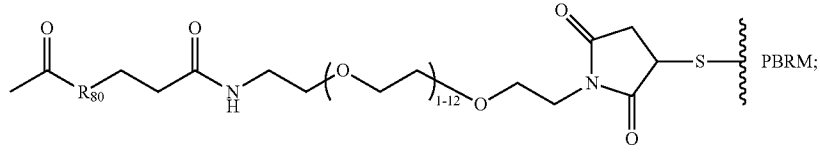 (20)
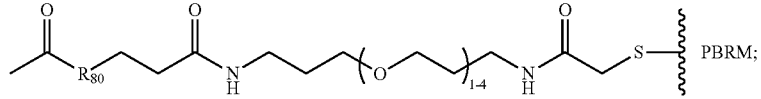 (21)
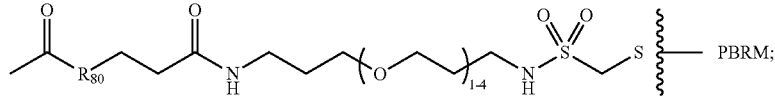 (22)

wherein:

$R_{80}$ is $CH_2$, NH or oxygen; and $R_{81}$ is

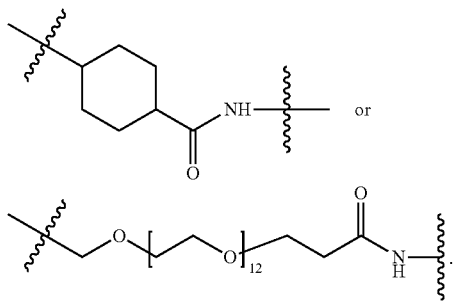

or

While biocleavable linkers preferably are used in the invention, a non-biocleavable linker also can be used to generate the above-described conjugate. A non-biocleavable linker is any chemical moiety that is capable of linking a drug or PBRM, to a polymer in a stable, covalent manner. Thus, non-biocleavable linkers are substantially resistant to acid-induced cleavage, light-induced cleavage, peptidase-induced cleavage, esterase-induced cleavage, and/or disulfide bond cleavage, at conditions under which the drug or polymer remains active.

In one embodiment, a substantial amount of the drug moiety is not cleaved from the conjugate until the protein-polymer-drug conjugate enters a cell with a cell-surface receptor specific for the PBRM of the protein-polymer-drug conjugate, and the drug moiety is cleaved from the protein-polymer-drug conjugate when the protein-polymer-drug conjugate does enter the cell.

In another embodiment, the bioavailability of the protein-polymer-drug conjugate or an intracellular metabolite of the protein-polymer-drug conjugate in a subject is improved when compared to a drug compound or conjugate comprising the drug moiety of the protein-polymer-drug conjugate, or when compared to an analog of the compound not having the drug moiety.

In another embodiment, the drug moiety is intracellularly cleaved in a subject from the protein-polymer-drug conjugate, or an intracellular metabolite of the protein-polymer-drug conjugate.

Conjugates or Polymeric Scaffolds

Conjugates of the invention comprise one or more occurrences of D, where D is a therapeutic agent, e.g., a drug, wherein the one or more occurrences of D may be the same or different.

In certain other embodiments, one or more occurrences of PBRM is attached to the polymeric carrier, wherein the one or more occurrences of PBRM may be the same or different. In certain other embodiments, one or more polymer carriers that contains one or more occurrences of D are connected to a PBRM (e.g., an antibody).

As discussed more generally above, in certain embodiments, each polymeric carrier independently, has about 0.1 to about 25% monomers comprising a D, more preferably about 0.5 to about 20%, more preferably about 1 to about 15%, and even more preferably about 2 to about 10%.

In certain embodiments, the conjugate of this invention is of Formula (I):

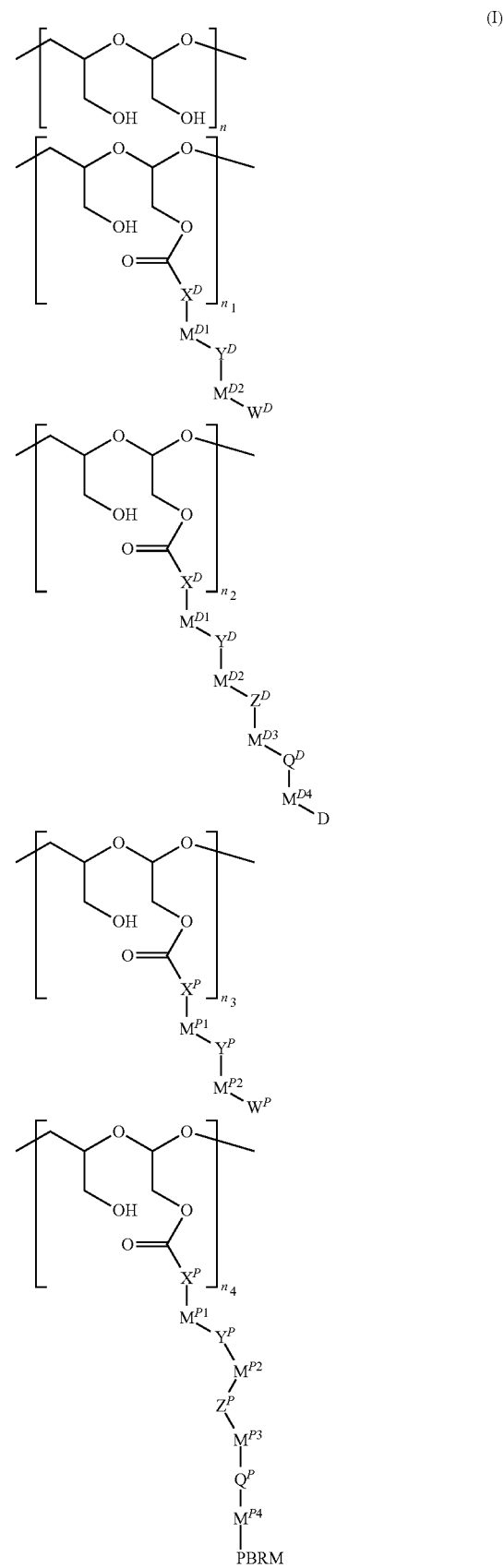

wherein:
each of n, $n_1$, $n_2$, $n_3$, and $n_4$, is the molar fraction of the corresponding polymer unit ranging between 0 and 1; $n+n_1+n_2+n_3+n_4=1$; provided that none of n, $n_2$, and $n_4$ is 0.

For example, the ratio between $n_2$ and $n_4$ is greater than 1:1 and ≤200:1.

For example, the ratio between $n_2$ and $n_4$ is between 10:1 and 50:1.

For example, the ratio between $n_2$ and $n_4$ is between 30:1 and 50:1.

For example, the ratio between $n_2$ and $n_4$ is about 50:1, 25:1, 10:1, 5:1 or 2:1.

In certain embodiments, the conjugates are formed in several steps. These steps include (1) modifying a polymer so that it contains a functional group that can react with a functional group of the drug or its derivative; (2) reacting the modified polymer with the drug or its derivative so that the drug is linked to the polymer; (3) modifying the polymer-drug conjugate so that the polymer contains a functional group that can react with a functional group of the PBRM or its derivative; and (4) reacting the modified polymer-drug conjugate with the PBRM or its derivative to form the conjugate of this invention. Step (3) may be omitted if the modified polymer produced by step (1) contains a functional group that can react with a functional group of the PBRM or its derivative.

In another embodiment the conjugates are formed in several steps: (1) modifying a polymer so that it contains a functional group that can react with a functional group of a first drug or its derivative; (2) reacting the modified polymer with the first drug or its derivative so that the first drug is linked to the polymer; (3) modifying the polymer-drug conjugate so that it contains a different functional group that can react with a functional group of a second drug or its derivative (4) reacting the modified polymer-drug conjugate with the second drug or its derivative so that the second drug is linked to the polymer-drug conjugate; (5) modifying the polymer-drug conjugate containing 2 different drugs so that the polymer contains a functional group that can react with a functional group of the PBRM or its derivative; and (6) reacting the modified polymer-drug conjugate of step (5) with the PBRM or its derivative to form the conjugate of this invention. Steps (5) and (6) may be repeated if 2 different PBRM or its derivatives are to be conjugated to form a polymer-drug conjugate comprising two different drugs and two different PBRMs.

In yet another embodiment, the conjugates are formed in several steps. These steps include (1) modifying a polymer so that it contains a functional group that can react with a functional group of the drug or its derivative; (2) further modifying the polymer so that it also contains a functional group that can react with a functional group of the PBRM or its derivative; (3) reacting the modified polymer with the drug or its derivative so that the drug is linked to the polymer; and (4) reacting the modified polymer-drug conjugate with the PBRM or its derivative to form the conjugate of this invention. The sequence of steps (1) and (2) or that of steps (3) and (4) can be reversed. Further either step (1) or (2) may be omitted if the modified polymer contains a functional group that can react with both a functional group of the drug or its derivatives and a functional group of the PBRM or its derivative.

In another embodiment the conjugates are formed in several steps: (1) modifying a polymer so that it contains a functional group that can react with a functional group of a first drug or its derivative; (2) further modifying a polymer so that it contains a functional group that can react with a functional group of the PBRM or its derivative; (3) reacting the modified polymer with the first drug or its derivative so that the first drug is linked to the polymer; (4) modifying the polymer-drug conjugate so that it contains a different functional group that can react with a functional group of a second drug or its derivative (5) reacting the modified polymer-drug conjugate with the second drug or its derivative so that the second drug is linked to the polymer-drug conjugate; (6) reacting the modified polymer-drug conjugate containing 2 different drugs so that the polymer with the PBRM or its derivative to form the conjugate of this invention. Step (6) may be repeated if 2 different PBRM or its derivatives are to be conjugated to form a polymer-drug conjugate comprising two different drugs and two different PBRMs. Step (4) may be carried out after step (1) so that the modified polymer contains two different functional groups that can react with two different drugs or their derivatives. In this embodiment, the modified polymer containing two different functional group that can react with two different drugs or their derivatives can be further modified so that it contains a functional group that can react with a functional group of the PBRM or its derivative; prior to the reaction of the modified polymer with either the two different drugs (step (3) and step (5) or PBRM (step (6).

The biodegradable biocompatible conjugates of the invention can be prepared to meet desired requirements of biodegradability and hydrophilicity. For example, under physiological conditions, a balance between biodegradability and stability can be reached. For instance, it is known that molecules with molecular weights beyond a certain threshold (generally, above 40-100 kDa, depending on the physical shape of the molecule) are not excreted through kidneys, as small molecules are, and can be cleared from the body only through uptake by cells and degradation in intracellular compartments, most notably lysosomes. This observation exemplifies how functionally stable yet biodegradable materials may be designed by modulating their stability under general physiological conditions (pH=7.5±0.5) and at lysosomal pH (pH near 5). For example, hydrolysis of acetal and ketal groups is known to be catalyzed by acids, therefore polyals will be in general less stable in acidic lysosomal environment than, for example, in blood plasma. One can design a test to compare polymer degradation profile at, for example, pH=5 and pH=7.5 at 37° C. in aqueous media, and thus to determine the expected balance of polymer stability in normal physiological environment and in the "digestive" lysosomal compartment after uptake by cells. Polymer integrity in such tests can be measured, for example, by size exclusion HPLC. One skilled on the art can select other suitable methods for studying various fragments of the degraded conjugates of this invention.

In many cases, it will be preferable that at pH=7.5 the effective size of the polymer will not detectably change over 1 to 7 days, and remain within 50% from the original for at least several weeks. At pH=5, on the other hand, the polymer should preferably detectably degrade over 1 to 5 days, and be completely transformed into low molecular weight fragments within a two-week to several-month time frame. Although faster degradation may be in some cases preferable, in general it may be more desirable that the polymer degrades in cells with the rate that does not exceed the rate of metabolization or excretion of polymer fragments by the cells. Accordingly, in certain embodiments, the conjugates of the present invention are expected to be biodegradable, in particular upon uptake by cells, and relatively "inert" in relation to biological systems. The products of carrier degradation are preferably uncharged and do not significantly shift the pH of the environment. It is proposed that the abundance of alcohol groups may provide low rate of polymer recognition by cell receptors, particularly of phagocytes. The polymer backbones of the present invention generally contain few, if any, antigenic determinants (characteristic, for example, for some polysaccharides and polypeptides) and generally do not comprise rigid structures capable of engaging in "key-and-lock" type interactions in vivo unless the latter are desirable. Thus, the soluble, crosslinked and solid conjugates of this invention are predicted to have low toxicity and bioadhesivity, which makes them suitable for several biomedical applications.

In certain embodiments of the present invention, the biodegradable biocompatible conjugates can form linear or branched structures. For example, the biodegradable biocompatible polyal conjugates of the present invention can be chiral (optically active). Optionally, the biodegradable biocompatible polyal conjugates of the present invention can be scalemic.

In certain embodiments, the conjugates of the invention are water-soluble. In certain embodiments, the conjugates of the invention are water-insoluble. In certain embodiments, the inventive conjugate is in a solid form. In certain embodiments, the conjugates of the invention are colloids. In certain embodiments, the conjugates of the invention are in particle form. In certain embodiments, the conjugates of the invention are in gel form.

This invention also features a polymeric scaffold useful for conjugating with a PBRM to form a polymer-drug-PBRM conjugate described herein. The scaffold comprises a polymeric carrier, one or more -$L^D$-D connected to the polymeric carrier, and one or more $L^P$ connected to the polymeric carrier which is suitable for connecting a PBRM to the polymeric carrier, wherein:

each occurrence of D is independently a therapeutic agent having a molecular weight ≤5 kDa;
the polymeric carrier is a polyacetal or polyketal,
$L^D$ is a linker having the structure:

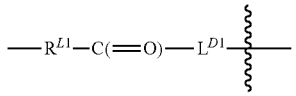

with $R^{L1}$ connected to an oxygen atom of the polymeric carrier and $L^{D1}$ connected to D, and

denotes direct or indirect attachment of D to $L^{D1}$, and $L^D$ contains a biodegradable bond so that when the bond is broken, D is released from the polymeric carrier in an active form for its intended therapeutic effect;
$L^{D1}$ is a carbonyl-containing moiety;
$L^P$ is a linker different from $L^D$ and having the structure: —$R^{L2}$—C(=O)-$L^{P1}$ with $R^{L2}$ connected to an oxygen atom of the polymeric carrier and $L^{P1}$ suitable for connecting directly or indirectly to a PBRM;
each of $R^{L1}$ and $R^{L2}$ independently is absent, alkyl, heteroalkyl, cycloalkyl, or heterocycloalkyl; and
$L^{P1}$ is a moiety containing a functional group that is capable of forming a covalent bond with a functional group of a PBRM.

For example, $L^P$ is a linker having the structure:

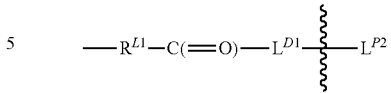

in which $L^{P2}$ is a moiety containing a functional group that is capable of forming a covalent bond with a functional group of a PBRM, and

denotes direct or indirect attachment of $L^{P2}$ to $L^{D1}$.

For example, the functional group of $L^{P1}$ or $L^{P2}$ is selected from —$SR^P$, —S—S-LG, maleimido, and halo, in which LG is a leaving group and $R^P$ is H or a sulfur protecting group.

For example, $L^{D1}$ comprises —X—$(CH_2)_v$—C(=O)— with X directly connected to the carbonyl group of $R^{L1}$—C(=O), in which X is $CH_2$, O, or NH, and v is an integer from 1 to 6.

For example, $L^{P1}$ or $L^{P2}$ contains a biodegradable bond.
For example, each of $R^{L1}$ and $R^{L2}$ is absent.
For example, the polymeric carrier of the scaffold of the invention is a polyacetal, e.g., a PHF having a molecular weight (i.e., MW of the unmodified PHF) ranging from about 2 kDa to about 300 kDa. The selection of a polymeric carrier with a specific MW range may depend on the size of the PBRM to be conjugated with.

For example, for conjugating a PBRM having a molecular weight of 40 kDa or greater (e.g., 60 kDa or greater, 80 kDa or greater, 100 kDa or greater, 120 kDa or greater, 140 kDa or greater, 160 kDa or greater or 180 kDa or greater), the polymeric carrier of the scaffold of the invention is a polyacetal, e.g., a PHF having a molecular weight (i.e., MW of the unmodified PHF) ranging from about 2 kDa to about 40 kDa (e.g., about 6-20 kDa or about 8-15 kDa).

For example, for conjugating a PBRM having a molecular weight of 40 kDa to 200 kDa, the polymeric carrier of the scaffold of the invention is a polyacetal, e.g., a PHF having a molecular weight (i.e., MW of the unmodified PHF) ranging from about 2 kDa to about 40 kDa (e.g., about 6-20 kDa or about 8-15 kDa).

For example, for conjugating a PBRM having a molecular weight of 60 kDa to 120 kDa, the polymeric carrier of the scaffold of the invention is a polyacetal, e.g., a PHF having a molecular weight (i.e., MW of the unmodified PHF) ranging from about 8 kDa to about 40 kDa (e.g., about 8-30 kDa, about 8-20 kDa or about 8-15 kDa). For example the PHF has a molecular weight of about 10 kDa, 20 kDa, 30 kDa or 40 kDa.

PBRMs in this molecular weight range, include but are not limited to, for example, camelids, Fab2, and the like.

For example, for conjugating a PBRM having a molecular weight of 140 kDa to 180 kDa, the polymeric carrier of the scaffold of the invention is a polyacetal, e.g., a PHF having a molecular weight (i.e., MW of the unmodified PHF) ranging from about 2 kDa to about 40 kDa (e.g., about 6-20 kDa or about 8-15 kDa). For example the PHF has a molecular weight of about 8 kDa, 10 kDa or 15 kDa.

PBRMs in this molecular weight range, include but are not limited to, for example, full length antibodies, such as, IgG, IgM.

For example, for conjugating a PBRM having a molecular weight of 200 kDa or less (e.g., 120 kDa or less, 80 kDa or less, 60 kDa or less, 40 kDa or less, 20 kDa or less or 10 kDa or less), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa, about 30-150 kDa, about 50-150 kDa, about 30-100 kDa, or about 50-100 kDa).

For example, for conjugating a PBRM having a molecular weight of 4 kDa to 80 kDa (e.g., 4-20 kDa, 20-30 kDa, or 30-70 kDa), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa, about 30-150 kDa, about 50-150 kDa, about 30-100 kDa, or about 50-100 kDa).

For example, for conjugating a PBRM having a molecular weight of 80 kDa or less (e.g., 70 kDa or less, 60 kDa or less, 50 kDa or less or 40 kDa or less), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa, about 30-150 kDa, about 50-150 kDa, about 30-100 kDa, or about 50-100 kDa). For example the PHF has a molecular weight of about 50 kDa, 70 kDa or 100 kDa.

PBRMs in this molecular weight range, include but are not limited to, for example, antibody fragments such as, for example Fabs.

For example, for conjugating a PBRM having a molecular weight of 30 kDa or less (e.g., about 20 kDa or less), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa, about 30-150 kDa, about 50-150 kDa, about 30-100 kDa, or about 50-100 kDa). For example the PHF has a molecular weight of about 30 kDa, 40 kDa, 50 kDa, 70 kDa, 100 kDa, 120 kDa or 150 kDa.

PBRMs in this molecular weight range, include but are not limited to, for example, antibody fragments, such as, scFv.

For example, for conjugating a PBRM having a molecular weight of 20 kDa or less (e.g., 10 kDa or less), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa, about 30-150 kDa, about 50-150 kDa, about 30-100 kDa, or about 50-100 kDa). For example the PHF has a molecular weight of about 30 kDa, 40 kDa, 50 kDa, 70 kDa, 100 kDa, 120 kDa or 150 kDa.

PBRMs in this molecular weight range, include but are not limited to, for example, small proteins and peptides.

For example, the scaffold is of Formula (Ia):

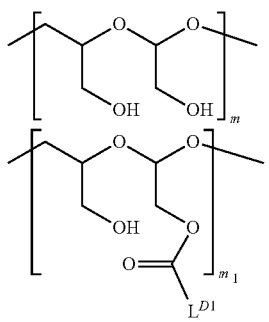
(Ia)

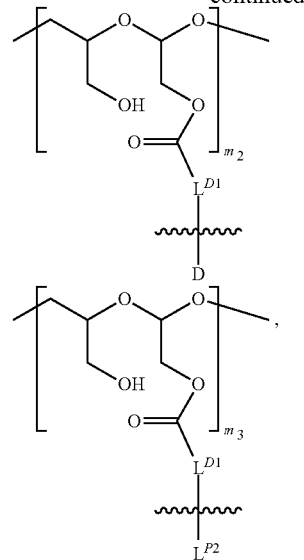
-continued wherein:
m is an integer from 1 to about 2200,
$m_1$ is an integer from 1 to about 660,
$m_2$ is an integer from 1 to about 300,
$m_3$ is an integer from 1 to about 110, and
the sum of m, $m_1$, $m_2$ and $m_3$ ranges from about 15 to about 2200.

For example, when the PHF in Formula (Ia) has a molecular weight ranging from about 2 kDa to about 40 kDa (i.e., the sum of m, $m_1$, $m_2$, and $m_3$ ranging from about 15 to about 300), $m_2$ is an integer from 1 to about 40, $m_3$ is an integer from 1 to about 18, and/or $m_1$ is an integer from 1 to about 140 (e.g., $m_1$ being about 1-90).

For example, when the PHF in Formula (Ia) has a molecular weight ranging from about 6 kDa to about 20 kDa (i.e., the sum of m, $m_1$, $m_2$, and $m_3$ ranging from about 45 to about 150), $m_2$ is an integer from 2 to about 20, $m_3$ is an integer from 1 to about 9, and/or $m_1$ is an integer from 1 to about 75 (e.g, $m_1$ being about 4-45).

For example, when the PHF in Formula (Ia) has a molecular weight ranging from about 8 kDa to about 15 kDa (i.e., the sum of m, $m_1$, $m_2$, and $m_3$ ranging from about 60 to about 110), $m_2$ is an integer from 2 to about 15, $m_3$ is an integer from 1 to about 7, and/or $m_1$ is an integer from 1 to about 55 (e.g, $m_1$ being about 4-30).

For example, when the PHF in Formula (Ia) has a molecular weight ranging from 20 kDa to 300 kDa (i.e., the sum of m, $m_1$, $m_2$, and $m_3$ ranging from about 150 to about 2200), $m_2$ is an integer from 3 to about 300, $m_3$ is an integer from 1 to about 110, and/or $m_1$ is an integer from 1 to about 660 (e.g, $m_1$ being about 10-250).

For example, when the PHF in Formula (Ia) has a molecular weight ranging from 20 kDa to 150 kDa (i.e., the sum of m, $m_1$, $m_2$, and $m_3$ ranging from about 150 to about 1100), $m_2$ is an integer from 3 to about 150, $m_3$ is an integer from 1 to about 75 (e.g., from 1 to about 55), and/or $m_1$ is an integer from 1 to about 330 (e.g., $m_1$ being about 10-330 or about 15-100). This scaffold can be used, for example, for conjugating a PBRM having a molecular weight of about 4 kDa to about 80 kDa.

For example, when the PHF in Formula (Ia) has a molecular weight ranging from 40 kDa to 150 kDa (i.e., the sum of m, $m_1$, $m_2$, and $m_3$ ranging from about 300 to about 1100), $m_2$ is an integer from 4 to about 150, $m_3$ is an integer from 1 to about 75 (e.g., from 1 to about 55), and/or $m_1$ is an integer from 1 to about 330 (e.g, $m_1$ being about 15-100).

For example, when the PHF in Formula (Ia) has a molecular weight ranging from 30 kDa to 100 kDa (i.e., the sum of m, $m_1$, $m_2$, and $m_3$ ranging from about 220 to about 740), $m_2$ is an integer from 3 to 100 (e.g., 5-100), $m_3$ is an integer from 1 to about 40, and/or $m_1$ is an integer from 1 to about 220 (e.g., $m_1$ being about 15-80).

For example, when the PHF in Formula (Ia) has a molecular weight ranging from about 50 kDa to about 100 kDa (i.e., the sum of m, $m_1$, $m_2$, and $m_3$ ranging from about 370 to about 740), $m_2$ is an integer from 5 to about 100, $m_3$ is an integer from 1 to about 40, and/or $m_1$ is an integer from 1 to about 220 (e.g, $m_1$ being about 15-80).

For example, the scaffold further comprises a PBRM connected to the polymeric carrier via $L^P$.

For example, when the PHF has a molecular weight ranging from 20 kDa to 300 kDa, (e.g., about 20-150 kDa, about 30-150 kDa, about 50-150 kDa, about 30-100 kDa, or about 50-100 kDa), the number of drugs per PHF (e.g., $m_2$) is an integer from about 3 to about 300, (e.g, about 3 to about 150 or about 3 to about 100). This scaffold can be used, for example, for conjugating a PBRM having a molecular weight of 200 kDa or less (e.g., 80 kDa or less, 60 kDa or less, 40 kDa or less, 20 kDa or less or 10 kDa or less). In this embodiment the ratio of PBRM per PHF is between about 1:1 and about 60:1, for example, between about 1:1 and about 30:1; between about 1:1 and about 20:1, between about 1:1 and about 10:1, between about 1:1 and about 9:1, between about 1:1 and about 8:1, between about 1:1 and about 7:1, between about 1:1 and about 6:1, between about 1:1 and about 5:1, between about 1:1 and about 4:1, between about 1:1 and about 3:1, or between about 1:1 and about 2:1. See, for example, Formula (Ib).

For example, the scaffold further comprises a PBRM connected to the polymeric carrier via $L^P$. For example, one or more PBRMs are connected to one drug-carrying polymeric carrier.

For example, the scaffold (e.g., a PBRM-polymer-drug conjugate) is of Formula (Ib):

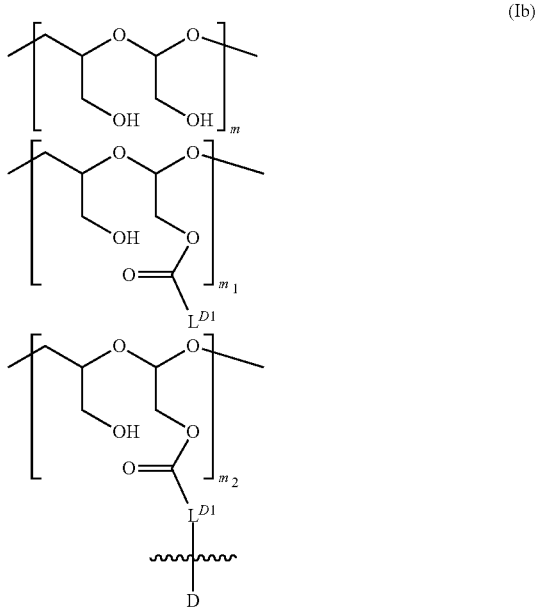

(Ib)

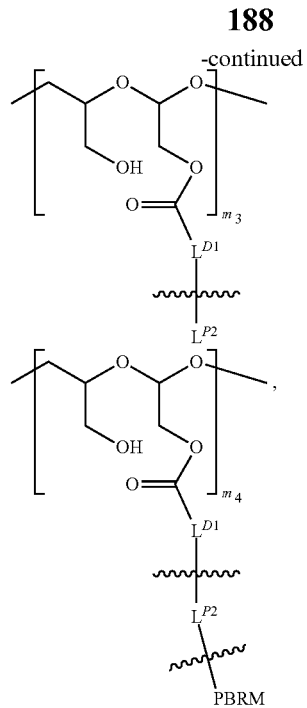

wherein:

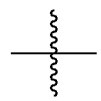

between $L^{P2}$ and PBRM denotes direct or indirect attachment of PBRM to $L^{P2}$, each occurrence of PBRM independently has a molecular weight of less than 200 kDa, m is an integer from 1 to about 2200, $m_1$ is an integer from 1 to about 660, $m_2$ is an integer from 3 to about 300, $m_3$ is an integer from 0 to about 110, $m_4$ is an integer from 1 to about 60; and the sum of m, $m_1$, $m_2$, $m_3$ and $m_4$ ranges from about 150 to about 2200.

For example, in Formula (Ib), $m_1$ is an integer from about 10 to about 660 (e.g., about 10-250).

For example, when the PHF in Formula (Ib) has a molecular weight ranging from 20 kDa to 150 kDa (i.e., the sum of m, $m_1$, $m_2$, $m_3$, and $m_4$ ranging from about 150 to about 1100), $m_2$ is an integer from 3 to about 150, $m_3$ is an integer from 1 to about 75 (e.g., from 1 to about 55), $m_4$ is an integer from 1 to about 30, and/or $m_1$ is an integer from 1 to about 330 (e.g., $m_1$ being about 10-330 or about 15-100). The PBRM in Formula (Ib), can have, for example, a molecular weight of about 4 kDa to about 70 kDa.

For example, when the PHF in Formula (Ib) has a molecular weight ranging from 40 kDa to 150 kDa (i.e., the sum of m, $m_1$, $m_2$, $m_3$, and $m_4$ ranging from about 300 to about 1100), $m_2$ is an integer from 4 to about 150, $m_3$ is an integer from 1 to about 75 (e.g., from 1 to about 55), $m_4$ is an integer from 1 to about 30, and/or $m_1$ is an integer from 1 to about 330 (e.g., $m_1$ being about 10-330 or about 15-100).

For example, when the PHF in Formula (Ib) has a molecular weight ranging from 50 kDa to 150 kDa, the number of drugs per PHF (e.g., $m_2$) is an integer from 3 to about 150).

The PBRM in Formula (Ib), can have, for example, a molecular weight of about 4 kDa to about 20 kDa. In this embodiment the ratio of PBRM per PHF is between about 1:1 to 10:1, between about 1:1 and about 9:1, between about 1:1 and about 8:1, between about 1:1 and about 7:1, between about 1:1 and about 6:1, between about 1:1 and about 5:1, between about 1:1 and about 4:1, between about 1:1 and about 3:1, or between about 1:1 and about 2:1.

PBRMs in this molecular weight range, include but are not limited to, for example, small proteins and peptides.

For example, when the PHF in Formula (Ib) has a molecular weight ranging from about 30 kDa to about 100 kDa (i.e., the sum of m, $m_1$, $m_2$, $m_3$, and $m_4$ ranging from about 225 to about 740), $m_2$ is an integer from 5 to about 100, $m_3$ is an integer from 1 to about 40, $m_4$ is an integer from 1 to about 20, and/or $m_1$ is an integer from 1 to about 220 (e.g., $m_1$ being about 15-80).

For example, when the PHF has a molecular weight ranging from 30 kDa to 150 kDa, (e.g., 50-100 kDa), the number of drugs per PHF (e.g., $m_2$) is an integer from about 3 to about 150 (e.g., about 3 to about 100). This scaffold can be used, for example, for conjugating a PBRM having a molecular weight of about 30 kDa to about 70 kDa In this embodiment the ratio of PBRM per PHF is between about 1:1 and about 30:1, between about 1:1 and about 10:1, between about 1:1 and about 9:1, between about 1:1 and about 8:1, between about 1:1 and about 7:1, between about 1:1 and about 6:1, between about 1:1 and about 5:1, between about 1:1 and about 4:1, between about 1:1 and about 3:1, or between about 1:1 and about 2:1.

PBRMs in this molecular weight range, include but are not limited to, for example, antibody fragments such as, for example Fab.

Alternatively or additionally, one or more drug-carrying polymeric carriers are connected to one PBRM. For example, the scaffold (e.g., a PBRM-polymer-drug conjugate) comprises a PBRM with a molecular weight of greater than 40 kDa and one or more D-carrying polymeric carriers connected to the PBRM, in which each of the D-carrying polymeric carrier independently is of Formula (Ic):

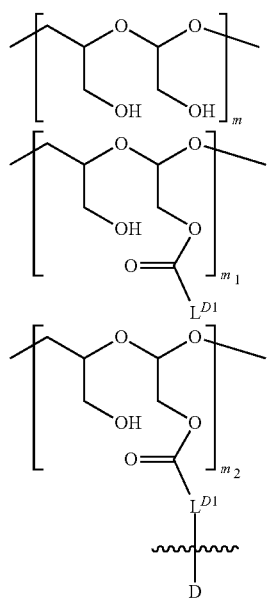

(Ic)

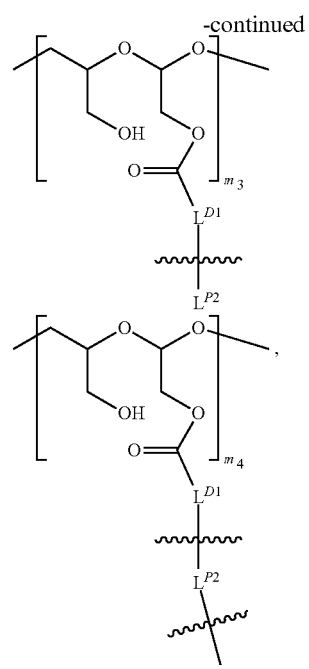

wherein:
terminal

attached to $L^{P2}$ denotes direct or indirect attachment of $L^{P2}$ to PBRM such that the D-carrying polymeric carrier is connected to the PBRM,
m is an integer from 1 to 300,
$m_1$ is an integer from 1 to 140,
$m_2$ is an integer from 1 to 40,
$m_3$ is an integer from 0 to 18,
$m_4$ is an integer from 1 to 10; and
the sum of m, $m_1$, $m_2$, $m_3$, and $m_4$ ranges from 15 to 300; provided that the total number of $L^{P2}$ attached to the PBRM is 10 or less.

For example, in Formula (Ic), $m_1$ is an integer from 1 to about 120 (e.g., about 1-90) and/or $m_3$ is an integer from 1 to about 10 (e.g., about 1-8).

For example, when the PHF in Formula (Ic) has a molecular weight ranging from about 6 kDa to about 20 kDa (i.e., the sum of m, $m_1$, $m_2$, $m_3$, and $m_4$ ranging from about 45 to about 150), $m_2$ is an integer from 2 to about 20, $m_3$ is an integer from 1 to about 9, and/or $m_1$ is an integer from 1 to about 75 (e.g., $m_1$ being about 4-45).

For example, when the PHF in Formula (Ic) has a molecular weight ranging from about 8 kDa to about 15 kDa (i.e., the sum of m, $m_1$, $m_2$, $m_3$, and $m_4$ ranging from about 60 to about 110), $m_2$ is an integer from 2 to about 15, $m_3$ is an integer from 1 to about 7, and/or $m_1$ is an integer from 1 to about 55 (e.g., $m_1$ being about 4-30).

For example, when the PHF has a molecular weight ranging from 2 kDa to 40 kDa, (e.g., about 6-20 kDa or about 8-15 kDa), the number of drugs per PHF (e.g., $m_2$) is an integer from 1 to about 40, (e.g., about 2-20 or about 2-15). This scaffold can be used, for example, for conjugating a PBRM having a molecular weight of 40 kDa or greater (e.g., 60 kDa or greater; 80 kDa or greater; or 100 kDa or greater; 120 kDa or greater; 140 kDa or greater; 160 kDa or greater or 180 kDa or greater). In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, or between about 1:1 and about 1:2.

For example, when the PHF has a molecular weight ranging from 2 kDa to 40 kDa, (e.g., about 6-20 kDa or about 8-15 kDa), the number of drugs per PHF (e.g., $m_2$) is an integer from 1 to about 40, (e.g., about 1:10 or about 1-15). This scaffold can be used, for example, for conjugating a PBRM having a molecular weight of 140 kDa to 180 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, or between about 1:1 and about 1:2.

PBRMs in this molecular weight range, include but are not limited to, for example, full length antibodies, such as, IgG, IgM.

For example, when the PHF has a molecular weight ranging from 2 kDa to 40 kDa, the number of drugs per PHF (e.g., $m_2$) is an integer from 1 to about 40, (e.g., about 1:20 or about 1:15). This scaffold can be used, for example, for conjugating a PBRM having a molecular weight of 60 kDa to 120 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, or between about 1:1 and about 1:2.

PBRMs in this molecular weight range, include but are not limited to, for example, antibody fragments such as, for example Fab2 and camelids.

In another aspect, the invention features a polymeric scaffold useful to conjugate with both a protein based recognition-molecule (PBRM) and a therapeutic agent (D). The D-free scaffold comprises a polymeric carrier, one or more $L^P$ connected to the polymeric carrier which is suitable for connecting a PBRM to the polymeric carrier, and one or more —$R^{L1}$—C(=O)-$L^{D1}$ connected to the polymeric carrier via $R^{L1}$, wherein:

the polymeric carrier is a polyacetal or polyketal, $R^{L1}$ is connected to an oxygen atom of the polymeric carrier, $L^{D1}$ is a linker suitable for connecting a D molecule to the polymeric carrier, in which each occurrence of D is independently a therapeutic agent having a molecular weight ≤5 kDa;

$L^P$ is a linker different from —$R^{L1}$—C(=O)-$L^{D1}$, and having the structure: —$R^{L2}$—C(=O)-$L^{P1}$ with $R^{L2}$ connected to an oxygen atom of the polymeric carrier and $L^{P1}$ suitable for connecting to a PBRM;

each of $R^{L1}$ and $R^{L2}$ independently is absent, alkyl, heteroalkyl, cycloalkyl, or heterocycloalkyl;

$L^{D1}$ is a moiety containing a functional group that is capable of forming a covalent bond with a functional group of D, and $L^{P1}$ is a moiety containing a functional group that is capable of forming a covalent bond with a functional group of a PBRM.

For example, the D-free scaffold useful to conjugate with a PBRM and a D can have one or more of the following features.

For example, $L^P$ is a linker having the structure:

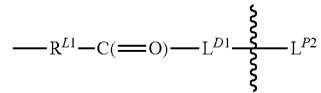

in which $L^{P2}$ is a moiety containing a functional group that is capable of forming a covalent bond with a functional group of a PBRM, and

denotes direct or indirect attachment of $L^{P2}$ to $L^{D1}$.

For example, the functional group of $L^{P1}$ or $L^{P2}$ is selected from —$SR^p$, —S—S-LG, maleimido, and halo, in which LG is a leaving group and $R^p$ is H or a sulfur protecting group.

For example, $L^{D1}$ comprises —X—(CH$_2$)$_v$—C(=O)— with X directly connected to the carbonyl group of $R^{L1}$—C (=O), in which X is CH$_2$, O, or NH, and v is an integer from 1 to 6.

For example, $L^{P1}$ or $L^{P2}$ contains a biodegradable bond.

For example, each of $R^{L1}$ and $R^{L2}$ is absent.

For example, the polymeric carrier of the D-free scaffold is a polyacetal, e.g., a PHF having a molecular weight (i.e., MW of the unmodified PHF) ranging from about 2 kDa to about 300 kDa.

The D-free scaffold is of Formula (Id):

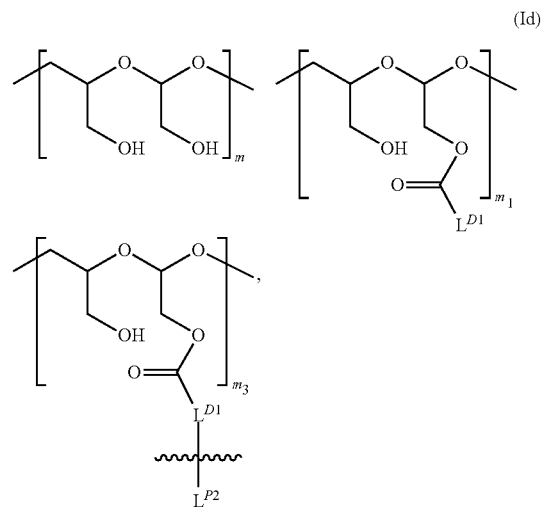

wherein:

m is an integer from 1 to about 2200, $m_1$ is an integer from 1 to about 660, $m_3$ is an integer from 1 to about 110, and the sum of m, $m_1$, and $m_3$ ranges from about 15 to about 2200.-

For example, when the PHF in Formula (Id) has a molecular weight ranging from about 2 kDa to about 40 kDa (i.e., the sum of m, $m_1$, and $m_3$ ranging from about 15 to about 300), $m_3$ is an integer from 1 to about 18, and/or $m_1$ is an integer from 1 to about 140 (e.g., $m_1$ being about 2-120).

For example, when the PHF in Formula (Id) has a molecular weight ranging from about 6 kDa to about 20 kDa (i.e., the sum of m, $m_1$, and $m_3$ ranging from about 45 to about 150), $m_3$ is an integer from 1 to about 9, and/or $m_1$ is an integer from 1 to about 75 (e.g., $m_1$ being about 6-60).

For example, when the PHF in Formula (Id) has a molecular weight ranging from about 8 kDa to about 15 kDa (i.e., the sum of m, $m_1$, and $m_3$ ranging from about 60 to about 110), $m_3$ is an integer from 1 to about 7, and/or $m_1$ is an integer from 1 to about 55 (e.g., $m_1$ being about 6-45).

For example, when the PHF in Formula (Id) has a molecular weight ranging from 20 kDa to 300 kDa (i.e., the sum of m, $m_1$, and $m_3$ ranging from about 150 to about 2200), $m_3$ is an integer from 1 to about 110, and/or $m_1$ is an integer from 1 to about 660 (e.g., $m_1$ being about 13-550).

For example, when the PHF in Formula (Id) has a molecular weight ranging from 40 kDa to 150 kDa (i.e., the sum of m, $m_1$, and $m_3$ ranging from about 300 to about 1100), $m_3$ is an integer from 1 to about 75, and/or $m_1$ is an integer from 1 to about 330 (e.g., $m_1$ being about 20-250).

For example, when the PHF in Formula (Id) has a molecular weight ranging from about 50 kDa to about 100 kDa (i.e., the sum of m, $m_1$, and $m_3$ ranging from about 370 to about 740), $m_3$ is an integer from 1 to about 40, and/or $m_1$ is an integer from 1 to about 220 (e.g., $m_1$ being about 20-180).

For example, the D-free scaffold further comprises a PBRM connected to the polymeric carrier via $L^P$.

For example, one or more PBRMs are connected to one D-free polymeric carrier.

For example, the D-free scaffold is of Formula (Ie):

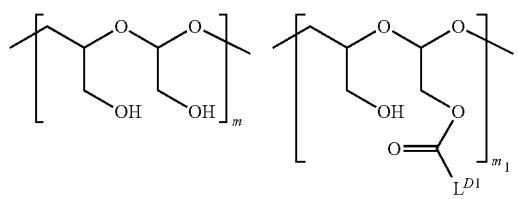

(Ie)

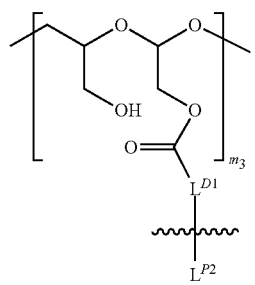

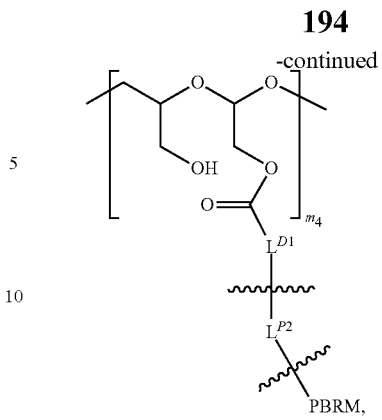

-continued wherein:

between $L^{P2}$ and PBRM denotes direct or indirect attachment of PBRM to $L^{P2}$, PBRM has a molecular weight of less than 200 kDa, m is an integer from 1 to 2200, $m_1$ is an integer from 1 to 660, $m_3$ is an integer from 0 to 110, $m_4$ is an integer from 1 to about 60; and the sum of m, $m_1$, $m_2$, $m_3$ and $m_4$ ranges from about 150 to about 2200.

For example, in Formula (Ie), $m_1$ is an integer from about 10 to about 660 (e.g., about 14-550).

For example, when the PHF in Formula (Ie) has a molecular weight ranging from 40 kDa to 150 kDa (i.e., the sum of m, $m_1$, $m_3$, and $m_4$ ranging from about 300 to about 1100), $m_3$ is an integer from 1 to about 75, $m_4$ is an integer from 1 to about 30, and/or $m_1$ is an integer from 1 to about 330 (e.g., $m_1$ being about 20-250).

For example, when the PHF in Formula (Ie) has a molecular weight ranging from about 50 kDa to about 100 kDa (i.e., the sum of m, $m_1$, $m_3$, and $m_4$ ranging from about 370 to about 740), $m_3$ is an integer from 1 to about 40, $m_4$ is an integer from 1 to about 20, and/or $m_1$ is an integer from 1 to about 220 (e.g., $m_1$ being about 20-180).

Alternatively or additionally, one or more D-free polymeric carriers are connected to one PBRM. For example, the scaffold comprises a PBRM with a molecular weight of greater than 40 kDa and one or more polymeric carriers connected to the PBRM, in which each of the polymeric carrier independently is of Formula (Ih):

(Ih)

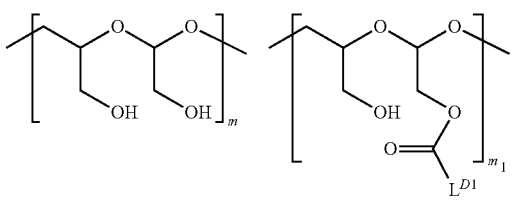

-continued

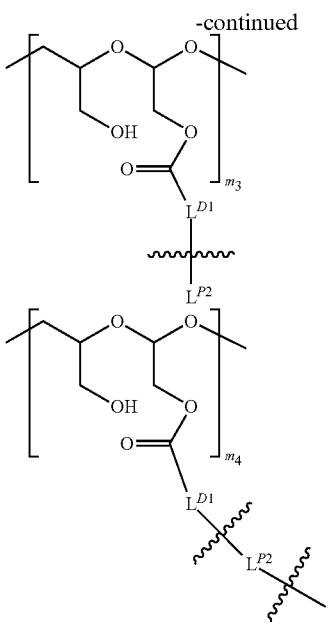

wherein:
terminal

attached to $L^{P2}$ denotes direct or indirect attachment of $L^{P2}$ to PBRM such that the D-carrying polymeric carrier is connected to the PBRM, m is an integer from 1 to 300,
$m_1$ is an integer from 1 to 140,
$m_3$ is an integer from 0 to 18,
$m_4$ is an integer from 1 to 10; and
the sum of m, $m_1$, $m_3$, and $m_4$ ranges from 15 to 300; provided that the total number of $L^{P2}$ attached to the PBRM is 10 or less For example, in Formula (Ih), $m_1$ is an integer from 2 to about 130 (e.g., about 3-120) and/or $m_3$ is an integer from 1 to about 10 (e.g., about 1-8).

For example, when the PHF in Formula (Ih) has a molecular weight ranging from about 6 kDa to about 20 kDa (i.e., the sum of m, $m_1$, $m_3$, and $m_4$ ranging from about 45 to about 150), $m_3$ is an integer from 1 to about 9, and/or $m_1$ is an integer from 6 to about 75 (e.g., $m_1$ being about 7-60).

For example, when the PHF in Formula (Ih) has a molecular weight ranging from about 8 kDa to about 15 kDa (i.e., the sum of m, $m_1$, $m_3$, and $m_4$ ranging from about 60 to about 110), $m_3$ is an integer from 1 to about 7, and/or $m_1$ is an integer from 6 to about 55 (e.g., $m_1$ being about 7-45).

In one embodiment the protein-polymer drug conjugate comprises a PBRM having a molecular weight of about 140 kDa to about 180 kDa (e.g., an antibody), the PHF has a molecular weight of about 8 to 15 kDa, and a load range of about 1 to about 15 of a therapeutic agent.

In one embodiment the protein-polymer drug conjugate comprises a PBRM having a molecular weight of about 60 kDa to about 120 kDa (e.g., Fab$_2$, camelids), the PHF has a molecular weight of about 8 to 40 kDa, and a load range of about 1 to about 20 of a therapeutic agent.

In one embodiment the protein-polymer drug conjugate comprises a PBRM having a molecular weight of about 30 kDa to about 70 kDa (e.g., Fab), the PHF has a molecular weight of about 50 to 100 kDa, and a load range of about 5 to about 100 of a therapeutic agent.

In one embodiment the protein-polymer drug conjugate comprises a PBRM having a molecular weight of about 20 kDa to about 30 kDa (e.g., scFv), the PHF has a molecular weight of about 50 to 150 kDa, and a load range of about 5 to about 150 of a therapeutic agent.

In one embodiment the protein-polymer drug conjugate comprises a PBRM having a molecular weight of about 4 kDa to about 20 kDa (e.g., a small protein), the PHF has a molecular weight of about 50 to 150 kDa, and a load range of about 5 to about 150 of a therapeutic agent.

In some embodiments, the protein-polymer drug conjugate is one of those characterized by Table 1 of FIG. 10.

In some embodiment, the protein-polymer drug conjugate is one of those characterized by Table 2 of FIG. 10.

In some embodiment, the protein-polymer drug conjugate is one of those characterized by Table 3 of FIG. 10.

In some embodiments, the protein-polymer drug conjugate includes PHF having a MW of up to 60 kDa (e.g., up to 50 kDa) and a drug to PHF ratio of up to 50:1 (e.g., about 45:1, 40:1, or 35:1).

In some embodiments, the polymeric scaffold (e.g., a polyacetal polymer such as PHF) is conjugated with PBRMs by utilizing random lysine modification. In other embodiments, the polymeric scaffold (e.g., a polyacetal polymer such as PHF) is conjugated with PBRMs by utilizing cysteine-based bioconjugation strategy. See, e.g., WO2010100430 and U.S. Pat. No. 7,595,292, the contents of which are hereby incorporated by reference in their entireties. In one embodiment, the polymeric scaffold (e.g., a polyacetal polymer such as PHF) conjugates with a PBRM (e.g., an antibody) via cysteines in the antibody hinge region. Without wishing to be bound by the theory, the resulting conjugate is stabilized through the formation of inter-chain bridge structures.

Accordingly, the invention also relates to a polymeric scaffold comprising at least two -$G^X$ moieties connected to the polymeric scaffold, in which each -$G^X$ is capable of conjugation to a thiol group from an amino acid (e.g., cysteine) in a PBRM so as to form a protein-polymer conjugate. In embodiments, -$G^X$ is a maleimide group, a disulfide group, a thiol group, a triflate group, a tosylate group, an aziridine group, a 5-pydriyl functional group, a vinylsulfone group, a vinyl pyridine group, an alkyl halide group, an acrylate group or a methacrylate group.

In embodiments, one or more free thiol groups of a PBRM are produced by reducing a protein. The one or more free thiol groups of the PBRM then react with the at least two -$G^X$ moieties contained in the polymer scaffold so as to conjugate the PBRM with the polymer scaffold.

In embodiments, the free thiol groups of the PBRM that are used for the conjugation are derived from a disulfide bridge of a native protein or a disulfide bridge of a protein complex consisting of two or more protein chains connected by the disulfide bridge. A disulfide bridge may be intrachain or interchain bridge. Alternatively, the free thiol groups of the PBRM are from cysteines or the unpaired thiol groups of the native protein that are not involved in inter or intra disulfide bridge formation.

Disulfide bonds can be reduced, for example, with dithiothreitol, mercaptoethanol, tris-carboxyethylphosphine, dehydroascorbic acid, copper sulfate, using conventional methods. A protein can contain one or more disulfide bridges. Reduction to give free thiol groups can be controlled to reduce one or more specific disulfide bridges in a protein. Depending on the extent of disulfide reduction and the stoichiometry of the -$G^X$ moieties on the polymeric scaffold polymeric, it is possible to conjugate one or more polymer scaffolds to the protein. Immobilized reducing agents may be used if it is desired to reduce less than the total number of disulfides, as can partial reduction using different reaction conditions or the addition of denaturants.

Advantages of conjugating a polymer to a protein via a thiol include, but are not limited to optimized efficacy, improved dose to dose consistency and homogeneity (as the number of conjugated polymer molecules per protein is the substantially the same for each protein molecule), specific conjugation directed to a specific residue or residues on each protein, and easier purification. Also, the protein-polymer conjugates via the thiol conjugation exhibits substantially improved half-life, mean residence time, and/or clearance rate in circulation as compared to the unconjugated protein.

In one embodiment, the scaffold for conjugating to thiol groups in a PBRM is of Formula (IIIa):

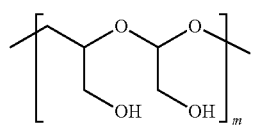
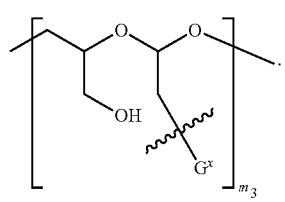

(IIIa)

The wavy line in Formula (IIIa) above denotes direct or indirect attachment of -$G^X$ to the backbone of PHF. m and $m_3$ are as defined herein. For example, -$G^X$ is connected to the polymeric scaffold by a linker -$L^S$ having the structure:

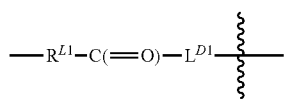

with $R^{L1}$ and $L^{D1}$ defined as herein and

denoting direct or indirect attachment of $L^{D1}$ to $G^X$.

For example, m is an integer from 1 to 2200.

For example, $m_3$ is an integer from 2 to 20 (e.g., an integer from 2 to 10, or an integer from 2 to 6).

In another embodiment, the scaffold for conjugating to thiol groups in a PBRM is of Formula (IIIb):

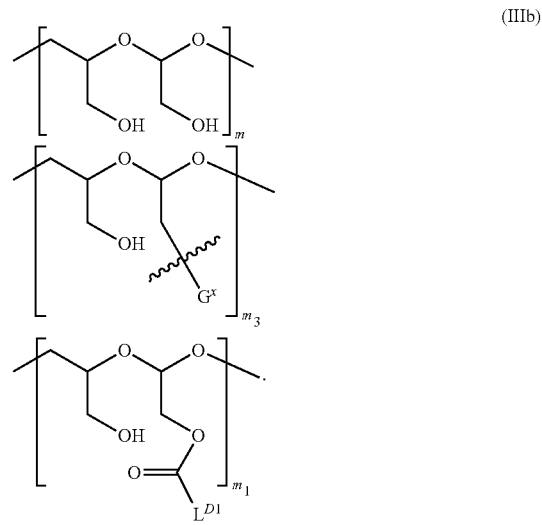

(IIIb)

The wavy line in Formula (IIIb) above denotes direct or indirect attachment of -$G^X$ to the backbone of PHF. For example, -$G^X$ is connected to the polymeric scaffold by a linker -$L^S$ having the structure:

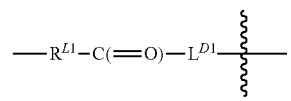

with $R^{L1}$ and $L^{D1}$ defined as herein and

denoting direct or indirect attachment of $L^{D1}$ to $G^X$. m, $m_1$, and $m_3$ are as defined herein.

For example, m is an integer from 1 to 2200.

For example, $m_3$ is an integer from 2 to 20 (e.g., an integer from 2 to 10, or an integer from 2 to 6).

For example, $m_1$ is an integer from 1 to 660.

In yet another embodiment, the scaffold for conjugating to thiol groups in a PBRM is of Formula (IIIc):

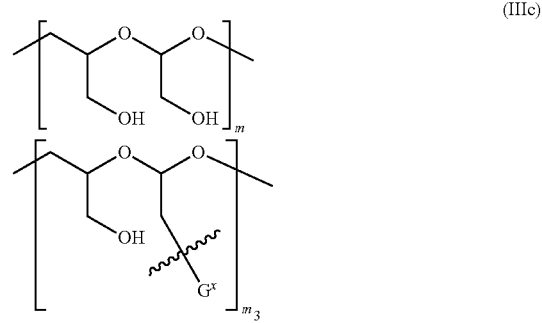

(IIIc)

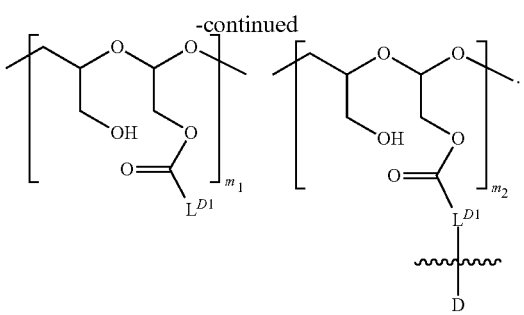

The wavy line in Formula (IIIc) above denotes direct or indirect attachment of -$G^X$ to the backbone of PHF. For example, -$G^X$ is connected to the polymeric scaffold by a linker -$L^S$ having the structure:

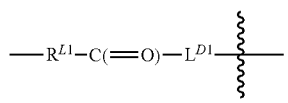

with $R^{L1}$ and $L^{D1}$ defined as herein and

denoting direct or indirect attachment of $L^{D1}$ to $G^X$. D, m, $m_1$, $m_2$, and $m_3$ are as defined herein.

For example, m is an integer from 1 to 2200.

For example, $m_3$ is an integer from 2 to 20 (e.g., an integer from 2 to 10, or an integer from 2 to 6).

For example, $m_1$ is an integer from 1 to 660.

For example, $m_2$ is an integer from 1 to 300.

In some embodiments, the drug-polymer-PBRM conjugates, drug-polymer conjugates, drug carrying-polymeric scaffolds, or PBRM-carrying polymer scaffolds described herein each have a polydispersity index (PDI) of less than 2.

PBRM-drug-polymer conjugates, drug carrying-polymeric scaffolds, or PBRM-carrying polymer scaffolds can be purified (i.e., removal of residual unreacted drug, PBRM, or polymeric starting materials) by extensive diafiltration. If necessary, additional purification by size exclusion chromatography can be conducted to remove any aggregated PBRM-drug polymer conjugates. In general, the PBRM-drug polymer conjugates as purified typically contain <5% aggregated PBRM-drug polymer conjugates as determined by SEC or SDS-PAGE; <1% polymer-drug conjugate as determined by SEC and <2% unconjugated PBRM as determined by RP HPLC.

Tables D and E below provide examples of the drug-carrying polymeric scaffolds and the polymer-drug-protein conjugates of the invention respectively.

TABLE D
| Ref # | Drug: PHF Ratio | Structure |
|---|---|---|
| Ex 9 | | 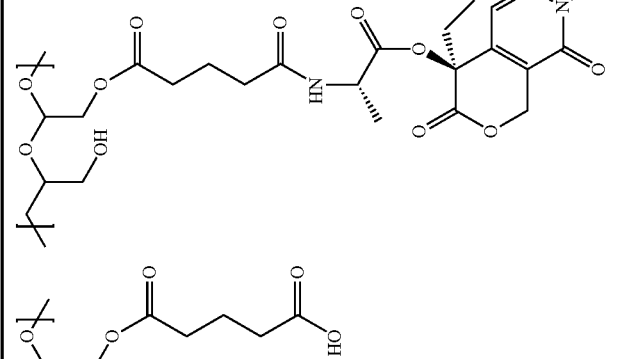 |

TABLE D-continued

| Ref # | Drug: PHF Ratio | Structure |
|---|---|---|
| Ex 9 | | 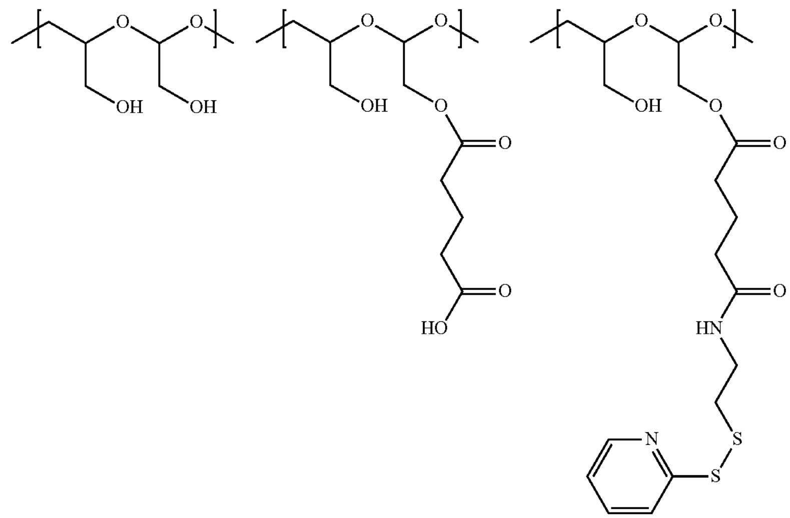 |

TABLE D-continued
| Ref # | Drug: PHF Ratio | Structure |
|---|---|---|
| | | 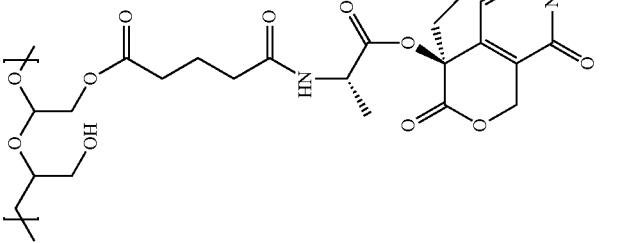 |

TABLE D-continued

| Ref # | Drug: PHF Ratio | Structure |
|---|---|---|
| | 7:1 to 11:1 | |

TABLE D-continued

| Ref # | Drug: PHF Ratio | Structure |
|---|---|---|
| | 11:1 to 15:1 | |

TABLE D-continued
| Ref # | Drug: PHF Ratio | Structure |
|---|---|---|
| Ex 6 | | 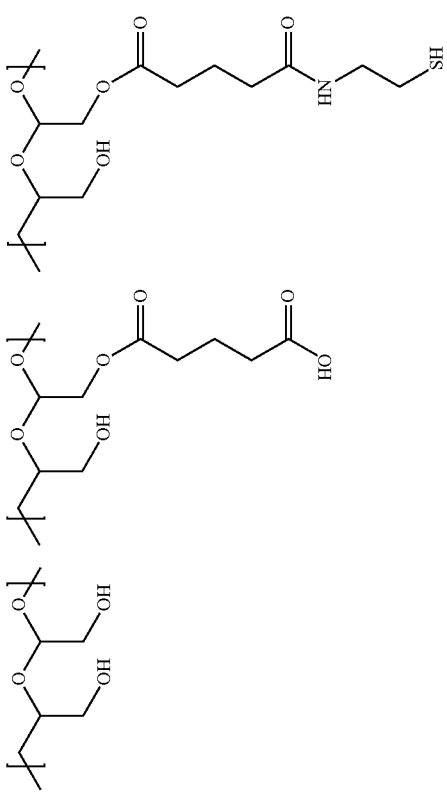 |

TABLE D-continued
| Ref # | Drug: PHF Ratio | Structure |
|---|---|---|
| Ex 18 | | 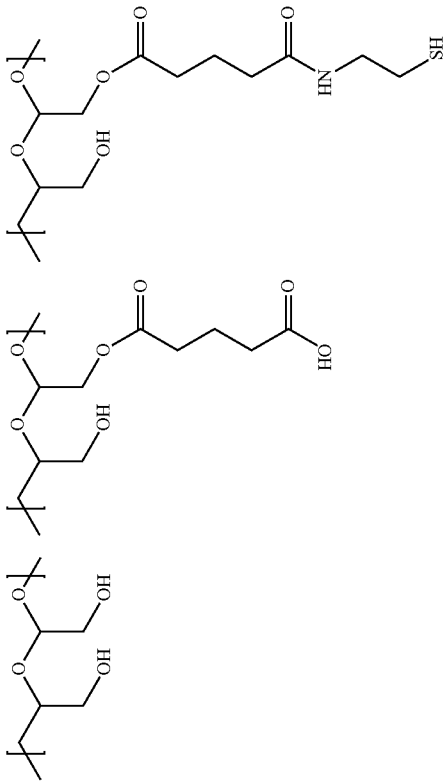 |

TABLE D-continued
| Ref # | Drug: PHF Ratio | Structure |
|---|---|---|
| Ex 13 | 24:1 to 28:1 | 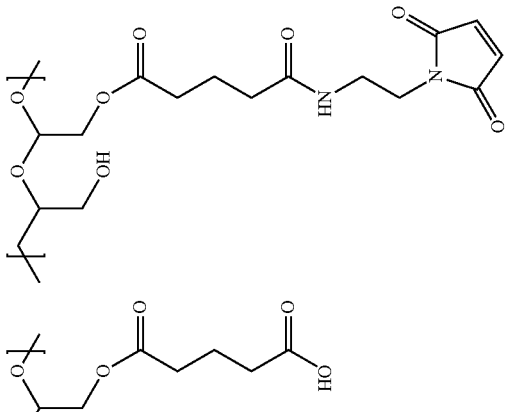 |

TABLE D-continued
| Ref # | Drug: PHF Ratio | Structure |
|---|---|---|
| Ex 59 | 11:1 to 15.1 | 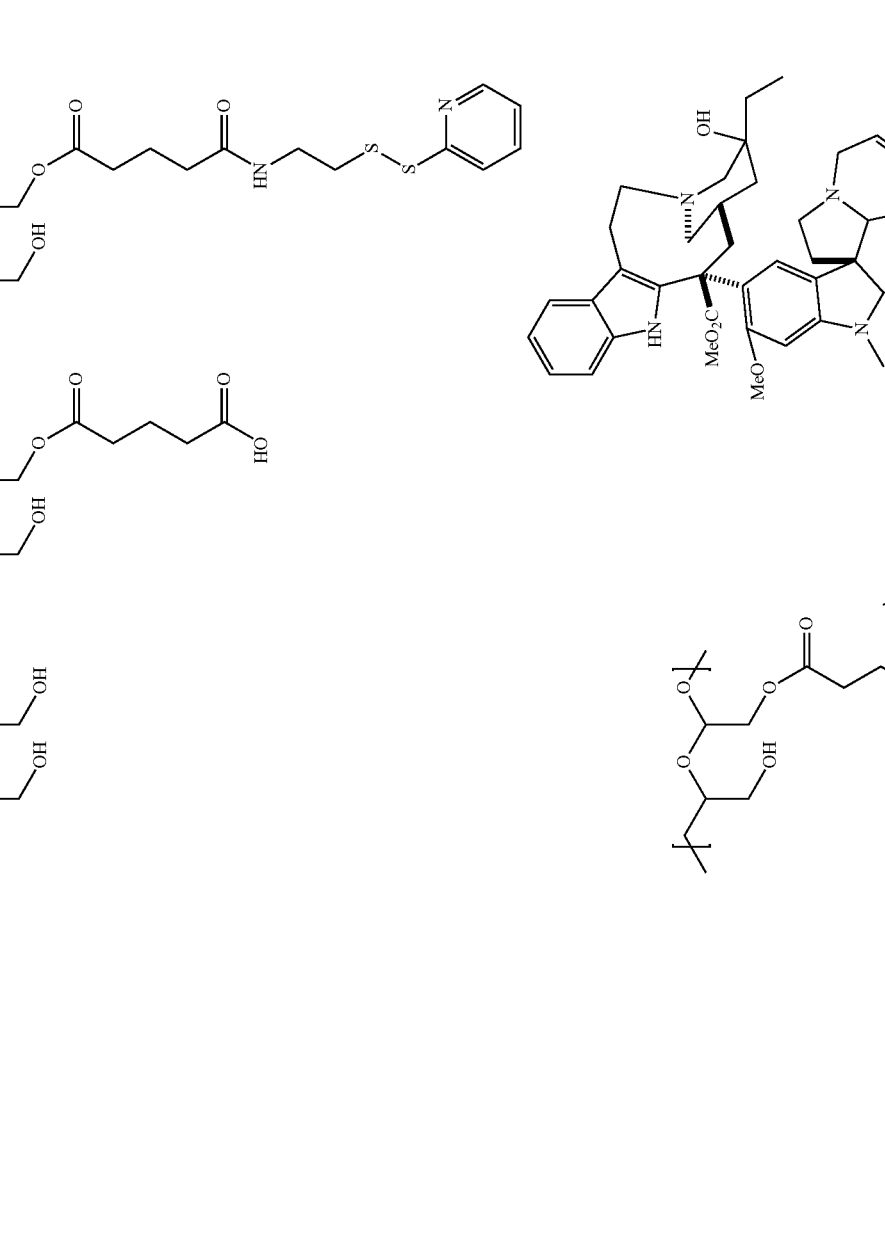 |

TABLE D-continued
| Ref # | Drug: PHF Ratio | Structure |
|---|---|---|
| Ex 20 | | 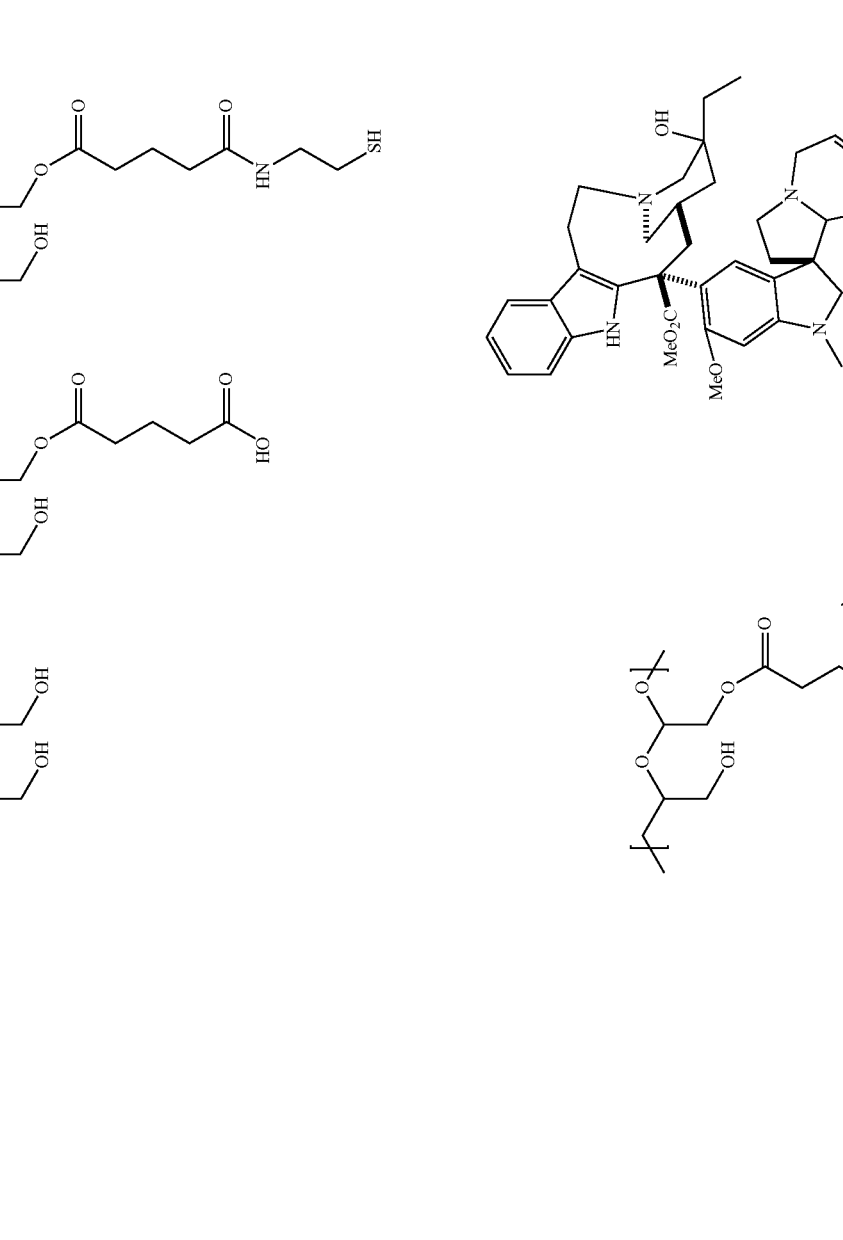 |

TABLE D-continued

| Ref # | Drug: PHF Ratio | Structure |
|---|---|---|
|  | 4:1 to 8:1 |  |

TABLE D-continued
| Ref # | Drug: PHF Ratio | Structure |
|---|---|---|
| | 11:1 to 15.1 | 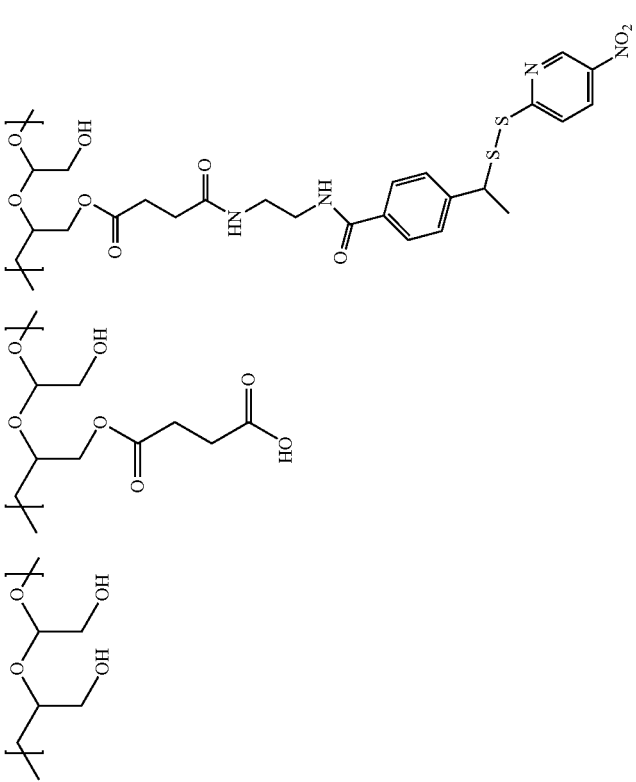 |

TABLE D-continued
| Ref # | Drug: PHF Ratio | Structure |
|---|---|---|
| | 1:1 to 5:1 | 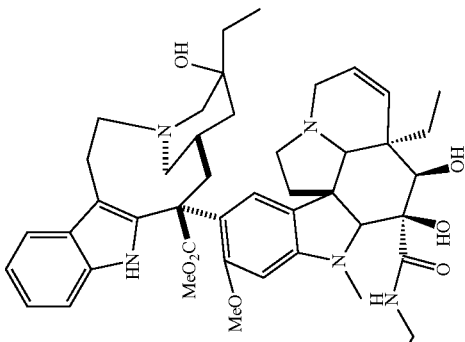 |

TABLE D-continued
| Ref # | Drug: PHF Ratio | Structure |
|---|---|---|
| | | 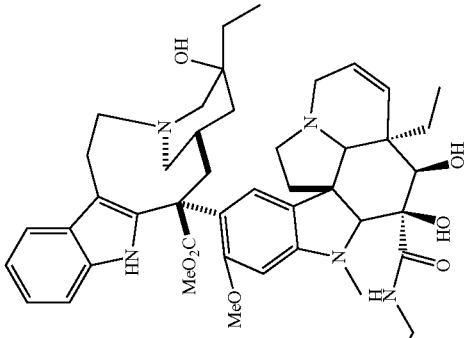 |

TABLE D-continued
| Ref # | Drug: PHF Ratio | Structure |
|---|---|---|
| | 1:1 to 5:1 | 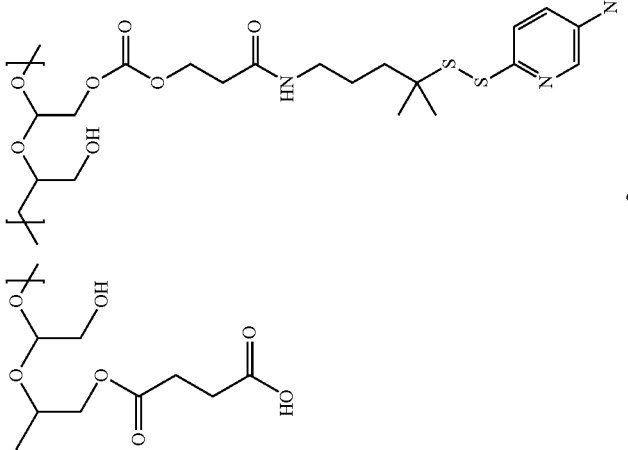 |

TABLE D-continued
| Ref # | Drug: PHF Ratio | Structure |
|---|---|---|
| | | 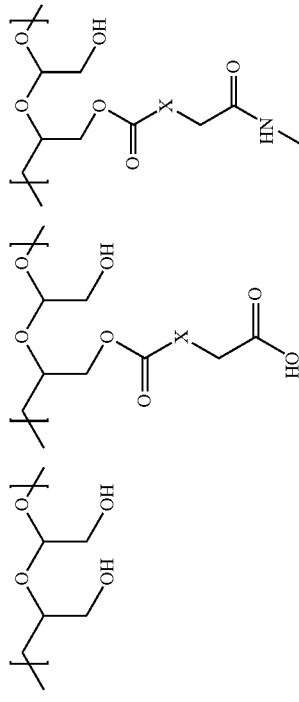 |

TABLE D-continued
| Ref # | Drug: PHF Ratio | Structure |
|---|---|---|
| Ex 26 | | 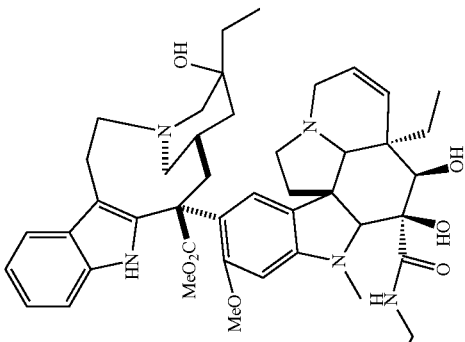 |

TABLE D-continued
| Ref # | Drug: PHF Ratio | Structure |
|---|---|---|
| Ex 28 | | 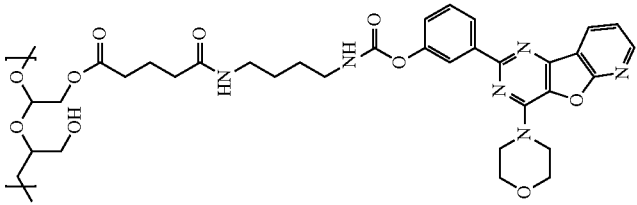 |

TABLE D-continued
| Ref # | Drug: PHF Ratio | Structure |
|---|---|---|
| Ex 31 | | 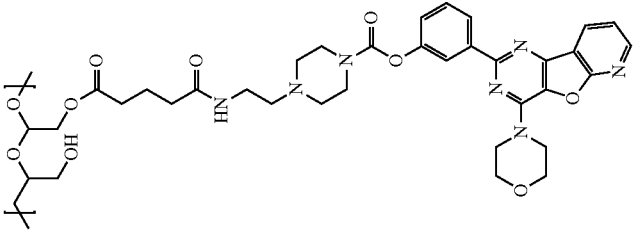 |

TABLE D-continued
| Ref # | Drug: PHF Ratio | Structure |
|---|---|---|
| Ex 34 | | 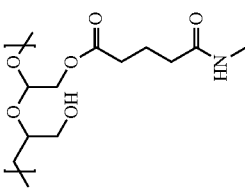 |

TABLE D-continued

| Ref # | Drug: PHF Ratio | Structure |
|---|---|---|

TABLE D-continued
| Ref # | Drug: PHF Ratio | Structure |
|---|---|---|
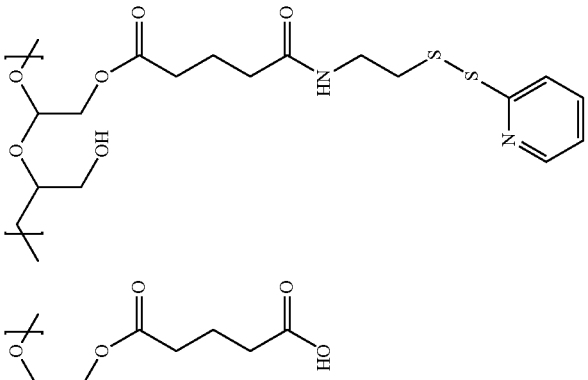

TABLE D-continued
| Ref # | Drug: PHF Ratio | Structure |
|---|---|---|
| Ex 37 | | 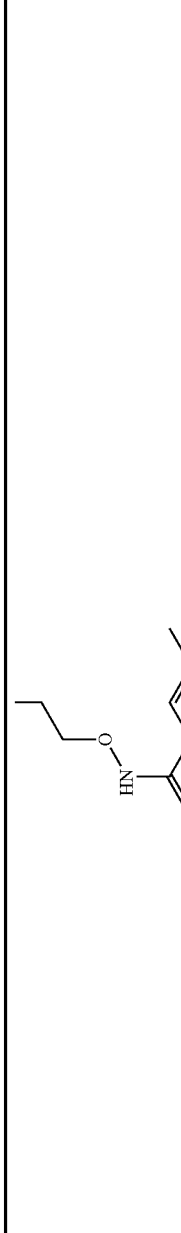 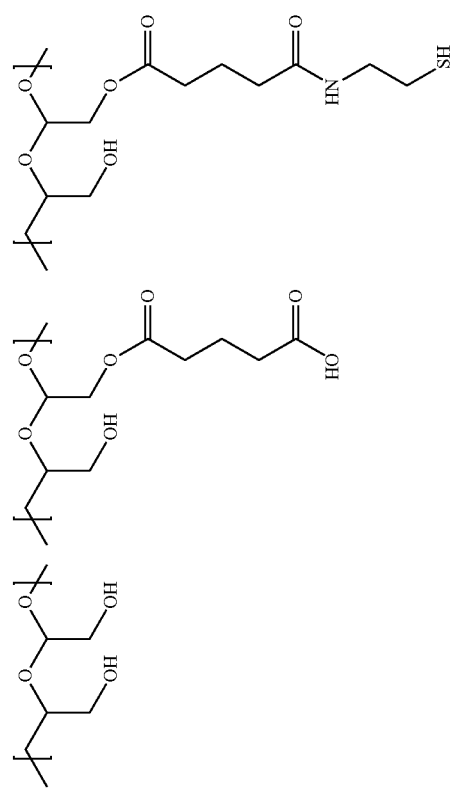 |

TABLE D-continued

| Ref # | Drug: PHF Ratio | Structure |
|---|---|---|

TABLE D-continued
| Ref # | Drug: PHF Ratio | Structure |
|---|---|---|
| Ex 47 | | 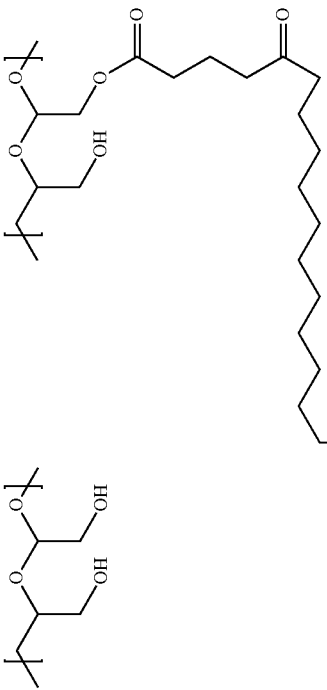 |

TABLE D-continued

| Ref # | Drug: PHF Ratio | Structure |
|---|---|---|
| Ex 44 | | 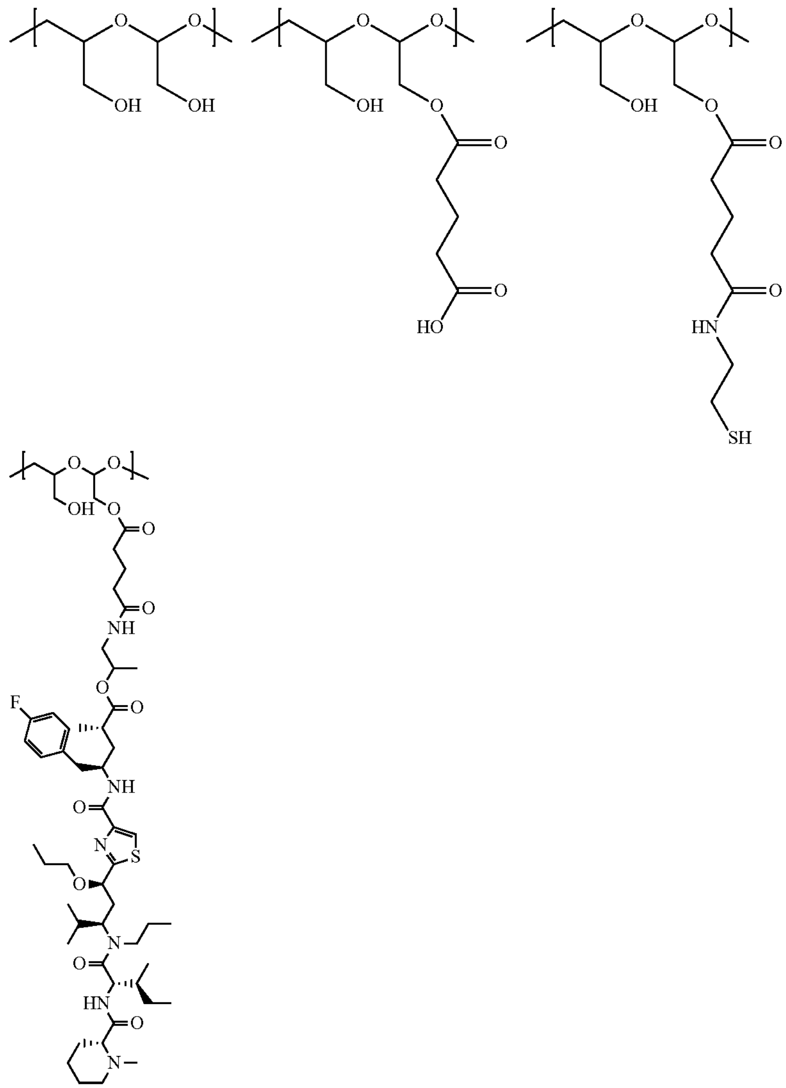 |

TABLE D-continued
| Ref # | Drug: PHF Ratio | Structure |
|---|---|---|
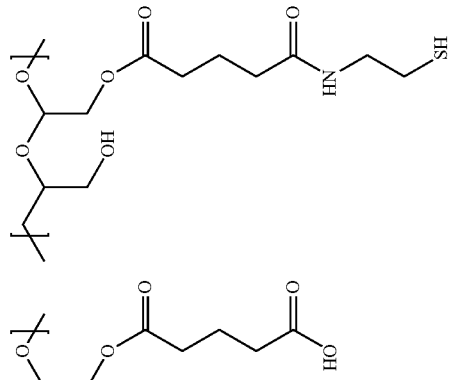
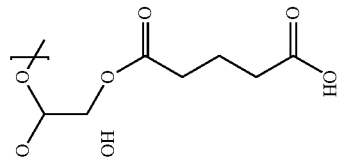
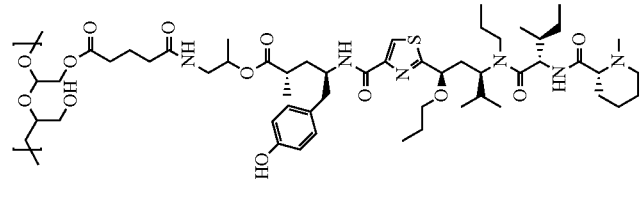

TABLE D-continued
| Ref # | Drug: PHF Ratio | Structure |
|---|---|---|
| | 11:1 to 15:1 | 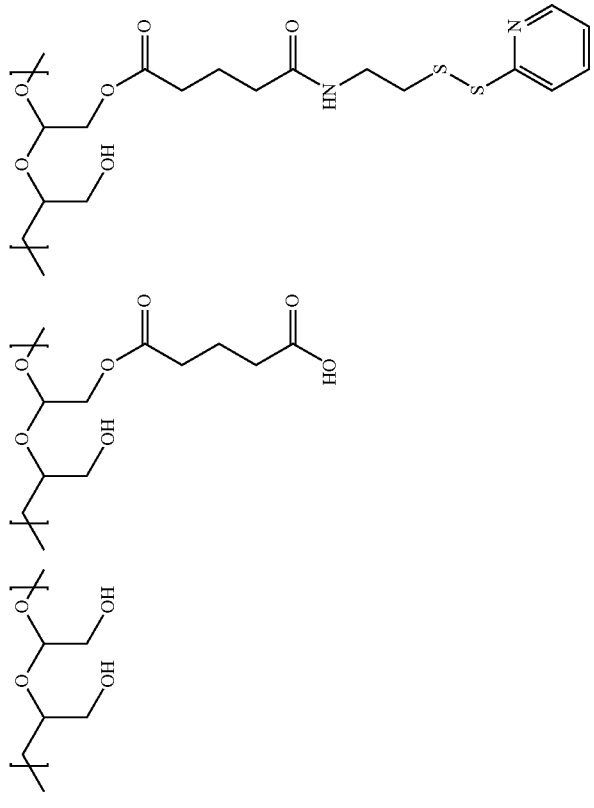 |

TABLE D-continued
| Ref # | Drug: PHF Ratio | Structure |
|---|---|---|
| | | 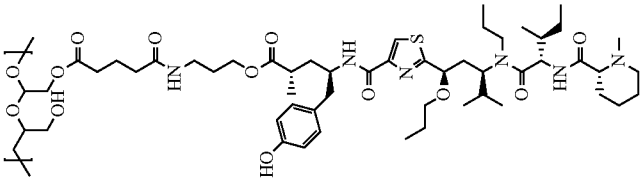 |

TABLE D-continued
| Ref # | Drug: PHF Ratio | Structure |
|---|---|---|
| Ex 74 | | 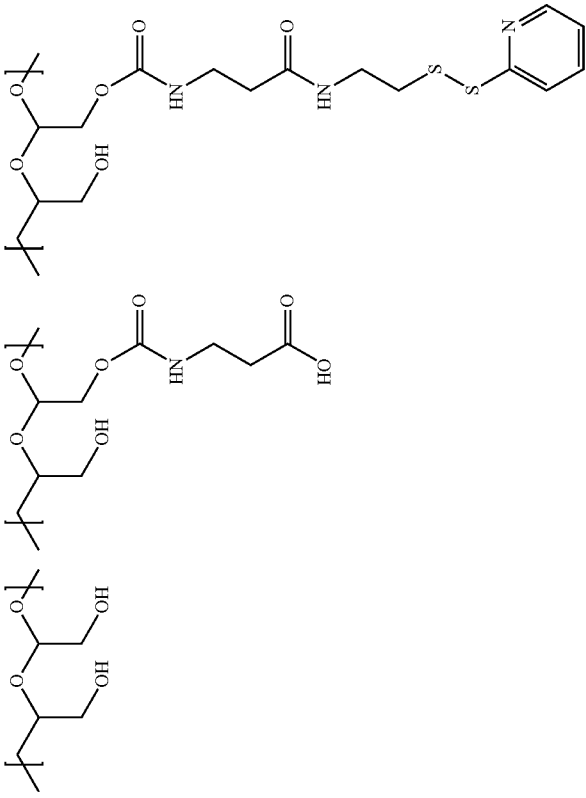 |

TABLE D-continued
| Ref # | Drug: PHF Ratio | Structure |
|---|---|---|
| | | 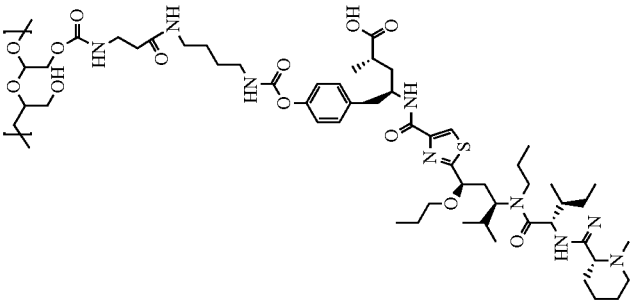 |

TABLE D-continued
| Ref # | Drug: PHF Ratio | Structure |
|---|---|---|
| Ex 77 | | 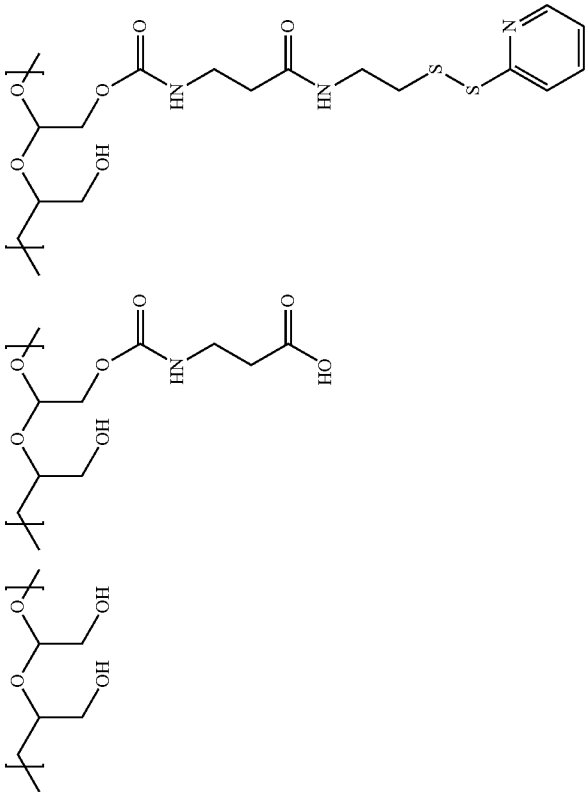 |

TABLE D-continued
| Ref # | Drug: PHF Ratio | Structure |
|---|---|---|
| | | 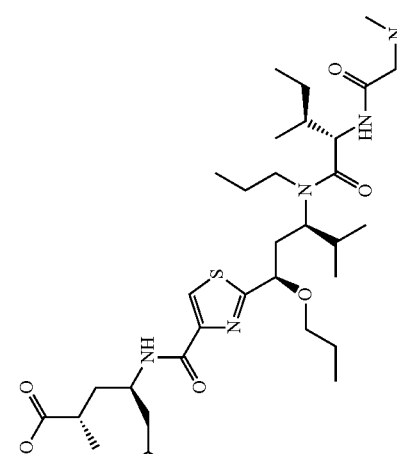 |

| Ref # | Drug: PHF Ratio | Structure |
|---|---|---|
| Ex 80 | | 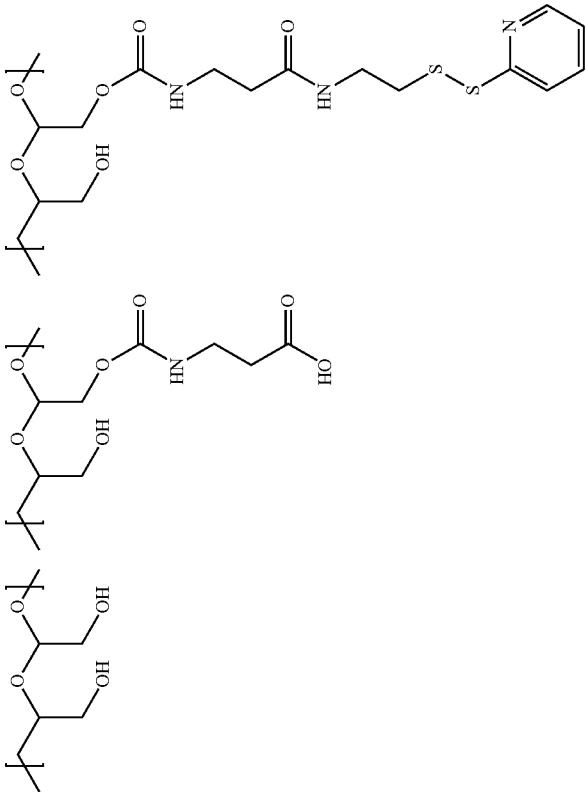 |

TABLE D-continued
| Ref # | Drug: PHF Ratio | Structure |
|---|---|---|
| | | 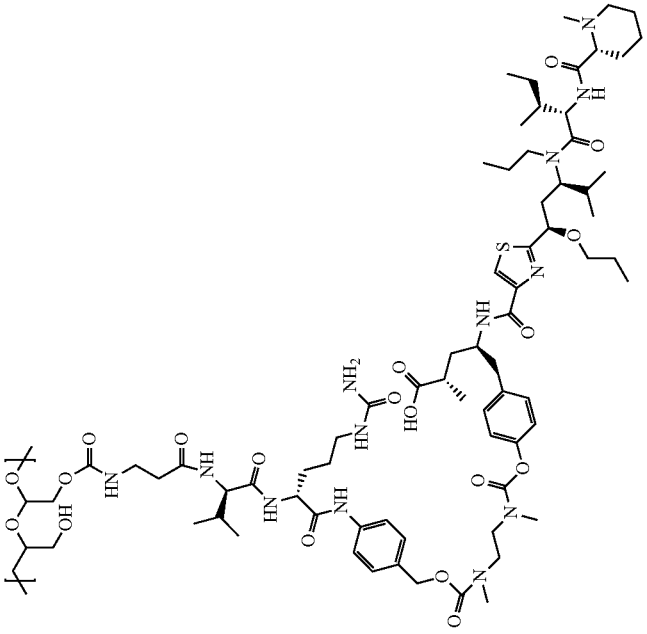 |

TABLE D-continued
| Ref # | Drug: PHF Ratio | Structure |
|---|---|---|
| Ex 40 | | 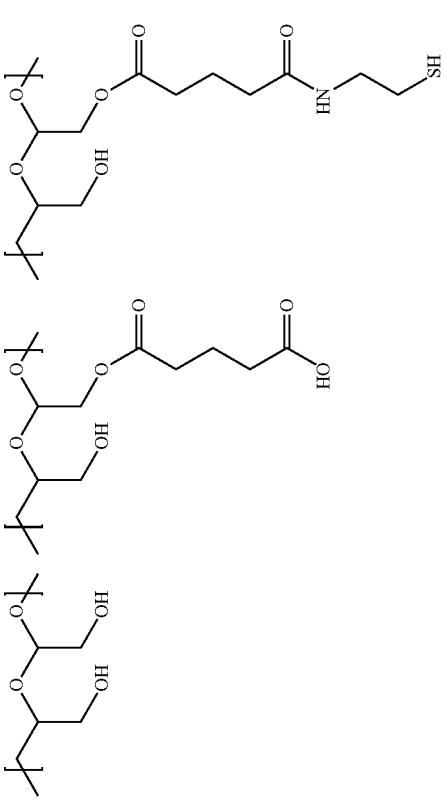 |

TABLE D-continued
| Ref # | Drug: PHF Ratio | Structure |
|---|---|---|
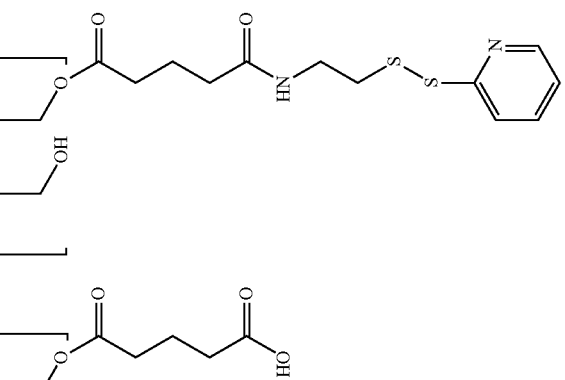

TABLE D-continued
| Ref # | Drug: PHF Ratio | Structure |
|---|---|---|
| | | 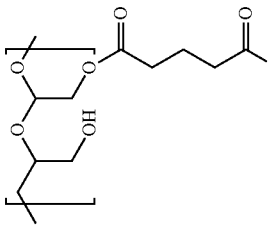 |

TABLE D-continued
| Ref # | Drug: PHF Ratio | Structure |
|---|---|---|
| | X = CH₂<br>1:1 to 4:1 |  |

TABLE D-continued

| Ref # | Drug: PHF Ratio | Structure |
|---|---|---|

TABLE D-continued
| Ref # | Drug: PHF Ratio | Structure |
|---|---|---|
| Ex 51 | | 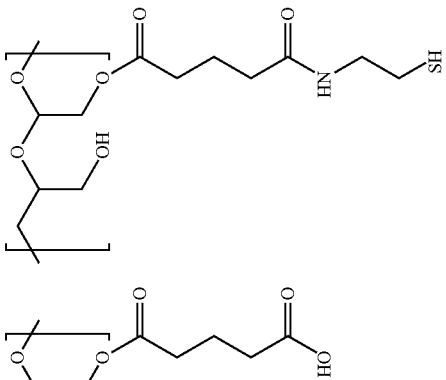 |

TABLE D-continued
| Ref # | Drug: PHF Ratio | Structure |
|---|---|---|
| | 1:1 to 4:1 | 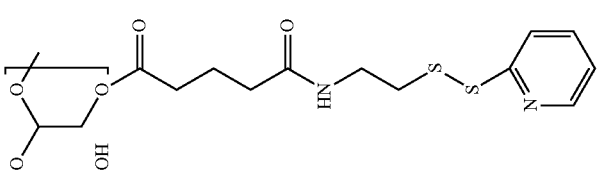 |

TABLE D-continued

| Ref # | Drug: PHF Ratio | Structure |
|---|---|---|

TABLE D-continued

| Ref # | Drug: PHF Ratio | Structure |
|---|---|---|
| Ex 65 | 3:1 to 7:1 | 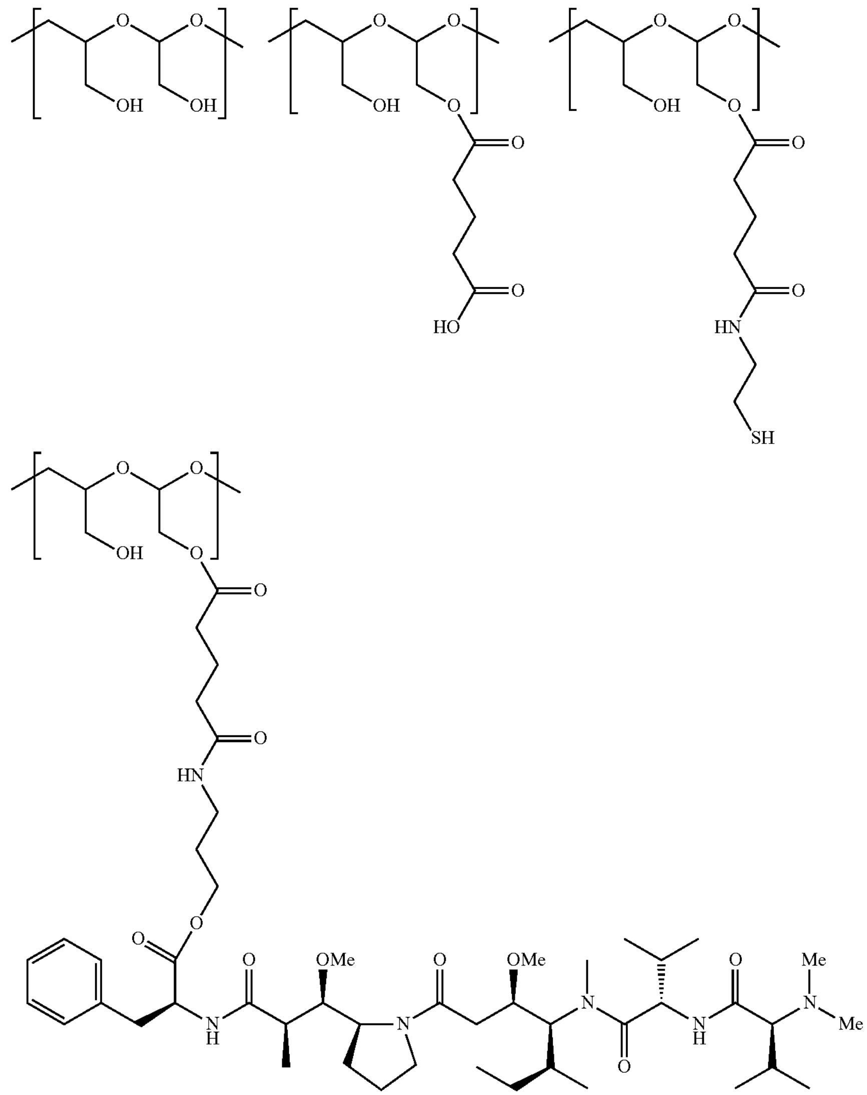 |

TABLE D-continued

| Ref # | Drug: PHF Ratio | Structure |
|---|---|---|
| | 1:1 to 5:1 | |

TABLE D-continued
| Ref # | Drug: PHF Ratio | Structure |
|---|---|---|
| | | 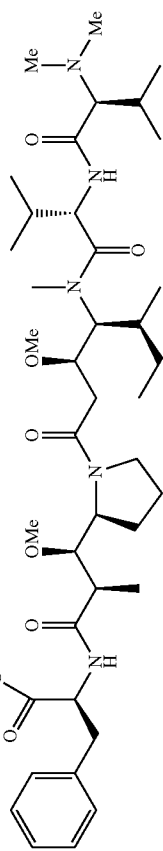 |

TABLE D-continued
| Ref # | Drug: PHF Ratio | Structure |
|---|---|---|
| Ex 69 | 1:1 to 5:1 | 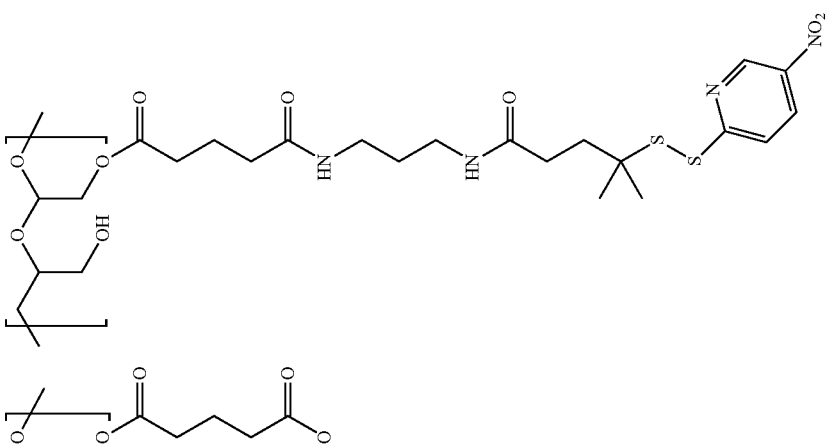 |

TABLE D-continued
| Ref # | Drug: PHF Ratio | Structure |
|---|---|---|
| | | 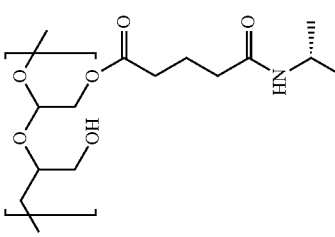 |

TABLE D-continued

| Ref # | Drug: PHF Ratio | Structure |
|---|---|---|
| Ex 71 | | (structure shown) |

TABLE D-continued
| Ref # | Drug: PHF Ratio | Structure |
|---|---|---|
| | 1:1 to 6:1 | 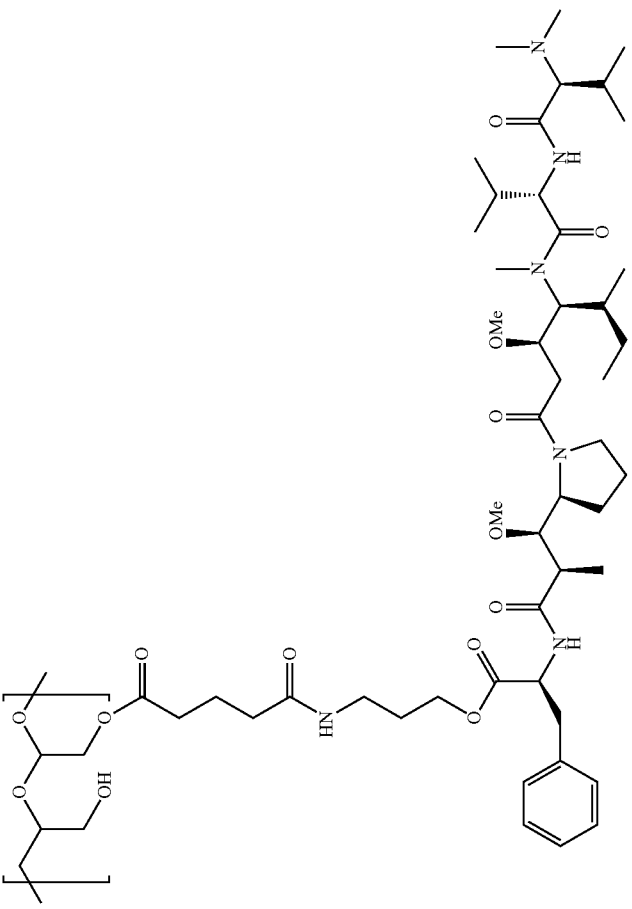 |

TABLE D-continued
| Ref # | Drug: PHF Ratio | Structure |
|---|---|---|
| | 1:1 to 6:1 | 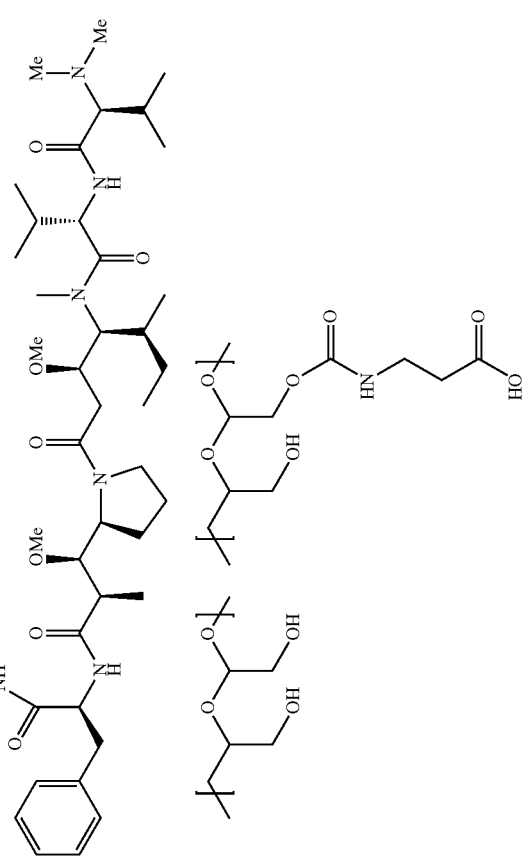 |

TABLE D-continued
| Ref # | Drug: PHF Ratio | Structure |
|---|---|---|
| | 8:1 to 12:1 | 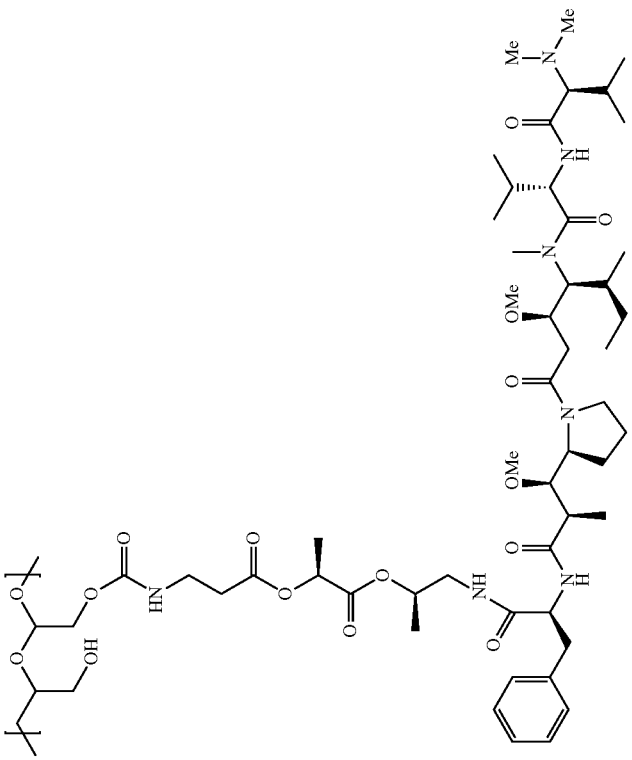 |

TABLE D-continued
| Ref # | Drug: PHF Ratio | Structure |
|---|---|---|
| | 1:1 to 5:1 | 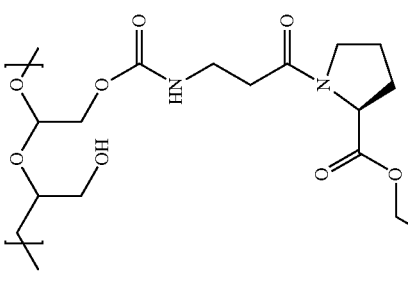 |

TABLE D-continued
| Ref # | Drug: PHF Ratio | Structure |
|---|---|---|
| | |  |

TABLE D-continued
| Ref # | Drug: PHF Ratio | Structure |
|---|---|---|
| | | 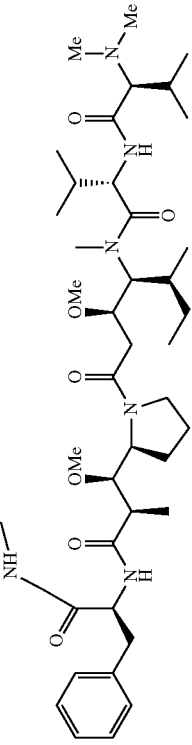 |

TABLE D-continued
| Ref # | Drug: PHF Ratio | Structure |
|---|---|---|
| | | 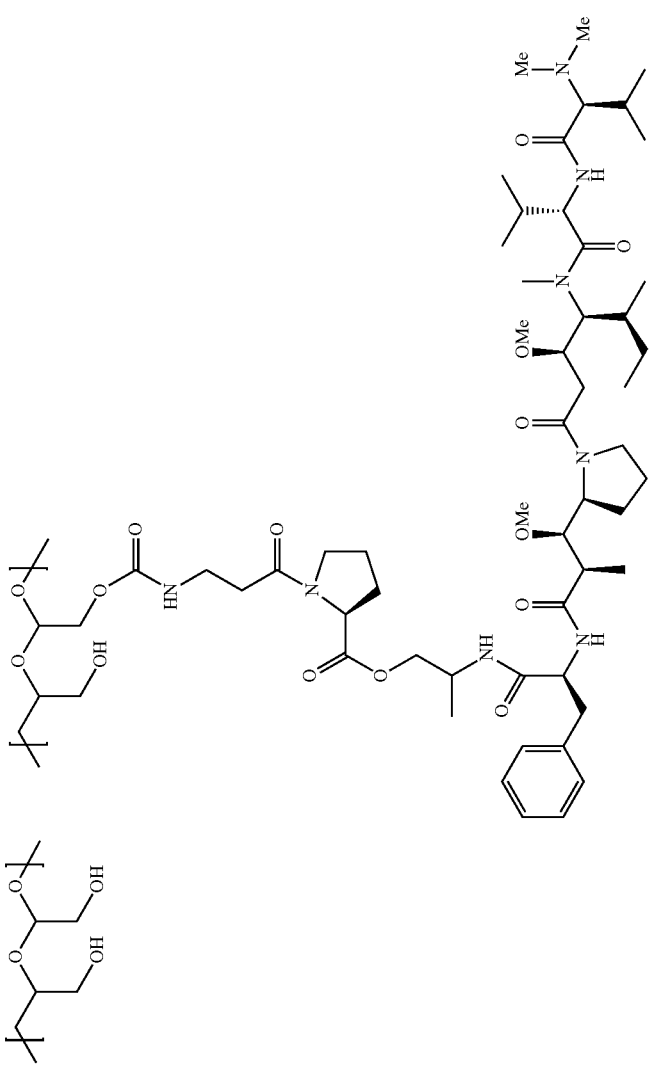 |

TABLE D-continued

| Ref # | Drug: PHF Ratio | Structure |
|---|---|---|

TABLE D-continued
| Ref # | Drug: PHF Ratio | Structure |
|---|---|---|
| Ex 90 Conjugate A | 8:1 to 12:1 | 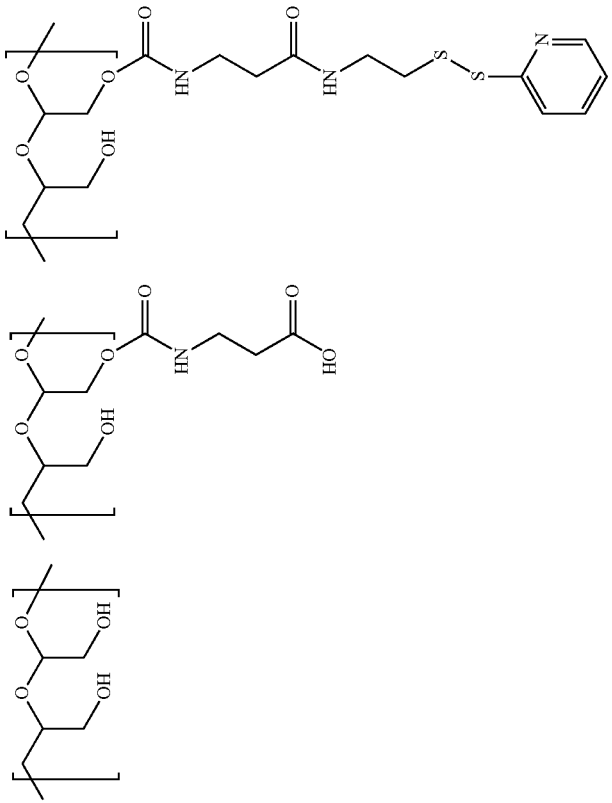 |

TABLE D-continued

| Ref # | Drug: PHF Ratio | Structure |
|---|---|---|

TABLE D-continued
| Ref # | Drug: PHF Ratio | Structure |
|---|---|---|
| | 1:1 to 5:1 | 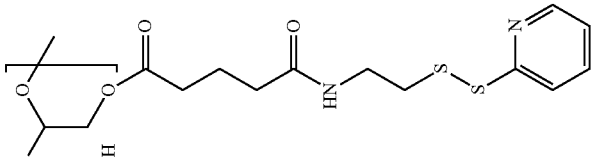 |

TABLE D-continued
| Ref # | Drug: PHF Ratio | Structure |
|---|---|---|
| | 1:1 to 5:1 | 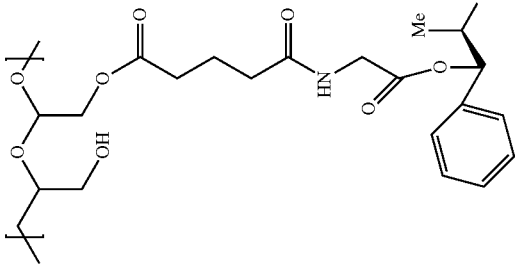 |

TABLE D-continued

| Ref # | Drug: PHF Ratio | Structure |
|---|---|---|

TABLE D-continued

| Ref # | Drug: PHF Ratio | Structure |
|---|---|---|

TABLE D-continued
| Ref # | Drug: PHF Ratio | Structure |
|---|---|---|
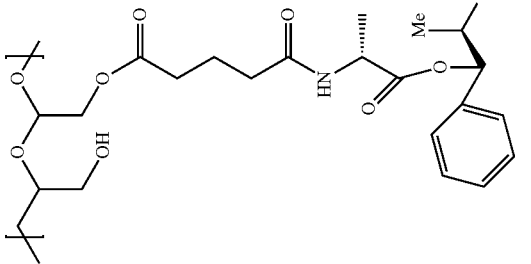

TABLE D-continued
| Ref # | Drug: PHF Ratio | Structure |
|---|---|---|
| | 5:1 to 10:1 | 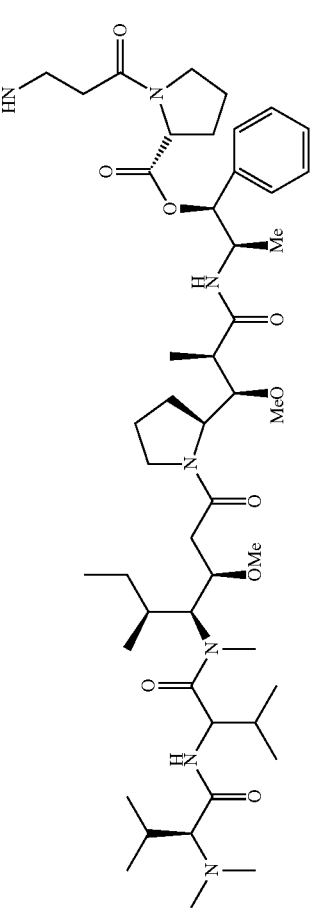 |

TABLE D-continued
| Ref # | Drug: PHF Ratio | Structure |
|---|---|---|
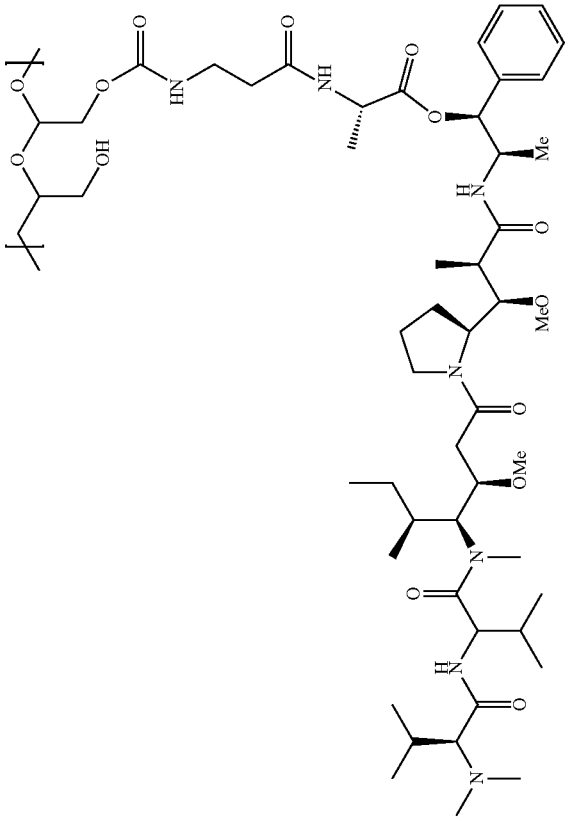

TABLE D-continued
| Ref # | Drug: PHF Ratio | Structure |
|---|---|---|
| | 1:1 to 5:1 | 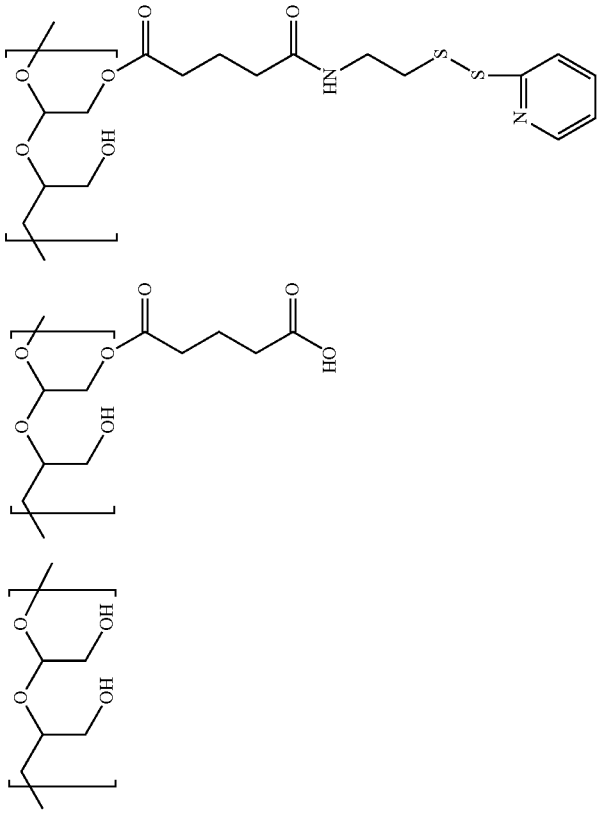 |

TABLE D-continued
| Ref # | Drug: PHF Ratio | Structure |
|---|---|---|
| | | 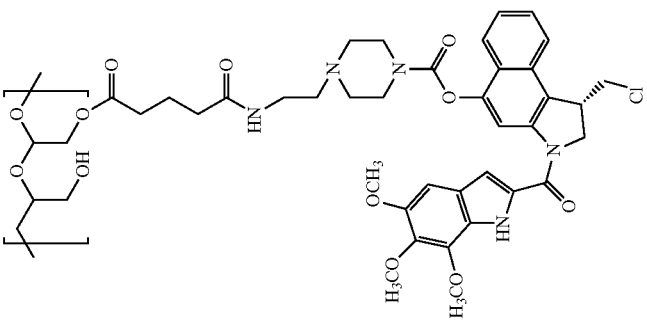 |

TABLE D-continued

| Ref # | Drug: PHF Ratio | Structure |
|---|---|---|
| | 12:1 to 16:1 | (structure image) |

TABLE D-continued

| Ref # | Drug: PHF Ratio | Structure |
|---|---|---|

TABLE D-continued

| Ref # | Drug: PHF Ratio | Structure |
|---|---|---|
|  | 5:1 to 9:1 |  |

TABLE D-continued
| Ref # | Drug: PHF Ratio | Structure |
|---|---|---|
| | 2:1 to 6:1 | 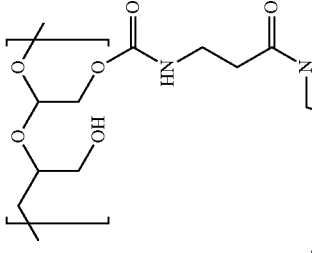 |

TABLE D-continued

| Ref # | Drug: PHF Ratio | Structure |
|-------|-----------------|-----------|

TABLE D-continued

| Ref # | Drug: PHF Ratio | Structure |
|---|---|---|

TABLE D-continued
| Ref # | Drug: PHF Ratio | Structure |
|---|---|---|
|  |  | 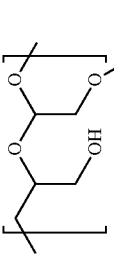 |

TABLE D-continued

| Ref # | Drug: PHF Ratio | Structure |
|---|---|---|
| | X = CH$_2$ or —N 1:1 to 5:1 | |

TABLE D-continued
| Ref # | Drug: PHF Ratio | Structure |
|---|---|---|
| | | 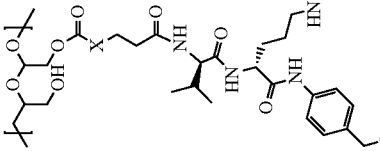 |

TABLE D-continued
| Ref # | Drug: PHF Ratio | Structure |
|---|---|---|
| Ex 85 | | 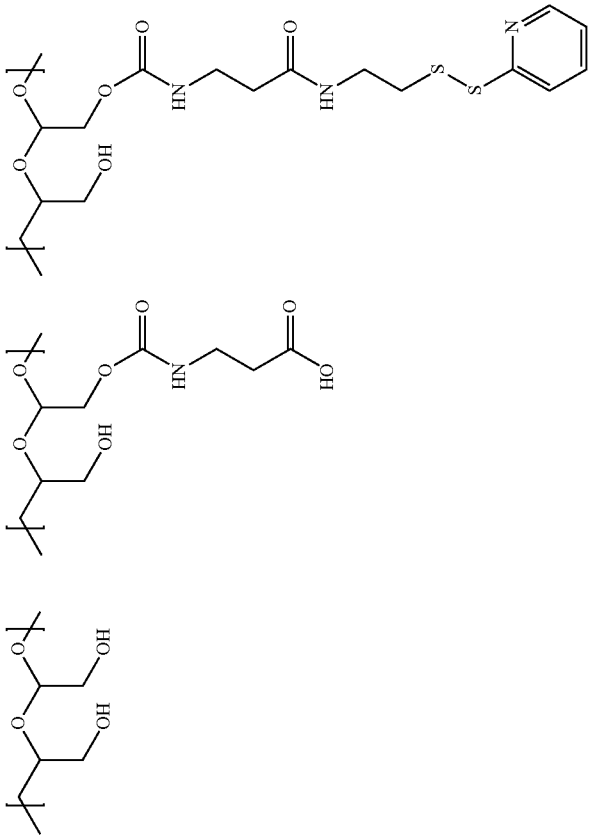 |

TABLE D-continued
| Ref # | Drug: PHF Ratio | Structure |
|---|---|---|
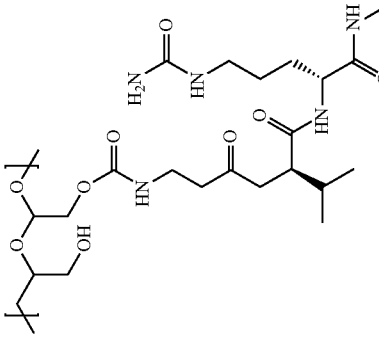

TABLE D-continued
| Ref # | Drug: PHF Ratio | Structure |
|---|---|---|
| Ex 88 | | 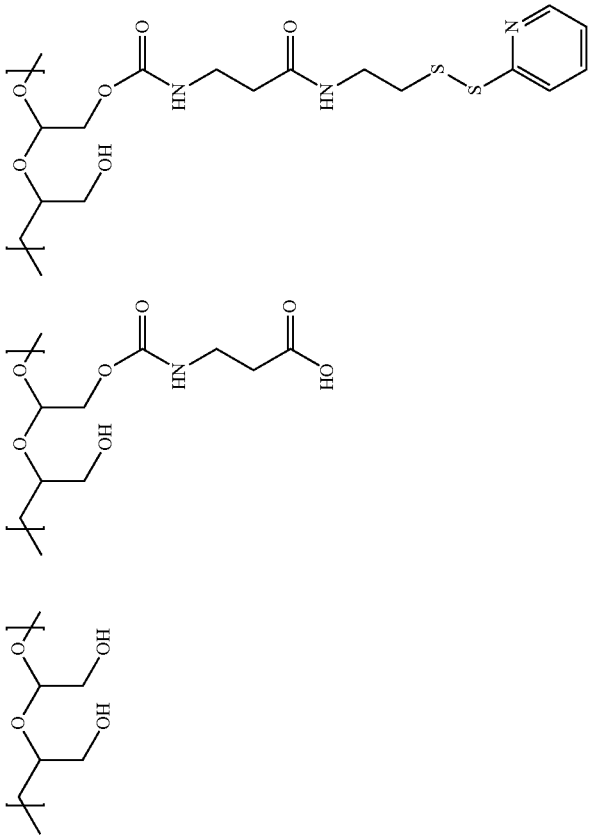 |

TABLE D-continued
| Ref # | Drug: PHF Ratio | Structure |
|---|---|---|
| | | 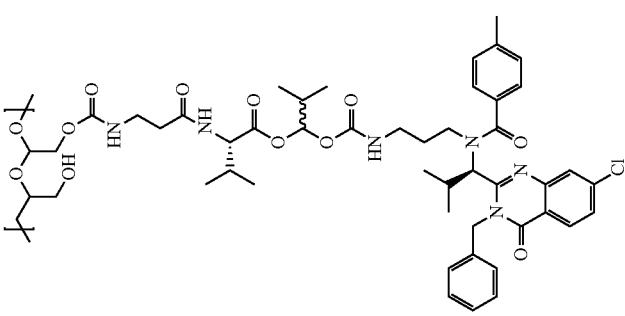 |

TABLE D-continued
| Ref # | Drug: PHF Ratio | Structure |
|---|---|---|
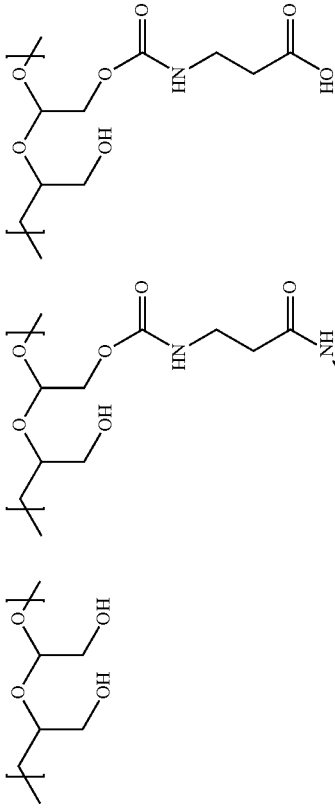

TABLE D-continued

| Ref # | Drug:PHF Ratio | Structure |
|---|---|---|

TABLE D-continued

| Ref # | Drug: PHF Ratio | Structure |
|---|---|---|

TABLE D-continued
| Ref # | Drug: PHF Ratio | Structure |
|---|---|---|
| | | 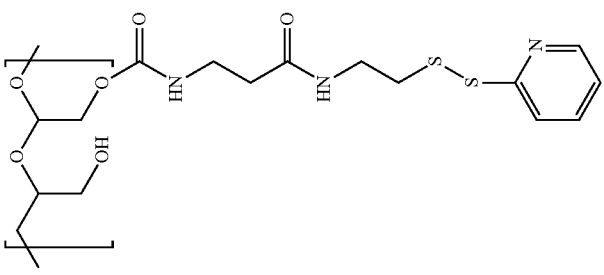 |

371 372
TABLE E
| Ref # | Drug: PBRM Ratio | Structure |
|---|---|---|
| Ex 11 | | 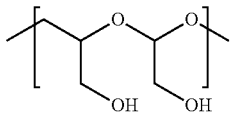 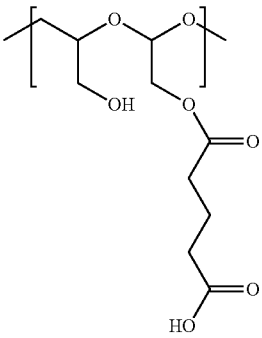 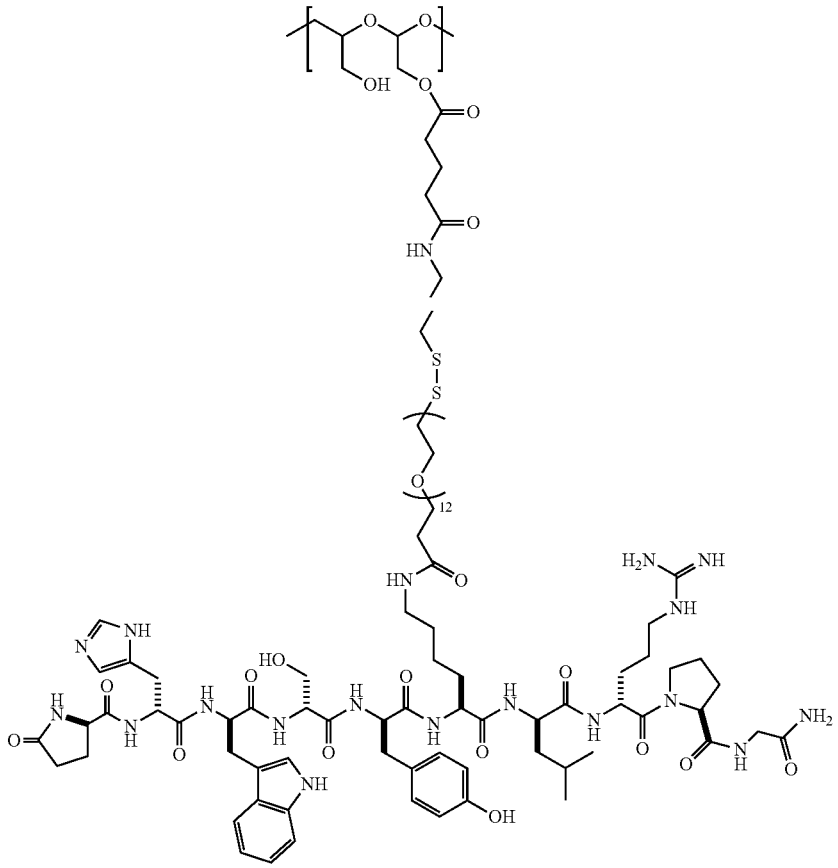 |

TABLE E-continued

| Ref # | Drug: PBRM Ratio | Structure |
|---|---|---|
| Ex 7 | 14.1 to 17:1<br>19.1 to 22:1 | 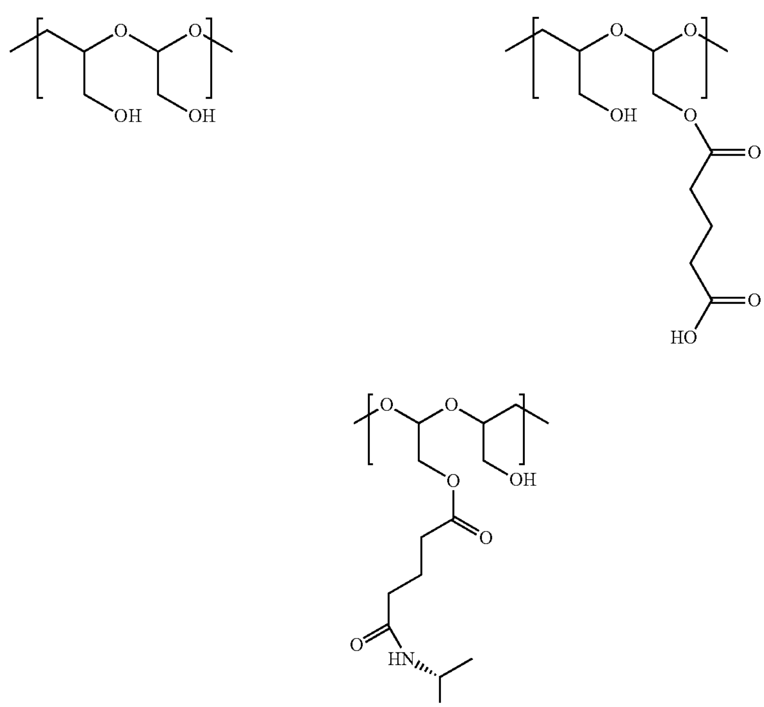 |

TABLE E-continued
| Ref # | Drug: PBRM Ratio | Structure |
|---|---|---|
| | | 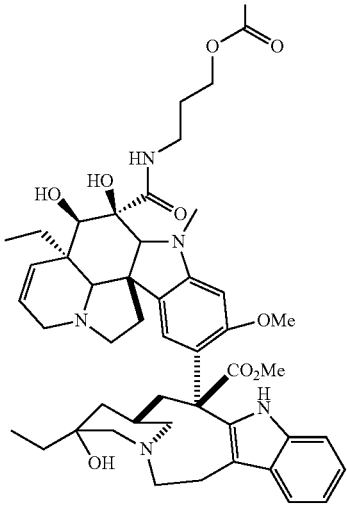 |
| Ex 19 | 10:1 to 12:1 | 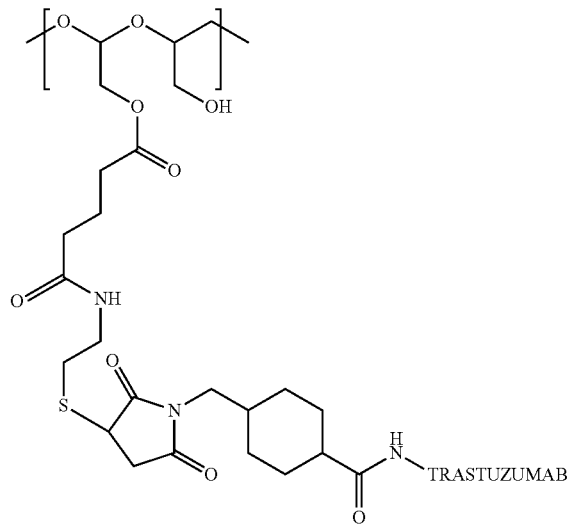 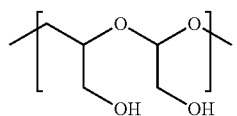 |

TABLE E-continued
| Ref # | Drug: PBRM Ratio | Structure |
|---|---|---|
| | | 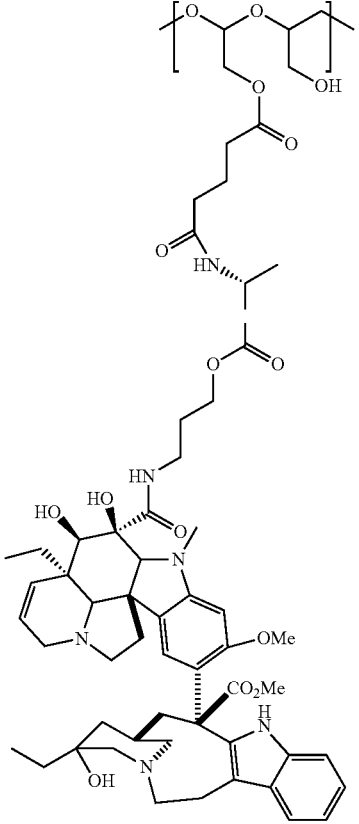 |
| | | 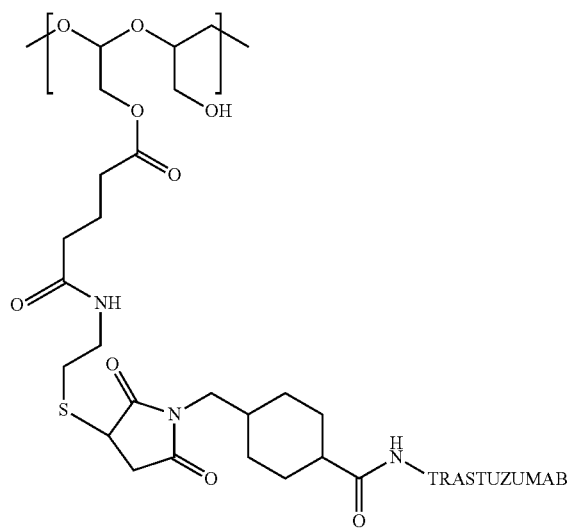 |

TABLE E-continued
| Ref # | Drug: PBRM Ratio | Structure |
|---|---|---|
| Ex 21 | 47:1 to 50:1 | 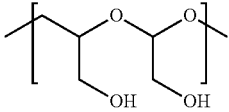 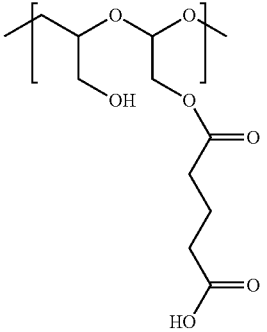 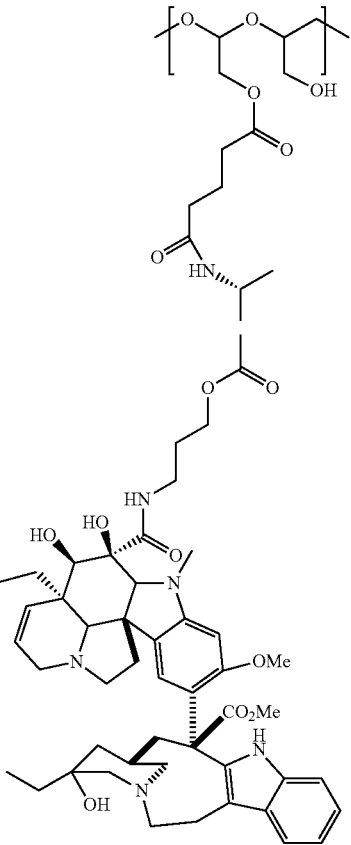 |

TABLE E-continued
| Ref # | Drug: PBRM Ratio | Structure |
|---|---|---|
| | | 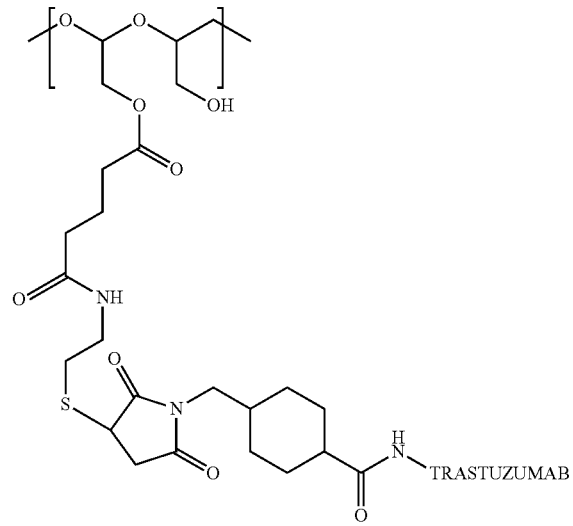 |
| Ex 8 | 16.1 to 18.1 | 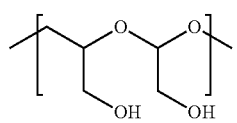 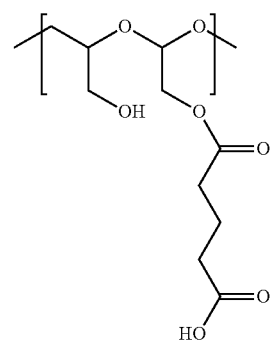 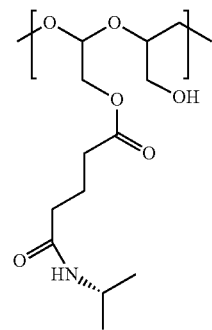 |

TABLE E-continued
| Ref # | Drug: PBRM Ratio | Structure |
|---|---|---|
| | | 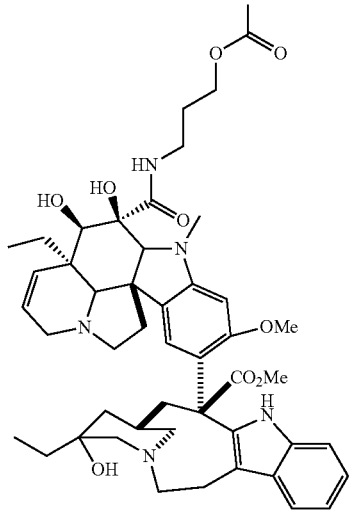 |
| Ex 15 | | 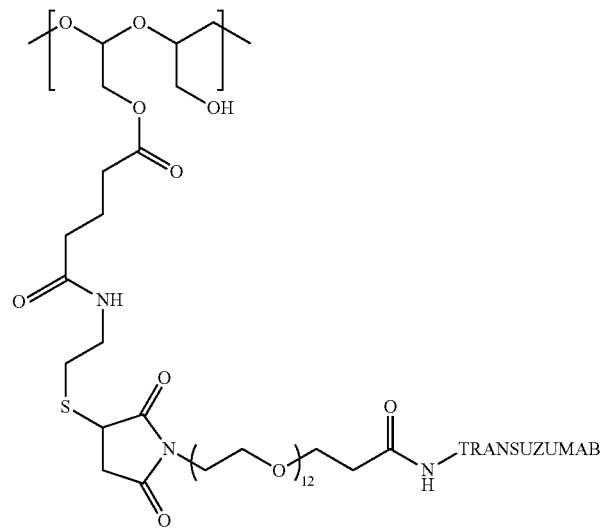 |

TABLE E-continued
| Ref # | Drug: PBRM Ratio | Structure |
|---|---|---|
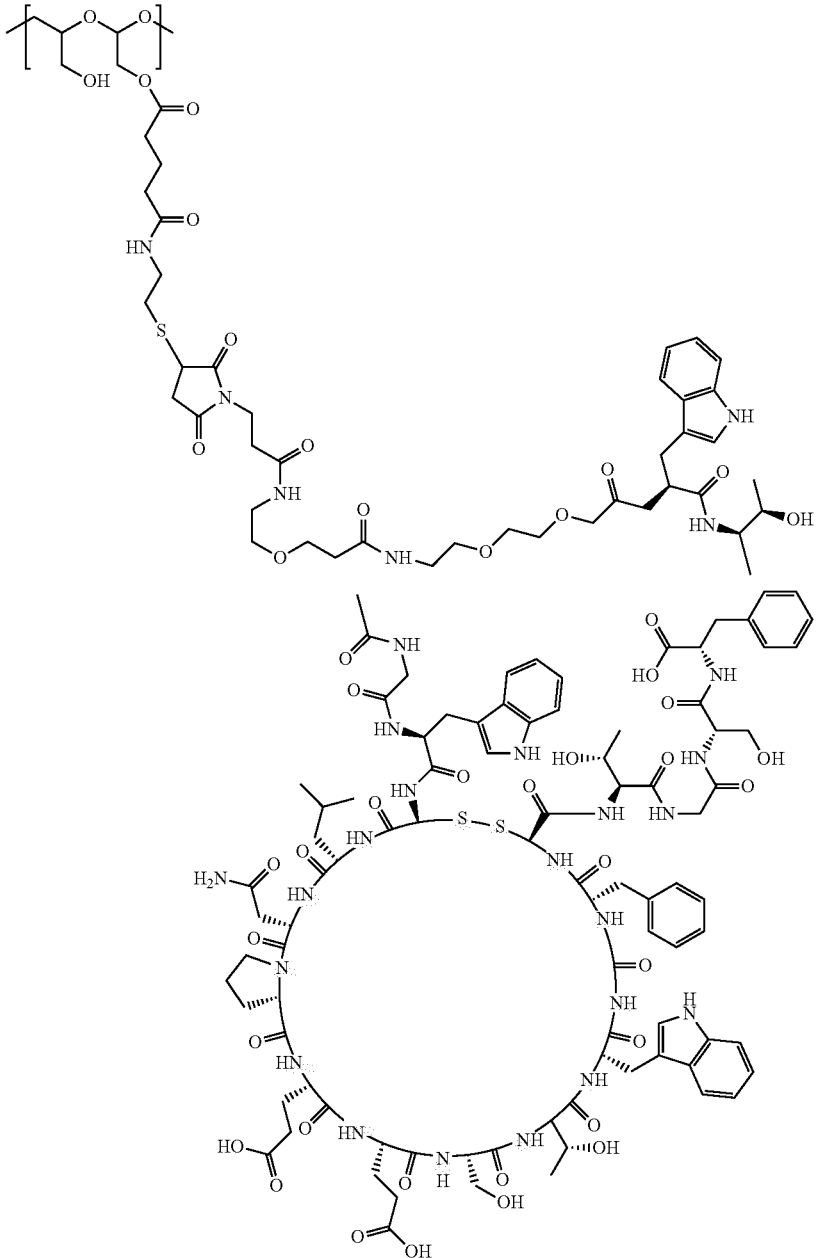

TABLE E-continued

| Ref # | Drug: PBRM Ratio | Structure |
|---|---|---|
| Ex 17 | | 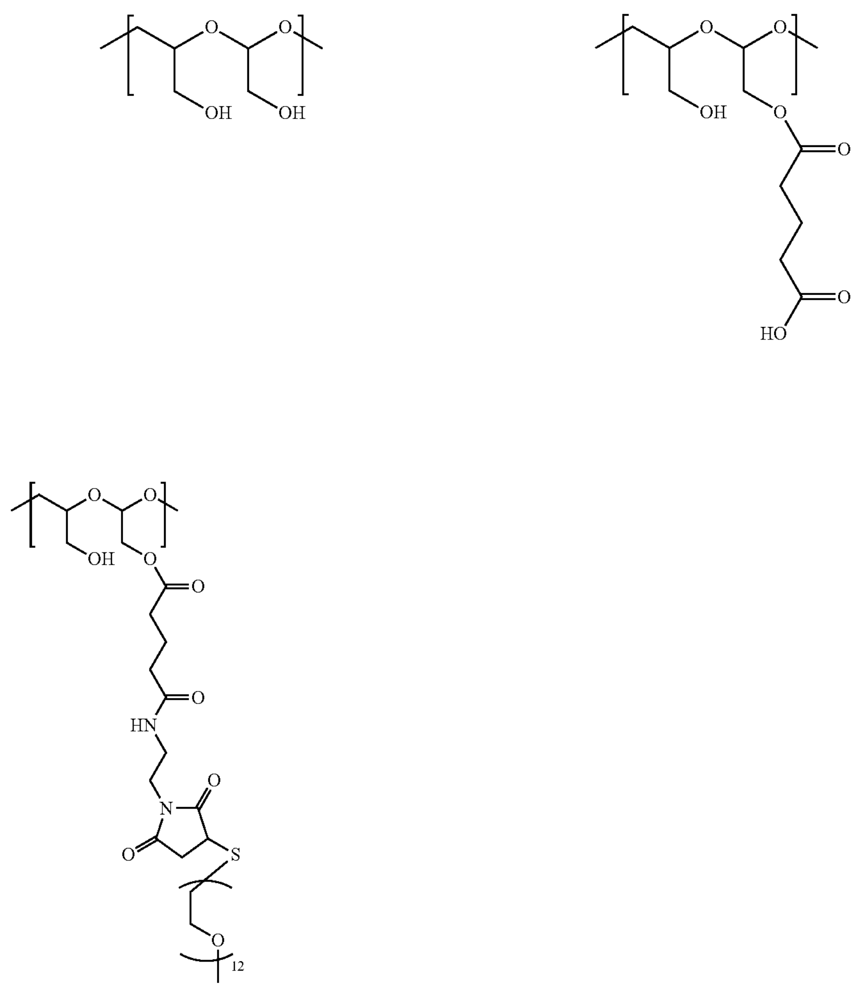 |

TABLE E-continued
| Ref # | Drug: PBRM Ratio | Structure |
|---|---|---|
|  |  | 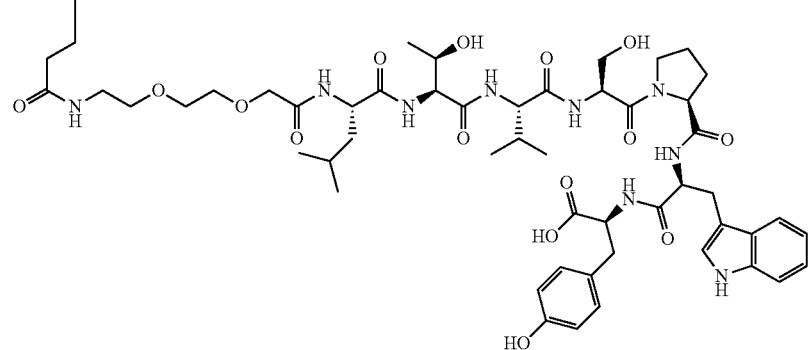 |
|  |  | 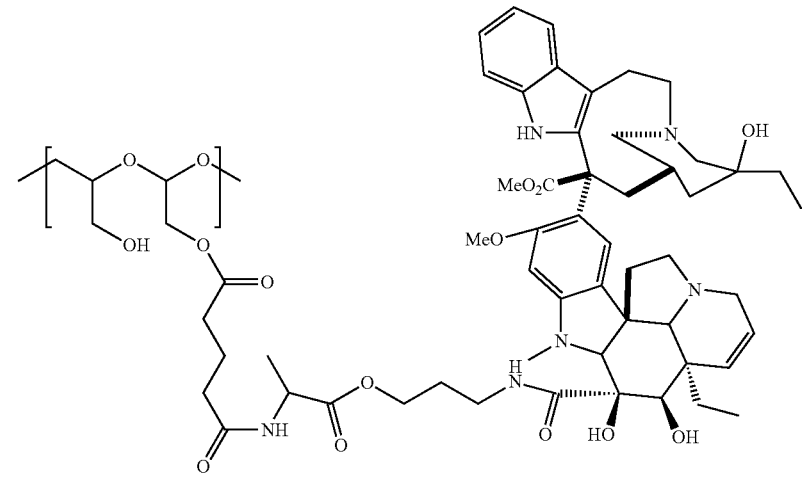 |
| Ex 54 | 12.1 to 15:1 | 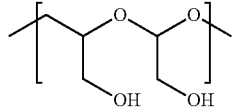 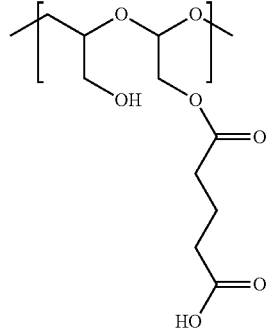 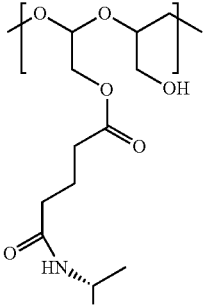 |

TABLE E-continued
| Ref # | Drug: PBRM Ratio | Structure |
|---|---|---|
| | | 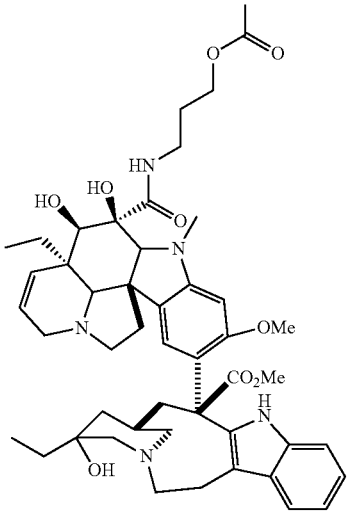 |
| Ex 55 | ~5:1 | 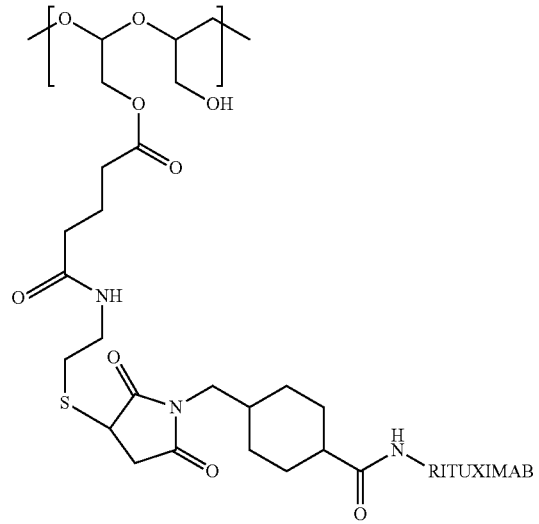 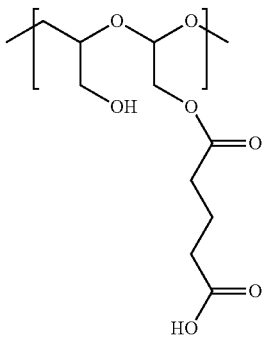 |

TABLE E-continued

| Ref # | Drug: PBRM Ratio | Structure |
|---|---|---|

TABLE E-continued

| Ref # | Drug: PBRM Ratio | Structure |
|---|---|---|
| Ex 56 | ~10:1 | 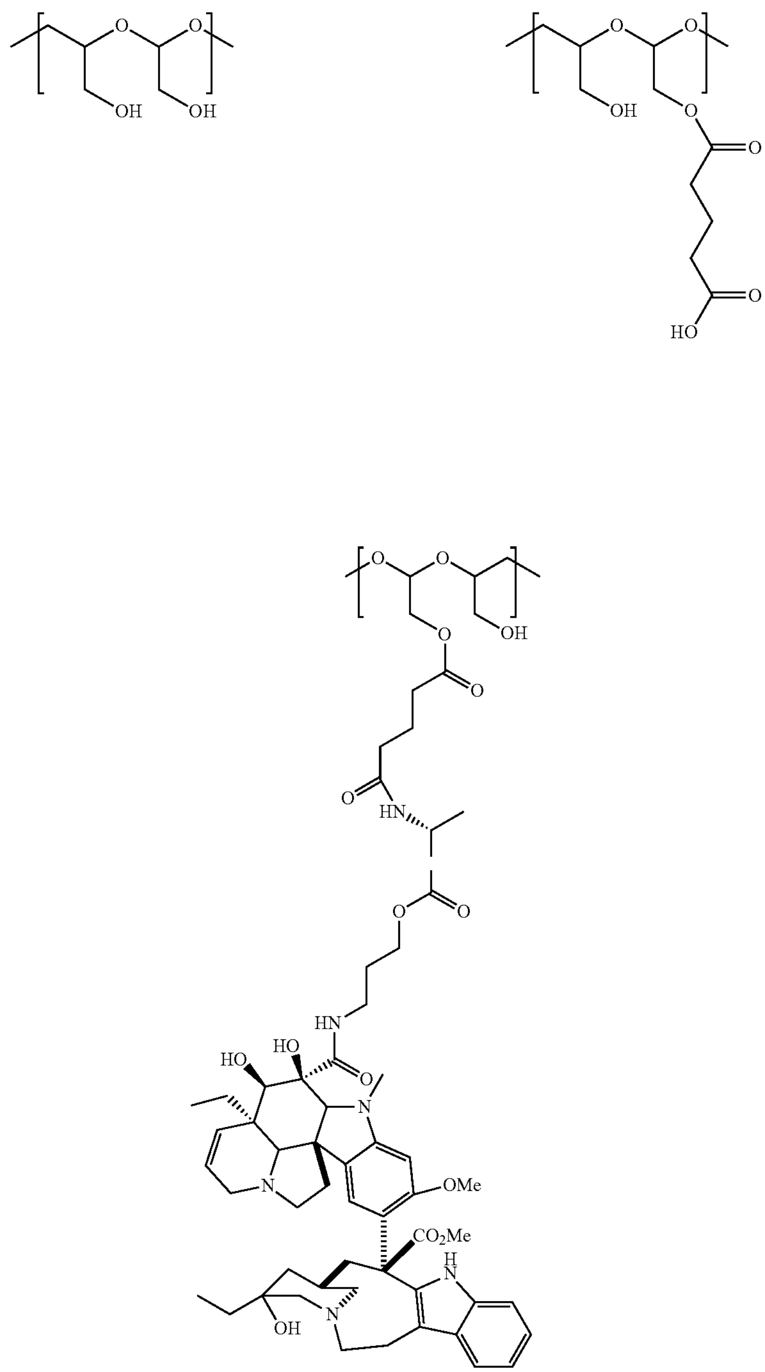 |

TABLE E-continued

| Ref # | Drug: PBRM Ratio | Structure |
|---|---|---|
| Ex 57 | ~20:1 | 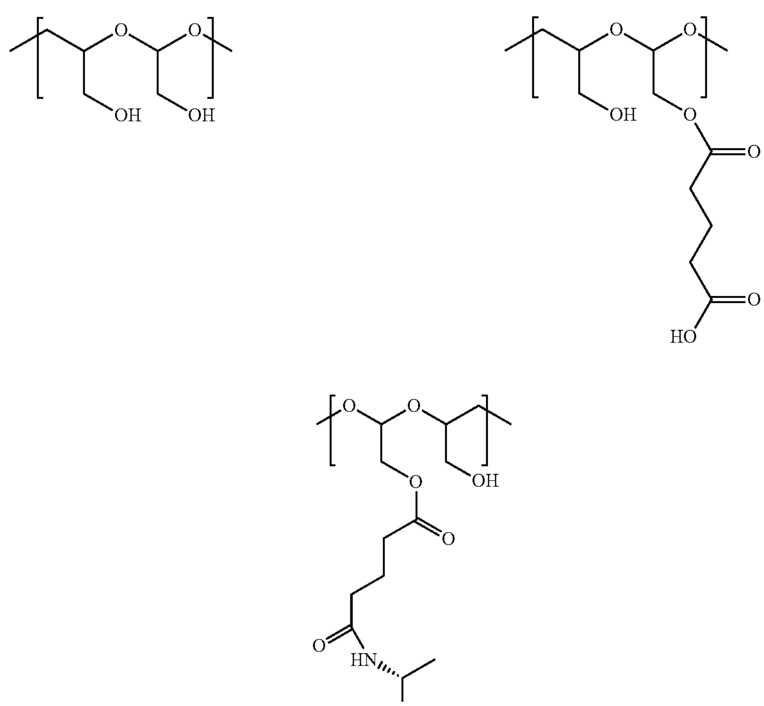 |

TABLE E-continued

| Ref # | Drug: PBRM Ratio | Structure |
|---|---|---|
| Ex 60 | 10:1 to 14:1 | |

401 402
TABLE E-continued
| Ref # | Drug: PBRM Ratio | Structure |
|---|---|---|
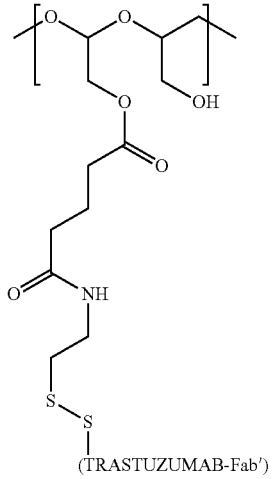

TABLE E-continued
| Ref # | Drug: PBRM Ratio | Structure |
|---|---|---|
| | | 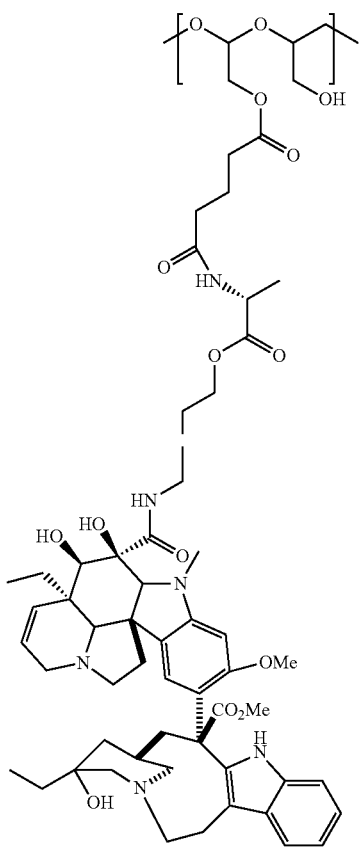 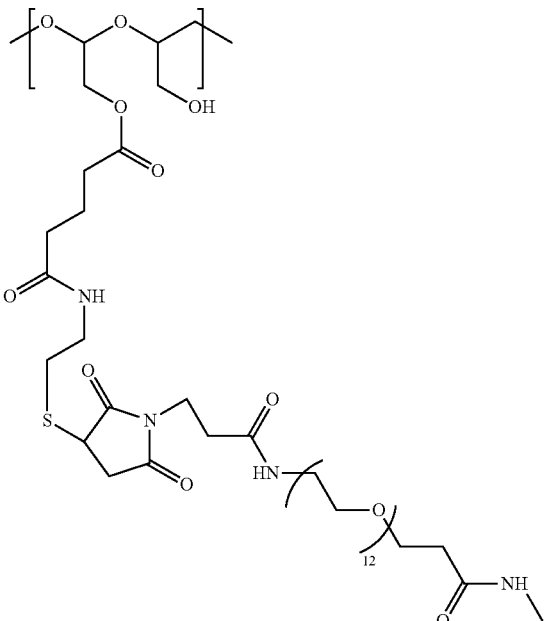 (TRASTUZUMAB-Fab) |

TABLE E-continued
| Ref # | Drug: PBRM Ratio | Structure |
|---|---|---|
| | 9:1 to 13:1 | 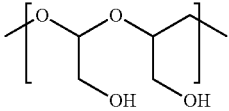 |

TABLE E-continued

| Ref # | Drug: PBRM Ratio | Structure |
|---|---|---|

TABLE E-continued

| Ref # | Drug: PBRM Ratio | Structure |
|---|---|---|

TABLE E-continued
| Ref # | Drug: PBRM Ratio | Structure |
|---|---|---|
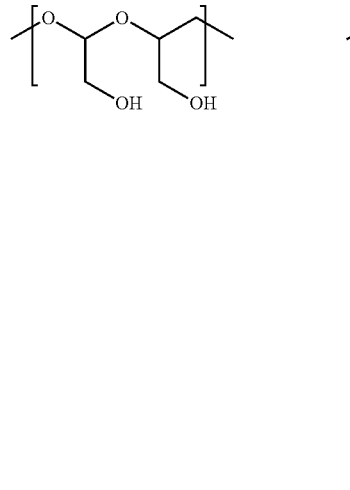

TABLE E-continued

| Ref # | Drug: PBRM Ratio | Structure |
|---|---|---|
| Ex 27 | | 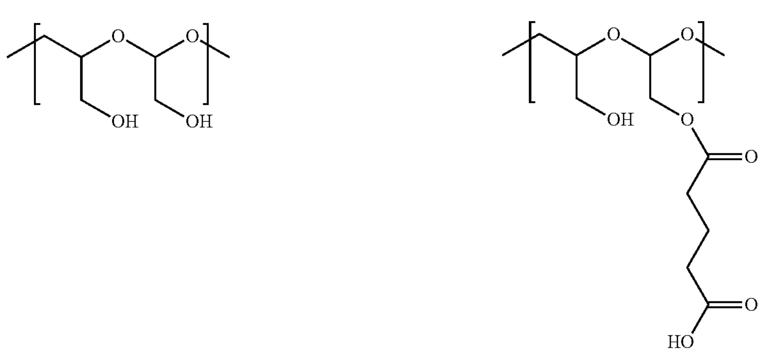 |

| Ref # | Drug: PBRM Ratio | Structure |
|---|---|---|
| | | 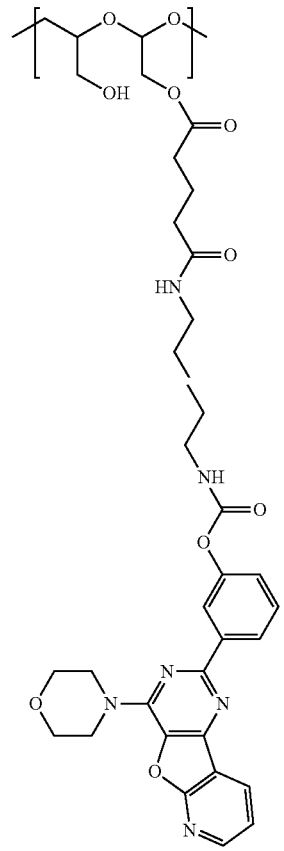 |
| | | 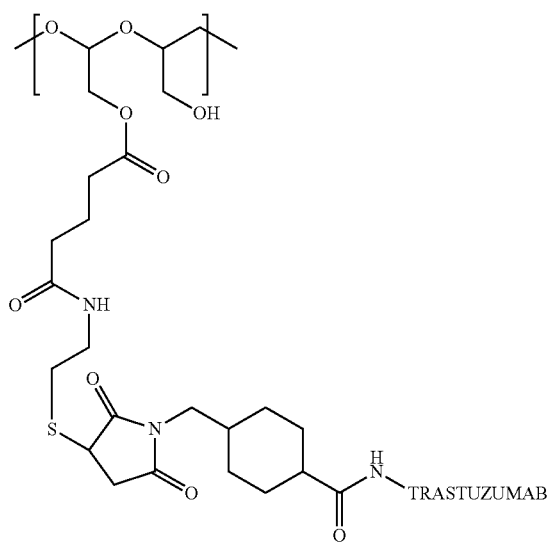 |

TABLE E-continued

| Ref # | Drug: PBRM Ratio | Structure |
|---|---|---|
| Ex 29 | | |

TABLE E-continued
| Ref # | Drug: PBRM Ratio | Structure |
|---|---|---|
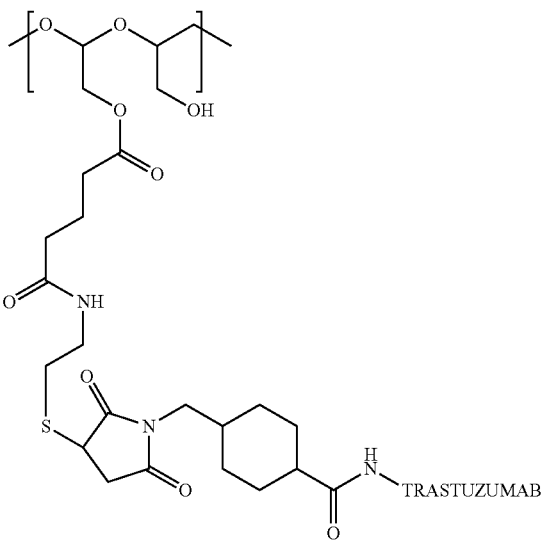
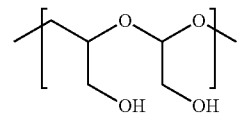
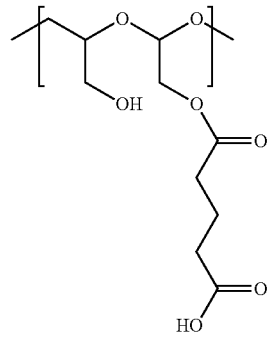
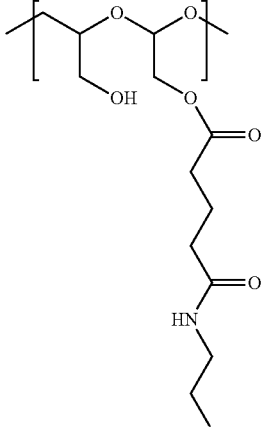

TABLE E-continued
| Ref # | Drug: PBRM Ratio | Structure |
|---|---|---|
| Ex 32 | | 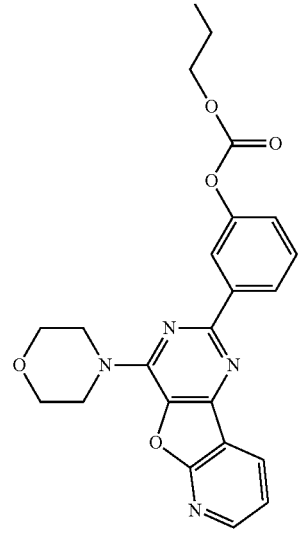 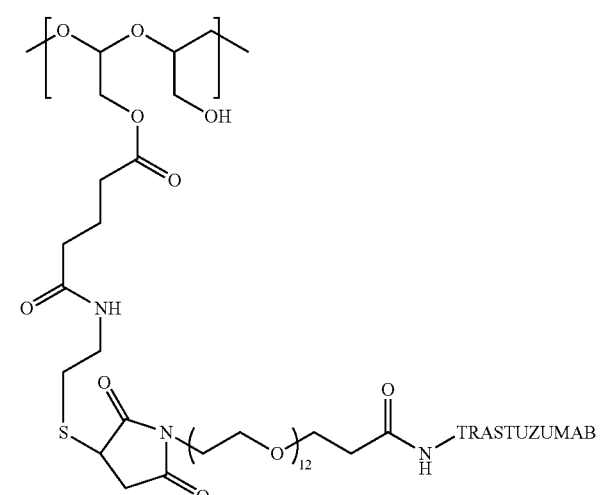 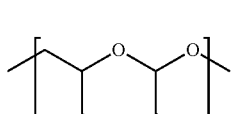 |

TABLE E-continued

| Ref # | Drug: PBRM Ratio | Structure |
|---|---|---|

TABLE E-continued

| Ref # | Drug: PBRM Ratio | Structure |
|---|---|---|
| Ex 35 | | 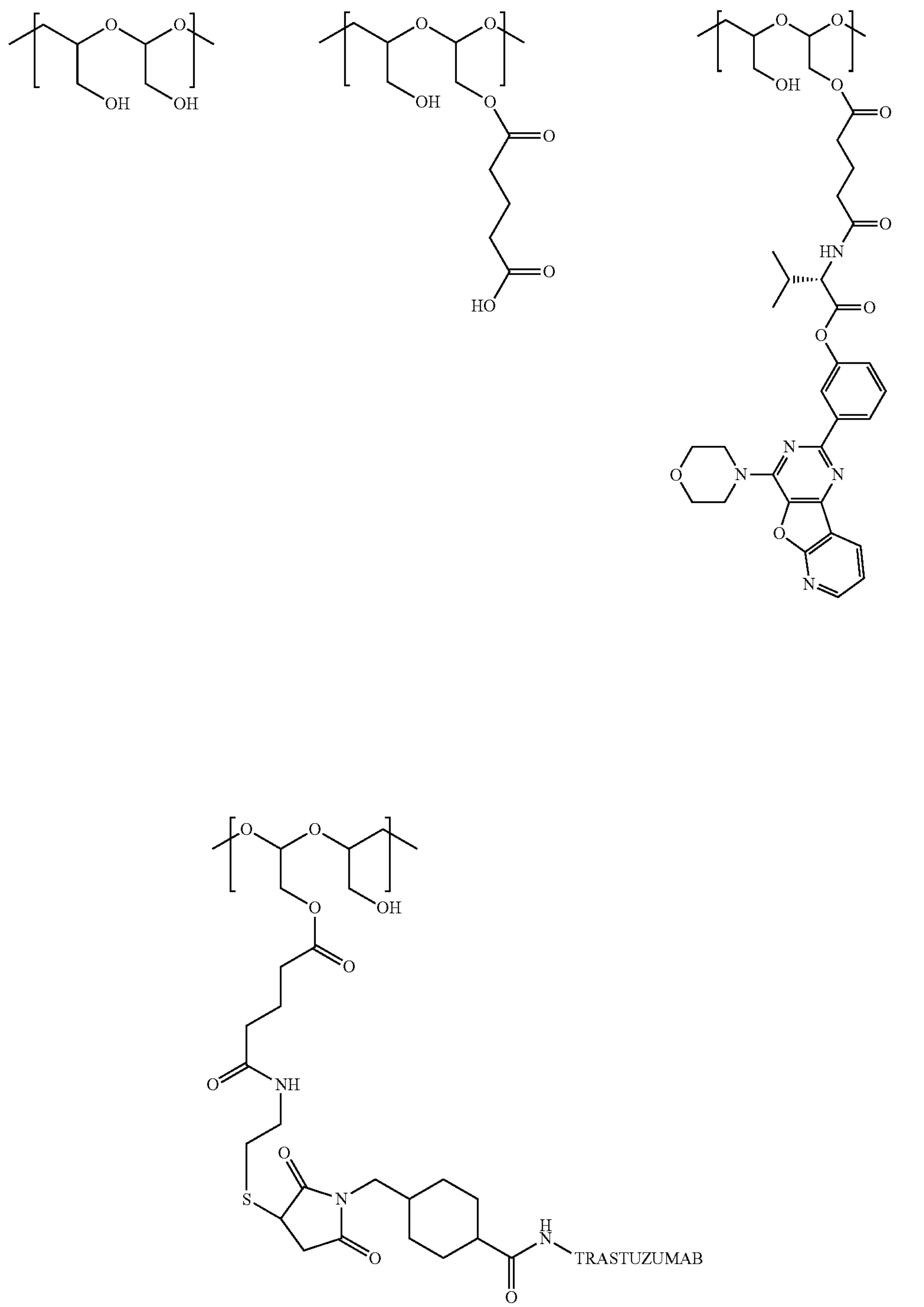 |

TABLE E-continued
| Ref # | Drug: PBRM Ratio | Structure |
|---|---|---|
| Ex 38 | 2:1 to 6:1 | 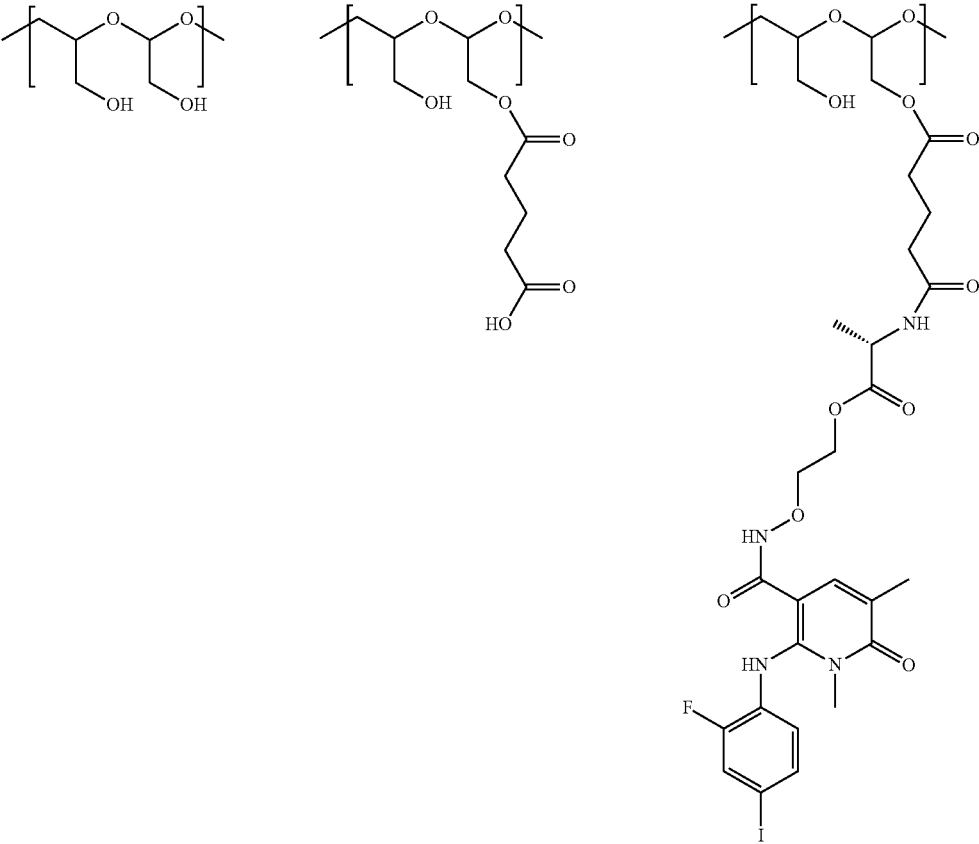 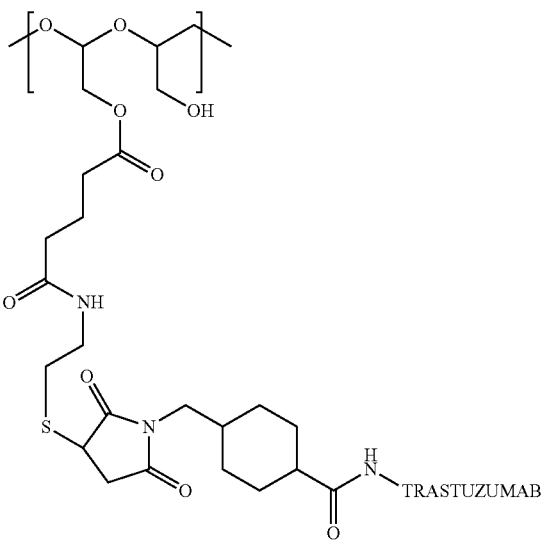 |

TABLE E-continued
| Ref # | Drug: PBRM Ratio | Structure |
|---|---|---|
| | 2:1 to 6:1 | 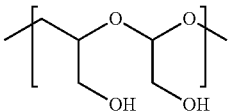 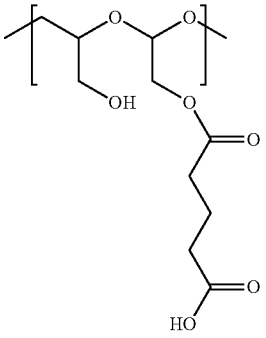 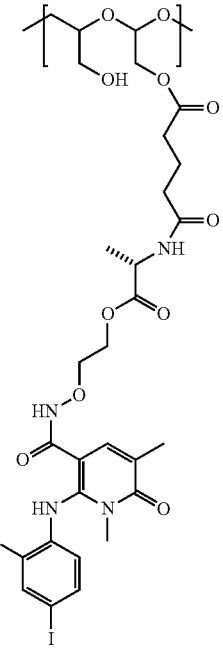 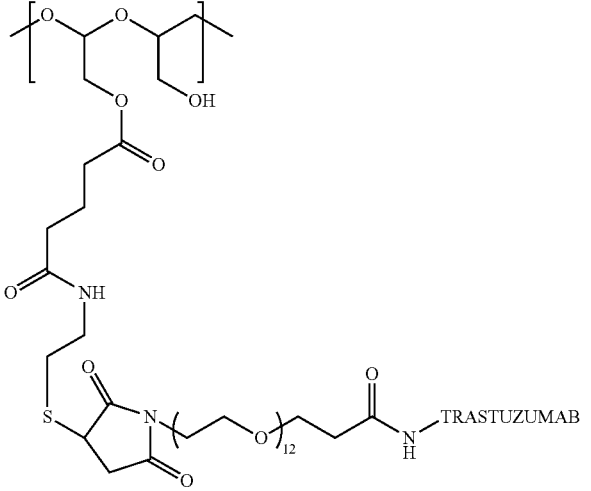 |

TABLE E-continued
| Ref # | Drug: PBRM Ratio | Structure |
|---|---|---|
| | 14:1 to 18:1 | 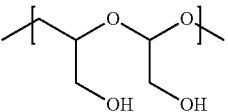 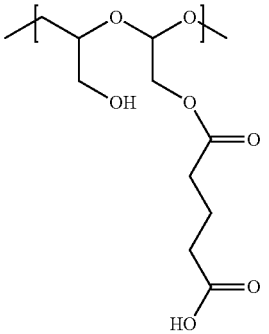 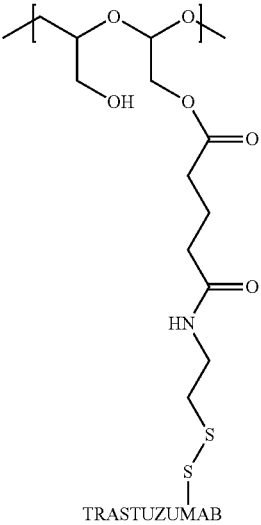 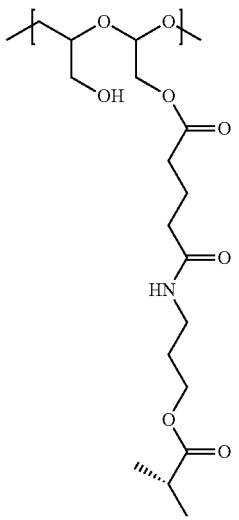 |

TABLE E-continued
| Ref # | Drug: PBRM Ratio | Structure |
|---|---|---|
| Ex 41 | | 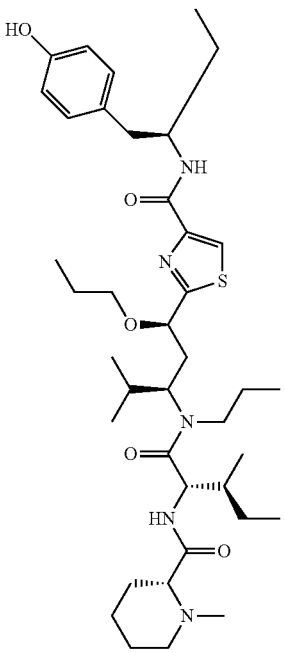 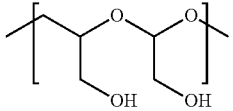 |

TABLE E-continued
| Ref # | Drug: PBRM Ratio | Structure |
|---|---|---|
|  |  | 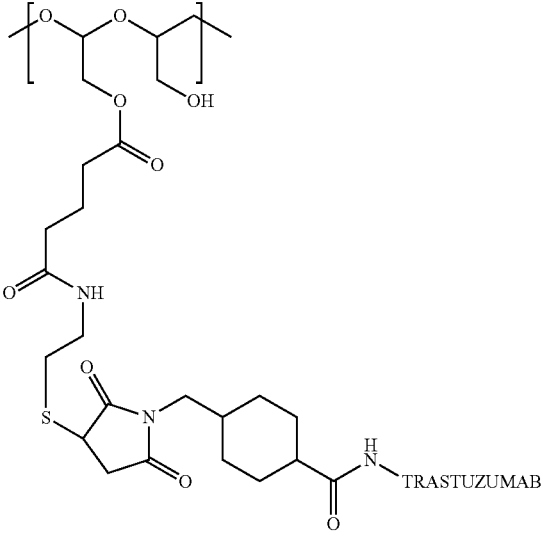 |
| Ex 52 | 19:1 to 23:1 24:1- 28:1 | 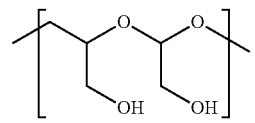 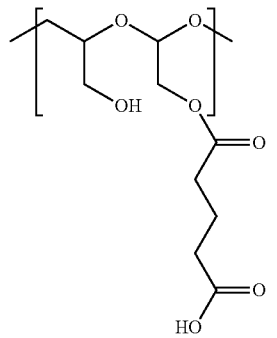 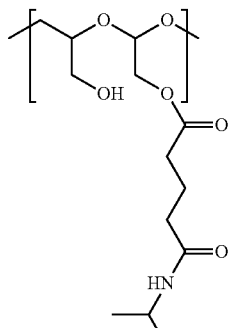 |

TABLE E-continued

| Ref # | Drug: PBRM Ratio | Structure |
|---|---|---|
| | | (structure showing polymer with OH, linked via ester to glutaryl-amide-ethyl-thio-succinimide-N-methyl-cyclohexyl-C(O)NH-TRASTUZUMAB) |
| Ex 105 Conjugate 1 | 8:1 to 12:1 | (three polymer fragment structures: diol repeat unit; mono-ester with pendant —CH₂CH₂CH₂COOH; and mono-ester with pendant —CH₂CH₂CH₂C(O)NH-CH₂CH₂-S-S-TRASTUZUMAB) |

TABLE E-continued
| Ref # | Drug: PBRM Ratio | Structure |
|---|---|---|
| Ex 66 | 9:1 to 13:1 21:1 to 25:1 | 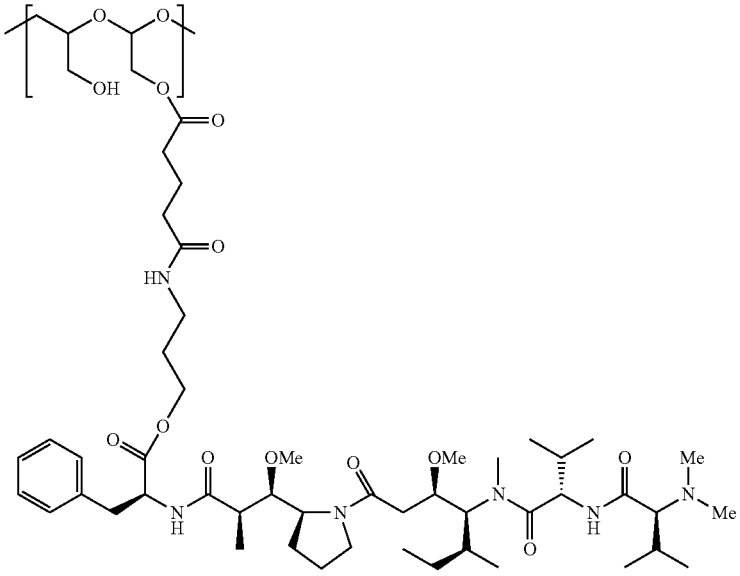 |

TABLE E-continued
| Ref # | Drug: PBRM Ratio | Structure |
|---|---|---|
| Ex 70 | 9:1 to 13:1 | 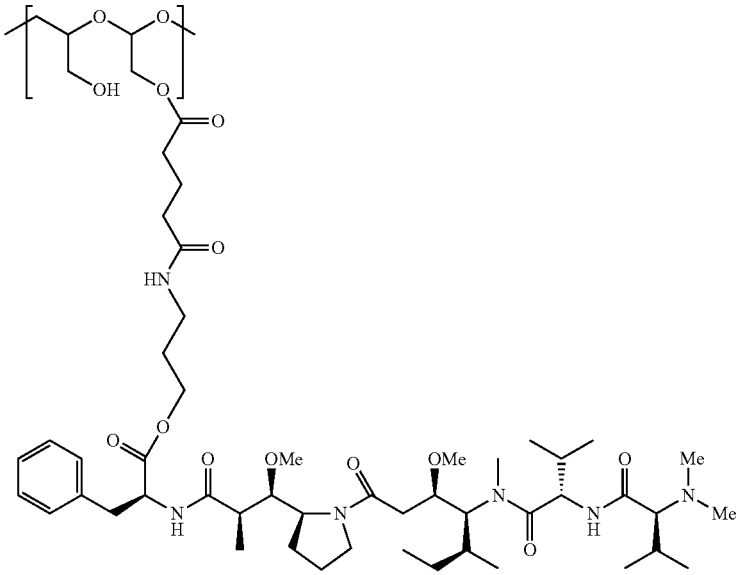 |

TABLE E-continued
| Ref # | Drug: PBRM Ratio | Structure |
|---|---|---|
| | | 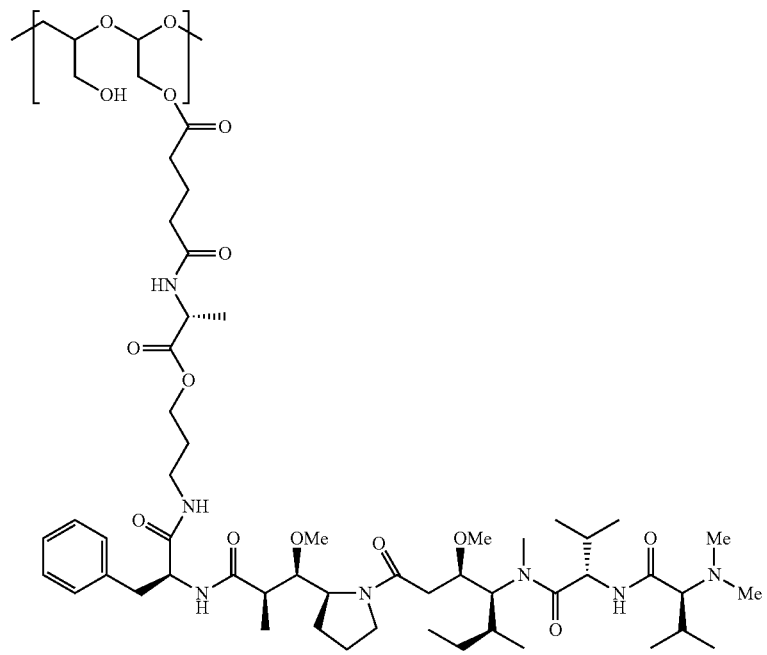 |
| Ex 72 | 11:1 to 15:1 | 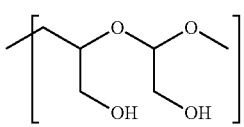 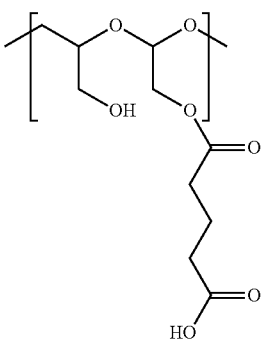 |

TABLE E-continued
| Ref # | Drug: PBRM Ratio | Structure |
|---|---|---|
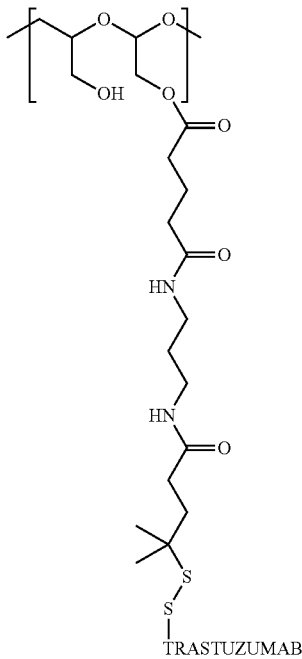
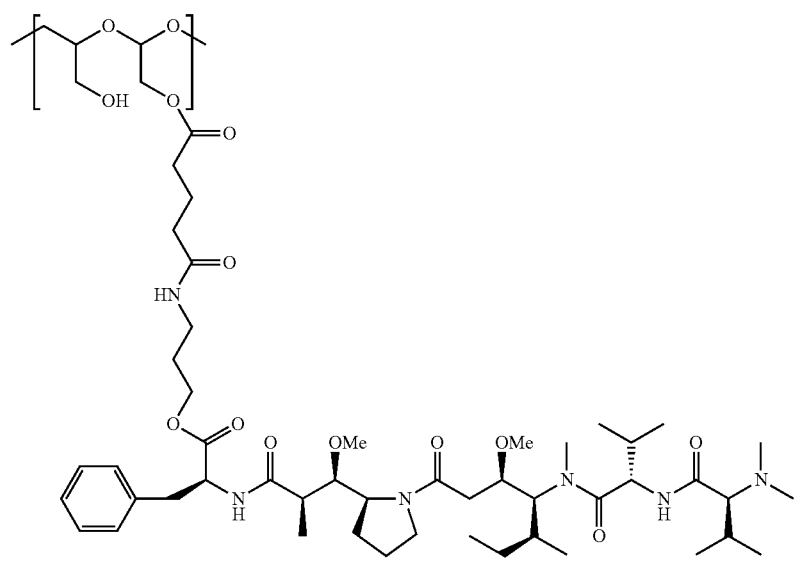

TABLE E-continued
| Ref # | Drug: PBRM Ratio | Structure |
|---|---|---|
| Ex 105 Conjugate 2 | X = NH 7:1 to 11:1 | 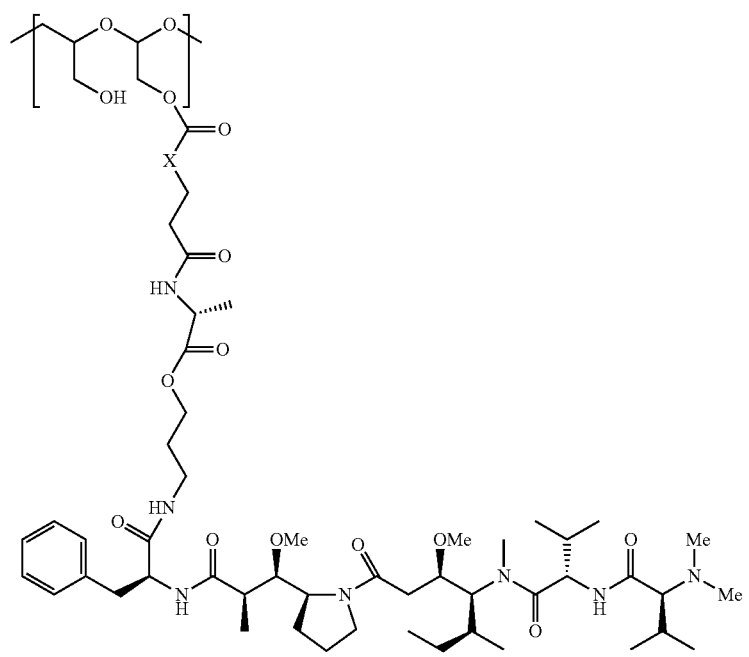 |

TABLE E-continued
| Ref # | Drug: PBRM Ratio | Structure |
|---|---|---|
| Ex 94 X = NH₂ | 40:1 to 45:1 (PHF 22 kDa) 44:1 to 48:1 (PHF 47 kDa) | 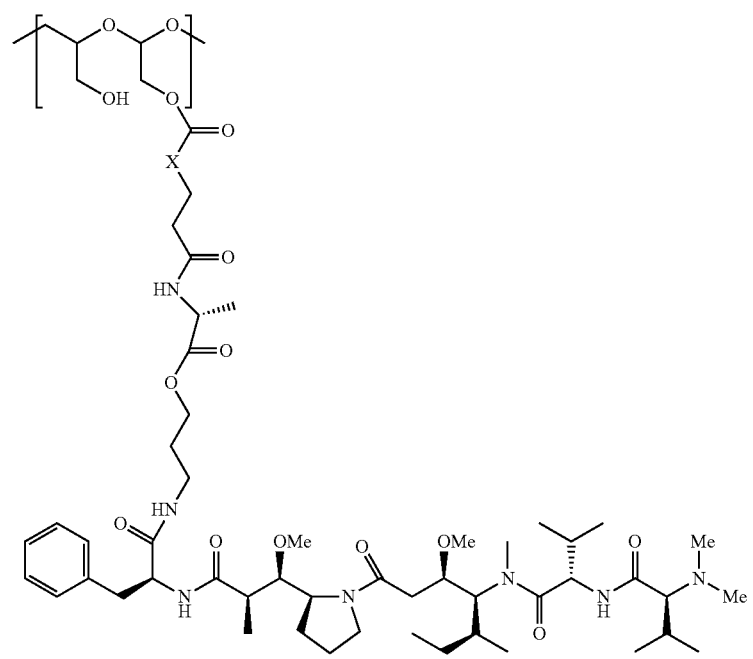 |

TABLE E-continued
| Ref # | Drug: PBRM Ratio | Structure |
|---|---|---|
| Ex 94 X = NH₂ | 37:1 to 41:1 (PHF 22 kDa) 47:1 to 51:1 (PHF 47 kDa) | 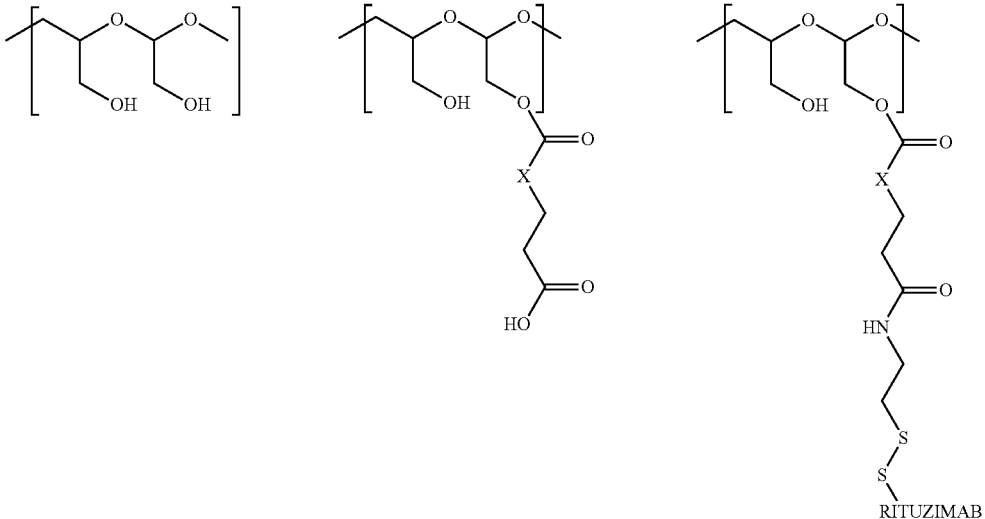 |
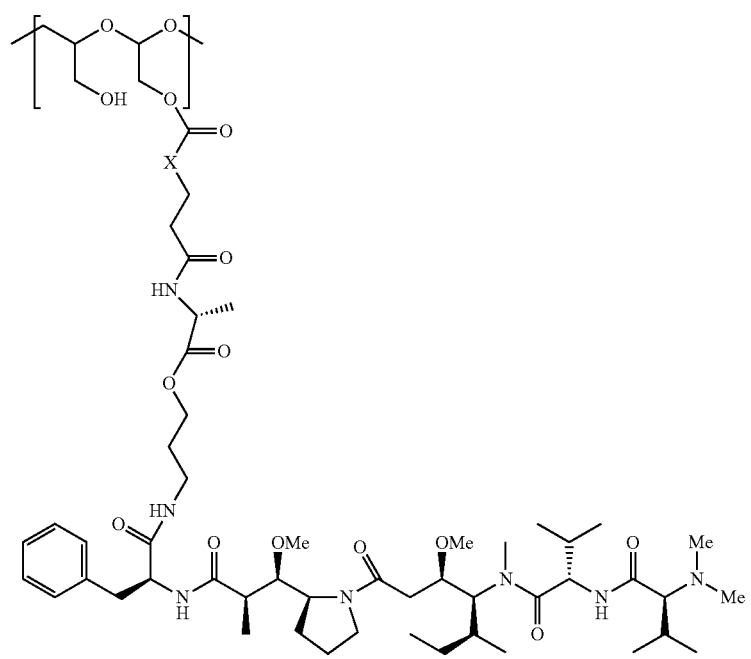

TABLE E-continued

| Ref # | Drug: PBRM Ratio | Structure |
|---|---|---|
| Ex 92 | 16:1 to 20:1 | |

455 456
TABLE E-continued
| Ref # | Drug: PBRM Ratio | Structure |
|---|---|---|
| Ex 93 | 6:1 to 8:1 (PHF 47 kDa) 6:1 to 10:1 (PHF 105 kDa) | 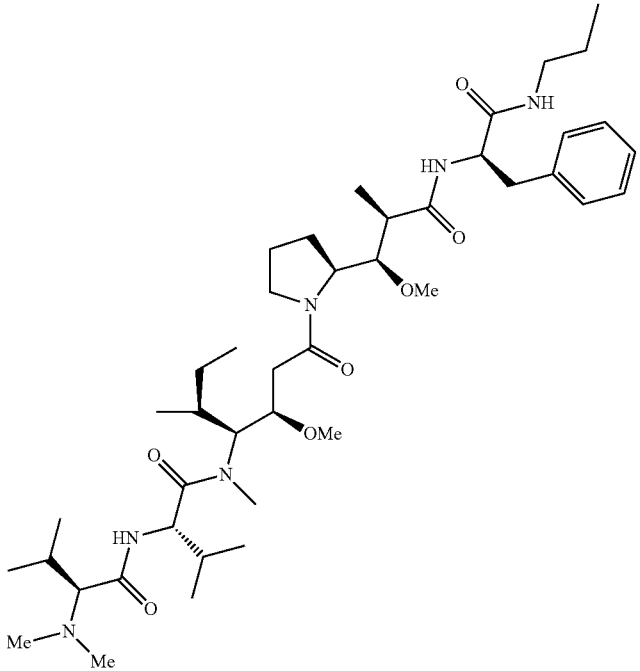 |

US 8,821,850 B2

457                                                                                     458

TABLE E-continued

| Ref # | Drug: PBRM Ratio | Structure |
|---|---|---|
| Ex 96 | 6:1 to 10:1 (PHF 105 kDa or 156 kDa) | 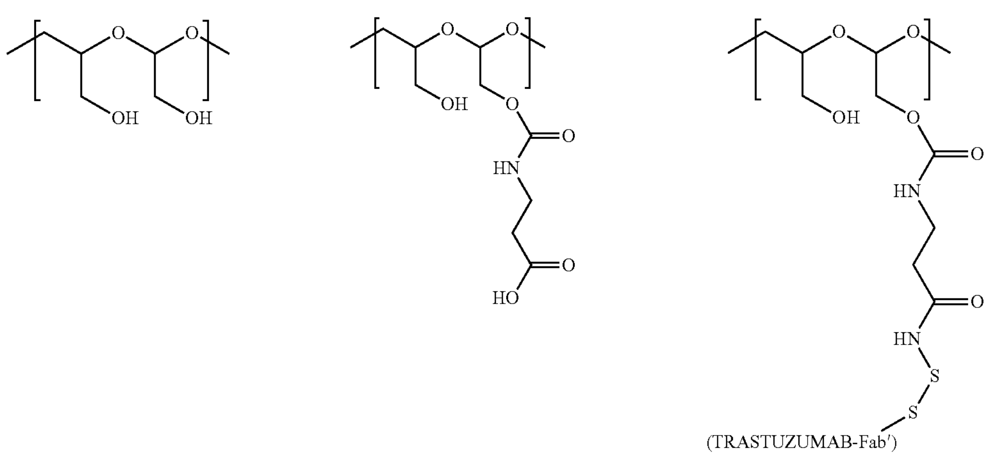 |

(TRASTUZUMAB-Fab')

TABLE E-continued

| Ref # | Drug: PBRM Ratio | Structure |
|---|---|---|
| | 2:1 to 6:1 | |

TABLE E-continued
| Ref # | Drug: PBRM Ratio | Structure |
|---|---|---|
| | | 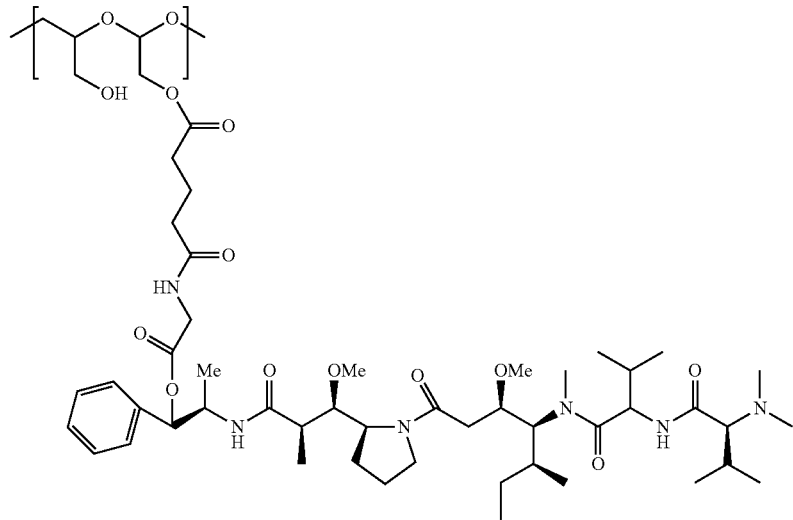 |
| | 12:1 to 16:1 | 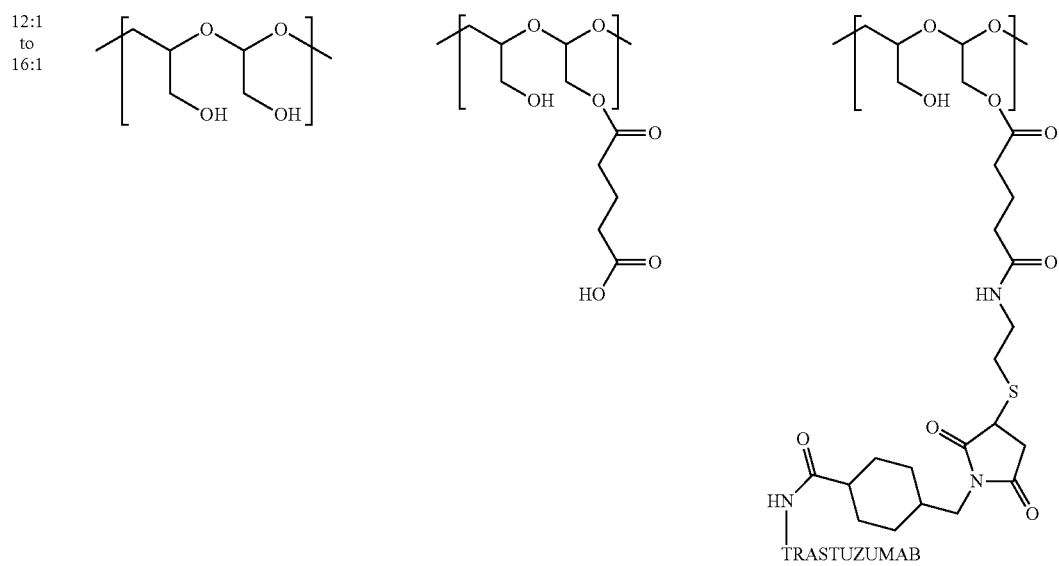 |

TABLE E-continued

| Ref # | Drug: PBRM Ratio | Structure |
|---|---|---|
| Ex 105 Conjugate 3 | | 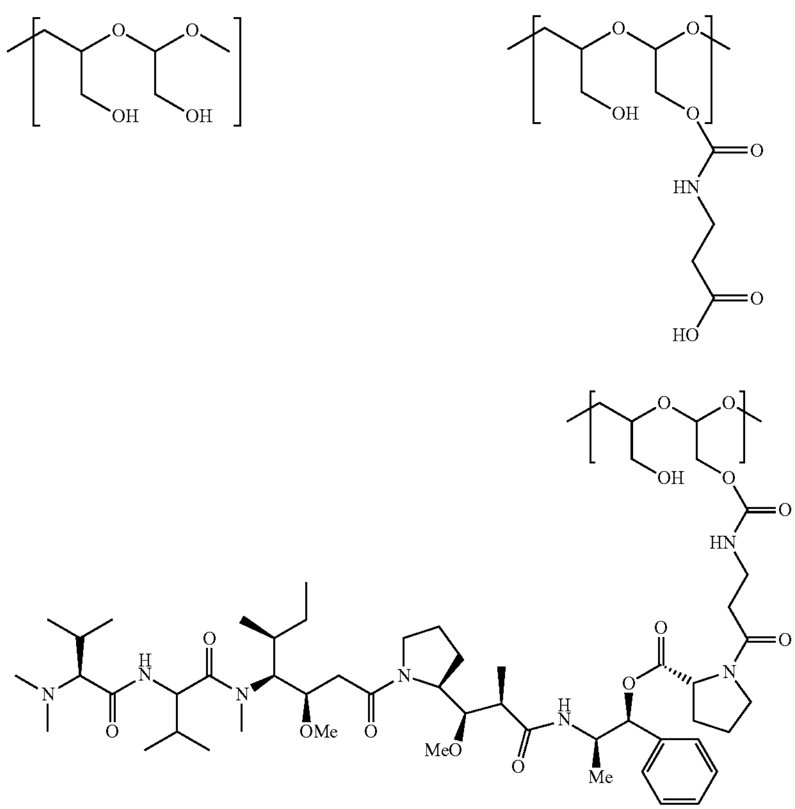 |

TABLE E-continued
| Ref # | Drug: PBRM Ratio | Structure |
|---|---|---|
| | | 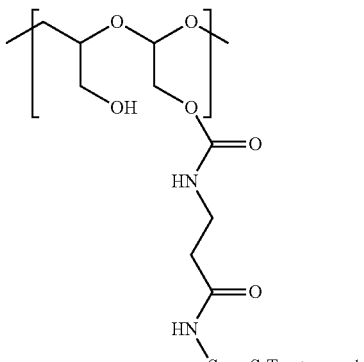 |
| | 11:1 to 15:1 | 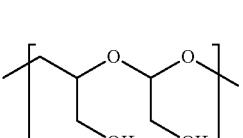 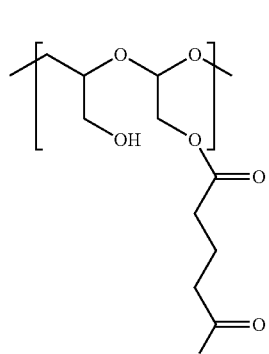 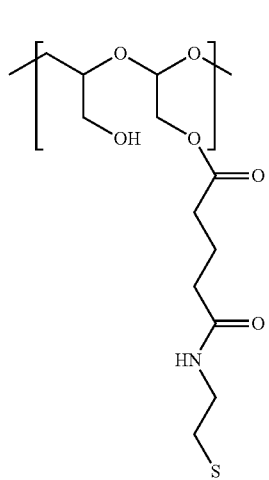 |

TABLE E-continued
| Ref # | Drug: PBRM Ratio | Structure |
|---|---|---|
| | | 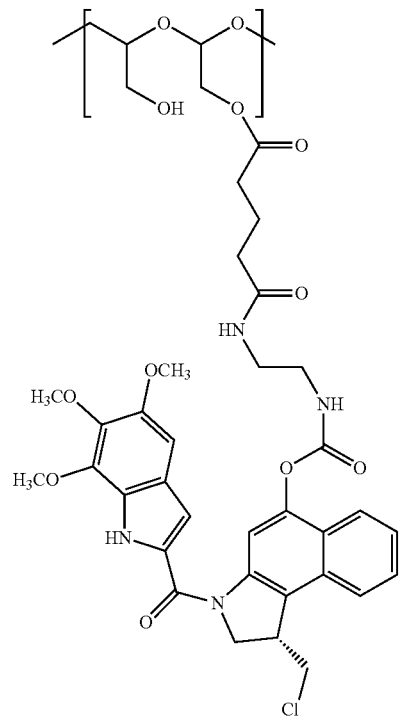 |
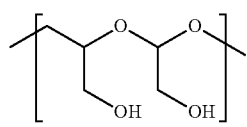 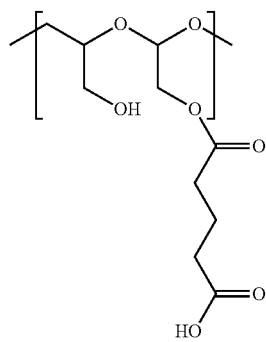 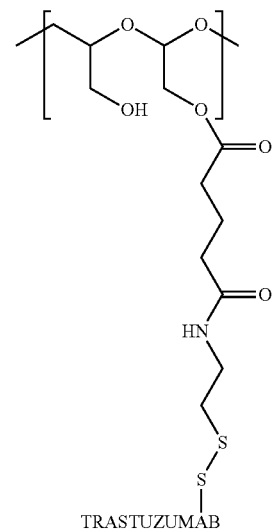

TABLE E-continued
| Ref # | Drug: PBRM Ratio | Structure |
|---|---|---|
| | | 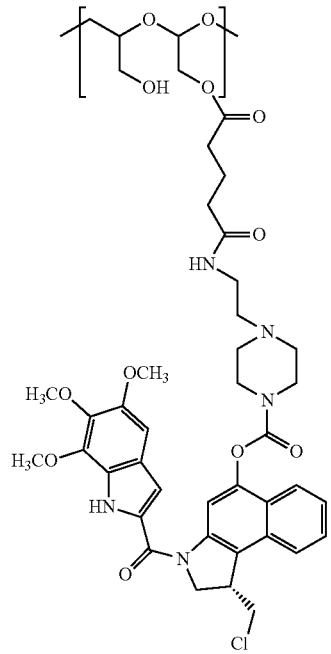 |
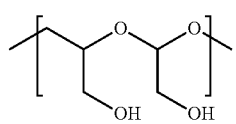
X = CH₂ or —NH
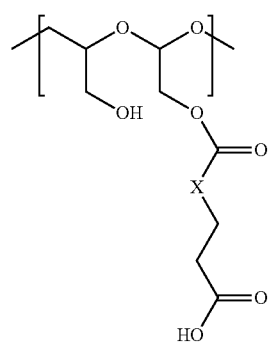
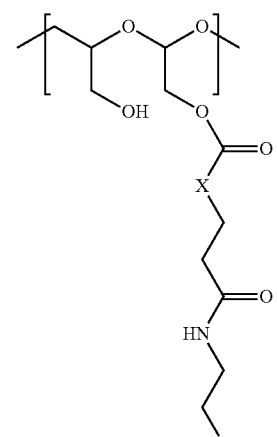

TABLE E-continued
| Ref # | Drug: PBRM Ratio | Structure |
|---|---|---|
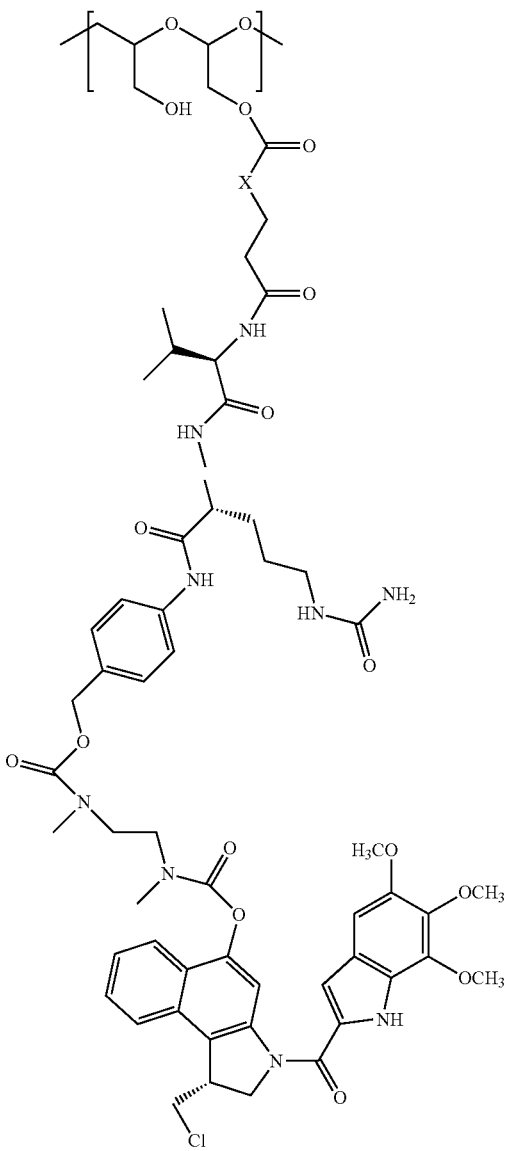

TABLE E-continued

| Ref # | Drug: PBRM Ratio | Structure |
|---|---|---|
| Ex 75 | 12:1 to 15:1 | 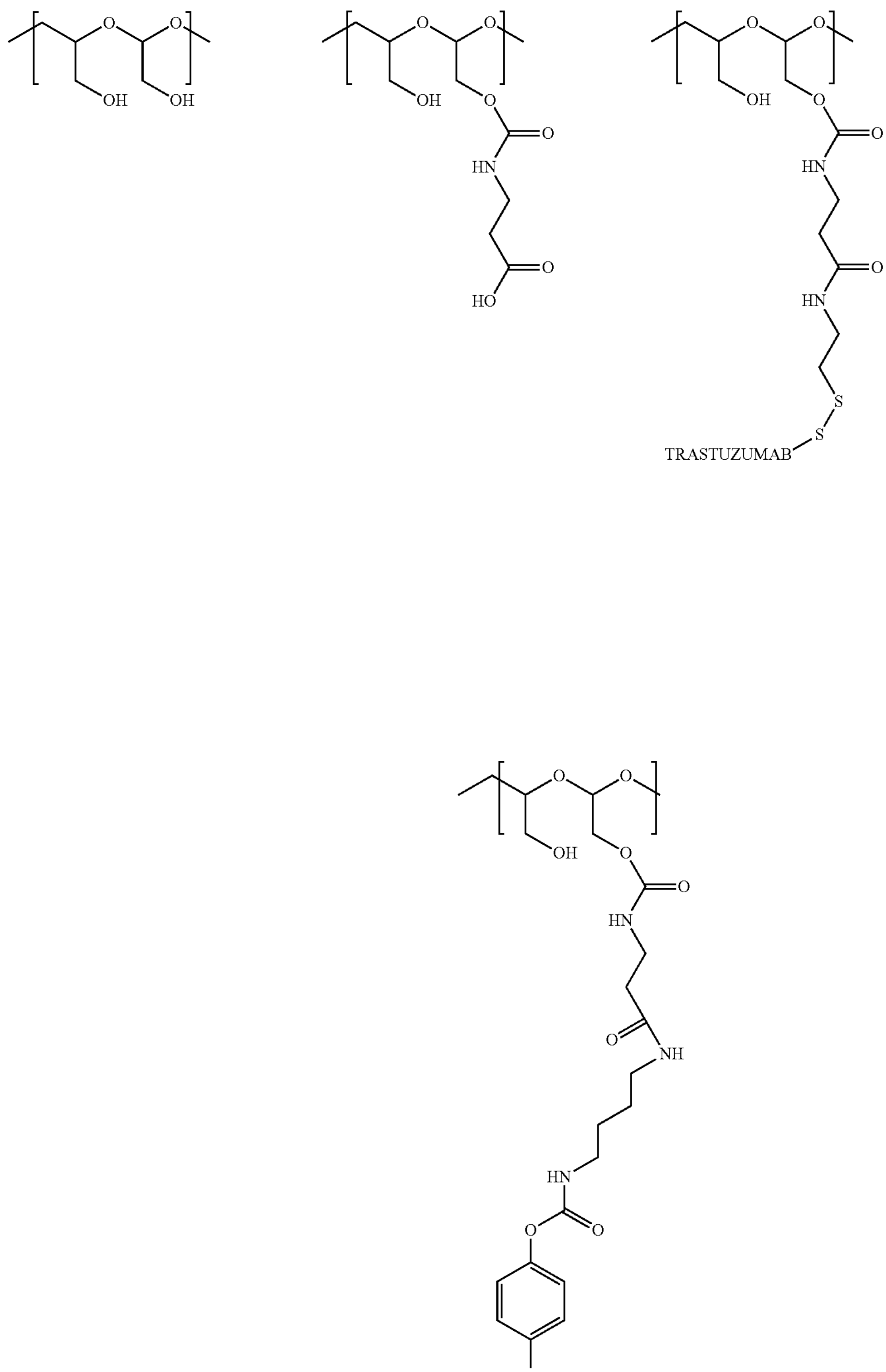 |

TABLE E-continued

| Ref # | Drug: PBRM Ratio | Structure |
|---|---|---|
| Ex 78 | 6:1 to 10:1 | 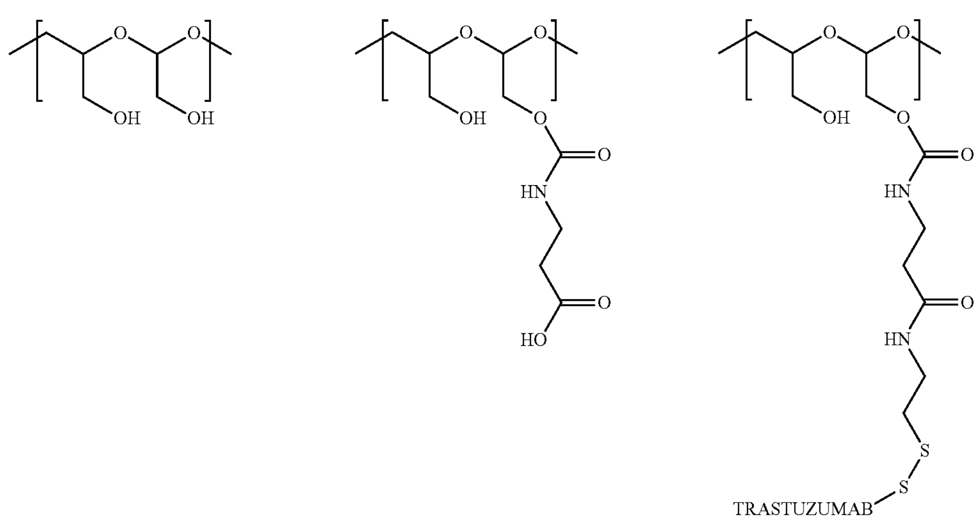 |

TABLE E-continued
| Ref # | Drug: PBRM Ratio | Structure |
|---|---|---|
| Ex 81 | 6:1 to 10:1 | 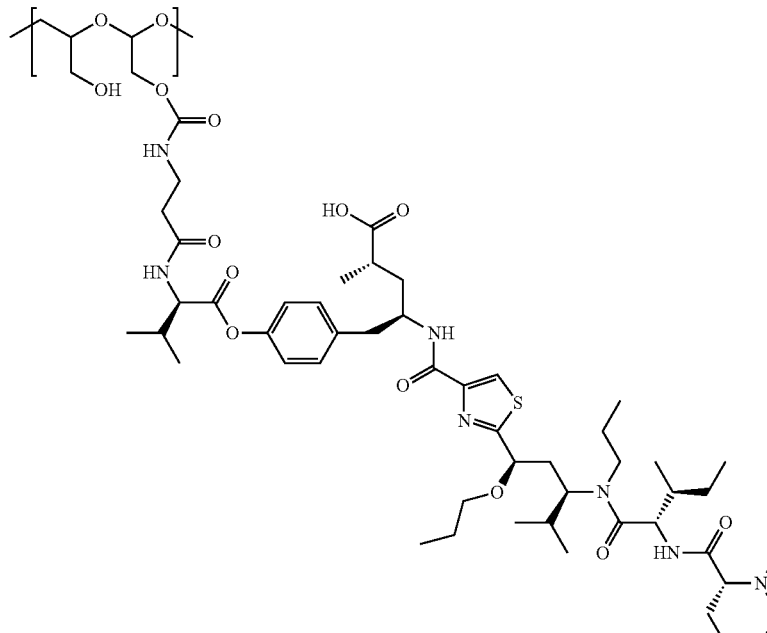 |

TABLE E-continued
| Ref # | Drug: PBRM Ratio | Structure |
|---|---|---|
| | | 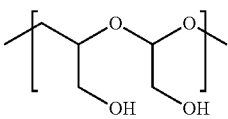 |
| Ex 86 | 6:1 to 10:1 | 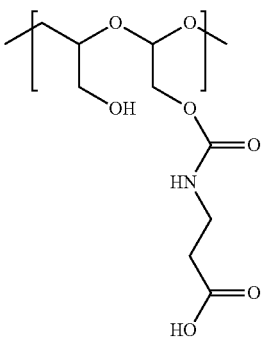 |

TABLE E-continued

| Ref # | Drug: PBRM Ratio | Structure |
|---|---|---|
| Ex 89 | 10:1 to 20:1 | 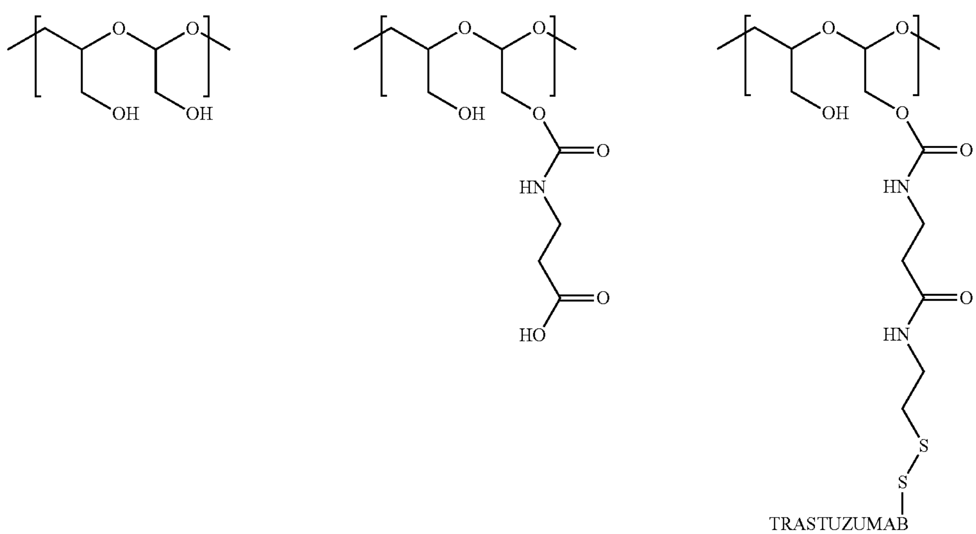 |

TABLE E-continued

| Ref # | Drug: PBRM Ratio | Structure |
|---|---|---|
| | | 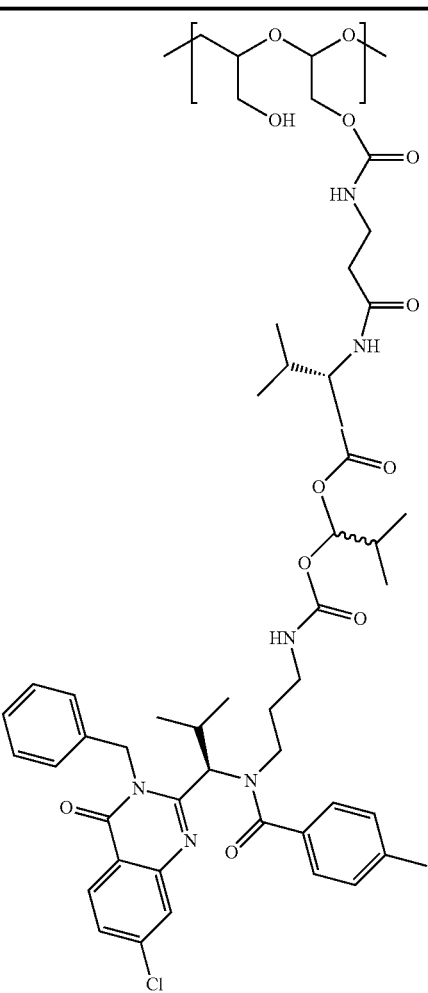 |

Synthetic Methods

According to the present invention, any available techniques can be used to make the inventive conjugates or compositions including them, and intermediates and components (e.g., carriers and modifiers) useful for making them. For example, semi-synthetic and fully synthetic methods such as those discussed in detail below may be used.

Carriers

Methods for preparing polymer carriers (e.g., biocompatible, biodegradable polymer carriers) suitable for conjugation to modifiers are known in the art. For example, synthetic guidance can be found in U.S. Pat. Nos. 5,811,510; 5,863,990; 5,958,398; 7,838,619; and 7,790,150; and U.S. Publication No. 2006/0058512. The skilled practitioner will know how to adapt these methods to make polymer carriers for use in the practice of the invention.

For example, semi-synthetic polyals may be prepared from polyaldoses and polyketoses via complete lateral cleavage of carbohydrate rings with periodate in aqueous solutions, with subsequent conversion into hydrophilic moieties (e.g., via borohydride reduction) for conjugation of hydroxyl groups with one or more drug molecules or PBRMs, via a dicarboxylic acid linker (e.g., glutaric acid or β-alanine linker). In an exemplary embodiment, the carbohydrate rings of a suitable polysaccharide can be oxidized by glycol-specific reagents, resulting in the cleavage of carbon-carbon bonds between carbon atoms that are each connected to a hydroxyl group. An example of application of this methodology to dextran B-512 is illustrated below:

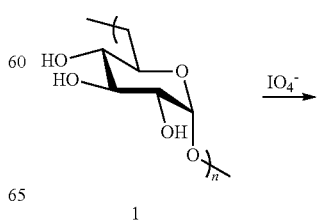

1

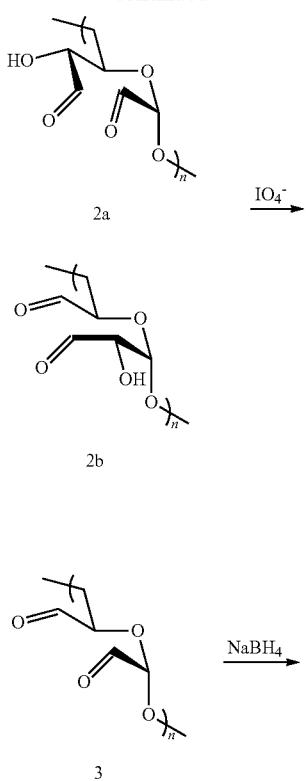
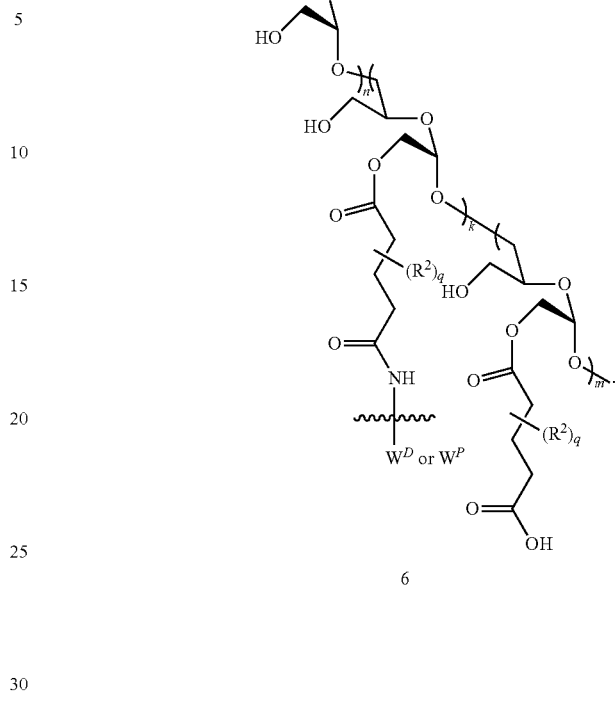
A similar approach may be used with Levan:
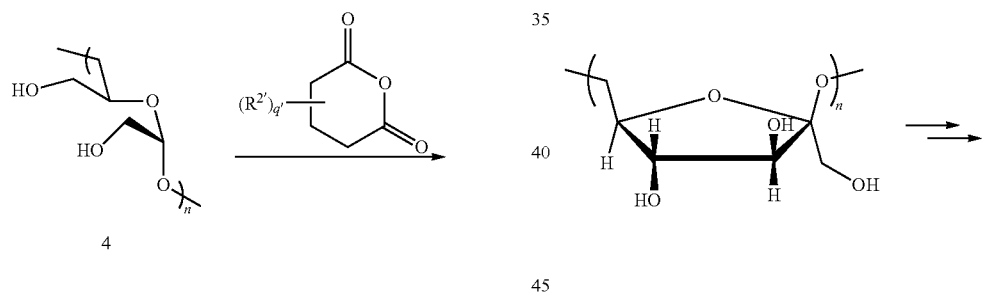
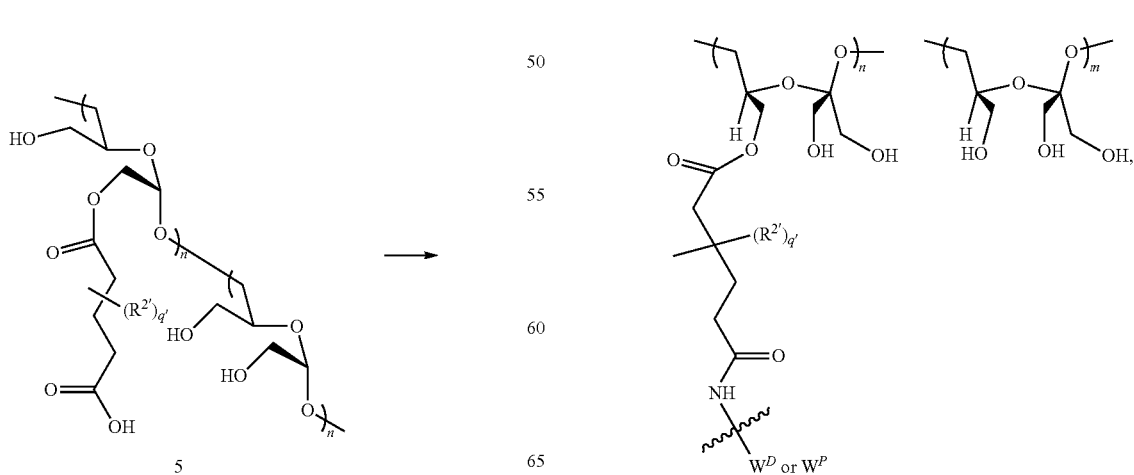

and Inulin:

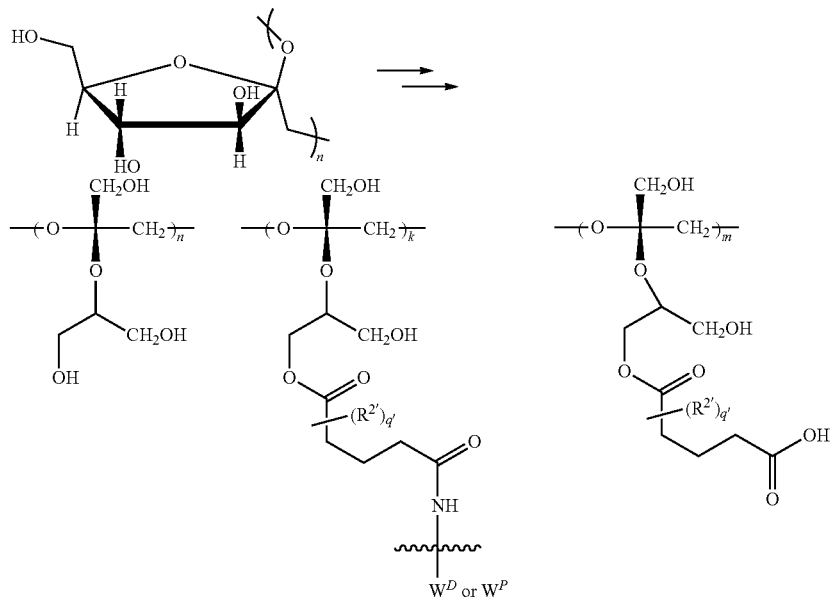

In the above schemes, the wavy bond indicates that $W^D$ or $W^P$ are connected directly as shown or via another moiety such as $M^{D2}$ or $M^{P2}$ respectively.

In the above schemes, q' is an integer from 0 to 4; and each occurrence of $R^{2'}$ is independently hydrogen, halogen, —CN, $NO_2$, an aliphatic, heteroaliphatic, carbocyclic, or heterocycloalkyl moiety, or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ is independently hydrogen, halogen, or an aliphatic, heteroaliphatic, carbocyclic, or heterocycloalkyl moiety, each of which is optionally substituted.

In certain embodiments, each occurrence of $R^{2'}$ is independently hydrogen, alkyl, alkenyl, alkynyl, cycloalkyl, heteroalkyl, heteroalkenyl, heteroalkynyl, heterocycloalkyl, aryl, heteroaryl, —C(=O)$R^{2A}$ or —$ZR^{2A}$, wherein Z is O, S, $NR^{2B}$, wherein each occurrence of $R^{2A}$ and $R^{2B}$ is independently hydrogen, or an alkyl, alkenyl, alkynyl, cycloalkyl, heteroalkyl, heteroalkenyl, heteroalkynyl, heterocycloalkyl, aryl or heteroaryl moiety. In certain embodiments, each occurrence of $R^2$ is hydrogen. In certain embodiments, one or more occurrences of $R^{2'}$ is a $C_{1-10}$ alkyl moiety. In certain embodiments, one or more occurrences of $R^{2'}$ is lower alkyl. In certain embodiments, one or more occurrences of $R^{2'}$ is a hydrophobic group. In certain embodiments, one or more occurrences of $R^2$ is a hydrophilic group. In certain embodiments, one or more occurrences of $R^{2'}$ is an anionic group. In certain embodiments, one or more occurrences of $R^{2'}$ is a cationic group. In certain embodiments, one or more occurrences of $R^{2'}$ is a receptor ligand.

In one embodiment, a method for forming the biodegradable biocompatible polyal conjugates of the present invention comprises a process by which a suitable polysaccharide is combined with an efficient amount of a glycol-specific oxidizing agent to form an aldehyde intermediate. The aldehyde intermediate, which is a polyal itself, may then be reduced to the corresponding polyol, succinulated, and coupled with one or more suitable modifiers to form a biodegradable biocompatible polyal conjugate comprising succinamide-containing linkages.

In another preferred embodiment, fully synthetic biodegradable biocompatible polyals for used in the present invention can be prepared by reacting a suitable initiator with a suitable precursor compound.

For example, fully synthetic polyals may be prepared by condensation of vinyl ethers with protected substituted diols. Other methods, such as cycle opening polymerization, may be used, in which the method efficacy may depend on the degree of substitution and bulkiness of the protective groups.

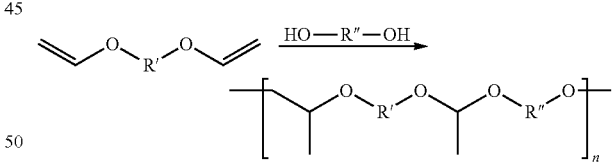

One of ordinary skill in the art will appreciate that solvent systems, catalysts and other factors may be optimized to obtain high molecular weight products.

In certain embodiments, the carrier is PHF.

In embodiments, the polymer carrier is PHF having a polydispersity index (PDI) of less than 2.

Drugs and Drug Derivatives

In certain embodiments, the drug may be modified before conjugation to the polymeric carrier. Schemes 1 and 2 are illustrative methods for modifying a Vinca alkaloid. Scheme 3 shows a method for modifying a non-natural camptothecin derivative. Scheme 4 shows a method for modifying auristatin F. More modification methods are described in US 2010/0305149, which is hereby incorporated by reference.

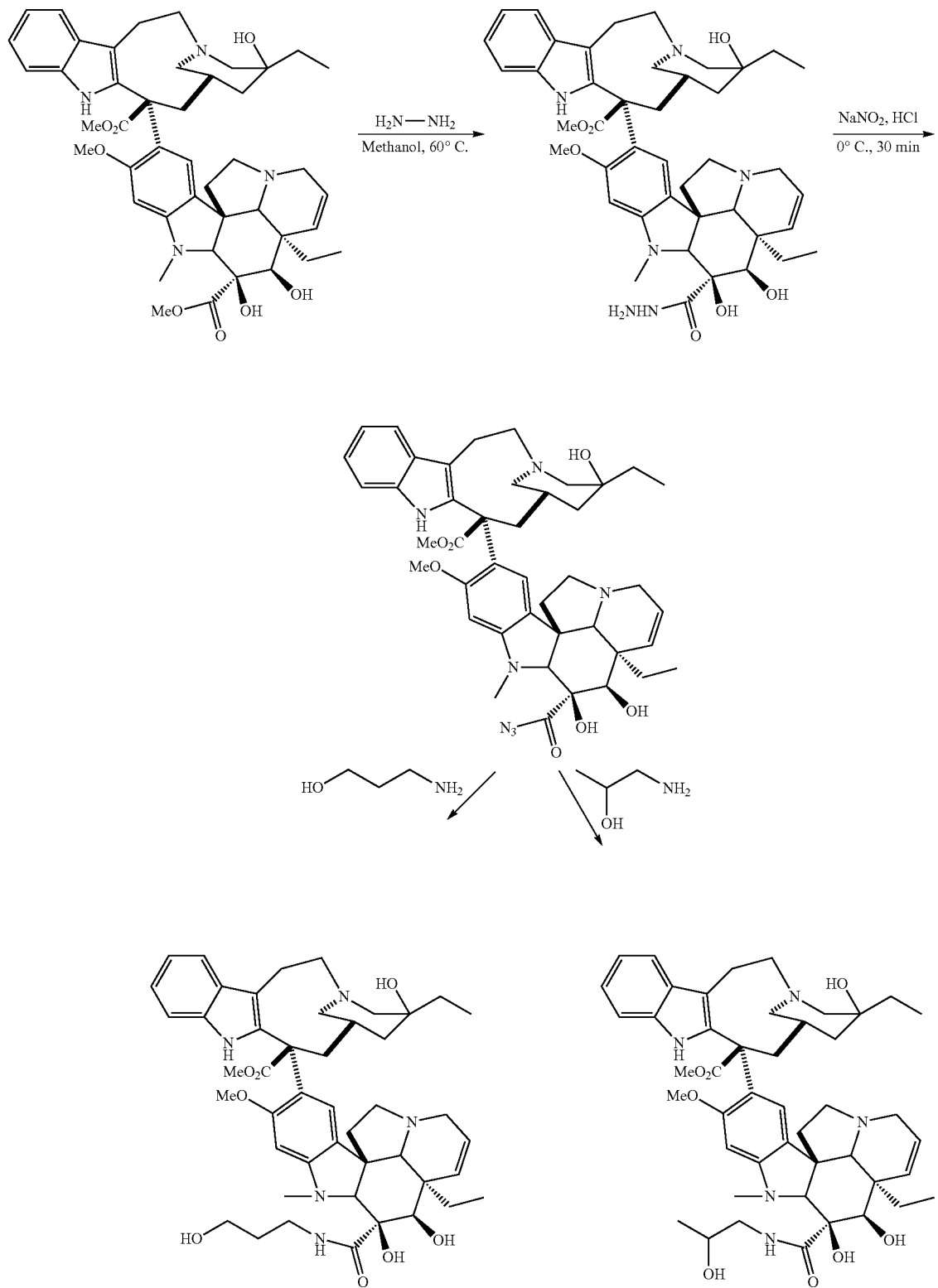
Scheme 1

491

Reaction of the $C_{23}$ ester of a Vinca alkaloid with hydrazine followed by treatment with $NaNO_2$ results in an active azido ester. Reaction of the azido ester with an amino compound such as propanolamine or 1-aminopropan-2-ol results in a Vinca alkaloid derivative with a functionalized hydroxyl which can be further derivatized with amino containing compounds, such as, for example, alanine or methyl alanine derivates, for conjugation with polymers (see Scheme 1).

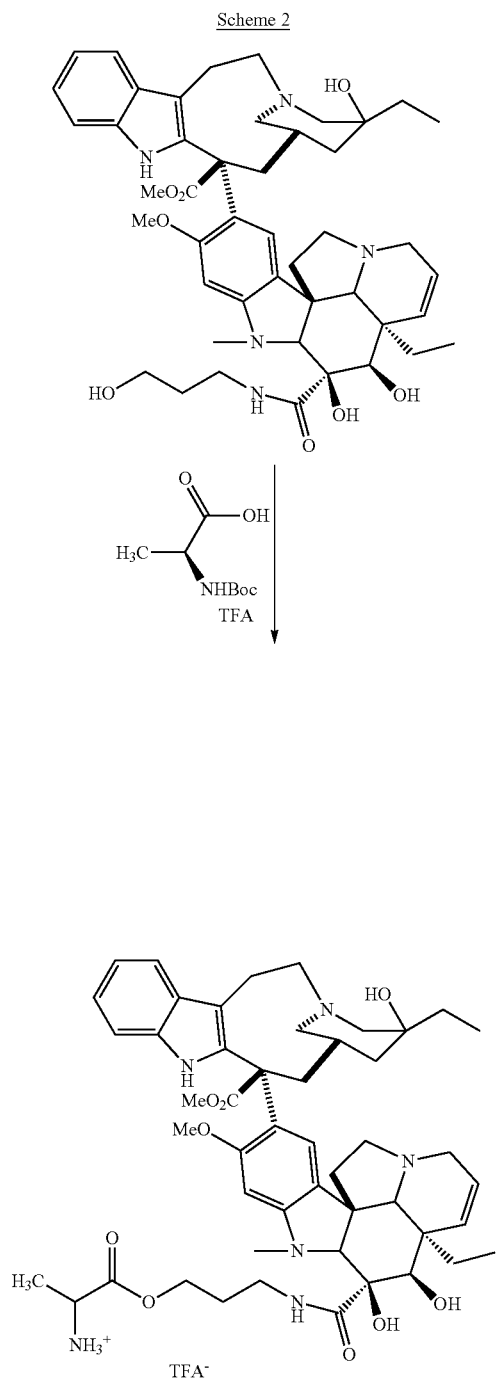

Scheme 2

492

-continued

Treatment of the hydroxyl derivative of the Vinca alkaloid with a protected amino containing tether such as t-butoxy esterified amino acid followed by TFA hydrolysis of the ester gives the triflate salt of the vinca alkaloid. (Scheme 2) Conjugation of the vinca alkaloid to functionalized polymers results in drug-polymer conjugates that can be further conjugated with a PBRM or its derivative to result in protein-drug polymer conjugates.

Scheme 3

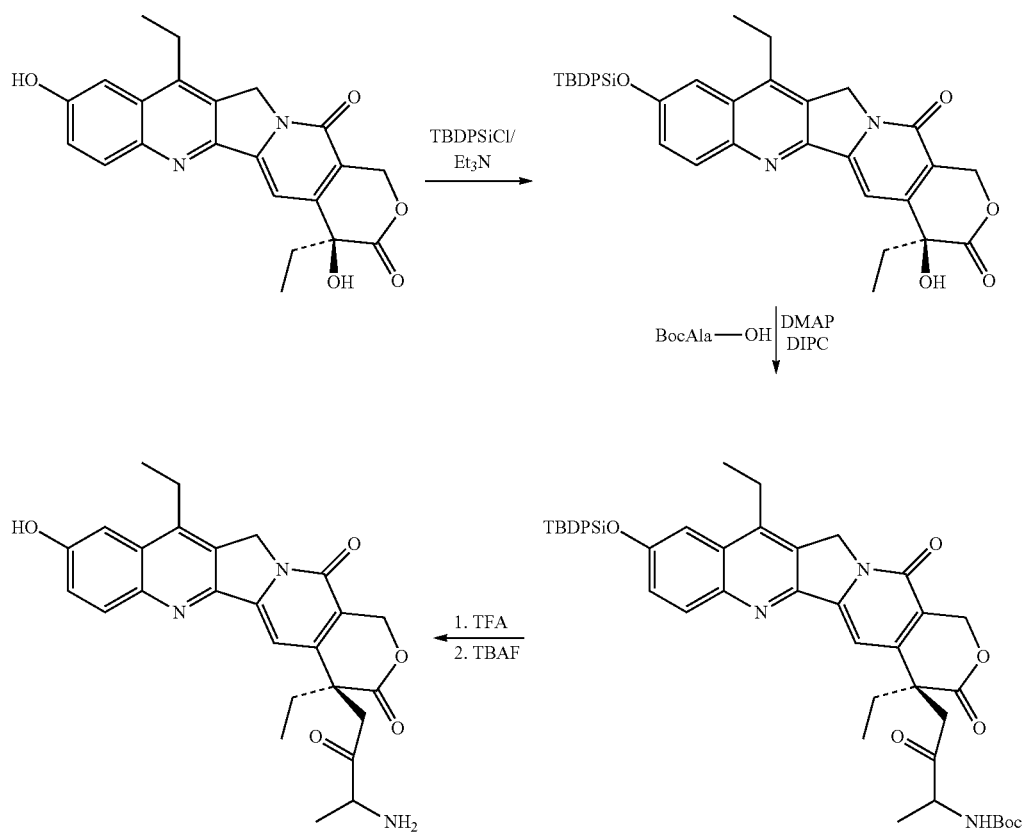

The 10-hydroxy group of non-natural camptothecin derivative, for example, SN38, is selectively protected by reacting the derivative with tert-butyldiphenylsilyl chloride (TBDPSiCl) in the presence of triethylamine. The 20-hydroxy group can be by reacted with t-butylcarbonyl-alanine to form the alanine derivative using the procedure described in Sapra, P. et al., Clin. Cancer Res., 14: 1888-1896 (2008). Alternatively, other amino acids can be employed, e.g., glycine. The primary amine is unmasked by removing the Boc protecting group by treatment with trifluoroacetic acid, followed by removing the TBDPS protecting group with tetrabutylammonium fluoride (see Scheme 3). The resulting amino derivatized SN38 compound can be conjugated with a functionalized polymer to form a drug-polymer conjugate.

Scheme 4

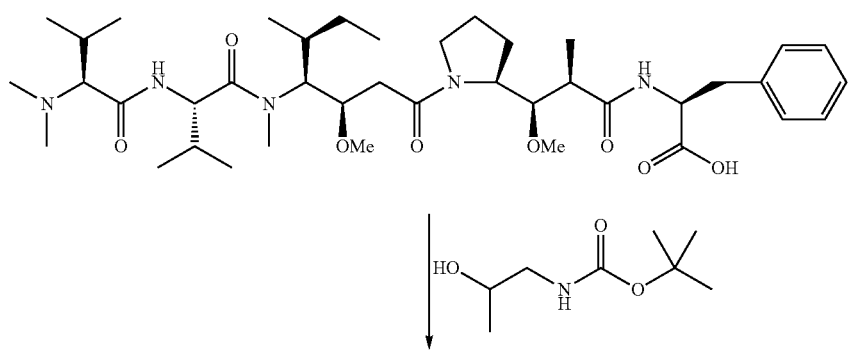

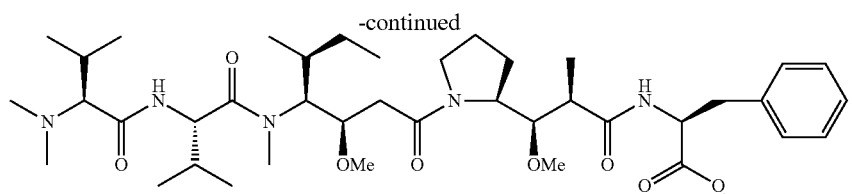

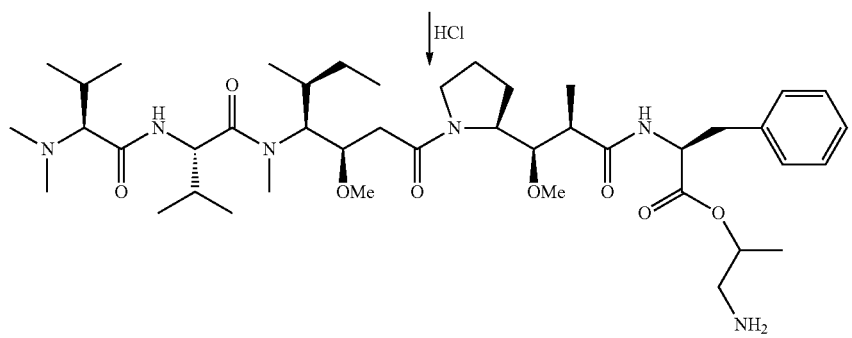

Treatment of auristatin F with a protected amino containing tether such as t-butoxy esterified 2-hydroxypropyl amine followed by HCl hydrolysis of the ester gives the 2-hydroxylpropyl amino derivative of auristatin F (see Scheme 4). Conjugation of the auristatin F derivative to functionalized polymers results in drug-polymer conjugates that can be further conjugated with a PBRM or its derivative to result in protein-polymer-drug conjugates.

This invention also relates to a drug derivative so modified that it can be directly conjugated to a PBRM absent a polymeric carrier, and the drug-PBRM conjugates thereof. For example, the drug derivative is a compound of Formula (XXII), wherein $R_{47}$ comprises a terminal maleimido group, i.e.,

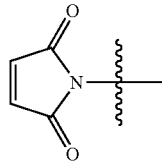

(see, e.g., Example 83).

Conjugates or Polymeric Scaffolds

The general methods of producing the conjugates or polymeric scaffolds of this invention have been described above. Schemes 5-10 below exemplify how the conjugates or polymeric scaffolds are synthesized. The variables (e.g., X, $X^D$, $X^P$, $L^{D1}$, and $L^{P2}$ etc) in these schemes have the same definitions as described herein unless otherwise specified. Each $W^{D1}$ is a function moiety that is capable of reacting with $W^D$ to form $Z^D$-$M^{D3}$ and each $W^{P1}$ is a function moiety that is capable of reacting with $W^P$ to form $Z^P$-$M^{P3}$. —$X^D$-$M^{D1}$-$Y^D$-$M^{D2}$-$W^D$ and —$X^P$-$M^{P1}$-$Y^P$-$M^{P2}$-$W^P$ may be different (such as in Schemes 5 and 5A) or the same (such as in Scheme 6). In some embodiments —$X^P$-$M^{P1}$-$Y^P$-$M^{P2}$-$W^P$ is formed by further modification of —$X^D$-$M^{D1}$-$Y^D$-$M^{D2}$-$W^D$.

Scheme 5

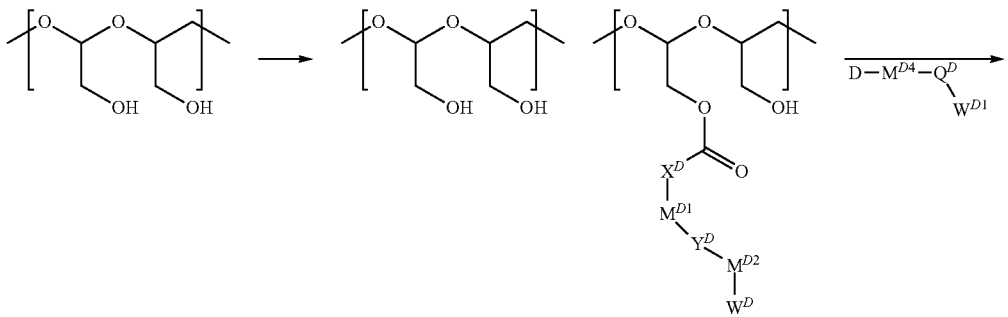

497 498
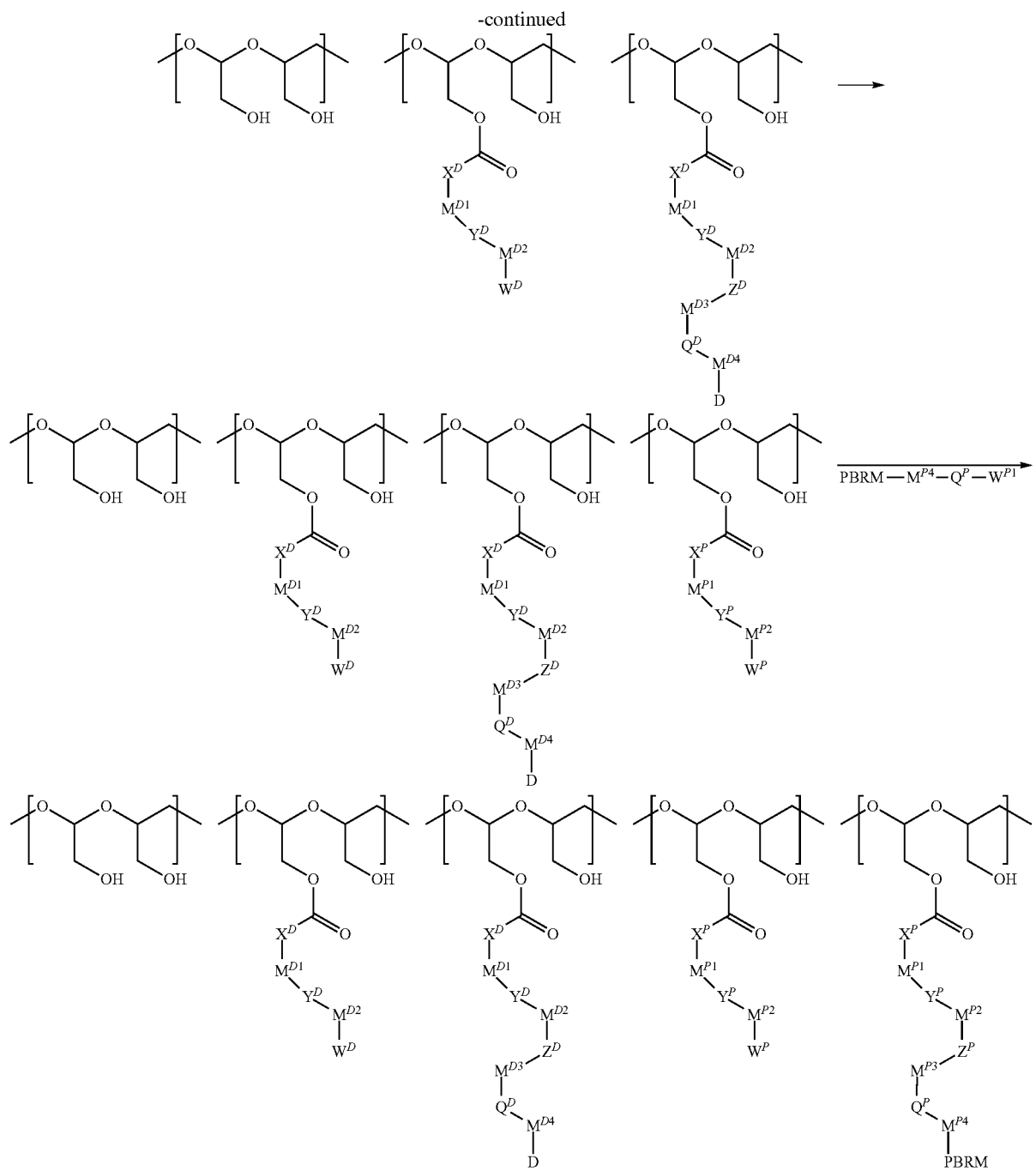
Scheme 5A
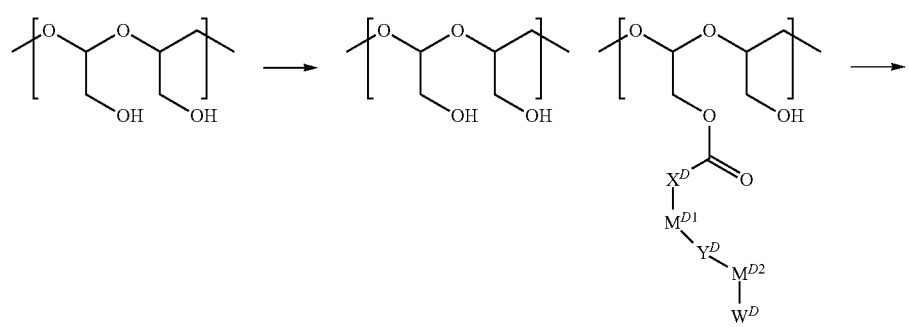

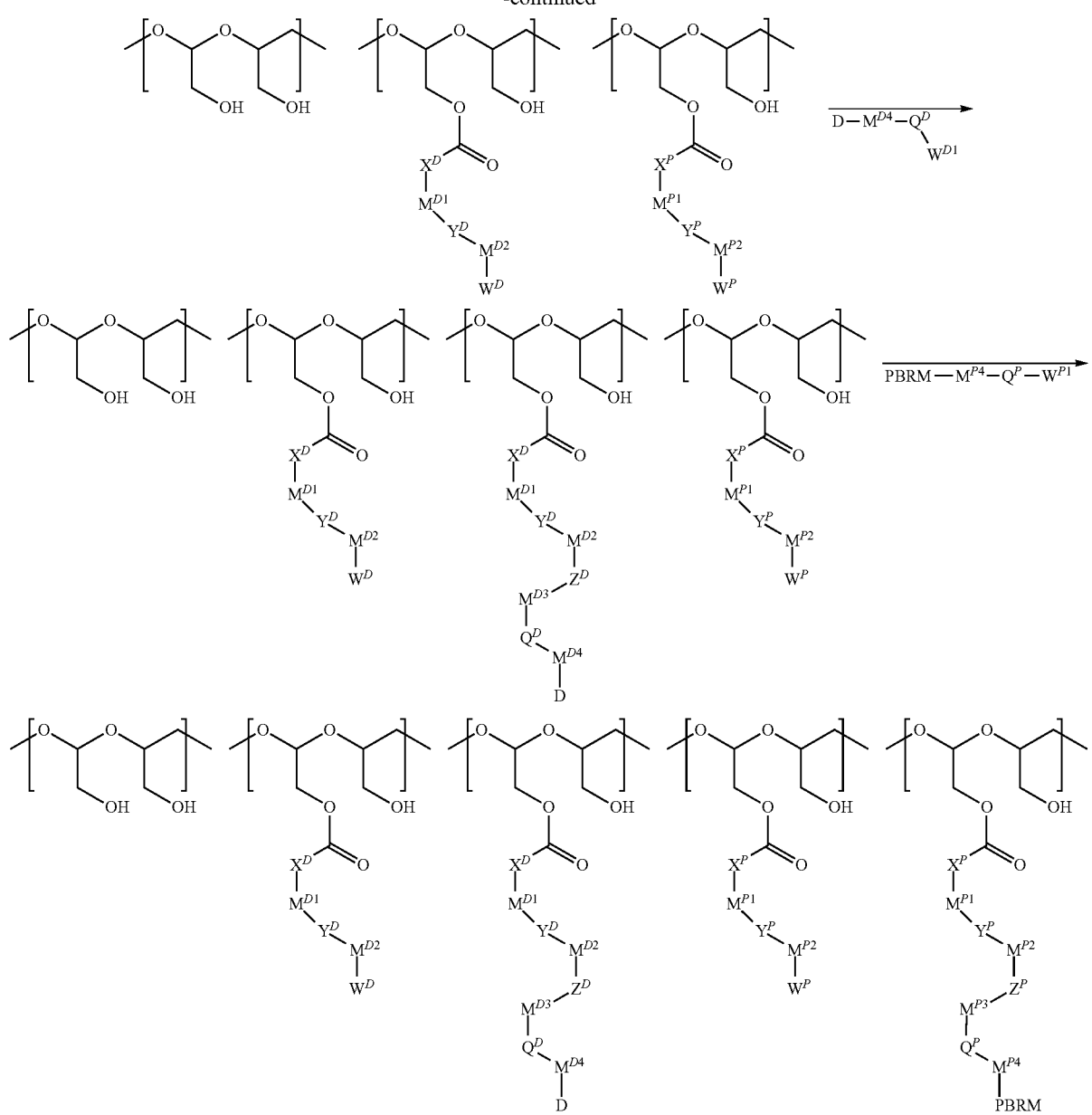
Scheme 6
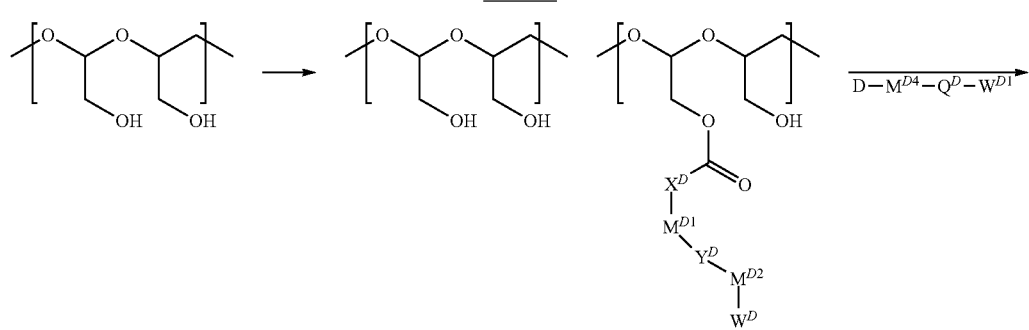

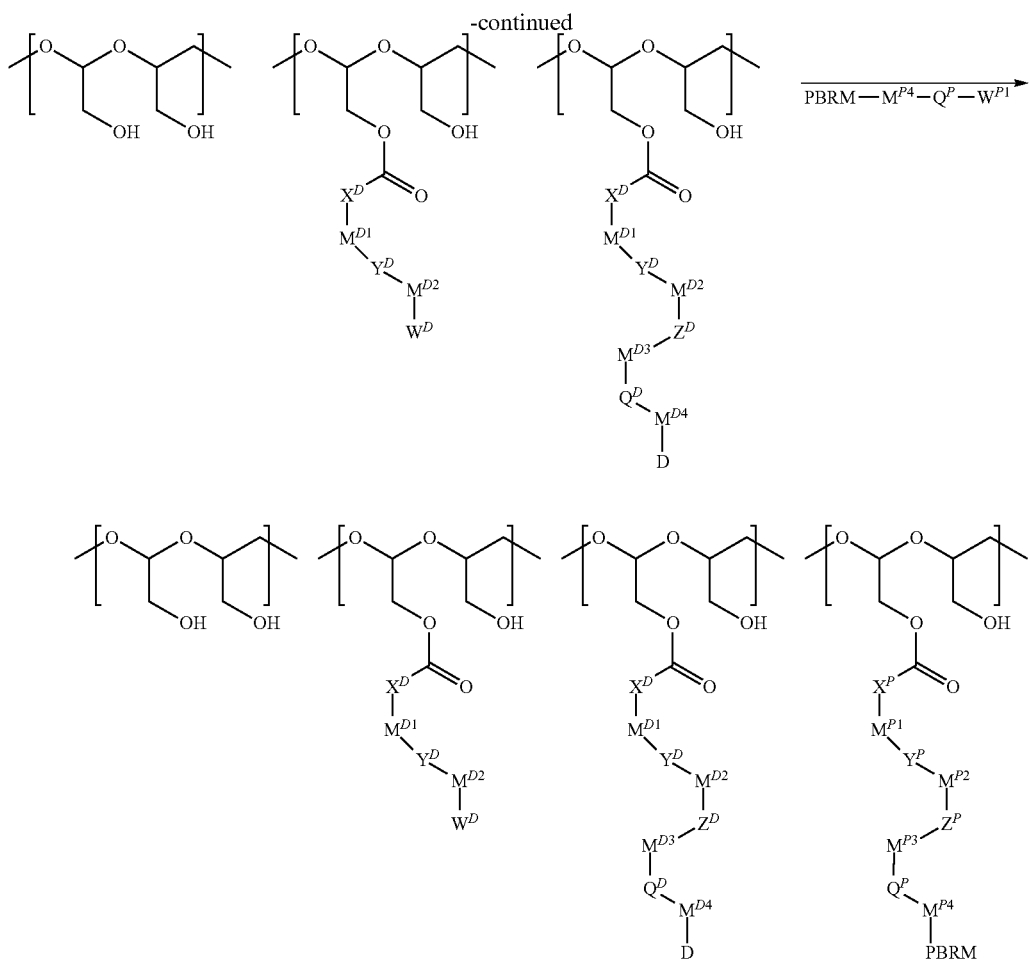

The PBRM can be linked to the drug-polymer conjugate to form the protein-drug polymer conjugate using standard synthetic methods for protein conjugation, including, but not limited to, reactions based on reductive amination, Staudinger ligation, oxime formation, thiazolidine formation and the methods and reactions described herein.

Scheme 7 below shows the synthesis of a PBRM-drug-polymer conjugate in which the PBRM is linked to the drug polymer conjugate using click chemistry.

Scheme 7

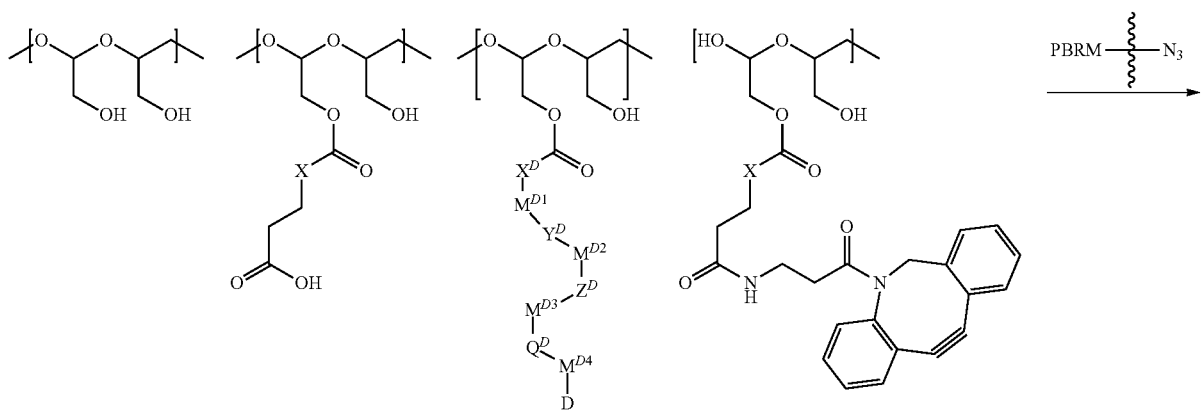

503
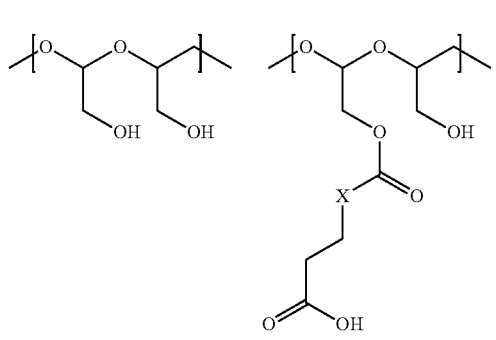
-continued
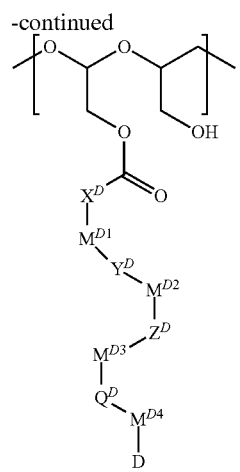
504
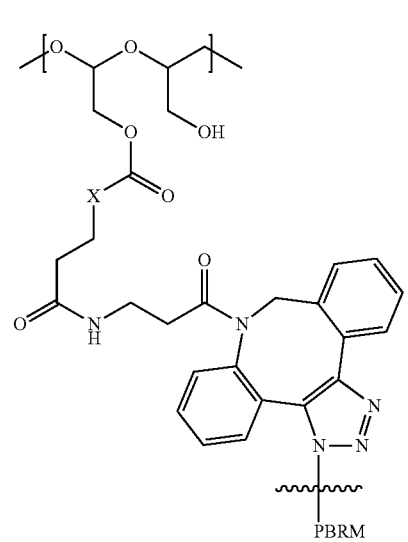
Scheme 8 below shows the synthesis of a PBRM-drug-polymer conjugate is which the PBRM is linked to the drug polymer conjugate by a Mannich reaction.
Scheme 9 below shows the synthesis of a PBRM-drug-polymer conjugate is which the PBRM is linked to the drug polymer conjugate by palladium catalyzed cross coupling.
Scheme 8
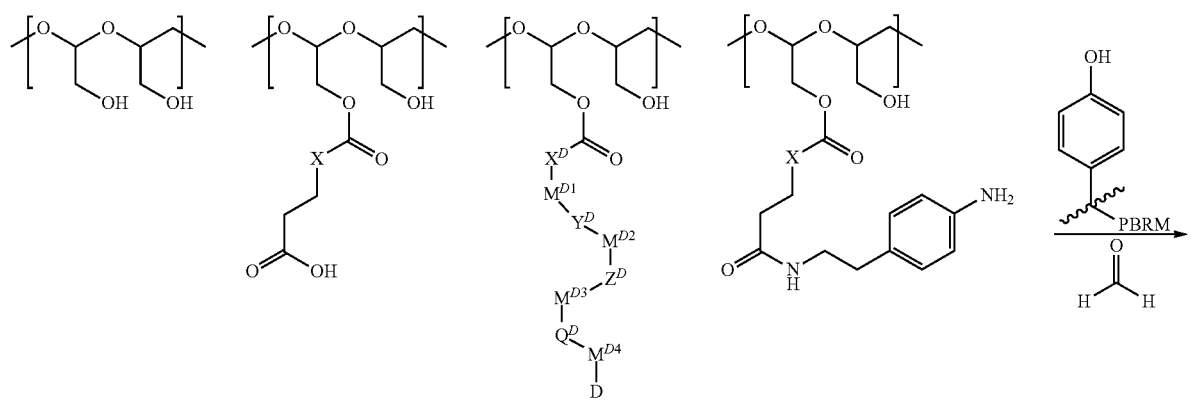
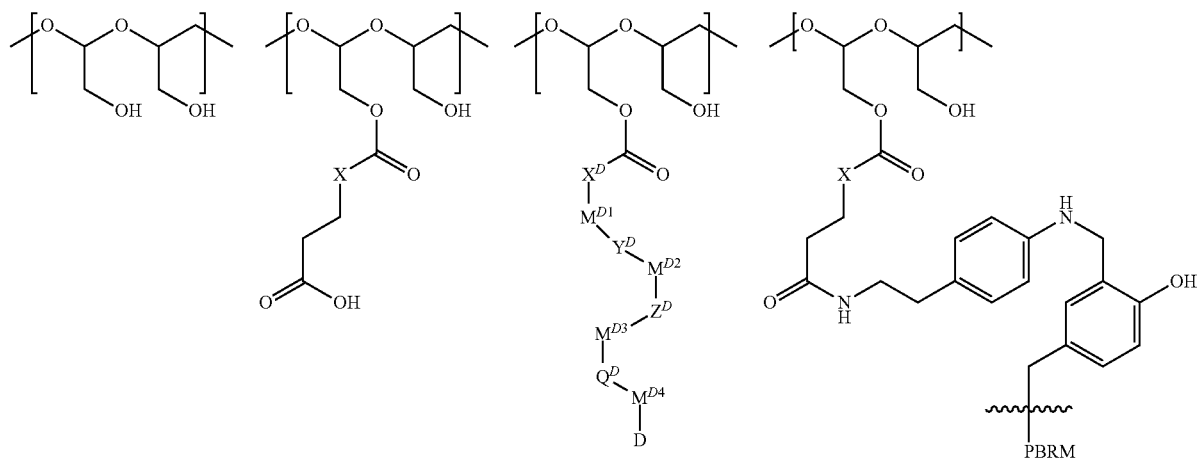

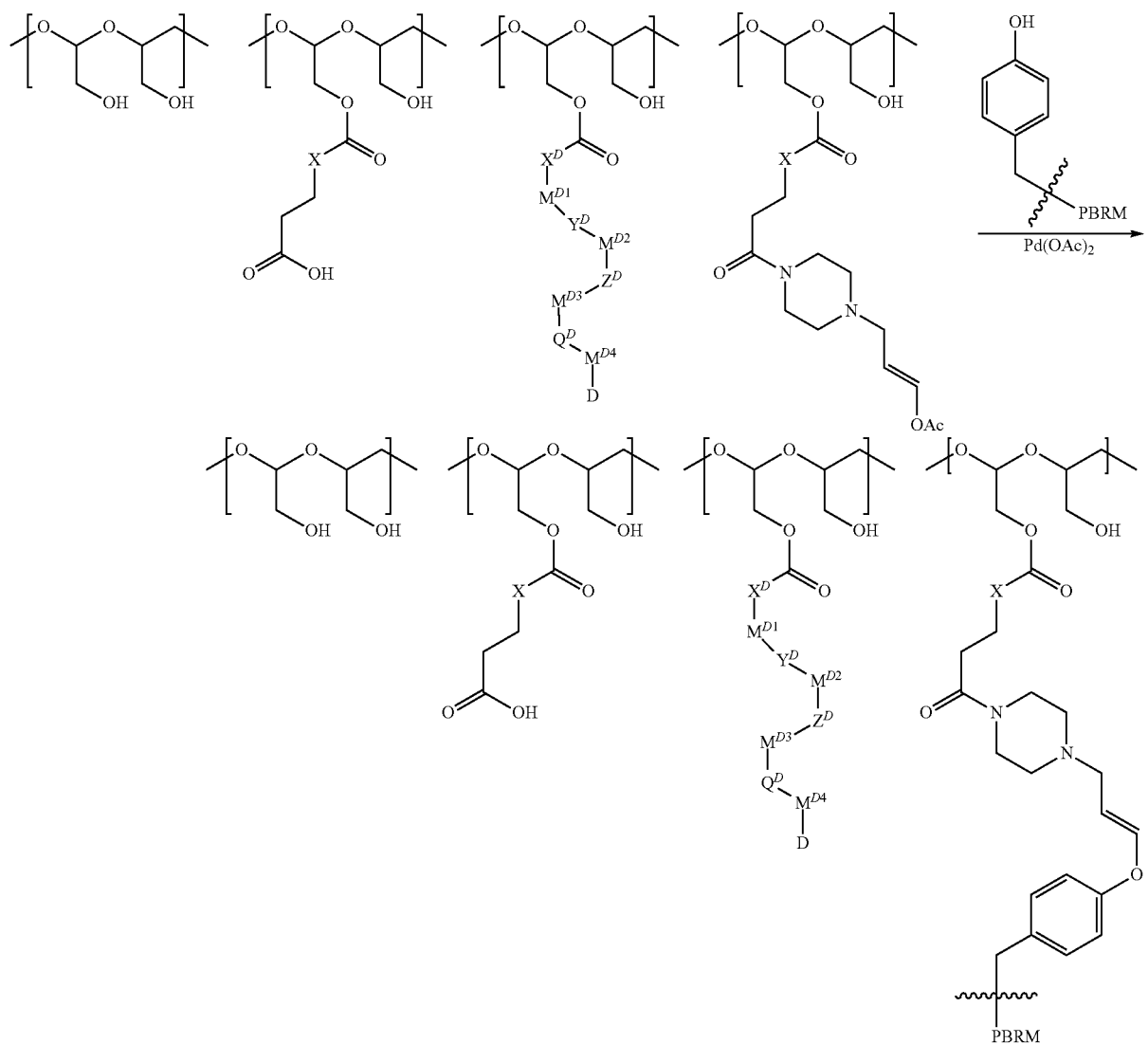
In Schemes 7-9 above, the wavy bond indicates that PBRM is either connected to the functional modifier directly or via another moiety such as alkyl, cycloalkyl, aryl, etc.
Schemes 10 below shows a general synthetic scheme of making the polymeric scaffolds of the invention. The wavy bond indicates direct or indirect connection between $L^{D1}$ and D or $L^{P2}$.
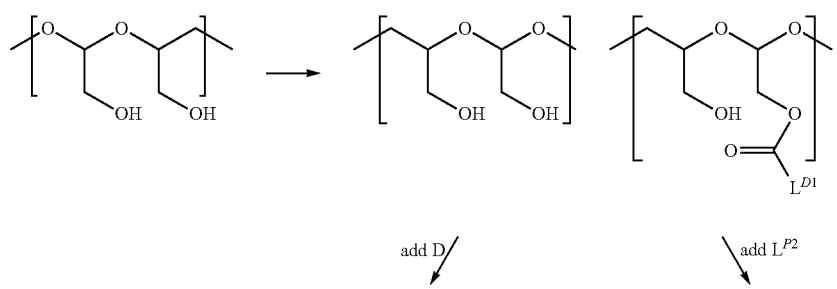

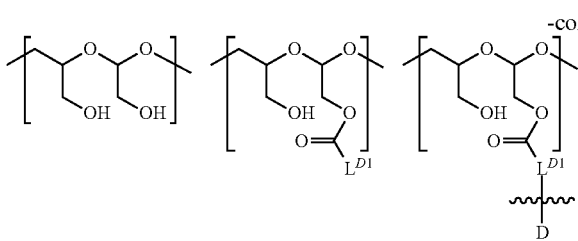
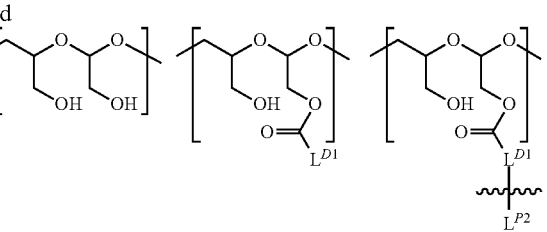
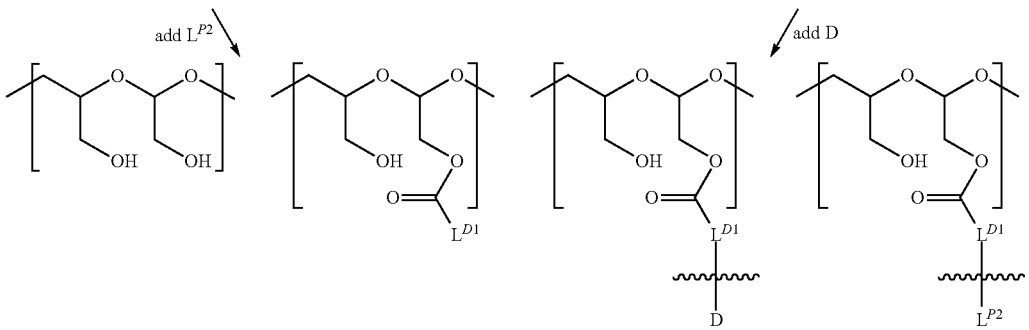

The PBRM can be linked to the drug-polymer conjugate to form the protein-drug polymer conjugate using standard synthetic methods for protein conjugation, including, but not limited to, reactions based on reductive amination, Staudinger ligation, oxime formation, thiazolidine formation and the methods and reactions described herein.

Pharmaceutical Compositions

Also included are pharmaceutical compositions comprising one or more protein-polymer-drug conjugates as disclosed herein in an acceptable carrier, such as a stabilizer, buffer, and the like. The conjugates can be administered and introduced into a subject by standard means, with or without stabilizers, buffers, and the like, to form a pharmaceutical composition. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral administration including intravenous, intraarterial, subcutaneous, intraperitoneal or intramuscular injection or infusion or intracranial, e.g., intrathecal or intraventricular, administration. The conjugates can be formulated and used as sterile solutions and/or suspensions for injectable administration; lyophilized powders for reconstitution prior to injection/infusion; topical compositions; as tablets, capsules, or elixirs for oral administration; or suppositories for rectal administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, inhaled, transdermal, or by injection/infusion. Such forms should not prevent the composition or formulation from reaching a target cell (i.e., a cell to which the drug is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of the modified polymer in the blood stream followed by distribution throughout the entire body. Administration routes that lead to systemic absorption include, without limitation: intravenous, subcutaneous, intraperitoneal, inhalation, oral, intrapulmonary, and intramuscular. Each of these administration routes exposes the modified polymers to an accessible diseased tissue. The rate of entry of an active agent into the circulation has been shown to be a function of molecular weight or size. The use of a conjugate of this invention can localize the drug delivery in certain cells, such as cancer cells via the specificity of PBRMs.

A "pharmaceutically acceptable formulation" means a composition or formulation that allows for the effective distribution of the conjugates in the physical location most suitable for their desired activity. In one embodiment, effective delivery occurs before clearance by the reticuloendothelial system or the production of off-target binding which can result in reduced efficacy or toxicity. Non-limiting examples of agents suitable for formulation with the conjugates include: P-glycoprotein inhibitors (such as Pluronic P85), which can enhance entry of active agents into the CNS; biodegradable polymers, such as poly(DL-lactide-coglycolide) microspheres for sustained release delivery after intracerebral implantation; and loaded nanoparticles, such as those made of polybutylcyanoacrylate, which can deliver active agents across the blood brain barrier and can alter neuronal uptake mechanisms.

Also included herein are pharmaceutical compositions prepared for storage or administration, which include a pharmaceutically effective amount of the desired conjugates in a pharmaceutically acceptable carrier or diluent. Acceptable carriers, diluents, and/or excipients for therapeutic use are well known in the pharmaceutical art. For example, buffers, preservatives, bulking agents, dispersants, stabilizers, dyes, can be provided. In addition, antioxidants and suspending agents can be used Examples of suitable carriers, diluents and/or excipients include, but are not limited to: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The term "pharmaceutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Pharmaceutically effective amounts for a given situation can be determined by routine experimentation that is within the skill and judgment of the clinician. In a preferred aspect, the disease or condition to can be treated via gene silencing.

For any conjugate, the pharmaceutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

For example, a drug or its derivatives, drug-polymer conjugates or PBRM-drug-polymer conjugates can be evaluated for their ability to inhibit tumor growth in several cell lines using Cell titer Glo. Dose response curves can be generated using SoftMax Pro software and $IC_{50}$ values can be determined from four-parameter curve fitting. Cell lines employed can include those which are the targets of the PBRM and a control cell line that is not the target of the PBRM contained in the test conjugates.

In one embodiment, the conjugates are formulated for parenteral administration by injection including using conventional catheterization techniques or infusion. Formulations for injection may be presented in unit dosage form, e.g., in ampules or in multi-dose containers, with an added preservative. The conjugates can be administered parenterally in a sterile medium. The conjugate, depending on the vehicle and concentration used, can either be suspended or dissolved in the vehicle. Advantageously, adjuvants such as local anesthetics, preservatives, and buffering agents can be dissolved in the vehicle. The term "parenteral" as used herein includes percutaneous, subcutaneous, intravascular (e.g., intravenous), intramuscular, or intrathecal injection or infusion techniques and the like. In addition, there is provided a pharmaceutical formulation comprising conjugates and a pharmaceutically acceptable carrier. One or more of the conjugates can be present in association with one or more non-toxic pharmaceutically acceptable carriers and/or diluents and/or adjuvants, and if desired other active ingredients.

The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, a bland fixed oil can be employed including synthetic mono- or diglycerides. In addition, fatty acids such as oleic acid find use in the preparation of injectables.

The conjugates and compositions described herein may be administered in appropriate form, preferably parenterally, more preferably intravenously. For parenteral administration, the conjugates or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

Dosage levels of the order of from between about 0.01 mg and about 140 mg per kilogram of body weight per day are useful in the treatment of the above-indicated conditions (between about 0.05 mg and about 7 g per subject per day). In some embodiments, the dosage administered to a patient is between about 0.01 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. The amount of conjugate that can be combined with the carrier materials to produce a single dosage form varies depending upon the host treated and the particular mode of administration. Dosage unit forms can generally contain from between about 0.01 mg and about 100 mg; between about 0.01 mg and about 75 mg; or between about 0.01 mg and about 50 mg; or between about 0.01 mg and about 25 mg; of a conjugate.

For intravenous administration, the dosage levels can comprise from about 0.01 to about 200 mg of a conjugate per kg of the animal's body weight. In one aspect, the composition can include from about 1 to about 100 mg of a conjugate per kg of the animal's body weight. In another aspect, the amount administered will be in the range from about 0.1 to about 25 mg/kg of body weight of a compound.

In some embodiments, the conjugates can be administered are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period.

In some embodiments about one to about four weeks after treatment, the patient can receive a second course of treatment. Specific clinical protocols with regard to route of administration, excipients, diluents, dosages, and times can be determined by the skilled artisan as the clinical situation warrants.

It is understood that the specific dose level for a particular subject depends upon a variety of factors including the activity of the specific conjugate, the age, body weight, general health, sex, diet, time of administration, route of administration, and rate of excretion, combination with other active agents, and the severity of the particular disease undergoing therapy.

For administration to non-human animals, the conjugates can also be added to the animal feed or drinking water. It can be convenient to formulate the animal feed and drinking water so that the animal takes in a therapeutically appropriate quantity of the conjugates along with its diet. It can also be convenient to present the conjugates as a premix for addition to the feed or drinking water.

The conjugates can also be administered to a subject in combination with other therapeutic compounds to increase the overall therapeutic effect. The use of multiple compounds to treat an indication can increase the beneficial effects while reducing the presence of side effects. In some embodiment the conjugates are used in combination with chemotherapeutic agents, such as those disclosed in U.S. Pat. No. 7,303,749. In other embodiments the chemotherapeutic agents, include, but are not limited to letrozole, oxaliplatin, docetaxel, 5-FU, lapatinib, capecitabine, leucovorin, erlotinib, pertuzumab, bevacizumab, and gemcitabine.

The present invention also provides pharmaceutical kits comprising one or more containers filled with one or more of the conjugates and/or compositions of the present invention, including, one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products.

Methods of Use
Methods of Treating

In certain preferred embodiments of the invention, the protein-polymer-drug conjugate of the invention are used in methods of treating animals (preferably mammals, most preferably humans and includes males, females, infants, children and adults). In one embodiment, the conjugates of the present invention may be used in a method of treating animals which comprises administering to the animal a biodegradable biocompatible conjugate of the invention. For example, conjugates in accordance with the invention can be administered in the form of soluble linear polymers, copolymers, conjugates, colloids, particles, gels, solid items, fibers, films, etc. Biodegradable biocompatible conjugates of this invention can be used as drug carriers and drug carrier components, in systems of controlled drug release, preparations for low-invasive surgical procedures, etc. Pharmaceutical formulations can be injectable, implantable, etc.

In yet another aspect, the invention provides a method of treating a disease or disorder in a subject in need thereof, comprising administering to the subject an efficient amount of at least one conjugate of the invention; wherein said conjugate releases one or more therapeutic agents upon biodegradation.

In another embodiment the conjugates can be administered in vitro, in vivo and/or ex vivo to treat patients and/or to modulate the growth of selected cell populations including, for example, cancer. In some embodiments, the particular types of cancers that can be treated with the conjugates include, but are not limited to: (1) solid tumors, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; (2) blood-borne cancers, including but not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma, acute and chronic leukemias, e.g., lymphoblastic myelogenous and lymphocytic myelocytic leukemias; and (3) lymphomas such as Hodgkin's disease, non-Hodgkin's Lymphoma, Multiple myeloma, Waldenstrom's macroglobulinemia, Heavy chain disease, and Polycythemia vera.

In another embodiment the conjugates can be administered in vitro, in vivo and/or ex vivo to treat autoimmune diseases, such as systemic lupus, rheumatoid arthritis, psoriasis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like.

In certain embodiments the conjugates can also be used for the manufacture of a medicament useful for treating or lessening the severity of disorders, such as, characterized by abnormal growth of cells (e.g., cancer).

In certain embodiments, the therapeutic agent is locally delivered to a specific target cell, tissue, or organ.

In certain embodiments, in practicing the method of the invention, the conjugate further comprises or is associated with a diagnostic label. In certain exemplary embodiments, the diagnostic label is selected from the group consisting of: radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves and microwaves and fluorophores. In certain exemplary embodiments, the conjugate is further monitored in vivo.

Examples of diagnostic labels include, but are not limited to, diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include γ-emitting radionuclides, e.g., indium-111, technetium-99m and iodine-131, etc. Contrast agents for MRI (Magnetic Resonance Imaging) include magnetic compounds, e.g., paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron and gadolinium. Further, labels can be employed which can reflect, refract, scatter, or otherwise affect X-rays, ultrasound, radiowaves, microwaves and other rays useful in diagnostic procedures. Fluorescent labels can be used for photoimaging. In certain embodiments a modifier comprises a paramagnetic ion or group.

In another aspect, the invention provides a method of treating a disease or disorder in a subject, comprising preparing an aqueous formulation of at least one conjugate of the invention and parenterally injecting said formulation in the subject.

In another aspect, the invention provides a method of treating a disease or disorder in a subject, comprising preparing an implant comprising at least one conjugate of the invention, and implanting said implant into the subject. In certain exemplary embodiments, the implant is a biodegradable gel matrix.

In another aspect, the invention provides a method for treating of an animal in need thereof, comprising administering a conjugate according to the methods described above.

In another aspect, the invention provides a method for eliciting an immune response in an animal, comprising administering a conjugate as in the methods described above.

In another aspect, the invention provides a method of diagnosing a disease in an animal, comprising steps of:
administering a conjugate as in the methods described above, wherein said conjugate comprises a detectable molecule; and
detecting the detectable molecule.

In certain exemplary embodiments, the step of detecting the detectable molecule is performed non-invasively. In certain exemplary embodiments, the step of detecting the detectable molecule is performed using suitable imaging equipment.

In one embodiment, a method for treating an animal comprises administering to the animal a biodegradable biocompatible conjugate of the invention as a packing for a surgical wound from which a tumor or growth has been removed. The biodegradable biocompatible conjugate packing will replace the tumor site during recovery and degrade and dissipate as the wound heals.

In certain embodiments, the conjugate is associated with a diagnostic label for in vivo monitoring.

The conjugates described above can be used for therapeutic, preventative, and analytical (diagnostic) treatment of animals. The conjugates are intended, generally, for parenteral administration, but in some cases may be administered by other routes.

In one embodiment, soluble or colloidal conjugates are administered intravenously. In another embodiment, soluble or colloidal conjugates are administered via local (e.g., subcutaneous, intramuscular) injection. In another embodiment, solid conjugates (e.g., particles, implants, drug delivery systems) are administered via implantation or injection.

In another embodiment, conjugates comprising a detectable label are administered to study the patterns and dynamics of label distribution in animal body.

In certain embodiments, any one or more of the conjugates disclosed herein may be used in practicing any of the methods described above. In certain exemplary embodiments, the conjugate is a Trastuzumab-PHF-, Rituximab-PHF- or LHRH-PHF-drug conjugate.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Drug compounds used for the conjugates of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5$^{th}$ edition, John Wiley & Sons: New York, 2001; and Greene, T. W., Wuts, P. G. M., *Protective Groups in Organic Synthesis,* 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Conjugates of the present invention and the drug compounds included therein can be conveniently prepared by a variety of methods familiar to those skilled in the art. The conjugates or compounds of this invention with each of the formulae described herein may be prepared according to the following procedures from commercially available starting materials or starting materials which can be prepared using literature procedures. These procedures show the preparation of representative conjugates of this invention.

Conjugates designed, selected and/or optimized by methods described above, once produced, can be characterized using a variety of assays known to those skilled in the art to determine whether the conjugates have biological activity. For example, the conjugates can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the conjugate molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Conjugates described herein can be prepared by the schemes generally outlined above and by methods described in the Examples below. The term "content" as used in certain examples below, unless otherwise specified, means the molar fraction of the polymer units that are substituted with the intended moiety, such as the linker, the drug molecule, or PBRM.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

Adoa 8-amino-3,6-dioxa-octanoic acid
AF HPA Auristatin F-hydroxypropylamide
AZD 8330 2-[(2-fluoro-4-iodophenyl)amino]-1,6-dihydro-N-(2-hydroxyethoxy)-1,5-dimethyl-6-oxo-3-pyridinecarboxamide
BA β-Alanine
BOC tert-Butyloxycarbonyl
DIC N,N'-Diisopropylcarbodiimide
DIEA N,N-Diisopropylethylamine
DIPEA N-Ethyl-N-isopropylpropan-2-amine
DCM Dichloromethane
DMA Dimethylacetamide
DMAP 4-Dimethylaminopyridine
DMF Dimethylformamide
DMSO Dimethylsulfoxide
DTT (2S,3S)-1,4-dimercaptobutane-2,3-diol
EDC 1-Ethyl-3-[3-dimethylaminopropyl]carbodiimide hydrochloride
GA Glutaric acid
HATU 2-(1H-7-Azabenzotriazol-1-yl)-1,1,3,3-tetramethyluronoium hexafluorophosphate
HOAt 3H-[1,2,3]-Triazolo[4,5-b]pyridin-3-ol
HOBt Hydroxybenzotriazole
HPLC High pressure liquid chromatography
HPSEC High performance size exclusion chromatography
HPV Hydroxypropylvindesine
2HPV 2-Hydroxypropylvindesine
MCC (N-maleimidomethyl) 1,4-cyclohexyl carbamate
M-(PEG)$_{12}$ N-maleimido-PEG$_{12}$-propionamide
MWCO Molecular Weight Cut-Off
NHS 1-Hydroxypyrrolidine-2,5-dione
NMP N-methyl-2-pyrrolidone
PABA p-Amino benzoic acid
PBS Phosphate buffered saline, 0.9% NaCl
PHF poly(1-hydroxymethylethylene hydroxylmethylformal), or FLEXIMER®
PI-103 3-[4-(4-morpholinyl)pyrido[3',':4,5]furo[3,2-d]pyrimidin-2-yl]-phenol
PNP p-Nitrophenoxide
RP-HPLC reverse-phase high performance liquid chromatography
SATA N-Succinimidyl-5-acetylthioacetate
SEC Size exclusion chromatography
SMCC Succinimidyl-4-(N-maleimidomethyl)cyclohexane-1-carboxylate
SM(PEG)$_{12}$ Succinimidyl-([N-maleimidopropionamide]-PEG$_{12}$)-ester
—SS— Indicates a covalently bound disulfide group
SSPy 2-(pyridine-2-yldisulfanyl)
TCEP Tris[2-carboxyethyl]phosphine
TEA Triethylamine
TFA Trifluoroacetic acid

General Information

Peptides EC-1-Adoa-NH$_2$ and LTVSPNY-Adoa-NH$_2$ were purchased from CreoSalus, Louisville, Ky.

Linkers M-(PEG)$_{12}$-NHS and S-Acetyl-(PEG)$_{12}$-NHS ester were purchased from Quanta Biodesign, Powell, Ohio.

Fmoc-Val-Cit-PABA-PNP, auristatin E and auristatin F were purchased from Concortis Biosystems.

6-Maleimidohexanoic acid N-hydroxysuccinimide ester was purchased from Aldrich Chemicals.

N-Boc-D-valine was purchased from Alfa Aesar.

N-Boc-L-Val-OH was purchased from Novabiochem.

Anti-Her2 affibody, 14 kDa, was purchased from Affibody AB.

Ispinesib was purchased from Shanghai Race Chemical Co.

AZD8330 and PI-103 kinase were purchased from Selleck.

HPLC purification was performed on a Phenomenex Gemini 5 μm 110 Å, 250×10 mm, 5 micron, semi-preparation column using the following solvent system: Solvent A: water (0.1% TFA); Solvent B: CH$_3$CN (0.1% TFA).

Whenever possible the drug content of the conjugates was determined spectrophotometrically otherwise LC/MS was performed for quantitative determination of the drug content. For spectrophotometric determination HPV and 2 HPV were monitored at 310 nm; SN38 at 370 nm; ispinesib at 318 nm; PI-103 at 330 nm and duocarmycin derivatives at 353 nm.

Protein content of the conjugates was determined spectrophotometrically at 280 nm.

Disulfide content in —SSPy conjugates was determined spectrophotometrically at 340 nm after pyridinethione release (10 mM DTT, 10 min, ambient temperature).

The molecular weights of the polymer conjugates were determined by SEC with either polysaccharide or protein molecular weight standards. More specifically, for the polymer or polymer drug conjugates, polysaccharide molecular weights standard are used, and for protein-drug polymer conjugates, protein standards are used. Unless specifically indicated the reported polymer carrier molecular weight is the weight average molecular weight of PHF. The polymer and polymer conjugates synthesized/measured all had a polydispersity <2.

PBRM-drug polymer conjugates were isolated from residual unreacted drug polymer conjugates by extensive diafiltration. If necessary, additional purification by size exclusion chromatography was conducted to remove any aggregated PBRM-drug polymer conjugates. In general the PBRM-drug polymer conjugates typically contained <5% aggregated PBRM-drug polymer conjugates as determined by SEC or SDS-PAGE; <1% free (unconjugated) drug as determined by SEC and <2% unconjugated PBRM as determined by HPLC.

Reduced or partially reduced antibodies were prepared using procedures described in the literature, see, for example, Francisco et al., Blood 102 (4): 1458-1465 (2003).

Example 1

Synthesis of PHF-β-Alanine

A. Synthesis of 30 kDa PHF-β-Alanine:

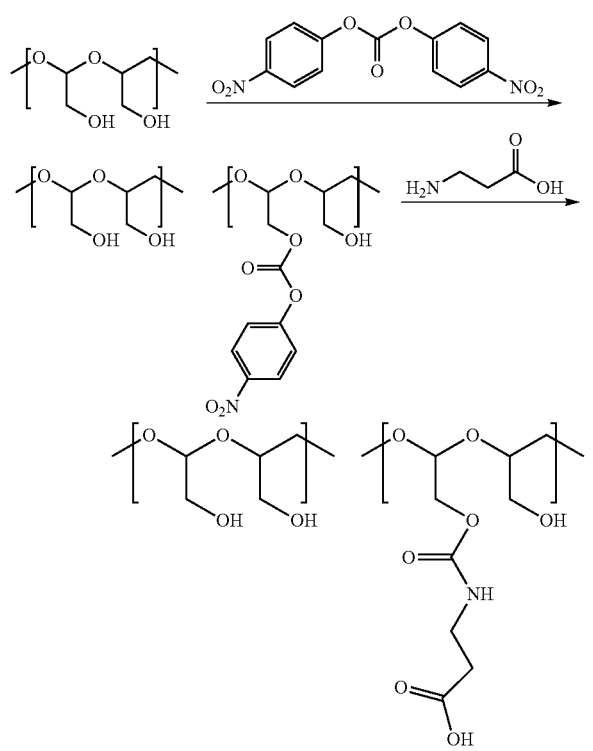

PHF (30 kDa, 4.54 g, 33.6 mmol PHF monomer) was dissolved in 150 mL anhydrous DMF, followed by the addition of bis(nitrophenol) carbonate (3.07 g, 10.1 mmol). The solution was stirred at 40° C. for 4 h. β-Alanine (1.50 g, 16.8 mmol) dissolved in water (10 mL) was added to the PHF mixture. The pH was adjusted to 7.5-8 with TEA and the reaction mixture stirred at 23° C. for 18 h, diluted to 400 mL with water and the pH adjusted to 11 with 5N NaOH. The resulting mixture was stirred for 1 h at ambient temperature, the pH was adjusted to 6.5 and then the mixture was diluted to 10% organics with water. The product (30 kDa PHF-β-Alanine) was purified using ultrafiltration cartridge equipped with 5K Biomax membrane filter. The purified product was lyophilized to give the title compound as a white solid (2.07 g, 36% yield). The molar fraction of the PHF monomer units substituted with β-alanine was 13%, as determined by $^1$H NMR.

B. Synthesis of 13 kDa PHF-β-Alanine:

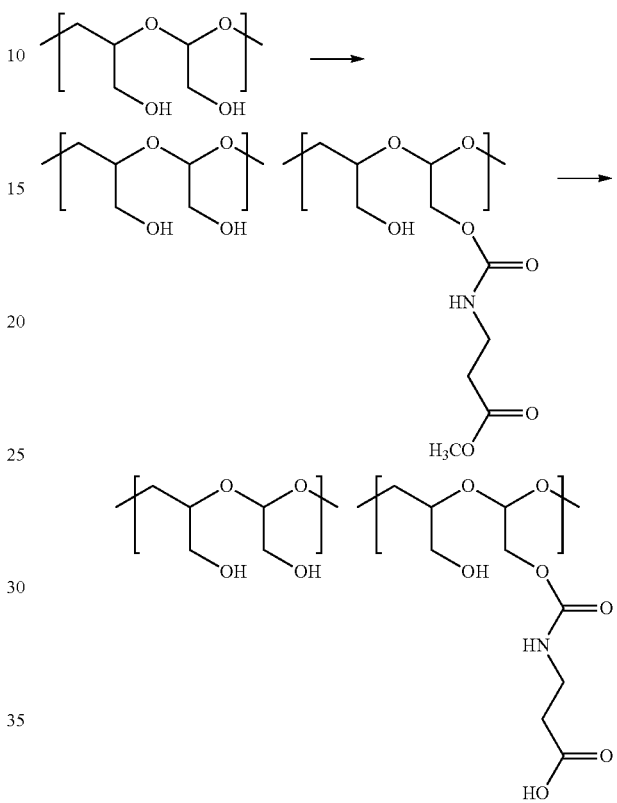

PHF (12 g), DMA (100 g) and pyridine (7.4 g) were stirred at 40° C. for ~3 hours. To the clear solution was added methyl-3-isocyanatopropanoate (3.8 g, 0.33 mole % to PHF) over a period of 5 minutes and the stirring continued for an additional 24 hours at 45° C. The reaction mixture was then diluted with water (320 g) and 5N NaOH (32 g) at 25° C. was added over 2 minutes, final pH 13. The mixture was stirred at 25° C. for 18 h, the pH of the reaction mixture was adjusted to 7 with 1N HCl, followed by dilution to ~3.5 L with water, concentrated by diafiltration using a membrane filter, 3 kDa MWCO, followed by purification on a Sephadex G-25 column. The resulting PHF BA was characterized to have a molecular weight of ~13 kDa. (BA ~31%, 14 g, yield 90%).

Example 2

Synthesis of 30 kDa PHF-GA

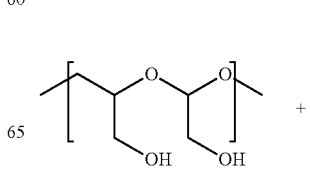

-continued

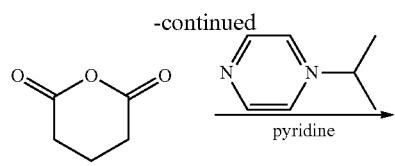

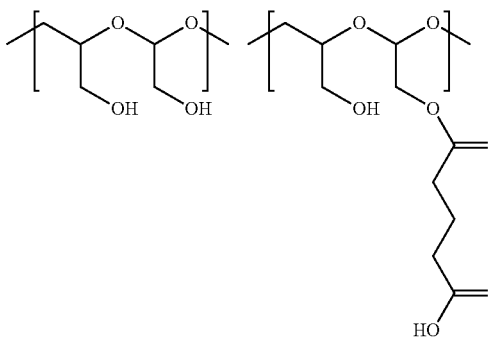

N,N-Dimethylpyridin-4-amine (0.268 g, 2.91 mmol) and glutaric anhydride (1.375 g, 12.06 mmol) was added to a solution of PHF (30 kDa, 1.48 g, 10.96 mmol PHF monomer) in DMA (300 mL) and anhydrous pyridine (33.3 mL). The reaction mixture was stirred at 60° C. for 18 h. The solvents were removed under reduced pressure and the resulting thick oil was taken up in water (100 mL). The pH was adjusted to pH 6.0-6.5 with 5N NaOH. The resulting clear solution was diluted to 200 mL with water, filtered through a 0.2 micron filter, and purified by diafiltration using a membrane filter, 5000 molecular weight cut-off. The water was removed by lyophilization to give 30 kDa PHF-GA as a white solid (1.28 g, 48% yield). The fraction of the total PHF monomer units substituted with glutaric acid as determined by $^1$H NMR was 96%.

Example 3

Synthesis of Trastuzumab-MCC Derivative

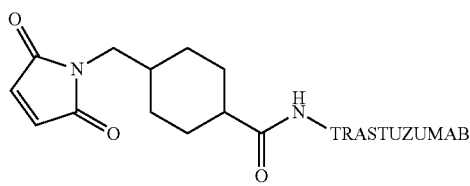

Trastuzumab (10 mg) was dissolved in PBS buffer (1 ml, pH 7.0), then a solution of SMCC in DMSO (5 µL, 30 mg/ml) was added. The resulting solution was stirred at room temperature for 2 h. The trastuzumab-MCC was purified by gel filtration using a PBS equilibrated PD-10 column (90% yield). Analysis showed that on average 5 to 6 MCC groups were linked to one trastuzumab.

Other PBRM-MCC derivatives, such as, MCC derivatives of cetuximab, rituximab, bevacizumab, nimotuzumab, gemtuzumab or alemtuzumab, are synthesized with methods similar to the procedure described above.

Example 4

Synthesis of Trastuzumab-M-(PEG)$_{12}$ Derivative

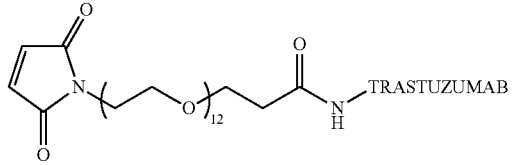

Trastuzumab (10 mg) was dissolved in PBS buffer (1 ml, pH 7.0), then a solution of SM-(PEG)$_{12}$ in DMSO (4 µL, 100 mg/ml) was added. The resulting solution was stirred at room temperature for 2 h. Trastuzumab-M-(PEG)$_{12}$ was purified by gel filtration using a PBS equilibrated PD-10 column (~90% yield). Analysis showed that on average 5 to 6 polyethylene groups were linked to one trastuzumab.

Other PBRM-M-(PEG)$_{12}$ derivatives, such as, M-(PEG)$_{12}$ derivatives of cetuximab, rituximab, bevacizumab, nimotuzumab, gemtuzumab or alemtuzumab, are synthesized with methods similar to the procedure described above.

Example 5

Synthesis of 10 kDa PHF-GA-SSpy

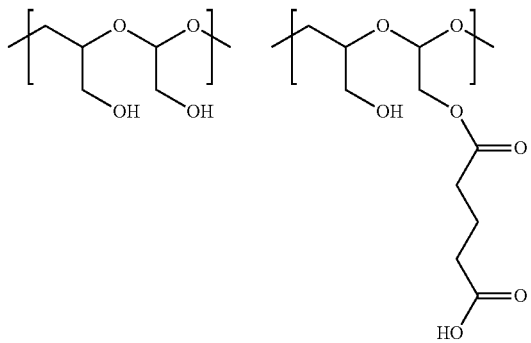

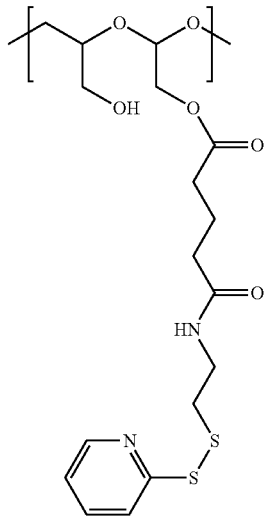

10 kDa PHF-GA (1.63 g 11.12 mmol, prepared using the procedure described in Example 2 with PHF 10,000 Da, 25% GA) was dissolved in water (10 mL) and NHS (0.154 g, 1.33 mmol) was added. The mixture was cooled to 0° C. and then an aqueous solution of EDC (0.256 g, 1.33 mmol) was added followed by 2-(pyridine-2-yldisulfanyl)ethaneamine hydrochloride (0.297 g, 1.33 mmol). The pH of the resulting mixture was adjusted to 5.5-6.0 then stirred at 23° C. for 18 h, followed by purification by dialysis through a Regenerated Cellulose membrane, and lyophilization to give the title compound (1.66 g, 86%) as a white solid. The SSPy content was 3%.

Example 6

Synthesis of 10 kDa PHF-GA-(HPV-Alanine)-SH

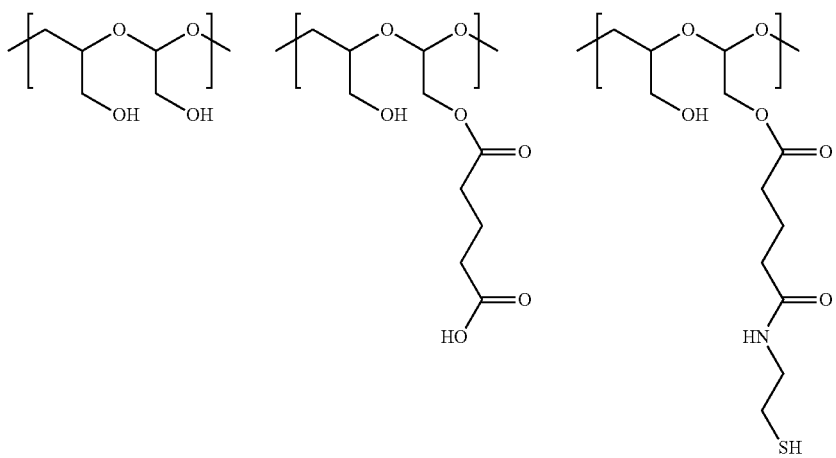

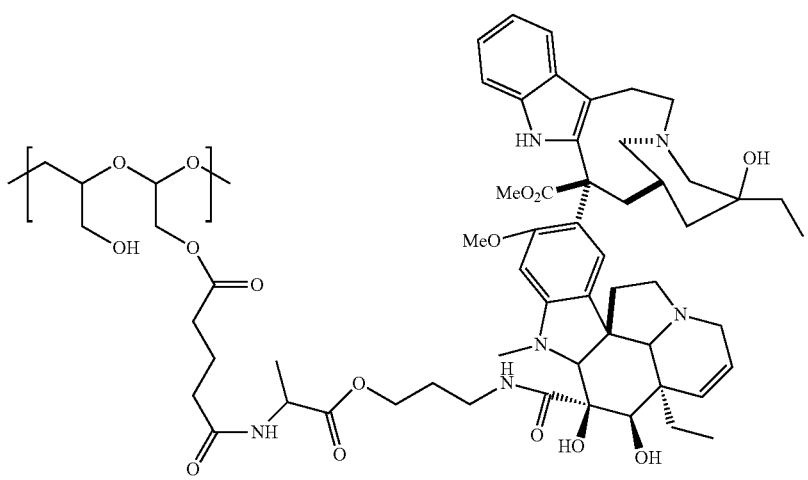

10 kDa PHF-GA-SSpy (289.0 mg, 0.023 mmol, prepared as described in Example 5) was taken up in a mixture of water (8 mL) and acetonitrile (4 mL) and cooled to 0° C. NHS (26.4 mg, 0.230 mmol) was added followed by an aqueous solution of EDC (44.0 mg, 0.230 mmol) and HPV-Alanine (131.45 mg, 0.138 mmol, prepared as described in U.S. Publication No. 2010/0305149, Example 1). The pH of the resulting mixture was adjusted to 6, and then the mixture was stirred at room temperature overnight. The pH was adjusted to 7.5 with 1M NaHCO$_3$ and DTT (37.8 mg, 0.245 mmol) was added. The reaction mixture was stirred at 23° C. for 30 min, diluted to 15 mL with water and purified by dialysis using a Regenerated cellulose membrane (3 K MW cut-off). Yield 57% (based on HPV); 7.3% wt HPV, as determined by HPLC.

By substituting HPV-Alanine with other drug moieties or drug derivatives in the procedure described above it is possible to synthesize other drug-polymer conjugates.

Example 7

Synthesis of 10 kDa PHF-GA-(HPV-Alanine)-(Trastuzumab-MCC)

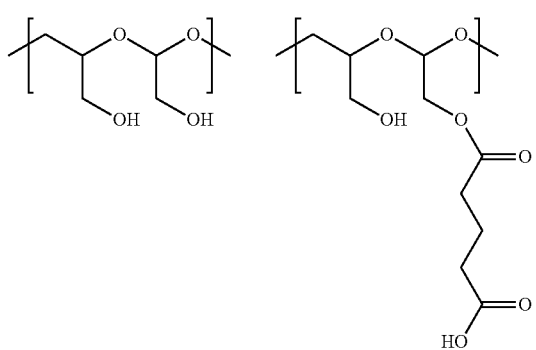

-continued

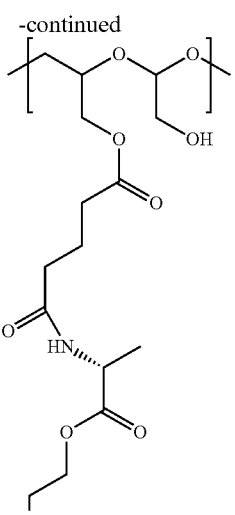

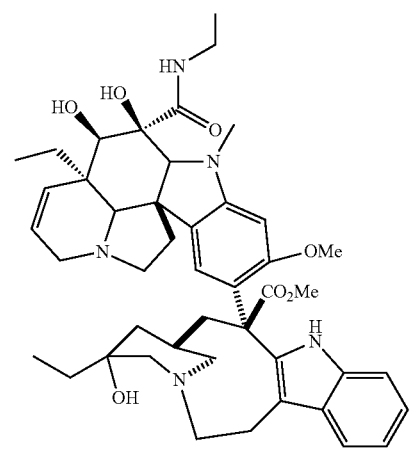

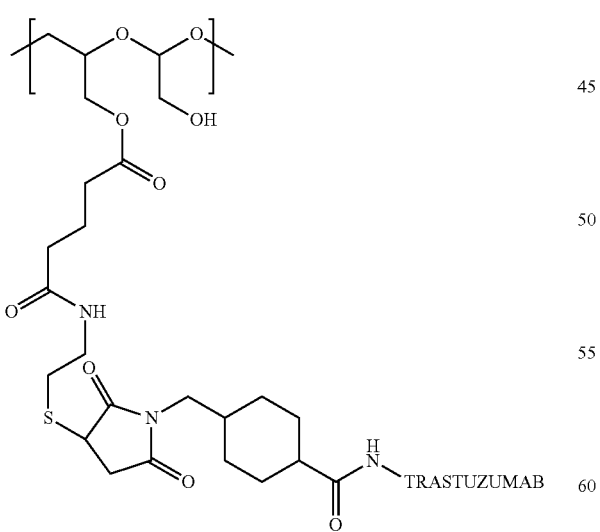

To Trastuzumab-MCC (20 mg, prepared as described in Example 3) in PBS (2 mL, pH 7.0) was added 10 kDa PHF-GA-(HPV-Alanine)-SH (11.2 mg, prepared as described in Example 6) in water (0.5 mL). The solution was stirred at room temperature for 4 h at pH 7.0. The resulting conjugate was purified by gel filtration using a Superpose-6 column with PBS as the eluant (75% yield). The molecular weight of the PHF-GA-(HPV-Alanine)-(Trastuzumab-MCC) as determined by SEC was about 170 kDa. The HPV content as determined by HPLC showed an average HPV to trastuzumab molar ratio of about 14:1 to 17:1. For the 10 kDa PHF-GA-(HPV-Alanine)-(Trastuzumab-MCC) used in FIGS. 2 and 4 the HPV to trastuzumab ratio was about 19:1 to 22:1.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab or alemtuzumab as described in Example 3 above. Also PBRM-drug polymer conjugates with varying ratios of drug to PBRM are obtained by varying the amount of PBRM and drug-polymer scaffold used in the Examples above.

Example 8

Synthesis of 10 kDa PHF-GA-(HPV-Alanine)-(Trastuzumab-M-(PEG)$_{12}$)

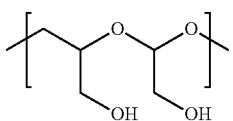

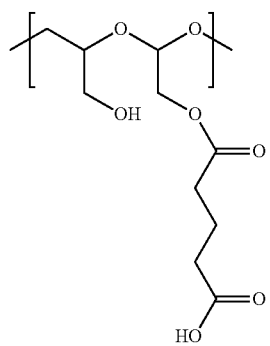

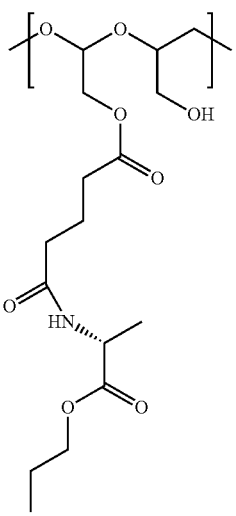

525

-continued

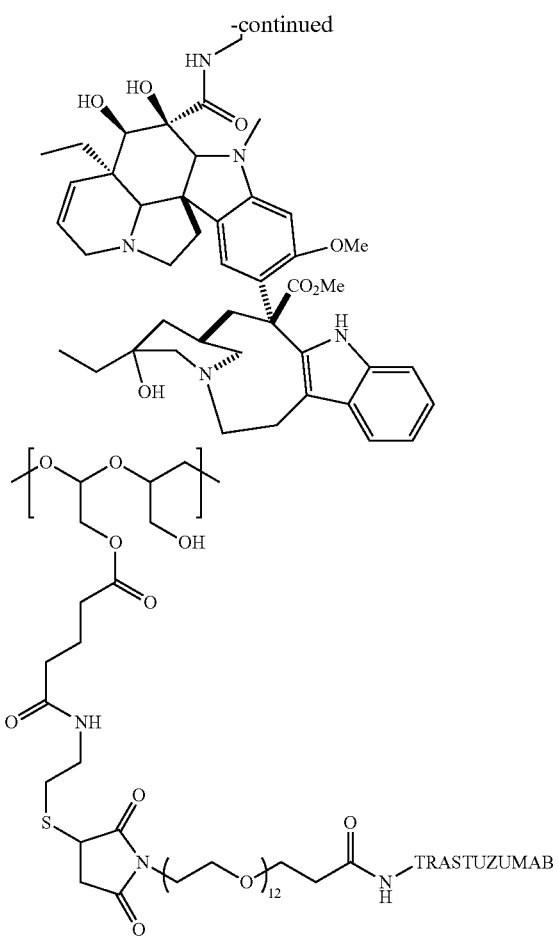

10 kDa PHF-GA-(HPV-Alanine)-(Trastuzumab-M-(PEG)$_{12}$) was prepared as described in Example 7 except Trastuzumab-MCC was replaced by Trastuzumab-M-(PEG)$_{12}$ (prepared as described in Example 4). The molecular weight of the PHF-GA-(HPV-Alanine)-(Trastuzumab-M-(PEG)$_{12}$) conjugate as determined by SEC was about 200 kDa. The HPV content as determined by HPLC showed an average HPV to trastuzumab molar ratio of about 16:1 to 18:1.

Example 9

Synthesis of 70 kDa PHF-GA-SN-38-Alanine-SSpy

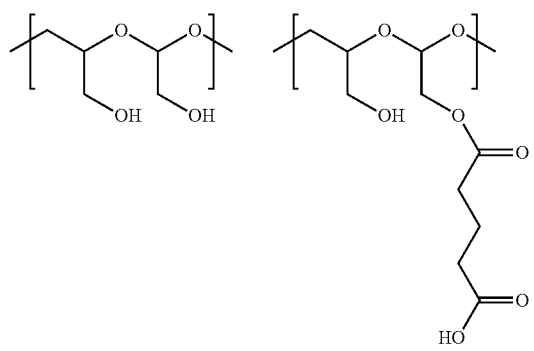

526

-continued

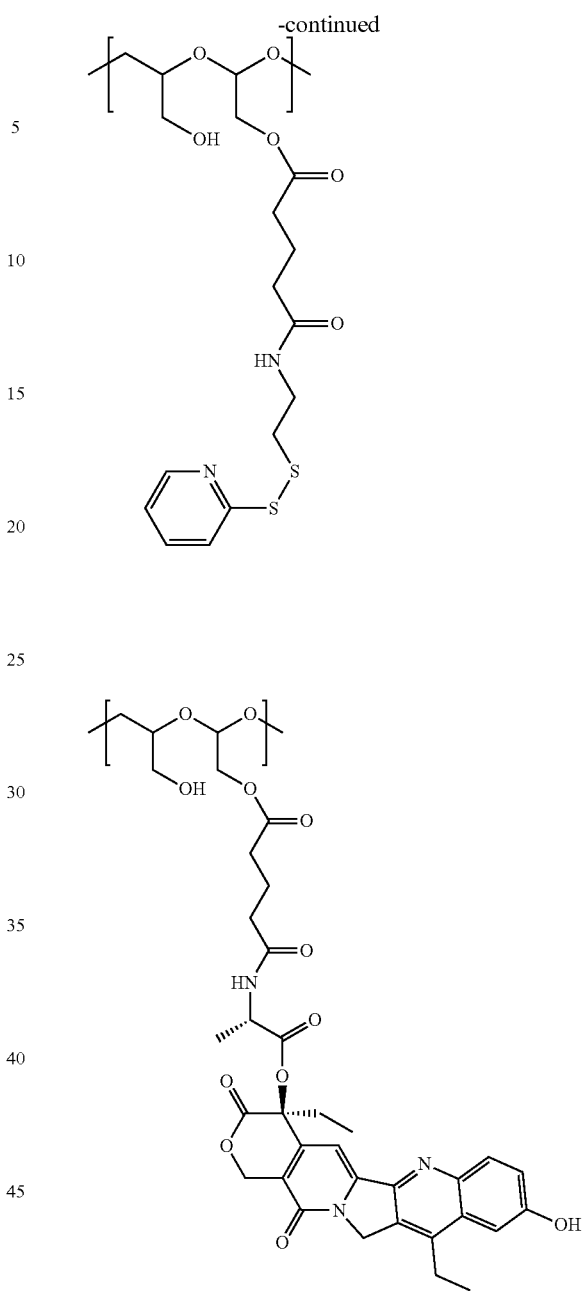

70 kDa PHF-GA-Alanine-SN38 (37.4 mg, 0.254 mmol, prepared as described in US 2010/0305149, using PHF 70,000 Da, GA 20%) was placed in a vial and 2-(pyridine-2-yldisulfanyl)ethaneamine hydrochloride (2.83 mg, 0.013 mmol) and NHS (2.93 mg, 0.025 mmol) were added followed by EDC (7.32 mg, 0.038 mmol). Additional aliquots of EDC (7.32 mg, 0.038 mmol) were added at 30 min, 2 h, 4 h, and 6 h, and the reaction mixture was stirred for an additional 12 h. The product was purified by dialysis through a 10 kDa regenerated cellulose membrane filter (SSPy 2%; SN38 4.8% (wt)).

Example 10

Synthesis of LHRH-PEG$_{12}$-SH

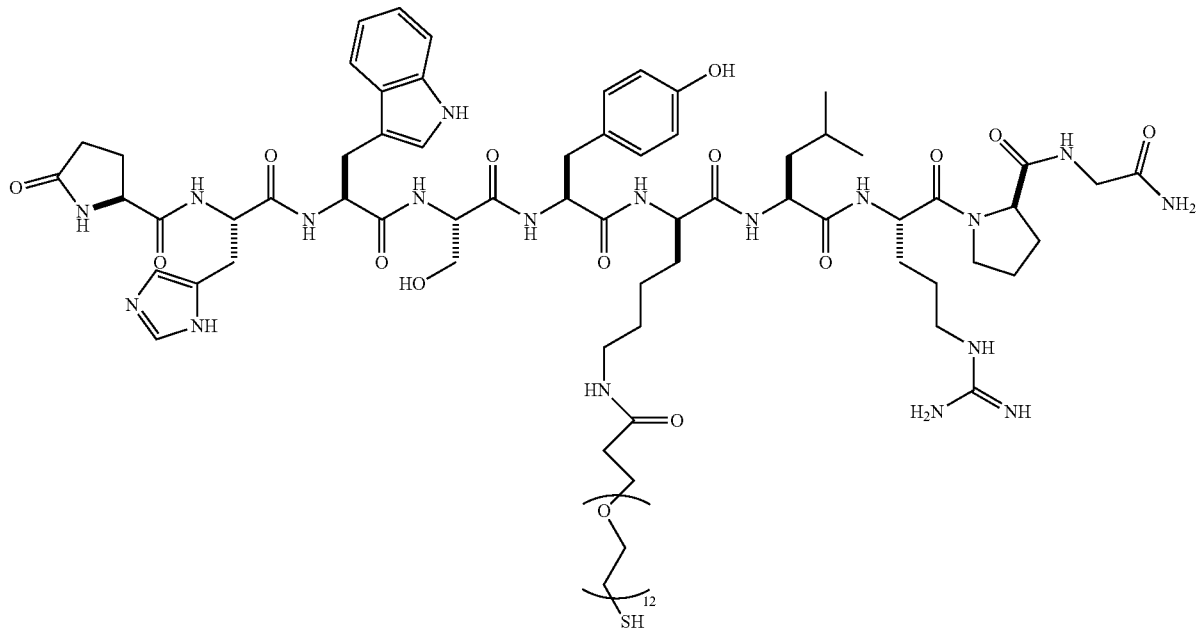

LHRH (10 mg) was dissolved in a mixture of acetonitrile:water (1:1, 500 μL) and to it was added PEG$_{12}$-SATA stock solution (9.2 μL, 0.0025 mmol, 1.9 mg). The resulting mixture was stirred for 3 h at ambient temperature. The product was purified by RP-HPLC followed by lyophilization (60% yield).

Purified LHRH-PEG$_{12}$-SH (2 mg) was dissolved in water (400 μL), pH was adjusted to 11.8 with TEA, and the mixture was stir for 40 min under argon and used in the next step.

Example 11

Synthesis of 70 kDa PHF-GA-SN-38-Alanine-(SS-PEG$_{12}$-LHRH)

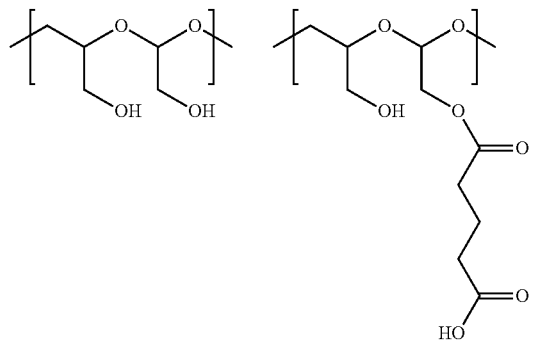

-continued
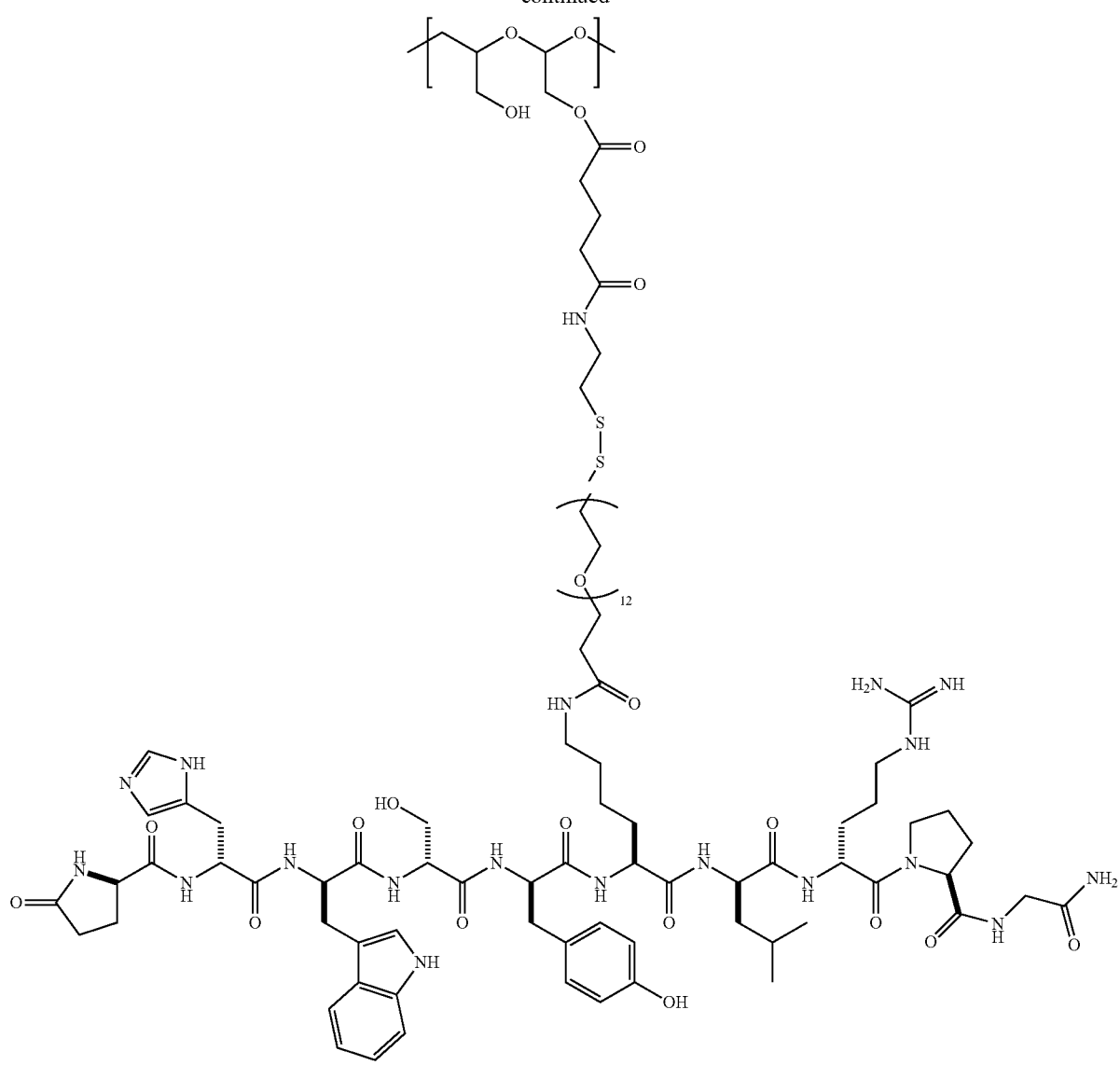

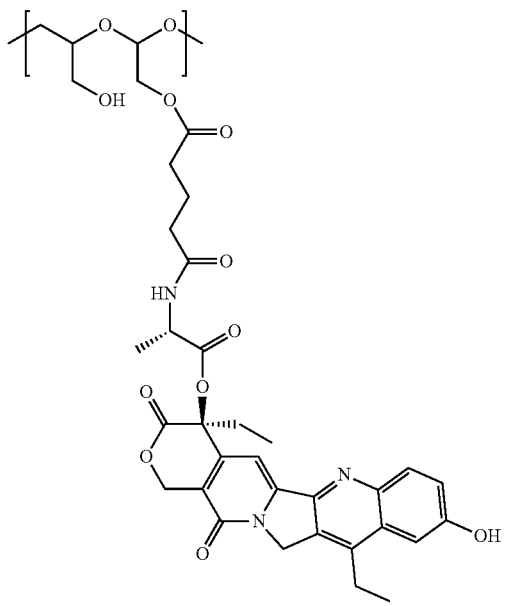

70 kDa PHF-GA-SN-38-Alanine-SSpy (2 mg, prepared as described in Example 9) was dissolved in PBS (0.5 mL, 50 mM, pH=7.5). Then LHRH-PEG$_{12}$-SH (0.8 mg, prepared as described in Example 10) was added. The mixture was stirred at room temperature for 4 h at pH 7.0. The conjugate was purified by dialysis against PBS (pH 7.0) using a 10 kDa cut-off regenerated cellulose membrane filter. LHRH content estimated by HPSEC was 65% with quantitative retention of SN38.

Example 12

Synthesis of 30 kDa PHF-GA-Maleimide

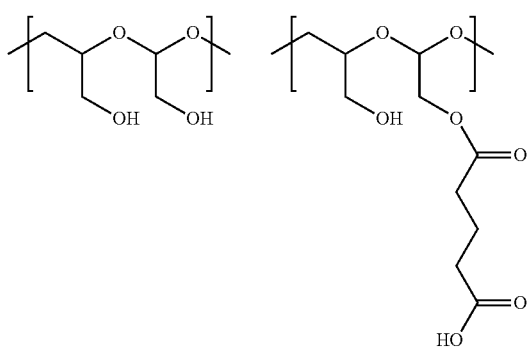

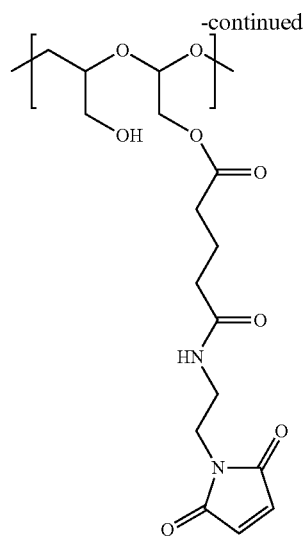

30 kDa PHF-GA (7.98 g, 50.2 mmol, prepared as described in Example 2, GA 15%) was taken up in water (502 mL) and cooled to 0° C. NHS (0.087 g, 0.752 mmol) was added followed by an aqueous solution of EDC (0.144 g, 0.752 mmol). The pH was adjusted to pH 7 to 8 with 1N NaOH and the reaction mixture stirred for 1 h at room temperature. N-aminoethyl-maleimide (0.080 g, 0.451 mmol) was added at 0° C. and the reaction mixture was warmed to room temperature and then left stirring overnight. The mixture was filtered through a 2 micron filter, concentrated to 200 mL, purified by dialysis through a Biomax (polyethersulfone) cartridge (5K) by washing with 1 liter of water, followed by lyophilization to give the title compound (2.19 g, 28% yield) as a white solid. Maleimide content as determined by CHN elemental analysis was 2.6%: (CHN average): C, 44.81; H, 6.91, N, 0.49.

Example 13

Synthesis of 30 kDa
PHF-GA-(HPV-Alanine)-Maleimide

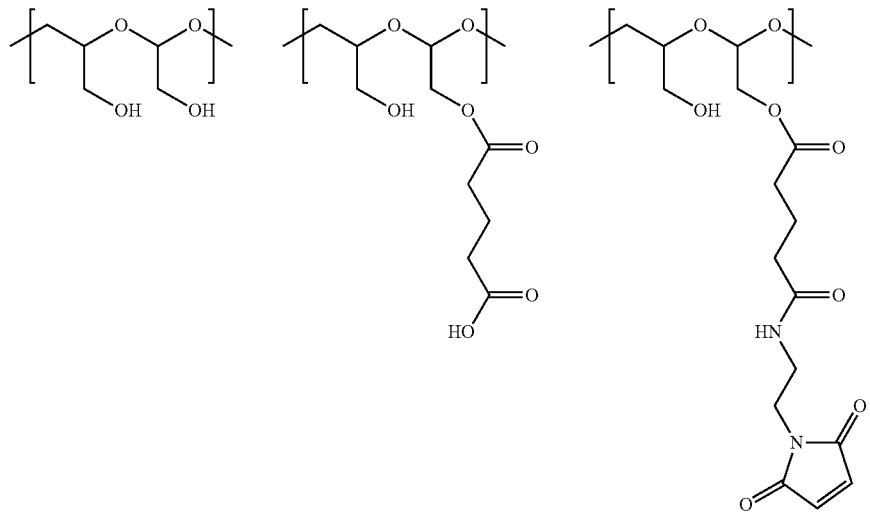

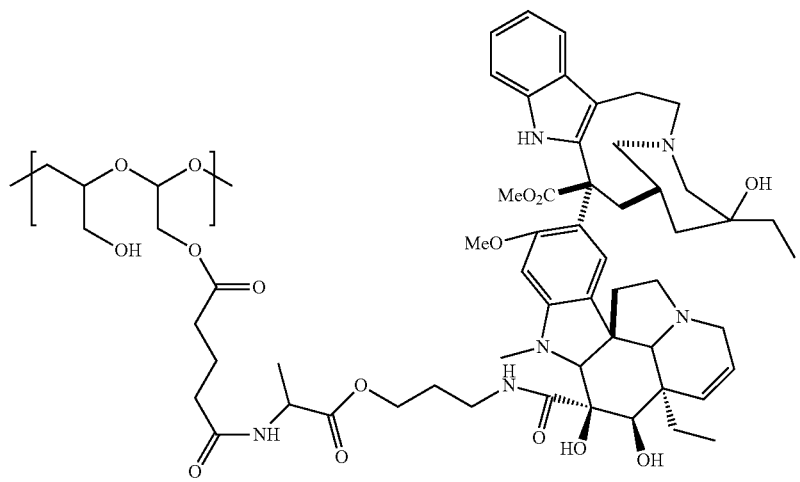

30 kDa PHF-GA-Maleimide (271 mg, 7.86 μmol, prepared as described in Example 12) was taken up in a mixture of water (8 mL) and CH$_3$CN (4 mL) and cooled to 0° C. NHS (9.04 mg, 0.079 mmol) was added followed by an aqueous solution of EDC (15.1 mg, 0.079 mmol) and HPV-Alanine (104 mg, 0.109 mmol, prepared as described in U.S. Publication No. 2010/0305149, Example 1) in water (2 mL). The pH of the resulting mixture was adjusted to 6.0, and then stirred at room temperature overnight. Progress of the reaction was monitored by HPLC analysis, 245 nm detection, and additional aliquots of EDC (15.1 mg, 0.079 mmol) in water were added at 19 and 22 h. The reaction mixture was diluted to 15 mL with water and the resulting mixture purified by dialysis through a Regenerated Cellulose membrane (5K) eluting with 5% NaCl/10% CH$_3$CN (3×10 mL) and water (2×10 mL). The sample was diluted to 10 mL and frozen to give 245 mg of the title compound, 93% yield. The HPV to polymer molar ratio was on average about 24:1 to 28:1

Example 14

Synthesis of EC-1-Adoa-M-(PEG)$_{12}$

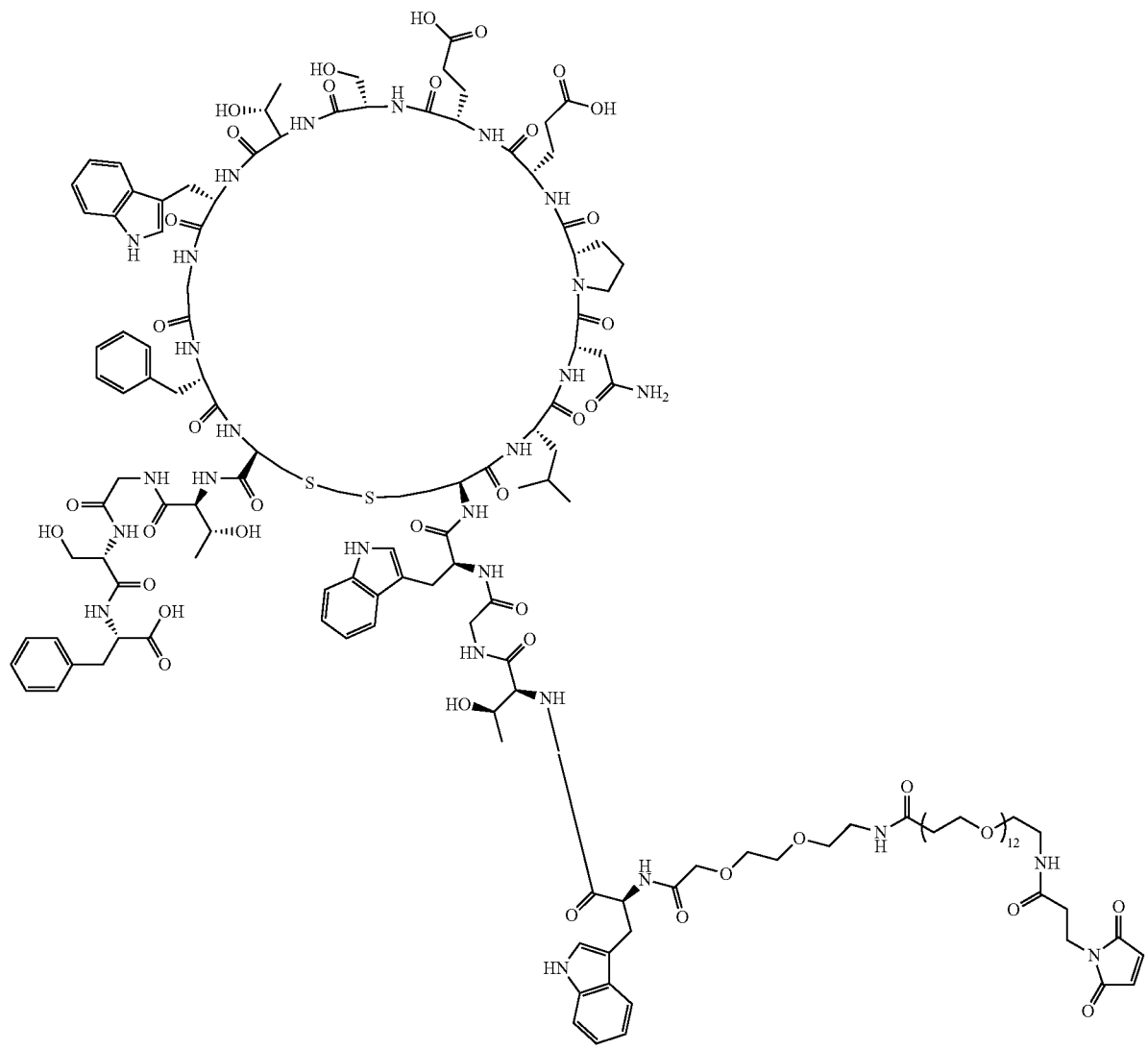

To a mixture of EC-1-Adoa-NH$_2$ (10 mg, 4 15 μmol) in CH$_3$CN/H$_2$O/DMSO (750 μL, 7:7:1) was added M-(PEG)$_{12}$-NHS (63 μL, 4.1 mg, 4.7 μmol) stock solution (0.064 mg/mL) in CH$_3$CN. The pH was adjusted to 7.4 and then DMSO (50 μL) and NMP (50 μL) were added to make the mixture more homogenous. The mixture was stirred under argon overnight, protected from light. An additional aliquot (13 μL, 1 mg) of freshly prepared M-(PEG)$_{12}$-NHS stock (0.077 mg/mL) was added and the resulting mixture was stirred for 30 min. The crude product was purified by HPLC (Gradient: 10% solvent B to 90% solvent B over 25 min). The title compound eluted at 16 min. and was concentrated to give 2 mg of a colorless solid. ESI-MS calc for C$_{146}$H$_{209}$N$_{27}$O$_{50}$S$_2$ 801.1 (M+4H$^+$), found 802.1.

Example 15
Synthesis of 10 kDa PHF-GA-(HPV-Alanine)-(EC-1-Adoa-M-(PEG)$_{12}$)
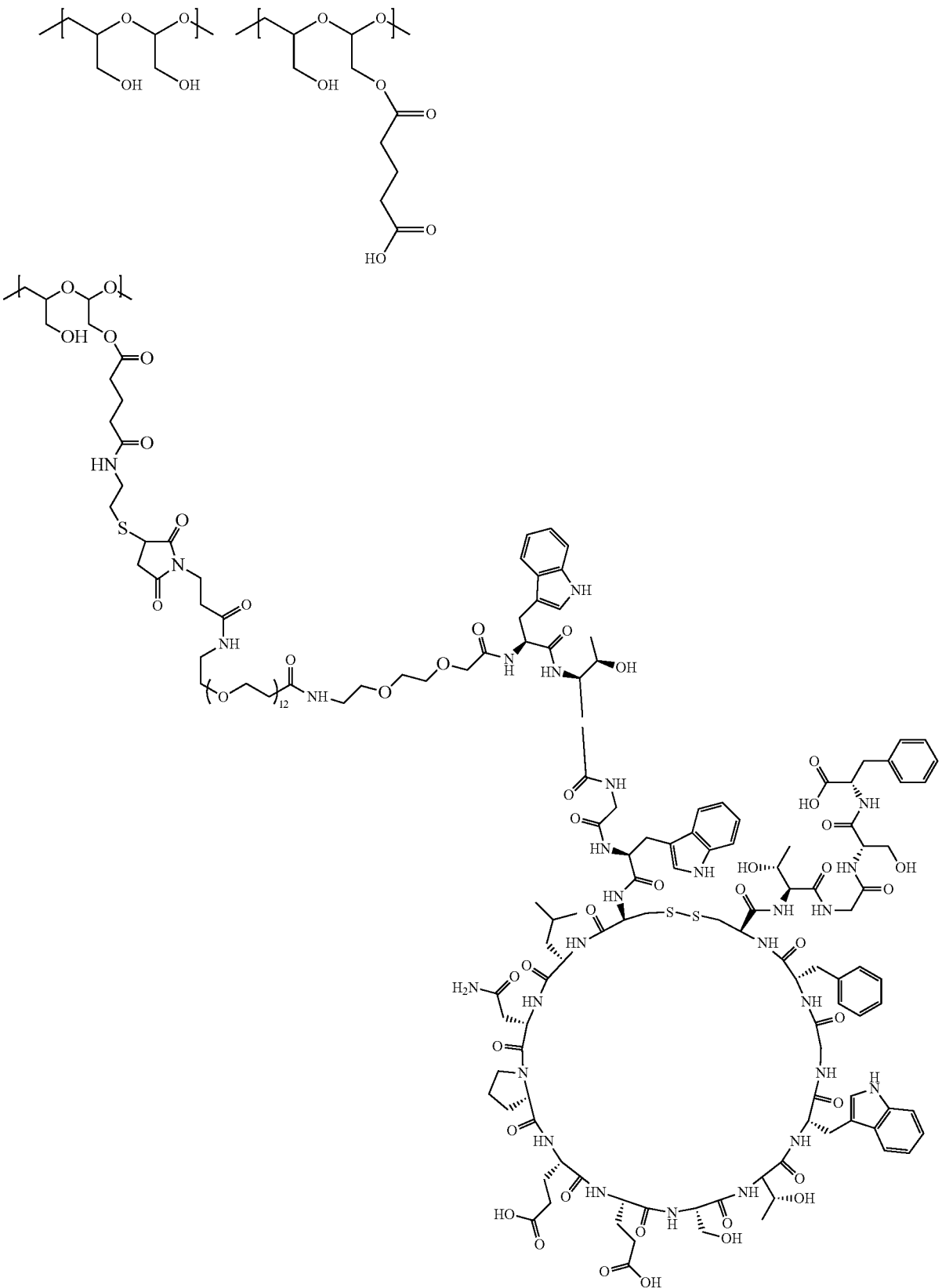

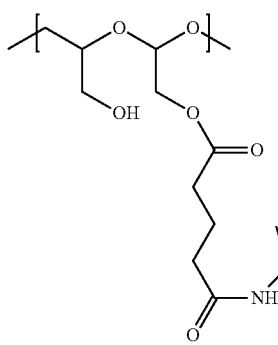

To a solution of 10 kDa PHF-GA-(HPV-Alanine)-SH (2 mg, 0.12 µmol, prepared as described in Example 6, 10 kDa PHF, GA 26%, HPV 7.4%, SH 3%) in 400 µL water was added a solution of the peptide EC-1-Adoa-M-(PEG)$_{12}$ (1 mg, 0.31 µmol, prepared as described in Example 14) in NMP (50 µL). The pH was adjusted to 7.4 and the reaction mixture was stirred under argon until no further incorporation of peptide was observed by HPSEC (2 h, 37% peptide). The reaction mixture was diluted with NaCl (1%, 10 mL) and then concentrated to 2 mL by centrifugal filtration (3000 Da cut off membrane). The solution was diluted with PBS (25 mM, 8 mL) and concentrated to 1.5 mL to give the title compound containing 0.373 mM HPV.

Example 16

Synthesis of LTVSPNY-Adoa-PEG$_{12}$-Thioester

To a solution of LTVSPNY-Adoa-NH$_2$ (10 mg, 10.7 µmol) in a mixture of CH$_3$CN/H$_2$O (500 µL, 1:1) was added (46 µL, 20.8 µmol, 16.1 mg) of a freshly prepared stock solution of S-Acetyl-PEG$_{12}$-NHS (350 mg/mL) in DMSO. The pH was adjusted to 6.5-7.0 and the reaction mixture stirred overnight. The pH was then adjusted to 7.5-8.0 and the reaction mixture was stirred for ~2 h. The crude product was purified by HPLC (Gradient: 10% solvent B to 70% solvent B over 25 min) to afford, after concentration, 9 mg of the title compound as a colorless solid (51% yield). ESI-MS calc for $C_{78}H_{126}N_9NaO_{28}S$ 845.9, found 845.9 (M+H$^+$+Na$^+$).

Example 17
Synthesis of 30 kDa PHF-GA-(HPV-Alanine)-(LTVSPNY-Adoa-PEG$_{12}$)
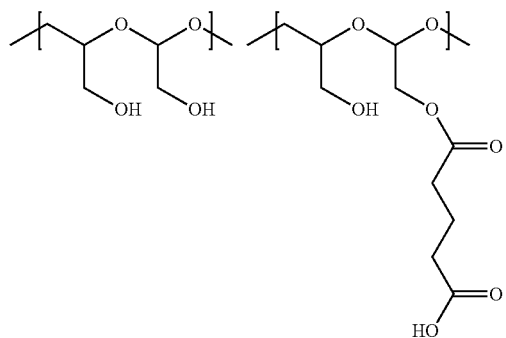
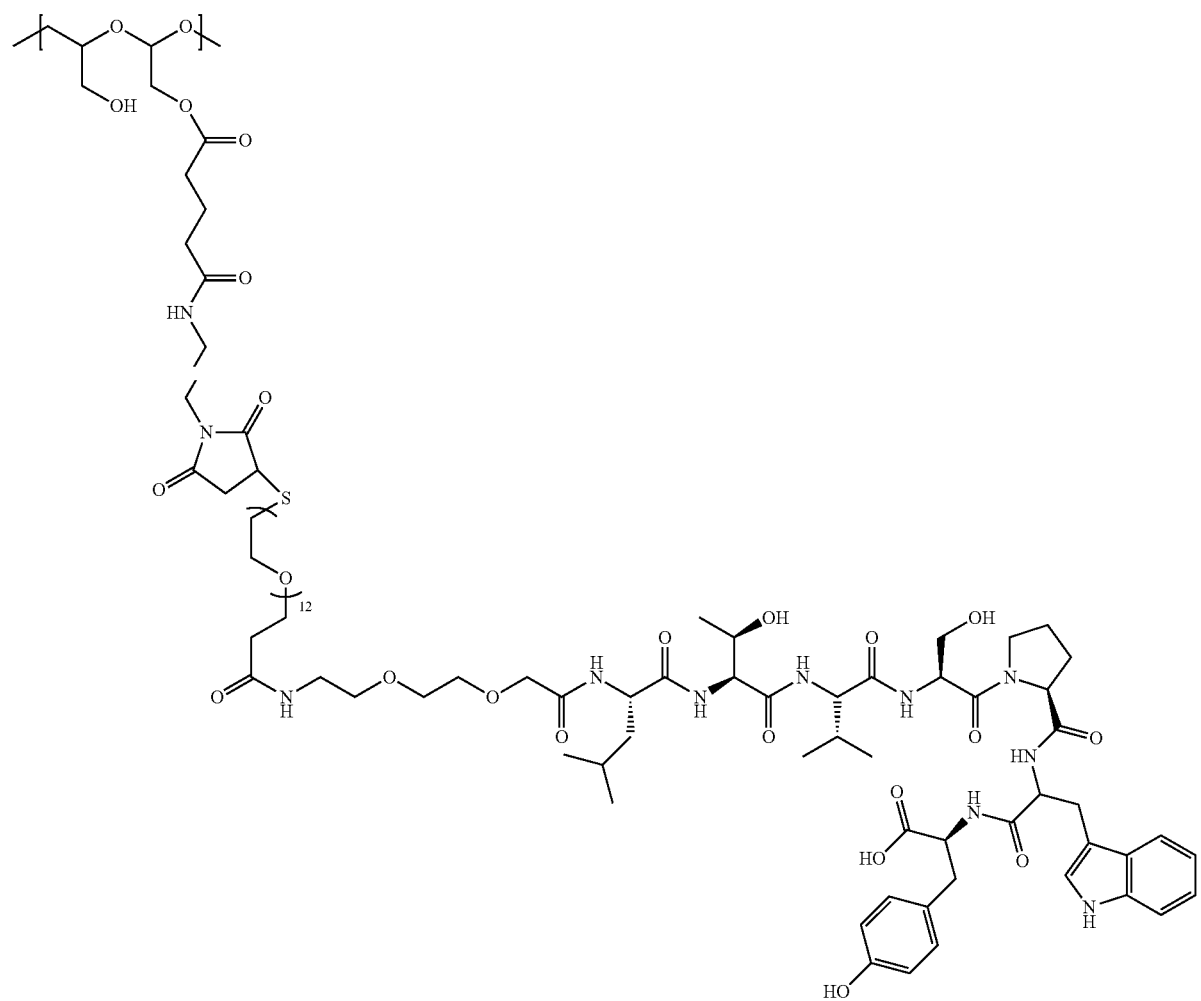

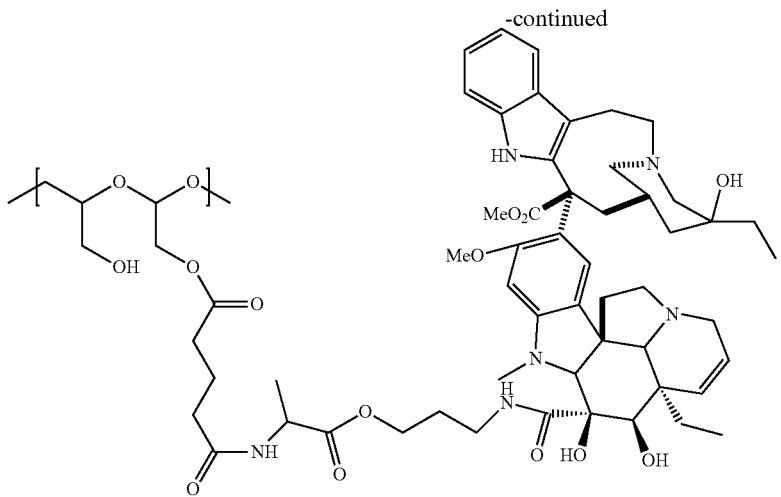

LTVSPNY-Adoa-PEG$_{12}$-thioester (0.57 mg, 0.34 µmol, prepared as described in Example 16) was dissolved in water (500 µL) and the pH adjusted to 11.8. The solution was stirred under argon for 30 min and the pH lowered to 5-5.5. To it was added a solution of 30 kDa PHF-GA-(HPV-Alanine)-Maleimide (2.5 mg, 0.057 mmol, prepared as described in Example 13, GA 15%, maleimide 2.6%, HPV 5%) in water (62.5 µL). The pH was adjusted to 7.6 and then the reaction mixture was stirred under argon until no further incorporation of peptide was observed by HPSEC (3 h, 15% incorporation of peptide). The reaction mixture was then diluted with 1% NaCl and filtered through 0.2 µM syringe filter. The crude material was purified by stir cell filtration through a 5 kDa MW cut off membrane to afford a solution of the title compound.

Example 18

Synthesis of 30 kDa PHF-GA-(HPV-Alanine)-SH

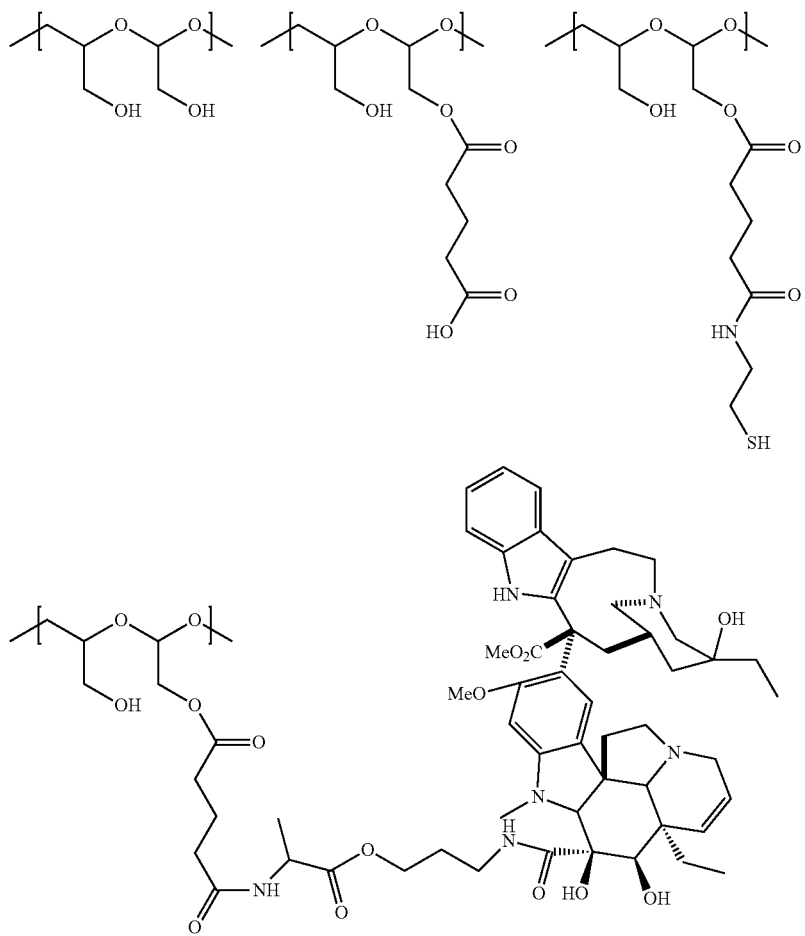

30 kDa PHF-GA-SSpy (26.2 mg, 0.72 µmol, prepared as described in Example 5 using 30 kDa PHF, GA 10%, SSPy 4.8%) was taken up in a mixture of water (3 mL) and acetonitrile (3 mL) and cooled to 0° C. NHS (0.83 mg, 7.16 µmol) was added followed by an aqueous solution of EDC (1.37 mg, 7.16 µmol) and HPV-Alanine (10.2 mg, 10.7 µmol, prepared as described in U.S. Publication No. 2010/0305149, Example 1). The pH of the resulting mixture was adjusted to 6.0, and then the mixture was stirred at room temperature overnight. The pH was adjusted to 7.5 with 1M NaHCO₃ and DTT (11.7 mg, 0.076 mmol) was added. The reaction mixture was stirred at 23° C. for 30 min, diluted to 15 mL with water and purified by dialysis using a Regenerated cellulose membrane (30 kDa MW cut-off). Yield 82% (based on HPV); 20.6% wt HPV, as determined by HPLC.

Example 19

Synthesis of 30 kDa PHF-GA-(HPV-Alanine)-(Trastuzumab-MCC)

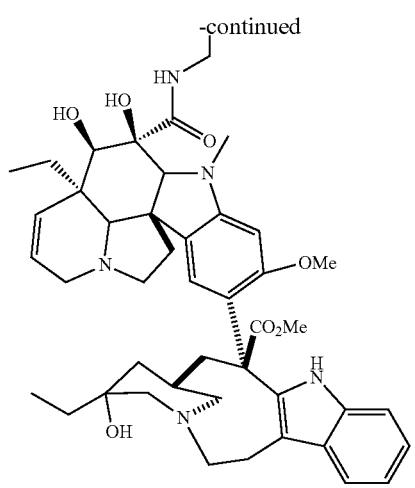

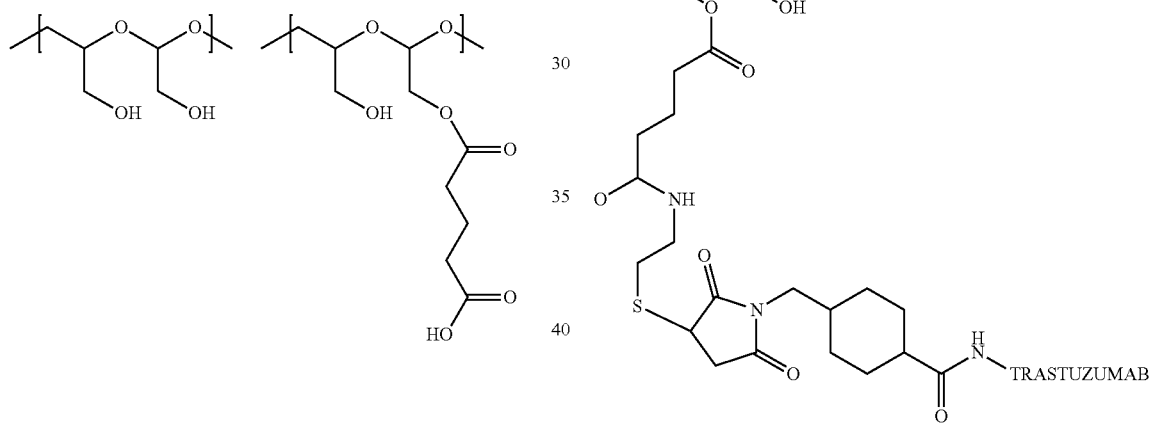

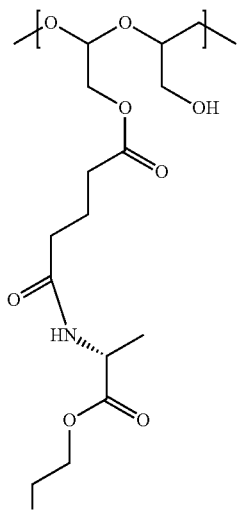

To Trastuzumab-MCC (20 mg, prepared as described in Example 3) in PBS (2 mL, pH 7.0) was added 30 kDa PHF-GA-(HPV-Alanine)-SH (11.2 mg, prepared as described in Example 18) in water (0.5 mL). The solution was stirred at room temperature for 4 h at pH 7.0. The resulting conjugate was purified by gel filtration using a Superpose-6 column with PBS as the eluant. The HPV content as determined by HPLC was on average HPV to antibody molar ratio of about 10:1 to 12:1.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab or alemtuzumab as described in Example 3 above. Also PBRM-drug polymer conjugates with varying ratios of drug to PBRM are obtained by varying the amount of PBRM and drug-polymer scaffold used in the Examples above.

Example 20
Synthesis of 70 kDa PHF-GA-(HPV-Alanine)-SH
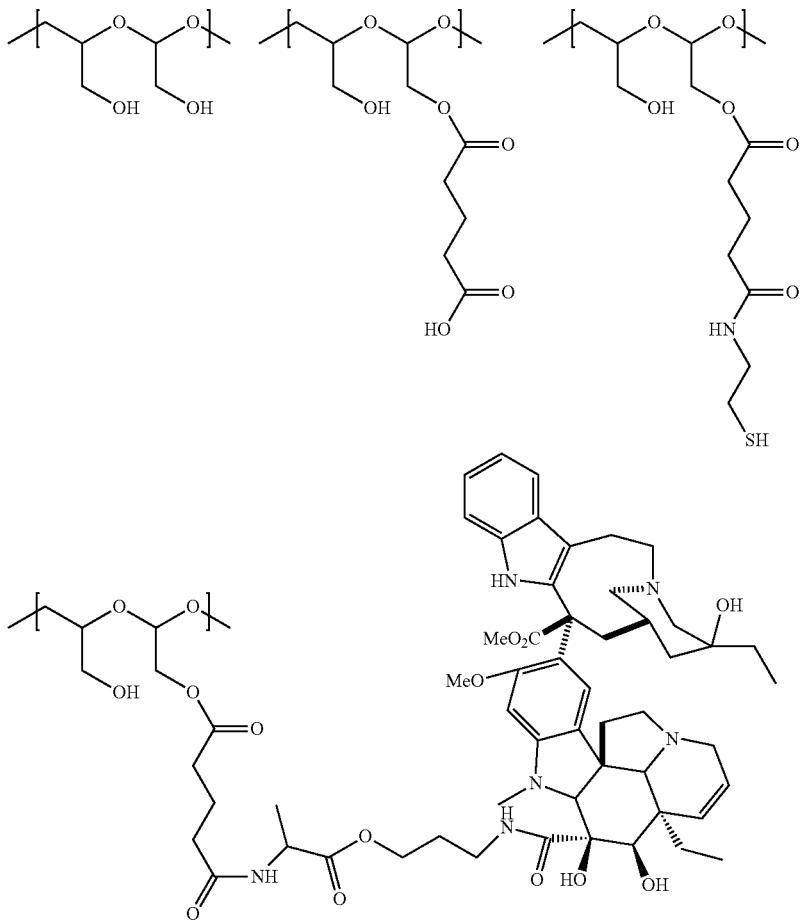
70 kDa PHF-GA-(HPV-Alanine)-SH was prepared as described in Example 18 except 70 kDa PHF-GA-SSPy (GA 10%, SSPy 4.8%, 58.2 mg, 0.727 μmol, prepared as described in Example 5), NHS (0.843 mg, 7.27 μmol), EDC (1.39 mg, 7.27 μmol) and HPV-Alanine (10.4 mg, 10.9 μmol) were used. Yield 82% (based on polymer); 10.9% wt HPV.
Example 21
Synthesis of 70 kDa PHF-GA-(HPV-Alanine)-(Trastuzumab-MCC)
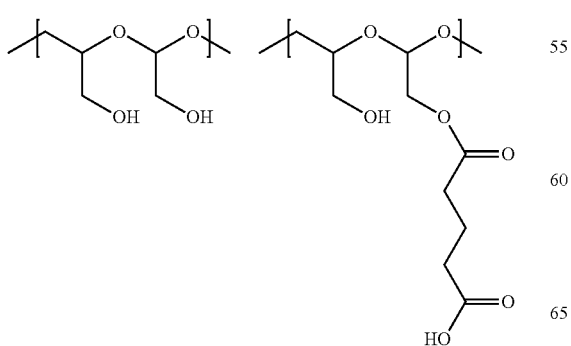
-continued
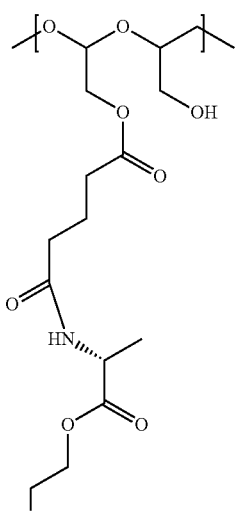

-continued

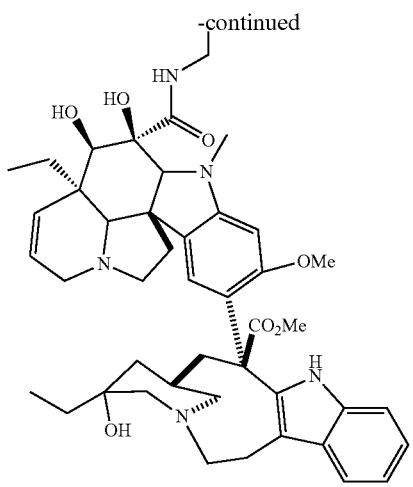

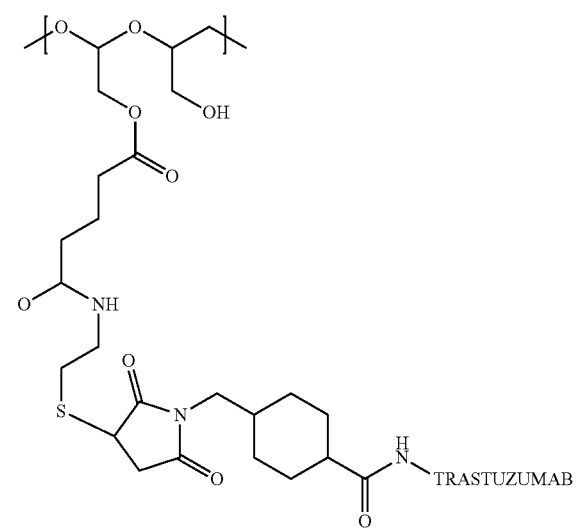

The title compound was prepared as described in Example 19 except trastuzumab-MCC (20 mg, prepared as described in Example 3) and 70 kDa PHF-GA-(HPV-Alanine)-SH (11.2 mg, prepared as described in Example 20) were used. The HPV content as determined by HPLC showed an average HPV to antibody molar ratio of about 47:1 to 50:1.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab or alemtuzumab as described in Example 3 above. Also PBRM-drug polymer conjugates with varying ratios of drug to PBRM are obtained by varying the amount of PBRM and drug-polymer scaffold used in the Examples above.

Example 22

Synthesis of (S)-2HPV

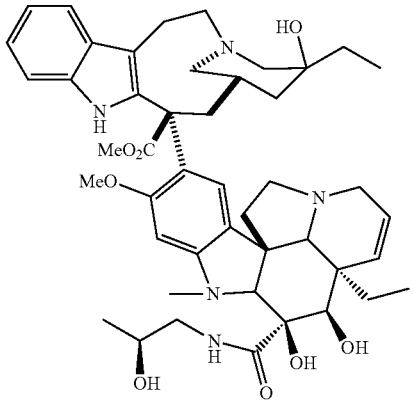

Vinblastine desacetyl hydrazide (400 Mg, 0.520 mmol, prepared as described in J. Med. Chem., 21, 88-96, 1978) in MeOH (5 mL) was combined with 1N HCl (15 mL) at 0° C., then sodium nitrite (93 mg, 1.353 mmol) was added in one portion. The reaction mixture was stirred for 12 min followed by pH adjustment to 7.6 at 0° C. with saturated $NaHCO_3$. The reaction mixture was extracted with DCM (3×50 ml). The combined DCM fractions were washed with brine, dried over $MgSO_4$ and filtered through a pad of $MgSO_4$. The volume was reduced to 10 ml and 5 ml was used for coupling with (S)-1-aminopropan-2-ol.

(S)-1-aminopropan-2-ol (205 µl, 2.6 mmol) in anhydrous DCM (2 mL) was added drop wise to a cold stirred solution of vinblastine desacetyl diazide (prepared as described above) under argon. The reaction mixture was stirred at 0° C. for several hours and then brought to room temperature. LC/MS showed conversion to the title compound. The crude reaction mixture was applied directly to a CombiFlash column (40 g column) for purification The CombiFlash column was conditioned with ethyl acetate (1% TEA). Following sample injection the initial conditions were continued for 2 min followed by a gradient from 10% MeOH (1% TEA) to ethyl acetate (1% TEA) over 10 minutes and then held. The title compound eluted at ~12 minutes. The eluant was concentrated to obtain 96 mg (46% yield). m/z(+) 812.4.

Example 23

Synthesis of (R)-2HPV

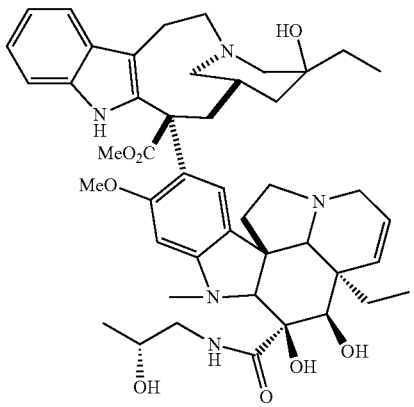

The title compound was prepared as described in Example 21 except (R)-1-aminopropan-2-ol (205 µl, 2.6 mmol) was used instead of (S)-1-aminopropan-2-ol to give 97 mg (46% yield)

Example 24

Synthesis of (PI-103)-4-(2-aminoethyl)piperazine-1-carboxylate dihydrochloride

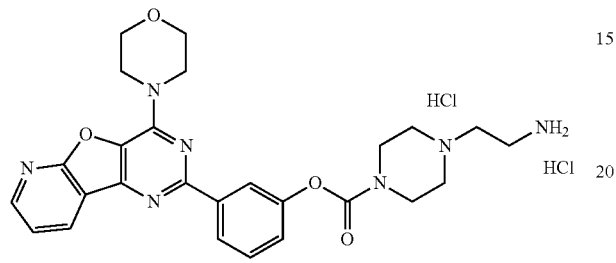

To a mixture of P1-103 (50 mg, 0.144 mmol) and TEA (60 µL, 0.431 mmol) in dry DMF (2.5 mL) was added 4-nitrophenyl chloroformate (35 mg, 0.172 mmol) and the resulting mixture was stirred at room temperature. After 45 min 2-piperazin-1-yl-ethyl-carbamic acid t-butyl ester (56 mg, 0.244 mmol) was added and the reaction mixture was then stirred overnight at room temperature followed by the removal of the solvent under high vacuum. The residue was dissolved in DCM (50 mL) and then washed successively with water (15 mL) and brine (15 mL). The organic phase was dried over $Na_2SO_4$ and concentrated under vacuum. Crude product was purified on silica gel (4 g CombiFlash column, MeOH: DCM (0% MeOH 1-2 min followed by a gradient to 7% MeOH over 15 min) to give the BOC-protected carbamate as a colorless film. ESI-MS calc for $C_{31}H_{38}N_7O_6$ 604.3 (M+H$^+$), found 604.3.

To the purified BOC-protected carbamate was added DCM (5 mL) and 4 M HCl in dioxane (5 mL). The mixture was stirred for 1 h at room temperature and then concentrated under vacuum. The deprotected PI-103 product was dissolved in water and then lyophilized to afford the title compound as a pale yellow solid (69 mg, 83% overall yield). ESI-MS calc for $C_{26}H_{30}N_7O_4$ 504.2 (M+H$^+$), found 504.2.

Example 25

Synthesis of (PI-103)-4-aminobutylcarbamate hydrochloride

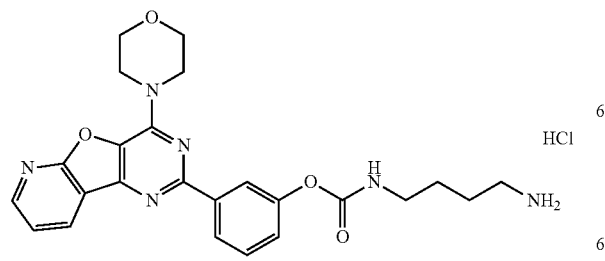

The title compound was prepared as described in Example 24 except the synthesis was conducted on a smaller scale with PI-103 (25 mg) and BOC-1,4-diaminobutane (23 mg, 0.122 mmol) was used instead of 2-piperazin-1-yl-ethyl-carbamic acid t-butyl ester to give the title compound (13 mg, 36% overall yield). ESI-MS calc for $C_{24}H_{27}N_6O_4$ 463.2 (M+H$^+$), found 463.2.

Example 26

Synthesis of 10 kDa PHF-GA-(PI-103)-4-aminobutylcarbamate-SH

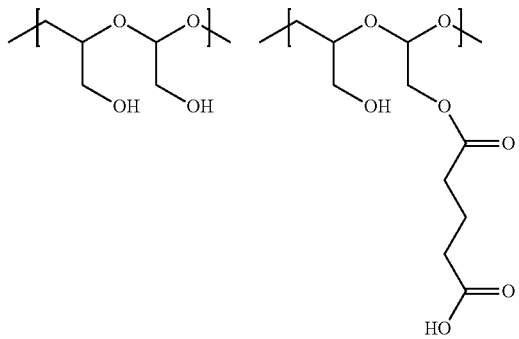

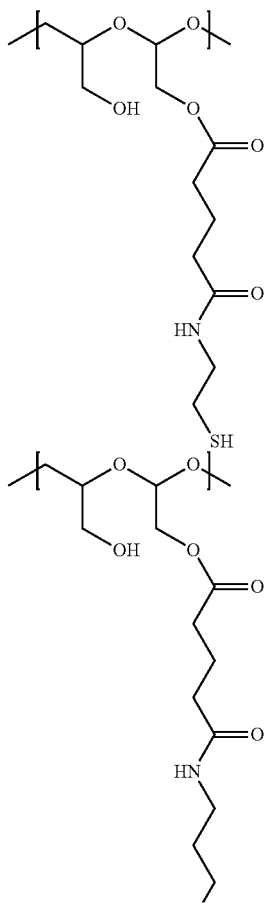

-continued

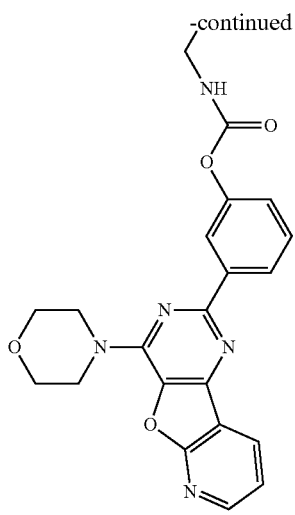

To a solution of 10 kDa PHF-GA-SSpy (GA 25%, SSPy 3.8%, 30 mg, 2.38 μmol, prepared as described in Example 5) in 1:1 CH$_3$CN/H$_2$O (400 μL) was added NHS (18 μL of 96 mg/mL stock in CH$_3$CN, 1.7 mg), EDC (78 μL of freshly prepared stock in water, 37.3 mg/mL, 2.9 mg), followed by a solution of (PI-103)-4-aminobutylcarbamate hydrochloride (5.35 mg, 10.7 μmol, prepared as described in Example 25) in 1:1 CH$_3$CN/H$_2$O (200 μL). Additional CH$_3$CN (100 μL) was added to improve the solubility. The pH was adjusted to 5.7-5.8 and the mixture was stirred for 1 h at room temperature. Additional CH$_3$CN (100 μL) was added and stirring was continued overnight. HPLC analysis of the crude reaction mixture indicated 92% incorporation of (PI-103)-4-aminobutylcarbamate. The pH was adjusted to 6.0 and then the crude mixture was diluted with 1% aqueous NaCl (10 mL) and filtered through a 0.2 μm syringe filter. The crude product was purified by stir cell filtration on a 3 kDa MWCO regenerated cellulose membrane followed by lyophilization to afford a colorless solid (26 mg, 1.82 μmol, 76% yield). The product (26 mg, 1.82 μmol) was dissolved in PBS (25 mM, pH 7, 1 mL) and then treated with DTT (10.4 mg, 0.067 mmol). The mixture was stirred for approx 1 h at room temperature and then purified by stir cell filtration through 3 kDa MWCO regenerated cellulose membrane to give an aqueous solution of the title compound.

Example 27

Synthesis of 10 kDa PHF-GA-(PI-103)-4-aminobutylcarbamate-(Trastuzumab-MCC)

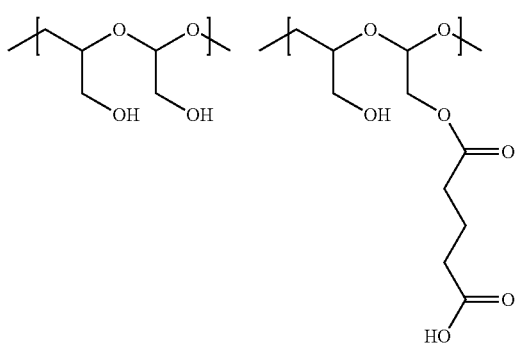

-continued

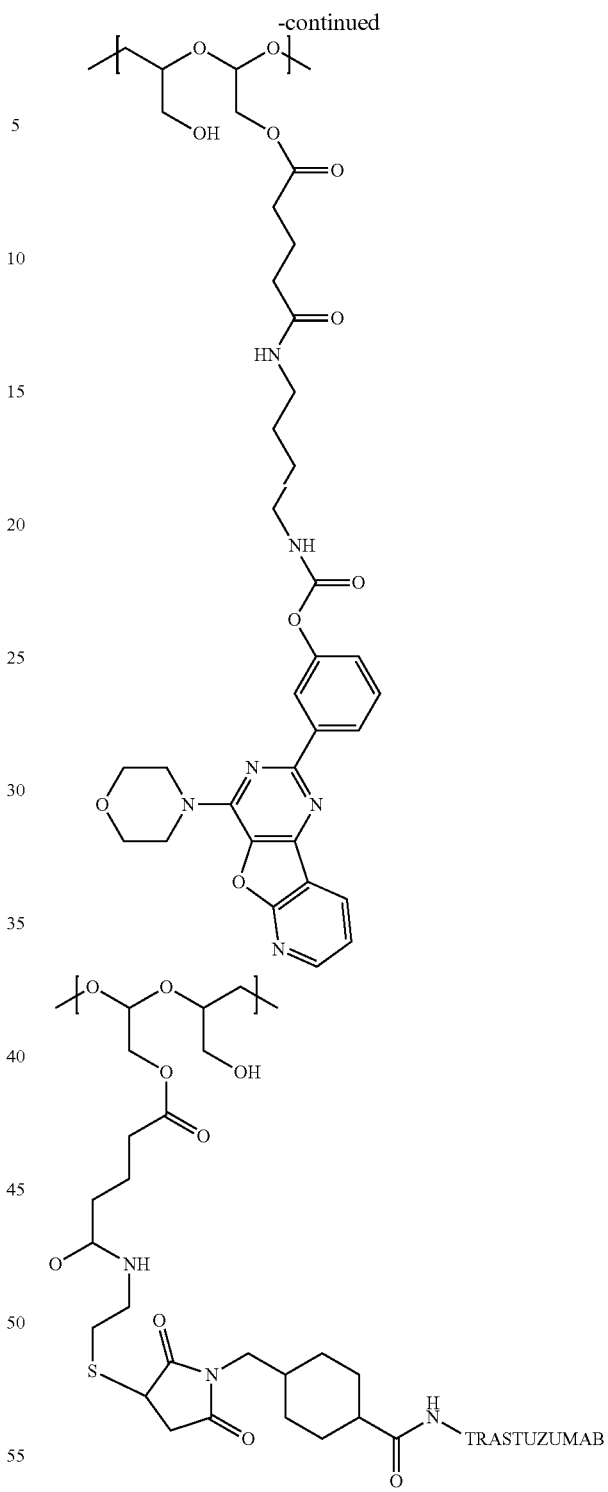

The title conjugate was prepared in a manner similar to that described in Example 7 except that trastuzumab-MCC (10 mg, prepared as described in Example 3) and 10 kDa PHF-GA-(PI-103)-4-aminobutylcarbamate-SH (11.2 mg, prepared as described in Example 26) were used.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab or alemtuzumab as described in Example 3 above. Also PBRM-drug polymer conjugates with varying ratios of drug to PBRM are obtained by varying the amount of PBRM and drug-polymer scaffold used in the Examples above.

Example 28

Synthesis of 10 kDa PHF-GA-(PI-103)-4-(2-amino-ethyl)piperazine-1-carbamate-SH

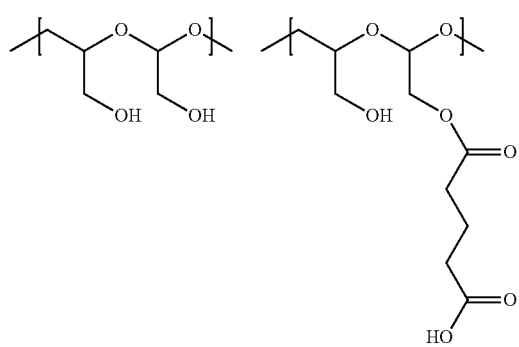

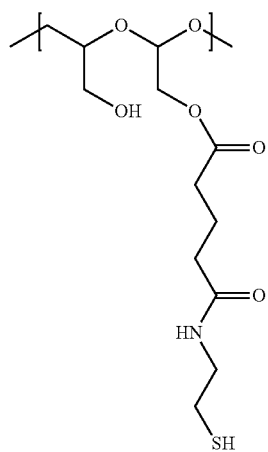

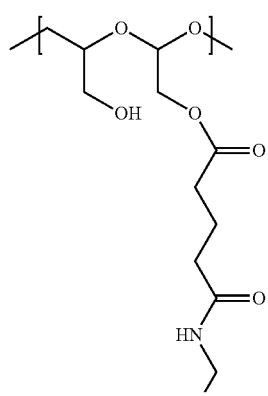

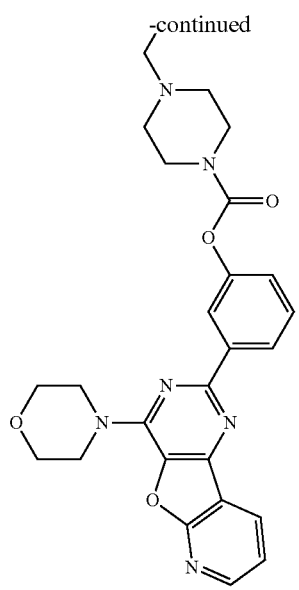

The title compound was prepared in a manner similar to that described in Example 26 except that 10 kDa PHF-GA-SSPy (GA 25%, SSPy 3.8%, 30 mg, 3.38 μmol, prepared as described in Example 5), NHS (1.7 mg, 15 μmol), EDC (2.88 mg, 15 μmol) and (PI-103)-4-(2-aminoethyl)piperazine-1-carboxylate dihydrochloride (5.49 mg, 9.52 μmol, prepared as described in Example 24) were used. Yield 80%.

Example 29

Synthesis of 10 kDa PHF-GA-(PI-103)-4-(2-amino-ethyl)piperazine-1-carbamate-(Trastuzumab-MCC)

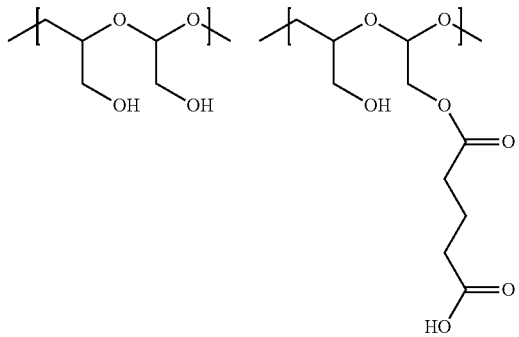

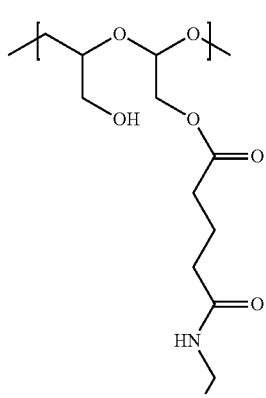

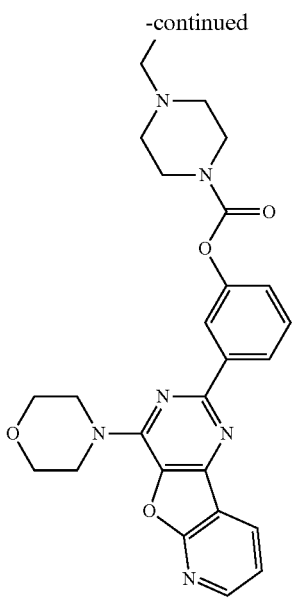

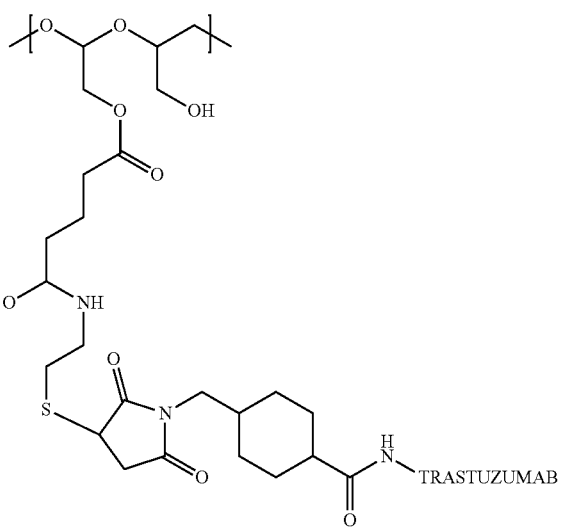

The title conjugate was prepared in a manner similar to that described in Example 7 except that trastuzumab-MCC (10 mg, prepared as described in Example 3) and 10 kDa PHF-GA-(PI-103)-4-(2-aminoethyl)piperazine-1-carbamate-SH (11.2 mg, prepared as described in Example 28) were used.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab or alemtuzumab as described in Example 3 above. Also PBRM-drug polymer conjugates with varying ratios of drug to PBRM are obtained by varying the amount of PBRM and drug-polymer scaffold used in the Examples above.

Example 30

Synthesis of (PI-103)-4-aminobutylcarbonate hydrochloride

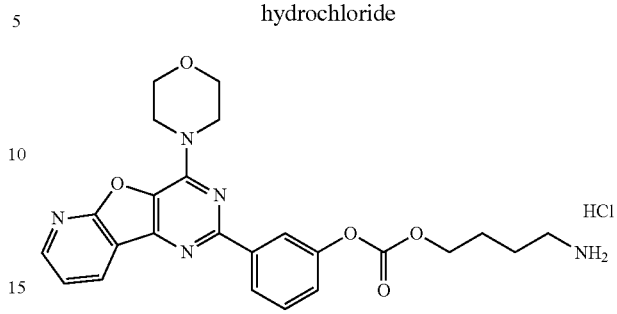

To an ice-cold solution of triphosgene (13.6 mg, 0.046 mmol) in dry THF (0.5 mL) was added a solution of t-butyl 4-hydroxybutylcarbamate (24.2 mg, 0.128 mmol) and TEA (18.1 μL, 0.13 mmol) in dry THF (1 mL) under argon. After stirring for 1 h at 0° C., the crude chloroformate was slowly added to a solution of PI-103 (25 mg, 0.072 mmol) and TEA (15.1 μL, 0.108 mmol) in NMP (0.5 mL). After several minutes THF was removed under vacuum and NMP (0.5 mL) was added to make the mixture more homogenous. The resulting mixture was stirred overnight at room temperature. Additional chloroformate (from 45 mg BOC-alcohol, prepared as described above) and TEA (15 μL) were added and the reaction mixture was stirred for 40 min at which point LC/MS indicated 95% conversion to the desired product. The reaction mixture was diluted with DCM (150 mL) and then washed with water (2×50 mL) and brine (50 mL). The organic phase was dried over $Na_2SO_4$ and concentrated under vacuum. The crude product was purified on silica gel (4 g CombiFlash column, EtOAc:Hex, 0% EtOAc 1 min, then gradient to 80% EtOAc over 16 min) to give 26 mg of a colorless film. Yield 64%. ESI-MS calc for $C_{29}H_{34}N_5O_7$ 564.3 (M+H$^+$), found 564.1.

The BOC-protected carbonate was dissolved in DCM (2 mL) and then treated with 4 M HCl in dioxane (4 mL). The resulting mixture was stirred for 3.5 h and then concentrated under vacuum. The deprotected carbonate was lyophilized from water:$CH_3CN$ to afford the title compound as a pale yellow solid (21.9 mg, 96% yield). ESI-MS calc for $C_{24}H_{26}N_5O_5$ 464.2 (M+H$^+$), found 464.1.

Example 31

Synthesis of 10 kDa PHF-GA-(PI-103)-4-aminobutylcarbonate-SH

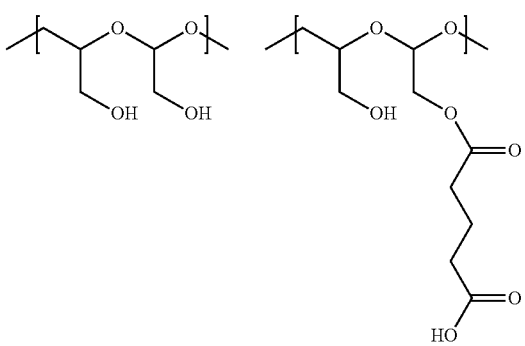

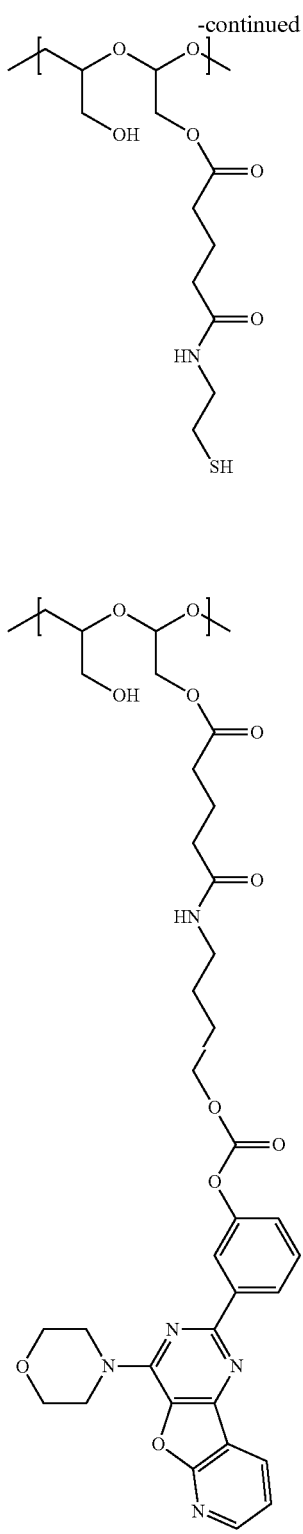
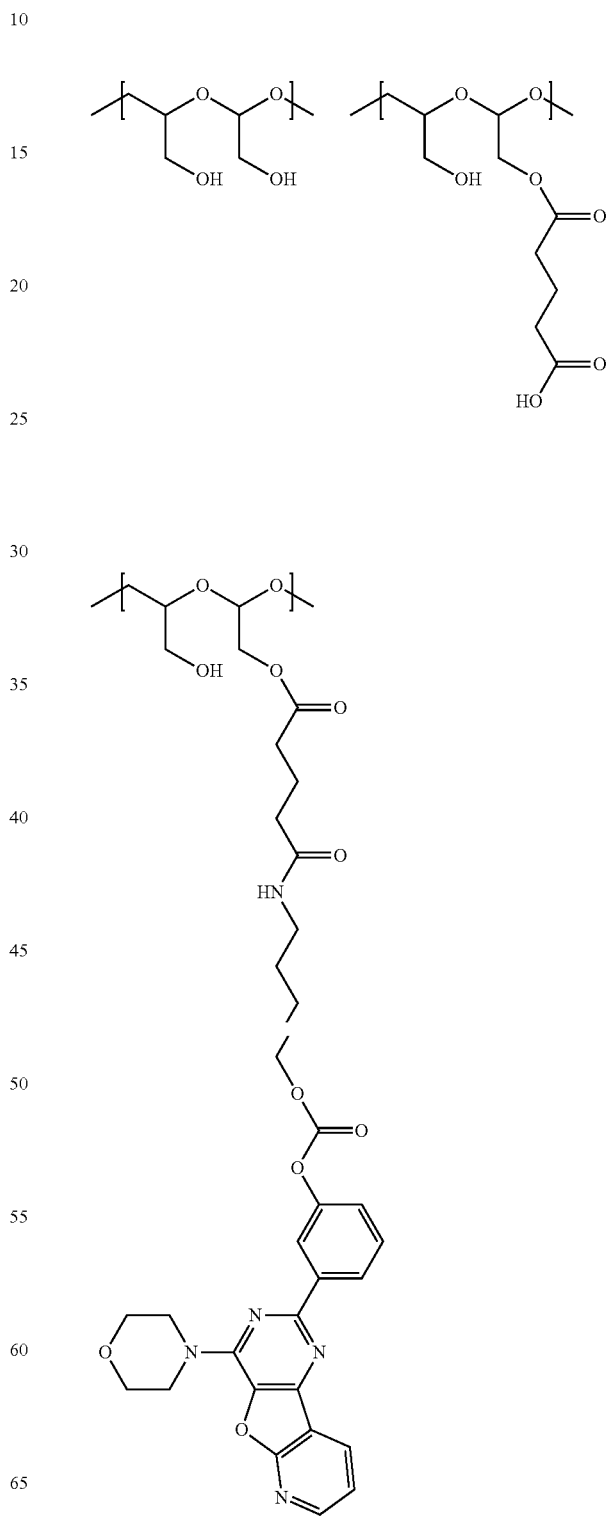
chloride (5.35 mg, 10.7 μmol, prepared as described in Example 30) were used. Yield 76%.
Example 32
Synthesis of 10 kDa PHF-GA-(PI-103)-4-aminobutylcarbonate-(Trastuzumab-MCC)
The title compound was prepared in a manner similar to that described in Example 26 except that 10 kDa PHF-GA-SSpy (GA 25%, SSPy 3.8%, 30 mg, 3.38 μmol, prepared as described in Example 5), NHS (1.7 mg, 15 μmol), EDC (2.88 mg, 15 μmol) and (PI-103)-4-aminobutylcarbonate hydro-

561

-continued

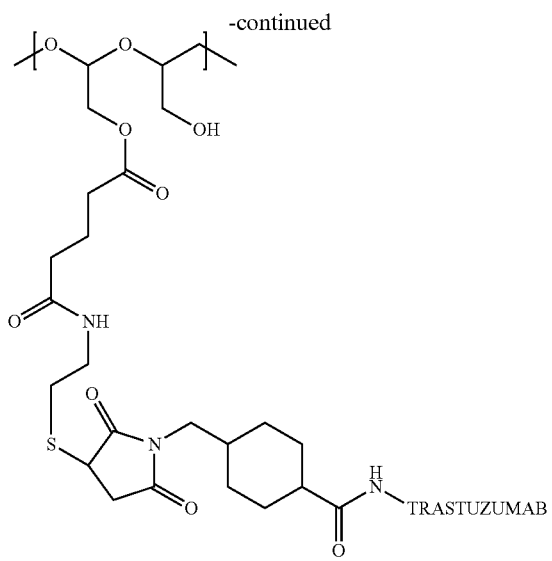

The title conjugate was prepared in a manner similar to that described in Example 7 except that trastuzumab-MCC (10 mg, prepared as described in Example 3) and 10 kDa PHF-GA-(PI-103)-(4-aminobutylcarbonate)-SH (11.2 mg, prepared as described in Example 31) were used. Yield 30%.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab or alemtuzumab as described in Example 3 above. Also PBRM-drug polymer conjugates with varying ratios of drug to PBRM are obtained by varying the amount of PBRM and drug-polymer scaffold used in the Examples above.

Example 33

Synthesis of (PI-103)-(S)-2-amino-3-methylbutanoate hydrochloride

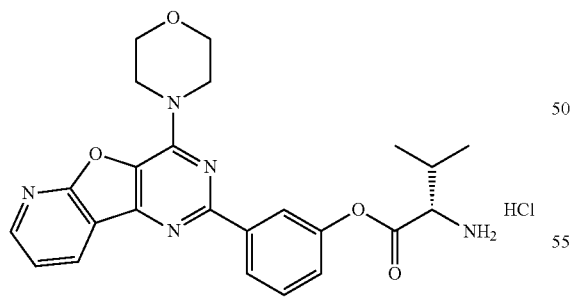

To a solution of PI-103 (25 mg, 0.072 mmol) in NMP (~750 μL) was added a mixture of HATU (32.7 mg, 0.086 mmol), DIEA (30.2 μL, 0.173 mmol), and BOC-Val-OH (0.086 mmol, 18.7 mmol) in NMP. The resulting mixture was stirred, protected from light, for 3 days at room temperature. A solution of BOC-Val-OH (15.6 mg, 0.072 mmol), HATU (27.4 mg, 0.072 mmol), and DIEA (25.1 μL, 0.144 mmol) in

562

NMP (200 μL) was then added. The reaction mixture was stirred for ~18 h at 50° C. and then DMAP (0.072 mmol, 8.8 mg) was added. The mixture was stirred for an additional 1.5 h at 50° C. followed by quenching the reaction with dilute acid. The reaction mixture was diluted with DCM and then washed with water (2×50 mL) and brine (50 mL). The BOC-protected valine ester was purified on silica gel (4 g Combiflash column, EtOAc:Hex, 0% EtOAc hold for 1 min then a gradient to 50% EtOAc over 16 min).

The BOC-protected valine ester was dissolved in DCM (5 mL) and then treated with 4 M HCl in dioxane (5 mL). The mixture was stirred for 6 h at room temperature and then concentrated to dryness under vacuum. The deprotected valine ester was lyophilized from water:CH$_3$CN to afford the title compound as a pale yellow solid (13.6 mg, overall yield 39%). ESI-MS calc for $C_{24}H_{26}N_5O_4$ 448.2 (M+H$^+$), found 448.2.

Example 34

Synthesis of 10 kDa PHF-GA-(PI-103)-(S)-2-amino-3-methylbutanoate-SH

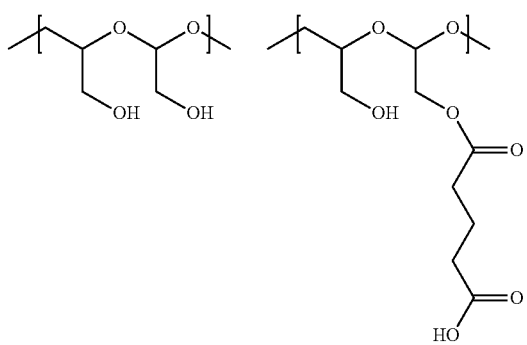

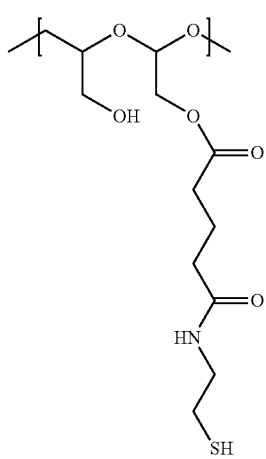

563

-continued

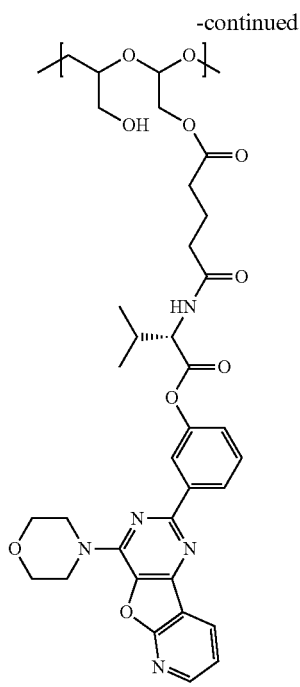

The title compound was prepared in a manner similar to that described in Example 26 except that 10 kDa PHF-GA-SSpy (GA 25%, SSPy 3.8%, 41.4 mg, 3.38 μmol, prepared as described in Example 5), NHS (2.81 mg, 25 μmol), EDC (4.85 mg, 25 μmol), and (PI-103)-(S)-2-amino-3-methylbutanoate hydrochloride (6.38 mg, 13 μmol, prepared as described in Example 33) were used.

Example 35

Synthesis of 10 kDa PHF-GA-((PI-103)-(S)-2-amino-3-methylbutanoate-(Trastuzumab-MCC)

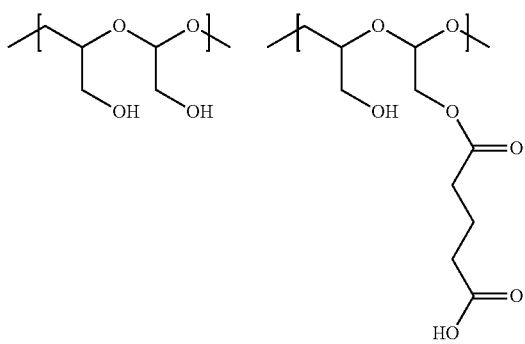

564

-continued

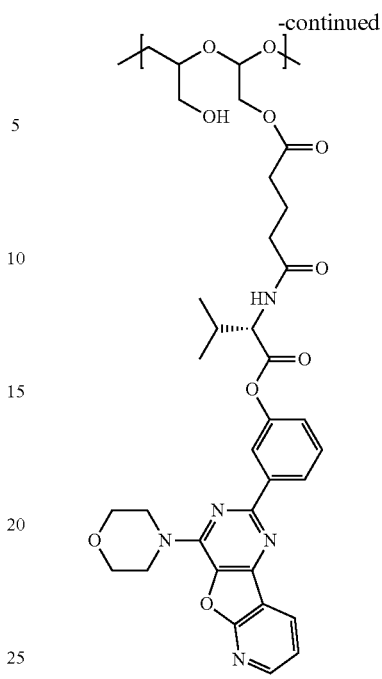

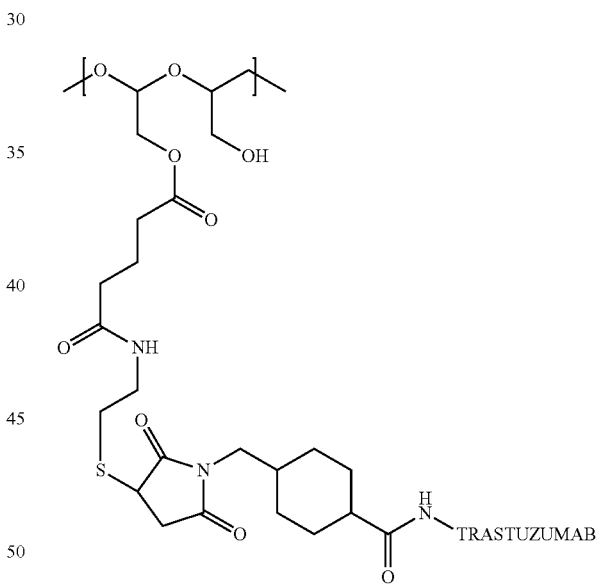

The title conjugate was prepared in a manner similar to that described in Example 7 except that trastuzumab-MCC (10 mg, prepared as described in Example 3) and 10 kDa PHF-GA-(PI-103)-(S)-2-amino-3-methylbutanoate-SH (11.2 mg, prepared as described in Example 34) were used.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab or alemtuzumab as described in Example 3 above. Also PBRM-drug polymer conjugates with varying ratios of drug to PBRM are obtained by varying the amount of PBRM and drug-polymer scaffold used in the Examples above.

Example 36

Synthesis of (AZD 8330)-(S)-2-aminopropanoate hydrochloride

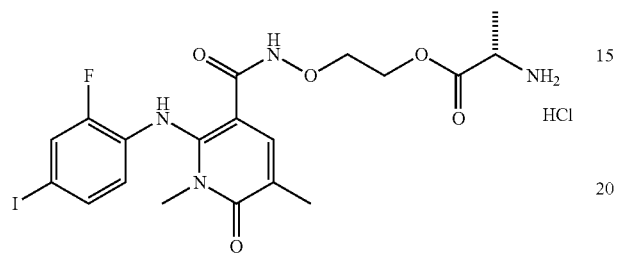

To a solution of BOC-Ala-OH (61.5 mg, 0.325 mmol) in dry THF (1.5 mL) was added DIC (20.5 mg, 0.163 mmol). The resulting mixture was cooled to 0° C. under argon and stirred for 10-15 min. A mixture of AZD 8330 (50 mg, 0.108 mmol) and DMAP (1.3 mg, 0.0108 mmol) in dry THF (1.5 mL) was added and the reaction mixture was stirred for 1.5 h at room temperature protected from light. The reaction mixture was diluted with EtOAc and then washed with saturated $NH_4Cl$ followed by brine. The organic phase was dried over $Na_2SO_4$ then concentrated under vacuum. The crude material was purified on silica gel (Combiflash column, acetone: DCM, 0% acetone hold for 1-2 min then gradient to 20% acetone) to afford 37 mg of a colorless solid. The solid was dissolved in DCM (5 mL) and then treated with 4 M HCl in dioxane (10 mL). The mixture was stirred, protected from light, at room temperature for approximately 5 h. Solvent was removed under vacuum and the residue was lyophilized to afford the title compound as a pale orange solid (22.4 mg, 39% overall yield).

Example 37

Synthesis of 10 kDa PHF-GA-(AZD 8330)-(S)-2-aminopropanoate-SH

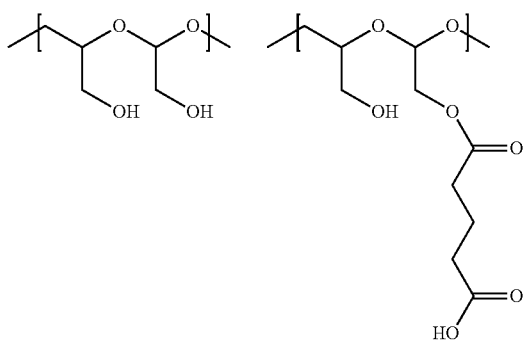

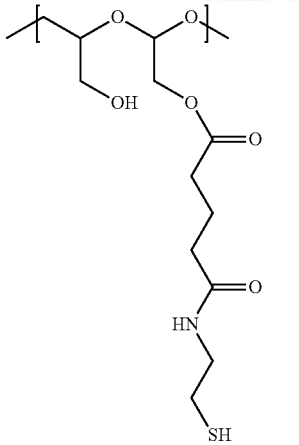

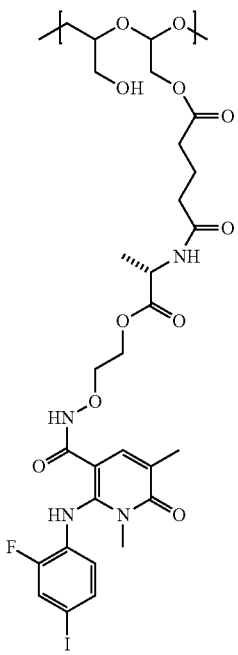

The title compound was prepared in a manner similar to that described in Example 26 except that 10 kDa PHF-GA-SSpy (GA 25%, SSPy 3.8%, 30 mg, 3.38 µmol, prepared as described in Example 5), NHS (1.7 mg, 15 µmol), EDC (2.88 mg, 15 µmol), and (AZD 8330)-(S)-2-aminopropanoate hydrochloride (6.44 mg, 9.9 µmol, prepared as described in Example 36) were used.

Example 38

Synthesis of 10 kDa PHF-GA-(AZD 8330)-(S)-2-aminopropanoate-(Trastuzumab-MCC)

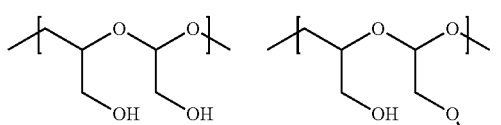

The title compound was prepared in a manner similar to that described in Example 7 except that trastuzumab-MCC (10 mg, prepared as described in Example 3) and 10 kDa PHF-GA-(AZD 8330)-(S)-2-aminopropanoate hydrochloride-SH (15.2 mg, prepared as described in Example 37) were used. The AZD 8330 to antibody molar ratio was on average about 2:1 to 6:1

Example 39

Synthesis of 1-Aminopropan-2-yl-Auristatin F trifluoroacetate

To Auristatin F (150.0 mg, 0.201 mmol) and HOBt (32.6 mg, 0.241 mmol) in 5 mL dichloromethane was added diisopropylcarbodiimide (68.5 µL, 0.442 mmol). The mixture was stirred at 0° C. for 10 minutes at which point a precipitate was observed. tert-Butyl-2-hydroxypropylcarbamate (881.0 mg, 5.03 mmol) in 2 mL dichloromethane was added. The reaction mixture was stirred at 45° C. in a sealed vial and the progress of the reaction monitored via LCMS. Additional HOBt (30.0 mg, 0.222 mmol) was added at 2.5 and 6 hours and the mixture stirred for 18 hours. Additional HOBt (54.3 mg, 0.402 mmol) and diisopropylcarbodiimide (43.1 mg, 0.342 mmol) were added and the mixture stirred at 45° C. for an additional 9 hours at which time LCMS analysis showed complete disappearance of the starting material. The solvent was removed under reduced pressure and the residue dissolved in 3 mL DMF. The sample was purified via preparatory HPLC; (10-90 solvent B gradient over 10 minutes, eluting with 0.1% TFA/Water, 0.1% TFA/CH$_3$CN). The water was removed via lyophilization to give the title compound as a white solid.

1-(Tert-butoxycarbonylamino)propan-2-yl-auristatin F (150 mg, 0.166 mmol) was taken up in dichloromethane (5 mL) and 2,2,2-trifluoroacetic acid (0.256 mL, 3.32 mmol) was added. The mixture was stirred at 23° C. for 30 minutes at which time LC/MS indicated complete conversion. The solvent was reduced to 1 mL under reduced pressure. Dropwise addition of the solution to stirring diethyl ether gave the title compound (27.5 mg, 0.027 mmol. 16%) as a white solid which was collected via filtration.

Example 40

Synthesis of 10 kDa PHF-GA-(1-aminopropan-2-yl-Auristatin F)-SH

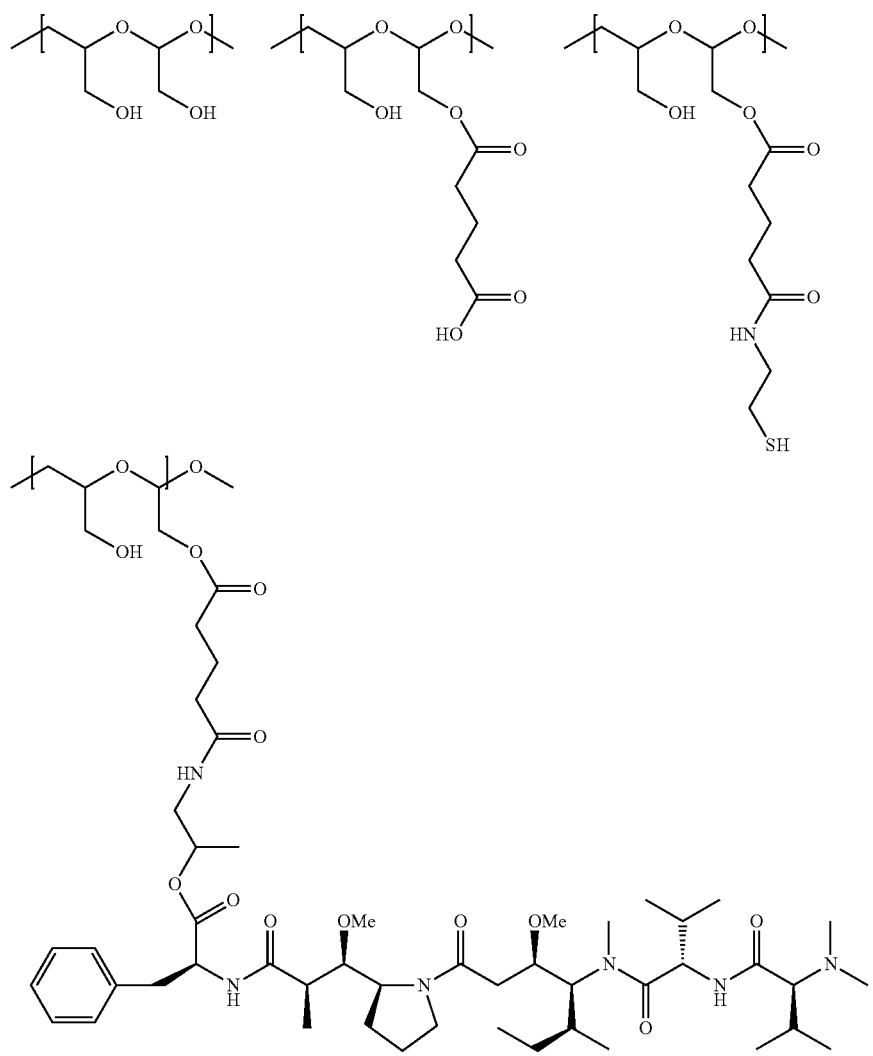

10K PHF-GA(28%)-SSPyr(10%) (76.0 mg, 5.93 µmol), prepared as described in Example 5, was taken up in water (5 mL) and acetonitrile (3 mL) and cooled to 0° C. NHS (6.82 mg, 0.059 mmol in 500 µL water) was added followed by 1-aminopropan-2-yl-auristatin F trifluoroacetate (27.5 mg, 0.027 mmol, prepared as described in Example 39) and EDC (11.4 mmol, 0.059 mmol in 500 µL water). The pH was adjusted to 6 with 0.1N NaOH and the reaction mixture warmed to room temperature and stirred overnight. The pH was adjusted to 7.5 with 1M NaHCO$_3$ and (2S,3S)-1,4-dimercaptobutane-2,3-diol (100 mg, 0.648 mmol) was added. The mixture was stirred at 23° C. for 30 minutes, diluted to 15 mL with water and purified via dialysis through a 3K regenerated cellulose membrane eluting with 1% NaCl/water (3×10 mL) and water (3×10 mL). The sample (76 mg) was diluted to 5 mL and stored at 2-8° C.

Example 41

Synthesis of 10 kDa PHF-GA-(1-aminopropan-2-yl-Auristatin F)-(Trastuzumab-MCC)

(1-aminopropan-2-yl-Auristatin F)-SH (4.44 mg, prepared as described in Example 40, GA 19%, SH 4.8%) were used.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab or alemtuzumab as described in Example 3 above. Also PBRM-drug polymer conjugates with

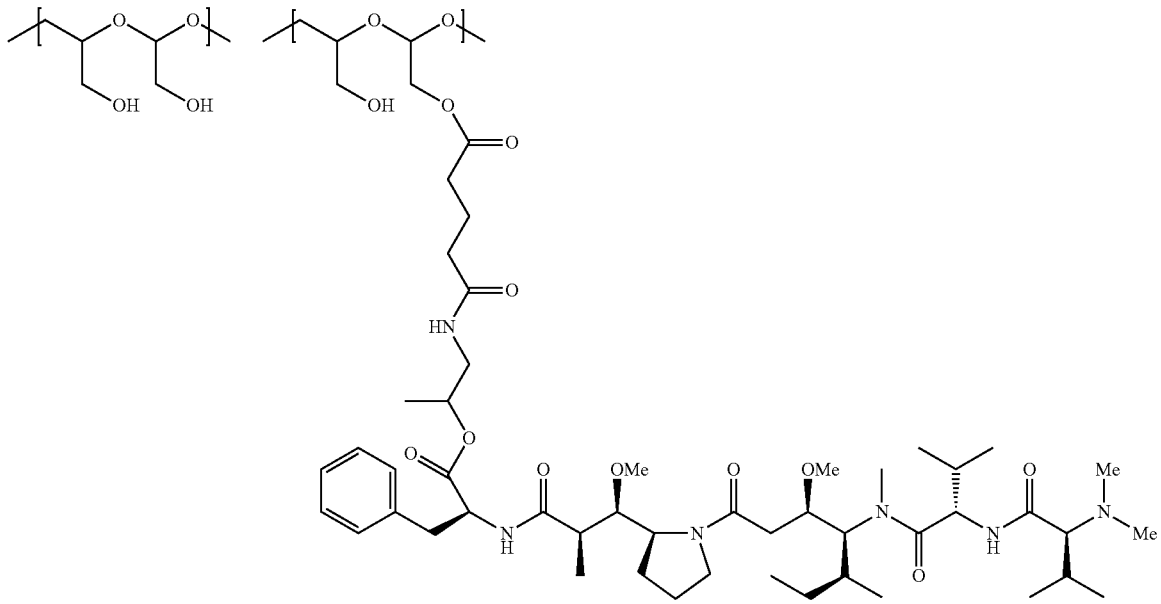

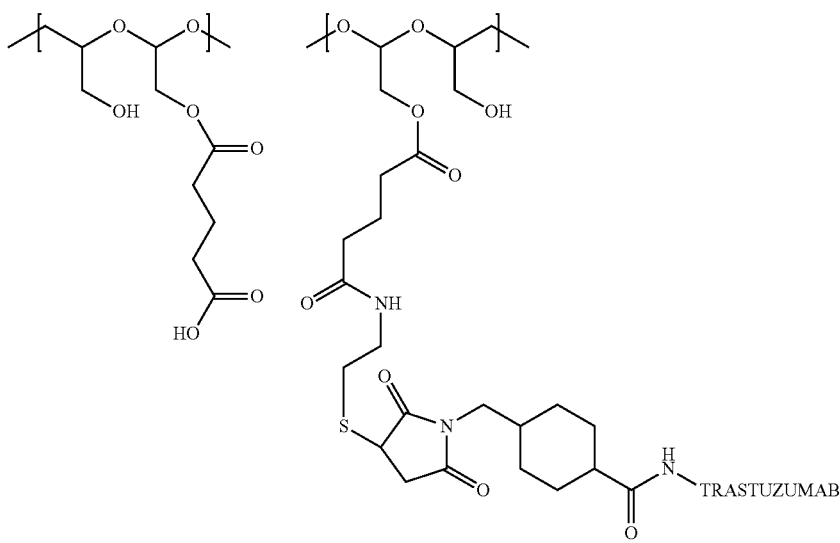

The title conjugate was prepared in a manner similar to that described in Example 7 except that trastuzumab-MCC (5 mg, prepared as described in Example 3) and 10 kDa PHF-GA- varying ratios of drug to PBRM are obtained by varying the amount of PBRM and drug-polymer scaffold used in the Examples above.

Example 42

Synthesis of RD-S1-BOC-amine

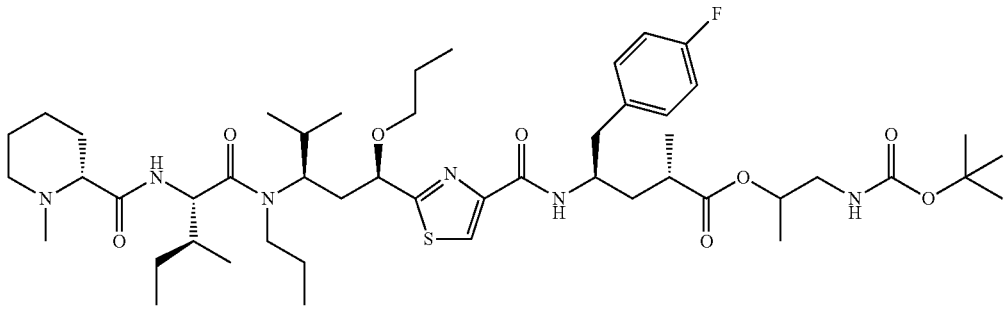 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(F)cc2)C[C@H](C)C(=O)OC(C)CNC(=O)OC(C)(C)C)cs1]

RD-S1 (48.5 mg, 0.055 mmol, prepared according to procedures described in WO 2008/138561) was taken up in $CH_2Cl_2$ (1 mL) and the solution cooled to 0° C. EDC (0.127 mL, 0.82 mmol) and N,N-dimethylpyridin-4-amine (33.4 mg, 0.273 mmol) were added. The reaction mixture was stirred at 0° C. for 20 min and then t-butyl 2-hydroxypropylcarbamate (0.094 mL, 0.546 mmol) was added. The reaction mixture was allowed to warm to room temperature and stirred for 24 h. The sample was purified by preparative HPLC, eluting with 0.1% $TFA/CH_3CN$ and 0.1% TFA/water, followed by lyophilization to give the title compound (20.3 mg, 40% yield) as a beige solid.

Example 43

Synthesis of RD-S1-amine

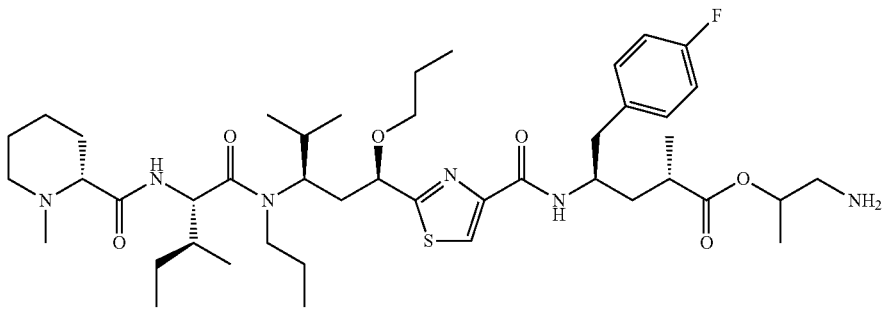 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(F)cc2)C[C@H](C)C(=O)OC(C)CN)cs1]

RD-S1-BOC-Amine (20.3 mg, 0.022 mmol, prepared as described in Example 42) was taken up in $CH_2Cl_2$ (0.500 mL) and cooled to 0° C. 2,2,2-Trifluoroacetic acid (200 μL, 2.61 mmol) was added dropwise, then stirred at room temperature for 30 min. The solvent was removed under reduced pressure. The resulting oil was taken up in $CH_2Cl_2$ followed by the addition of ether to give the title compound as a beige solid (18.1 mg, 100% yield).

Example 44

Synthesis of PHF-GA-RD-S1-Amine-SH

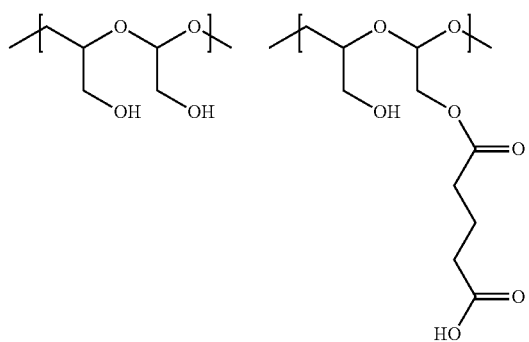

-continued

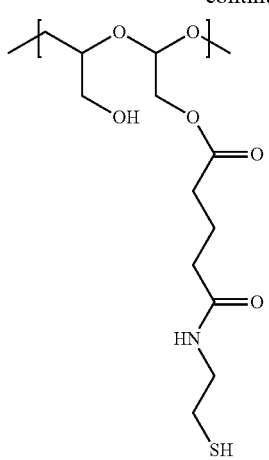

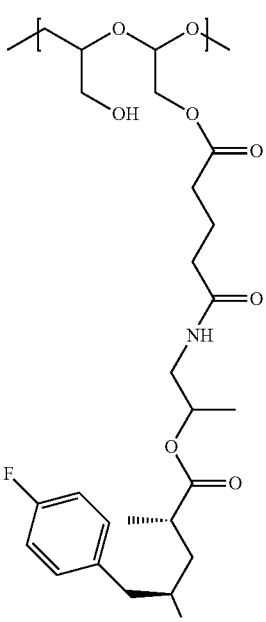

-continued

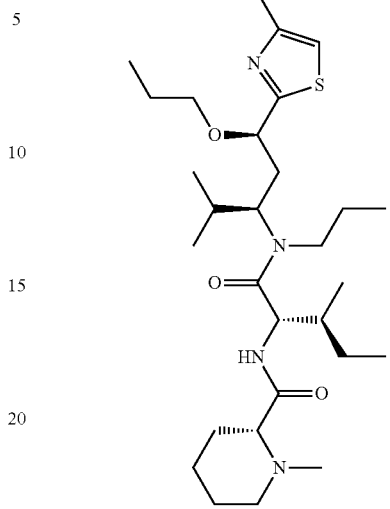

PHF-GA-SSpy (40.2 mg, 3.19 μmol, PHF-GA-SSpy prepared as described in Example 5) was taken up in a mixture of water (2 mL) and $CH_3CN$ (2 mL) and cooled to 0° C. NHS (3.67 mg, 0.032 mmol) was added followed by an aqueous solution of EDC (6.12 mg, 0.032 mmol) and RD-S1-amine (18.1 mg, 0.019 mmol, prepared as described in Example 43) in water (1 mL). The pH of the resulting mixture was adjusted to 6.0 to 6.5, and then stirred at room temperature overnight. The pH was adjusted to 7.5 with 1M $NaHCO_3$ and DTT (10 mg, 0.065 mmol) was added. The reaction mixture was stirred at room temperature for 30 min, diluted to 15 mL with water, filtered through a 2 micron filter and purified by dialysis using a Regenerated cellulose membrane (3 K MW cut-off) by washing with 1% NaCl/water (3×10 mL) followed by water (2×10 mL). The title product was obtained in 61% yield (based on Tubulysin), 3.8% SH content.

By substituting RD-S1-amine with other drug moieties or drug derivatives in the procedures described above it is possible to synthesize other drug-polymer conjugates.

Example 45

Synthesis of XMT-A2

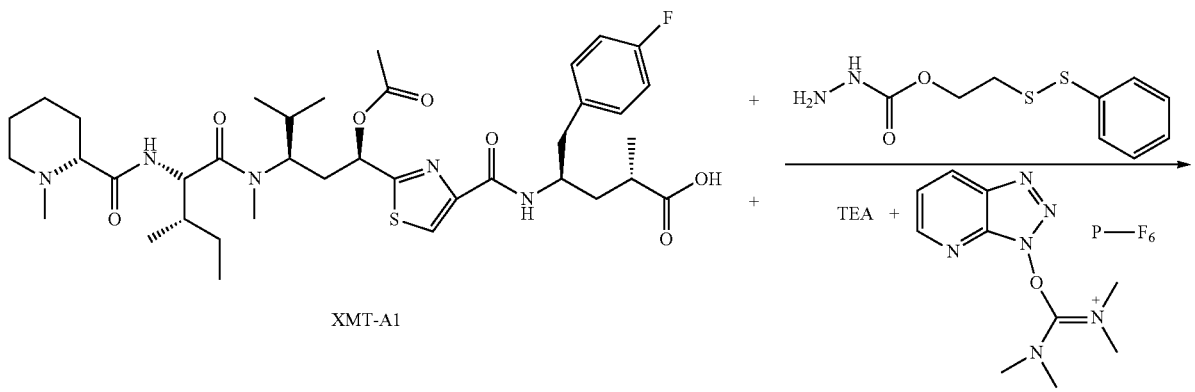

XMT-A1

-continued

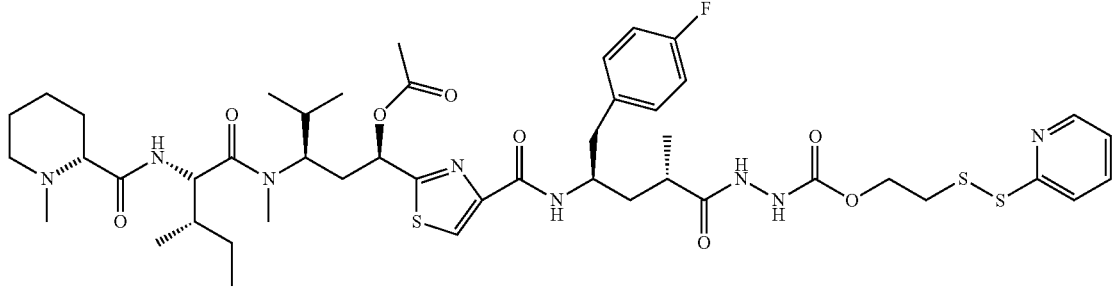

XMT-A2

To a solution of XMT-A1 (5.03 mg, 6.74 μmol) in DMF (33 μL) at 0° C. under argon was added TEA (1.88 μL, 0.013 mmol). The mixture was stirred for 5 min and then (2-(pyridine-2-yldisulfanyl)ethyl hydrazinecarboxylate (2.48 mg, 10.1 μmol) in DMF (20 μL) and HATU (3.85 mg, 10.1 μmol) were added. The reaction mixture was allowed to warm to room temperature, stirred for 2.5 h, diluted with a mixture of water (750 μL) and $CH_3CN$ (1 mL) and then purified by preparative HPLC eluting with 0.1% TFA/$CH_3CN$ and 0.1% TFA/water, followed by lyophilized to give the title compound (8.64 mg, 65.2% yield) as a white solid.

Example 46

Synthesis of XMT-A3

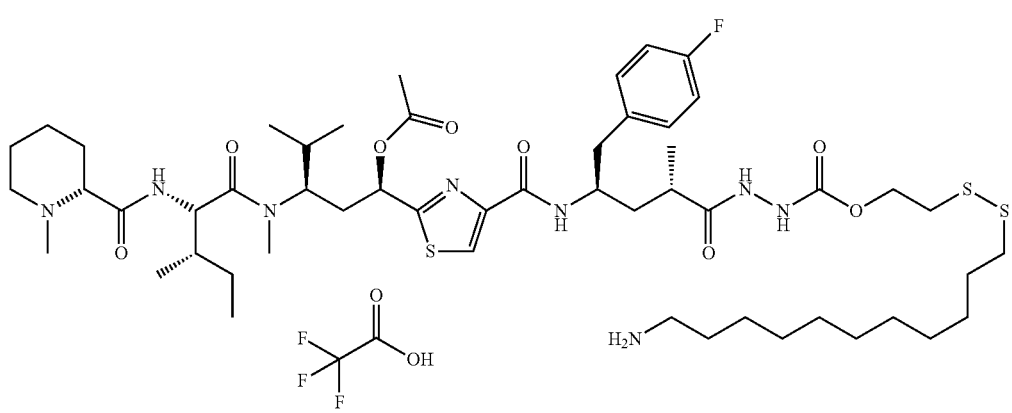

XMT-A3

XMT-A2 (11.9 mg, 0.012 mmol, prepared as described in Example 45) was dissolved in DMF (0.3 mL) and 11-aminoundecane-1-thiol hydrochloride (29.5 mg, 0.123 mmol) in DMF (0.3 mL) was added at 0° C. The reaction mixture was allowed to warm to room temperature and stirred for 2 days, diluted with water (2 mL) and purified by preparative HPLC, followed by lyophilization to give the title compound (6.02 mg, 46% yield) as a white solid.

Example 47

Synthesis of 70 kDa PHF-GA-(XMT-A3)

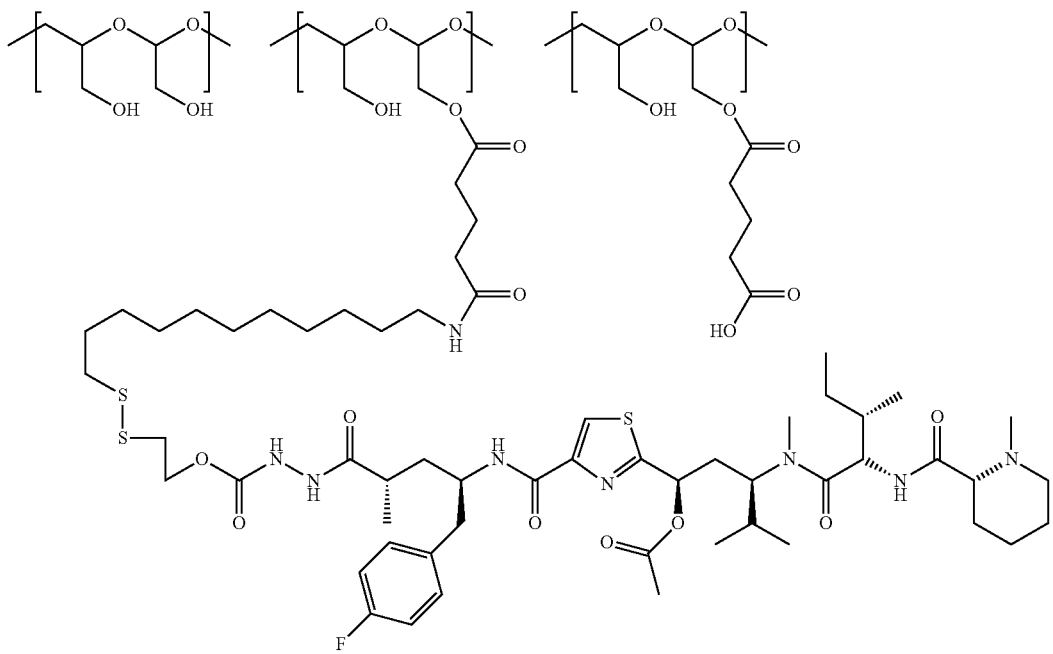

70 KDa PHF-GA (57.4 mg, 0.217 mmol, prepared using the procedure described in Example 2 with 70 KDa PHF, 9% GA) was dissolved in a mixture of water (2.17 mL) and DMF (0.05 mL). XMT-A3 (12.8 mg, 10.9 μmol, prepared as described in Example 46) in DMF (0.05 mL) was added and the pH adjusted to 5 to 6. The resulting solution was cooled to 0° C. and EDC (4.16 mg, 0.022 mmol) was added portionwise over 4 h. The reaction mixture was stirred for 6 h at pH 5.0 to 6.0. Purification by size exclusion chromatography eluting with water gave the title compound (40 mg, 5% (wt) Tubulysin).

Example 48

Synthesis of Auristatin F-hydroxypropylamide (AF HPA)

Auristatin F (150 mg, 0.201 mmol), HATU (153.0 mg, 0.402 mmol), and diisopropylethylamine (108 μL, 0.603 mmol) were taken up in DMF (5 mL) and 3-aminopropan-1-ol (45.9 μL, 0.603 mmol) was added. The mixture was stirred at 23° C. for 45 minutes at which time LCMS analysis showed complete disappearance of the starting material. Reduction of the volume to 1.4 mL under high vacuum followed by purification via preparative HPLC (10-90 solvent B gradient over 20 minutes eluting with 0.1% TFA/Water, 0.1% TFA/CH₃CN) afforded the title compound as white solid (109 mg, 68% yield).

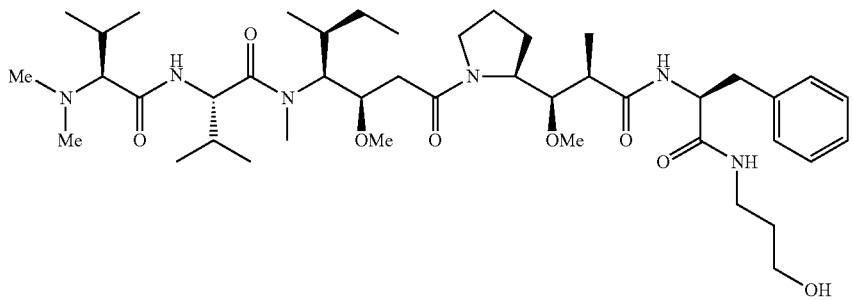 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCCO)OC)N(C)C(=O)[C@@H](NC(=O)[C@H](C(C)C)N(C)C)C(C)C]

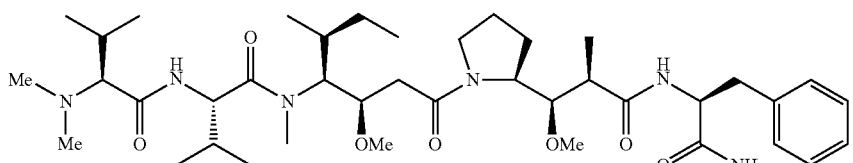
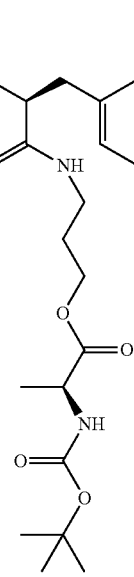

BOC-L-alanine (117.0 mg, 0.618 mmol) and DMAP (94.0 mg, 0.772 mmol) were taken up in dichloromethane and then diisopropylcarbodiimide (52.6 µL, 0.340 mmol) was added. The reaction mixture was cooled to 0° C. and stirred for 10 minutes after which AF HPA (124 mg, 0.154 mmol, prepared as described in Example 48) was added. The reaction mixture was warmed to 23° C. and stirred for 18 hours. Purification via preparative HPLC followed by removal of the water via lyophilization afforded the title compound as beige solid (112 mg, 75% yield).

Example 50

Synthesis of AF HPA-L-Alanine

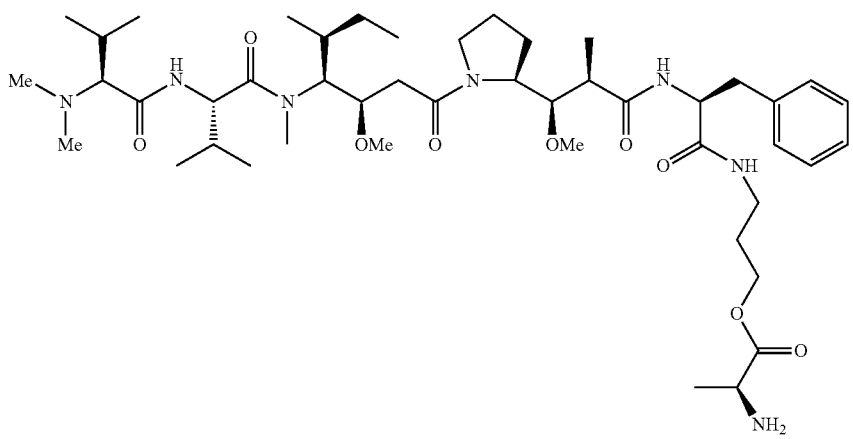 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCCOC(=O)[C@H](C)N)OC)N(C)C(=O)[C@@H](NC(=O)[C@H](C(C)C)N(C)C)C(C)C]

AF HPA-Boc-L-Alanine (112 mg, 0.115 mmol, prepared as described in Example 49) was taken up in dichloromethane (3 mL) and excess trifluoroacetic acid was added. The mixture was stirred at 23° C. for 1 hour and the solvent removed under high vacuum. The resulting oil was taken up in dichloromethane (1.5 mL) and precipitation from diethyl ether (30 mL to give the title compound as white solid (96.2 mg, 85%).

Example 51

Synthesis of 10K PHF-GA-5H-(AF HPA-L-Alanine)

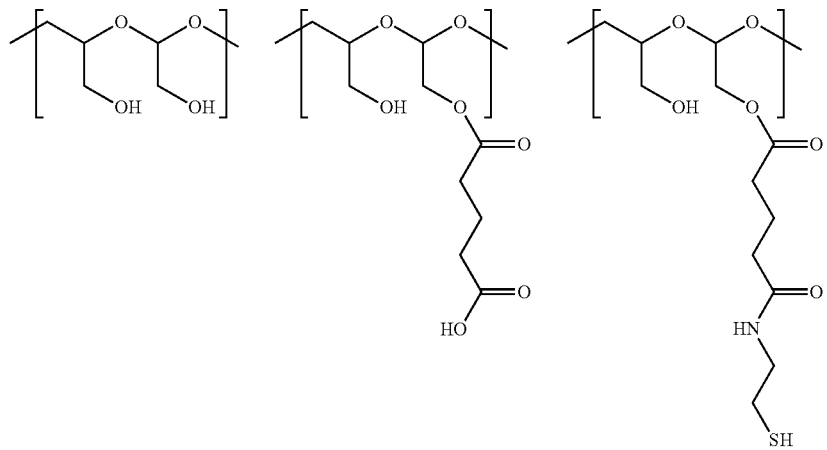

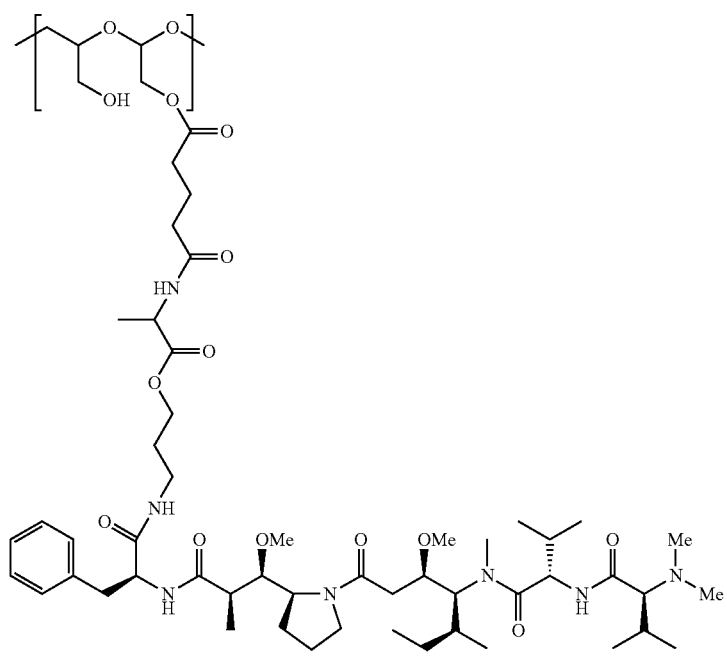

10K PHF-GA(28%)-SSPyr(10%) (135.0 mg, 10.49 µL, prepared as described in Example 5) was taken up in water (8 mL) and acetonitrile (4 mL) and cooled to 0° C. 1-NHS (12.07 mg, 0.105 mmol) was added followed by EDC (20.11 mg, 0.105 mmol) and AF HPA-L-alanine (52.02 mg, 0.047 mmol, prepared as described in Example 50). The pH was adjusted to 6 with 0.1N NaOH and the mixture stirred at 23° C. for 18 hours. The pH was adjusted to 7.5 with 1M NaHCO$_3$ and (2S,3S)-1,4-dimercaptobutane-2,3-diol (90 mg, 0.583 mmol) was added. The mixture was stirred at 23° C. for 30 minutes then diluted to 15 mL with water. The material was purified via dialysis through a 3K regenerated cellulose membrane eluting with 1% NaCl/water (3×10 mL) and water (3×10 mL). The sample was diluted to 5 mL and stored at 2-8° C. (145.0 mg, Auristatin F 14.06 mg/mL).

Example 52

Synthesis of 10 kDa PHF-GA-(AF HPA-L-Alanine)-(Trastuzumab-MCC)

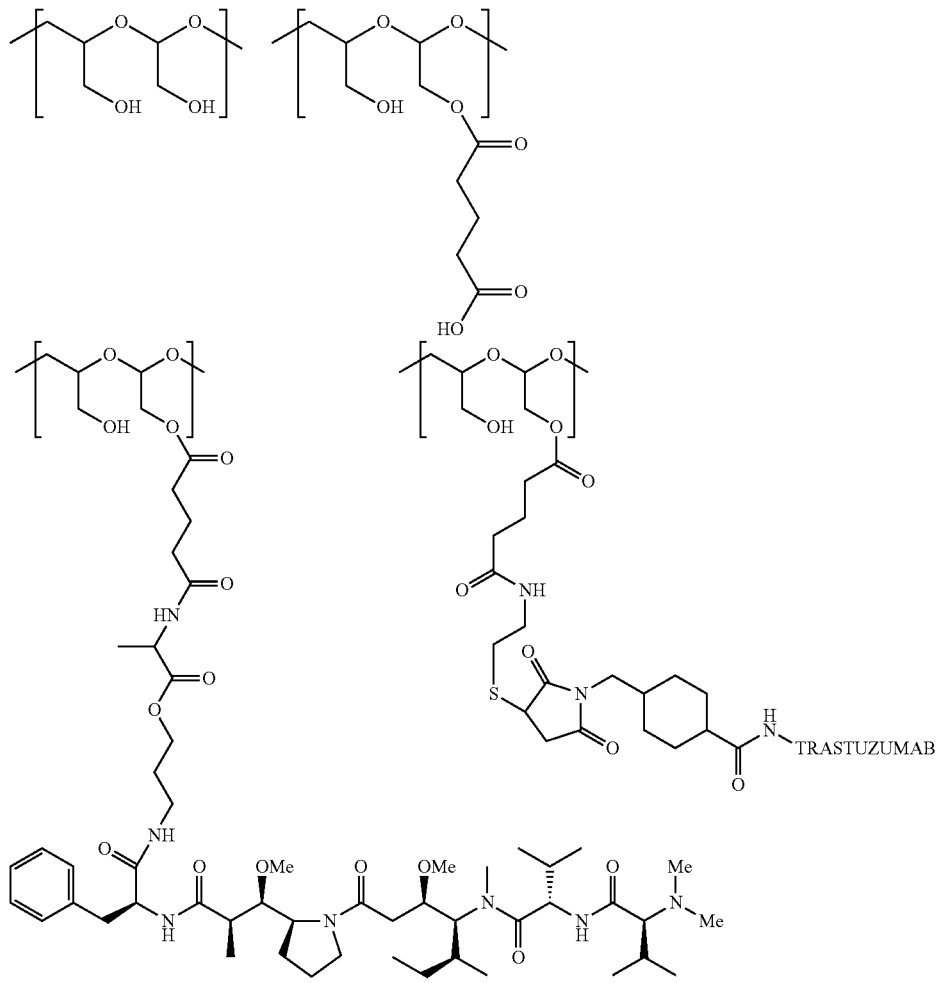

To trastuzumab-MCC (400 mg, prepared as described in Example 3) in PBS (20 mL, pH 7.0) was added 10 kDa PHF-GA-5H-(AF HPA-L-Alanine) (106 mg, prepared as described in Example 51) in water (10 mL). The solution was stirred at room temperature for 4 h at pH 7.0. The resulting product was purified by gel filtration using a Superpose-6 column with PBS as the eluant (50% yield). The molecular weight of the PHF-GA-(AF HPA-L-Alanine)-(Trastuzumab-MCC) as determined by SEC was about 170 kDa. The auristatin F content as determined by LC-MS showed an average auristatin F to antibody molar ratio of about 20:1 to 22:1. For the 10 kDa PHF-GA-(AF HPA-L-Alanine)-(Trastuzumab-MCC) used in FIG. 3 the auristatin F to trastuzumab ratio was about 20:1 to 22:1 and for that used in FIG. 8 the auristatin F to trastuzumab ratio was about 24:1 to 28:1.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab or alemtuzumab as described in Example 3 above. Also PBRM-drug polymer conjugates with varying ratios of drug to PBRM are obtained by varying the amount of PBRM and drug-polymer scaffold used in the Examples above.

Example 53

Synthesis of Rituximab-MCC Derivative

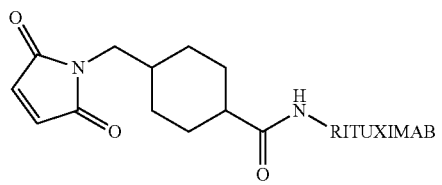

The title compound was prepared as described in Example 3 except Rituximab was used instead of trastuzumab. Analysis showed that on average 5 to 6 MCC groups were linked to one Rituximab.

Other PBRM-MCC derivatives, such as, MCC derivatives of cetuximab, bevacizumab, nimotuzumab, gemtuzumab or alemtuzumab, are synthesized with methods similar to the procedure described above Example 54

Synthesis of 10 kDa PHF-GA-(HPV-Alanine)-(Rituximab-MCC)

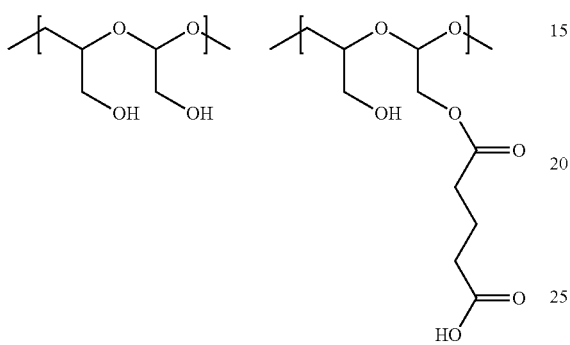

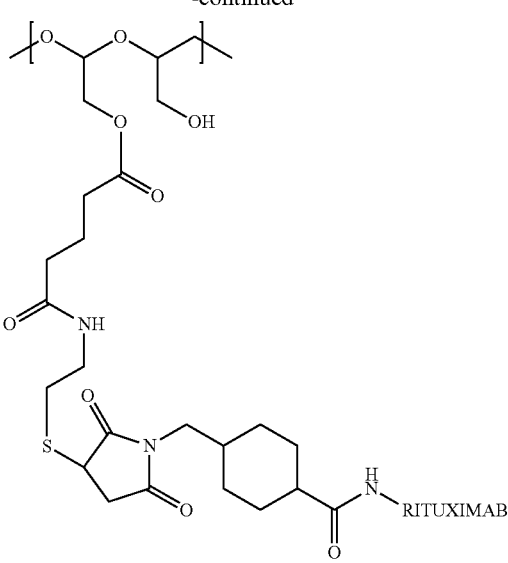

The title compound was prepared using the procedure described in Example 7, except Rituximab-MCC (prepared as described in Example 53) was used instead of Trastuzumab-MCC. The HPV content as determined by HPLC showed an average HPV to Rituximab molar ratio of about 12:1 to 15:1.

Other protein-drug-polymer conjugates are synthesized with methods similar to the procedure described above, involving other PBRM derivatives, such as, for example, MCC derivatives of cetuximab, bevacizumab, nimotuzumab, gemtuzumab or alemtuzumab as described in Example 3 above. Also PBRM-drug polymer conjugates with varying ratios of drug to PBRM are obtained by varying the amount of PBRM and drug-polymer scaffold used in the Examples above.

Example 55

Synthesis of 10 kDa PHF-GA-(HPV-Alanine)-(Trastuzumab-MCC) (5:1)

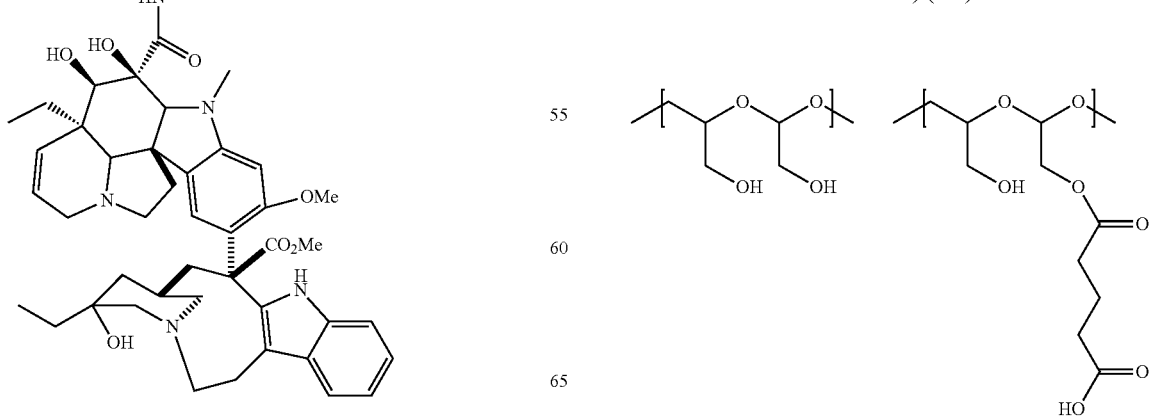

589
-continued
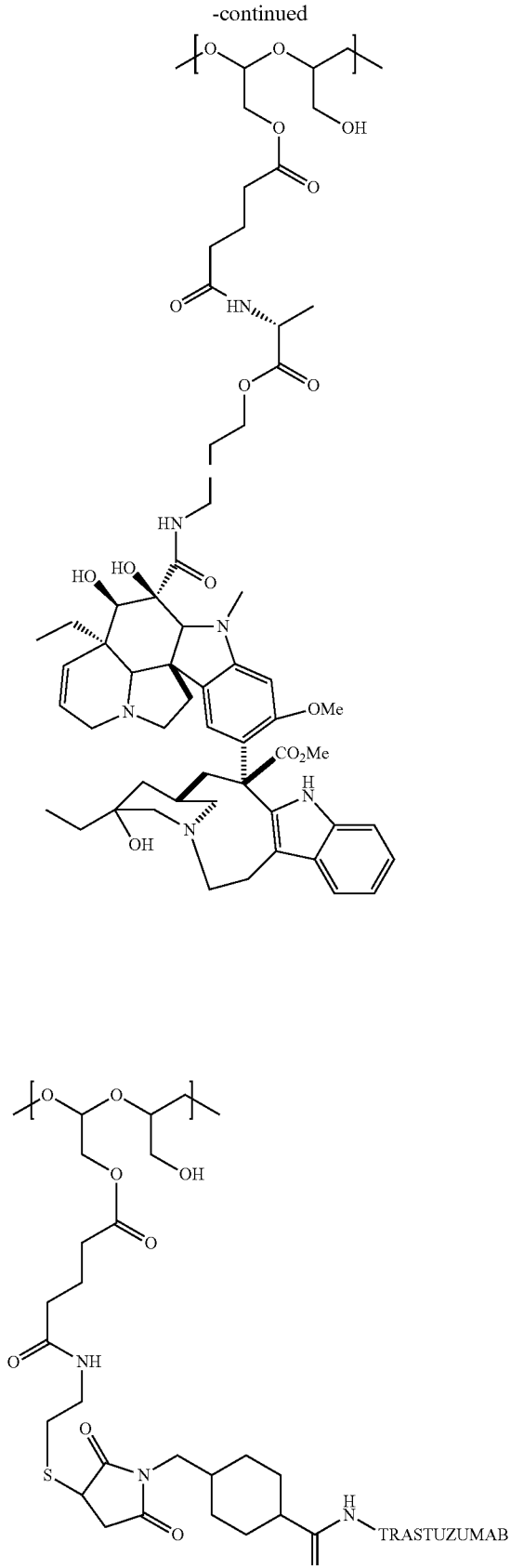
590
The title compound was prepared using the procedure described in Example 7 except HPV content as determined by HPLC showed an average HPV to antibody molar ratio of about 5:1.
Example 56
Synthesis of 10 kDa PHF-GA-(HPV-Alanine)-(Trastuzumab-MCC) (10:1)
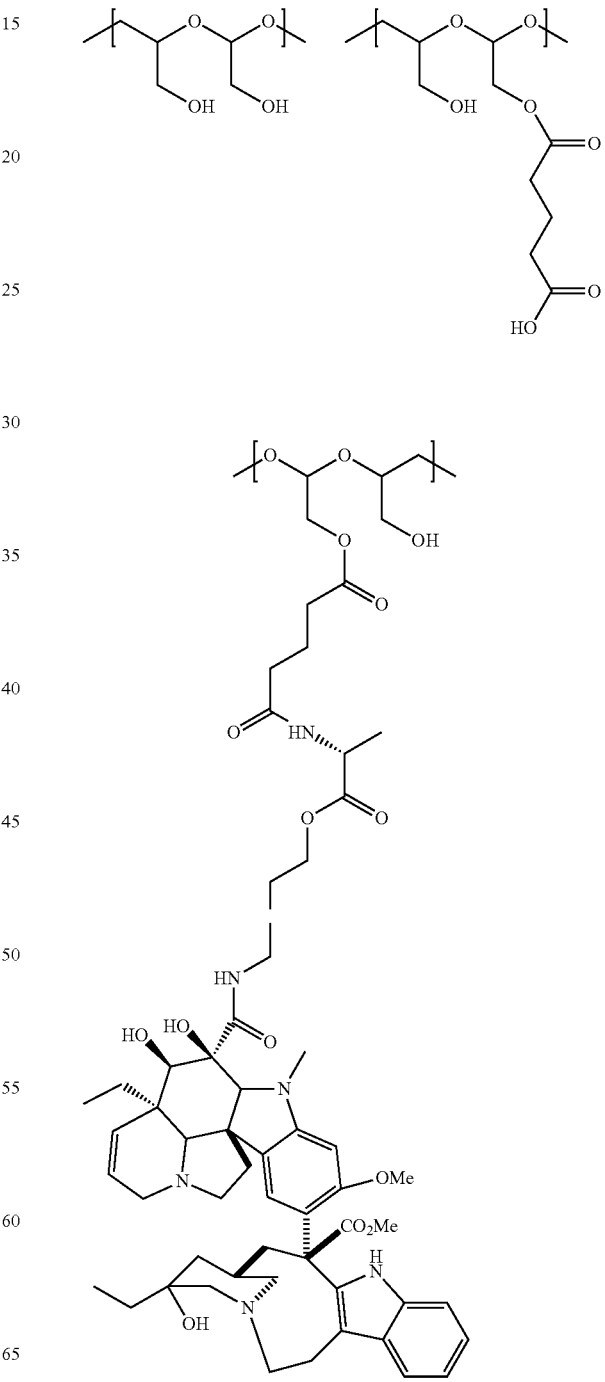

591

-continued

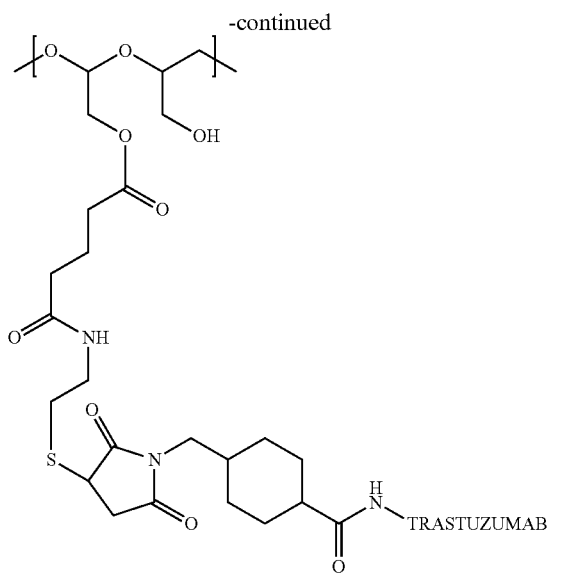

The title compound was prepared using the procedure described in Example 7 except HPV content as determined by HPLC showed an average HPV to antibody molar ratio of about 10:1.

Example 57

Synthesis of 10 kDa PHF-GA-(HPV-Alanine)-(Trastuzumab-MCC) (20:1)

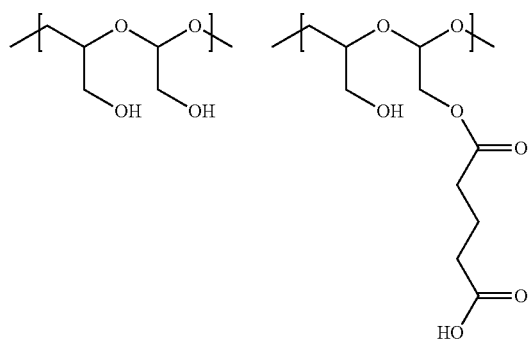

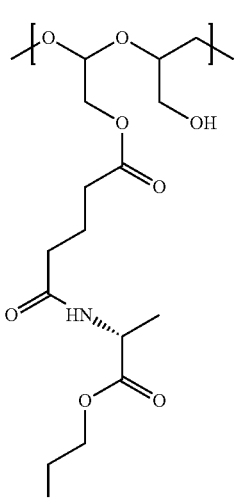

592

-continued

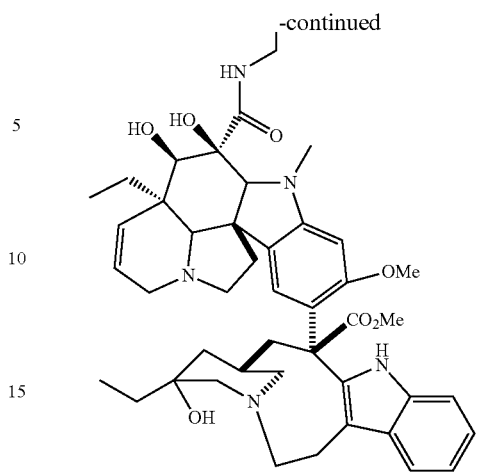

The title compound was prepared using the procedure described in Example 7 except HPV content as determined by HPLC showed an average HPV to antibody molar ratio of about 20:1.

Example 58

Synthesis of Trastuzumab-F(ab')$_2$

Trastuzumab-F(ab')$_2$ was prepared from immobilized pepsin (15 mL settled gel) and trastuzumab (440 mg, 2.4 µmol) according to the manufacturer's (Pierce) instructions to give the title compound (265.2 mg, 92% yield).

By substituting trastuzumab with other PBRMs, such as, for example, cetuximab, rituximab, bevacizumab, nimotuzumab, gemtuzumab or alemtuzumab in the procedure described above it is possible to synthesize other PBRM F(ab')$_2$ fragments.

Example 59

Synthesis of 30 kDa PHF-GA-SSPyr-(HPV-Alanine)

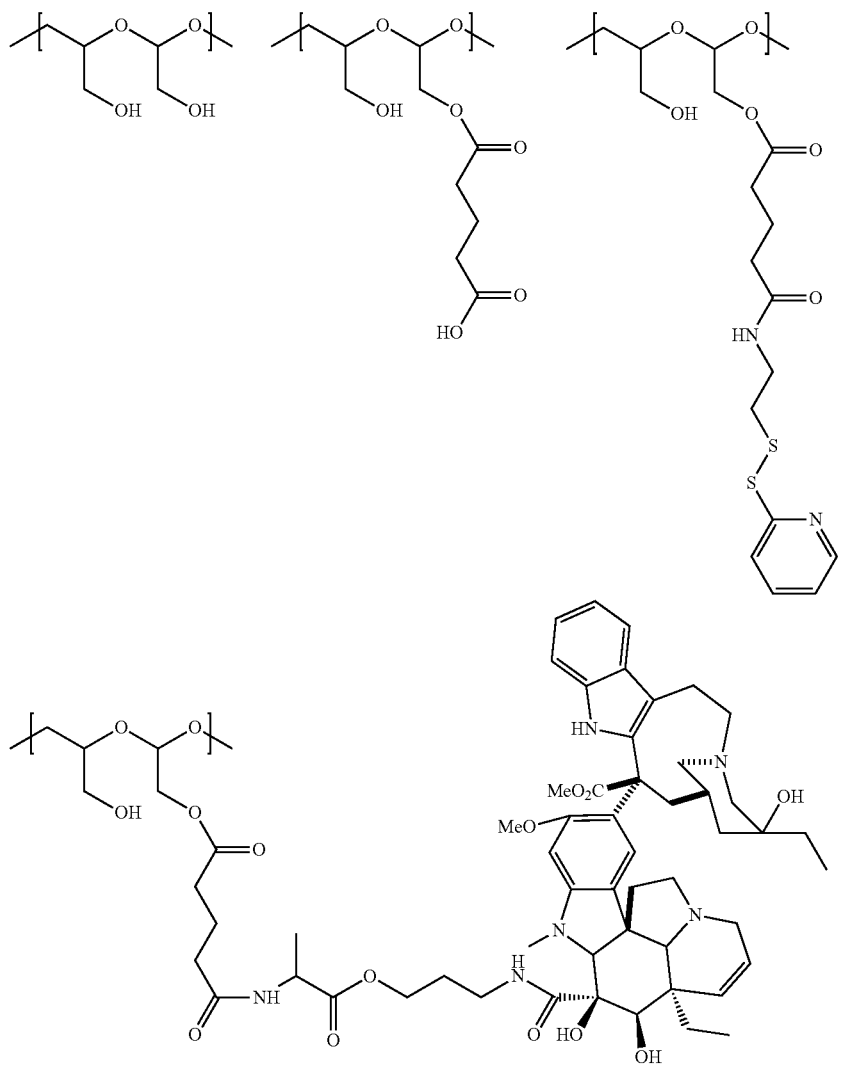

To a solution of 30 kDa PHF-GA (54 mg, 1.49 μmol, prepared as described in Example 2) in 2 mL CH$_3$CN:H$_2$O (1:1)) was added 69 μL (37 μmol) freshly prepared NHS stock solution (62.4 mg/mL in CH$_3$CN) followed by EDC stock solution (150 μL (37 μmol) of 47.3 mg/mL in water). A solution of HPV-alanine hydrochloride (21.3 mg, 22 μmol, prepared as described in U.S. Publication No. 2010/0305149, Example 1) in 500 μL CH$_3$CN:water (1:1) was added and then the pH of the reaction mixture was adjusted to 5.8. The reaction was monitored by SEC HPLC (270 nm detection), and additional EDC was added at 18 h (7 mg, 0.037 mmol) and 19 h (4.5 mg, 0.023 mmol). The reaction mixture was diluted with 30 mL 1% NaCl to bring CH$_3$CN down to 4% of total reaction volume. The crude mixture was filtered through a 0.2 μm membrane by syringe and then purified by stir cell filtration on a 5000 MWCO membrane (regenerated cellulose) washing with 1% NaCl until no small molecules were observed by SEC HPLC. The purified material was finally concentrated to 2.5 mL and stored as a 1% NaCl solution at −20° C. Yield 86% (based on HPV). The HPV to polymer molar ratio was on average about 11:1 to 15:1

Example 60

Synthesis of 30 kDa PHF-GA-(HPV-Alanine)-(Trastuzumab-Fab')

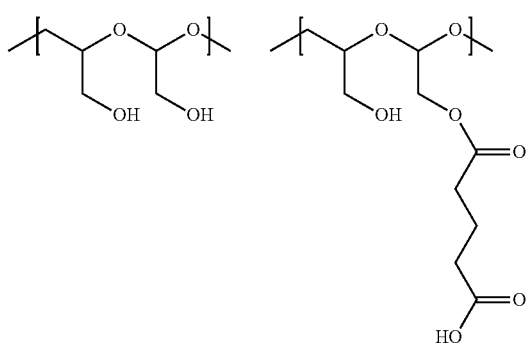

-continued

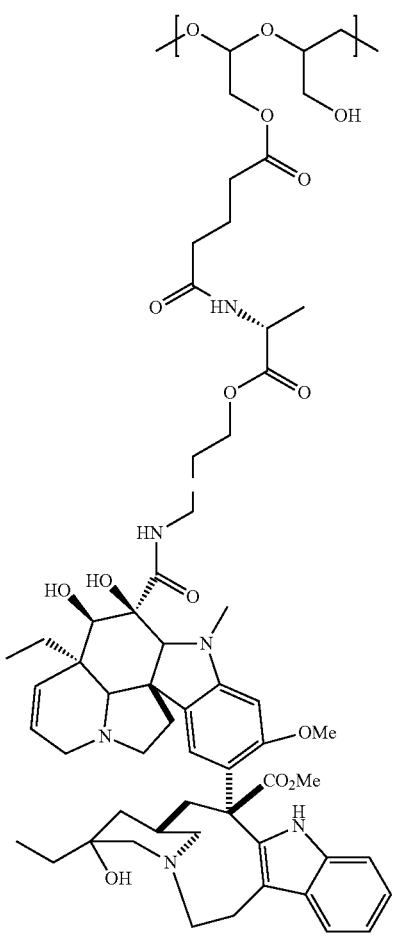

-continued

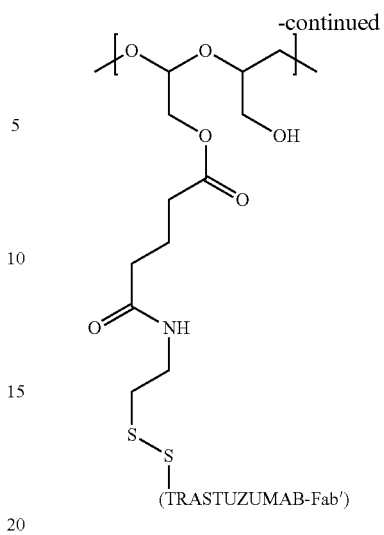

To trastuzumab-F(ab')₂ (3.44 mL, 0.325 µmol of 10.4 mg/mL stock, prepared as described in Example 58) in PBS, pH 7.4 was added an aliquot (138 µL, 0.467 mg) of freshly prepared TCEP stock (3.38 mg/mL in Et₃NHOAc buffer). The mixture was incubated 1 h at 37° C. The reaction mixture was cooled to room temperature and then purified on a PD10 column which was preequilibrated with Et₃NHOAc buffer to give trastuzumab-Fab', MW (SDS PAGE), about 50 to 55 kDa. A solution of 30 kDa PHF-GA-(HPV-Alanine)-SSPyr (600 µL of 6.2 mg HPV equivalents/mL stock, 3.72 mg HPV equivalents) in 1% NaCl was added and the solution was mixed at room temp several hours. The resulting conjugate was first purified by centrifugation on a 10 kDa MWCO membrane and optionally purified by gel filtration. The molecular weight of the PHF-GA-(HPV-Alanine)-(Trastuzumab-Fab') conjugate as determined by SEC was about 108 kDa with polysaccharides as the molecular weight standards. The HPV content as determined by HPLC showed an average HPV to trastuzumab-Fab' molar ratio of about 5:1 to 8:1. For the 30 kDa PHF-GA-(HPV-Alanine)-(Trastuzumab-Fab') used in FIG. 5 the HPV to trastuzumab-Fab' ratio was about 10:1 to 14:1.

By substituting trastuzumab-F(ab')₂ with other PBRM F(ab')₂ fragments, such as, for example, cetuximab, rituximab, bevacizumab, nimotuzumab, gemtuzumab or alemtuzumab F(ab)₂ fragments in the procedure described above it is possible to synthesize other protein-drug conjugates. Also PBRM-drug polymer conjugates with varying ratios of drug to PBRM can be obtained by varying the amount of PBRM and drug polymer used in the Examples above.

Example 61

Synthesis of (S) 2-Hydroxypropylamide-Auristatin F

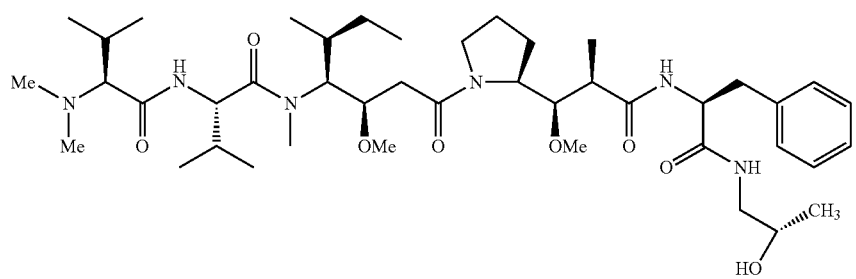 [SMILES: CC[C@H](C)[C@@H]([C@@H](CC(=O)N1CCC[C@H]1[C@H](OC)[C@@H](C)C(=O)N[C@@H](Cc1ccccc1)C(=O)NC[C@H](C)O)OC)N(C)C(=O)[C@@H](NC(=O)[C@H](C(C)C)N(C)C)C(C)C]

To an ice cold solution of auristatin F (50 mg, 0.067 mmol) in DMF (4 ml) was added HATU (51.0 mg, 0.134 mmol) and the resulting mixture was stirred cold for 20 mins. To this was added (S)-1-aminopropan-2-ol (10.07 mg, 0.134 mmol) followed by DIEA (0.035 ml, 0.201 mmol) and the mixture was stirred cold for 1 h and then overnight at room temperature. Purification via preparative HPLC followed by lyophilization gave the title compound as a white amorphous solid as the TFA salt (47 mg, 76% yield) M/z=803.4.

Example 62

Synthesis of (R) 2-Hydroxypropylamide-Auristatin F

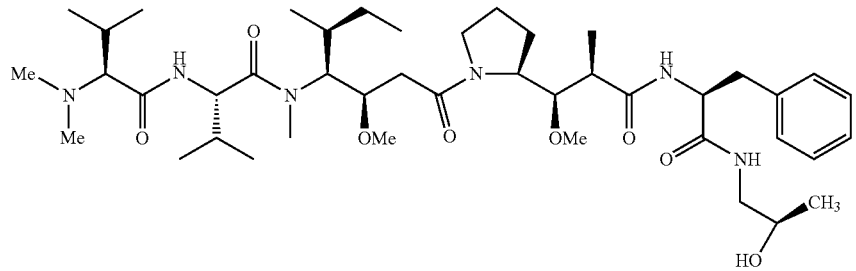 [SMILES: CC[C@H](C)[C@@H]([C@@H](CC(=O)N1CCC[C@H]1[C@H](OC)[C@@H](C)C(=O)N[C@@H](Cc1ccccc1)C(=O)NC[C@@H](C)O)OC)N(C)C(=O)[C@@H](NC(=O)[C@H](C(C)C)N(C)C)C(C)C]

The title compound was prepared as described in Example 61 except (R)-1-aminopropan-2-ol (10.07 mg, 0.134 mmol) was used instead of (S)-1-aminopropan-2-ol. (49 mg, 80% yield) M/z=803.4.

Example 63

Synthesis of XMT-A4 proline ester

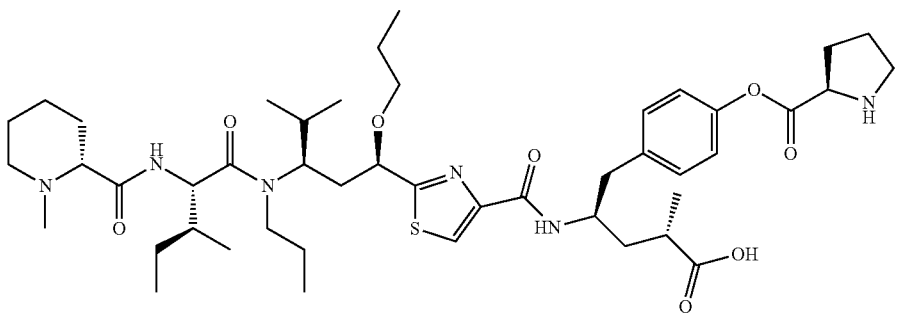 [SMILES: CCCO[C@H](C[C@H](C(C)C)N(CCC)C(=O)[C@@H](NC(=O)[C@H]1CCCCN1C)[C@@H](C)CC)c1nc(C(=O)N[C@@H](Cc2ccc(OC(=O)[C@H]3CCCN3)cc2)C[C@H](C)C(=O)O)cs1]

To an ice cold solution of (S)-1-(tert-butoxycarbonyl)pyrrolidine-2-carboxylic acid (2.79 mg, 0.013 mmol) in DMF (250 µL) was added DIC (2.018 µL, 0.013 mmol) and the resulting mixture was stirred for 15 mins and then added to a solution of XMT-A4 (5 mg, 6.48 µmol) and DMAP (2.374 mg, 0.019 mmol) in DMF (250 µL). The reaction mixture was stirred cold and then at room temperature. After 4 h another aliquot of (S)-1-(tert-butoxycarbonyl) pyrrolidine-2-carboxylic acid (2.79 mg, 0.013 mmol), DIC (2.018 µL, 0.013 mmol) in 100 µL of DMF was added and the stirring was continued overnight at room temperature. The crude product was purified by HPLC followed by lyophilized to give the Boc-protected XMT-A4 as a white amorphous solid (4.4 mg, 63% yield). M/z=969.4.

To an ice cold solution of the Boc-protected XMT-A4 compound with 2,2,2-trifluoroacetic acid (1:1) (4.4 mg, 4.06 µmol) in DCM (300 µL) was added TFA (31.3 µL, 0.406 mmol) and the resulting mixture was stirred cold for 1 h followed by stirring at room temperature for 1 h. The reaction mixture was concentrated, dissolved in acetonitrile and lyophilized to a give the title compound as a white solid (2.3 mg, 58% yield). M/z=869.4.

Example 64

Synthesis of Auristatin F hydroxypropyl amide (AF HPA)

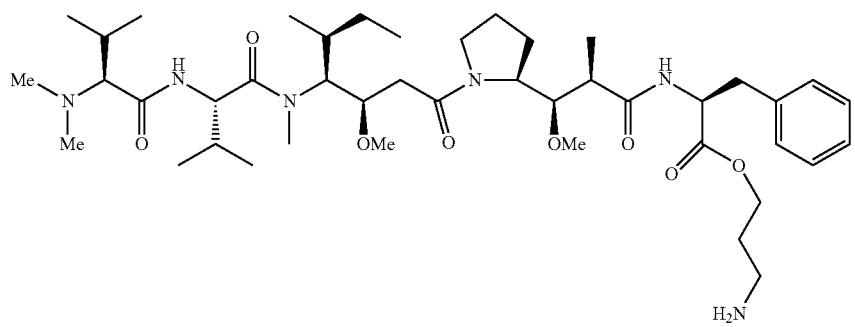 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCCCN)OC)N(C)C(=O)[C@@H](NC(=O)[C@H](C(C)C)N(C)C)C(C)C]

To a solution of auristain F (100 mg, 0.134 mmol) in DCM (5 ml) cooled in an ice/salt bath was added DIC (0.052 ml, 0.335 mmol), tert-butyl 3-hydroxypropylcarbamate (117 mg, 0.670 mmol) and DMAP (82 mg, 0.670 mmol) and the resulting mixture was stirred cold for 2 h and then overnight at room temperature. The reaction mixture was purified by HPLC followed by lyophilized to give the tert-butyl carbamate protected title compound as a white amorphous solid (121 mg, 89% yield) M/z=903.5.

To an ice cold solution of the tert-butyl carbamate protected title compound 2,2,2-trifluoroacetate (121 mg, 0.119 mmol) in DCM (4 ml) was added TFA (500 μl, 6.49 mmol) and the resulting mixture was stirred cold for 1 h and then at room temperature for 1 h. After removal of the excess TFA, the title compound was isolated by precipitation into ethyl ether as a white amorphous solid (109 mg, 93% yield); M/z=803.4.

Example 65

Synthesis of 10K PHF-GA-5H-AF HPA

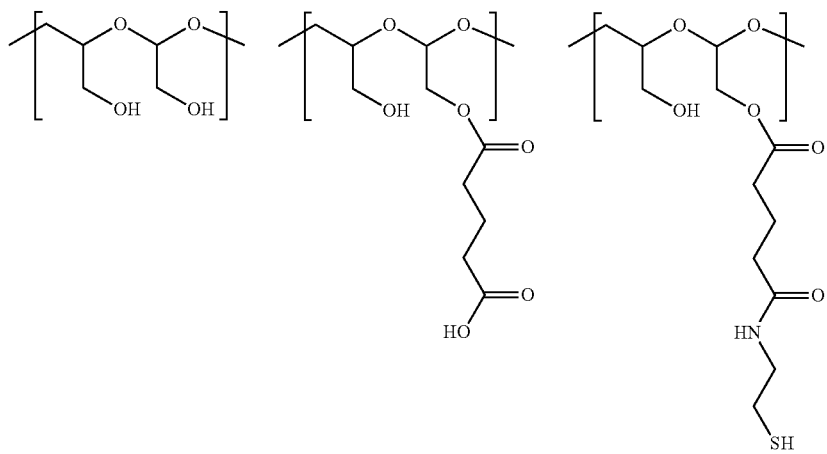

-continued
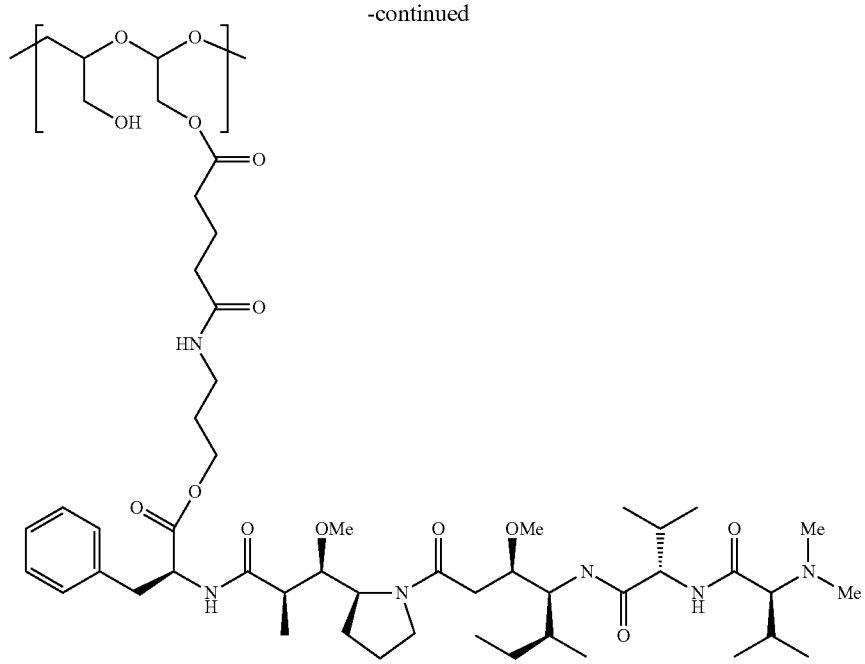
The title compound was prepared as described in Example 51 except AF HPA (Example 64) was used instead of AF HPA-L-Alanine (Example 50).
Example 66
Synthesis of 10K PHF-GA-5H-(AF HPA)-(Trastuzumab-MCC)
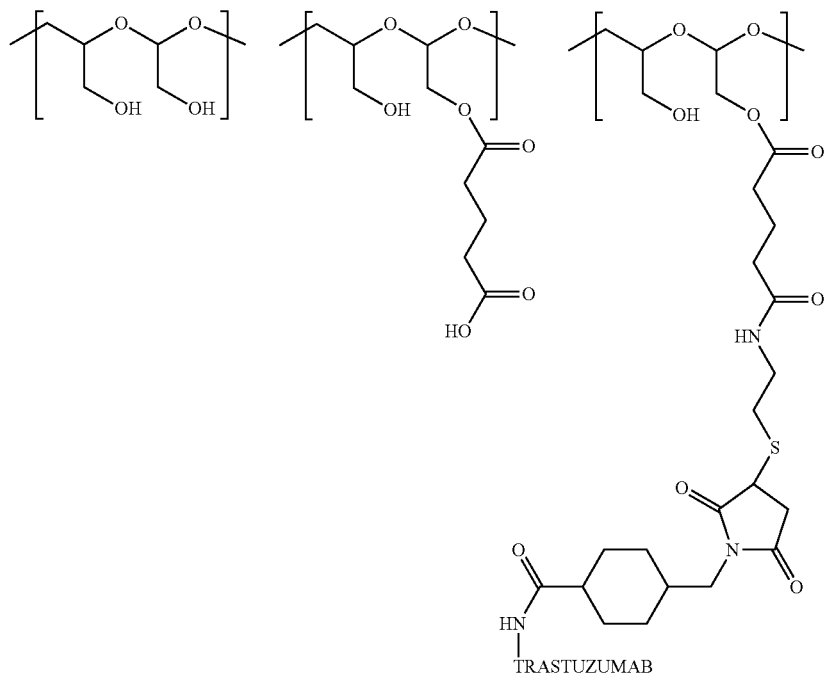

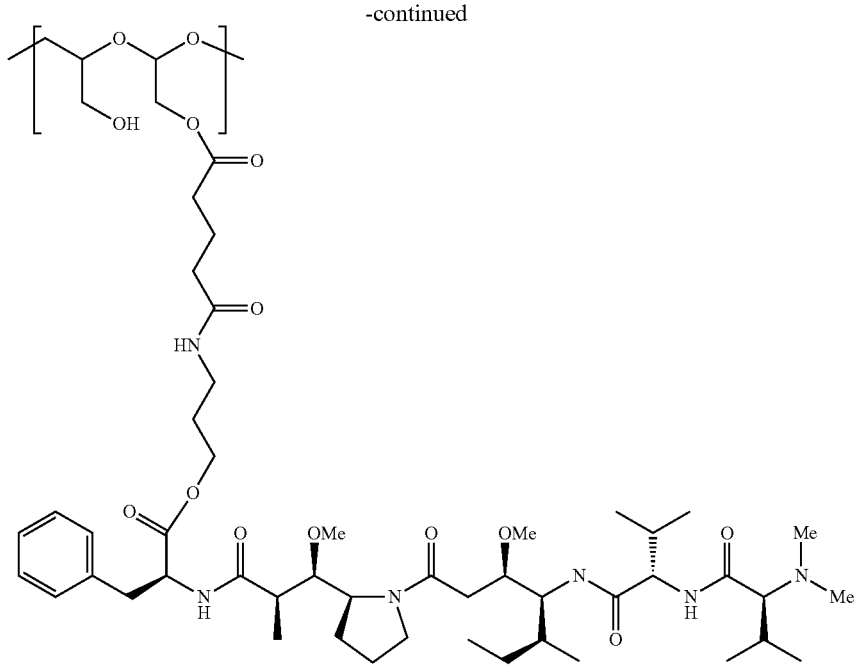

The title compound was prepared as described in Example 52 except 10K PHF-GA-5H-(AF HPA) (Example 66) was used. The auristatin F content as determined by LC-MS showed an average auristatin F to antibody molar ratio of about 21:1 to 25:1.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab or alemtuzumab as described in Example 3 above. Also PBRM-drug polymer conjugates with varying ratios of drug to PBRM are obtained by varying the amount of PBRM and drug-polymer scaffold used in the Examples above.

Example 67

Synthesis of N-3(aminopropyl)-4-methyl-4-((5-nitro-pyridin-2-yl)disulfanyl)pentanamide

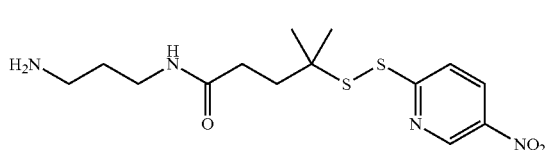

To tert-butyl 3-aminopropylcarbamate (0.437 mL, 2.50 mmol) in DMF (1 mL) was added N-ethyl-N-isopropylpropan-2-amine (0.437 mL, 2.50 mmol) and 1H-benzo[d][1,2,3]triazol-1-ol (846 mg, 6.26 mmol). The reaction mixture was stirred for 10 minutes at 25° C. and 2,5-dioxopyrrolidin-1-yl-4-methyl-4-((5-nitropyridin-2-yl)disulfanyl)pentanoate (500 mg, 1.25 mmol) in DMF (1 mL) was added. The reaction mixture was stirred at 25° C. for 18 hours. Purification by HPLC afforded the title compound as its tert butyl carbamate (476.7 mg, 1.04 mmol, 83%) as a beige solid: m/z 459 [M+H]$^+$.

To the title compound as its tert butyl carbamate (699.7 mg, 1.53 mmol) in DMF (5.00 mL) was added 2,2,2-trifluoroacetic acid (2.35 mL, 30.5 mmol). The mixture was stirred at 25° C. for 1 hour. After removal of the solvent the resulting title compound was used without further purification: m/z 359 [M+H]$^+$.

Example 68

10K PHF-GA (25%)-SS-Dimethyl-NO$_2$ (5%)

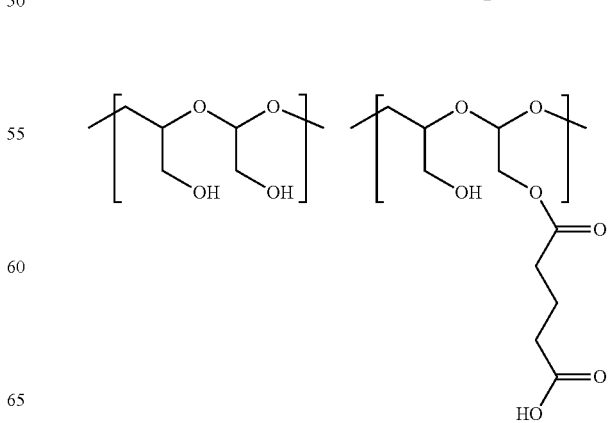

-continued

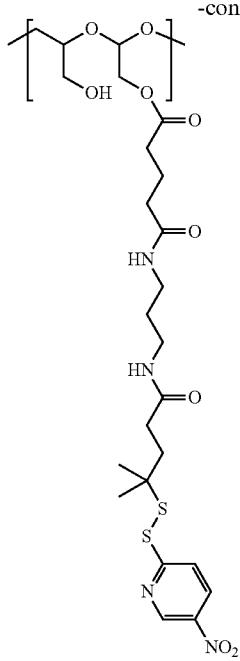

10 kDa PHF-GA (2.37 g, 14.5 mmol, prepared using the procedure described in Example 2 with PHF 10,000 Da, 25% GA) was diluted to 100 mL with water and NHS (0.133 g, 1.16 mmol) was added. The mixture was cooled to 0° C., pH adjusted to 5.5-6.0 and then N-3(aminopropyl)-4-methyl-4-((5-nitropyridin-2-yl)disulfanyl)pentanamide (547.0 mg, 1.16 mmol, Example 67) in CH$_3$CN (4 mL) and DMF (0.5 mL) were added followed by EDC (0.222 g, 1.16 mmol). The pH of the reaction mixture was again adjusted to 5.5-6.0 and stirred at room temperature for 18 hours. Additional EDC (0.150 mg, 0.782 mmol) was added and the mixture stirred for an additional 1.5 hours. The sample was purified via dialysis through a Regenerated Cellulose membrane to give the title compound (2.05 g).

Example 69

10K PHF-GA-SS-Dimethyl-NO$_2$-(AF HPA-L-Alanine

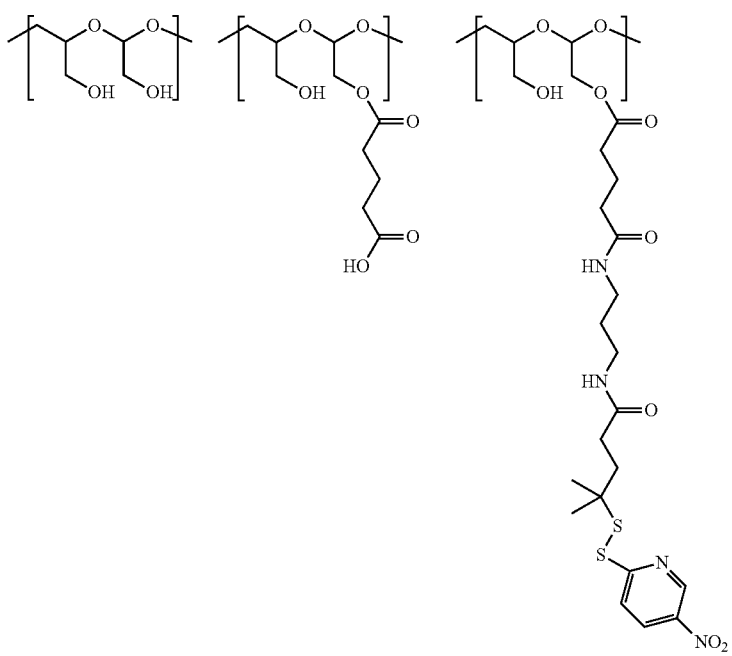

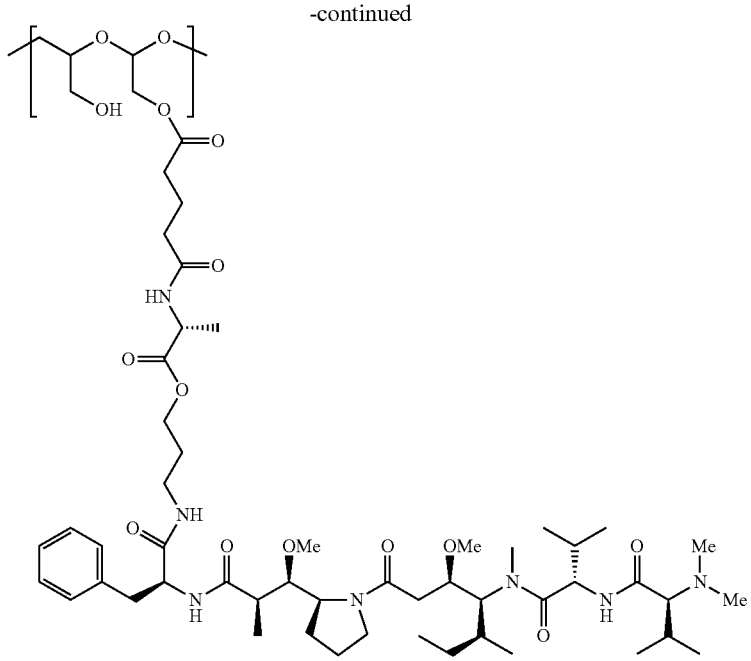
The title compound was prepared as described in Example 51 except 10K PHF-GA(25%)-SS-Dimethyl-NO₂ (5%) (Example 68) was used instead of 10K PHF-GA-SS-Pyr (Example 5) and (2S,3S)-1,4-dimercaptobutane-2,3-diol (90 mg, 0.583 mmol) was not added.
Example 70
10K PHF-GA (AF HPA-L-Alanine)-(Dimethyl S-S-Trastuzumab)
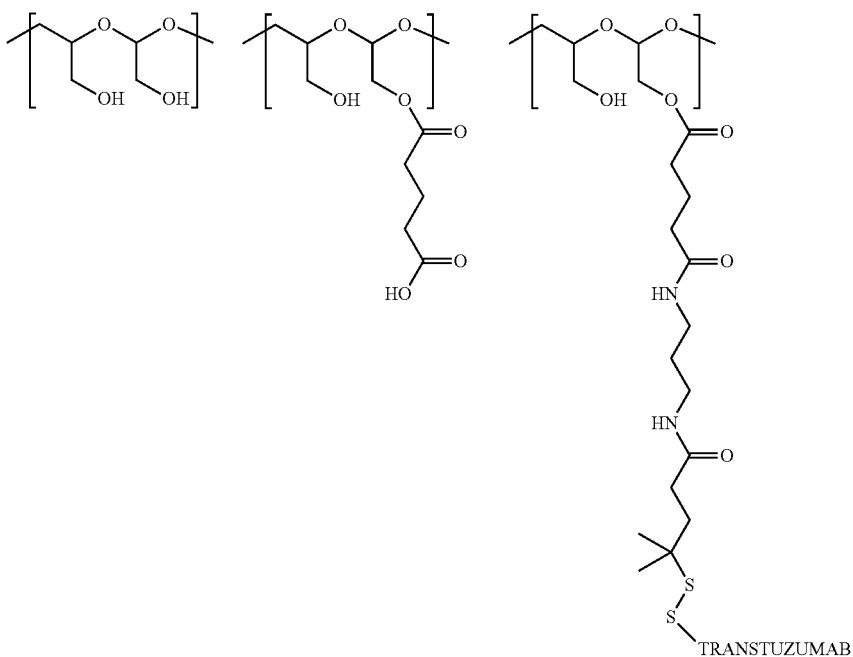

-continued

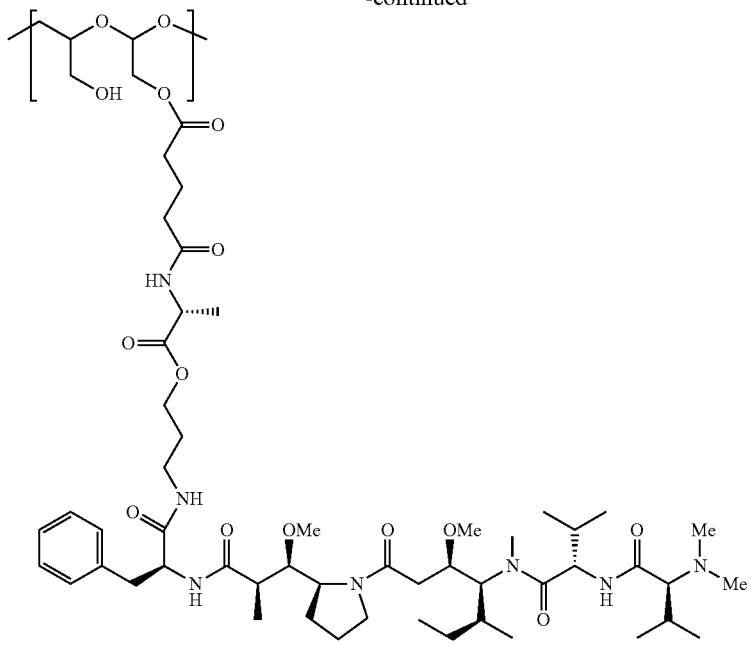

The title compound was prepared from 10K PHF-GA-SS-Dimethyl-NO$_2$-(AF HPA-L-Alanine) (Example 69) using the procedure described in Example 60 except reduced Trastuzumab was used instead of Trastuzumab-F(ab')$_2$. The auristatin F content as determined by LC-MS showed an average auristatin F to antibody molar ratio of about 9:1 to 13:1.

Other protein-drug-polymer conjugates are synthesized with methods similar to the procedure described above, involving other PBRM derivatives, such as, for example, reduced form of cetuximab, rituximab, bevacizumab, nimotuzumab, gemtuzumab or alemtuzumab as described in Example 60 above. Also PBRM-drug polymer conjugates with varying ratios of drug to PBRM are obtained by varying the amount of PBRM and drug-polymer scaffold used in the Examples above.

Example 71

10K PHF-GA-SS-Dimethyl-NO$_2$-(AF HPA)

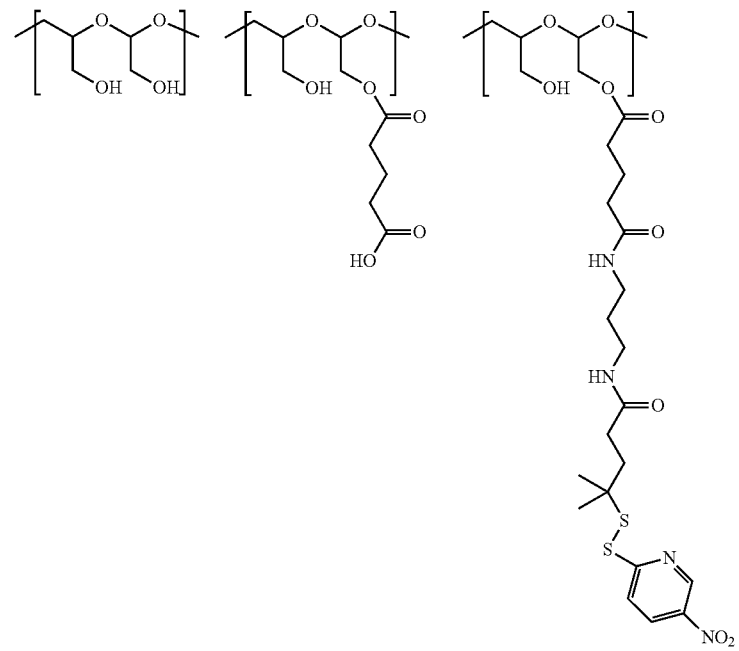

-continued
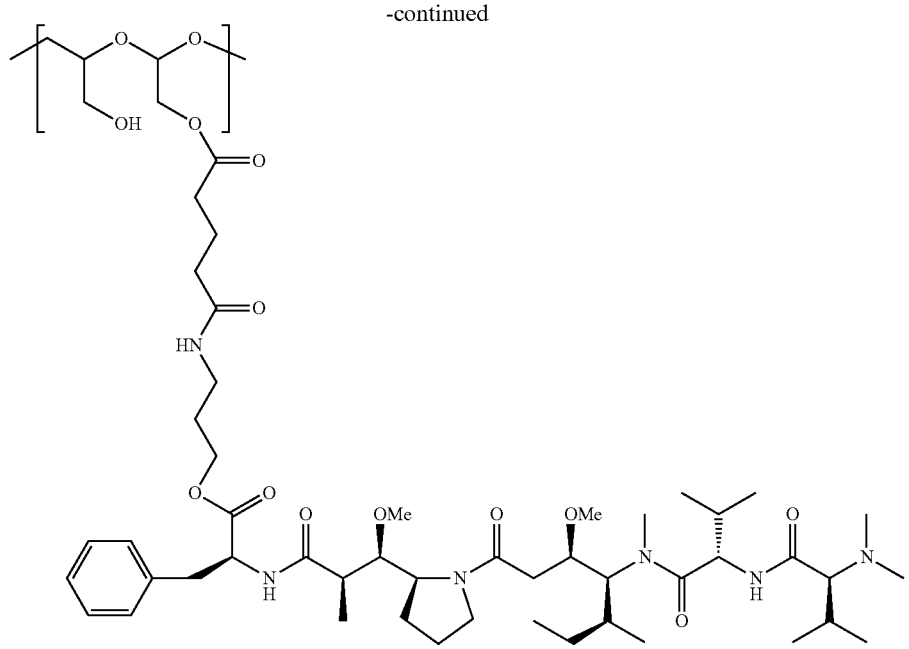
The title compound was prepared as described in Example 69 except 10K PHF-GA-SS-Dimethyl-NO₂ (Example 68) and AF HPA were used.
Example 72
10K PHF-GA-(AF HPA)-(Dimethyl-S-S-Trastuzumab)
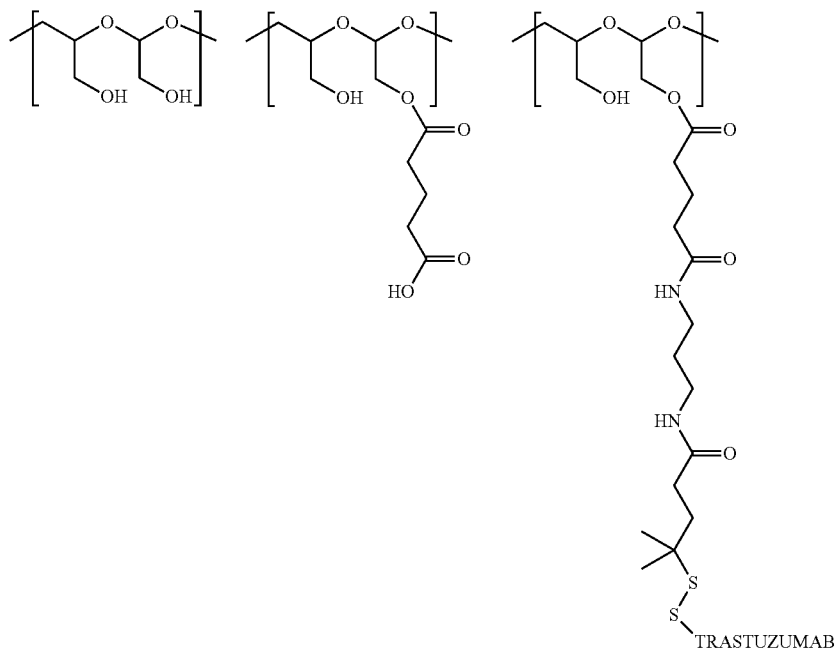

-continued
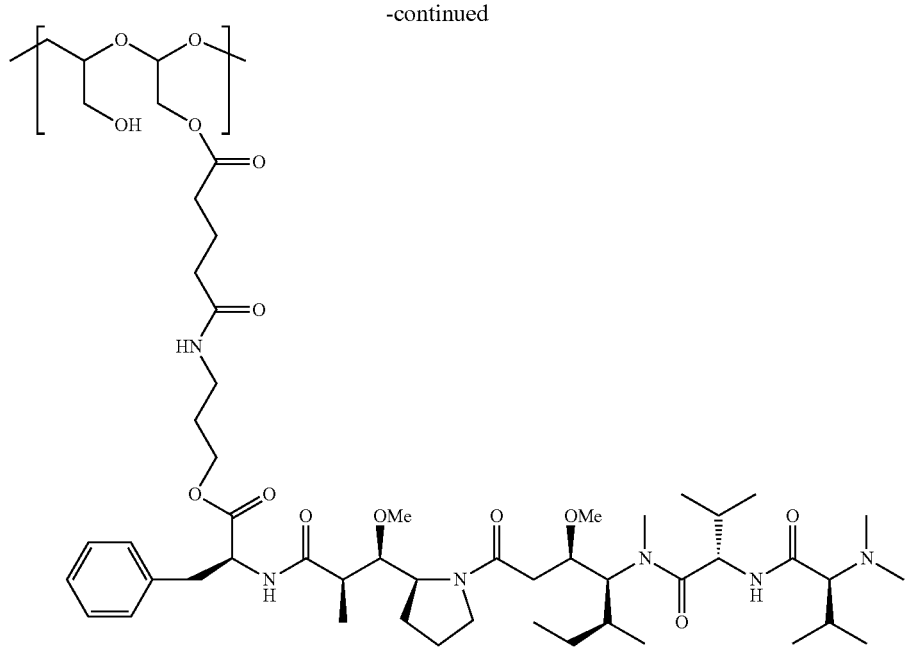
The title compound was prepared using the procedure described in Example 70 except 10K PHF-GA-SS-Dimethyl-NO$_2$-(AF HPA) (Example 71) was used. The auristatin F content as determined by LC-MS showed an average auristatin F to antibody molar ratio of about 11:1 to 15:1
Example 73
Synthesis of XMT-A4 diaminobutyl carbamate

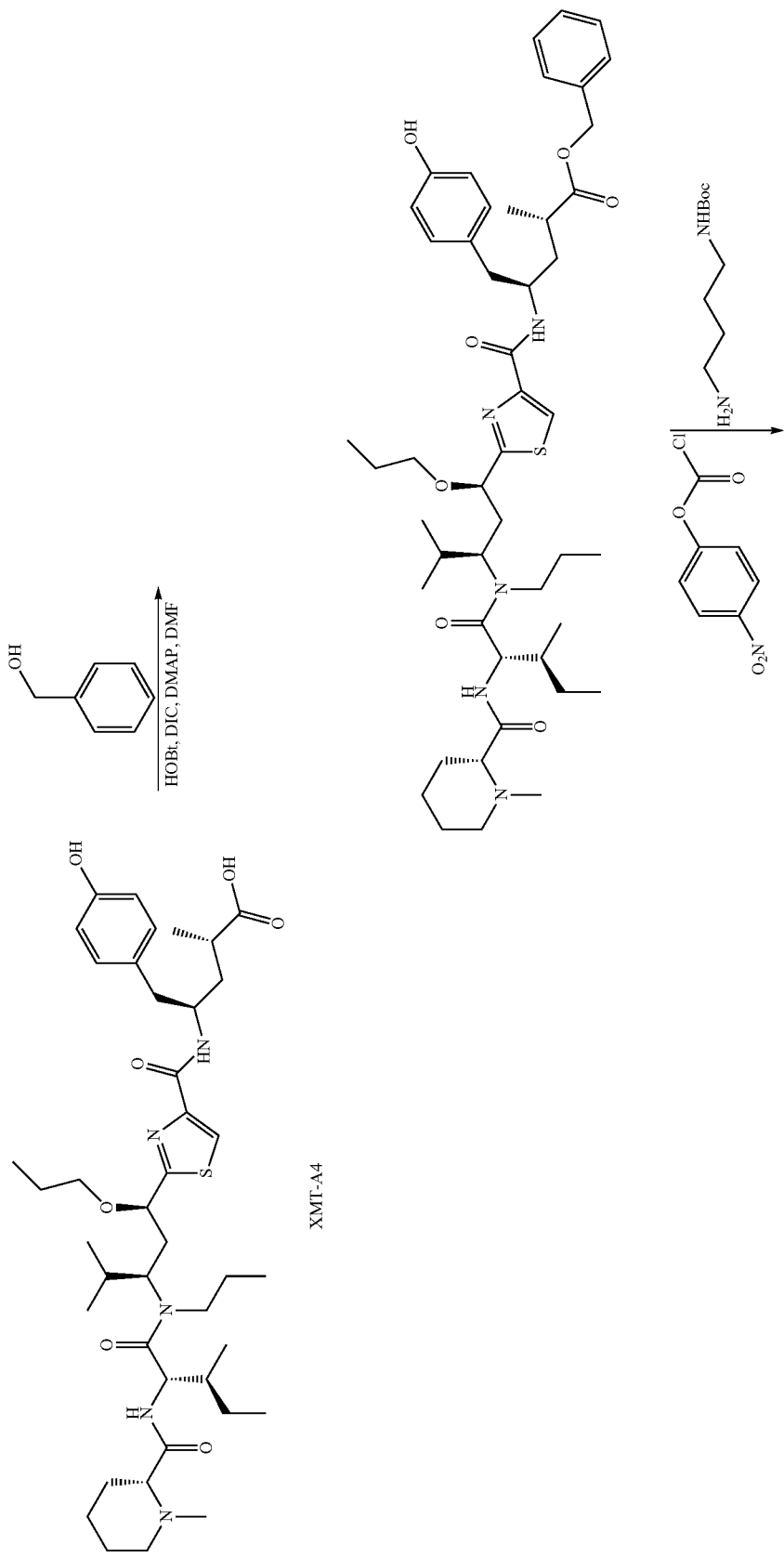

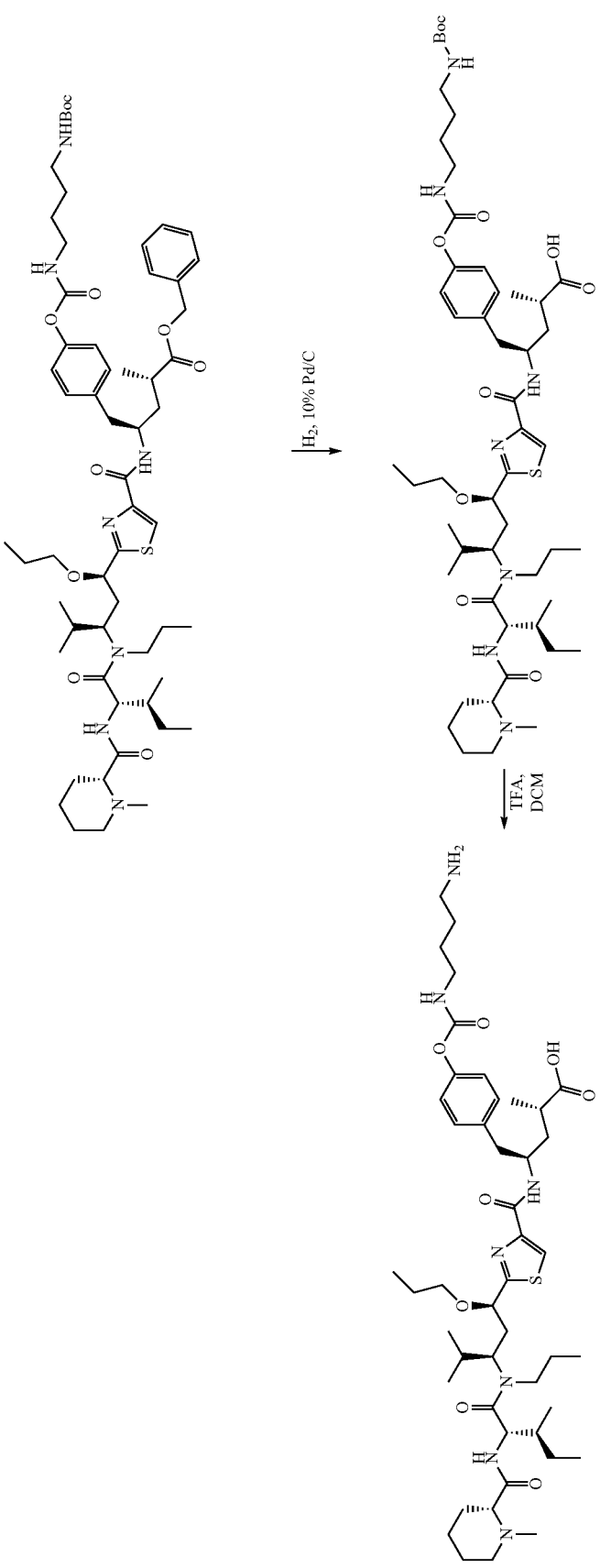

XMT-A4 (114 mg, 0.129 mmol), HOBt (39.4 mg, 0.257 mmol) and DMF (5 ml) were combined at room temperature with stirring. After 15 min phenylmethanol (69.6 mg, 0.643 mmol) and DMAP (47.2 mg, 0.386 mmol) were added. After 10 min DIC (0.030 ml, 0.193 mmol) was added. After 16 h at room temperature the crude reaction mixture was purified to give XMT-A4 benzyl ester as a white amorphous solid (60 mg, 47.8% yield). M/z=862.5.

To a solution of XMT-A4 benzyl ester (23 mg, 0.024 mmol) in THF (4 ml) at room temperature was added HOBt (7.22 mg, 0.047 mmol), 4-nitrophenyl carbonochloridate (9.50 mg, 0.047 mmol), and triethylamine (0.033 ml, 0.236 mmol). The reaction was monitored by LC/MS or HPLC for the appearance of the p-nitrophenyl carbonate XMT-A4 intermediate. A second aliquot of HOBt (7.22 mg, 0.047 mmol), 4-nitrophenyl carbonochloridate (9.50 mg, 0.047 mmol) and triethylamine (0.033 ml, 0.236 mmol) was added. After 45 min, to the reaction mixture was added tert-butyl 4-aminobutylcarbamate (22.18 mg, 0.118 mmol) and triethylamine (0.033 ml, 0.236 mmol). After ~30 minutes, the reaction mixture was purified to give XMT-A4 Boc-amino butylcarbamate benzyl ester as a white amorphous solid (17.5 mg, 62.4% yield). M/z=1076.4.

To an argon bubbled solution of XMT-A4 Boc-diamino butylcarbamate benzyl ester (17.5 mg, 0.015 mmol) in THF (2 mL) and ethanol (2.000 ml) was added palladium on carbon (1.564 mg, 0.015 mmol) followed by attachment of a balloon to the flask to deliver hydrogen (0.030 mg, 0.015 mmol). The reaction mixture was stirred vigorously until LC/MS or HPLC indicated that the reaction was complete. The crude reaction mixture was purified to give XMT-A4 Boc-amino butylcarbamate as a white amorphous solid (6.5 mg, 40.2% yield). M/z=986.5

To an ice cold solution of XMT-A4 Boc-diamino butylcarbamate (6.5 mg, 5.91 μmol) in DCM (1 mL) was added TFA (0.455 μl, 5.91 μmol) and the reaction mixture stirred cold for 1 h and then at room temperature for 1 h. After LC/MS or HPLC indicated that the reaction was complete the reaction mixture was concentrated and the residue taken up in acetonitrile and water with 0.1% TFA and then lyophilized to give the title compound as a white amorphous solid (5.2 mg, 88% yield) M/z=886.3.

Example 74

Synthesis of 22 kDa PHF-BA-SSPyr-(XMT-A4 diaminobutyl carbamate)

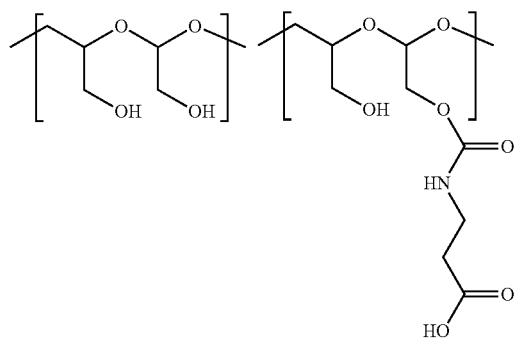

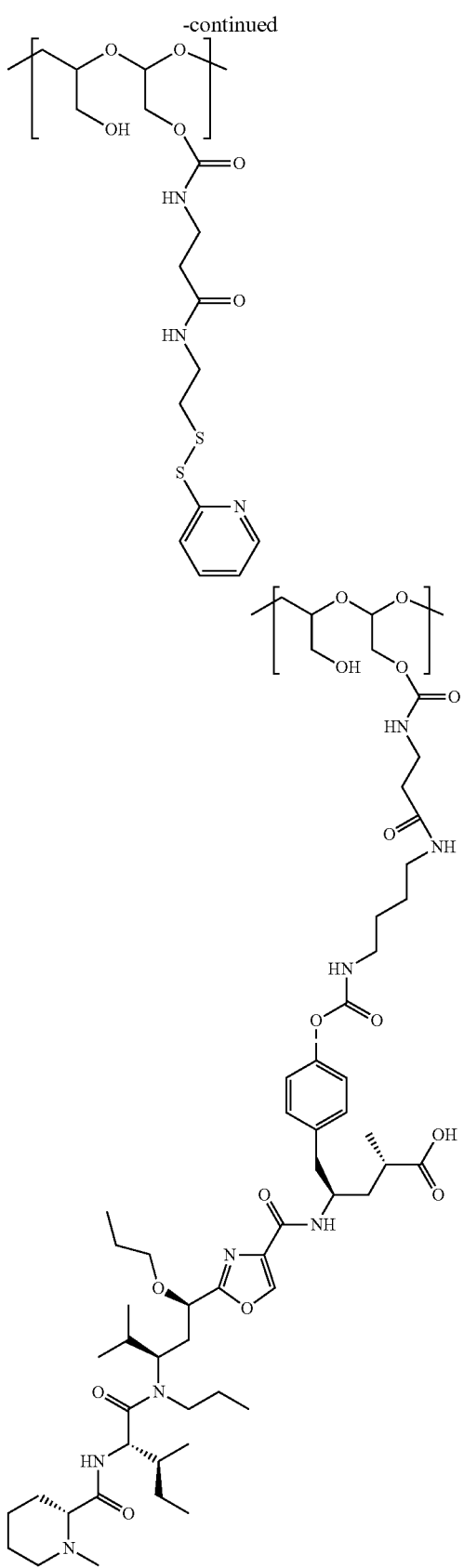

22 kDa PHF-BA (29%)-SSPy (5%) (10.9 mg, 0.492 μmol, prepared using the procedure described in Example 5 with PHF-BA (29%) (MW ~22 kDa) which was prepared as described in Example 1) was dissolved in NMP (0.5 mL) with heating. The reaction mixture was cooled to room temperature and HOAt (1.67 mg, 0.012 mmol) in NMP (0.1 mL) and EDC (2.356 mg, 0.012 mmol) in NMP (0.2 mL) were added. The mixture was stirred for 10 minutes and a solution of DIPEA (1.35 μl, 7.86 μmol) and XMT-A4-butylcarbamate (5.90 mg, 5.90 μmol, prepared as described in Example 73) in NMP (0.300 mL) were added. After stirring at room temperature for 18 h the mixture was diluted to 5% organics with deionized water, concentrated via dialysis using a Regenerated cellulose membrane (3K) followed by purification by HPLC to give the title compound.

Example 75

Synthesis of 22 kDa PHF-BA (29%) (XMT-A4 diaminobutyl carbamate)-(S—S-Trastuzumab)

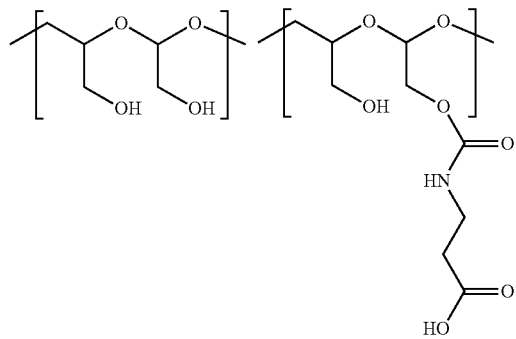

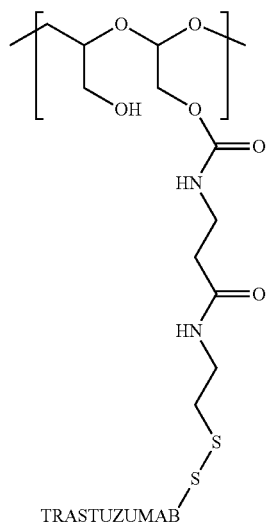

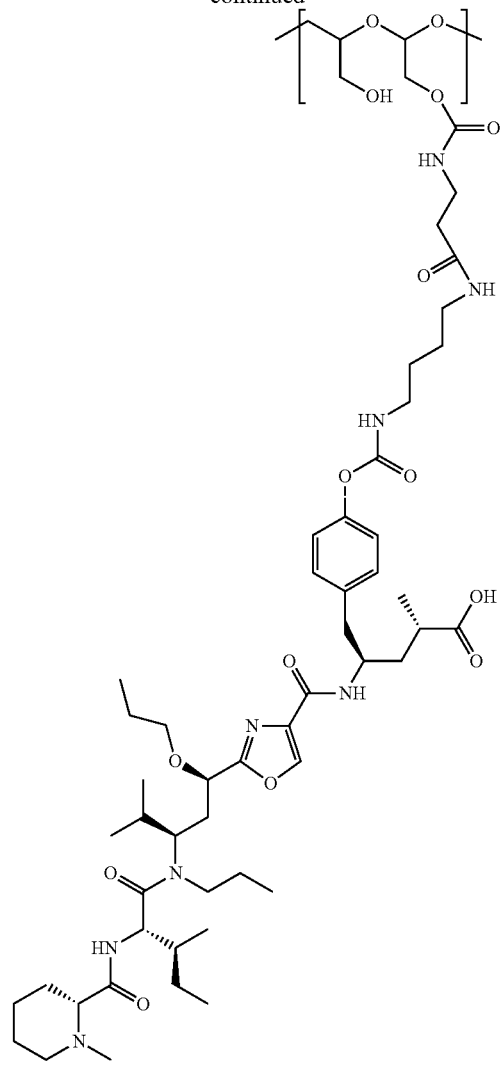

To reduced trastuzumab (5 mg, prepared using the procedure described in Example 60) in triethylamine acetate buffer (1 mL, 50 mM, containing 1 mM EDTA, pH=7.0) was added 22 kDa PHF-BA (29%)-SSPy (5%)—(XMT-A4 diaminobutyl carbamate) (3.5 mg, prepared as described in Example 74). After 18 h at room temperature the resulting conjugate was isolated and purified by diafitration (30% yield). The XMT-A4 to Trastuzumab ratio was about 12:1 to about 15:1.

Other protein-drug-polymer conjugates are synthesized with methods similar to the procedure described above, involving other PBRM derivatives, such as, for example, reduced form of cetuximab, rituximab, bevacizumab, nimotuzumab, gemtuzumab or alemtuzumab as described in Example 60 above. Also PBRM-drug polymer conjugates with varying ratios of drug to PBRM are obtained by varying the amount of PBRM and drug-polymer scaffold used in the Examples above.

Example 76

Synthesis of XMT-A4 Valine ester

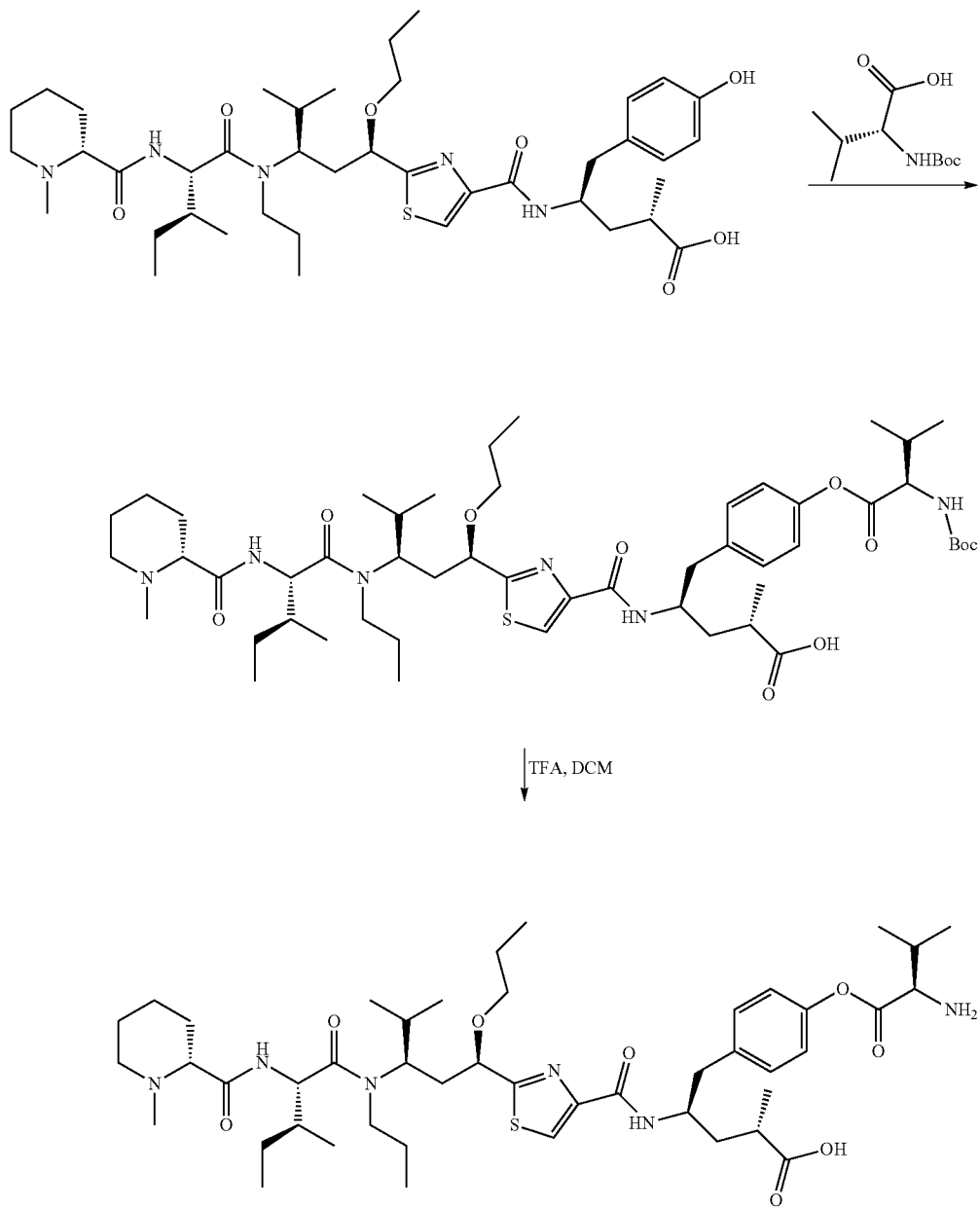

To an ice cold solution of N-Boc-D-valine (17.3 mg, 0.080 mmol) in DMF (500 μL) was added DIC (11.28 μL, 0.072 mmol) and the resulting solution was stirred cold for 15 min, then it was added to a solution of XMT-A4 (30 mg, 0.034 mmol) and DMAP (13.27 mg, 0.109 mmol) in DMF (500 μL). The resulting mixture was stirred cold for 15 min and then overnight at room temperature. The crude reaction mixture was purified to give XMT-A4 N-Boc-D-valine ester as a white amorphous solid (20 mg, 50% yield). M/z=971.4.

To an ice cold solution of XMT-A4 N-Boc-D-valine ester (20 mg, 0.018 mmol) and 2,2,2-trifluoroacetic acid (1:1) in DCM (3 mL) was added TFA (0.284 ml, 3.69 mmol). The resulting mixture stirred cold for 1 h then at room temperature for 1 h, followed by purification to give the title compound (11 mg, 60% yield). M/z=871.4.

Example 77
Synthesis of 7 kDa PHF-BA-SSPyr-(XMT-A4 valine)
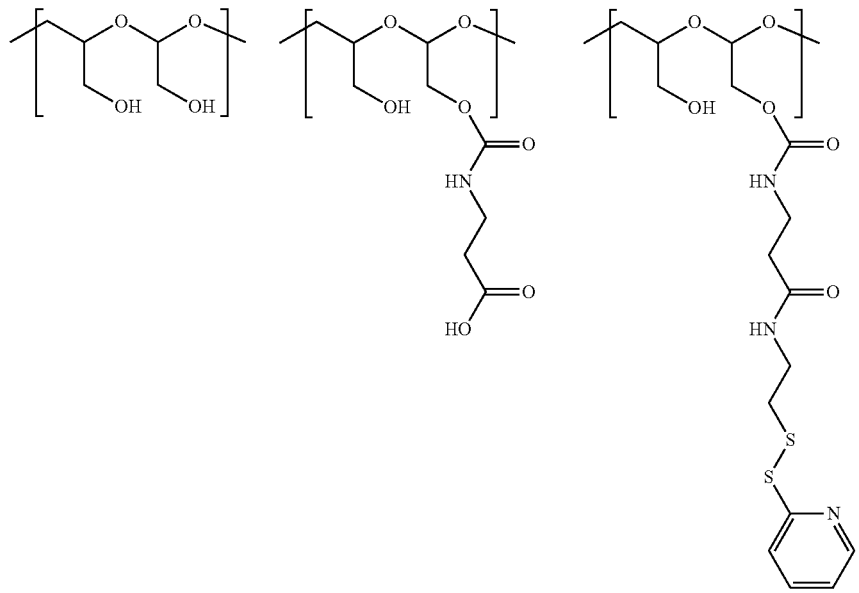
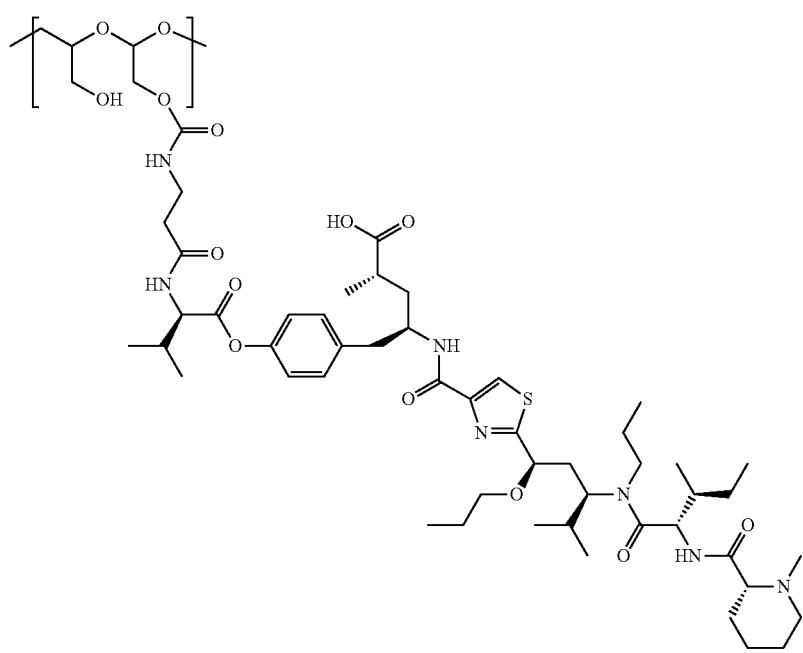
7K PHF-BA(29%)-SSPyr(6%) (258 mg, 0.378 mmol, prepared using the procedure described in Example 5 with PHF BA (29%) (MW ~7 kDa) which was prepared as described in Example 1) was reacted with XMT-A4 valine ester (10.2 mg, 0.011 mmol, prepared as described in Example 76) using the procedure of Example 59. MW 7.9 kDa.

Example 78
Synthesis of 7 kDa PHF-BA (29%) (XMT-A4 valine)-(S-S-Trastuzumab)
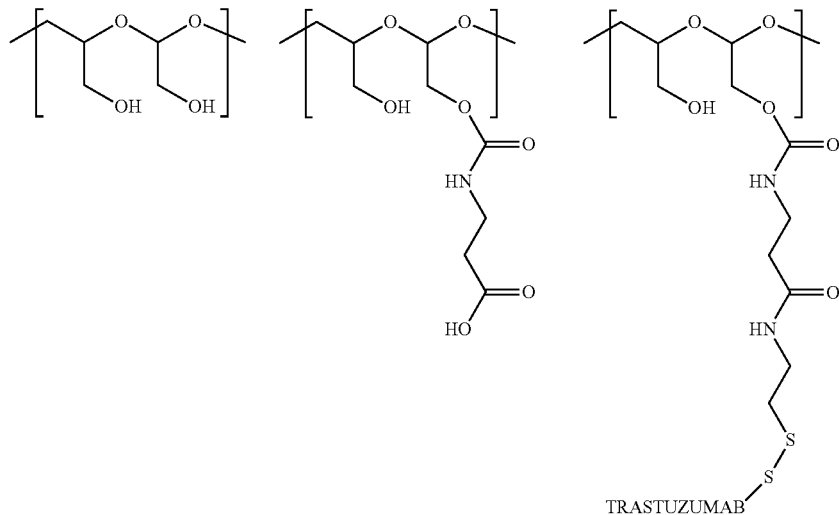
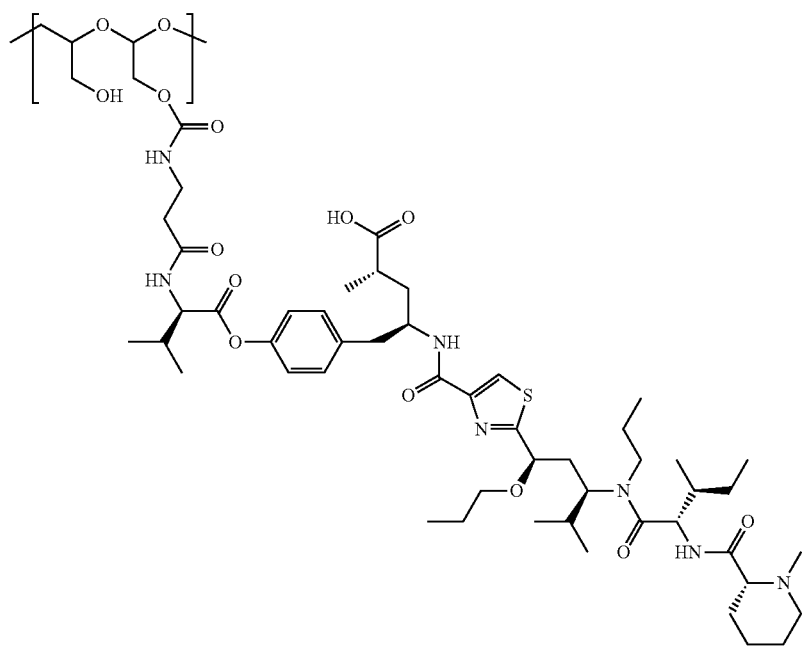
The title compound was prepared using the procedure described in Example 75 except 7 kDa PHF-BA-SSPyr-(XMT-A4 valine) was used (18% yield). The XMT-A4 to Trastuzumab ratio was about 6:1 to about 10:1.

Example 79

Synthesis of XMT-A4
Dimethyl-diaminoethyl-PABA-Val Cit-NH₂

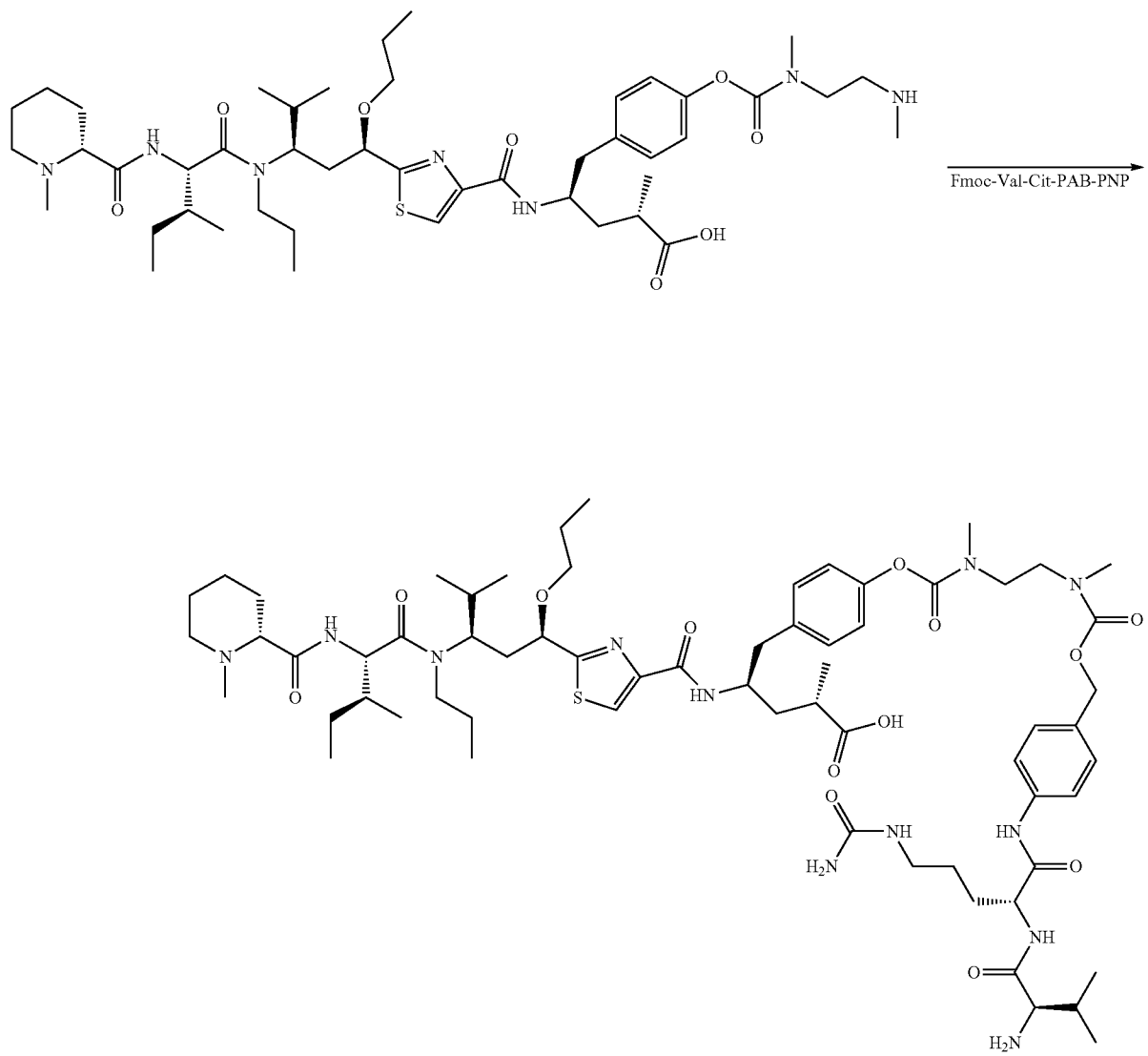

Fmoc-Val-Cit-PABA-PNP (20.93 mg, 0.027 mmol), XMT-A4 dimethyl-diamino ethyl carbamate (22.75 mg, 0.023 mmol, prepared as described in Example 73 except tert-butyl methyl(2-methylamino)ethylcarbamate was used instead of tert-butyl 4-methylamino)butyl carbamate), m/z 886.4), 2,2,2-trifluoroacetic acid (1:1) and HOBt (3.83 mg, 0.025 mmol) in DMF (2 mL) were stirred at room temperature under argon. To the reaction mixture was added triethylamine (0.016 ml, 0.114 mmol). After 16 h the crude reaction mixture was purified to give the title compound as to a white amorphous solid (17.5 mg, 54% yield). M/z=1291.7.

Example 80

Synthesis of 13 kDa PHF-BA-SSPyr-(XMT-A4-Dimethy

633
13K PHF-BA(31%)-SSPyr(6%) (17.4 mg, 1.38 μmol, prepared using the procedure described in Example 5 with PHF BA (31%) (MW ~13 kDa), prepared as described in Example 1) was reacted with XMT-A4-Dimethyl-diaminoethyl-PABA-Val Cit NH₂ (9.70 mg, 6.90 μmol, prepared as described in Example 79) using the procedure of Example 59.
634
Example 81
Synthesis of 13 kDa PHF-BA-(XMT-A4-Dimethyl-diaminoethyl-PABA-Val Cit)-(S-S-Trastuzumab)
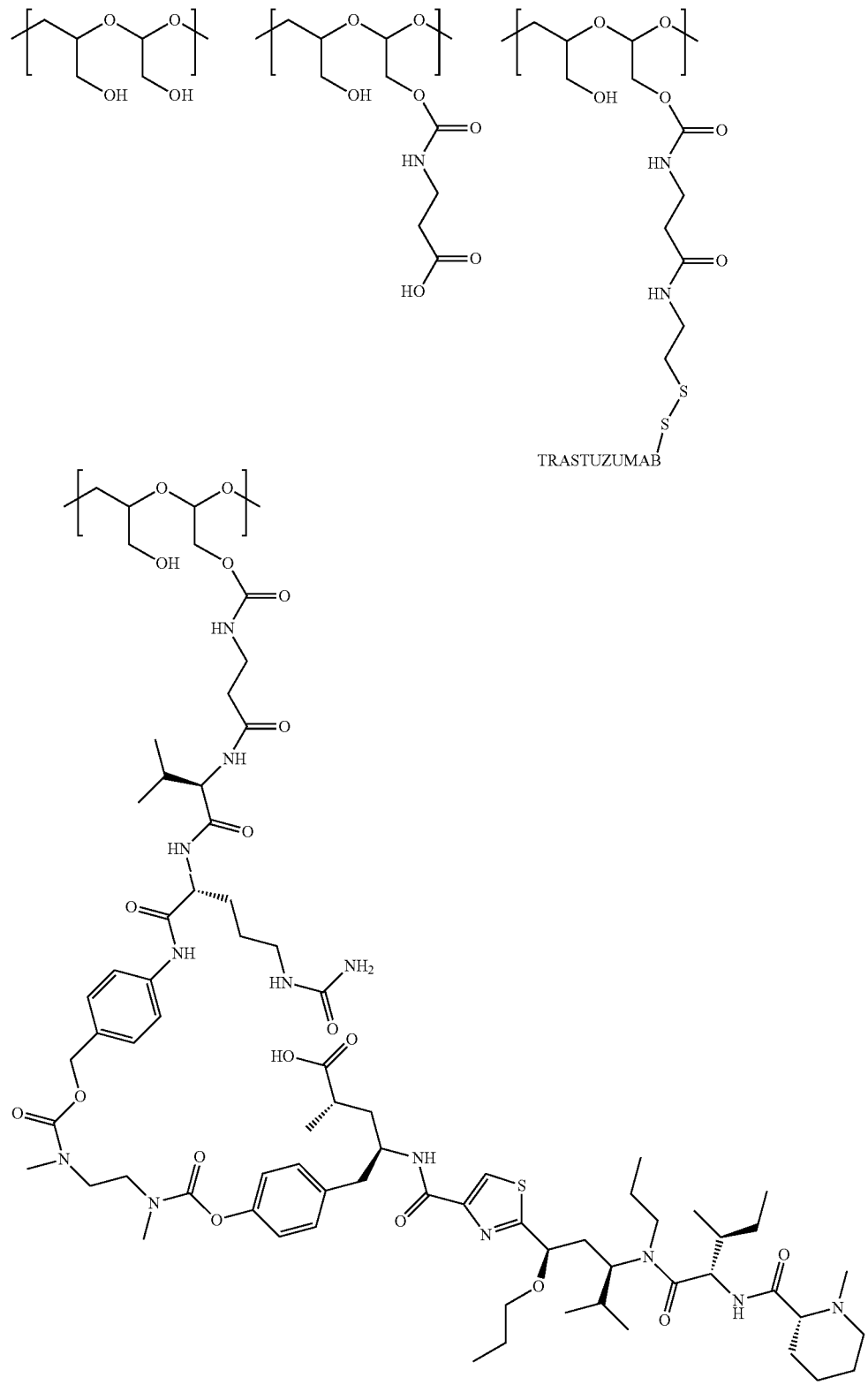

The title compound was prepared using the procedure described in Example 75 except 13 kDa PHF-BA-SSPyr-(XMT-A4-Dimethyl-diaminoethyl-PABA-Val Cit) was used. The XMT-A4 to Trastuzumab ratio was about 6:1 to about 10:1.

Example 82

Synthesis of XMT-A4-dimethyldiamino ethyl-PABA-Val Cit-Maleimide

XMT-A4 Dimethyl-diaminoethyl-PABA-Val Cit-NH$_2$ (11.2 mg, 9.05 μmol, prepared as described in Example 79), 2,5-dioxopyrrolidin-1-yl 6-(2,5-dioxo-2,5-dihydro-1H-pyrrol-1-yl)hexanoate (5.58 mg, 0.018 mmol) and HOBt (2.77 mg, 0.018 mmol) in DMF (1 mL) were stirred at room temperature, followed by the addition of triethylamine (0.013 ml, 0.091 mmol). After 4 h the reaction mixture was purified to give the title compound as a white amorphous solid (6 mg, 46% yield). M/z=1316.7.

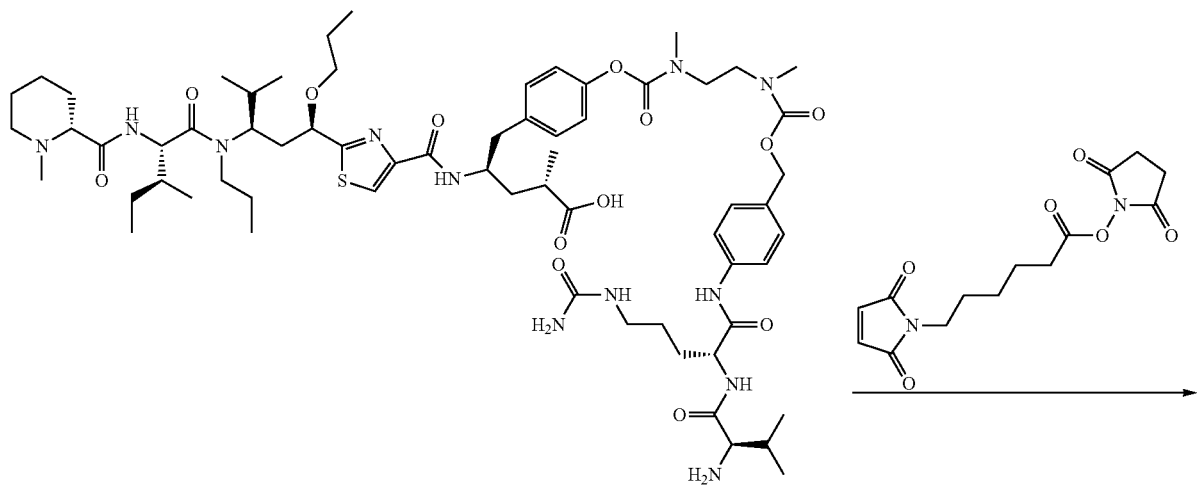

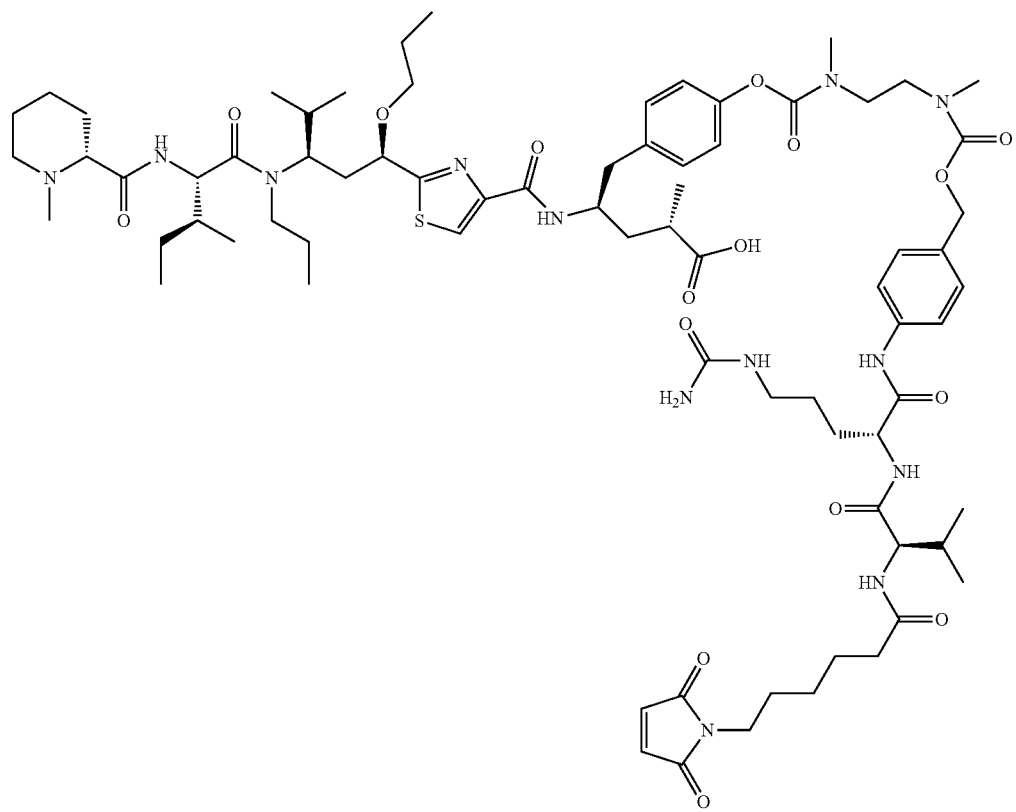

Example 83

Synthesis of XMT-A4-dimethyldiamino ethyl-PABA-Val Cit-Maleimido-(S-Trastuzumab

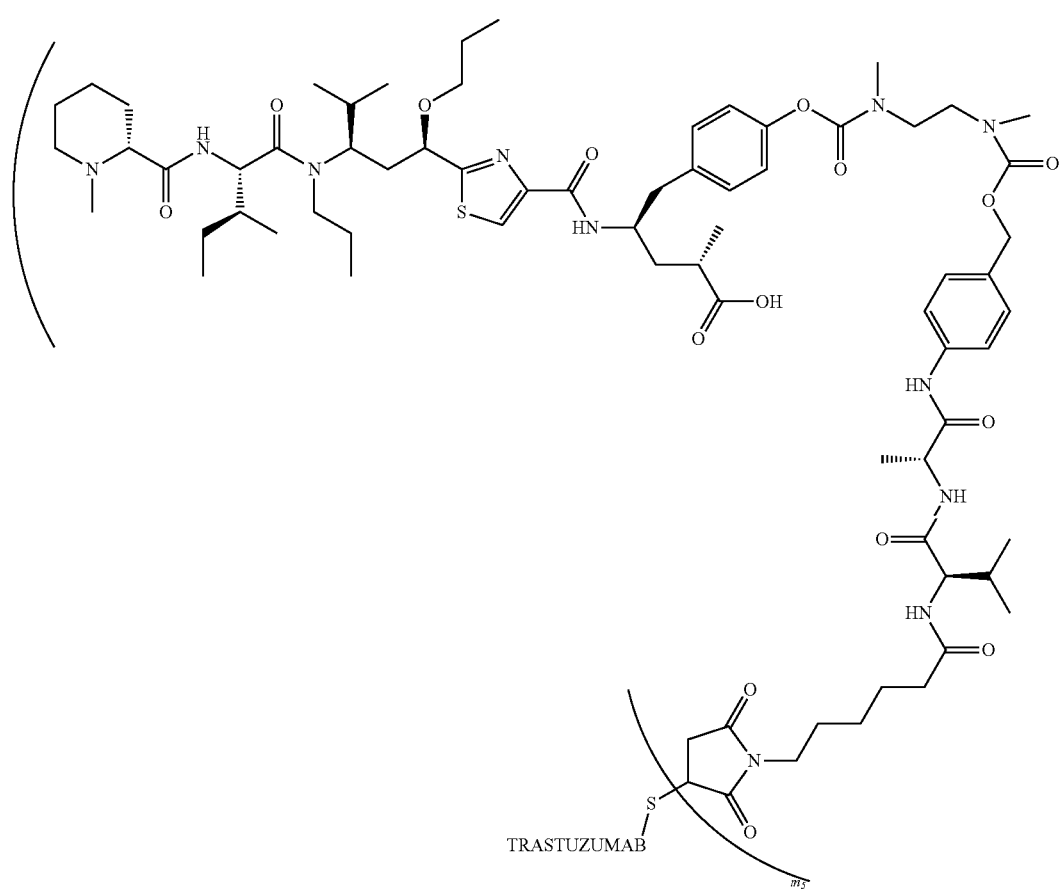

Reduced trastuzumab was reacted with XMT-A4-dimethyldiamino ethyl-PABA-Val Cit-Maleimide using the procedure described in Example 75. The XMT-A4 to Trastuzumab ratio obtained was about 9:1 to about 13:1.

By substituting reduced rituximab in the procedure described above, XMT-A4-dimethyldiamino ethyl-PABA-Val Cit-Maleimido-5-rituximab was synthesized. The XMT-A4 to Rituxiumab ratio was about 6:1 to about 11:1.

Other protein-drug-polymer conjugates are synthesized with methods similar to the procedure described above, involving other PBRM derivatives, such as, for example, reduced form of cetuximab, rituximab, bevacizumab, nimotuzumab, gemtuzumab or alemtuzumab as described in Example 60 above. Also PBRM-drug polymer conjugates with varying ratios of drug to PBRM are obtained by varying the amount of PBRM and drug-polymer scaffold used in the Examples above.

Example 84
Synthesis of Ispinesib-PABA-Val-Cit-NH$_2$
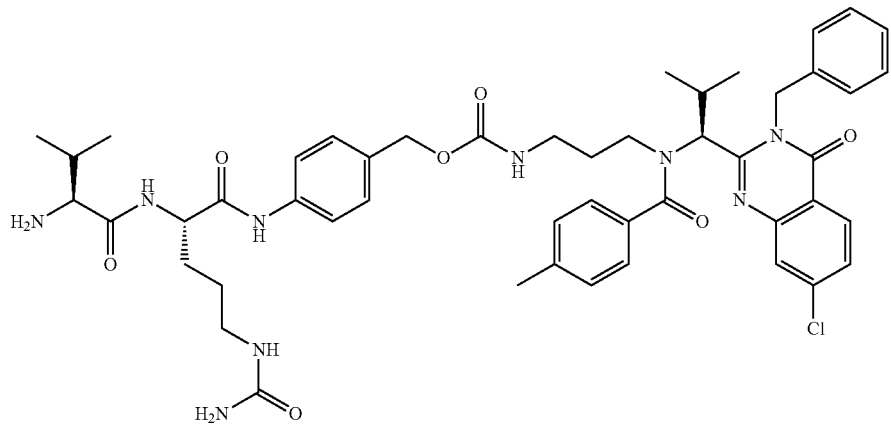 [SMILES: Cc1ccc(C(=O)N(CCCNC(=O)OCc2ccc(NC(=O)[C@H](CCCNC(N)=O)NC(=O)[C@@H](N)C(C)C)cc2)[C@H](c2nc3cc(Cl)ccc3c(=O)n2Cc2ccccc2)C(C)C)cc1]
The title compound was prepared using the procedure described in Example 79. to give a white amorphous solid (75.4 mg, 75% yield). M/z=922.3.
Example 85
13 kDa PHF-BA-SSPyr-Ispinesib-PABA-Val-Cit
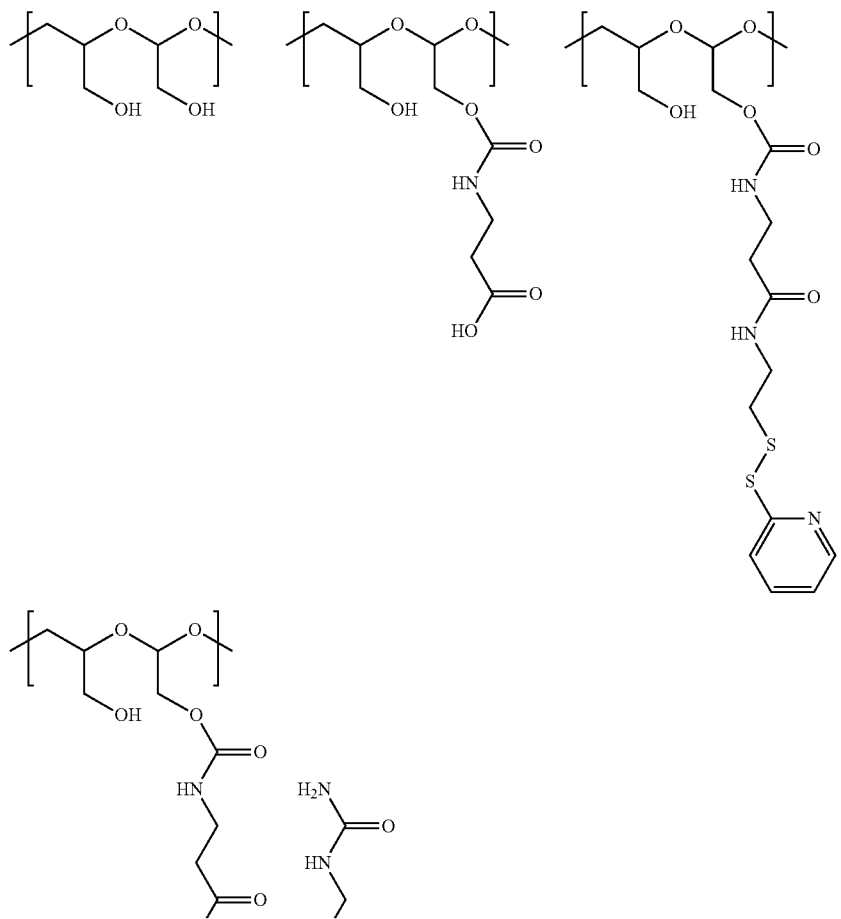

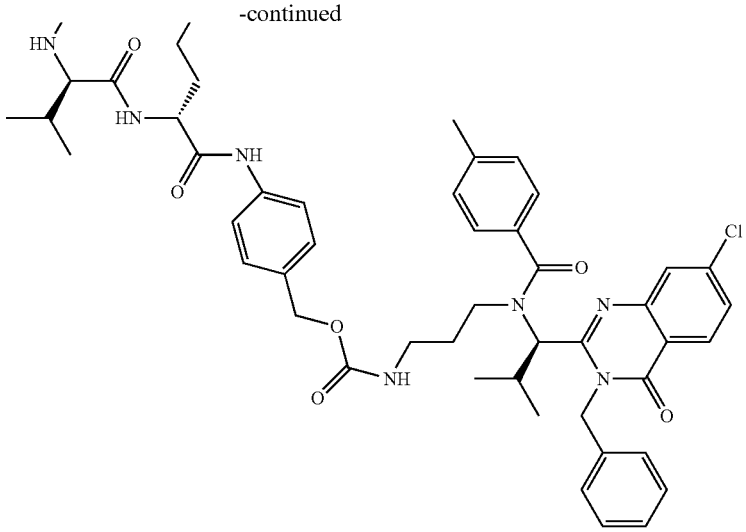

To a solution of 13 kDa PHF-BA(31%)-SSPyr(6%) (124.8 mg, prepared using the procedure described in Example 5 with PHF BA (31%) (MW ~13 kDa), prepared as described in Example 1) was added Ispinesib-PABA-Val-Cit-NH$_2$ (30 mg, prepared as described in Example 84) in NMP (0.7 mL). To this mixture was added HATU (16.4 mg) in NMP (0.7 mL) followed by DIEA (11.4 mg). The reaction mixture was stirred 5-10 min at room temperature and then added slowly to a stirring aqueous solution of NaCl (1%, ~200 mL). The crude mixture was purified to give the title compound (Yield: 23%, based on Ispinesib).

Example 86

Synthesis of 13 kDa PHF-BA-Ispinesib-PABA-Val-Cit-(S-S-Trastuzumab)

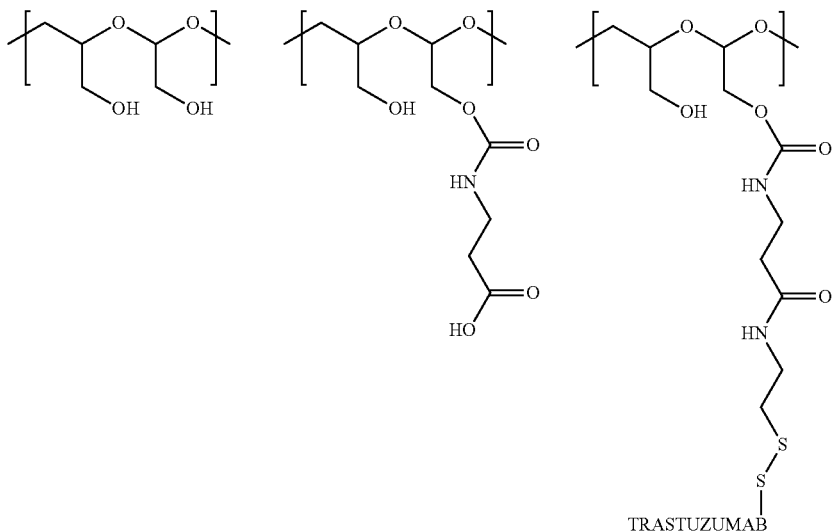

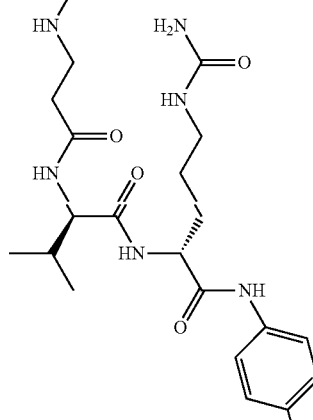

The title compound was prepared using the procedure described in Example 75 except 13 kDa PHF-BA-SSPyr-Ispinesib-PABA-Val-Cit was used (yield 20%). The Ispinesib to Trastuzumab ratio was about 6:1 to about 10:1.

Other protein-drug-polymer conjugates are synthesized with methods similar to the procedure described above, involving other PBRM derivatives, such as, for example, reduced form of cetuximab, rituximab, bevacizumab, nimotuzumab, gemtuzumab or alemtuzumab as described in Example 60 above. Also PBRM-drug polymer conjugates with varying ratios of drug to PBRM are obtained by varying the amount of PBRM and drug-polymer scaffold used in the Examples above.

Example 87

Ispinesib-N-(acyloxyisopropyloxy)-Val-NH$_2$

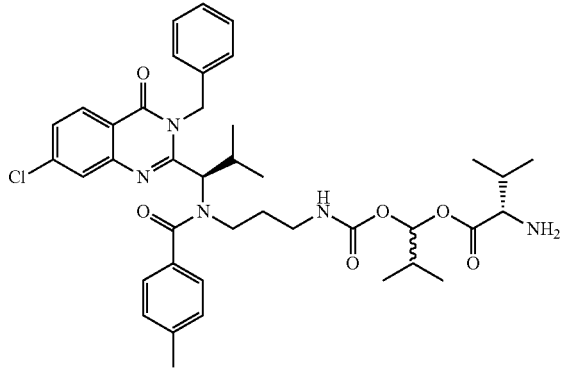 [SMILES: Cc1ccc(C(=O)N(CCCNC(=O)OC(OC(=O)[C@@H](N)C(C)C)C(C)C)[C@@H](c2nc3cc(Cl)ccc3c(=O)n2Cc2ccccc2)C(C)C)cc1]

To an ice-cold solution of Ispinesib (100 mg) in dry THF (3 mL) was added DIEA (37.7 µL) followed by 1-chloro-2-methylpropyl chloroformate (30.8 µL). After the addition was complete, the reaction mixture was stirred at room temperature for 30 min under argon, then extracted with DCM (20 mL) and concentrated to give crude Ispinesib-N-(acyloxyisopropyloxy)-chloride as a racemic mixture. M/z 651.3.

To a solution of Ispinesib-N-(acyloxyisopropyloxy)-chloride in DMA (5 mL) was added Boc-Val-OCs salt (prepared by reacting Boc-(L)Val-OH (387 mg) with CsHCO$_3$) and the resulting mixture was stirred at room temperature. After 1.5 h, tetrabutylammonium iodide (14.3 mg) was added and the reaction mixture was stirred for an additional 3 h at 45° C. then purified to afford the partially pure Ispinesib-N-(acyloxyisopropyloxy)-Val-NH-Boc (160 mg). M/z 832.2.

To an ice-cold solution of partially pure Ispinesib-N-(acyloxyisopropyloxy)-Val-NH-Boc (160 mg) in DCM (5 mL) was added TFA (5 mL). The mixture was stirred for 2 h at 0° C. and then purified to give the title compound as a colorless solid (18.1 mg, 11% overall yield). M/z 732.3.

Example 88
13 kDa
PHF-BA-SSPyr-Ispinesib-N-(acyloxyisopropyloxy)-Val
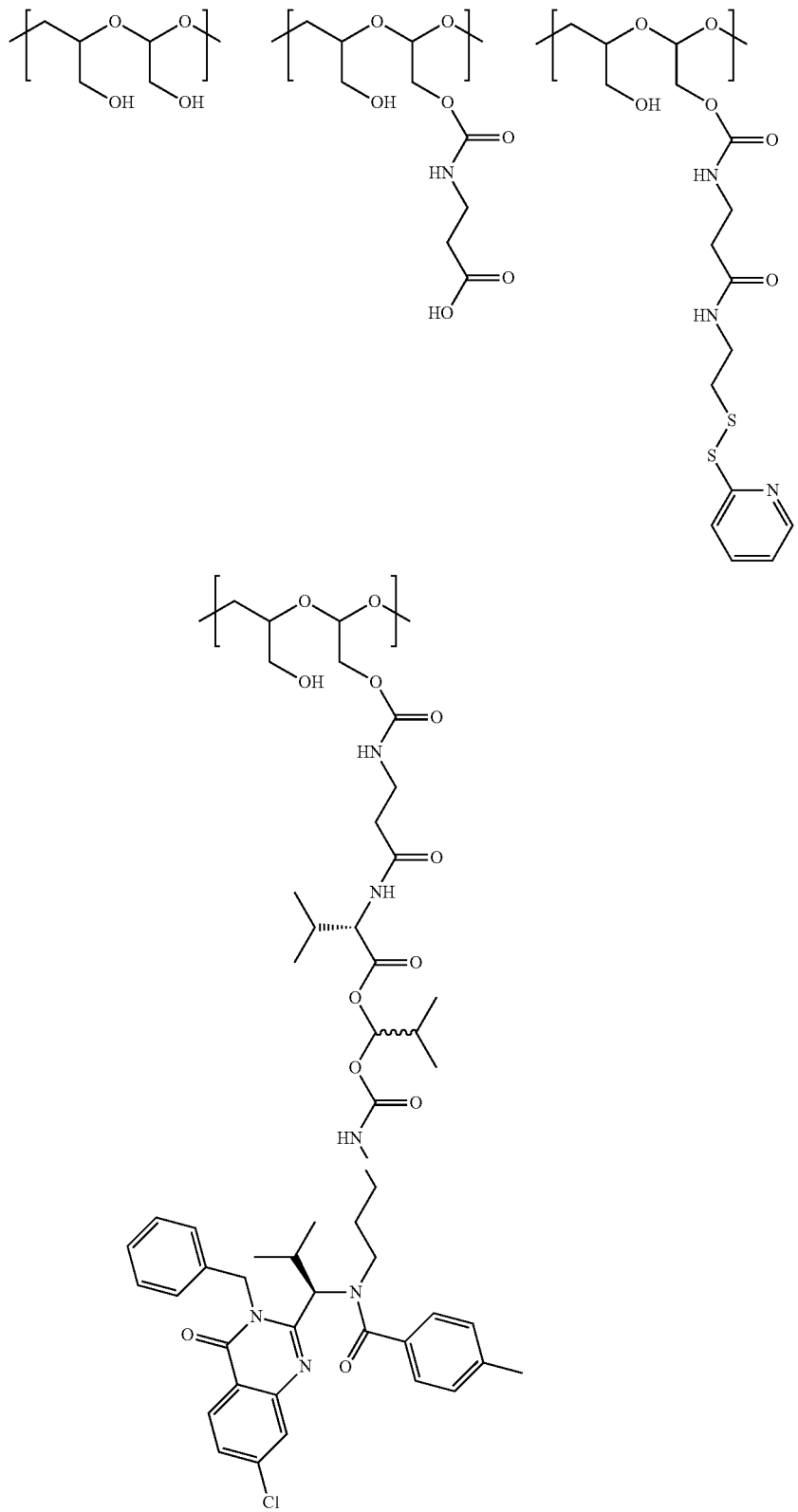

To a solution of 13 kDa PHF-BA(31%)-SSPyr(6%) (79.3 mg, prepared using the procedure described in Example 5 with PHF BA (31%) (MW ~13 kDa), prepared as described in Example 1) in NMP (6.9 mL) was added Ispinesib-N-(acyloxyisopropyloxy)-Val-NH$_2$ trifluoroacetate (15.4 mg, prepared as described in Example 87) in NMP (1 mL) followed by HOAt (7.9 mg) and EDC (11.1 mg). The mixture was stirred overnight at room temperature and then purified to give the title compound. (Yield: 38%, based on Ispinesib); 9% Ispinesib; MW=2.9 kDa.

Example 89

13 kDa PHF-BA-Ispinesib-N-(acyloxyisopropyloxy)-Val-(S-S-Trastuzumab)

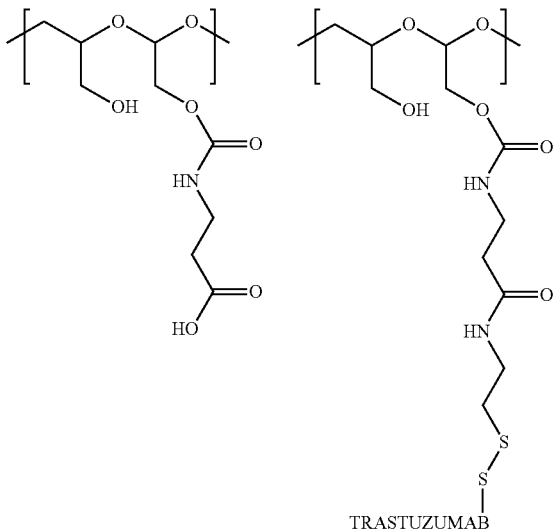

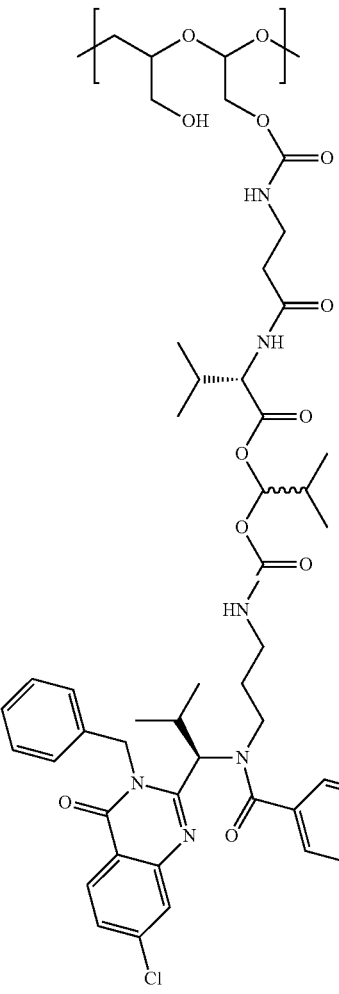

The title compound was prepared using the procedure described in Example 75 except 13 kDa PHF-BA-SSPyr-Ispinesib-N-(acyloxyisopropyloxy)-Val was used (20% yield). The Ispinesib to Trastuzumab ratio was about 10:1 to about 20:1.

Other protein-drug-polymer conjugates are synthesized with methods similar to the procedure described above, involving other PBRM derivatives, such as, for example, reduced form of cetuximab, rituximab, bevacizumab, nimotuzumab, gemtuzumab or alemtuzumab as described in Example 60 above. Also PBRM-drug polymer conjugates with varying ratios of drug to PBRM are obtained by varying the amount of PBRM and drug-polymer scaffold used in the Examples above.

Example 90

PHF-BA-SSPy-(AF HPA-L-Alanine)

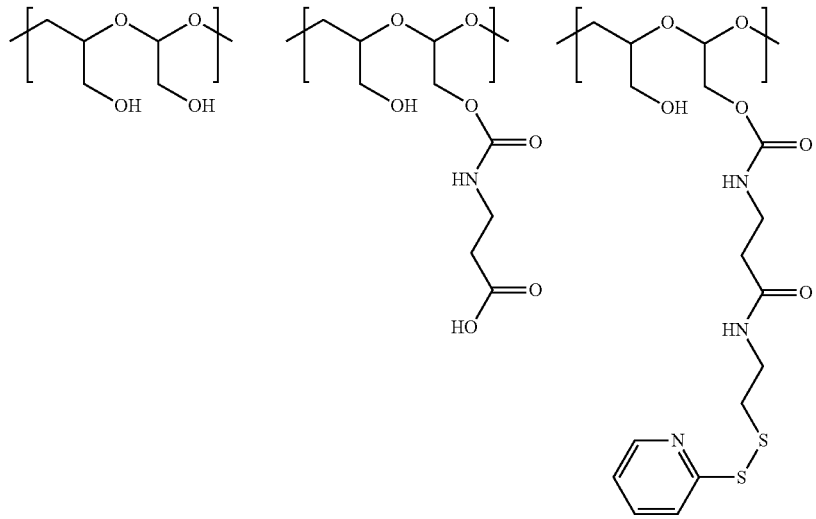

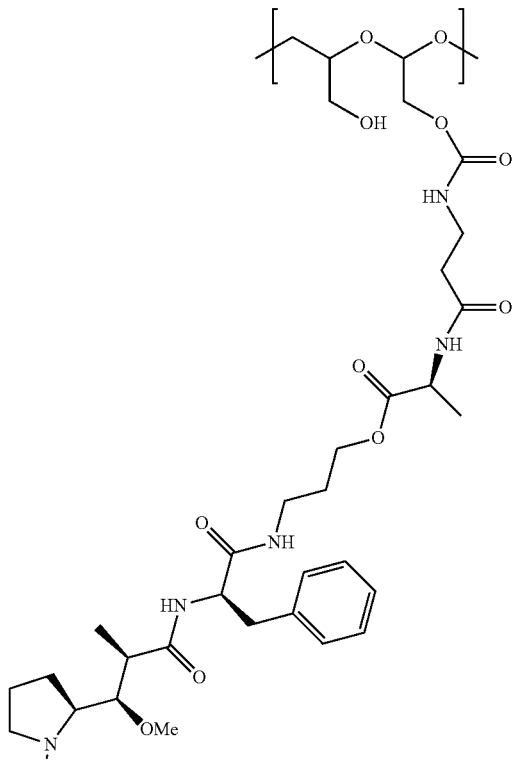

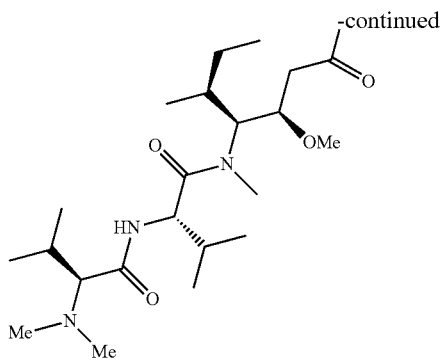
-continued

Conjugate A—47 kDa PHF-BA-(18%) SSPy (2.2%)-(AF HPA-L-Alanine)

47 kDa PHF-BA-(18%) SSPy (2.2%)-(AF HPA-L-Alanine was prepared by the reaction of 47 kDa PHF-BA(18%)-SSPyr(2.2%) (44.6 mg, 0.96 μmol, prepared using the procedure described in Example 5 with PHF-BA (18%) (MW ~47 kDa) which was prepared as described in Example 1) with AF HPA-L-Alanine (25 mg, 0.024 mmol, prepared as described in Example 50) using the procedure of Example 59. The AF-HPA to polymer molar ratio was on average about 8:1 to about 12:1.

Conjugate B—13 kDa PHF-BA-(29%) SSPy (5%)-(AF HPA-L-Alanine)

Using the procedure described above 13 kDa PHF-BA-(29%) SSPy (5%)-(AF HPA-L-Alanine) with an AF-HPA to polymer molar ratio of about 5:1 to about 9:1 was prepared.

Conjugate C—22 kDa PHF-BA-(29%) SSPy (5%)-(AF HPA-L-Alanine)

Using the procedure described above 22 kDa PHF-BA-(29%) SSPy (5%)-(AF HPA-L-Alanine) with an AF-HPA to polymer molar ratio of about 10:1 to about 14:1 was prepared.

Conjugate D—62 kDa PHF-BA(16%)-SSPy(1.3%)-(AF HPA-L-Alanine)

Using the procedure described above 62 kDa PHF-BA (16%)-SSPy(1.3%)-(AF HPA-L-Alanine) with an AF-HPA to polymer molar ratio of about 13:1 to about 17:1 was prepared.

Conjugate E—110 kDa PHF-BA(9%)-SSPy(1.0%)-(AF HPA-L-Alanine)

Using the procedure described above 110 kDa PHF-BA (9%)-SSPy(1.0%)-(AF HPA-L-Alanine) with an AF-HPA to polymer molar ratio of about 13:1 to about 17:1 was prepared.

Example 91

Synthesis of Trastuzumab-Fab

Trastuzumab-Fab was prepared from immobilized papain (6.5 mL resin) and trastuzumab (192 mg) to give two Fab fragments and an Fc fragments. Purification resulted in Trastuzumab Fab (51.4 mg). MW (SDS PAGE), ~45 kDa.

Other PBRM-Fab fragments, such as, Fab fragments of cetuximab, rituximab, bevacizumab, nimotuzumab, gemtuzumab or alemtuzumab, are synthesized with methods similar to the procedure described above.

Example 92

47 kDa PHF-BA (AF HPA-L-Alanine)-SS-(Trastuzumab-Fab)

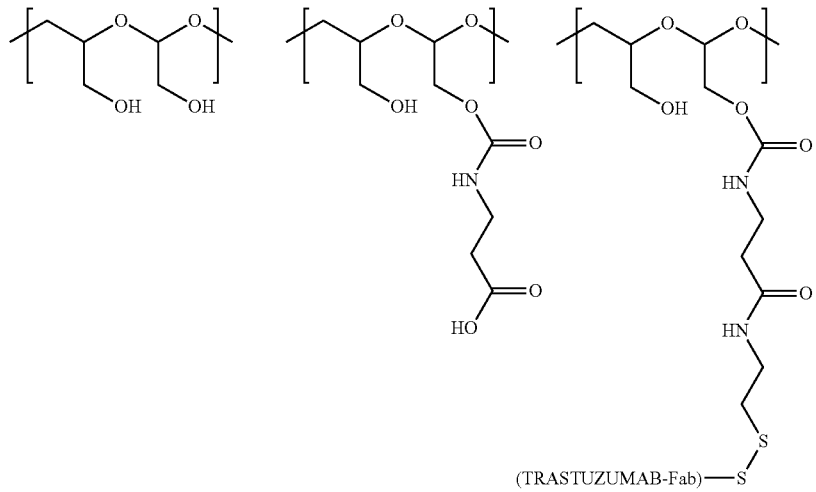

-continued

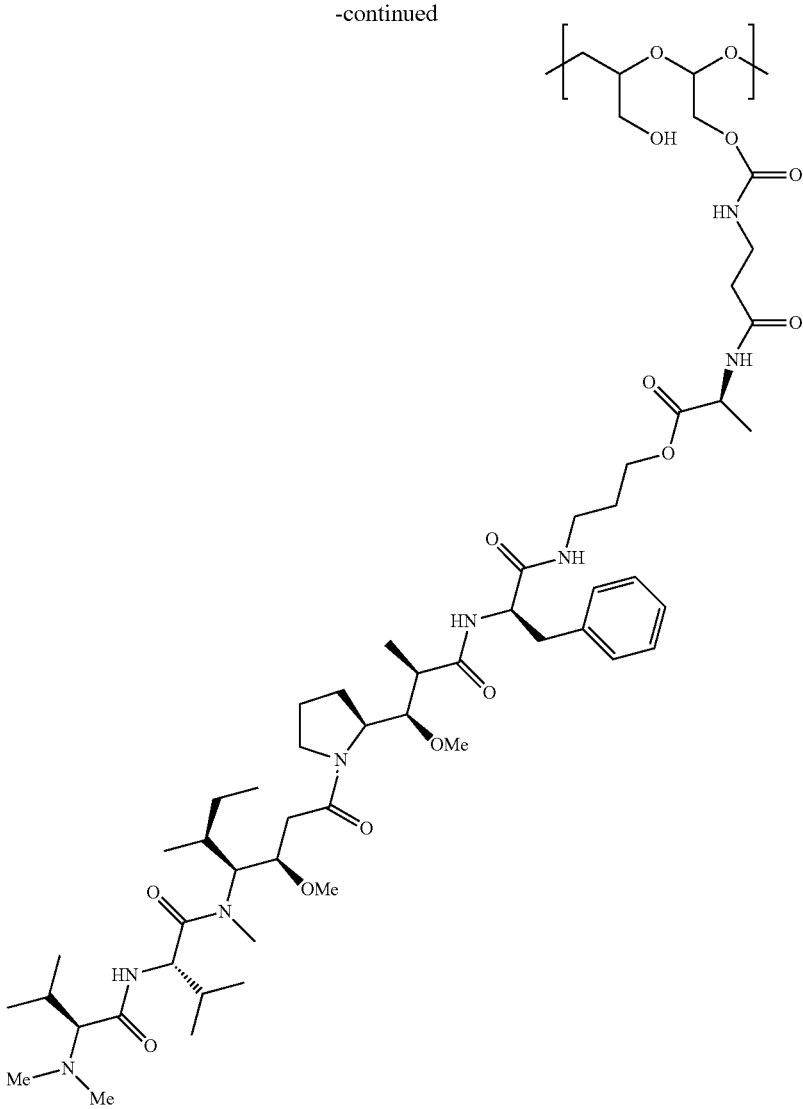

The title compound was prepared using the procedure described in Example 60 except Trastuzumab Fab (0.095 mg, prepared as described in Example 91) and 47 K PHF-BA (18%)-SSPyr(2.2%)-(AF HPA-L-Alanine) (2.4%) (3.14 mg, prepared as described in Example 90) were used in the synthesis. AF-HPA to trastuzumab-Fab ratio was about 16:1 to 20:1.

Other protein-drug-polymer conjugates are synthesized with methods similar to the procedure described above, involving other PBRM derivatives, such as, for example, reduced form of cetuximab, rituximab, bevacizumab, nimotuzumab, gemtuzumab or alemtuzumab as described in Example 60 above. Also PBRM-drug polymer conjugates with varying ratios of drug to PBRM are obtained by varying the amount of PBRM and drug-polymer scaffold used in the Examples above.

Example 93
47 kDa PHF-BA (AF
HPA-L-Alanine)-SS-(Anti-Her2 Affibody)
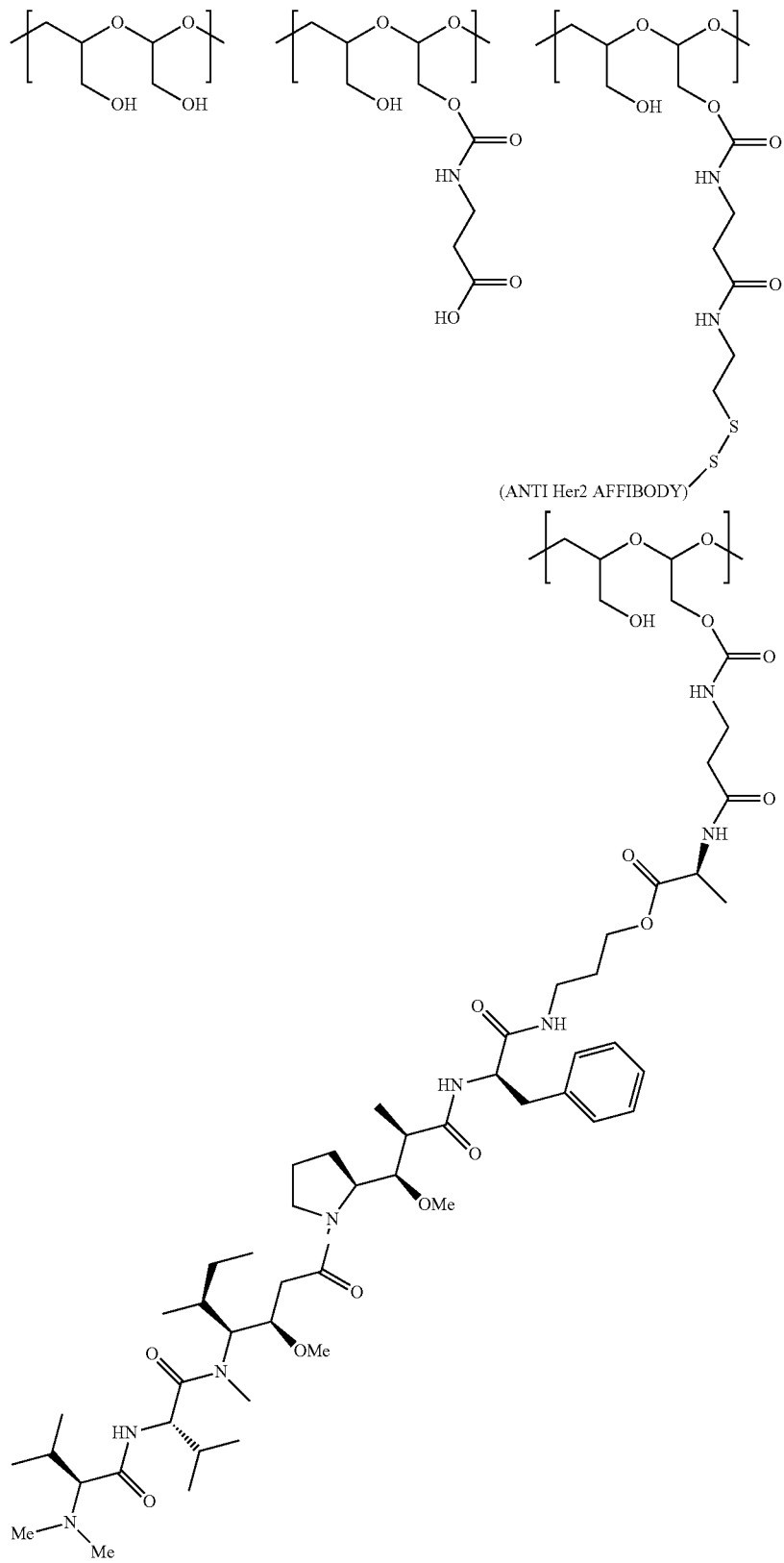

Conjugate A—47 kDa PHF-BA(18%)-SSPyr(2.2%)-(AF HPA-L-Alanine)

The title compound was prepared using the procedure describe in Example 60 except anti-Her2 Affibody (0.5 mg) and 47 kDa PHF-BA(18%)-SSPyr(2.2%)-(AF HPA-L-Alanine) (0.68 mg, prepared as described in Example 90) were used in the synthesis. AF-HPA to anti-Her2-Affibody ratio was about 6:1 to 8:1.

Conjugate B—105 kDa PHF-BA (AF HPA-L-Alanine)-SS-(anti-Her2-Affibody)

Using the procedure described above 105 kDa PHF-BA (AF HPA-L-Alanine)-SS-(anti-Her2-Affibody) was synthesized except 105 kDa PHF-BA(9%)-SSPyr(1.5%)-(AF HPA-L-Alanine)(0.97%) was used. AF-HPA to anti-Her2-Affibody ratio was about 6:1 to 10:1.

By substituting anti-Her2-Affibody with other PBRMs, such as, for example, affibodies derived from anti EGFR, anti-Her3, anti IL-8, anti TNF-α in the procedure described above it is possible to synthesize other protein-drug polymer conjugates. Also PBRM-drug polymer conjugates with varying ratios of drug to PBRM can be obtained by varying the amount of PBRM and drug polymer used in the Examples above.

Example 94

High loading PHF-BA (AF HPA-L-Alanine)-SS-Trastuzumab or Rituximab

The following conjugates were prepared using the procedure described in Example 75 except 22 kDa PHF-BA-(29%) SSPy (5%)-(AF HPA-L-Alanine) or 47 kDa PHF-BA(18%)-SSPyr(2.2%)-(AF HPA-L-Alanine) (prepared as described in Example 90) and reduced trastuzumab or reduced rituximab were used.

Conjugate A
22 kDa PHF-BA-(AF HPA-L-Alanine)-SS-Trastuzumab; ratio of AF HPA to trastuzumab is about 40:1 to about 45:1.
Conjugate B
47 kDa PHF-BA-(AF HPA-L-Alanine)-SS-Trastuzumab; ratio of AF HPA to trastuzumab is about 44:1 to about 48:1.
Conjugate C
22 kDa PHF-BA-(AF HPA)-SS-Rituximab; ratio of AF HPA to rituximab is about 37:1 to about 41:1.
Conjugate D
47 kDa PHF-BA-(AF HPA-L-Alanine)-SS-Rituximab; ratio of AF HPA to rituximab is about 47:1 to about 51:1.

In Conjugates A, B, C and D about 3 to about 5 PHF polymers chains comprising AF HPA-L-Alanine are conjugated to one antibody.

Other protein-drug-polymer conjugates are synthesized with methods similar to the procedure described above, involving other PBRM derivatives, such as, for example, reduced form of cetuximab, bevacizumab, nimotuzumab, gemtuzumab or alemtuzumab as described in Example 60 above. Also PBRM-drug polymer conjugates with varying ratios of drug to PBRM are obtained by varying the amount of PBRM and drug-polymer scaffold used in the Examples above.

Example 95

PHF-BA (AF HPA-L-Alanine)-SS-scFv

Reduced scFv is prepared by adding TCEP (0.006 mg) in Et$_3$NHOAc buffer) to scFv (1.0 mg) in Et$_3$NHOAc buffer(500 μL). The mixture is incubated for 1 h at 37° C. and the progress of the reduction is monitored by reverse phase HPLC or SEC followed by purification. To the reduced purified scFv is added a solution of PHF-BA-SSPyr-AF-HPA-Ala (1.1 mg, prepared as described in Example 90) in DI water (96 μL) is added and the mixture is stirred for 3 h at room temperature. The progress of the reaction can be monitored by HPLC or SEC by observing the decrease in the UV signal at 280 nm corresponding to scFv. The resulting conjugate can be purified.

Example 96

PHF-BA (AF HPA-L-Alanine)-SS-(Trastuzumab-Fab')

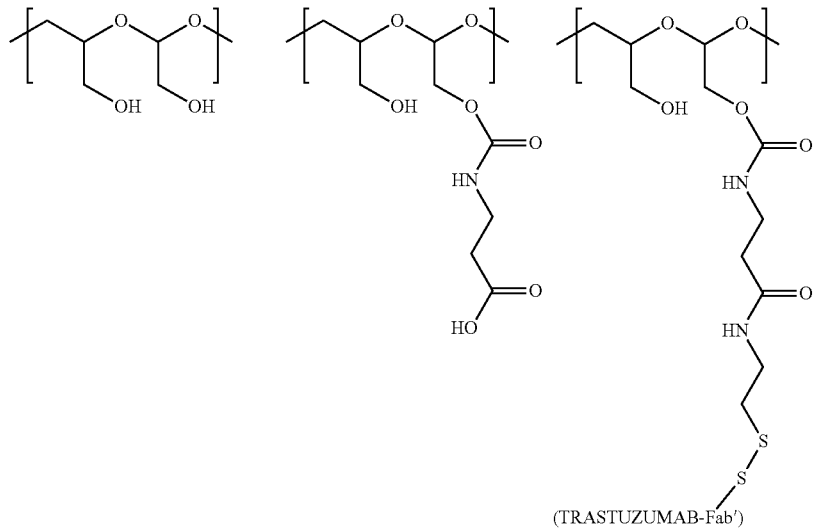

-continued

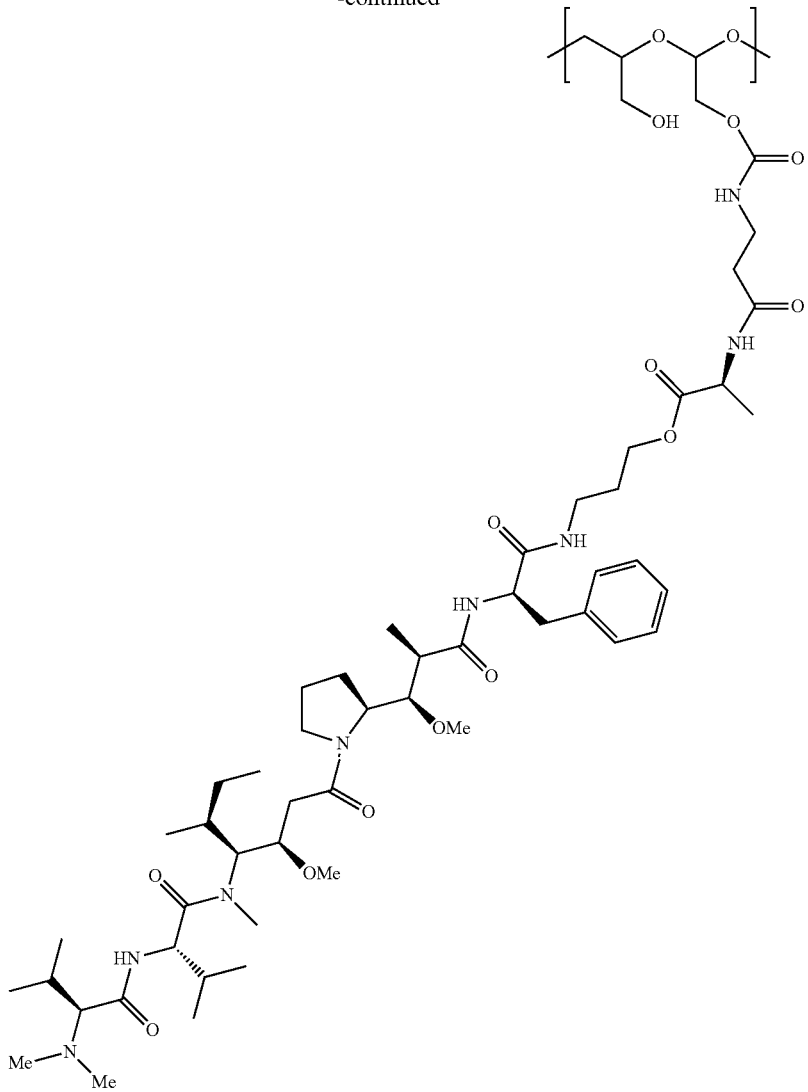

Conjugate A—105 kDa PHF-BA (AF HPA-L-Alanine)-SS-(Trastuzumab-Fab')

The title compound was prepared using the procedure describe in Example 60 except 105 kDa PHF-BA(9%)-SSPyr (1.5%)-(AF HPA-L-Alanine) (0.97%) were used in the synthesis. AF-HPA to trastuzumab-Fab' ratio was about 6:1 to 10:1.

Conjugate B—156 kDa PHF-BA (AF HPA-L-Alanine)-SS-(Trastuzumab-Fab')

Using the procedure described above 156 kDa PHF-BA (AF HPA-L-Alanine)-SS-(Trastuzumab-Fab') was synthesized except 156 kDa PHF-BA(9%)-SSPyr(1.5%)-(AF HPA-L-Alanine) (1.3%) were used in the synthesis. AF-HPA to trastuzumab-Fab' ratio was about 6:1 to 10:1.

Example 97

Cell Viability Assay for PBRM-Drug Polymer Conjugates

PBRM-drug polymer conjugates were evaluated for their tumor viability using Cell Titer-Glo (Promega Corp). Cells were plated in black walled 96-well plate and allowed to adhere overnight at 37° C. in a humidified atmosphere of 5% $CO_2$. HER2 expressing cells SKBR3, BT474, NCI-N87 and cells expressing low levels of HER2-$MCF_7$ were plated at a density of 5,000 cells per well. The next day the medium was replaced with 50 µL fresh medium and 50 µL of 2× stocks of PBRM-drug polymer conjugate, drug polymer conjugate or drug were added to appropriate wells, mixed and incubated for 72 h. Cell Titer-Glo reagent was added to the wells at room temperature and the luminescent signal was measured after 10 min using a SpectraMax M5 plate reader (Molecular Devices). Dose response curves were generated using SoftMax Pro software. $IC_{50}$ values were determined from four-parameter curve fitting.

CD20 expressing cell lines Raji and Ramos were plated and analyzed using the same procedure described above for HER2 expressing cells.

Tables I to VII, XII and XIII are illustrative results for the antiproliferation properties of the PBRM-drug polymer conjugate in either HER2 expressing cells (Tables I to IV, VI, VII, XII and XIII) or CD20 expressing cells (Table V).

Table I lists the results for PBRM-drug polymer conjugate (PHF-GA-(HPV-Alanine)-(Trastuzumab-MCC), Example 7, (HPV:trastuzumab about 14:1 to 17:1) and PHF-GA-(HPV-Alanine)-(Trastuzumab-M-(PEG)$_{12}$), Example 8, (HPV:trastuzumab about 16:1 to 18:1), drug polymer conjugate (PHF-GA-(HPV-Alanine)-SH, Example 6, and drug alone (HPV).

TABLE I

|  | SKBR3 IC$_{50}$ (nmol/L) | BT474 IC$_{50}$ (nmol/L) | MCF7 IC$_{50}$ (nmol/L) |
|---|---|---|---|
| Example 6 | 9.58 | 11.90 | 131 |
| Example 7 | 1.43 | 1.5 | 912 |
| Example 8 | 1.54 | 1.55 | 31.6 |
| HPV | 0.52 | 0.61 | 8.26 |

The results in Table I shows that, for the HER2 expressing cell lines SKBR3 and BT474, the PBRM-drug polymer conjugates (Examples 7 and 8) exhibited enhanced antiproliferative activity relative to the drug polymer conjugate (Example 6) and drug alone (HPV). In these cell lines the drug polymer conjugate (Example 6) is less potent than the drug alone (HPV).

Table II lists the results for (S)-2HPV (Example 22) and (R)-2HPV (Example 23).

TABLE II

|  | SKBR3 IC$_{50}$ (nmol/L) | BT474 IC$_{50}$ (nmol/L) | MCF7 IC$_{50}$ (nmol/L) |
|---|---|---|---|
| Example 22 | 0.76 | 0.41 | 1.83 |
| Example 23 | 0.71 | 0.39 | 1.71 |

The results in Table II show that, for the HER2 expressing cell lines SKBR3 and BT474, the Vinca derivatives (Examples 22 and 23) exhibited similar antiproliferative activity.

Table III lists the results for PBRM-drug polymer conjugate (PHF-GA-SSPyr-(HPV-Alanine)), Example 59) and drug polymer conjugate (PHF-GA-(HPV-Alanine)-(Trastuzumab-Fab')), Example 60, HPV:trastuzumab-Fab' about 6:1 to 8:1).

TABLE III

|  | SKBR3 IC$_{50}$ (nmol/L) | BT474 IC$_{50}$ (nmol/L) | N87 IC$_{50}$ (nmol/L) | MCF7 IC$_{50}$ (nmol/L) |
|---|---|---|---|---|
| Example 59 | 17.35 | 7.35 | 35.85 | 31.60 |
| Example 60 | 1.2 | 0.4 | 7.0 | 28.7 |

The results in Table III show that, for the HER2 expressing cell lines SKBR3, BT474 and N87 the PBRM-drug polymer conjugate (Example 60) exhibited higher antiproliferative activity comparatively to drug polymer conjugate (Example 59).

Table IV lists the results for PBRM-drug polymer conjugate (PHF-GA-(HPV-Alanine)-(Trastuzumab-MCC)), Example 7 (HPV:trastuzumab about 19:1 to 22:1) and PHF-GA-(HPV-Alanine)-(Trastuzumab-M-(PEG)$_{12}$), Example 8, HPV:trastuzumab about 16:1 to 18:1) and drug polymer conjugate (PHF-GA-(HPV-Alanine)-SH, Example 6).

TABLE IV

|  | SKBR3 IC$_{50}$ (nmol/L) | BT474 IC$_{50}$ (nmol/L) | N87 IC$_{50}$ (nmol/L) | MCF7 IC$_{50}$ (nmol/L) |
|---|---|---|---|---|
| Example 6 | 19 | 10 | 43 | 54 |
| Example 7 | 1.3 | 0.8 | 8.0 | 69.3 |
| Example 8 | 2.17 | 1.44 | 4.44 | 30.75 |

The results in Table IV show that, for the HER2 expressing cell lines SKBR3, BT474 and N87 both PBRM-drug polymer conjugates (Example 7 and Example 8) exhibited higher antiproliferative activity comparatively to drug polymer conjugate (Example 6).

Table V lists the results for the PBRM-drug polymer conjugate (PHF-GA-(HPV-Alanine)-(Rituximab-MCC), (Example 54, HPV:Rituximab about 12 to 15:1) and drug polymer conjugate (PHF-GA-(HPV-Alanine)-SH, Example 6) for CD20 expressing cell lines Raji and Ramos.

TABLE V

|  | Raji IC$_{50}$ (nmol/L) | Ramos IC$_{50}$ (nmol/L) |
|---|---|---|
| Example 54 | 17.57 | 1.54 |
| Example 6 | 48.20 | 11.60 |

The results in Table V show that, for the CD20 expressing cell lines Raji and Ramos the PBRM-drug polymer conjugate (Example 54) exhibited higher antiproliferative activity comparatively to drug polymer conjugates (Example 6).

Table VI lists the results for PBRM-drug polymer conjugates PHF-GA-(HPV-Alanine)-(Trastuzumab-MCC) (about 5:1) (Example 55); PHF-GA-(HPV-Alanine)-(Trastuzumab-MCC) (about 10:1) (Example 56); and PHF-GA-(HPV-Alanine)-(Trastuzumab-MCC) (about 20:1) (Example 57).

TABLE VI

|  | Drug/Antibody Ratio | SKBR3 IC$_{50}$ (µg/mL) | BT474 IC$_{50}$ (µg/mL) |
|---|---|---|---|
| Example 57 | 20:1 | 0.0079 | 0.0037 |
| Example 56 | 10:1 | 0.0121 | 0.0083 |
| Example 55 | 5:1 | 0.0492 | 0.0302 |

The results in Table VI show that, for the HER2 expressing cell lines SKBR3 and BT474 the antiproliferation effect is dependent on the drug load. The PBRM-drug polymer conjugates with higher drug loading (Example 57) exhibited higher antiproliferative activity comparatively to conjugates with lower drug loading (Example 56 and Example 55).

Table VII lists the results for PBRM-drug polymer conjugates PHF-GA-(AF HPA-L-Alanine)-(Trastuzumab-MCC) (Example 52, Auristatin F:trastuzumab about 20:1 to 22:1); drug polymer conjugate PHF-GA-5H-(AF HPA-L-Alanine) (Example 51) and AF HPA (Example 48).

TABLE VII

|  | SKBR3 IC$_{50}$ (nmol/L) | BT474 IC$_{50}$ (nmol/L) | N87 IC$_{50}$ (nmol/L) | MCF7 IC$_{50}$ (nmol/L) |
|---|---|---|---|---|
| Example 52 | 2.8 | 2.9 | 11.2 | 120.5 |
| Example 51 | 46 | 56 | 128 | 369 |
| Example 48 | 0.6 | 1.0 | 1.6 | 2.5 |

The results in Table VII show that for the HER2 expressing cell lines SKBR3, BT474 and N87 the PBRM-drug polymer conjugates (Example 52) and drug alone (Example 48) exhibited higher antiproliferative activity compared to drug polymer conjugate (Example 51). The PBRM-drug polymer conjugate retains the potency of the drug alone.

Table XII lists the results for PBRM-drug polymer conjugates with PBRM MW<80 kDa. These PBRM-drug polymer conjugates are (i) 47 kDa PHF-BA (AF HPA-L-Alanine)-SS-(Trastuzumab-Fab) (Example 92); (ii) 105 kDa PHF-BA (AF HPA-L-Alanine)-SS-(Trastuzumab-Fab') (Example 96, Conjugate A); (iii) 156 kDa PHF-BA (AF HPA-L-Alanine)-SS-(Trastuzumab-Fab') (Example 96, Conjugate B); (iv) 47 kDa PHF-BA (AF HPA-L-Alanine)-SS-(Anti Her2-Affibody) (Example 93, Conjugate A); and (v) 105 kDa PHF-BA (AF HPA-L-Alanine)-SS-(Anti Her2-Affibody) (Example 93, conjugate B). Also included as a control was the drug-polymer conjugate 47 kDa PHF-BA-SSPy-(AF HPA-L-Alanine) (Example 90).

TABLE XII

| | PBRM MW | PHF MW | SKBR3 $IC_{50}$ (nmol/L) | MCF7 $IC_{50}$ (nmol/L) |
|---|---|---|---|---|
| Example 92 | ~45 kDa | 47 | 0.3 | >100 |
| Example 96 Conjugate A | ~45 kDa | 105 | 0.6 | >100 |
| Example 96 Conjugate B | ~45 kDa | 156 | 1.0 | >100 |
| Example 93 Conjugate A | ~14 kDa | 47 | 0.4 | >100 |
| Example 93 Conjugate B | ~14 kDa | 105 | 0.5 | >100 |
| Example 90 | Not applicable | Not applicable | 7.1 | >100 |

The results in Table XII show that for the HER2 expressing cell line, the PBRM-drug polymer conjugates (Examples 92, 93 and 96) exhibited higher antiproliferative activity compared to drug polymer conjugate (Example 90). All the conjugates were selective and did not show any antiproliferative activity in the non-HER2 expressing cell line.

Table XIII lists the results for PBRM-drug polymer conjugates with high drug loading. These PBRM-drug polymer conjugates are (i) 22 kDa PHF-BA-SSPyr-(AF HPA-L-Alanine)-SS-Trastuzumab (Example 94, Conjugate A AF HPA: trastuzumab about 40:1 to 45:1); (ii) 22 kDa PHF-BA-SSPy-(AF HPA-L-Alanine)-SS-Rituximab (Example 94, Conjugate C, AF HPA:rituximab about 37:1 to 41:1); (iii) 47 kDa PHF-BA-SSPyr-(AF HPA-L-Alanine)-SS-Trastuzumab (Example 94, conjugate B, Auristatin F—HPA:trastuzumab about 44:1 to 48:1); and (iv) 47 kDa PHF-BA(18%)-SSPyr (2.2%)-(AF HPA-L-Alanine)-SS-Rituximab (Example 94, conjugate D; AF HPA:rituximab about 47:1 to 51:1). Also included as a control was the drug alone: Auristatin F.

TABLE XIII

| | PHF MW (kDa) | Drug:PBRM | SKBR3 $IC_{50}$ (nmol/L) | BT474 $IC_{50}$ (nmol/L) | N87 $IC_{50}$ (nmol/L) | MCF7 $IC_{50}$ (nmol/L) |
|---|---|---|---|---|---|---|
| Example 94, Conjugate A | 22 | 40:1 to 45:1 | 0.008 | 0.05 | 0.12 | 9.5 |
| Example 94, Conjugate C | 22 | 37:1 to 41:1 | 0.83 | 2.82 | 5.84 | 4.17 |
| Example 50 | NA | NA | 0.32 | 0.85 | 1.00 | 8.5 |
| Example 94, Conjugate B | 47 | 44:1 to 48:1 | <0.05 | <0.05 | ~0.30 | 7.4 |
| Example 94, Conjugate D | 47 | 47:1 to 51:1 | 0.26 | 1.1 | 10.9 | 8.8 |
| Example 50 | NA | NA | 0.28 | 1.5 | 1.6 | 8.2 |

NA = not applicable.

Example 98

Cell Viability Assay for Drug Compounds

Drug compounds were evaluated for their ability to inhibit tumor growth using Cell Titer-Glo (Promega Corp) as described in Example 97. Table VIII are illustrative results for the antiproliferation properties of the drug compounds in HER2 expressing cells ("ND"=not determined).

TABLE VIII

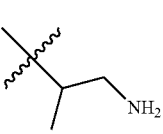 [SMILES: *C(C)CN]

| $R_{42}$ | SKBR3 $IC_{50}$ (nmol/L) | BT474 $IC_{50}$ (nmol/L) | MCF7 $IC_{50}$ (nmol/L) | N87 $IC_{50}$ (nmol/L) | HCT15 $IC_{50}$ (nmol/L) |
|---|---|---|---|---|---|
| —H | 103 | 160 | 619 | ND | ND |
| —CH$_3$ | 0.05 | 0.09 | 0.27 | 0.03 | 0.41 |
| (CH(CH$_3$)CH$_2$NH$_2$) | 0.72 | 1.07 | 3.29 | ND | ND |

TABLE VIII-continued
| R40 | SKBR3 IC$_{50}$ (nmol/L) | BT474 IC$_{50}$ (nmol/L) | MCF7 IC$_{50}$ (nmol/L) | N87 IC$_{50}$ (nmol/L) | HCT15 IC$_{50}$ (nmol/L) |
|---|---|---|---|---|---|
| 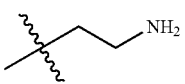 [SMILES: *CCN] | 0.73 | 1.17 | 3.28 | 0.89 | ND |
| 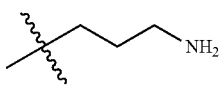 [SMILES: *CCCN] | 2.04 | 2.84 | 11.5 | 3.72 | ND |
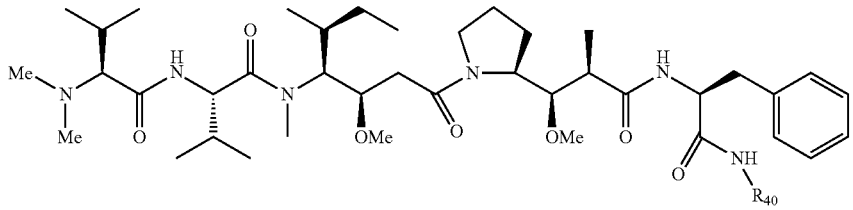
| R40 | SKBR3 IC$_{50}$ (nmol/L) | BT474 IC$_{50}$ (nmol/L) | MCF7 IC$_{50}$ (nmol/L) | N87 IC$_{50}$ (nmol/L) | HCT15 IC$_{50}$ (nmol/L) |
|---|---|---|---|---|---|
| H | 0.32 | 0.67 | 1.78 | ND | ND |
| 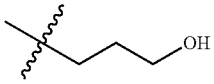 [SMILES: *CCCO] | 0.60 | 1.00 | 2.50 | 1.60 | 36.32 |
| 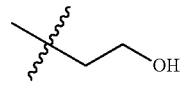 [SMILES: *CCO] | 1.11 | 1.74 | 4.92 | ND | ND |
| 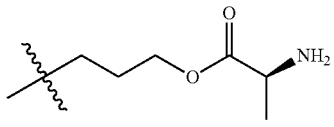 [SMILES: *CCCOC(=O)[C@H](C)N] | 1.40 | 1.66 | 6.77 | 2.47 | ND |
| 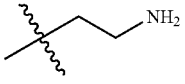 | 0.73 | 1.17 | 3.28 | 0.89 | ND |
| 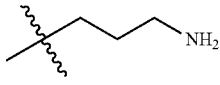 [SMILES: *CCCN] | 2.04 | 2.84 | 11.5 | 3.72 | ND |
| —OH | 12.0 | 20.6 | 39 | ND | ND |
| 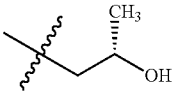 | 0.44 | 1.27 | 1.88 | 0.69 | 31.8 |
| 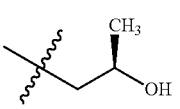 [SMILES: *C[C@@H](C)O] | 0.5 | 1.5 | 2.06 | 0.78 | 32.42 |
| 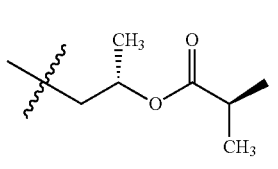 | 0.67 | 2.04 | 2.53 | 1.08 | 46.06 |
| 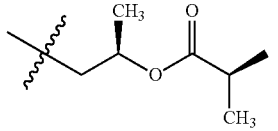 | 0.75 | 2.33 | 3.02 | 1.22 | 101.2 |

TABLE VIII-continued
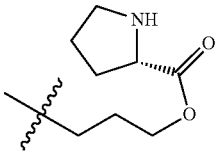 [SMILES: *CCCOC(=O)[C@@H]1CCCN1] 0.88 3.5 3.3 1.51 85.7
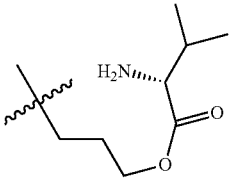 [SMILES: *CCCOC(=O)[C@H](N)C(C)C] 0.63 ND 3.85 1.64 42.2
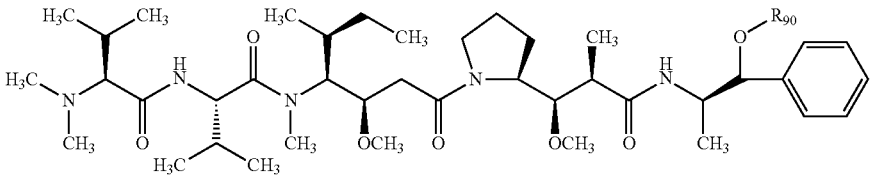
| $R_{90}$ | SKBR3 $IC_{50}$ (nmol/L) | BT474 $IC_{50}$ (nmol/L) | MCF7 $IC_{50}$ (nmol/L) | N87 $IC_{50}$ (nmol/L) | HCT15 $IC_{50}$ (nmol/L) |
|---|---|---|---|---|---|
| —H | 0.14 | 0.14 | 0.41 | 0.24 | 10.11 |
| 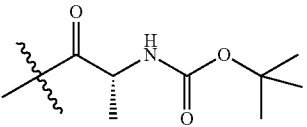 [SMILES: *C(=O)[C@@H](C)NC(=O)OC(C)(C)C] | 2.79 | 1.81 | 6.60 | 4.50 | 35.5 |
| 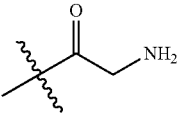 | 0.25 | 0.21 | 0.83 | 0.41 | 13.8 |
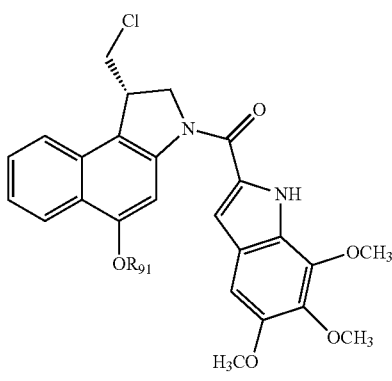
| $R_{91}$ | SKBR3 $IC_{50}$ (nmol/L) | BT474 $IC_{50}$ (nmol/L) | MCF7 $IC_{50}$ (nmol/L) | N87 $IC_{50}$ (nmol/L) | HCT15 $IC_{50}$ (nmol/L) |
|---|---|---|---|---|---|
| H | 1.05 | 3.7 | 0.99 | 0.80 | 1.75 |
| 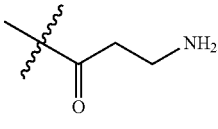 [SMILES: *C(=O)CCN] | 2.07 | 6.54 | 1.40 | 1.50 | 2.50 |

TABLE VIII-continued
| Structure | | | | | |
|---|---|---|---|---|---|
| (pyrrolidine-CO-) | 1.34 | 4.55 | 0.67 | 0.93 | 1.53 |
| (valine-CO-, NH₂) | 0.95 | 3.47 | 0.79 | 0.96 | 1.44 |
| (N-methyl-N-(2-hydroxyethyl)amide) | 21.5 | 68 | 100 | 30 | 100 |
| (piperazinyl-ethylamine amide) | 100 | 100 | 100 | 77 | 68 |
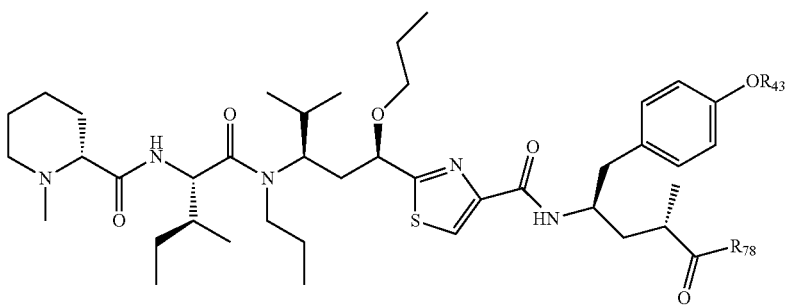
| $R_{43}$ | $R_{78}$ | SKBR3 $IC_{50}$ (nmol/L) | BT474 $IC_{50}$ (nmol/L) | MCF7 $IC_{50}$ (nmol/L) | N87 $IC_{50}$ (nmol/L) | HCT15 $IC_{50}$ (nmol/L) |
|---|---|---|---|---|---|---|
| H | —OH | 0.06 | 0.04 | 0.76 | 0.10 | 0.29 |
| (prolyl-CO-) | —OH | 0.13 | 0.15 | 0.44 | 0.19 | 1.91 |
| H | —OCH₃ | 0.71 | 0.21 | 3.02 | ND | ND |
| H | —O-(CH₂)₃-NH₂ | ND | 0.40 | ND | 1.5 | 23.0 |
| H | —NH₂ | 1.6 | 1.35 | 3.3 | 3.2 | |
| (valyl-CO-, NH₂) | —OH | 0.15 | ND | 0.67 | ND | 2.8 |

TABLE VIII-continued

| Structure | | | | | | |
|---|---|---|---|---|---|---|
| ![structure: C(=O)-NH-(CH2)4-NH2] | —OH | 0.08 | 0.10 | 0.68 | 0.24 | 4.6 |

Example 99

In Vivo Efficacy, Pharmacokinetic and Biodistribution Studies

In order to evaluate the efficacy and pharmacokinetics of the protein drug conjugate mouse and rat subcutaneous and orthotopic xenograft models are used.

Test articles, along with appropriate controls are administered intravenously (IV) via tail-vein injection or intraperitoneally. To assess circulating levels of test article blood sample is collected at designated times via terminal cardiac-puncture. Samples are kept at room temperature for 30 min to coagulate, then centrifuged for 10 min at 1,000×g at 4° C. and immediately frozen at −80° C. Total PBRM concentrations in serum samples are measured using ELISA. Circulating drug concentration (conjugated and free) is determined by LC/MS/MS methods.

To assess efficacy of the PBRM-drug polymer conjugates the tumor size are measured using digital calipers. Tumor volume is calculated and used to determine the delay in tumor growth.

For the determination of drug biodistribution, tumor, and major organs such as, for example, liver, kidney, spleen, lung, heart, muscles, and brain are harvested, immediately frozen in liquid nitrogen, stored at −80° C. PBRM and/or drug levels are determined in tissue homogenates by standard methods, such as, for example, ELISA or LC/MS/MS methods respectively.

Example 100

Tumor Growth Response to Administration of PBRM-Drug Polymer Conjugates

Female CB-17 SCID mice were inoculated subcutaneously with NCI-N87 cells (n=10 for each group) or BT474 tumors (n=12 or n=10 for each group). Test compounds or vehicle were dosed IV as a single dose on day 1; once every week for 3 weeks on day 1, day 8 and day 15 respectively; or once every week for 3 weeks on day 17, day 24 and day 31 respectively. The drug polymer conjugate dose was determined such that it delivered the same amount of drug as that present in the highest dose of the corresponding PBRM-drug polymer conjugate administered Tumor size was measured at the times indicated in FIGS. 1, 2, 3, 4 and 5 using digital calipers. Tumor volume was calculated and was used to determine the delay in tumor growth. Mice were sacrificed when tumors reached a size of 1000 mm³, 800 mm³, or 700 mm³. Tumor volumes are reported as the mean±SEM for each group.

FIG. 1 provides the results for the tumor response in mice inoculated subcutaneously with NCI-N87 cells (n=10 for each group) after IV administration of vehicle; PBRM-drug polymer conjugate PHF-GA-(HPV-Alanine)-(Trastuzumab-M-(PEG)$_{12}$), (Example 8, HPV:trastuzumab about 16:1 to 18:1) at 15.6 mg/kg, 5.2 mg/kg, 1.6 mg/kg and 0.5 mg/kg respectively and drug polymer conjugate PHF-GA-(HPV-Alanine)-SH (Example 6) (dosed at a Vinca dose that was equivalent to that present in Example 8 at 15.6 mg/kg) dosed once every week for 3 weeks on day 1, day 8 and day 15 respectively. The results show a dose response for PBRM-drug polymer conjugate (Example 8) with the highest dose of 15.6 mg/kg showing reduction of tumor volume with 80% partial responses (8/10); 20% complete responses (2/10) and 0% tumor free survival (0/10). The vehicle, drug-polymer conjugate (Example 6) and PBRM-drug polymer conjugate (Example 8) at doses of 5.2 mg/kg, 1.6 mg/kg and 0.5 mg/kg all showed increase of tumor volume.

Figure 2:
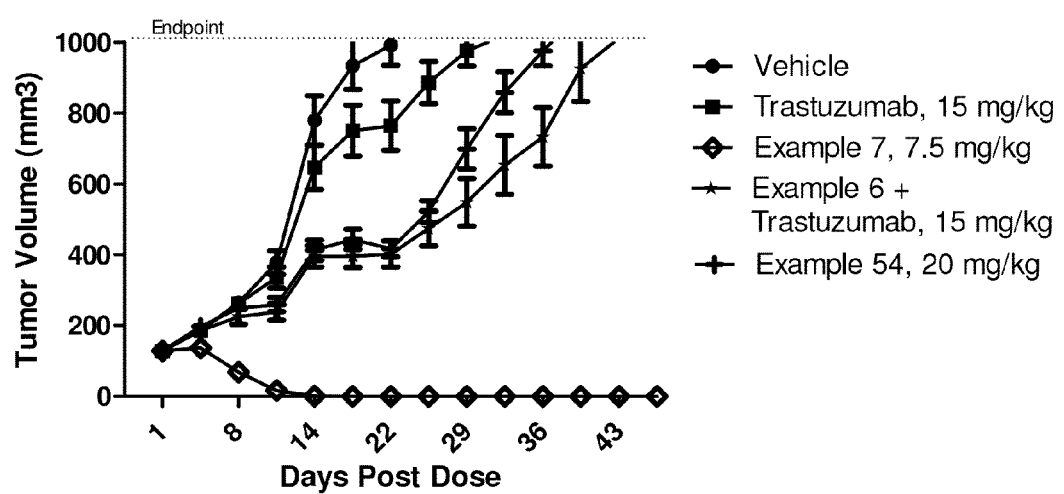
FIG. 2 is a graph showing the tumor response in mice inoculated subcutaneously with BT474 tumors (n=12 for each group) after IV administration of vehicle; PBRM (trastuzumab) at 15 mg/kg; PBRM-drug polymer conjugates PHF-GA-(HPV-Alanine)-(trastuzumab-MCC) (Example 7, HPV:trastuzumab about 19:1 to 22:1) at 7.5 mg/kg and PHF-GA-(HPV-Alanine)-(Rituximab-MCC) (Example 54, HPV:Rituximab about 12:1 to 15:1) at 20 mg/kg; drug polymer conjugate PHF-GA-(HPV-Alanine)-SH (Example 6) (dosed at a Vinca dose that was equivalent to that present in Example 7 at 15 mg/kg) in combination with trastuzumab at 15 mg/kg dosed once every week for 3 weeks on day 1, day 8 and day 15 respectively.

FIG. 2 provides the results for the tumor response in mice inoculated subcutaneously with BT474 tumors (n=12 for each group) after IV administration of vehicle; PBRM (trastuzumab) at 15 mg/kg; PBRM-drug polymer conjugates PHF-GA-(HPV-Alanine)-(Trastuzumab-MCC) (Example 7, HPV:trastuzumab about 19:1 to 22:1) at 7.5 mg/kg and PHF-GA-(HPV-Alanine)-(Rituximab-MCC) (Example 54, HPV: Rituximab about 12:1 to 15:1) at 20 mg/kg; drug polymer conjugate PHF-GA-(HPV-Alanine)-SH (Example 6) (dosed at a Vinca dose that was equivalent to that present in Example 7 at 15 mg/kg) in combination with trastuzumab at 15 mg/kg dosed once every week for 3 weeks on day 1, day 8 and day 15 respectively. The results show reduction of tumor volume for Example 7 with 100% complete responses and 100% tumor free survival. The vehicle, trastuzumab alone, combination of Example 6 and trastuzumab; and Example 54 all showed an increase of tumor volume. The conjugation of a PBRM specific for HER2 cell (trastuzumab) to a drug polymer conjugate was necessary for the reduction of tumor volume as neither a drug polymer conjugate in combination with a PBRM (Example 6 in combination with trastuzumab) nor conjugation of a HER2 cell non-specific PBRM (Rituximab, Example 54) showed reduction in tumor volume).

Figure 3:
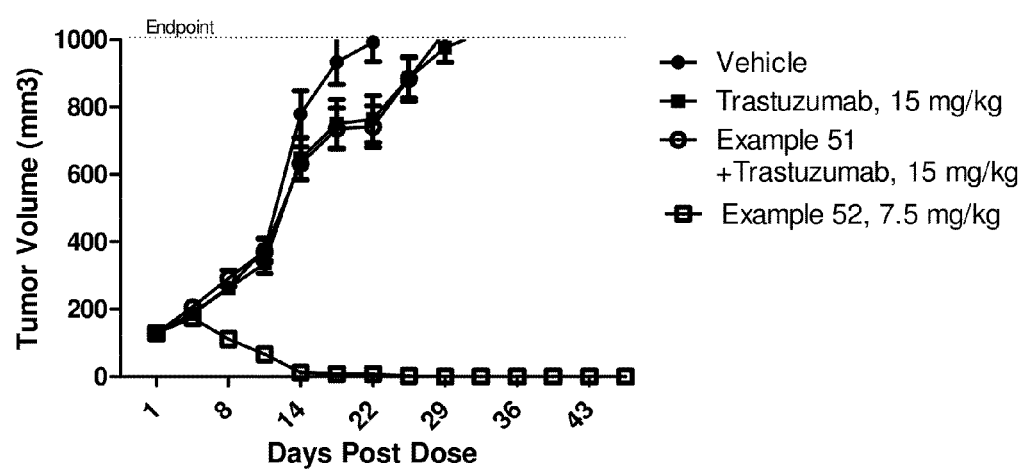
FIG. 3 is a graph showing the tumor response in mice inoculated subcutaneously with BT474 tumors (n=12 for each group) after IV administration of vehicle; PBRM (trastuzumab) at 15 mg/kg; PBRM-drug polymer conjugates PHF-GA-(Auristatin F-hydroxypropylamide-L-Alanine)-(Trastuzumab-MCC) (Example 52, Auristatin F:Trastuzumab about 20:1 to 22:1) at 7.5 mg/kg; drug polymer conjugate PHF-GA-5H-(Auristatin F-propylamide-L-Alanine) (Example 51) (dosed at an auristatin dose that was equivalent to that present in Example 52 at 15 mg/kg) in combination with trastuzumab at 15 mg/kg dosed once every week for 3 weeks on day 1, day 8 and day 15 respectively.

FIG. 3 provides the results for the tumor response in mice inoculated subcutaneously with BT474 tumors (n=12 for each group) after IV administration of vehicle; PBRM (trastuzumab) at 15 mg/kg; PBRM-drug polymer conjugates PHF-GA-(AF HPA-L-Alanine)-(Trastuzumab-MCC) (Example 52, Auristatin F:Trastuzumab about 20:1 to 22:1) at 7.5 mg/kg; drug polymer conjugate PHF-GA-5H-(AF HPA-L-Alanine) (Example 51) (dosed at an auristatin dose that was equivalent to that present in Example 52 at 15 mg/kg) in combination with trastuzumab at 15 mg/kg dosed once every week for 3 weeks on day 1, day 8 and day 15 respectively. The results show reduction of tumor volume for Example 52 with 100% complete responses (11/11) and 100% tumor free survival (11/11). The vehicle, trastuzumab alone, combination of Example 51 and trastuzumab all showed an increase of tumor volume. The conjugation of PBRM to drug-polymer conjugate was necessary for the reduction of tumor volume as neither a drug-polymer conjugate in combination with a PBRM (Example 51 in combination with trastuzumab) nor PBRM (trastuzumab) alone showed reduction in tumor volume.

Figure 4:
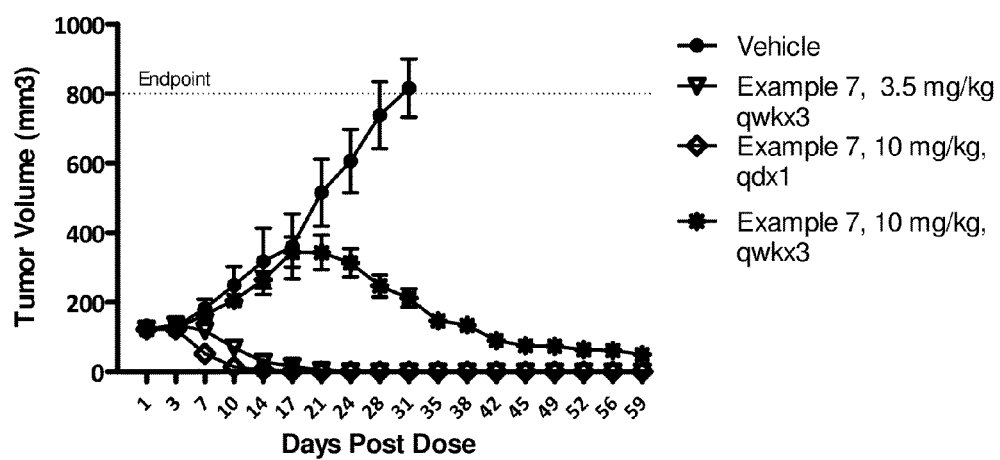
FIG. 4 is a graph showing the tumor response in mice inoculated subcutaneously with BT474 tumors (n=10 for each group) after IV administration of vehicle; PBRM-drug polymer conjugates PHF-GA-(HPV-Alanine)-(Trastuzumab-MCC) (Example 7, HPV:trastuzumab about 19:1 to 22:1) at 3.5 mg/kg dosed once every week for 3 weeks on day 1, day 8 and day 15 respectively; PBRM-drug polymer conjugates PHF-GA-(HPV-Alanine)-(Trastuzumab-MCC) (Example 7, HPV:trastuzumab about 19:1 to 22:1) at 10 mg/kg dosed as a single dose on day 1; PBRM-drug polymer conjugates PHF-GA-(HPV-Alanine)-(Trastuzumab-MCC) (Example 7, HPV:trastuzumab about 19:1 to 22:1) at 10 mg/kg dosed once every week for 3 weeks on day 17, day 24 and day 31 respectively.

FIG. 4 provides the results for the tumor response in mice inoculated subcutaneously with BT474 tumors (n=10 for each group) after IV administration of vehicle; PBRM-drug polymer conjugates PHF-GA-(HPV-Alanine)-(Trastuzumab-MCC) (Example 7, HPV:trastuzumab about 19:1 to 22:1) at 3.5 mg/kg dosed once every week for 3 weeks on day 1, day 8 and day 15 respectively; PBRM-drug polymer conjugates PHF-GA-(HPV-Alanine)-(Trastuzumab-MCC) (Example 7, HPV:trastuzumab about 19:1 to 22:1) at 10 mg/kg dosed as a single dose on day 1; PBRM-drug polymer conjugates PHF-GA-(HPV-Alanine)-(Trastuzumab-MCC) (Example 7, HPV:trastuzumab about 19:1 to 22:1) at 10 mg/kg dosed once every week for 3 weeks on day 17, day 24 and day 31 respectively. The results show reduction of tumor volume for Example 7 for all dosing regimens and all dosing concentrations tested with 100% complete responses (10/10) and 100% tumor free survival (10/10) dosed at 3.5 mg/kg once every week for 3 weeks; with 90% partial responses (9/10); 10% complete responses (1/10) and 10% tumor free survival (1/10) dosed at 10 mg/kg once every week for 3 weeks in mice with large tumors; and with 100% complete responses (10/10) and 100% tumor free survival (10/10) dosed at 10 mg/kg as a single dose. The vehicle, showed an increase of tumor volume.

Figure 5:
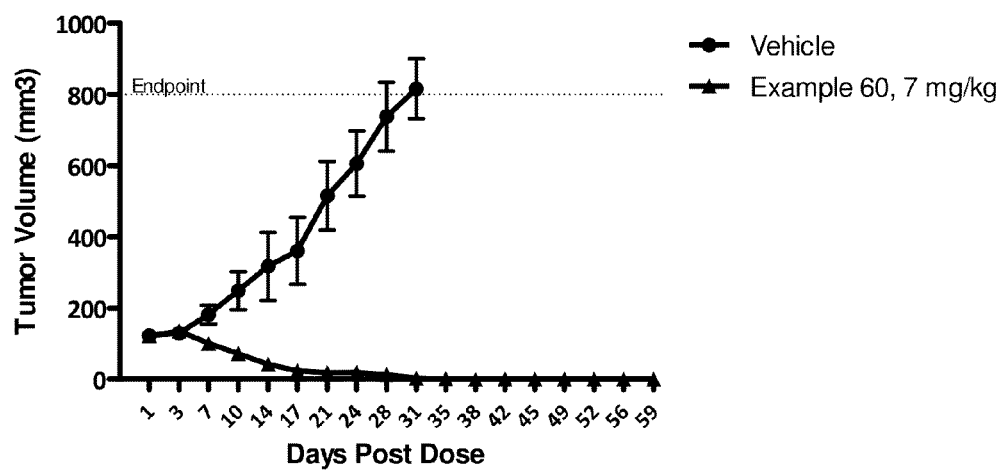
FIG. 5 is a graph showing the tumor response in mice inoculated subcutaneously with BT474 tumors (n=10 for each group) after IV administration of vehicle or 30 kDa PHF-GA-(HPV-Alanine)-(Trastuzumab-Fab) (Example 60, HPV:trastuzumab-Fab about 10:1 to 14:1) at 7 mg/kg dosed once every week for 3 weeks on day 1, day 8 and day 15 respectively.

FIG. 5 provides the results for the tumor response in mice inoculated subcutaneously with BT474 tumors (n=10 for each group) after IV administration of vehicle or 30 kDa PHF-GA-(HPV-Alanine)-(Trastuzumab-Fab') (Example 60, HPV:trastuzumab-Fab' about 10:1 to 14:1) at 7 mg/kg dosed once every week for 3 weeks on day 1, day 8 and day 15 respectively. The results show reduction of tumor volume for Example 60 with 100% complete responses (10/10) and 100% tumor free survival (10/10) compared to an increase of tumor volume for the vehicle.

Figure 8:
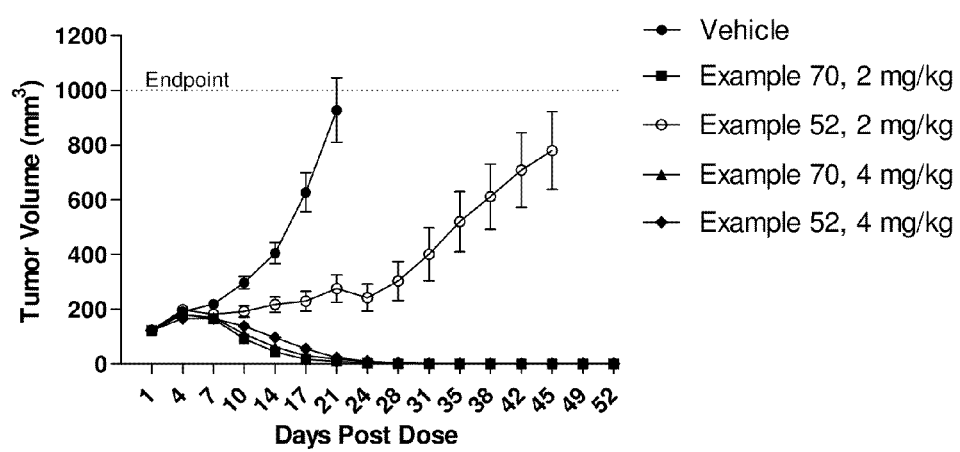
FIG. 8 is a graph showing the tumor response in mice inoculated subcutaneously with BT474 tumors (n=10 for each group) after IV administration of vehicle; PBRM-drug polymer conjugates PHF-GA-(Auristatin F-hydroxypropylamide-L-Alanine)-(Trastuzumab-MCC) (Example 52, Auristatin F:Trastuzumab about 24:1 to 28:1) and drug polymer conjugate PHF-GA-SS-Dimethyl-NO$_2$-(Auristatin F-hydroxypropylamide-L-Alanine)-(S-S-Trastuzumab) (Example 70, Auristatin F:Trastuzumab about 9:1 to 13:1) at 2 mg/kg and 4 mg/kg dosed once every week for 3 weeks on day 1, day 8 and day 15 respectively.

FIG. 8 provides the results for the tumor response in mice inoculated subcutaneously with BT474 tumors (n=10 for each group) after IV administration of vehicle; PBRM-drug polymer conjugates PHF-GA-(AF HPA-L-Alanine)-(Trastuzumab-MCC) (Example 52, Auristatin F:Trastuzumab about 24:1 to 28:1) and drug polymer conjugate PHF-GA-SS-Dimethyl-NO$_2$-(AF HPA-L-Alanine)-(S-S-Trastuzumab) (Example 70, Auristatin F:Trastuzumab about 9:1 to 13:1) at 2 mg/kg and 4 mg/kg dosed once every week for 3 weeks on day 1, day 8 and day 15 respectively. The results show complete reduction of tumor volume for Example 70 at doses 2 mg/kg and 4 mg/kg and for Example 52 at 4 mg/kg.

In all the in vitro or in vivo experiments described herein, unless otherwise specified, the doses used were all based on the PBRM (e.g., antibodies of antibody fragments) of the PBRM-drug polymer conjugates.

Example 101

In Vitro Stability of PBRM-Drug Polymer Conjugates

The in vitro stability of PBRM-drug polymer conjugates was evaluated by incubation of the PBRM-drug polymer conjugate in physiological saline or animal plasma at 37° C., pH 7.4. The rate of PBRM-drug polymer conjugate degradation was determined by monitoring the amount of drug released into the matrix by LC/MS analysis after isolation of released drug from the PBRM-drug polymer conjugate by liquid-liquid extraction.

Table IX lists the half life ($T_{1/2}$) of the PBRM-drug-conjugate, PHF-GA-(HPV-Alanine)-(Trastuzumab-M-(PEG)$_{12}$) of Example 8 (HPV:trastuzumab about 16:1 to 18:1) in mouse plasma, rat plasma and dog plasma.

TABLE IX

| Medium | $T_{1/2}$ (Days) |
|---|---|
| PBS | 6.4 |
| Mouse Plasma | 3.5 |
| Rat Plasma | 5.0 |
| Dog Plasma | 4.8 |

The results show that the PBRM-drug polymer conjugate of Example 8 was stable in animal plasma and released the drug as intended.

Example 102

Ligand Binding Studies by BIAcore Surface Plasmon Resonance (SPR)

The kinetic binding of the PBRM-drug polymer conjugate to an immobilized receptor was determined by BIAcore SPR. The binding constants for the PBRM in the PBRM-drug-conjugate PHF-GA-(HPV-Alanine)-(Trastuzumab-M-(PEG)$_{12}$) Example 8 (HPV:trastuzumab about 16:1 to 18:1) and PBRM (i.e., trastuzumab) alone were determined using standard BIAcore procedures.

Using standard amine coupling chemistry, hErbB2 was immobilized in three flow channels to the surface Plasmon resonance sensor chip surface at three similar densities. trastuzumab readily bound to the immobilized hErbB2 thereby demonstrating that both binding partners were active. Table X provides the binding parameters ka (association or affinity constant) and $K_D$ (dissociation constant) measured at 25° C. for the conjugate of Example 8 and trastuzumab using a BioRad ProteOn XPR36 optical biosensor equipped with a GLC sensor chip and equilibrated with running buffer.

TABLE X

| | ka ($M^{-1}s^{-1}$) | $K_D$ (pM) |
|---|---|---|
| Trastuzumab | 9.39 × 10$^5$ | 1.07 |
| Example 8 | 3.06 × 10$^5$ | 3.27 |

The results show that the PBRM in the PBRM-drug-conjugate was recognized by the PBRM receptor.

Example 103

Mouse Plasma PK and Tissue Distribution after Administration of PBRM-Drug Polymer Conjugates The plasma PK stability and the tissue distribution of PBRM-drug-conjugate was determined after administration of PBRM-drug-conjugate in female CB-17 SCID mice with NCI-N87 tumors (n=3). The conjugated HPV concentrations were determined by LC/MS analysis. The concentration of the HPV-trastuzumab-conjugate was estimated from the conjugated HPV data. Total trastuzumab concentration was determined by ELISA The mice received an IV bolus of PBRM-drug-conjugate PHF-GA-(HPV-Alanine)-(Trastuzumab-M-(PEG)$_{12}$) as in Example 8 (HPV:trastuzumab about 16:1 to 18:1) at 15 mg/kg (based on trastuzumab).

Figure 6:
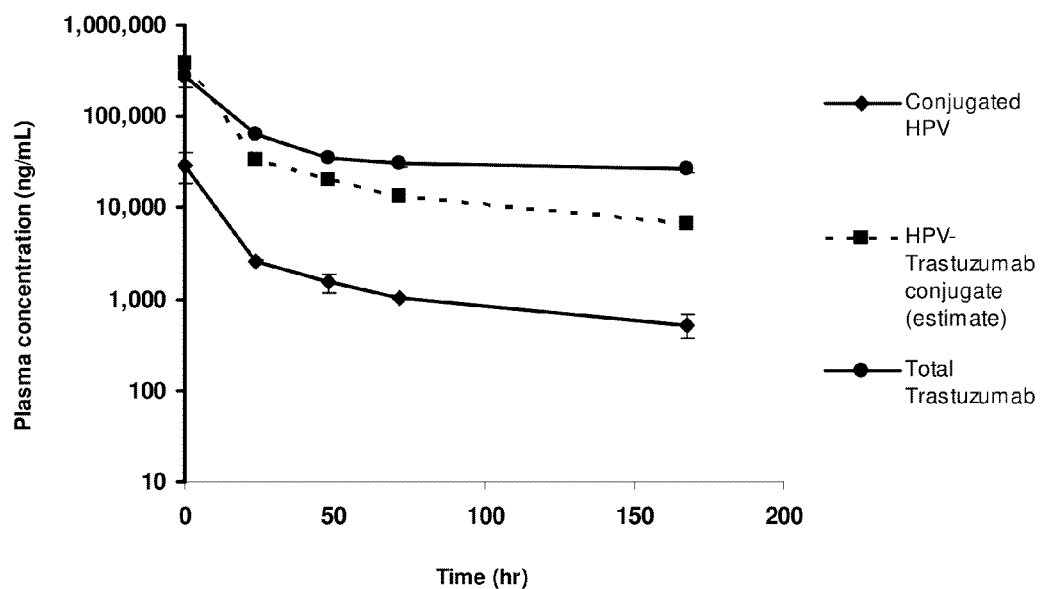
FIG. 6 is a graph showing the plasma PK for the conjugated HPV and trastuzumab after IV bolus administration of PBRM-drug-conjugate PHF-GA-(HPV-Alanine)-(Trastuzumab-M-(PEG)$_{12}$) as in Example 8 (HPV:trastuzumab about 16:1 to 18:1) at 15 mg/kg (based on trastuzumab).

FIG. 6 shows the plasma PK for the conjugated HPV and trastuzumab after IV bolus administration of PBRM-drug-conjugate PHF-GA-(HPV-Alanine)-(Trastuzumab-M-(PEG)$_{12}$) as in Example 8 (HPV:trastuzumab about 16:1 to 18:1) at 15 mg/kg (based on trastuzumab).

Figure 7:
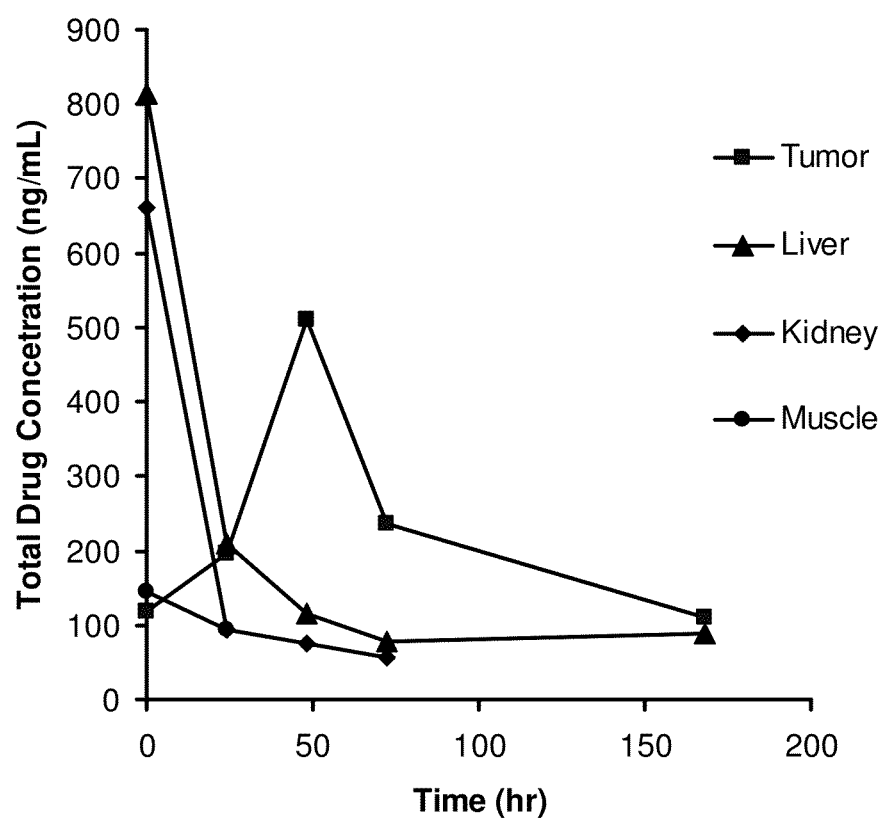
FIG. 7 is a graph showing the accumulation of HPV in various organs of the mice after IV bolus administration of PBRM-drug-conjugate PHF-GA-(HPV-Alanine)-(Trastuzumab-M-(PEG)$_{12}$) as in Example 8 (HPV:trastuzumab about 16:1 to 18:1) at 15 mg/kg (based on trastuzumab).

FIG. 7 shows the amount of HPV that accumulated in the various organs of the mice after IV bolus administration of PBRM-drug-conjugate PHF-GA-(HPV-Alanine)-(Trastuzumab-M-(PEG)$_{12}$) as in Example 8 (HPV:trastuzumab about 16:1 to 18:1) at 15 mg/kg (based on trastuzumab).

The results show that the PBRM-drug-conjugate was stable in plasma and that the drug reached the tumor. Peak tumor accumulation of HPV was observed between 24 and 72 hours.

Example 104

Mouse Plasma PK after Administration of PBRM-Drug Polymer Conjugates

The plasma PK stability of PBRM-drug-conjugate was determined after administration of PBRM-drug-conjugate in female CB-17 SCID mice with N87 tumors (n=3) or BT474 tumors (n=3). The conjugated HPV concentration was determined by LC/MS analysis. Total trastuzumab concentration was determined by ELISA.

Table XI provides the half life ($T_{1/2}$) and area under the curve (AUC) of the PBRM-drug-conjugate, PHF-GA-(HPV-Alanine)-(Trastuzumab-M-(PEG)$_{12}$) Example 8 (HPV:trastuzumab about 16:1 to 18:1) at 15.6 mg/kg based on trastuzumab in a N87 xenograft model and PBRM-drug polymer conjugates PHF-GA-(HPV-Alanine)-(Trastuzumab-MCC) (Example 7, HPV:trastuzumab about 19:1 to 22:1) at 15.0 mg/kg based on trastuzumab in BT474 xenograft model.

TABLE XI

|  | $T_{1/2}$ (hr) Conjugated HPV | AUC (0 to α) Conjugated HPV µg day/mL | AUC (0 to α) Total ADC µg day/mL |
| --- | --- | --- | --- |
| Example 7 BT474 xenograft model | 83 (β) | 19.5 | 205 |
| Example 8 N87 xenograft model | 81 (β) | 25.6 | 332 |

The results show that the PBRM-drug polymer conjugate of Examples 7 and 8 were stable in plasma.

Example 105

SDS-PAGE of PBRM-Polymer Drug Conjugates

PBRM-polymer drug conjugates (2.5 µg) were subjected to SDS-PAGE i.e., sodium dodecyl sulfate polyacrylamide gel electrophoresis) under non-reducing and reducing conditions and visualized with Odyssey IRDye® Blue Protein Stain Buffer. Under non-reducing conditions samples were either heated at 70° C. for 10 minutes, or not heated prior to SDS-PAGE analysis.

Figure 9:
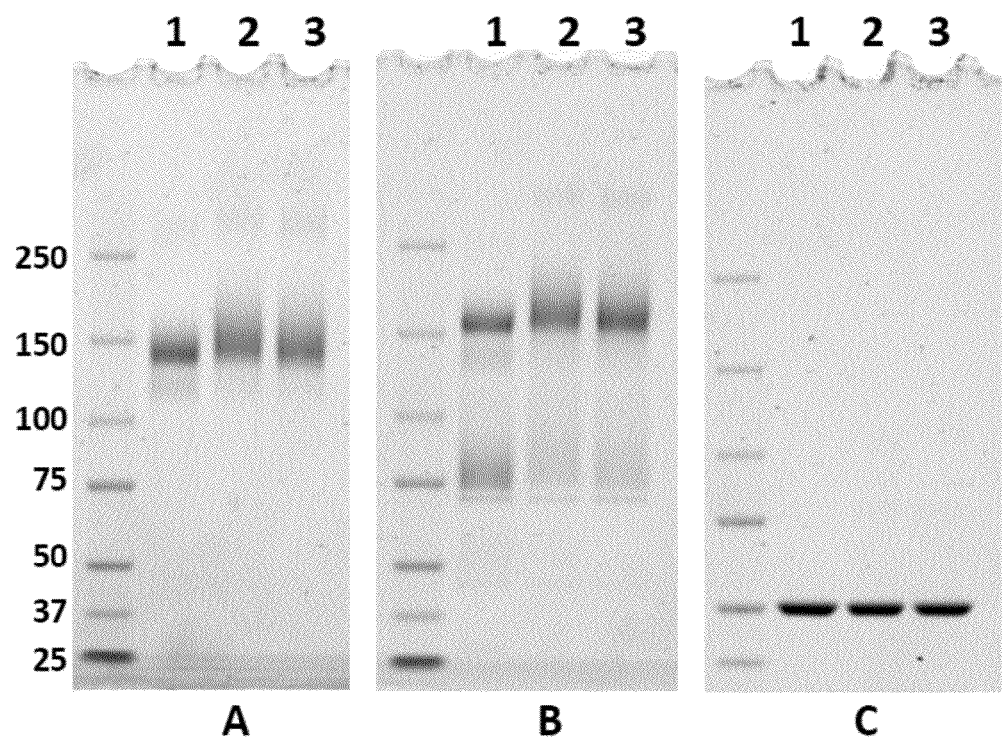
FIG. 9 is a group of SDS-PAGE (i.e., sodium dodecyl sulfate polyacrylamide gel electrophoresis) pictures of PBRM-drug-polymer conjugates 10 kDa PHF-GA-Auristatin F-hydroxylpropyl amide-SS-Trastuzumab (labeled as "1"); 14 kDa PHF-BA-Auristatin F-hydroxypropylamide-L-alanine-SS-Trastuzumab (labeled as "2") and 7 kDa PHF-BA-Auristatin E-proline SS-Trastuzumab (labeled as "3") under three different conditions: A—non-reducing and non-denaturing condition; B—non-reducing denaturing conditions, such as 70° C. for 10 minutes; and C—reducing conditions.

FIG. 9 shows a picture of SDS-PAGE of the following PBRM-polymer drug-conjugates:
Conjugate 1: 10 kDa PHF-GA-AF HPA-SS-Trastuzumab
Conjugate 2: 14 kDa PHF-BA-AF HPA-L-alanine-SS-Trastuzumab
Conjugate 3: 7 kDa PHF-BA-Auristatin E-proline-SS-Trastuzumab The SGS-PAGE gels shows that the PBRM-drug-polymer conjugates PHF-conjugates are stable under non-reducing conditions (FIG. 9A) and do not dissociate even under non-reducing denaturing conditions, such as 70° C. for 10 minutes. (FIG. 9B).

Under reducing conditions the conjugates dissociate in to heavy and light chain fragments. (FIG. 9C). Conjugates without PHF, i.e., Her2-auristatin conjugates, were also tested under the same conditions. It was found that those conjugates dissociated under non-reducing conditions even at room temperature. Under reducing conditions all tested conjugates (conjugates with or without PHF) dissociated in to heavy and light chain fragments.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A conjugate comprising an antibody and one or more D-carrying polymeric scaffolds connected to the antibody, each polymeric scaffold having Formula (Ic):

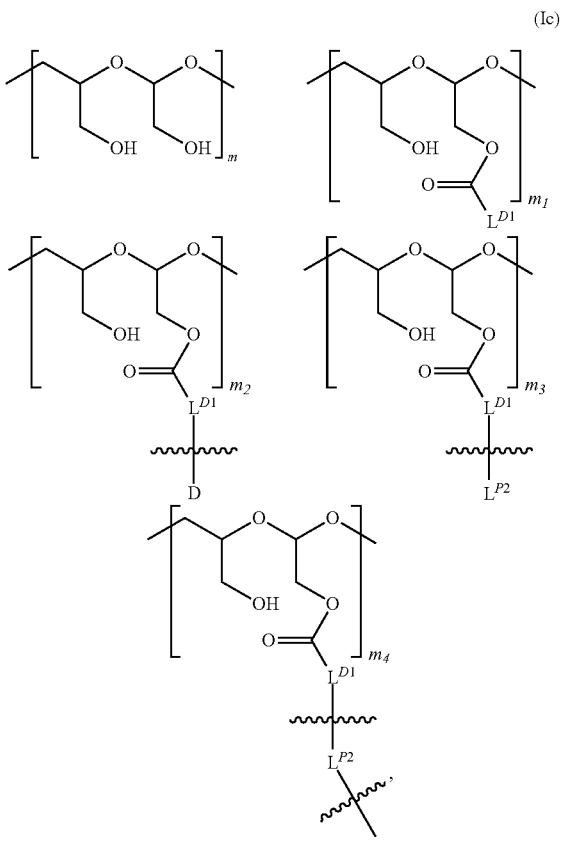

wherein:
each occurrence of D is independently a therapeutic agent having a molecular weight of ≤5 kDa;
each D-carrying polymeric scaffold comprises poly(1-hydroxymethylethylene hydroxymethyl-formal) (PHF) having a molecular weight ranging from about 2 kDa to about 40 kDa;
$L^{D1}$ is a carbonyl-containing moiety;
each occurrence of

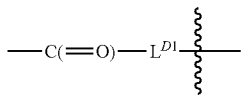

in

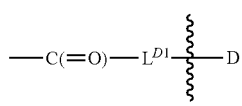

is independently a first linker that contains a biodegradable bond so that when the bond is broken, D is released in an active form for its intended therapeutic effect; and the

in

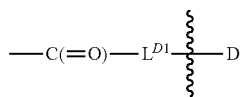

between $L^{D1}$ and D denote's direct or indirect attachment of D to $L^{D1}$;
each occurrence of

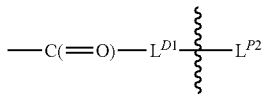

is independently a second linker not yet connected to the antibody, in which $L^{P2}$ is a moiety containing a functional group that is yet to form a covalent bond with a functional group of the antibody, and the

between $L^{D1}$ and $L^{P2}$ denotes direct or indirect attachment of $L^{P2}$ to $L^{D1}$, and each occurrence of the second linker is distinct from each occurrence of the first linker;

each occurrence of

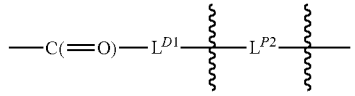

is independently a third linker that connects each D-carrying polymeric scaffold to the antibody in which the terminal

attached to $L^{P2}$ denotes direct or indirect attachment of $L^{P2}$ to the antibody upon formation of a covalent bond between a functional group of $L^{P2}$ and a functional group of the antibody; and each occurrence of the third linker is distinct from each occurrence of the first linker;
m is an integer from 1 to 300,
$m_1$ is an integer from 1 to 140,
$m_2$ is an integer from 1 to 40,
$m_3$ is an integer from 0 to 18,
$m_4$ is an integer from 1 to 10; and
the sum of m, $m_1$, $m_2$, $m_3$, and $m_4$ ranges from 15 to 300; provided that the total number of $L^{P2}$ connected to the antibody is 10 or less.

2. The conjugate of claim 1, wherein the sum of m, $m_1$, $m_2$, $m_3$ and $m_4$ ranges from 45 to 150, $m_1$ is an integer from 1 to 75, $m_2$ is an integer from 2 to 20, $m_3$ is an integer from 1 to 9, and PHF has a molecular weight ranging from about 6 kDa to about 20 kDa.

3. The conjugate of claim 1, wherein the sum of m, $m_1$, $m_2$, $m_3$ and $m_4$ ranges from 60 to 110, $m_1$ is an integer from 1 to 55, $m_2$ is an integer from 2 to 15, $m_3$ is an integer from 1 to 7; and PHF has a molecular weight ranging from about 8 kDa to about 15 kDa.

4. The conjugate of claim 1, wherein the functional group of $L^{P2}$ is selected from —$SR^p$, —S—S-LG, maleimido, and halo, in which LG is a leaving group and $R^p$ is H or a sulfur protecting group.

5. The conjugate of claim 1, wherein $L^{D1}$ comprises —X—$(CH_2)_v$—C(=O)— with X directly connected to the carbonyl group of

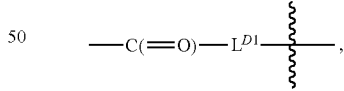

in which X is $CH_2$, O, or NH, and v is an integer from 1 to 6.

6. The conjugate of claim 1, wherein $L^{P2}$ contains a biodegradable bond.

7. The conjugate of claim 1, wherein each occurrence of D independently is an anticancer drug selected from vinca alkaloids, auristatins, tubulysins, duocarmycins, phosphatidylinositide 3 (PI3) kinase inhibitors, mitogen-activated protein kinase/extracellular signal-regulated kinase kinase (MEK) inhibitors, Kinesin Spindle Protein (KSP) inhibitors, pyrrolobenzodiazepines, DNA-binding drugs, and analogs thereof.

8. The conjugate of claim 1, wherein the antibody has a molecular weight of greater than 40 kDa.

9. The conjugate of claim 8, wherein the antibody has a molecular weight of greater than 80 kDa.
10. The conjugate of claim 9, wherein the antibody has a molecular weight of 140 kDa to 180 kDa.
11. The conjugate of claim 1, wherein each
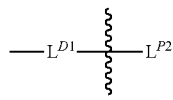
in the second linker, comprises a terminal group $W^P$, in which each $W^P$ independently is:
(1)
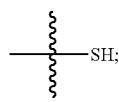
(2)
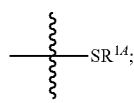
(3)
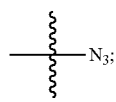
(4)
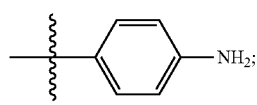
(5)
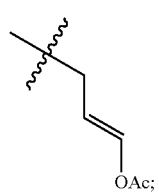
(6)
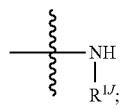
(7)
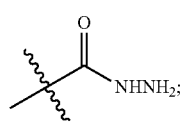
(8)
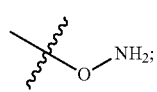
(9)
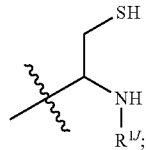
(10)
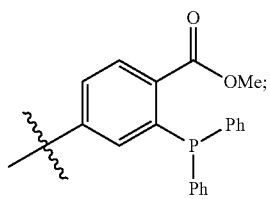
(11)
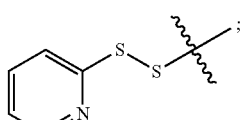
(12)
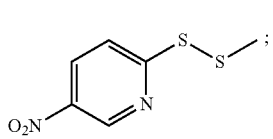
(13)
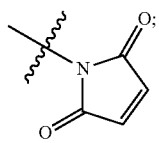
(14)
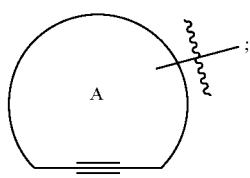
(15)
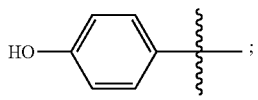
(16)
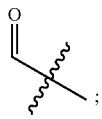
(17)
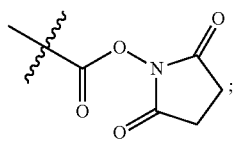
(18)
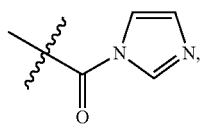
(19)
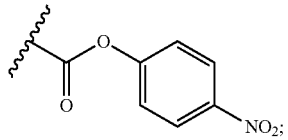
(20)
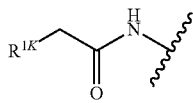

-continued (21)

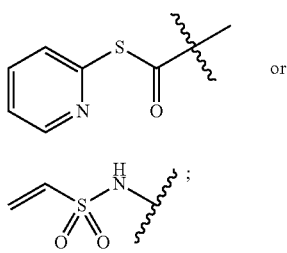

or (22)

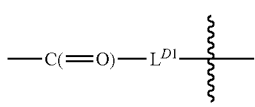

in which $R^{1K}$ is a leaving group, $R^{1A}$ is a sulfur protecting group, and ring A is cycloalkyl or heterocycloalkyl, and $R^{1J}$ is hydrogen, an aliphatic, heteroaliphatic, carbocyclic, or heterocycloalkyl moiety.

12. The conjugate of claim 11, wherein $R^{1A}$ is

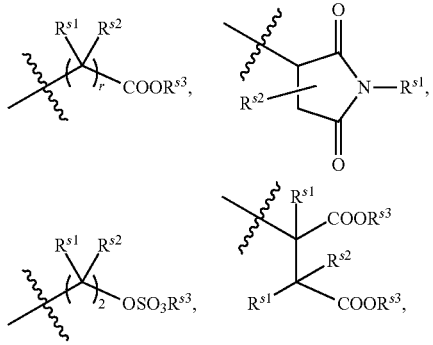

in which r is 1 or 2 and each of $R^{s1}$, $R^{s2}$, and $R^{s3}$ is hydrogen, an aliphatic, heteroaliphatic, carbocyclic, or heterocycloalkyl moiety.

13. The conjugate of claim 1, wherein each

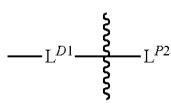

in the third linker is independently —$X^P$-$M^{P1}$-$Y^P$-$M^{P2}$-$Z^P$-$M^{P3}$-$Q^P$-$M^{P4}$-, with $X^P$ directly connected to the carbonyl group of —C(=O)—$L^{D1}$—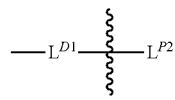

and $M^{P4}$ directly connected to the antibody, in which
  $X^P$ is —O—, —S—, —N($R^1$)—, or absent, in which $R^1$ is hydrogen, an aliphatic, heteroaliphatic, carbocyclic, or heterocycloalkyl moiety, —C(=O)$R^{1B}$, —C(=O)O$R^{1B}$, or —SO$_2$$R^{1B}$, or —N($R^1$)— is a heterocycloalkyl moiety, wherein $R^{1B}$ is hydrogen, an aliphatic, heteroaliphatic, carbocyclic, or heterocycloalkyl moiety;
  each of $Y^P$, $Z^P$, and $Q^P$, independently, is absent or a biodegradable linker moiety selected from the group consisting of —S—S—, —C(=O)O—, —C(=O)NR$^2$—, —OC(=O)—, —NR$^2$C(=O)—, —OC(=O)O—, —OC(=O)NR$^2$—, —NR$^2$C(=O)O—, —NR$^2$C(=O)NR$^3$—, —C(OR$^2$)O—, —C(OR$^2$)S—, —C(OR$^2$)NR$^3$—, —C(SR$^2$)O—, —C(SR$^2$)S—, —C(SR$^2$)NR$^3$—, —C(NR$^2$R$^3$)O—, —C(NR$^2$R$^3$)S—, —C(NR$^2$R$^3$)NR$^4$—, —C(=O)S—, —SC(=O)—, —SC(=O)S—, —OC(=O)S—, —SC(=O)O—, —C(=S)S—, —SC(=S)—, —OC(=S)—, —C(=S)O—, —SC(=S)O—, —OC(=S)S—, —OC(=S)O—, —SC(=S)S—, —C(=NR$^2$)O—, —C(=NR$^2$)S—, —C(=NR$^2$)NR$^3$—, —OC(=NR$^2$)—, —SC(=NR$^2$)—, —NR$^3$C(=NR$^2$)—, —NR$^2$SO$_2$—, —NR$^2$NR$^3$—, —C(=O)NR$^2$NR$^3$—, —NR$^2$NR$^3$C(=O)—, —OC(=O)NR$^2$NR$^3$—, —NR$^2$NR$^3$C(=O)O—, —C(=S)NR$^2$NR$^3$—, —NR$^2$NR$^3$C(=S)—, —C(=NR$^4$)NR$^2$NR$^3$—, —NR$^2$NR$^3$C(=NR$^4$)—, —O(N=CR$^3$)—, —(CR$^3$=N)O—, —C(=O)NR$^2$—(N=CR$^3$)—, —(CR$^3$=N)—NR$^2$C(=O)—, —SO$_3$—, —NR$^2$SO$_2$NR$^3$—, —SO$_2$NR$^2$—, and polyamide, wherein each occurrence of R$^2$, R$^3$, and R$^4$ independently is hydrogen or an aliphatic, heteroaliphatic, carbocyclic, or heterocyclic moiety, or each occurrence of —NR$^2$— or —NR$^2$NR$^3$— is a heterocycloalkyl moiety; and
  each of $M^{P1}$, $M^{P2}$, $M^{P3}$, and $M^{P4}$ independently, is absent or a non-biodegradable linker moiety selected from the group consisting of alkyl, alkenyl, alkynyl, heteroalkyl, heteroalkenyl, heteroalkynyl, a carbocyclic moiety, a heterocyclic moiety, and a combination thereof, and each of $M^{P1}$, $M^{P2}$, and $M^{P3}$ optionally contains one or more —(C=O)— but does not contain any said biodegradable linker moiety;
  provided that for each —$L^{D1}$—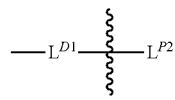—$L^{P2}$ connected to the antibody, at least one of $X^P$, $Y^P$, $Z^P$, and $Q^P$ is not absent.

14. The conjugate of claim 13, wherein each

—$L^{D1}$—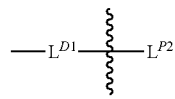—$L^{P2}$ in the third linker independently comprises one of the following structures:

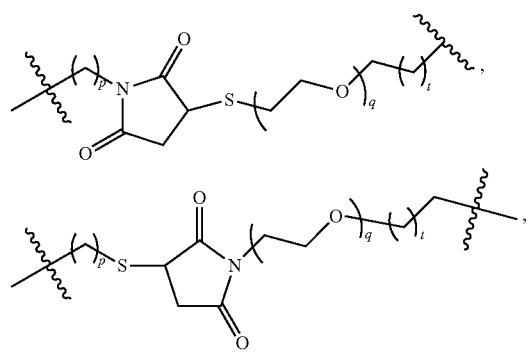

-continued

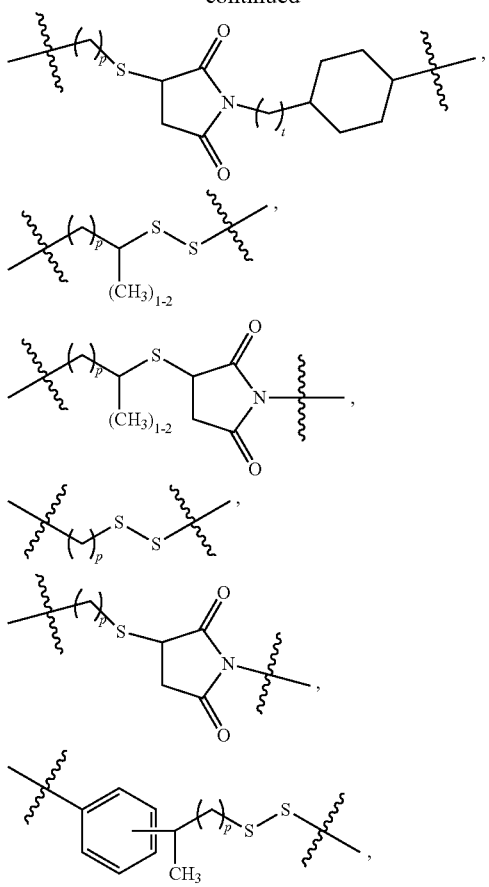

-continued

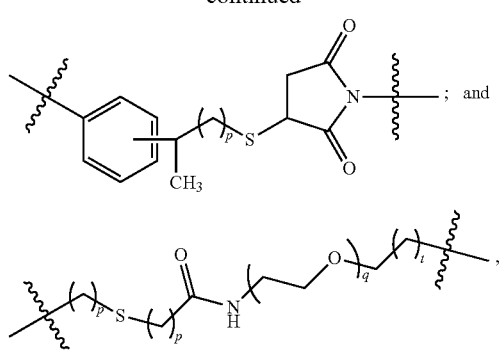

in which q is an integer from 0 to 12 and each of p and t independently is an integer from 0 to 3.

15. A pharmaceutical composition comprising a conjugate of claim 1 and a pharmaceutically acceptable carrier.

16. A method of treating cancer in a subject in need thereof, comprising administering to the subject an effective amount of the conjugate of claim 7.

17. The method of claim 16, wherein D is locally delivered to a target cell to which the antibody is capable of binding.

18. The method of claim 16, wherein the cancer is selected from the group consisting of anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, and gastric cancer.

* * * * *